US012486517B2

(12) United States Patent
Parks et al.

(10) Patent No.: US 12,486,517 B2
(45) Date of Patent: Dec. 2, 2025

(54) PESTICIDAL GENES AND METHODS OF USE

(71) Applicant: AGBIOME, INC., Durham, NC (US)

(72) Inventors: Jessica Parks, Apex, NC (US); Kira Bulazel Roberts, Bahama, NC (US); Rebecca E. Thayer, Morrisville, NC (US)

(73) Assignee: AgBiome, Inc., Durham, NC (US)

( * ) Notice: Subject to any disclaimer, the term of this patent is extended or adjusted under 35 U.S.C. 154(b) by 0 days.

(21) Appl. No.: 18/460,134

(22) Filed: Sep. 1, 2023

(65) Prior Publication Data

US 2024/0026373 A1 Jan. 25, 2024

Related U.S. Application Data

(62) Division of application No. 17/242,883, filed on Apr. 28, 2021, now abandoned, which is a division of application No. 16/388,061, filed on Apr. 18, 2019, now Pat. No. 11,021,717.

(60) Provisional application No. 62/774,515, filed on Dec. 3, 2018, provisional application No. 62/660,502, filed on Apr. 20, 2018.

(51) Int. Cl.
*C12N 15/82* (2006.01)
*C07K 14/195* (2006.01)

(52) U.S. Cl.
CPC ........ *C12N 15/8286* (2013.01); *C07K 14/195* (2013.01); *Y02A 40/146* (2018.01)

(58) Field of Classification Search
None
See application file for complete search history.

(56) References Cited

U.S. PATENT DOCUMENTS 8,829,279 B2 * 9/2014 Carozzi .............. C12N 15/8286 514/4.5

FOREIGN PATENT DOCUMENTS

| | | |
|---|---|---|
| WO | WO 1995/02694 | 1/1995 |
| WO | WO 2001/14417 | 3/2001 |
| WO | WO 2017/112538 | 6/2017 |

OTHER PUBLICATIONS

Moar et al, 2017, J. Invert. Pathol. 142:50-59.*
Argolo-Filho et al, 2014, Insects 5:62-91.*
GenBank Accession No. EWH35106 (2014, https://www.ncbi.nlm.nih.gov/protein/EWH35106).*
Bravo et al., "*Bacillus thuringiensis*: A story of a successful bioinsecticide," Insect Biochemistry and Molecular Biology, 2011, 41(7):423-431.
GenBank SCX27936.1, hypothetical protein DSM25558_4335 [*Agrobacterium* sp. DSM 25558], 2017.
Moar et al., "The sequence, structural, and functional diversity within a protein family and implications for specificity and safety: The case for ETX_MTX2 insecticidal proteins," J. Invert. Pathol., 2017, 142:50-59.
NCBI WP_077106733.1, "hypothetical protein [*Agrobacterium* sp. DSM 25558]," Feb. 8, 2017.
NCBI WP_103583963.1, "hypothetical protein [*Agrobacterium rosae*]," Feb. 6, 2018.
Schnepf et al., "Characterization of Cry34/Cry35 Binary Insecticidal Proteins from Diverse *Bacillus thuringiensis* Strain Collection," Appl Environ Microbiol, Apr. 2005, 71(4):1765-1774.
UniProtKB A0A1B8ZQ11, *Chryseobacterium arthrosphaerae*, 2016.
UniProtKB Accession No. R8R5P5, "Bacilluscereus HuB4-4," 2013.
GenBank: ACA38725.1, "hypothetical protein Bsph_1115 [Lysinibacillus sphaericus C3-41]," Jan. 20, 2015.
GenBank: APG02401.1, "hypothetical protein BFR06_29240 [Burkholderia pseudomallei]," Nov. 30, 2016.
GenBank: APG03947.1, "peptidase M23 [Luteibacter rhizovicinus DSM 16549]," Jul. 21, 2020.
GenBank: APG05834.1, "RND transporter [Luteibacter rhizovicinus DSM 16549]," Jul. 21, 2020.
GenBank: APG09110.1, "potassium-transporting ATPase subunit C [Bradyrhizobium japonicum]," Feb. 4, 2021.
NCBI Reference Sequence: WP_018673409.1, "ETX/MTX2 family pore-forming toxin [Brevibacillus laterosporus]," Sep. 5, 2024.
NCBI Reference Sequence: WP_051563179.1, "Multispecies: ETX/MTX2 family pore-forming toxin [Lysinibacillus]," Sep. 5, 2024.
NCBI Reference Sequence: WP_051800214.1, "ETX/MTX2 family pore-forming toxin [Lysinibacillus sphaericus]," Sep. 5, 2024.

(Continued)

*Primary Examiner* — Anne Kubelik
(74) *Attorney, Agent, or Firm* — Womble Bond Dickinson (US) LLP

(57) ABSTRACT

Compositions having pesticidal activity and methods for their use are provided. Compositions include isolated and recombinant polypeptide sequences having pesticidal activity, recombinant and synthetic nucleic acid molecules encoding the pesticidal polypeptides, DNA constructs comprising the nucleic acid molecules, vectors comprising the nucleic acid molecules, host cells comprising the vectors, and antibodies to the pesticidal polypeptides. Nucleotide sequences encoding the polypeptides provided herein can be used in DNA constructs or expression cassettes for transformation and expression in organisms of interest. The compositions and methods provided herein are useful for the production of organisms with enhanced pest resistance or tolerance. Transgenic plants and seeds comprising a nucleotide sequence that encodes a pesticidal protein of the invention are also provided. Methods are provided for producing the polypeptides disclosed herein, and for using those polypeptides for controlling a pest. Methods and kits for detecting polypeptides of the invention in a sample are also included.

19 Claims, No Drawings

Specification includes a Sequence Listing.

(56) References Cited

OTHER PUBLICATIONS

NCBI Reference Sequence: WP_051889583.1, "ETX/MTX2 family pore-forming toxin [Lysinibacillus sphaericus]," Sep. 5, 2024.
NCBI Reference Sequence: WP_051889585.1, "ETX/MTX2 family pore-forming toxin [Lysinibacillus sphaericus]," Sep. 5, 2024.
NCBI Reference Sequence: WP_051891081.1, "ETX/MTX2 family pore-forming toxin [Lysinibacillus sphaericus]," Sep. 5, 2024.
NCBI Reference Sequence: WP_104030950.1, "ETX/MTX2 family pore-forming toxin [Brevibacillus laterosporus]," Sep. 5, 2024.
NCBI Reference Sequence: WP_104064947.1, "ETX/MTX2 family pore-forming toxin [Brevibacillus laterosporus]," Sep. 5, 2024.

* cited by examiner

PESTICIDAL GENES AND METHODS OF USE

CROSS-REFERENCE TO RELATED APPLICATIONS

This application is a divisional of U.S. patent application Ser. No. 17/242,883, filed Apr. 28, 2021, which is a divisional of U.S. patent application Ser. No. 16/388,061, filed Apr. 18, 2019, which issued on Jun. 1, 2021 as U.S. Pat. No. 11,021,717, which claims priority from U.S. Provisional Application Nos. 62/774,515, filed Dec. 3, 2018, and 62/660,502, filed Apr. 20, 2018, which applications are hereby incorporated in their entirety by referenced in this application.

FIELD OF THE INVENTION

The invention is drawn to methods and compositions for controlling pests, particularly plant pests.

STATEMENT REGARDING THE SEQUENCE LISTING

The official copy of the sequence listing is submitted electronically concurrently with the specification as an XML formatted sequence listing with a file name of A101100_1150 US_D2_SL.xml, a creation date of Aug. 28, 2023, and a size of 824,162 bytes. The sequence listing contained in this XML formatted document is part of the specification and is hereby incorporated in its entirety by reference herein.

BACKGROUND

Pests, plant diseases, and weeds can be serious threats to crops. Losses due to pests and diseases have been estimated at 37% of the agricultural production worldwide, with 13% due to insects, bacteria and other organisms.

Toxins are virulence determinants that play an important role in microbial pathogenicity and/or evasion of the host immune response. Toxins from the gram-positive bacterium *Bacillus*, particularly *Bacillus thuringiensis*, have been used as insecticidal proteins. Current strategies use the genes expressing these toxins to produce transgenic crops. Transgenic crops expressing insecticidal protein toxins are used to combat crop damage from insects.

While the use of *Bacillus* toxins has been successful in controlling insects, resistance to Bt toxins has developed in some target pests in many parts of the world where such toxins have been used intensively. One way of solving this problem is sowing Bt crops with alternating rows of regular non Bt crops (refuge). An alternative method to avoid or slow down development of insect resistance is stacking insecticidal genes with different modes of action against insects in transgenic plants. The current strategy of using transgenic crops expressing insecticidal protein toxins is placing increasing emphasis on the discovery of novel toxins, beyond those already derived from the bacterium *Bacillus thuringiensis*. These toxins may prove useful as alternatives to those derived from *B. thuringiensis* for deployment in insect- and pest-resistant transgenic plants. Thus, new toxin proteins are needed.

SUMMARY

Compositions having pesticidal activity and methods for their use are provided. Compositions include isolated and recombinant polypeptide sequences having pesticidal activity, recombinant and synthetic nucleic acid molecules encoding the pesticidal polypeptides, DNA constructs comprising the nucleic acid molecules, vectors comprising the nucleic acid molecules, host cells comprising the vectors, and antibodies to the pesticidal polypeptides. Nucleotide sequences encoding the polypeptides provided herein can be used in DNA constructs or expression cassettes for transformation and expression in organisms of interest, including microorganisms and plants.

The compositions and methods provided herein are useful for the production of organisms with enhanced pest resistance or tolerance. These organisms and compositions comprising the organisms are desirable for agricultural purposes. Transgenic plants and seeds comprising a nucleotide sequence that encodes a pesticidal protein of the invention are also provided. Such plants are resistant to insects and other pests.

Methods are provided for producing the various polypeptides disclosed herein, and for using those polypeptides for controlling or killing a pest. Methods and kits for detecting polypeptides of the invention in a sample are also included.

DETAILED DESCRIPTION OF THE INVENTION

The present inventions now will be described more fully hereinafter with reference to the accompanying drawings, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

I. Polynucleotides and Polypeptides

Compositions and method for conferring pesticidal activity to an organism are provided. The modified organism exhibits pesticidal resistance or tolerance. Recombinant pesticidal proteins, or polypeptides and fragments and variants thereof that retain pesticidal activity, are provided and include those set forth in SEQ ID NOs: 1, 2, 3, 4, 5, 6, 7, 8, 9, 10, 11, 12, 13, 14, 15, 16, 17, 18, 19, 20, 21, 22, 23, 24, 25, 26, 27, 28, 29, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, and/or 525. The pesticidal proteins are biologically active (e.g., pesticidal) against pests including insects, fungi, nematodes, and the like. Nucleotides encoding the pesticidal polypeptides, including for example, SEQ ID NOs: 1, 2, 3, 4, 5, 6, 7, 8, 9, 10, 11, 12, 13, 14, 15, 16, 17, 18, 19, 20, 21, 22, 23, 24, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, and/or 525, or active fragments or variants thereof, can be used to produce transgenic organisms, such as plants and microorganisms. The pesticidal proteins are biologically active (for example, are pesticidal) against pests including insects, fungi, nematodes, and the like. In specific embodiments, the pesticidal polypeptides and the active variant and fragments thereof have an improved pesticidal activity when compared to other polypeptides in the art. Polynucleotides encoding the pesticidal polypeptides, including for example, SEQ ID NOs: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, and/or 525, or active fragments or variants thereof, can be used to produce transgenic organisms, such as plants and microorganisms. The transformed organisms are characterized by genomes that comprise at least one stably incorporated DNA construct comprising a coding sequence for a pesticidal protein disclosed herein. In some embodiments, the coding sequence is operably linked to a promoter that drives expression of the encoded pesticidal polypeptide. Accordingly, transformed microorganisms, plant cells, plant tissues, plants, seeds, and plant parts are provided. A summary of various polypeptides, active variants and fragments thereof, and polynucleotides encoding the same are set forth below in Table 1. As noted in Table 1, various forms of polypeptides are provided. Full length pesticidal polypeptides, as well as, modified versions of the original full-length sequence (i.e., variants) are provided. Table 1 further denotes "CryBP1" sequences. Such sequences (SEQ ID NOs: 3, 9, 57, 143, 220, 365, 404, and 449) comprise accessory polypeptides that can be associated with some of the toxin genes. In such instances, the CryBP1 sequences can be used alone or in combination with any of the pesticidal polypeptides provided herein. Table 1 further provides Split-Cry C-terminus polypeptides (SEQ ID NO: 27, 48, 85, 139, 271, 374, 430, and 497). Such sequences comprise the sequence of a downstream protein that has homology to the C-terminal end of the Cry class of toxin genes and are usually found after a Cry gene that is not full-length and is missing the expected C-terminal region.

TABLE 1

Summary of SEQ ID NOs, Gene Class, and Variants thereof

| APG ID | Seq ID | Modified Seq ID(s) | CryBP1 Seq ID | Split-Cry C-terminus Seq ID | Gene Class | % Identity | % Similarity | Homologs |
|---|---|---|---|---|---|---|---|---|
| APG00751.0 | 1 | 2 | 3 | | Cry | 55, 60, 65, 70, 75, 80, 85, 90, 91, 92, 93, 94, 95, 96, 97, 98, 99, 100 | 70, 75, 80, 85, 90, 91, 92, 93, 94, 95, 96, 97, 98, 99, 100 | APG08884.0 (54.39% identity, 68.5% similarity)<br>APG02841.0 (44.17% identity, 58.16% similarity)<br>APG00162.0 US_2016_0177333_A1-82 (43.57% identity, 59.16% similarity)<br>WP_098826687.1 (43.57% identity, 59.16% similarity)<br>APG03056.0 (42.69% identity, 58.27% similarity)<br>APG00374.0 US_2016_0366881_A1-40 (40.36% identity, 55.78% similarity)<br>US_6056953_A-28 (38.67% identity, 54.85% similarity)<br>ASO64551.1 (38.43% identity, 54.51% similarity)<br>CA_2516349-38 (38.39% identity, 54.6% similarity)<br>AND28677.1 (38.39% identity, 54.45% similarity) |
| APG00831.0 | 4 | 5, 6 | | | Cry | 60, 65, 70, 75, 80, 85, 90, 91, 92, 93, 94, 95, 96, 97, 98, 99, 100 | 70, 75, 80, 85, 90, 91, 92, 93, 94, 95, 96, 97, 98, 99, 100 | CA_2844913-48 (58.85% identity, 60.27% similarity)<br>APG06942.0 (58.22% identity, 60.19% similarity)<br>APG00688.0 US_2017_0175134_A1-104 (49.52% identity, 66.55% similarity)<br>WP_098088433.1 (47.28% identity, 63.15% similarity)<br>WP_098098942.1 (47.19% identity, 63.46% similarity)<br>US_9695440_B2-14 (41.35% identity, 52.76% similarity)<br>APG00103.0 US_2016_0304898_A1-132 (41.31% identity, 55.71% similarity)<br>US_9695440_B2-13 (41.24% identity, 52.56% similarity)<br>US_8461421_B2-168 (40.9% identity, 52.56% similarity)<br>US_8759619_B2-28 (40.59% identity, 54.47% similarity) |
| APG00832.0 | 7 | 8 | 9 | | Cry | 45, 50, 55, 60, 65, 70, 75, 80, 85, 90, 91, 92, 93, 94, 95, 96, 97, 98, 99, 100 | 60, 65, 70, 75, 80, 85, 90, 91, 92, 93, 94, 95, 96, 97, 98, 99, 100 | APG01634.0 (40.14% identity, 55.49% similarity)<br>WP_016099738.1 (39.15% identity, 56.6% similarity) |

TABLE 1-continued

Summary of SEQ ID NOs, Gene Class, and Variants thereof

| APG ID | Seq ID | Modified Seq ID(s) | CryBP1 Seq ID | Split-Cry C-terminus Seq ID | Gene Class | % Identity | % Similarity | Homologs |
|---|---|---|---|---|---|---|---|---|
| | | | | | | | | US_8318900_B2-111 (37.05% identity, 51.93% similarity)<br>WP_103574454.1 (36.88% identity, 53.62% similarity)<br>US_8318900_B2-80 (36.8% identity, 51.57% similarity)<br>US_8461415_B2-28 (36.31% identity, 52.79% similarity)<br>APG09227.0 (36.08% identity, 53.01% similarity)<br>APG07799.0 (35.47% identity, 51.98% similarity)<br>US_8461415_B2-1 (35.38% identity, 51.61% similarity)<br>APG00864.0 US_2017_0175134_A1-174 (31.74% identity, 44.13% similarity) |
| APG00842.0 | 10 | 11 | | | MTX | 5, 10, 15, 20, 25, 30, 35, 40, 45, 50, 55, 60, 65, 70, 75, 80, 85, 90, 91, 92, 93, 94, 95, 96, 97, 98, 99, 100 | 5, 10, 15, 20, 25, 30, 35, 40, 45, 50, 55, 60, 65, 70, 75, 80, 85, 90, 91, 92, 93, 94, 95, 96, 97, 98, 99, 100 | WP_004801413.1 (94.08% identity, 94.08% similarity)<br>WP_033133379.1 (94.08% identity, 94.08% similarity)<br>WP_005202252.1 (93.75% identity, 94.08% similarity)<br>WP_005322969.1 (93.42% identity, 94.08% similarity)<br>WP_016162910.1 (93.42% identity, 93.75% similarity)<br>WP_063645785.1 (65.13% identity, 65.79% similarity)<br>WP_090386676.1 (28.23% identity, 44.74% similarity)<br>WP_018616622.1 (26.99% identity, 43.56% similarity)<br>PCJ91616.1 (25.31% identity, 45.0% similarity) |
| APG00887.0 | 12 | 13 | | | MTX | 85, 90, 91, 92, 93, 94, 95, 96, 97, 98, 99, 100 | 90, 91, 92, 93, 94, 95, 96, 97, 98, 99, 100 | APG02970.0 (82.08% identity, 87.57% similarity)<br>APG02808.0 (81.79% identity, 87.57% similarity)<br>APG05239.0 (80.64% identity, 89.02% similarity)<br>APG01367.0 (80.35% identity, 86.99% similarity)<br>APG05140.0 (80.06% identity, 86.71% similarity)<br>APG05040.0 (78.32% identity, 86.13% similarity) |

TABLE 1-continued

Summary of SEQ ID NOs, Gene Class, and Variants thereof

| APG ID | Seq ID | Modified Seq ID(s) | CryBP1 Seq ID | Split-Cry C-terminus Seq ID | Gene Class | % Identity | % Similarity | Homologs |
|---|---|---|---|---|---|---|---|---|
| | | | | | | | | APG00793.0 US_2016_0355842_A1-170 (46.31% identity, 64.2% similarity)<br>APG07753.0 (41.11% identity, 55.28% similarity)<br>APG09460.0 (41.05% identity, 54.82% similarity)<br>APG00416.0 US_2016_0355842_A1-82 (40.22% identity, 53.72% similarity)<br>WP_098425282.1 (40.22% identity, 53.72% similarity) |
| APG00961.0 | 14 | 15 | | | Cry | 85, 90, 91, 92, 93, 94, 95, 96, 97, 98, 99, 100 | 90, 91, 92, 93, 94, 95, 96, 97, 98, 99, 100 | APG00084.0 US_2016_0311864_A1-15 (82.22% identity, 87.03% similarity)<br>APG06921.0 (61.73% identity, 73.75% similarity)<br>APG00152.0 US_2016_0311864_A1-36 (57.82% identity, 68.87% similarity)<br>WP_098381669.1 (56.94% identity, 69.1% similarity)<br>APG07954.0 (56.78% identity, 69.04% similarity)<br>WP_098377949.1 (56.78% identity, 69.04% similarity)<br>APG00164.0 US_2016_0311864_A1-41 (55.11% identity, 69.37% similarity)<br>EEM92570.1 (55.06% identity, 67.86% similarity)<br>CA_2844913-12 (54.1% identity, 67.34% similarity)<br>WP_098209375.1 (54.1% identity, 67.34% similarity) |
| APG00973.0 | 16 | 17, 18 | | | MTX | 40, 45, 50, 55, 60, 65, 70, 75, 80, 85, 90, 91, 92, 93, 94, 95, 96, 97, 98, 99, 100 | 50, 55, 60, 65, 70, 75, 80, 85, 90, 91, 92, 93, 94, 95, 96, 97, 98, 99, 100 | ANN35812.1 (45.86% identity, 59.34% similarity)<br>APG06236.0 (36.64% identity, 48.76% similarity)<br>APG04375.0 (35.14% identity, 46.76% similarity)<br>APG03686.0 (34.79% identity, 46.58% similarity)<br>APG04793.0 (34.52% identity, 46.3% similarity)<br>WP_098162508.1 (34.52% identity, 46.3% similarity)<br>WP_098908549.1 (34.52% identity, 46.3% similarity)<br>APG05300.0 (34.44% identity, 46.83% similarity) |

TABLE 1-continued

| Summary of SEQ ID NOs, Gene Class, and Variants thereof | | | | | | | | |
|---|---|---|---|---|---|---|---|---|
| APG ID | Seq ID | Modified Seq ID(s) | CryBP1 Seq ID | Split-Cry C-terminus Seq ID | Gene Class | % Identity | % Similarity | Homologs |
| | | | | | | | | APG07676.0 (34.25% identity, 46.03% similarity)<br>APG08525.0 (34.25% identity, 45.75% similarity) |
| APG01038.0 | 19 | 20 | | | MTX | 65, 70, 75, 80, 85, 90, 91, 92, 93, 94, 95, 96, 97, 98, 99, 100 | 80, 85, 90, 91, 92, 93, 94, 95, 96, 97, 98, 99, 100 | APG09572.0 (61.83% identity, 74.76% similarity)<br>APG03867.0 (61.61% identity, 74.61% similarity)<br>APG00143.0 US_2016_0355842_A1-4 (60.44% identity, 75.39% similarity)<br>APG00441.0 US_2016_0355842_A1-91 (60.0% identity, 74.69% similarity)<br>APG00833.0 US_2016_0355842_A1-175 (59.81% identity, 75.7% similarity)<br>WP_098858716.1 (59.81% identity, 75.7% similarity)<br>APG00444.0 US_2016_0355842_A1-93 (59.69% identity, 75.0% similarity)<br>APG03227.0 (58.07% identity, 73.29% similarity)<br>APG04037.0 (57.72% identity, 70.99% similarity)<br>APG07682.0 (57.4% identity, 69.49% similarity)<br>WP_098268663.1 (57.4% identity, 69.49% similarity)<br>WP_098768822.1 (57.4% identity, 69.49% similarity) |
| APG01063.0 | 21 | 22 | | | Bin | 75, 80, 85, 90, 91, 92, 93, 94, 95, 96, 97, 98, 99, 100 | 80, 85, 90, 91, 92, 93, 94, 95, 96, 97, 98, 99, 100 | APG04208.0 (71.64% identity, 81.17% similarity)<br>WP_098412831.1 (71.32% identity, 81.13% similarity)<br>APG00295.0 US_2016_0311864_A1-128 (70.99% identity, 79.25% similarity)<br>APG00308.0 US_2016_0311864_A1-135 (70.32% identity, 78.1% similarity)<br>WP_098386694.1 (65.38% identity, 75.54% similarity)<br>WP_098858722.1 (64.75% identity, 74.34% similarity)<br>APG00369.0 US_2016_0311864_A1-149 (64.67% identity, 73.56% similarity)<br>APG00419.0 US_2016_0311864_A1-176 (63.99% identity, 75.43% similarity)<br>WP_098634587.1 (63.99% identity, 75.43% similarity) |

TABLE 1-continued

Summary of SEQ ID NOs, Gene Class, and Variants thereof

| APG ID | Seq ID | Modified Seq ID(s) | CryBP1 Seq ID | Split-Cry C-terminus Seq ID | Gene Class | % Identity | % Similarity | Homologs |
|---|---|---|---|---|---|---|---|---|
| | | | | | | | | WP_098205870.1 (63.88% identity, 75.43% similarity) |
| APG01092.0 | 23 | 24 | | | Cry | 60, 65, 70, 75, 80, 85, 90, 91, 92, 93, 94, 95, 96, 97, 98, 99, 100 | 75, 80, 85, 90, 91, 92, 93, 94, 95, 96, 97, 98, 99, 100 | APG01686.0 (75.19% identity, 82.77% similarity)<br>APG04682.0 (56.32% identity, 70.7% similarity)<br>APG02630.0 (56.0% identity, 70.61% similarity)<br>US_8759619_B2-17 (34.43% identity, 49.34% similarity)<br>US_8759619_B2-3 (34.43% identity, 49.34% similarity)<br>CA_2595901-4 (33.75% identity, 49.63% similarity)<br>US_8759619_B2-15 (33.02% identity, 50.84% similarity)<br>APG00070.0 US_2016_0177333_A1-37 (32.39% identity, 45.82% similarity)<br>APG02391.0 (32.02% identity, 46.14% similarity)<br>US_8759619_B2-13 (31.85% identity, 45.26% similarity) |
| APG01102.0 | 25 | 26 | | 27 | Cry | 70, 75, 80, 85, 90, 91, 92, 93, 94, 95, 96, 97, 98, 99, 100 | 80, 85, 90, 91, 92, 93, 94, 95, 96, 97, 98, 99, 100 | APG00383.0 US_2017_0175134_A1-6 (66.21% identity, 75.71% similarity)<br>APG00101.0 US_2016_0177333_A1-57 (64.86% identity, 74.35% similarity)<br>WP_098976575.1 (64.86% identity, 74.35% similarity)<br>APG05886.0 (56.42% identity, 69.71% similarity)<br>OPA06342.1 (55.47% identity, 67.98% similarity)<br>WP_078401734.1 (55.1% identity, 67.53% similarity)<br>APG03555.0 (54.34% identity, 67.15% similarity)<br>APG00048.0 US_2016_0177333_A1-22 (54.24% identity, 64.72% similarity)<br>WP_098139461.1 (54.24% identity, 64.72% similarity)<br>APG08578.0 (53.9% identity, 67.26% similarity) |
| APG01127.0 | 28 | | | | MTX | 95, 96, 97, 98, 99, 100 | 98, 99, 100 | APG07655.0 (94.61% identity, 97.31% similarity)<br>APG00155.0 US_2016_0311864_A1-40 (92.93% identity, 96.97% similarity) |

TABLE 1-continued

Summary of SEQ ID NOs, Gene Class, and Variants thereof

| APG ID | Seq ID | Modified Seq ID(s) | CryBP1 Seq ID | Split-Cry C-terminus Seq ID | Gene Class | % Identity | % Similarity | Homologs |
|---|---|---|---|---|---|---|---|---|
| | | | | | | | | APG03504.0 (92.93% identity, 96.97% similarity)<br>APG03379.0 (82.94% identity, 89.3% similarity)<br>APG00749.0 (81.4% identity, 87.38% similarity)<br>APG01506.0 (80.47% identity, 87.54% similarity)<br>APG09682.0 (80.27% identity, 87.63% similarity)<br>APG09416.0 (80.0% identity, 86.33% similarity)<br>APG08241.0 (79.8% identity, 86.2% similarity)<br>APG02638.0 (79.33% identity, 87.67% similarity) |
| APG01141.0 | 29 | 30 | | | Bin | 85, 90, 91, 92, 93, 94, 95, 96, 97, 98, 99, 100 | 90, 91, 92, 93, 94, 95, 96, 97, 98, 99, 100 | APG00591.0 US_2016_0311864_A1-194 (84.36% identity, 88.55% similarity)<br>WP_098290048.1 (84.36% identity, 88.55% similarity)<br>APG00844.0 US_2016_0311864_A1-221 (47.31% identity, 59.85% similarity)<br>APG01059.0 (46.8% identity, 59.34% similarity)<br>APG01810.0 (46.62% identity, 59.4% similarity)<br>APG00353.0 US_2016_0311864_A1-144 (46.43% identity, 59.44% similarity)<br>WP_099003921.1 (46.43% identity, 59.44% similarity)<br>APG00203.0 US_2016_0311864_A1-69 (46.43% identity, 58.67% similarity)<br>WP_098475832.1 (46.43% identity, 58.67% similarity)<br>WP_033679178.1 (46.19% identity, 59.14% similarity) |
| APG01163.0 | 31 | 32 | | | MTX | 50, 55, 60, 65, 70, 75, 80, 85, 90, 91, 92, 93, 94, 95, 96, 97, 98, 99, 100 | 65, 70, 75, 80, 85, 90, 91, 92, 93, 94, 95, 96, 97, 98, 99, 100 | APG07249.0 (60.92% identity, 73.85% similarity)<br>APG00580.0 US_2016_0355842_A1-132 (45.61% identity, 61.4% similarity)<br>WP_098146720.1 (45.61% identity, 61.4% similarity)<br>APG00594.0 US_2016_0355842_A1-137 (42.11% identity, 54.02% similarity)<br>WP_097795410.1 (42.11% identity, 54.02% similarity) |

TABLE 1-continued

Summary of SEQ ID NOs, Gene Class, and Variants thereof

| APG ID | Seq ID | Modified Seq ID(s) | CryBP1 Seq ID | Split-Cry C-terminus Seq ID | Gene Class | % Identity | % Similarity | Homologs |
|---|---|---|---|---|---|---|---|---|
| | | | | | | | | APG00154.0 US_2016_0355842_A1-5 (42.11% identity, 53.74% similarity) US_8461415_B2-38 (41.92% identity, 55.07% similarity) APG00414.0 US_2016_0355842_A1-81 (41.53% identity, 57.67% similarity) APG00995.0 US_2016_0355842_A1-200 (41.53% identity, 57.14% similarity) APG00593.0 US_2016_0355842_A1-136 (41.53% identity, 56.88% similarity) WP_097899326.1 (41.53% identity, 56.88% similarity) |
| APG01165.0 | 33 | 34 | | | Cry | 70, 75, 80, 85, 90, 91, 92, 93, 94, 95, 96, 97, 98, 99, 100 | 80, 85, 90, 91, 92, 93, 94, 95, 96, 97, 98, 99, 100 | APG09773.0 (95.13% identity, 96.43% similarity) APG00296.0 US_2016_0355842_A1-52 (67.09% identity, 77.95% similarity) WP_098926211.1 (67.09% identity, 77.95% similarity) APG07033.0 (65.78% identity, 76.3% similarity) APG03264.0 (57.83% identity, 71.57% similarity) APG06221.0 (52.83% identity, 70.11% similarity) APG00553.0 US_2016_0355842_A1-124 (51.05% identity, 69.31% similarity) WP_098926212.1 (51.05% identity, 69.31% similarity) APG04454.0 (50.72% identity, 68.26% similarity) APG09727.0 (50.57% identity, 68.29% similarity) |
| APG01201.0 | 35 | 36 | | | MTX | 50, 55, 60, 65, 70, 75, 80, 85, 90, 91, 92, 93, 94, 95, 96, 97, 98, 99, 100 | 70, 75, 80, 85, 90, 91, 92, 93, 94, 95, 96, 97, 98, 99, 100 | APG03218.0 (52.54% identity, 68.08% similarity) APG00479.0 US_2016_0355842_A1-101 (47.75% identity, 63.48% similarity) WP_098139684.1 (47.75% identity, 63.48% similarity) WP_098139851.1 (47.58% identity, 67.52% similarity) APG00966.0 US_2016_0355842_A1-195 (47.29% identity, 63.82% similarity) WP_098976737.1 (47.29% identity, 63.82% similarity) APG00283.0 US_2016_0355842_A1-50 (46.52% identity, 66.02% similarity) |

TABLE 1-continued

| Summary of SEQ ID NOs, Gene Class, and Variants thereof | | | | | | | | |
|---|---|---|---|---|---|---|---|---|
| APG ID | Seq ID | Modified Seq ID(s) | CryBP1 Seq ID | Split-Cry C-terminus Seq ID | Gene Class | % Identity | % Similarity | Homologs |
| | | | | | | | | APG03623.0 (40.88% identity, 57.18% similarity)<br>APG00411.0 US_2016_0355842_A1-80 (39.89% identity, 55.59% similarity)<br>WP_065486138.1 (37.82% identity, 59.66% similarity)<br>WP_065487080.1 (37.82% identity, 59.66% similarity) |
| APG01281.0 | 37 | 38 | | | MTX | 65, 70, 75, 80, 85, 90, 91, 92, 93, 94, 95, 96, 97, 98, 99, 100 | 75, 80, 85, 90, 91, 92, 93, 94, 95, 96, 97, 98, 99, 100 | APG05341.0 (64.8% identity, 71.68% similarity)<br>APG00324.0 US_2016_0355842_A1-61 (63.96% identity, 74.37% similarity)<br>APG05481.0 (61.44% identity, 70.69% similarity)<br>APG00253.0 US_2016_0355842_A1-39 (44.83% identity, 60.48% similarity)<br>APG04342.0 (44.56% identity, 62.86% similarity)<br>APG00020.0 US_2016_0304898_A1-33 (44.56% identity, 60.48% similarity)<br>WP_098539891.1 (44.56% identity, 60.48% similarity)<br>WP_098178928.1 (44.56% identity, 59.68% similarity)<br>WP_098908888.1 (44.56% identity, 59.42% similarity)<br>APG01508.0 (44.3% identity, 59.95% similarity)<br>WP_098322759.1 (44.3% identity, 59.95% similarity) |
| APG01352.0 | 39 | 40 | | | Bin | 50, 55, 60, 65, 70, 75, 80, 85, 90, 91, 92, 93, 94, 95, 96, 97, 98, 99, 100 | 65, 70, 75, 80, 85, 90, 91, 92, 93, 94, 95, 96, 97, 98, 99, 100 | APG00729.0 US_2017_0175134_A1-142 (45.1% identity, 61.76% similarity)<br>APG00880.0 US_2016_0366881_A1-134 (34.5% identity, 49.0% similarity)<br>APG00215.0 US_2016_0311864_A1-78 (34.16% identity, 51.49% similarity)<br>APG00837.0 (33.5% identity, 50.37% similarity)<br>WP_002167240.1 (32.68% identity, 48.54% similarity)<br>APG04536.0 (32.67% identity, 48.38% similarity)<br>WP_016093722.1 (32.67% identity, 48.38% similarity)<br>APG05475.0 (32.33% identity, 48.62% similarity) |

TABLE 1-continued

Summary of SEQ ID NOs, Gene Class, and Variants thereof

| APG ID | Seq ID | Modified Seq ID(s) | CryBP1 Seq ID | Split-Cry C-terminus Seq ID | Gene Class | % Identity | % Similarity | Homologs |
|---|---|---|---|---|---|---|---|---|
| | | | | | | | | WP_048517129.1 (32.24% identity, 50.88% similarity)<br>APG08193.0 (32.18% identity, 50.74% similarity) |
| APG01380.0 | 41 | | | | Cry34 | 5, 10, 15, 20, 25, 30, 35, 40, 45, 50, 55, 60, 65, 70, 75, 80, 85, 90, 91, 92, 93, 94, 95, 96, 97, 98, 99, 100 | 5, 10, 15, 20, 25, 30, 35, 40, 45, 50, 55, 60, 65, 70, 75, 80, 85, 90, 91, 92, 93, 94, 95, 96, 97, 98, 99, 100 | APG05078.0 (96.52% identity, 98.26% similarity)<br>WP_077106733.1 (91.3% identity, 93.91% similarity)<br>WP_103583963.1 (91.3% identity, 93.91% similarity) |
| APG01385.0 | 42 | | | | MTX | 97, 98, 99, 100 | 98, 99, 100 | APG00641.0 US_2017_0175134_A1-66 (96.69% identity, 97.68% similarity)<br>APG00807.0 US_2017_0175134_A1-169 (75.08% identity, 83.06% similarity)<br>APG00434.0 US_2016_0366881_A1-58 (50.48% identity, 67.52% similarity)<br>US_9567381_B2-446 (32.49% identity, 47.95% similarity)<br>APG00866.0 US_2016_0355842_A1-183 (32.32% identity, 50.3% similarity)<br>WP_098072344.1 (32.32% identity, 50.3% similarity)<br>APG02068.0 (32.22% identity, 47.11% similarity)<br>APG00112.0 US_2016_0311864_A1-23 (31.83% identity, 46.85% similarity)<br>WP_098162515.1 (31.83% identity, 46.85% similarity)<br>APG00360.0 US_2016_0355842_A1-69 (31.78% identity, 47.98% similarity) |
| APG01396.0 | 43 | 44 | | | MTX | 70, 75, 80, 85, 90, 91, 92, 93, 94, 95, 96, 97, 98, 99, 100 | 80, 85, 90, 91, 92, 93, 94, 95, 96, 97, 98, 99, 100 | US_8829279_B2-42 (69.11% identity, 79.2% similarity)<br>WP_098228105.1 (32.56% identity, 52.62% similarity)<br>APG00218.0 US_2016_0355842_A1-26 (32.28% identity, 52.16% similarity)<br>APG00245.0 US_2016_0355842_A1-34 (32.08% identity, 52.02% similarity)<br>APG03900.0 (31.01% identity, 50.28% similarity)<br>APG01189.0 (30.95% identity, 46.42% similarity)<br>APG00187.0 US_2016_0355842_A1-20 (29.23% identity, 46.13% similarity)<br>WP_098228102.1 (29.23% identity, 46.13% similarity) |

TABLE 1-continued

Summary of SEQ ID NOs, Gene Class, and Variants thereof

| APG ID | Seq ID | Modified Seq ID(s) | CryBP1 Seq ID | Split-Cry C-terminus Seq ID | Gene Class | % Identity | % Similarity | Homologs |
|---|---|---|---|---|---|---|---|---|
| APG01434.0 | 45 | 46, 47 | | 48 | Cry | 85, 90, 91, 92, 93, 94, 95, 96, 97, 98, 99, 100 | 90, 91, 92, 93, 94, 95, 96, 97, 98, 99, 100 | AGV55019.1 (81.33% identity, 87.65% similarity)<br>APG00986.0 US_2017_0175134_A1-190 (80.54% identity, 87.48% similarity)<br>WP_098223384.1 (65.63% identity, 77.04% similarity)<br>CA_2658677-2 (64.37% identity, 75.95% similarity)<br>APG00518.0 US_2016_0366881_A1-104 (58.32% identity, 60.57% similarity)<br>WP_103592286.1 (58.04% identity, 72.17% similarity)<br>APG03018.0 (56.48% identity, 71.09% similarity)<br>WP_085313394.1 (56.18% identity, 70.79% similarity)<br>WP_050845711.1 (55.34% identity, 69.29% similarity)<br>US_9567381_B2-427 (55.03% identity, 68.93% similarity) |
| APG01455.0 | 49 | | | | MTX | 97, 98, 99, 100 | 98, 99, 100 | US_7214788_B2-4 (96.83% identity, 97.62% similarity)<br>US_9328356_B2-34 (92.06% identity, 96.03% similarity)<br>CA_2267665-4 (80.16% identity, 88.1% similarity)<br>AHA43421.1 (80.16% identity, 87.3% similarity)<br>US_9328356_B2-6 (66.67% identity, 73.33% similarity)<br>US_7214788_B2-10 (30.81% identity, 31.06% similarity)<br>US_7214788_B2-6 (30.81% identity, 31.06% similarity)<br>US_7214788_B2-14 (30.58% identity, 30.83% similarity)<br>US_7214788_B2-33 (30.5% identity, 30.75% similarity)<br>US_7214788_B2-8 (30.5% identity, 30.75% similarity) |
| APG01516.0 | 50 | 51 | | | MTX | 75, 80, 85, 90, 91, 92, 93, 94, 95, 96, 97, 98, 99, 100 | 85, 90, 91, 92, 93, 94, 95, 96, 97, 98, 99, 100 | APG04687.0 (72.39% identity, 84.45% similarity)<br>APG06242.0 (72.3% identity, 83.91% similarity)<br>US_8829279_B2-11 (61.85% identity, 75.75% similarity) |

TABLE 1-continued

| Summary of SEQ ID NOs, Gene Class, and Variants thereof | | | | | | | | |
|---|---|---|---|---|---|---|---|---|
| APG ID | Seq ID | Modified Seq ID(s) | CryBP1 Seq ID | Split-Cry C-terminus Seq ID | Gene Class | % Identity | % Similarity | Homologs |
| | | | | | | | | APG09338.0 (57.07% identity, 67.74% similarity)<br>APG06273.0 (56.39% identity, 70.28% similarity)<br>APG00051.0 US_2016_0304898_A1-81 (55.89% identity, 70.93% similarity)<br>WP_098425241.1 (55.89% identity, 70.93% similarity)<br>APG01858.0 (55.47% identity, 67.66% similarity)<br>WP_098229435.1 (54.1% identity, 65.3% similarity)<br>APG07055.0 (54.0% identity, 64.16% similarity) |
| APG01549.0 | 52 | | | | MTX | 55, 60, 65, 70, 75, 80, 85, 90, 91, 92, 93, 94, 95, 96, 97, 98, 99, 100 | 70, 75, 80, 85, 90, 91, 92, 93, 94, 95, 96, 97, 98, 99, 100 | US_8318900_B2-96 (51.1% identity, 67.82% similarity)<br>WP_044797748.1 (48.09% identity, 64.65% similarity)<br>APG03053.0 (44.41% identity, 62.84% similarity)<br>APG00098.0 US_2016_0304898_A1-128 (44.19% identity, 60.34% similarity)<br>APG00899.0 US_2016_0355842_A1-188 (44.19% identity, 60.34% similarity)<br>WP_098162516.1 (44.19% identity, 60.34% similarity)<br>WP_098908554.1 (44.19% identity, 60.34% similarity)<br>APG01885.0 (44.13% identity, 60.63% similarity)<br>US_9328356_B2-46 (32.84% identity, 48.36% similarity)<br>US_9567381_B2-441 (32.84% identity, 48.06% similarity) |
| APG01617.0 | 53 | 54 | | | MTX | 85, 90, 91, 92, 93, 94, 95, 96, 97, 98, 99, 100 | 90, 91, 92, 93, 94, 95, 96, 97, 98, 99, 100 | CA_2844913-54 (81.85% identity, 88.69% similarity)<br>APG00509.0 US_2016_0355842_A1-113 (35.03% identity, 46.33% similarity)<br>APG00541.0 US_2016_0355842_A1-119 (34.46% identity, 46.05% similarity)<br>WP_097855808.1 (34.46% identity, 46.05% similarity)<br>WP_098581475.1 (34.18% identity, 45.76% similarity)<br>CA_2844913-102 (33.05% identity, 47.29% similarity) |

TABLE 1-continued

| Summary of SEQ ID NOs, Gene Class, and Variants thereof | | | | | | | | |
|---|---|---|---|---|---|---|---|---|
| APG ID | Seq ID | Modified Seq ID(s) | CryBP1 Seq ID | Split-Cry C-terminus Seq ID | Gene Class | % Identity | % Similarity | Homologs |
| | | | | | | | | APG06228.0 (32.96% identity, 47.21% similarity)<br>APG00387.0 US_2016_0366881_A1-45 (32.78% identity, 45.0% similarity)<br>APG09155.0 (32.77% identity, 46.89% similarity)<br>APG04477.0 (32.71% identity, 45.74% similarity) |
| APG01681.0 | 55 | 56 | 57 | | Bin | 40, 45, 50, 55, 60, 65, 70, 75, 80, 85, 90, 91, 92, 93, 94, 95, 96, 97, 98, 99, 100 | 55, 60, 65, 70, 75, 80, 85, 90, 91, 92, 93, 94, 95, 96, 97, 98, 99, 100 | US_9321814_B2-2 (38.46% identity, 52.04% similarity)<br>US_9321814_B2-3 (38.46% identity, 52.04% similarity)<br>WP_098876539.1 (38.46% identity, 52.04% similarity)<br>APG06920.0 (37.92% identity, 51.47% similarity)<br>APG09069.0 (37.64% identity, 52.38% similarity)<br>APG07930.0 (37.56% identity, 52.76% similarity)<br>US_9321814_B2-4 (37.56% identity, 50.9% similarity)<br>APG00413.0 US_2016_0311864_A1-174 (37.44% identity, 52.51% similarity)<br>APG07511.0 (37.41% identity, 52.61% similarity)<br>APG03859.0 (37.35% identity, 52.67% similarity) |
| APG01686.0 | 58 | 59 | | | Cry | 55, 60, 65, 70, 75, 80, 85, 90, 91, 92, 93, 94, 95, 96, 97, 98, 99, 100 | 70, 75, 80, 85, 90, 91, 92, 93, 94, 95, 96, 97, 98, 99, 100 | APG01092.0 (75.19% identity, 82.77% similarity)<br>APG04682.0 (54.27% identity, 69.18% similarity)<br>APG02630.0 (53.67% identity, 67.84% similarity)<br>US_8759619_B2-17 (34.23% identity, 47.88% similarity)<br>US_8759619_B2-3 (34.23% identity, 47.88% similarity)<br>CA_2595901-4 (32.67% identity, 49.33% similarity)<br>APG00070.0 US_2016_0177333_A1-37 (32.1% identity, 45.86% similarity)<br>CA_2595901-2 (31.82% identity, 48.81% similarity)<br>APG02391.0 (31.57% identity, 45.74% similarity) |

TABLE 1-continued

| Summary of SEQ ID NOs, Gene Class, and Variants thereof | | | | | | | | |
|---|---|---|---|---|---|---|---|---|
| APG ID | Seq ID | Modified Seq ID(s) | CryBP1 Seq ID | Split-Cry C-terminus Seq ID | Gene Class | % Identity | % Similarity | Homologs |
| | | | | | | | | US_8759619_B2-13 (31.49% identity, 44.89% similarity) |
| APG01710.0 | 60 | 61 | | | Cry | 85, 90, 91, 92, 93, 94, 95, 96, 97, 98, 99, 100 | 90, 91, 92, 93, 94, 95, 96, 97, 98, 99, 100 | EJQ96305.1 (86.63% identity, 91.64% similarity)<br>WP_085962534.1 (86.15% identity, 91.14% similarity)<br>APG00616.0 US_2016_0366881_A1-120 (81.22% identity, 88.95% similarity)<br>US_8461421_B2-112 (38.93% identity, 55.74% similarity)<br>AFI42041.1 (38.11% identity, 55.58% similarity)<br>APG00618.0 US_2016_0366881_A1-123 (37.92% identity, 53.98% similarity)<br>AEX63666.1 (37.8% identity, 53.32% similarity)<br>APG05865.0 (30.44% identity, 44.83% similarity)<br>WP_033728958.1 (29.55% identity, 46.11% similarity)<br>ETT84679.1 (29.17% identity, 45.48% similarity) |
| APG01788.0 | 62 | 63 | | | Cry | 40, 45, 50, 55, 60, 65, 70, 75, 80, 85, 90, 91, 92, 93, 94, 95, 96, 97, 98, 99, 100 | 55, 60, 65, 70, 75, 80, 85, 90, 91, 92, 93, 94, 95, 96, 97, 98, 99, 100 | APG00473.0 US_2016_0366881_A1-87 (35.45% identity, 53.55% similarity)<br>APG07564.0 (29.99% identity, 44.3% similarity)<br>APG02706.0 (29.57% identity, 43.57% similarity)<br>APG02706.0 (29.57% identity, 43.57% similarity)<br>WP_103655243.1 (28.49% identity, 45.08% similarity)<br>US_2011_0239334_A1-80 (28.49% identity, 44.76% similarity)<br>US_2017_0347664_A1-215 (28.41% identity, 44.68% similarity)<br>US_5670365_A-9 (28.41% identity, 44.68% similarity)<br>US_9567381_B2-1403 (28.41% identity, 44.68% similarity)<br>US_7923602_B2-35 (27.98% identity, 42.38% similarity) |
| APG01803.0 | 64 | 65 | | | Cry | 35, 40, 45, 50, 55, 60, 65, 70, 75, 80, 85, 90, 91, 92, 93, 94, 95, 96, 97, 98, 99, 100 | 55, 60, 65, 70, 75, 80, 85, 90, 91, 92, 93, 94, 95, 96, 97, 98, 99, 100 | APG00564.0 US_2016_0355842_A1-128 (34.04% identity, 50.57% similarity)<br>APG00239.0 US_2016_0311864_A1-91 (31.57% identity, 45.19% similarity) |

TABLE 1-continued

Summary of SEQ ID NOs, Gene Class, and Variants thereof

| APG ID | Seq ID | Modified Seq ID(s) | CryBP1 Seq ID | Split-Cry C-terminus Seq ID | Gene Class | % Identity | % Similarity | Homologs |
|---|---|---|---|---|---|---|---|---|
| | | | | | | | | APG04152.0 (30.08% identity, 44.96% similarity)<br>APG06420.0 (29.61% identity, 42.3% similarity)<br>APG00395.0 US_2016_0311864_A1-162 (29.57% identity, 43.81% similarity)<br>WP_098397014.1 (29.57% identity, 43.81% similarity)<br>APG02506.0 (27.7% identity, 40.94% similarity)<br>APG07866.0 (27.45% identity, 41.78% similarity)<br>APG05920.0 (27.44% identity, 38.72% similarity)<br>APG00285.0 US_2016_0311864_A1-118 (27.4% identity, 39.67% similarity) |
| APG01810.0 | 66 | 67 | | | Bin | 75, 80, 85, 90, 91, 92, 93, 94, 95, 96, 97, 98, 99, 100 | 85, 90, 91, 92, 93, 94, 95, 96, 97, 98, 99, 100 | APG00301.0 US_2016_0311864_A1-131 (70.59% identity, 83.12% similarity)<br>WP_033679178.1 (70.44% identity, 83.55% similarity)<br>APG01059.0 (70.23% identity, 82.7% similarity)<br>APG00353.0 US_2016_0311864_A1-144 (70.08% identity, 83.38% similarity)<br>WP_099003921.1 (70.08% identity, 83.38% similarity)<br>APG00203.0 US_2016_0311864_A1-69 (69.82% identity, 83.12% similarity)<br>WP_098475832.1 (69.82% identity, 83.12% similarity)<br>APG00844.0 US_2016_0311864_A1-221 (69.21% identity, 81.93% similarity)<br>APG00419.0 US_2016_0311864_A1-176 (69.14% identity, 80.99% similarity)<br>WP_098634587.1 (69.14% identity, 80.99% similarity)<br>WP_098205870.1 (69.14% identity, 80.74% similarity) |
| APG01817.0 | 68 | | | | Cry | 92, 93, 94, 95, 96, 97, 98, 99, 100 | 97, 98, 99, 100 | EP_2728007-45 (91.95% identity, 96.06% similarity)<br>AHB36886.1 (91.61% identity, 95.89% similarity)<br>WP_080989246.1 (88.36% identity, 92.55% similarity)<br>US_9567381_B2-470 (76.22% identity, 84.77% similarity) |

TABLE 1-continued

| Summary of SEQ ID NOs, Gene Class, and Variants thereof | | | | | | | | |
|---|---|---|---|---|---|---|---|---|
| APG ID | Seq ID | Modified Seq ID(s) | CryBP1 Seq ID | Split-Cry C-terminus Seq ID | Gene Class | % Identity | % Similarity | Homologs |
| | | | | | | | | AEA92303.1 (76.13% identity, 84.69% similarity)<br>AFI42036.1 (71.17% identity, 79.04% similarity)<br>EP_2728007-55 (54.03% identity, 68.15% similarity)<br>US_8829279_B2-21 (53.99% identity, 69.13% similarity)<br>US_8829279_B2-23 (53.94% identity, 69.3% similarity)<br>WP_088065221.1 (53.83% identity, 69.05% similarity)<br>APG00960.0 US_2017_0175134_A1-179 (53.83% identity, 68.83% similarity) |
| APG01819.0 | 69 | 70 | | | Cry | 70, 75, 80, 85, 90, 91, 92, 93, 94, 95, 96, 97, 98, 99, 100 | 75, 80, 85, 90, 91, 92, 93, 94, 95, 96, 97, 98, 99, 100 | APG02667.0 (69.05% identity, 70.51% similarity)<br>APG00787.0 US_2017_0175134_A1-156 (28.77% identity, 42.92% similarity)<br>APG03986.0 (27.36% identity, 43.87% similarity)<br>APG00564.0 US_2016_0355842_A1-128 (27.32% identity, 43.61% similarity)<br>APG00702.0 US_2017_0175134_A1-115 (27.29% identity, 43.6% similarity)<br>APG05538.0 (26.96% identity, 40.21% similarity)<br>APG09947.0 (26.94% identity, 41.65% similarity)<br>APG08243.0 (26.69% identity, 44.32% similarity)<br>APG03699.0 (26.61% identity, 39.21% similarity)<br>APG00435.0 US_2016_0366881_A1-59 (26.32% identity, 41.02% similarity)<br>WP_086420153.1 (26.32% identity, 41.02% similarity) |
| APG01860.0 | 71 | 72 | | | Cry | 75, 80, 85, 90, 91, 92, 93, 94, 95, 96, 97, 98, 99, 100 | 75, 80, 85, 90, 91, 92, 93, 94, 95, 96, 97, 98, 99, 100 | APG09282.0 (70.13% identity, 72.08% similarity)<br>APG00787.0 US_2017_0175134_A1-156 (59.16% identity, 67.39% similarity)<br>APG05538.0 (57.65% identity, 63.19% similarity)<br>APG02533.0 (57.1% identity, 63.71% similarity)<br>KXH80331.1 (49.46% identity, 57.98% similarity) |

TABLE 1-continued

| Summary of SEQ ID NOs, Gene Class, and Variants thereof | | | | | | | | |
|---|---|---|---|---|---|---|---|---|
| APG ID | Seq ID | Modified Seq ID(s) | CryBP1 Seq ID | Split-Cry C-terminus Seq ID | Gene Class | % Identity | % Similarity | Homologs |
| | | | | | | | | WP_082770008.1 (47.97% identity, 56.24% similarity)<br>WP_098395829.1 (46.46% identity, 55.43% similarity)<br>APG05689.0 (45.7% identity, 57.56% similarity)<br>APG05439.0 (45.03% identity, 57.71% similarity)<br>APG09630.0 (44.97% identity, 52.9% similarity) |
| APG01967.0 | 73 | 74 | | | MTX | 80, 85, 90, 91, 92, 93, 94, 95, 96, 97, 98, 99, 100 | 90, 91, 92, 93, 94, 95, 96, 97, 98, 99, 100 | US_2015_0047076_A1-8 (76.33% identity, 85.87% similarity)<br>US_2015_0047076_A1-4 (68.06% identity, 76.39% similarity)<br>US_2015_0047076_A1-10 (67.49% identity, 77.39% similarity)<br>AQM56940.1 (65.37% identity, 72.44% similarity)<br>US_2015_0047076_A1-2 (64.81% identity, 75.96% similarity)<br>US_8461421_B2-42 (64.44% identity, 74.65% similarity)<br>US_8461421_B2-102 (64.08% identity, 74.65% similarity)<br>US_2015_0047076_A1-12 (64.01% identity, 76.47% similarity)<br>US_8461421_B2-220 (63.73% identity, 73.94% similarity)<br>US_9567381_B2-384 (62.94% identity, 74.83% similarity) |
| APG02071.0 | 75 | 76 | | | Cry | 45, 50, 55, 60, 65, 70, 75, 80, 85, 90, 91, 92, 93, 94, 95, 96, 97, 98, 99, 100 | 60, 65, 70, 75, 80, 85, 90, 91, 92, 93, 94, 95, 96, 97, 98, 99, 100 | APG05073.0 (45.78% identity, 58.49% similarity)<br>CA_2595901-12 (44.9% identity, 56.86% similarity)<br>US_5281530-4 (44.64% identity, 57.26% similarity)<br>CA_2595901-11 (44.52% identity, 57.37% similarity)<br>US_5281530-3 (44.52% identity, 57.37% similarity)<br>WP_097983832.1 (44.24% identity, 55.97% similarity)<br>US_9567381_B2-433 (44.17% identity, 55.9% similarity)<br>WP_098856496.1 (44.17% identity, 55.83% similarity) |

TABLE 1-continued

| Summary of SEQ ID NOs, Gene Class, and Variants thereof | | | | | | | | |
|---|---|---|---|---|---|---|---|---|
| APG ID | Seq ID | Modified Seq ID(s) | CryBP1 Seq ID | Split-Cry C-terminus Seq ID | Gene Class | % Identity | % Similarity | Homologs |
| | | | | | | | | US_9567381_B2-434 (44.03% identity, 55.83% similarity)<br>APG00622.0 US_2017_0175134_A1-58 (43.68% identity, 55.38% similarity)<br>APG00622.0 US_2017_0175134_A1-58 (43.68% identity, 55.38% similarity) |
| APG02105.0 | 77 | | | | MTX | 97, 98, 99, 100 | 99, 100 | WP_088080922.1 (97.05% identity, 97.7% similarity)<br>APG06465.0 (96.72% identity, 97.7% similarity)<br>APG01882.0 (96.41% identity, 97.39% similarity)<br>WP_098290464.1 (96.41% identity, 97.39% similarity)<br>APG08138.0 (96.39% identity, 98.36% similarity)<br>APG04483.0 (96.39% identity, 97.38% similarity)<br>WP_098908548.1 (96.39% identity, 97.38% similarity)<br>APG00696.0 US_2016_0355842_A1-160 (96.39% identity, 97.05% similarity)<br>WP_098222384.1 (96.39% identity, 97.05% similarity)<br>WP_098162507.1 (96.07% identity, 97.05% similarity)<br>WP_098778568.1 (95.74% identity, 97.05% similarity)<br>APG01265.0 (95.41% identity, 97.38% similarity)<br>APG06195.0 (95.08% identity, 96.07% similarity)<br>APG03715.0 (91.25% identity, 92.5% similarity)<br>WP_087969960.1 (90.6% identity, 91.85% similarity) |
| APG02110.0 | 78 | 79 | | | Cry | 85, 90, 91, 92, 93, 94, 95, 96, 97, 98, 99, 100 | 90, 91, 92, 93, 94, 95, 96, 97, 98, 99, 100 | APG06213.0 (95.78% identity, 97.89% similarity)<br>APG07811.0 (95.61% identity, 97.54% similarity)<br>APG06606.0 (95.08% identity, 97.19% similarity)<br>APG04108.0 (83.45% identity, 88.33% similarity)<br>APG00235.0 US_2016_0311864_A1-89 (82.87% identity, 88.75% similarity) |

TABLE 1-continued

| Summary of SEQ ID NOs, Gene Class, and Variants thereof | | | | | | | | |
|---|---|---|---|---|---|---|---|---|
| APG ID | Seq ID | Modified Seq ID(s) | CryBP1 Seq ID | Split-Cry C-terminus Seq ID | Gene Class | % Identity | % Similarity | Homologs |
| | | | | | | | | WP_050845493.1 (64.12% identity, 75.51% similarity)<br>APG08681.0 (55.49% identity, 66.3% similarity)<br>WP_048536324.1 (55.49% identity, 66.3% similarity)<br>APG00702.0 US_2017_0175134_A1-115 (37.52% identity, 50.72% similarity)<br>APG00401.0 US_2016_0311864_A1-168 (33.78% identity, 45.05% similarity)<br>APG00401.0 US_2016_0311864_A1-168 (33.78% identity, 45.05% similarity) |
| APG02115.0 | 80 | | | | MTX | 85, 90, 91, 92, 93, 94, 95, 96, 97, 98, 99, 100 | 90, 91, 92, 93, 94, 95, 96, 97, 98, 99, 100 | APG04978.0 (80.08% identity, 87.22% similarity)<br>APG08577.0 (42.81% identity, 62.23% similarity)<br>SHH89794.1 (37.28% identity, 55.91% similarity)<br>WP_073006288.1 (35.56% identity, 55.99% similarity)<br>WP_084723762.1 (34.33% identity, 52.0% similarity)<br>APG07463.0 (31.4% identity, 52.22% similarity)<br>WP_073008904.1 (30.8% identity, 49.83% similarity)<br>WP_073006284.1 (27.18% identity, 50.17% similarity) |
| APG02143.0 | 81 | | | | MTX | 50, 55, 60, 65, 70, 75, 80, 85, 90, 91, 92, 93, 94, 95, 96, 97, 98, 99, 100 | 70, 75, 80, 85, 90, 91, 92, 93, 94, 95, 96, 97, 98, 99, 100 | WP_098099663.1 (49.39% identity, 65.55% similarity)<br>WP_098087996.1 (49.39% identity, 65.24% similarity)<br>US_9328356_B2-26 (49.09% identity, 65.55% similarity)<br>WP_098179800.1 (49.09% identity, 65.55% similarity)<br>WP_098643733.1 (49.09% identity, 65.24% similarity)<br>WP_098072309.1 (48.78% identity, 65.24% similarity)<br>APG00866.0 US_2016_0355842_A1-183 (47.15% identity, 63.66% similarity)<br>WP_098072344.1 (47.15% identity, 63.66% similarity)<br>US_9567381_B2-328 (42.51% identity, 60.18% similarity) |

TABLE 1-continued

| Summary of SEQ ID NOs, Gene Class, and Variants thereof | | | | | | | | |
|---|---|---|---|---|---|---|---|---|
| APG ID | Seq ID | Modified Seq ID(s) | CryBP1 Seq ID | Split-Cry C-terminus Seq ID | Gene Class | % Identity | % Similarity | Homologs |
| | | | | | | | | US_9238678_B2-123 (34.77% identity, 49.43% similarity)<br>US_9238678_B2-125 (34.77% identity, 49.43% similarity) |
| APG02166.0 | 82 | | | | MTX | 45, 50, 55, 60, 65, 70, 75, 80, 85, 90, 91, 92, 93, 94, 95, 96, 97, 98, 99, 100 | 60, 65, 70, 75, 80, 85, 90, 91, 92, 93, 94, 95, 96, 97, 98, 99, 100 | APG06578.0 (44.26% identity, 60.98% similarity)<br>APG09957.0 (40.65% identity, 57.74% similarity)<br>APG02633.0 (32.4% identity, 50.17% similarity)<br>APG06768.0 (30.72% identity, 48.28% similarity)<br>APG02714.0 (29.15% identity, 49.83% similarity)<br>APG05793.0 (25.08% identity, 41.69% similarity) |
| APG02206.0 | 83 | 84 | | 85 | MTX | 90, 91, 92, 93, 94, 95, 96, 97, 98, 99, 100 | 94, 95, 96, 97, 98, 99, 100 | APG00932.0 (89.95% identity, 93.47% similarity)<br>APG03217.0 (76.63% identity, 85.18% similarity)<br>APG08029.0 (76.13% identity, 85.18% similarity)<br>WP_098069633.1 (75.63% identity, 84.17% similarity)<br>WP_098099018.1 (75.63% identity, 84.17% similarity)<br>WP_098087707.1 (75.38% identity, 84.17% similarity)<br>WP_099010057.1 (75.38% identity, 83.92% similarity)<br>APG01797.0 (75.13% identity, 84.42% similarity)<br>APG04119.0 (62.41% identity, 77.19% similarity)<br>APG06283.0 (61.19% identity, 75.12% similarity) |
| APG02221.0 | 86 | 87 | | | Cry | 60, 65, 70, 75, 80, 85, 90, 91, 92, 93, 94, 95, 96, 97, 98, 99, 100 | 75, 80, 85, 90, 91, 92, 93, 94, 95, 96, 97, 98, 99, 100 | APG01288.0 (59.56% identity, 70.17% similarity)<br>WP_098214356.1 (59.56% identity, 70.17% similarity)<br>APG07636.0 (52.3% identity, 66.81% similarity)<br>APG00801.0 US_2017_0175134_A1-160 (49.38% identity, 61.98% similarity)<br>APG00784.0 US_2017_0175134_A1-148 (48.35% identity, 60.23% similarity) |

TABLE 1-continued

| Summary of SEQ ID NOs, Gene Class, and Variants thereof | | | | | | | | |
|---|---|---|---|---|---|---|---|---|
| APG ID | Seq ID | Modified Seq ID(s) | CryBP1 Seq ID | Split-Cry C-terminus Seq ID | Gene Class | % Identity | % Similarity | Homologs |
| | | | | | | | | APG00099.0 US_2016_0177333_A1-55 (46.67% identity, 58.75% similarity)<br>WP_098487817.1 (46.67% identity, 58.75% similarity)<br>US_2011_0239334_A1-82 (31.0% identity, 43.74% similarity)<br>US_2011_0239334_A1-84 (30.99% identity, 44.12% similarity)<br>APG00217.0 US_2016_0355842_A1-24 (30.25% identity, 39.51% similarity) |
| APG02256.0 | 88 | 89 | | | MTX | 99, 100 | 99, 100 | APG07058.0 (98.4% identity, 98.94% similarity)<br>WP_078404291.1 (97.87% identity, 98.4% similarity)<br>APG04807.0 (32.41% identity, 50.5% similarity)<br>OPA24196.1 (31.92% identity, 49.63% similarity)<br>WP_078404344.1 (30.7% identity, 47.72% similarity)<br>APG05429.0 (30.62% identity, 47.85% similarity)<br>APG09864.0 (30.16% identity, 46.34% similarity)<br>APG08307.0 (30.0% identity, 50.5% similarity)<br>APG00940.0 US_2016_0355842_A1-191 (28.57% identity, 45.76% similarity)<br>WP_098783549.1 (28.57% identity, 45.76% similarity) |
| APG02309.0 | 90 | 91, 92 | | | Cry | 40, 45, 50, 55, 60, 65, 70, 75, 80, 85, 90, 91, 92, 93, 94, 95, 96, 97, 98, 99, 100 | 50, 55, 60, 65, 70, 75, 80, 85, 90, 91, 92, 93, 94, 95, 96, 97, 98, 99, 100 | APG09289.0 (65.9% identity, 75.48% similarity)<br>APG09289.0 (65.9% identity, 75.48% similarity)<br>US_5281530-4 (35.25% identity, 49.16% similarity)<br>US_5281530-4 (35.25% identity, 49.16% similarity)<br>US_5281530-4 (35.25% identity, 49.16% similarity)<br>CA_2595901-11 (35.21% identity, 49.43% similarity)<br>CA_2595901-11 (35.21% identity, 49.43% similarity)<br>US_5281530-3 (35.21% identity, 49.43% similarity) |

TABLE 1-continued

Summary of SEQ ID NOs, Gene Class, and Variants thereof

| APG ID | Seq ID | Modified Seq ID(s) | CryBP1 Seq ID | Split-Cry C-terminus Seq ID | Gene Class | % Identity | % Similarity | Homologs |
|---|---|---|---|---|---|---|---|---|
| | | | | | | | | US_5281530-3 (35.21% identity, 49.43% similarity)<br>CA_2595901-10 (34.97% identity, 49.87% similarity)<br>CA_2595901-10 (34.97% identity, 49.87% similarity) |
| APG02315.0 | 93 | 94 | | | MTX | 75, 80, 85, 90, 91, 92, 93, 94, 95, 96, 97, 98, 99, 100 | 80, 85, 90, 91, 92, 93, 94, 95, 96, 97, 98, 99, 100 | APG00541.0 US_2016_0355842_A1-119 (70.91% identity, 79.39% similarity)<br>WP_097855808.1 (70.91% identity, 79.39% similarity)<br>WP_098581475.1 (70.91% identity, 79.39% similarity)<br>APG00569.0 US_2016_0355842_A1-129 (70.38% identity, 78.01% similarity)<br>WP_098115624.1 (70.38% identity, 78.01% similarity)<br>APG00509.0 US_2016_0355842_A1-113 (70.3% identity, 79.09% similarity)<br>APG00244.0 US_2016_0355842_A1-33 (66.97% identity, 76.67% similarity)<br>WP_098381606.1 (66.97% identity, 76.67% similarity)<br>WP_098213528.1 (66.67% identity, 76.67% similarity)<br>APG06371.0 (66.08% identity, 74.56% similarity) |
| APG02319.0 | 95 | | | | MTX | 85, 90, 91, 92, 93, 94, 95, 96, 97, 98, 99, 100 | 92, 93, 94, 95, 96, 97, 98, 99, 100 | APG00614.0 US_2016_0355842_A1-144 (81.54% identity, 91.15% similarity)<br>WP_098072343.1 (81.54% identity, 91.15% similarity)<br>PEJ82417.1 (81.23% identity, 90.04% similarity)<br>US_9328356_B2-22 (79.23% identity, 88.46% similarity)<br>AAL26870.1 (64.66% identity, 78.95% similarity)<br>APG05300.0 (34.77% identity, 52.33% similarity)<br>APG08525.0 (34.39% identity, 51.93% similarity)<br>US_5308760_A-9 (34.29% identity, 48.25% similarity)<br>APG02740.0 (34.28% identity, 55.12% similarity)<br>APG06236.0 (33.82% identity, 50.91% similarity) |

TABLE 1-continued

Summary of SEQ ID NOs, Gene Class, and Variants thereof

| APG ID | Seq ID | Modified Seq ID(s) | CryBP1 Seq ID | Split-Cry C-terminus Seq ID | Gene Class | % Identity | % Similarity | Homologs |
|---|---|---|---|---|---|---|---|---|
| APG02380.0 | 96 | 97 | | | Vip3 | 92, 93, 94, 95, 96, 97, 98, 99, 100 | 96, 97, 98, 99, 100 | CA_2442594-2 (91.89% identity, 95.44% similarity)<br>US_9567381_B2-1539 (91.89% identity, 95.44% similarity)<br>AIT93171.1 (91.89% identity, 95.18% similarity)<br>AIT93180.1 (91.89% identity, 95.06% similarity)<br>CA_2442594-3 (91.76% identity, 95.31% similarity)<br>AIT93181.1 (91.76% identity, 95.06% similarity)<br>AIT93176.1 (91.76% identity, 94.8% similarity)<br>AIT93170.1 (91.63% identity, 95.06% similarity)<br>CA_2479769-2 (91.63% identity, 94.8% similarity)<br>US_9567381_B2-1536 (91.51% identity, 95.18% similarity)<br>KIP27841.1 (91.51% identity, 95.06% similarity)<br>CA_2327266-54 (90.75% identity, 94.8% similarity)<br>US_7129212_B2-27 (90.62% identity, 94.68% similarity)<br>CA_2442594-7 (90.24% identity, 94.3% similarity) |
| APG02451.0 | 98 | 99 | | | MTX | 95, 96, 97, 98, 99, 100 | 98, 99, 100 | APG00987.0 US_2016_0366881_A1-223 (94.88% identity, 97.95% similarity)<br>APG00506.0 US_2016_0366881_A1-102 (91.3% identity, 94.98% similarity)<br>APG04821.0 (91.3% identity, 94.98% similarity)<br>US_8461415_B2-57 (50.83% identity, 69.77% similarity)<br>APG00697.0 US_2016_0366881_A1-222 (48.49% identity, 68.9% similarity)<br>APG00346.0 US_2016_0366881_A1-24 (48.16% identity, 68.9% similarity)<br>US_8461415_B2-56 (45.27% identity, 67.91% similarity)<br>APG00450.0 US_2016_0366881_A1-72 (43.41% identity, 63.34% similarity)<br>APG01761.0 (43.09% identity, 62.7% similarity) |

TABLE 1-continued

Summary of SEQ ID NOs, Gene Class, and Variants thereof

| APG ID | Seq ID | Modified Seq ID(s) | CryBP1 Seq ID | Split-Cry C-terminus Seq ID | Gene Class | % Identity | % Similarity | Homologs |
|---|---|---|---|---|---|---|---|---|
| | | | | | | | | APG05804.0 (41.88% identity, 61.04% similarity) |
| APG02475.0 | 100 | 101, 102 | | | MTX | 97, 98, 99, 100 | 98, 99, 100 | APG04431.0 (96.18% identity, 97.71% similarity)<br>CA_2844913-120 (88.55% identity, 92.62% similarity)<br>APG05346.0 (88.04% identity, 92.62% similarity)<br>APG00202.0 US_2016_0304898_A1-195 (87.12% identity, 92.93% similarity)<br>WP_098111055.1 (86.77% identity, 92.11% similarity)<br>APG01443.0 (86.55% identity, 92.89% similarity)<br>APG00208.0 US_2016_0304898_A1-201 (82.91% identity, 90.45% similarity)<br>APG00352.0 US_2016_0366881_A1-29 (77.47% identity, 87.09% similarity)<br>APG07094.0 (76.96% identity, 86.84% similarity)<br>WP_000715637.1 (75.89% identity, 83.5% similarity) |
| APG02506.0 | 103 | 104 | | | Cry | 65, 70, 75, 80, 85, 90, 91, 92, 93, 94, 95, 96, 97, 98, 99, 100 | 75, 80, 85, 90, 91, 92, 93, 94, 95, 96, 97, 98, 99, 100 | US_8318900_B2-91 (62.64% identity, 72.07% similarity)<br>PGZ56209.1 (58.82% identity, 66.39% similarity)<br>APG08243.0 (55.56% identity, 67.0% similarity)<br>APG01679.0 (42.06% identity, 55.62% similarity)<br>WP_048536362.1 (42.06% identity, 55.62% similarity)<br>APG00375.0 US_2016_0311864_A1-152 (41.38% identity, 55.07% similarity)<br>WP_098805991.1 (41.38% identity, 55.07% similarity)<br>APG05139.0 (39.74% identity, 53.96% similarity)<br>APG07224.0 (39.48% identity, 52.69% similarity)<br>US_8318900_B2-90 (39.07% identity, 53.7% similarity) |
| APG02511.0 | 105 | 106, 107 | | | MTX | 55, 60, 65, 70, 75, 80, 85, 90, 91, 92, 93, 94, 95, 96, 97, 98, 99, 100 | 70, 75, 80, 85, 90, 91, 92, 93, 94, 95, 96, 97, 98, 99, 100 | APG02659.0 (56.98% identity, 67.88% similarity)<br>WP_078401252.1 (53.93% identity, 64.89% similarity) |

TABLE 1-continued

Summary of SEQ ID NOs, Gene Class, and Variants thereof

| APG ID | Seq ID | Modified Seq ID(s) | CryBP1 Seq ID | Split-Cry C-terminus Seq ID | Gene Class | % Identity | % Similarity | Homologs |
|---|---|---|---|---|---|---|---|---|
| | | | | | | | | US_8461415_B2-32 (53.33% identity, 65.51% similarity)<br>WP_098213667.1 (53.3% identity, 69.63% similarity)<br>WP_098487632.1 (53.3% identity, 69.63% similarity)<br>JP_2016_516397-59 (53.07% identity, 65.64% similarity)<br>ANS51604.1 (52.79% identity, 65.36% similarity)<br>AGC39300.1 (52.23% identity, 64.04% similarity)<br>JP_2016_516397-60 (51.96% identity, 64.25% similarity)<br>WP_023524027.1 (51.69% identity, 62.43% similarity) |
| APG02587.0 | 108 | 109 | | | Cry | 91, 92, 93, 94, 95, 96, 97, 98, 99, 100 | 95, 96, 97, 98, 99, 100 | US_7923602_B2-2 (90.97% identity, 94.85% similarity)<br>US_7923602_B2-17 (90.8% identity, 94.77% similarity)<br>US_7923602_B2-33 (90.66% identity, 94.53% similarity)<br>US_7923602_B2-38 (88.42% identity, 92.28% similarity)<br>APG00052.0 US_2016_0177333_A1-25 (87.5% identity, 93.16% similarity)<br>US_7923602_B2-13 (84.78% identity, 89.91% similarity)<br>US_2011_0231963_A1-6 (84.63% identity, 89.76% similarity)<br>US_5589382_A-4 (84.61% identity, 89.82% similarity)<br>US_9139843_B2-1 (84.5% identity, 90.23% similarity)<br>US_5959080_A-3 (84.19% identity, 89.32% similarity) |
| APG02592.0 | 110 | | | | MTX | 35, 40, 45, 50, 55, 60, 65, 70, 75, 80, 85, 90, 91, 92, 93, 94, 95, 96, 97, 98, 99, 100 | 55, 60, 65, 70, 75, 80, 85, 90, 91, 92, 93, 94, 95, 96, 97, 98, 99, 100 | APG07732.0 (45.49% identity, 66.32% similarity)<br>APG02088.0 (33.64% identity, 52.47% similarity)<br>APG07824.0 (32.61% identity, 50.62% similarity)<br>APG05918.0 (32.24% identity, 50.33% similarity)<br>APG09455.0 (31.69% identity, 48.62% similarity) |

TABLE 1-continued

| Summary of SEQ ID NOs, Gene Class, and Variants thereof | | | | | | | | |
|---|---|---|---|---|---|---|---|---|
| APG ID | Seq ID | Modified Seq ID(s) | CryBP1 Seq ID | Split-Cry C-terminus Seq ID | Gene Class | % Identity | % Similarity | Homologs |
| | | | | | | | | APG09675.0 (31.33% identity, 50.32% similarity)<br>APG00598.0 US_2016_0355842_A1-140 (30.87% identity, 50.16% similarity)<br>APG06880.0 (28.66% identity, 44.48% similarity)<br>APG02633.0 (28.43% identity, 46.08% similarity)<br>APG00236.0 US_2016_0355842_A1-32 (25.63% identity, 46.84% similarity) |
| APG02656.0 | 111 | 112 | | | Cry | 5, 10, 15, 20, 25, 30, 35, 40, 45, 50, 55, 60, 65, 70, 75, 80, 85, 90, 91, 92, 93, 94, 95, 96, 97, 98, 99, 100 | 5, 10, 15, 20, 25, 30, 35, 40, 45, 50, 55, 60, 65, 70, 75, 80, 85, 90, 91, 92, 93, 94, 95, 96, 97, 98, 99, 100 | WP_039580723.1 (74.55% identity, 81.91% similarity)<br>WP_023629461.1 (60.82% identity, 72.9% similarity)<br>WP_094012300.1 (60.62% identity, 72.71% similarity)<br>WP_104444565.1 (60.43% identity, 72.51% similarity)<br>WP_073183820.1 (30.93% identity, 49.03% similarity)<br>WP_074623349.1 (28.18% identity, 44.55% similarity)<br>WP_088716757.1 (27.69% identity, 43.39% similarity)<br>WP_043145958.1 (27.26% identity, 43.01% similarity)<br>WP_088671570.1 (27.26% identity, 43.01% similarity)<br>WP_069210391.1 (27.26% identity, 42.83% similarity) |
| APG02659.0 | 113 | 114 | | | MTX | 60, 65, 70, 75, 80, 85, 90, 91, 92, 93, 94, 95, 96, 97, 98, 99, 100 | 75, 80, 85, 90, 91, 92, 93, 94, 95, 96, 97, 98, 99, 100 | JP_2016_516397-59 (58.94% identity, 70.39% similarity)<br>WP_078401252.1 (58.47% identity, 69.49% similarity)<br>ANS51604.1 (58.38% identity, 69.83% similarity)<br>JP_2016_516397-60 (57.26% identity, 68.72% similarity)<br>APG02511.0 (56.98% identity, 67.88% similarity)<br>WP_098213667.1 (56.5% identity, 68.64% similarity)<br>WP_098487632.1 (56.5% identity, 68.36% similarity)<br>JP_2016_516397-61 (56.42% identity, 67.6% similarity) |

TABLE 1-continued

Summary of SEQ ID NOs, Gene Class, and Variants thereof

| APG ID | Seq ID | Modified Seq ID(s) | CryBP1 Seq ID | Split-Cry C-terminus Seq ID | Gene Class | % Identity | % Similarity | Homologs |
|---|---|---|---|---|---|---|---|---|
| | | | | | | | | WP_023524027.1 (56.02% identity, 69.47% similarity)<br>JP_2016_516397-63 (53.54% identity, 64.59% similarity) |
| APG02671.0 | 115 | 116 | | | Cyt | 85, 90, 91, 92, 93, 94, 95, 96, 97, 98, 99, 100 | 90, 91, 92, 93, 94, 95, 96, 97, 98, 99, 100 | APG00015.0 US_2016_0304898_A1-25 (84.27% identity, 89.16% similarity)<br>WP_098207008.1 (84.27% identity, 89.16% similarity)<br>APG00468.0 US_2016_0366881_A1-81 (84.27% identity, 88.81% similarity)<br>APG01301.0 (76.77% identity, 82.83% similarity)<br>APG01121.0 (75.61% identity, 84.32% similarity)<br>APG00168.0 US_2016_0311864_A1-44 (61.02% identity, 73.56% similarity)<br>APG00790.0 (59.33% identity, 73.33% similarity)<br>APG00431.0 US_2016_0366881_A1-56 (59.06% identity, 74.16% similarity)<br>APG01257.0 (59.06% identity, 73.15% similarity)<br>US_2017_0058293_A1-4 (58.94% identity, 69.87% similarity) |
| APG02676.0 | 117 | | | | MTX | 5, 10, 15, 20, 25, 30, 35, 40, 45, 50, 55, 60, 65, 70, 75, 80, 85, 90, 91, 92, 93, 94, 95, 96, 97, 98, 99, 100 | 5, 10, 15, 20, 25, 30, 35, 40, 45, 50, 55, 60, 65, 70, 75, 80, 85, 90, 91, 92, 93, 94, 95, 96, 97, 98, 99, 100 | WP_078782981.1 (94.07% identity, 95.36% similarity)<br>WP_073552443.1 (89.02% identity, 90.24% similarity)<br>AIL46026.1 (64.97% identity, 81.22% similarity)<br>CDN80307.1 (64.72% identity, 80.96% similarity)<br>WP_024564198.1 (62.75% identity, 78.43% similarity)<br>WP_078724005.1 (62.75% identity, 78.43% similarity)<br>WP_035592229.1 (62.5% identity, 78.19% similarity)<br>WP_078675442.1 (62.25% identity, 78.19% similarity)<br>AQW99431.1 (62.25% identity, 77.94% similarity)<br>WP_078720018.1 (62.01% identity, 77.94% similarity) |
| APG02706.0 | 118 | 119, 120, 121, 123, | | | Cry | 50, 55, 60, 65, 70, 75, 80, 85, 90, 91, 92, | 60, 65, 70, 75, 80, 85, 90, 91, 92, 93, 94, | APG00651.0 US_2017_0175134_A1-77 (45.86% identity, 59.49% similarity) |

TABLE 1-continued

| Summary of SEQ ID NOs, Gene Class, and Variants thereof | | | | | | | | |
|---|---|---|---|---|---|---|---|---|
| APG ID | Seq ID | Modified Seq ID(s) | CryBP1 Seq ID | Split-Cry C-terminus Seq ID | Gene Class | % Identity | % Similarity | Homologs |
| | | 124, 122 | | | | 93, 94, 95, 96, 97, 98, 99, 100 | 95, 96, 97, 98, 99, 100 | APG00524.0 US_2017_0175134_A1-17 (44.69% identity, 57.21% similarity)<br>APG00703.0 US_2017_0175134_A1-117 (42.5% identity, 56.25% similarity)<br>AHI15917.1 (41.41% identity, 57.03% similarity)<br>CA_2595901-15 (41.16% identity, 57.42% similarity)<br>AHI15915.1 (40.71% identity, 55.81% similarity)<br>US_8318900_B2-68 (40.37% identity, 56.1% similarity)<br>AEH76817.1 (40.15% identity, 56.18% similarity)<br>WP_080685557.1 (39.37% identity, 53.97% similarity)<br>US_2011_0239334_A1-79 (39.24% identity, 55.45% similarity)<br>US_2011_0239334_A1-79 (39.24% identity, 55.45% similarity)<br>US_5670365_A-9 (39.24% identity, 55.45% similarity)<br>US_5670365_A-9 (39.24% identity, 55.45% similarity)<br>US_9567381_B2-1403 (39.24% identity, 55.45% similarity)<br>US_9567381_B2-1403 (39.24% identity, 55.45% similarity) |
| APG02714.0 | 125 | | | | MTX | 75, 80, 85, 90, 91, 92, 93, 94, 95, 96, 97, 98, 99, 100 | 85, 90, 91, 92, 93, 94, 95, 96, 97, 98, 99, 100 | APG05793.0 (83.68% identity, 84.03% similarity)<br>APG06768.0 (71.48% identity, 84.19% similarity)<br>APG02633.0 (40.82% identity, 60.88% similarity)<br>APG04111.0 (31.21% identity, 50.34% similarity)<br>APG04977.0 (30.46% identity, 49.01% similarity)<br>APG09675.0 (30.0% identity, 50.0% similarity)<br>APG06578.0 (29.69% identity, 44.06% similarity)<br>APG00236.0 US_2016_0355842_A1-32 (28.76% identity, 51.31% similarity)<br>APG09957.0 (28.26% identity, 49.38% similarity) |

TABLE 1-continued

| Summary of SEQ ID NOs, Gene Class, and Variants thereof | | | | | | | | |
|---|---|---|---|---|---|---|---|---|
| APG ID | Seq ID | Modified Seq ID(s) | CryBP1 Seq ID | Split-Cry C-terminus Seq ID | Gene Class | % Identity | % Similarity | Homologs |
| APG02718.0 | 126 | 127 | | | MTX | 30, 35, 40, 45, 50, 55, 60, 65, 70, 75, 80, 85, 90, 91, 92, 93, 94, 95, 96, 97, 98, 99, 100 | 45, 50, 55, 60, 65, 70, 75, 80, 85, 90, 91, 92, 93, 94, 95, 96, 97, 98, 99, 100 | AQT70550.1 (51.15% identity, 65.14% similarity)<br>EFL12798.1 (50.8% identity, 65.9% similarity)<br>WP_030873518.1 (49.54% identity, 64.68% similarity)<br>WP_093835703.1 (45.35% identity, 60.32% similarity)<br>WP_078093242.1 (43.55% identity, 56.07% similarity)<br>WP_078857801.1 (41.51% identity, 53.51% similarity)<br>WP_082206325.1 (39.37% identity, 51.97% similarity)<br>WP_073808998.1 (34.15% identity, 46.54% similarity)<br>WP_100584951.1 (28.62% identity, 40.34% similarity)<br>PJN29953.1 (28.62% identity, 40.17% similarity) |
| APG02767.0 | 128 | 129 | | | Vip3 | 90, 91, 92, 93, 94, 95, 96, 97, 98, 99, 100 | 94, 95, 96, 97, 98, 99, 100 | WP_095210724.1 (89.7% identity, 93.55% similarity)<br>KMQ16234.1 (89.49% identity, 93.34% similarity)<br>APG00939.0 US_2017_0175134_A1-49 (88.76% identity, 93.55% similarity)<br>APG00077.0 US_2016_0304898_A1-99 (85.43% identity, 91.05% similarity)<br>APG00278.0 US_2016_0311864_A1-112 (83.94% identity, 88.39% similarity)<br>APG00175.0 US_2016_0311864_A1-48 (83.77% identity, 89.28% similarity)<br>WP_098343719.1 (83.77% identity, 89.28% similarity)<br>APG00173.0 US_2016_0311864_A1-46 (81.75% identity, 87.11% similarity)<br>WP_098839023.1 (81.75% identity, 87.11% similarity)<br>APG00875.0 US_2016_0366881_A1-133 (81.13% identity, 86.49% similarity) |
| APG02941.0 | 130 | | | | MTX | 85, 90, 91, 92, 93, 94, 95, 96, 97, 98, 99, 100 | 90, 91, 92, 93, 94, 95, 96, 97, 98, 99, 100 | APG02038.0 (84.19% identity, 89.03% similarity)<br>WP_098584414.1 (84.19% identity, 89.03% similarity)<br>APG03662.0 (83.01% identity, 87.18% similarity) |

TABLE 1-continued

Summary of SEQ ID NOs, Gene Class, and Variants thereof

| APG ID | Seq ID | Modified Seq ID(s) | CryBP1 Seq ID | Split-Cry C-terminus Seq ID | Gene Class | % Identity | % Similarity | Homologs |
|---|---|---|---|---|---|---|---|---|
| | | | | | | | | PGM93662.1 (67.48% identity, 76.69% similarity)<br>APG06508.0 US_2017_0175134_A1-217 (61.45% identity, 72.59% similarity)<br>US_8829279_B2-25 (61.38% identity, 73.05% similarity)<br>APG09801.0 US_2017_0175134_A1-218 (61.26% identity, 73.87% similarity)<br>APG00661.0 US_2017_0175134_A1-83 (60.6% identity, 71.94% similarity)<br>US_8318900_B2-62 (58.79% identity, 71.21% similarity)<br>US_8829279_B2-35 (58.01% identity, 70.69% similarity) |
| APG02947.0 | 131 | 132, 133 | | | Cry | 95, 96, 97, 98, 99, 100 | 96, 97, 98, 99, 100 | APG00536.0 US_2017_0175134_A1-24 (94.37% identity, 95.81% similarity)<br>APG00046.0 US_2016_0177333_A1-20 (87.19% identity, 92.54% similarity)<br>JP_2016_516397-52 (87.19% identity, 92.54% similarity)<br>JP_2016_516397-9 (87.19% identity, 92.54% similarity)<br>JP_2016_516397-53 (86.94% identity, 92.29% similarity)<br>WP_098712089.1 (83.58% identity, 88.56% similarity)<br>WP_098995610.1 (81.34% identity, 86.19% similarity)<br>JP_2016_516397-54 (79.1% identity, 83.58% similarity)<br>JP_2016_516397-55 (78.23% identity, 82.59% similarity)<br>JP_2016_516397-56 (76.74% identity, 81.09% similarity) |
| APG02956.0 | 134 | | | | MTX | 65, 70, 75, 80, 85, 90, 91, 92, 93, 94, 95, 96, 97, 98, 99, 100 | 80, 85, 90, 91, 92, 93, 94, 95, 96, 97, 98, 99, 100 | APG03565.0 (62.8% identity, 77.13% similarity)<br>APG06065.0 (62.33% identity, 77.05% similarity)<br>US_2003_0049243_A1-38 (36.67% identity, 56.33% similarity)<br>WP_042595209.1 (36.67% identity, 56.33% similarity)<br>US_9328356_B2-54 (33.02% identity, 52.02% similarity)<br>WP_002193629.1 (31.11% identity, 47.3% similarity) |

TABLE 1-continued

| Summary of SEQ ID NOs, Gene Class, and Variants thereof | | | | | | | | |
|---|---|---|---|---|---|---|---|---|
| APG ID | Seq ID | Modified Seq ID(s) | CryBP1 Seq ID | Split-Cry C-terminus Seq ID | Gene Class | % Identity | % Similarity | Homologs |
| | | | | | | | | APG00871.0 (29.02% identity, 45.43% similarity)<br>US__2003__0049243__A1-45 (29.02% identity, 44.59% similarity) |
| APG02986.0 | 135 | | | | Cry | 55, 60, 65, 70, 75, 80, 85, 90, 91, 92, 93, 94, 95, 96, 97, 98, 99, 100 | 65, 70, 75, 80, 85, 90, 91, 92, 93, 94, 95, 96, 97, 98, 99, 100 | APG00534.0 US__2017__0175134__A1-22 (51.79% identity, 61.85% similarity)<br>APG00120.0 US__2016__0177333__A1-68 (49.32% identity, 58.62% similarity)<br>WP__098164683.1 (49.21% identity, 58.62% similarity)<br>US__8461421__B2-204 (47.67% identity, 64.93% similarity)<br>WP__098905715.1 (47.2% identity, 59.01% similarity)<br>APG08350.0 (44.25% identity, 55.63% similarity)<br>APG06056.0 (43.8% identity, 56.08% similarity)<br>APG02109.0 (43.53% identity, 54.39% similarity)<br>WP__088125814.1 (42.48% identity, 54.28% similarity)<br>US__8461421__B2-264 (42.38% identity, 54.16% similarity) |
| APG03018.0 | 136 | 137, 138 | | 139 | Cry | 85, 90, 91, 92, 93, 94, 95, 96, 97, 98, 99, 100 | 90, 91, 92, 93, 94, 95, 96, 97, 98, 99, 100 | WP__085313394.1 (99.24% identity, 99.24% similarity)<br>WP__103592286.1 (85.93% identity, 89.86% similarity)<br>US__8318900__B2-9 (83.73% identity, 88.1% similarity)<br>US__8318900__B2-58 (83.58% identity, 88.1% similarity)<br>US__8318900__B2-113 (83.28% identity, 87.65% similarity)<br>US__7919272__B2-19 (81.54% identity, 85.33% similarity)<br>US__7919272__B2-35 (81.24% identity, 85.02% similarity)<br>WP__050845711.1 (76.16% identity, 83.51% similarity)<br>US__9567381__B2-427 (75.78% identity, 83.11% similarity)<br>AGE10586.1 (75.56% identity, 83.06% similarity) |
| APG03054.0 | 140 | | | | Cry | 45, 50, 55, 60, 65, 70, 75, 80, 85, 90, 91, | 65, 70, 75, 80, 85, 90, 91, 92, 93, 94, 95, | ANC11094.1 (66.62% identity, 79.06% similarity) |

TABLE 1-continued

Summary of SEQ ID NOs, Gene Class, and Variants thereof

| APG ID | Seq ID | Modified Seq ID(s) | CryBP1 Seq ID | Split-Cry C-terminus Seq ID | Gene Class | % Identity | % Similarity | Homologs |
|---|---|---|---|---|---|---|---|---|
| | | | | | | 92, 93, 94, 95, 96, 97, 98, 99, 100 | 96, 97, 98, 99, 100 | WP_080470008.1 (65.67% identity, 78.06% similarity)<br>APG04651.0 (61.03% identity, 74.92% similarity)<br>APG06921.0 (43.63% identity, 62.08% similarity)<br>CBL59394.1 (42.94% identity, 61.38% similarity)<br>CBL59393.1 (42.94% identity, 61.24% similarity)<br>CBL59395.1 (42.94% identity, 61.24% similarity)<br>CBL59396.1 (42.94% identity, 61.24% similarity)<br>CBL59397.1 (42.94% identity, 61.1% similarity)<br>APG09814.0 (41.57% identity, 57.0% similarity) |
| APG03056.0 | 141 | 142 | 143 | | Cry | 60, 65, 70, 75, 80, 85, 90, 91, 92, 93, 94, 95, 96, 97, 98, 99, 100 | 70, 75, 80, 85, 90, 91, 92, 93, 94, 95, 96, 97, 98, 99, 100 | APG08884.0 (57.11% identity, 68.45% similarity)<br>APG02841.0 (43.42% identity, 58.1% similarity)<br>APG00162.0 US_2016_0177333_A1-82 (43.36% identity, 56.56% similarity)<br>WP_098826687.1 (43.36% identity, 56.56% similarity)<br>APG00751.0 (42.69% identity, 58.27% similarity)<br>APG00374.0 US_2016_0366881_A1-40 (42.34% identity, 57.99% similarity)<br>US_9567381_B2-413 (39.08% identity, 54.93% similarity)<br>APG00326.0 US_2017_0175134_A1-1 (38.96% identity, 54.64% similarity)<br>US_9567381_B2-411 (38.63% identity, 54.17% similarity)<br>AAW55474.1 (38.37% identity, 55.46% similarity) |
| APG03182.0 | 144 | 145, 146 | | | MTX | 65, 70, 75, 80, 85, 90, 91, 92, 93, 94, 95, 96, 97, 98, 99, 100 | 80, 85, 90, 91, 92, 93, 94, 95, 96, 97, 98, 99, 100 | APG06372.0 (63.24% identity, 77.7% similarity)<br>WP_078185377.1 (63.24% identity, 77.7% similarity)<br>WP_098954578.1 (63.24% identity, 77.7% similarity)<br>APG00129.0 US_2016_0304898_A1-158 (63.24% identity, 77.21% similarity) |

TABLE 1-continued

Summary of SEQ ID NOs, Gene Class, and Variants thereof

| APG ID | Seq ID | Modified Seq ID(s) | CryBP1 Seq ID | Split-Cry C-terminus Seq ID | Gene Class | % Identity | % Similarity | Homologs |
|---|---|---|---|---|---|---|---|---|
| | | | | | | | | WP_097908072.1 (63.24% identity, 77.21% similarity)<br>OQR53340.1 (62.99% identity, 77.21% similarity)<br>KXY21848.1 (62.75% identity, 78.19% similarity)<br>CDN39409.1 (62.75% identity, 77.94% similarity)<br>APG00923.0 (62.75% identity, 77.45% similarity)<br>APG03337.0 (62.75% identity, 77.21% similarity) |
| APG03218.0 | 147 | 148 | | | MTX | 50, 55, 60, 65, 70, 75, 80, 85, 90, 91, 92, 93, 94, 95, 96, 97, 98, 99, 100 | 65, 70, 75, 80, 85, 90, 91, 92, 93, 94, 95, 96, 97, 98, 99, 100 | APG01201.0 (52.54% identity, 68.08% similarity)<br>APG00966.0 US_2016_0355842_A1-195 (45.74% identity, 62.78% similarity)<br>WP_098976737.1 (45.74% identity, 62.78% similarity)<br>WP_098139851.1 (44.35% identity, 62.15% similarity)<br>APG00479.0 US_2016_0355842_A1-101 (43.97% identity, 58.91% similarity)<br>WP_098139684.1 (43.97% identity, 58.91% similarity)<br>APG00283.0 US_2016_0355842_A1-50 (43.37% identity, 60.77% similarity)<br>APG03623.0 (41.41% identity, 58.59% similarity)<br>WP_065486138.1 (40.63% identity, 59.94% similarity)<br>WP_065487080.1 (40.63% identity, 59.94% similarity) |
| APG03247.0 | 149 | 150 | | | Cry | 90, 91, 92, 93, 94, 95, 96, 97, 98, 99, 100 | 90, 91, 92, 93, 94, 95, 96, 97, 98, 99, 100 | WP_069848556.1 (88.07% identity, 90.66% similarity)<br>WP_015892933.1 (87.68% identity, 90.4% similarity)<br>WP_017251277.1 (87.42% identity, 90.27% similarity)<br>APG05519.0 (87.42% identity, 89.88% similarity)<br>WP_087343164.1 (84.05% identity, 88.07% similarity)<br>APG08067.0 (83.92% identity, 87.55% similarity)<br>WP_016742208.1 (83.4% identity, 87.42% similarity) |

TABLE 1-continued

Summary of SEQ ID NOs, Gene Class, and Variants thereof

| APG ID | Seq ID | Modified Seq ID(s) | CryBP1 Seq ID | Split-Cry C-terminus Seq ID | Gene Class | % Identity | % Similarity | Homologs |
|---|---|---|---|---|---|---|---|---|
| | | | | | | | | APG00182.0 US_2016_0355842_A1-17 (26.59% identity, 39.66% similarity)<br>CA_2595901-6 (25.7% identity, 39.91% similarity)<br>APG05711.0 (25.6% identity, 39.43% similarity) |
| APG03361.0 | 151 | | | | Bin | 45, 50, 55, 60, 65, 70, 75, 80, 85, 90, 91, 92, 93, 94, 95, 96, 97, 98, 99, 100 | 60, 65, 70, 75, 80, 85, 90, 91, 92, 93, 94, 95, 96, 97, 98, 99, 100 | APG05955.0 (64.06% identity, 75.59% similarity)<br>APG09146.0 (42.31% identity, 57.09% similarity)<br>WP_016099737.1 (40.75% identity, 53.77% similarity)<br>US_8461415_B2-29 (36.69% identity, 50.47% similarity)<br>US_8461415_B2-44 (33.39% identity, 46.48% similarity)<br>APG06401.0 (32.13% identity, 45.63% similarity)<br>APG08101.0 (31.96% identity, 48.97% similarity)<br>APG07432.0 (31.53% identity, 46.83% similarity)<br>WP_098826686.1 (30.09% identity, 45.87% similarity)<br>APG00734.0 US_2016_0366881_A1-131 (30.02% identity, 45.72% similarity) |
| APG03392.0 | 152 | 153 | | | Cry | 75, 80, 85, 90, 91, 92, 93, 94, 95, 96, 97, 98, 99, 100 | 85, 90, 91, 92, 93, 94, 95, 96, 97, 98, 99, 100 | APG00266.0 US_2016_0311864_A1-105 (73.65% identity, 82.0% similarity)<br>APG00288.0 US_2016_0311864_A1-122 (58.78% identity, 72.19% similarity)<br>WP_098783882.1 (58.78% identity, 72.19% similarity)<br>APG06730.0 (48.6% identity, 61.2% similarity)<br>APG00043.0 US_2016_0304898_A1-69 (34.62% identity, 48.72% similarity)<br>APG00396.0 US_2016_0311864_A1-163 (33.06% identity, 44.35% similarity)<br>WP_098783217.1 (33.06% identity, 44.35% similarity)<br>APG06774.0 (31.87% identity, 48.59% similarity)<br>US_8318900_B2-91 (31.54% identity, 47.31% similarity)<br>APG00372.0 US_2016_0311864_A1-150 (31.25% identity, 46.14% similarity) |

TABLE 1-continued

Summary of SEQ ID NOs, Gene Class, and Variants thereof

| APG ID | Seq ID | Modified Seq ID(s) | CryBP1 Seq ID | Split-Cry C-terminus Seq ID | Gene Class | % Identity | % Similarity | Homologs |
|---|---|---|---|---|---|---|---|---|
| APG03415.0 | 154 | | | | MTX | 45, 50, 55, 60, 65, 70, 75, 80, 85, 90, 91, 92, 93, 94, 95, 96, 97, 98, 99, 100 | 65, 70, 75, 80, 85, 90, 91, 92, 93, 94, 95, 96, 97, 98, 99, 100 | APG00360.0 US_2016_0355842_A1-69 (44.38% identity, 60.79% similarity)<br>APG00907.0 US_2016_0311864_A1-225 (39.17% identity, 58.75% similarity)<br>WP_098908553.1 (39.17% identity, 58.75% similarity)<br>US_8318900_B2-191 (39.16% identity, 59.94% similarity)<br>APG01122.0 (39.02% identity, 57.62% similarity)<br>APG05358.0 (38.37% identity, 57.1% similarity)<br>APG01885.0 (38.18% identity, 57.58% similarity)<br>APG02548.0 (37.87% identity, 57.69% similarity)<br>APG07396.0 (37.83% identity, 54.25% similarity)<br>APG04690.0 (37.61% identity, 56.42% similarity) |
| APG03504.0 | 155 | | | | MTX | 93, 94, 95, 96, 97, 98, 99, 100 | 97, 98, 99, 100 | APG01127.0 (92.93% identity, 96.97% similarity)<br>APG07655.0 (92.91% identity, 96.62% similarity)<br>APG00155.0 US_2016_0311864_A1-40 (92.57% identity, 96.62% similarity)<br>APG03379.0 (82.21% identity, 89.6% similarity)<br>APG01506.0 (81.76% identity, 88.51% similarity)<br>APG00749.0 (81.13% identity, 88.08% similarity)<br>APG09416.0 (79.93% identity, 86.62% similarity)<br>APG08241.0 (79.73% identity, 86.49% similarity)<br>APG09682.0 (79.12% identity, 86.87% similarity)<br>APG02638.0 (79.07% identity, 88.04% similarity) |
| APG03505.0 | 156 | 157, 159, 160, 158, 161, 162 | | | Cry | 75, 80, 85, 90, 91, 92, 93, 94, 95, 96, 97, 98, 99, 100 | 85, 90, 91, 92, 93, 94, 95, 96, 97, 98, 99, 100 | US_7923602_B2-6 (72.6% identity, 81.87% similarity)<br>US_7923602_B2-35 (48.35% identity, 59.32% similarity)<br>US_8318900_B2-68 (46.78% identity, 59.51% similarity) |

TABLE 1-continued

| Summary of SEQ ID NOs, Gene Class, and Variants thereof | | | | | | | | |
|---|---|---|---|---|---|---|---|---|
| APG ID | Seq ID | Modified Seq ID(s) | CryBP1 Seq ID | Split-Cry C-terminus Seq ID | Gene Class | % Identity | % Similarity | Homologs |
| | | | | | | | | AHI15917.1 (46.73% identity, 59.29% similarity)<br>AHI15915.1 (46.44% identity, 58.34% similarity)<br>AEH76817.1 (46.2% identity, 59.36% similarity)<br>AHI15916.1 (45.71% identity, 57.14% similarity)<br>US_9567381_B2-1403 (45.29% identity, 55.0% similarity)<br>US_9567381_B2-1403 (45.29% identity, 55.0% similarity)<br>WO_2017_161181-215 (45.29% identity, 55.0% similarity)<br>WO_2017_161181-215 (45.29% identity, 55.0% similarity) |
| APG03527.0 | 163 | 164 | | | MTX | 90, 91, 92, 93, 94, 95, 96, 97, 98, 99, 100 | 94, 95, 96, 97, 98, 99, 100 | US_2015_0047076_A1-14 (88.77% identity, 93.84% similarity)<br>US_2015_0047076_A1-8 (57.14% identity, 70.73% similarity)<br>APG01967.0 (56.34% identity, 70.07% similarity)<br>US_2015_0047076_A1-12 (55.36% identity, 67.82% similarity)<br>US_2015_0047076_A1-10 (52.28% identity, 67.72% similarity)<br>US_2015_0047076_A1-4 (52.08% identity, 65.97% similarity)<br>AQM56940.1 (51.6% identity, 62.63% similarity)<br>US_2015_0047076_A1-2 (50.53% identity, 65.26% similarity)<br>US_2015_0047076_A1-6 (50.0% identity, 66.07% similarity)<br>US_8461421_B2-42 (49.82% identity, 67.26% similarity) |
| APG03584.0 | 165 | 166 | | | MTX | 40, 45, 50, 55, 60, 65, 70, 75, 80, 85, 90, 91, 92, 93, 94, 95, 96, 97, 98, 99, 100 | 60, 65, 70, 75, 80, 85, 90, 91, 92, 93, 94, 95, 96, 97, 98, 99, 100 | WP_075719043.1 (37.59% identity, 56.26% similarity)<br>APG05777.0 (37.36% identity, 56.26% similarity)<br>WP_100910639.1 (37.36% identity, 56.26% similarity)<br>APG00129.0 US_2016_0304898_A1-158 (36.94% identity, 53.38% similarity)<br>WP_097908072.1 (36.94% identity, 53.38% similarity) |

TABLE 1-continued

| Summary of SEQ ID NOs, Gene Class, and Variants thereof | | | | | | | | |
|---|---|---|---|---|---|---|---|---|
| APG ID | Seq ID | Modified Seq ID(s) | CryBP1 Seq ID | Split-Cry C-terminus Seq ID | Gene Class | % Identity | % Similarity | Homologs |
| | | | | | | | | APG04650.0 (36.71% identity, 53.6% similarity)<br>KXY21848.1 (36.04% identity, 53.38% similarity)<br>CDN39409.1 (36.04% identity, 53.15% similarity)<br>WP_078185377.1 (36.04% identity, 53.15% similarity)<br>APG02686.0 (35.81% identity, 53.6% similarity)<br>WP_080448724.1 (35.81% identity, 53.6% similarity)<br>APG02421.0 (35.81% identity, 53.38% similarity)<br>WP_080685552.1 (35.81% identity, 53.38% similarity)<br>APG03337.0 (35.81% identity, 53.15% similarity)<br>OQR53340.1 (35.81% identity, 53.15% similarity) |
| APG03587.0 | 167 | | | | MTX | 80, 85, 90, 91, 92, 93, 94, 95, 96, 97, 98, 99, 100 | 90, 91, 92, 93, 94, 95, 96, 97, 98, 99, 100 | APG09439.0 (92.83% identity, 96.42% similarity)<br>APG07780.0 (76.34% identity, 85.66% similarity)<br>APG05984.0 (75.99% identity, 85.3% similarity)<br>APG08576.0 (73.84% identity, 84.95% similarity)<br>APG01093.0 (72.4% identity, 81.72% similarity)<br>APG05943.0 (68.58% identity, 79.39% similarity)<br>APG01273.0 (67.02% identity, 78.25% similarity)<br>APG08917.0 (58.06% identity, 69.89% similarity)<br>APG01706.0 (52.69% identity, 66.31% similarity)<br>APG05992.0 (51.97% identity, 68.1% similarity) |
| APG03674.0 | 168 | 169 | | | Cyt | 96, 97, 98, 99, 100 | 100 | APG09444.0 (95.59% identity, 99.51% similarity)<br>APG01987.0 (94.12% identity, 98.53% similarity)<br>US_2016_0339078_A1-28662 (94.12% identity, 98.53% similarity) |

TABLE 1-continued

| Summary of SEQ ID NOs, Gene Class, and Variants thereof | | | | | | | | |
|---|---|---|---|---|---|---|---|---|
| APG ID | Seq ID | Modified Seq ID(s) | CryBP1 Seq ID | Split-Cry C-terminus Seq ID | Gene Class | % Identity | % Similarity | Homologs |
| | | | | | | | | WP_018782198.1 (94.12% identity, 98.53% similarity)<br>WP_033798332.1 (94.12% identity, 98.53% similarity)<br>WP_040119538.1 (94.12% identity, 98.53% similarity)<br>WP_016114769.1 (94.12% identity, 98.04% similarity)<br>WP_018766353.1 (94.12% identity, 98.04% similarity)<br>WP_098928754.1 (93.63% identity, 98.53% similarity)<br>US_2016_0339078_A1-28716 (93.63% identity, 98.04% similarity)<br>WP_097849755.1 (93.63% identity, 98.04% similarity)<br>WP_098114905.1 (93.63% identity, 98.04% similarity)<br>WP_097836653.1 (93.63% identity, 97.55% similarity)<br>APG05707.0 (93.14% identity, 97.55% similarity)<br>APG00770.0 (93.14% identity, 96.08% similarity)<br>APG01989.0 (91.67% identity, 96.08% similarity)<br>APG00456.0 US_2016_0311864_A1-180 (90.69% identity, 96.08% similarity) |
| APG03738.0 | 170 | | | | MTX | 75, 80, 85, 90, 91, 92, 93, 94, 95, 96, 97, 98, 99, 100 | 85, 90, 91, 92, 93, 94, 95, 96, 97, 98, 99, 100 | APG04977.0 (74.45% identity, 86.13% similarity)<br>APG02471.0 (71.74% identity, 82.97% similarity)<br>APG04111.0 (57.04% identity, 72.51% similarity)<br>APG00236.0 US_2016_0355842_A1-32 (48.28% identity, 67.24% similarity)<br>APG02633.0 (33.33% identity, 53.33% similarity)<br>APG00598.0 US_2016_0355842_A1-140 (31.7% identity, 50.65% similarity)<br>APG02714.0 (31.63% identity, 50.16% similarity)<br>APG05793.0 (29.77% identity, 46.49% similarity)<br>APG07732.0 (29.71% identity, 49.84% similarity) |

TABLE 1-continued

Summary of SEQ ID NOs, Gene Class, and Variants thereof

| APG ID | Seq ID | Modified Seq ID(s) | CryBP1 Seq ID | Split-Cry C-terminus Seq ID | Gene Class | % Identity | % Similarity | Homologs |
|---|---|---|---|---|---|---|---|---|
| APG03748.0 | 171 | 172 | | | Bin | 92, 93, 94, 95, 96, 97, 98, 99, 100 | 96, 97, 98, 99, 100 | APG00229.0 US_2016_0311864_A1-84 (91.58% identity, 95.3% similarity)<br>APG07334.0 (89.58% identity, 93.3% similarity)<br>WP_098205870.1 (89.36% identity, 93.07% similarity)<br>APG00419.0 US_2016_0311864_A1-176 (88.7% identity, 92.14% similarity)<br>WP_098634587.1 (88.7% identity, 92.14% similarity)<br>APG00203.0 US_2016_0311864_A1-69 (87.84% identity, 90.32% similarity)<br>WP_098475832.1 (87.84% identity, 90.32% similarity)<br>APG05411.0 (86.88% identity, 91.34% similarity)<br>APG00353.0 US_2016_0311864_A1-144 (86.1% identity, 88.83% similarity)<br>WP_099003921.1 (86.1% identity, 88.83% similarity) |
| APG03758.0 | 173 | | | | MTX/PI-PLC | 45, 50, 55, 60, 65, 70, 75, 80, 85, 90, 91, 92, 93, 94, 95, 96, 97, 98, 99, 100 | 55, 60, 65, 70, 75, 80, 85, 90, 91, 92, 93, 94, 95, 96, 97, 98, 99, 100 | OUB31138.1 (61.62% identity, 66.6% similarity)<br>WP_086396644.1 (60.3% identity, 63.96% similarity)<br>WP_098838879.1 (48.54% identity, 57.4% similarity)<br>WP_000358225.1 (48.44% identity, 57.3% similarity)<br>WP_098564358.1 (48.34% identity, 57.3% similarity)<br>EEM93103.1 (48.06% identity, 56.8% similarity)<br>APG00572.0 US_2017_0175134_A1-46 (40.65% identity, 54.38% similarity)<br>APG08081.0 (38.66% identity, 49.95% similarity)<br>WP_087876328.1 (38.47% identity, 50.0% similarity)<br>WP_000836979.1 (37.59% identity, 48.68% similarity) |
| APG03778.0 | 174 | | | | Bin | 50, 55, 60, 65, 70, 75, 80, 85, 90, 91, 92, 93, 94, 95, 96, 97, 98, 99, 100 | 60, 65, 70, 75, 80, 85, 90, 91, 92, 93, 94, 95, 96, 97, 98, 99, 100 | US_6555655_B1-14 (45.45% identity, 56.33% similarity)<br>APG07310.0 (43.49% identity, 55.28% similarity)<br>US_6555655_B1-13 (36.85% identity, 45.66% similarity) |

TABLE 1-continued

| Summary of SEQ ID NOs, Gene Class, and Variants thereof | | | | | | | | |
|---|---|---|---|---|---|---|---|---|
| APG ID | Seq ID | Modified Seq ID(s) | CryBP1 Seq ID | Split-Cry C-terminus Seq ID | Gene Class | % Identity | % Similarity | Homologs |
| | | | | | | | | US_7692068_B2-2 (35.98% identity, 53.32% similarity)<br>WP_098826686.1 (35.05% identity, 48.04% similarity)<br>APG00075.0 US_2016_0177333_A1-40 (34.87% identity, 47.79% similarity)<br>APG06401.0 (33.57% identity, 44.94% similarity)<br>APG08101.0 (33.04% identity, 46.19% similarity)<br>APG07432.0 (32.73% identity, 47.09% similarity)<br>APG00063.0 US_2016_0304898_A1-95 (32.43% identity, 47.64% similarity) |
| APG03789.0 | 175 | | | | Bin | 55, 60, 65, 70, 75, 80, 85, 90, 91, 92, 93, 94, 95, 96, 97, 98, 99, 100 | 65, 70, 75, 80, 85, 90, 91, 92, 93, 94, 95, 96, 97, 98, 99, 100 | APG00474.0 US_2016_0366881_A1-89 (53.33% identity, 62.96% similarity)<br>APG00629.0 US_2016_0366881_A1-126 (51.26% identity, 60.46% similarity)<br>APG00050.0 US_2016_0304898_A1-80 (46.8% identity, 57.08% similarity)<br>WP_098902696.1 (46.8% identity, 57.08% similarity)<br>APG00557.0 US_2017_0175134_A1-36 (41.14% identity, 55.23% similarity)<br>APG00167.0 US_2016_0304898_A1-180 (39.06% identity, 49.43% similarity)<br>WP_098326411.1 (39.06% identity, 49.43% similarity)<br>APG00461.0 US_2016_0311864_A1-182 (38.97% identity, 50.31% similarity)<br>WP_098902378.1 (38.97% identity, 50.31% similarity)<br>APG03964.0 (37.36% identity, 48.49% similarity) |
| APG03826.0 | 176 | | | | MTX | 30, 35, 40, 45, 50, 55, 60, 65, 70, 75, 80, 85, 90, 91, 92, 93, 94, 95, 96, 97, 98, 99, 100 | 50, 55, 60, 65, 70, 75, 80, 85, 90, 91, 92, 93, 94, 95, 96, 97, 98, 99, 100 | US_2015_0047076_A1-10 (28.2% identity, 45.57% similarity)<br>US_2015_0047076_A1-4 (28.19% identity, 46.98% similarity) |
| APG03887.0 | 177 | | | | MTX | 40, 45, 50, 55, 60, 65, 70, 75, 80, 85, 90, 91, 92, 93, 94, 95, 96, 97, 98, 99, 100 | 55, 60, 65, 70, 75, 80, 85, 90, 91, 92, 93, 94, 95, 96, 97, 98, 99, 100 | WP_073006286.1 (37.3% identity, 54.34% similarity)<br>APG07780.0 (35.71% identity, 54.76% similarity)<br>APG01273.0 (35.15% identity, 54.27% similarity)<br>APG08576.0 (35.12% identity, 53.51% |

TABLE 1-continued

| Summary of SEQ ID NOs, Gene Class, and Variants thereof | | | | | | | | |
|---|---|---|---|---|---|---|---|---|
| APG ID | Seq ID | Modified Seq ID(s) | CryBP1 Seq ID | Split-Cry C-terminus Seq ID | Gene Class | % Identity | % Similarity | Homologs |
| | | | | | | | | similarity)<br>APG05984.0 (34.9% identity, 53.02% similarity)<br>APG05943.0 (34.41% identity, 50.8% similarity)<br>APG03587.0 (32.66% identity, 49.83% similarity)<br>APG09439.0 (32.44% identity, 49.5% similarity)<br>APG01093.0 (32.32% identity, 51.52% similarity)<br>APG04296.0 (31.06% identity, 51.55% similarity) |
| APG03893.0 | 178 | | | | Cry | 90, 91, 92, 93, 94, 95, 96, 97, 98, 99, 100 | 93, 94, 95, 96, 97, 98, 99, 100 | WP_012259841.1 (95.06% identity, 97.07% similarity)<br>WP_088059022.1 (87.37% identity, 92.6% similarity)<br>CA_2844913-24 (87.17% identity, 90.11% similarity)<br>WP_088113460.1 (87.06% identity, 92.3% similarity)<br>APG00800.0 US_2016_0355842_A1-172 (86.9% identity, 92.3% similarity)<br>APG00643.0 US_2017_0175134_A1-68 (81.51% identity, 89.68% similarity)<br>AST51780.1 (69.5% identity, 81.94% similarity)<br>APG00088.0 US_2016_0304898_A1-116 (66.62% identity, 76.54% similarity)<br>WP_025988975.1 (62.92% identity, 66.41% similarity)<br>WP_088610578.1 (53.2% identity, 68.17% similarity) |
| APG03909.0 | 179 | 180 | | | Cry | 35, 40, 45, 50, 55, 60, 65, 70, 75, 80, 85, 90, 91, 92, 93, 94, 95, 96, 97, 98, 99, 100 | 55, 60, 65, 70, 75, 80, 85, 90, 91, 92, 93, 94, 95, 96, 97, 98, 99, 100 | APG05279.0 (40.56% identity, 57.52% similarity)<br>APG03045.0 (33.55% identity, 49.19% similarity)<br>APG02037.0 (30.61% identity, 51.48% similarity)<br>APG01146.0 (30.5% identity, 50.26% similarity)<br>APG05915.0 (29.76% identity, 44.23% similarity)<br>WP_098783120.1 (29.66% identity, 45.08% similarity)<br>CA_2844913-151 (26.06% identity, 44.63% |

TABLE 1-continued

| Summary of SEQ ID NOs, Gene Class, and Variants thereof | | | | | | | | |
|---|---|---|---|---|---|---|---|---|
| APG ID | Seq ID | Modified Seq ID(s) | CryBP1 Seq ID | Split-Cry C-terminus Seq ID | Gene Class | % Identity | % Similarity | Homologs |
| | | | | | | | | similarity)<br>CA_2844913-152 (25.9% identity, 44.63% similarity) |
| APG03959.0 | 181 | | | | Cyt | 95, 96, 97, 98, 99, 100 | 99, 100 | CA_2844913-98 (94.91% identity, 98.15% similarity)<br>WP_098524519.1 (94.44% identity, 98.15% similarity)<br>WP_098190289.1 (93.98% identity, 97.69% similarity)<br>APG05662.0 (91.67% identity, 95.83% similarity)<br>WP_076855475.1 (89.81% identity, 95.83% similarity)<br>WP_088326113.1 (89.81% identity, 95.37% similarity)<br>APG00394.0 US_2016_0366881_A1-48 (85.78% identity, 94.04% similarity)<br>WP_097961786.1 (28.63% identity, 54.63% similarity)<br>US_6093695_A-1 (27.35% identity, 54.27% similarity)<br>WP_061667230.1 (27.31% identity, 54.19% similarity)<br>WP_098300708.1 (27.31% identity, 54.19% similarity)<br>WP_098315775.1 (27.31% identity, 54.19% similarity) |
| APG04009.0 | 182 | | | | MTX | 45, 50, 55, 60, 65, 70, 75, 80, 85, 90, 91, 92, 93, 94, 95, 96, 97, 98, 99, 100 | 60, 65, 70, 75, 80, 85, 90, 91, 92, 93, 94, 95, 96, 97, 98, 99, 100 | APG05943.0 (43.61% identity, 57.32% similarity)<br>APG08576.0 (43.61% identity, 55.76% similarity)<br>APG05984.0 (42.77% identity, 55.97% similarity)<br>APG07780.0 (42.5% identity, 55.94% similarity)<br>APG03587.0 (41.36% identity, 53.7% similarity)<br>APG08917.0 (41.27% identity, 53.33% similarity)<br>APG01273.0 (40.24% identity, 53.05% similarity)<br>APG09439.0 (39.88% identity, 53.27% similarity)<br>APG01093.0 (39.81% identity, 53.29% similarity) |

TABLE 1-continued

| Summary of SEQ ID NOs, Gene Class, and Variants thereof | | | | | | | | |
|---|---|---|---|---|---|---|---|---|
| APG ID | Seq ID | Modified Seq ID(s) | CryBP1 Seq ID | Split-Cry C-terminus Seq ID | Gene Class | % Identity | % Similarity | Homologs |
| APG04019.0 | 183 | 184 | | | Bin | 40, 45, 50, 55, 60, 65, 70, 75, 80, 85, 90, 91, 92, 93, 94, 95, 96, 97, 98, 99, 100 | 55, 60, 65, 70, 75, 80, 85, 90, 91, 92, 93, 94, 95, 96, 97, 98, 99, 100 | APG05992.0 (39.17% identity, 53.18% similarity)<br>WP_051505009.1 (68.82% identity, 75.29% similarity)<br>AKG37966.1 (56.7% identity, 62.39% similarity)<br>WP_052756038.1 (56.5% identity, 62.15% similarity)<br>WP_087914274.1 (55.14% identity, 61.43% similarity)<br>WP_042162506.1 (49.86% identity, 58.08% similarity)<br>APG05946.0 (41.11% identity, 54.36% similarity)<br>APG07202.0 (38.48% identity, 49.86% similarity)<br>APG08348.0 (38.11% identity, 48.65% similarity)<br>US_8829279_B2-4 (36.83% identity, 51.43% similarity)<br>APG01809.0 (35.39% identity, 50.65% similarity) |
| APG04103.0 | 185 | 186 | | | MTX | 70, 75, 80, 85, 90, 91, 92, 93, 94, 95, 96, 97, 98, 99, 100 | 80, 85, 90, 91, 92, 93, 94, 95, 96, 97, 98, 99, 100 | WP_051889583.1 (71.39% identity, 82.08% similarity)<br>WP_051563179.1 (69.25% identity, 81.32% similarity)<br>WP_051800214.1 (69.25% identity, 81.03% similarity)<br>WP_051891081.1 (68.97% identity, 81.32% similarity)<br>WP_051889585.1 (68.97% identity, 81.03% similarity)<br>APG09110.0 (68.14% identity, 78.67% similarity)<br>ACA38725.1 (66.94% identity, 78.61% similarity)<br>APG03947.0 (66.94% identity, 78.61% similarity)<br>APG05834.0 (61.99% identity, 75.15% similarity)<br>APG02401.0 (55.33% identity, 70.61% similarity)<br>WP_018673409.1 (55.33% identity, 70.61% similarity)<br>WP_104030950.1 (55.33% identity, 70.61% similarity) |

TABLE 1-continued

| Summary of SEQ ID NOs, Gene Class, and Variants thereof | | | | | | | | |
|---|---|---|---|---|---|---|---|---|
| APG ID | Seq ID | Modified Seq ID(s) | CryBP1 Seq ID | Split-Cry C-terminus Seq ID | Gene Class | % Identity | % Similarity | Homologs |
| | | | | | | | | WP_104064947.1 (55.33% identity, 70.61% similarity) |
| APG04111.0 | 187 | | | | MTX | 60, 65, 70, 75, 80, 85, 90, 91, 92, 93, 94, 95, 96, 97, 98, 99, 100 | 75, 80, 85, 90, 91, 92, 93, 94, 95, 96, 97, 98, 99, 100 | APG04977.0 (63.92% identity, 74.23% similarity)<br>APG02471.0 (59.12% identity, 71.96% similarity)<br>APG03738.0 (57.04% identity, 72.51% similarity)<br>APG00236.0 US_2016_0355842_A1-32 (44.41% identity, 64.47% similarity)<br>APG02633.0 (32.76% identity, 51.19% similarity)<br>APG02714.0 (31.21% identity, 50.34% similarity)<br>APG00598.0 US_2016_0355842_A1-140 (30.84% identity, 46.71% similarity)<br>APG05793.0 (29.93% identity, 47.28% similarity) |
| APG04141.0 | 188 | | | | Cry | 95, 96, 97, 98, 99, 100 | 98, 99, 100 | APG09824.0 (94.19% identity, 97.44% similarity)<br>APG03438.0 (93.95% identity, 96.98% similarity)<br>APG09812.0 (93.72% identity, 96.51% similarity)<br>WP_103108858.1 (93.29% identity, 96.06% similarity)<br>KNB72291.1 (93.24% identity, 96.74% similarity)<br>APG04458.0 (93.24% identity, 96.5% similarity)<br>APG09936.0 (93.01% identity, 95.57% similarity)<br>APG05978.0 (92.47% identity, 94.98% similarity)<br>WP_084765780.1 (91.55% identity, 94.75% similarity)<br>WP_093871939.1 (37.61% identity, 58.33% similarity) |
| APG04162.0 | 189 | 190 | | | MTX | 55, 60, 65, 70, 75, 80, 85, 90, 91, 92, 93, 94, 95, 96, 97, 98, 99, 100 | 70, 75, 80, 85, 90, 91, 92, 93, 94, 95, 96, 97, 98, 99, 100 | WP_098228004.1 (100.0% identity, 100.0% similarity)<br>WP_097984959.1 (51.66% identity, 64.65% similarity)<br>WP_001267112.1 (51.36% identity, 64.05% similarity)<br>JP_2016_516397-59 (51.31% identity, 66.18% similarity)<br>ANS51604.1 (50.73% identity, 65.6% |

TABLE 1-continued

Summary of SEQ ID NOs, Gene Class, and Variants thereof

| APG ID | Seq ID | Modified Seq ID(s) | CryBP1 Seq ID | Split-Cry C-terminus Seq ID | Gene Class | % Identity | % Similarity | Homologs |
|---|---|---|---|---|---|---|---|---|
| | | | | | | | | similarity)<br>US_8461415_B2-32 (50.59% identity, 63.31% similarity)<br>WP_078401252.1 (50.15% identity, 64.43% similarity)<br>WP_023524027.1 (49.43% identity, 63.22% similarity)<br>JP_2016_516397-60 (49.27% identity, 64.14% similarity)<br>APG02659.0 (49.01% identity, 63.1% similarity) |
| APG04208.0 | 191 | 192 | | | Bin | 85, 90, 91, 92, 93, 94, 95, 96, 97, 98, 99, 100 | 90, 91, 92, 93, 94, 95, 96, 97, 98, 99, 100 | WP_098412831.1 (91.83% identity, 94.8% similarity)<br>APG00369.0 US_2016_0311864_A1-149 (83.18% identity, 85.87% similarity)<br>WP_098858722.1 (78.4% identity, 85.92% similarity)<br>APG00925.0 US_2016_0311864_A1-227 (76.58% identity, 82.43% similarity)<br>APG00282.0 US_2016_0311864_A1-116 (74.51% identity, 81.07% similarity)<br>WP_098386694.1 (72.06% identity, 81.37% similarity)<br>WP_002191947.1 (71.85% identity, 80.99% similarity)<br>APG01063.0 (71.64% identity, 81.17% similarity)<br>WP_002166959.1 (71.6% identity, 80.99% similarity)<br>APG00308.0 US_2016_0311864_A1-135 (69.29% identity, 80.1% similarity) |
| APG04302.0 | 193 | | | | Bin | 85, 90, 91, 92, 93, 94, 95, 96, 97, 98, 99, 100 | 90, 91, 92, 93, 94, 95, 96, 97, 98, 99, 100 | WP_098630027.1 (82.83% identity, 87.19% similarity)<br>APG00499.0 US_2016_0311864_A1-185 (82.56% identity, 87.19% similarity)<br>APG07930.0 (74.66% identity, 85.01% similarity)<br>APG00532.0 US_2016_0311864_A1-189 (70.7% identity, 81.72% similarity)<br>WP_098821682.1 (70.7% identity, 81.72% similarity)<br>APG03859.0 (63.49% identity, 77.38% similarity)<br>WP_098818616.1 (61.14% identity, 73.83% similarity)<br>WP_098838667.1 (60.62% identity, 73.58% |

TABLE 1-continued

Summary of SEQ ID NOs, Gene Class, and Variants thereof

| APG ID | Seq ID | Modified Seq ID(s) | CryBP1 Seq ID | Split-Cry C-terminus Seq ID | Gene Class | % Identity | % Similarity | Homologs |
|---|---|---|---|---|---|---|---|---|
| | | | | | | | | similarity)<br>CA_2844913-50 (60.36% identity, 73.58% similarity)<br>APG00413.0 US_2016_0311864_A1-174 (50.65% identity, 63.19% similarity) |
| APG04316.0 | 194 | 195 | | | MTX | 80, 85, 90, 91, 92, 93, 94, 95, 96, 97, 98, 99, 100 | 90, 91, 92, 93, 94, 95, 96, 97, 98, 99, 100 | WP_097969882.1 (100.0% identity, 100.0% similarity)<br>WP_098173426.1 (99.68% identity, 99.68% similarity)<br>WP_098707157.1 (99.68% identity, 99.68% similarity)<br>WP_098149421.1 (99.37% identity, 99.37% similarity)<br>WP_098125701.1 (94.95% identity, 97.16% similarity)<br>WP_097837258.1 (94.32% identity, 96.53% similarity)<br>WP_098425855.1 (93.06% identity, 96.21% similarity)<br>WP_098786706.1 (92.74% identity, 96.53% similarity)<br>APG09415.0 (92.74% identity, 96.21% similarity)<br>WP_070143005.1 (92.74% identity, 96.21% similarity)<br>WP_098157467.1 (92.74% identity, 96.21% similarity) |
| APG04323.0 | 196 | | | | MTX | 75, 80, 85, 90, 91, 92, 93, 94, 95, 96, 97, 98, 99, 100 | 80, 85, 90, 91, 92, 93, 94, 95, 96, 97, 98, 99, 100 | APG04375.0 (73.78% identity, 77.74% similarity)<br>APG05300.0 (73.78% identity, 77.44% similarity)<br>WP_098222386.1 (73.78% identity, 75.91% similarity)<br>APG04793.0 (73.17% identity, 77.13% similarity)<br>WP_088080923.1 (73.17% identity, 75.91% similarity)<br>WP_087969959.1 (72.87% identity, 75.61% similarity)<br>APG03686.0 (72.56% identity, 77.44% similarity)<br>APG03747.0 (72.56% identity, 76.22% similarity)<br>APG07676.0 (72.26% identity, 77.44% similarity)<br>WP_098908549.1 (71.95% identity, 76.83% |

TABLE 1-continued

Summary of SEQ ID NOs, Gene Class, and Variants thereof

| APG ID | Seq ID | Modified Seq ID(s) | CryBP1 Seq ID | Split-Cry C-terminus Seq ID | Gene Class | % Identity | % Similarity | Homologs |
|---|---|---|---|---|---|---|---|---|
| | | | | | | | | similarity)<br>WP_098290465.1 (71.95% identity, 75.61% similarity) |
| APG04360.0 | 197 | | | | Cyt | 95, 96, 97, 98, 99, 100 | 98, 99, 100 | APG00017.0 US_2016_0304898_A1-28 (94.63% identity, 97.07% similarity)<br>WP_098207009.1 (94.63% identity, 97.07% similarity)<br>APG01309.0 (92.2% identity, 96.1% similarity)<br>APG00464.0 US_2016_0366881_A1-78 (90.73% identity, 95.61% similarity)<br>APG01971.0 (68.16% identity, 79.82% similarity)<br>APG00194.0 US_2016_0311864_A1-65 (55.16% identity, 70.4% similarity)<br>OUB82185.1 (34.74% identity, 59.15% similarity)<br>US_9121035_B2-20 (33.48% identity, 54.46% similarity)<br>US_9121035_B2-6 (33.48% identity, 54.46% similarity)<br>WP_088071709.1 (33.04% identity, 56.25% similarity) |
| APG04439.0 | 198 | 199 | | | MTX | 30, 35, 40, 45, 50, 55, 60, 65, 70, 75, 80, 85, 90, 91, 92, 93, 94, 95, 96, 97, 98, 99, 100 | 45, 50, 55, 60, 65, 70, 75, 80, 85, 90, 91, 92, 93, 94, 95, 96, 97, 98, 99, 100 | US_8318900_B2-187 (25.06% identity, 43.91% similarity)<br>US_8318900_B2-43 (25.06% identity, 43.91% similarity)<br>US_8318900_B2-92 (25.06% identity, 43.91% similarity)<br>WP_087986663.1 (25.06% identity, 43.68% similarity) |
| APG04442.0 | 200 | 201 | | | MTX | 85, 90, 91, 92, 93, 94, 95, 96, 97, 98, 99, 100 | 91, 92, 93, 94, 95, 96, 97, 98, 99, 100 | APG06001.0 (84.83% identity, 90.45% similarity)<br>APG09232.0 (52.99% identity, 68.66% similarity)<br>APG02168.0 (49.16% identity, 66.01% similarity)<br>APG00441.0 US_2016_0355842_A1-91 (38.68% identity, 56.16% similarity)<br>APG00444.0 US_2016_0355842_A1-93 (37.57% identity, 55.49% similarity)<br>APG03867.0 (37.57% identity, 52.6% similarity)<br>APG00833.0 US_2016_0355842_A1-175 (37.28% identity, 54.34% similarity)<br>WP_098858716.1 (37.28% identity, 54.34% |

TABLE 1-continued

Summary of SEQ ID NOs, Gene Class, and Variants thereof

| APG ID | Seq ID | Modified Seq ID(s) | CryBP1 Seq ID | Split-Cry C-terminus Seq ID | Gene Class | % Identity | % Similarity | Homologs |
|---|---|---|---|---|---|---|---|---|
| | | | | | | | | similarity)<br>APG04037.0 (36.31% identity, 52.16% similarity)<br>APG03227.0 (35.92% identity, 50.86% similarity) |
| APG04476.0 | 202 | 203 | | | Cry | 90, 91, 92, 93, 94, 95, 96, 97, 98, 99, 100 | 94, 95, 96, 97, 98, 99, 100 | US_8461415_B2-14 (87.53% identity, 93.46% similarity)<br>US_8461415_B2-42 (87.42% identity, 93.46% similarity)<br>WP_097862021.1 (87.42% identity, 93.35% similarity)<br>WP_098329961.1 (87.42% identity, 93.25% similarity)<br>WP_098283907.1 (87.32% identity, 93.35% similarity)<br>WP_098980505.1 (87.32% identity, 93.25% similarity)<br>WP_097919094.1 (87.22% identity, 93.25% similarity)<br>WP_098213472.1 (87.12% identity, 93.25% similarity)<br>APG00096.0 US_2016_0304898_A1-125 (84.62% identity, 90.84% similarity)<br>WP_098720132.1 (84.52% identity, 90.73% similarity) |
| APG04568.0 | 204 | 205 | | | Bin | 91, 92, 93, 94, 95, 96, 97, 98, 99, 100 | 95, 96, 97, 98, 99, 100 | APG08004.0 (91.73% identity, 94.74% similarity)<br>APG05715.0 (90.98% identity, 94.74% similarity)<br>APG06331.0 (90.8% identity, 94.28% similarity)<br>APG04176.0 (89.5% identity, 93.5% similarity)<br>APG02445.0 (89.47% identity, 93.98% similarity)<br>WP_098807694.1 (89.47% identity, 93.98% similarity)<br>APG07911.0 (88.31% identity, 93.28% similarity)<br>CA_2844913-146 (84.94% identity, 90.62% similarity)<br>WP_070144216.1 (83.75% identity, 90.5% similarity)<br>APG00212.0 US_2016_0311864_A1-75 (83.54% identity, 87.89% similarity) |

TABLE 1-continued

| Summary of SEQ ID NOs, Gene Class, and Variants thereof | | | | | | | | |
|---|---|---|---|---|---|---|---|---|
| APG ID | Seq ID | Modified Seq ID(s) | CryBP1 Seq ID | Split-Cry C-terminus Seq ID | Gene Class | % Identity | % Similarity | Homologs |
| APG04602.0 | 206 | 207 | | | Vip4 | 55, 60, 65, 70, 75, 80, 85, 90, 91, 92, 93, 94, 95, 96, 97, 98, 99, 100 | 70, 75, 80, 85, 90, 91, 92, 93, 94, 95, 96, 97, 98, 99, 100 | WP_098537347.1 (100.0% identity, 100.0% similarity)<br>APG04931.0 (53.5% identity, 67.51% similarity)<br>WP_098546457.1 (53.5% identity, 67.51% similarity)<br>APG07526.0 (52.73% identity, 67.89% similarity)<br>US_2016_0339078_A1-29674 (48.98% identity, 64.66% similarity)<br>APG07790.0 (48.67% identity, 65.23% similarity)<br>WP_053512697.1 (48.6% identity, 63.8% similarity)<br>APG07577.0 (48.58% identity, 65.14% similarity)<br>WP_088063470.1 (48.51% identity, 63.8% similarity)<br>WP_048561796.1 (48.14% identity, 63.71% similarity) |
| APG04651.0 | 208 | | | | Cry | 45, 50, 55, 60, 65, 70, 75, 80, 85, 90, 91, 92, 93, 94, 95, 96, 97, 98, 99, 100 | 60, 65, 70, 75, 80, 85, 90, 91, 92, 93, 94, 95, 96, 97, 98, 99, 100 | APG03054.0 (61.03% identity, 74.92% similarity)<br>ANC11094.1 (60.95% identity, 75.8% similarity)<br>WP_080470008.1 (59.4% identity, 73.88% similarity)<br>CBL59394.1 (43.89% identity, 60.82% similarity)<br>CBL59393.1 (43.89% identity, 60.68% similarity)<br>CBL59395.1 (43.89% identity, 60.68% similarity)<br>CBL59396.1 (43.89% identity, 60.68% similarity)<br>CBL59397.1 (43.89% identity, 60.38% similarity)<br>APG07954.0 (41.35% identity, 57.06% similarity)<br>APG06921.0 (41.12% identity, 59.76% similarity) |
| APG04683.0 | 209 | 210, 211 | | | MTX | 55, 60, 65, 70, 75, 80, 85, 90, 91, 92, 93, 94, 95, 96, 97, 98, 99, 100 | 65, 70, 75, 80, 85, 90, 91, 92, 93, 94, 95, 96, 97, 98, 99, 100 | WP_098487632.1 (90.46% identity, 90.46% similarity)<br>WP_098213667.1 (90.19% identity, 90.19% similarity)<br>AGC39300.1 (61.4% identity, 71.76% similarity)<br>WP_023524027.1 (57.58% identity, 66.58% |

TABLE 1-continued

Summary of SEQ ID NOs, Gene Class, and Variants thereof

| APG ID | Seq ID | Modified Seq ID(s) | CryBP1 Seq ID | Split-Cry C-terminus Seq ID | Gene Class | % Identity | % Similarity | Homologs |
|---|---|---|---|---|---|---|---|---|
| | | | | | | | | similarity)<br>APG02659.0 (51.41% identity, 62.21% similarity)<br>APG02511.0 (50.67% identity, 67.12% similarity)<br>US_8461415_B2-32 (50.0% identity, 62.63% similarity)<br>WP_001267112.1 (49.19% identity, 61.83% similarity)<br>WP_078401252.1 (46.84% identity, 61.05% similarity)<br>JP_2016_516397-59 (46.21% identity, 59.79% similarity) |
| APG04687.0 | 212 | 213, 214 | | | MTX | 75, 80, 85, 90, 91, 92, 93, 94, 95, 96, 97, 98, 99, 100 | 85, 90, 91, 92, 93, 94, 95, 96, 97, 98, 99, 100 | APG01516.0 (72.39% identity, 84.45% similarity)<br>APG06242.0 (71.54% identity, 84.57% similarity)<br>US_8829279_B2-11 (64.4% identity, 76.36% similarity)<br>APG06273.0 (61.2% identity, 74.04% similarity)<br>APG09338.0 (58.4% identity, 71.18% similarity)<br>APG00051.0 US_2016_0304898_A1-81 (57.75% identity, 70.25% similarity)<br>WP_098425241.1 (57.75% identity, 70.25% similarity)<br>APG01858.0 (57.04% identity, 71.11% similarity)<br>APG00911.0 US_2016_0355842_A1-189 (55.91% identity, 67.19% similarity)<br>APG05896.0 (54.92% identity, 68.03% similarity) |
| APG04692.0 | 215 | 216, 217 | | | MTX | 40, 45, 50, 55, 60, 65, 70, 75, 80, 85, 90, 91, 92, 93, 94, 95, 96, 97, 98, 99, 100 | 60, 65, 70, 75, 80, 85, 90, 91, 92, 93, 94, 95, 96, 97, 98, 99, 100 | WP_065486138.1 (37.01% identity, 53.81% similarity)<br>WP_065487080.1 (37.01% identity, 53.81% similarity)<br>APG00228.0 US_2016_0355842_A1-31 (36.2% identity, 56.25% similarity)<br>WP_098139851.1 (34.62% identity, 51.28% similarity)<br>US_8461415_B2-37 (34.53% identity, 51.08% similarity)<br>APG00283.0 US_2016_0355842_A1-50 (34.43% identity, 51.14% similarity)<br>APG03623.0 (34.04% identity, 49.87% |

TABLE 1-continued

| Summary of SEQ ID NOs, Gene Class, and Variants thereof | | | | | | | | |
|---|---|---|---|---|---|---|---|---|
| APG ID | Seq ID | Modified Seq ID(s) | CryBP1 Seq ID | Split-Cry C-terminus Seq ID | Gene Class | % Identity | % Similarity | Homologs |
| | | | | | | | | similarity)<br>APG00479.0 US__2016__0355842__A1-101 (33.07% identity, 48.41% similarity)<br>WP__098139684.1 (33.07% identity, 48.41% similarity)<br>WP__086387329.1 (32.56% identity, 46.98% similarity) |
| APG04694.0 | 218 | 219 | 220 | | Cry | 55, 60, 65, 70, 75, 80, 85, 90, 91, 92, 93, 94, 95, 96, 97, 98, 99, 100 | 65, 70, 75, 80, 85, 90, 91, 92, 93, 94, 95, 96, 97, 98, 99, 100 | CA__2844913-48 (50.51% identity, 62.5% similarity)<br>APG06942.0 (49.96% identity, 62.38% similarity)<br>APG09805.0 (49.31% identity, 62.25% similarity)<br>APG09805.0 (49.31% identity, 62.25% similarity)<br>WP__087949412.1 (48.35% identity, 61.38% similarity)<br>WP__098343937.1 (47.4% identity, 58.72% similarity)<br>APG00912.0 US__2017__0175134__A1-175 (47.34% identity, 60.2% similarity)<br>WP__078205753.1 (46.76% identity, 59.73% similarity)<br>WP__078205753.1 (46.76% identity, 59.73% similarity)<br>WP__078205749.1 (46.54% identity, 58.25% similarity) |
| APG04786.0 | 221 | 222, 223 | | | Cry | 70, 75, 80, 85, 90, 91, 92, 93, 94, 95, 96, 97, 98, 99, 100 | 80, 85, 90, 91, 92, 93, 94, 95, 96, 97, 98, 99, 100 | WP__002169796.1 (73.87% identity, 82.45% similarity)<br>APG01013.0 (65.27% identity, 77.34% similarity)<br>APG00044.0 US__2016__0304898__A1-71 (50.0% identity, 63.14% similarity)<br>WP__098906559.1 (50.0% identity, 63.14% similarity)<br>CA__2844913-189 (48.13% identity, 50.75% similarity)<br>CA__2844913-190 (47.89% identity, 50.62% similarity)<br>US__8461421__B2-264 (47.58% identity, 60.74% similarity)<br>WP__088125814.1 (47.46% identity, 60.51% similarity)<br>US__9567381__B2-378 (47.09% identity, 61.8% similarity) |

TABLE 1-continued

| Summary of SEQ ID NOs, Gene Class, and Variants thereof | | | | | | | | |
|---|---|---|---|---|---|---|---|---|
| APG ID | Seq ID | Modified Seq ID(s) | CryBP1 Seq ID | Split-Cry C-terminus Seq ID | Gene Class | % Identity | % Similarity | Homologs |
| | | | | | | | | US_8461421_B2-140 (46.46% identity, 59.28% similarity) |
| APG04794.0 | 224 | | | | MTX | 5, 10, 15, 20, 25, 30 35, 40, 45, 50, 55, 60, 65, 70, 75, 80, 85, 90, 91, 92, 93, 94, 95, 96, 97, 98, 99, 100 | 5, 10, 15, 20, 25, 30, 35, 40, 45, 50, 55, 60, 65, 70, 75, 80, 85, 90, 91, 92, 93, 94, 95, 96, 97, 98, 99, 100 | WP_001063481.1 (87.86% identity, 90.17% similarity)<br>WP_100240422.1 (30.75% identity, 50.57% similarity) |
| APG04821.0 | 225 | 226 | | | MTX | 99, 100 | 100 | APG00506.0 US_2016_0366881_A1-102 (98.33% identity, 99.0% similarity)<br>APG00987.0 US_2016_0366881_A1-223 (93.65% identity, 95.99% similarity)<br>APG02451.0 (91.3% identity, 94.98% similarity)<br>US_8461415_B2-57 (49.51% identity, 68.4% similarity)<br>APG00697.0 US_2016_0366881_A1-222 (45.9% identity, 66.89% similarity)<br>APG00346.0 US_2016_0366881_A1-24 (45.25% identity, 66.56% similarity)<br>US_8461415_B2-56 (43.38% identity, 67.22% similarity)<br>APG01761.0 (41.32% identity, 62.46% similarity)<br>APG00450.0 US_2016_0366881_A1-72 (41.32% identity, 61.83% similarity)<br>APG05804.0 (40.76% identity, 61.15% similarity) |
| APG04822.0 | 227 | 228 | | | MTX | 85, 90, 91, 92, 93, 94, 95, 96, 97, 98, 99, 100 | 85, 90, 91, 92, 93, 94, 95, 96, 97, 98, 99, 100 | APG00991.0 (81.44% identity, 83.25% similarity)<br>APG00055.0 US_2016_0304898_A1-86 (81.19% identity, 82.99% similarity)<br>WP_098516321.1 (81.19% identity, 82.99% similarity)<br>US_9328356_B2-17 (70.9% identity, 76.84% similarity)<br>US_9328356_B2-18 (70.9% identity, 76.55% similarity)<br>US_8796026_B2-6 (69.09% identity, 75.84% similarity)<br>WP_061885068.1 (68.83% identity, 75.84% similarity)<br>US_8796026_B2-8 (68.52% identity, 76.72% similarity)<br>US_9328356_B2-9 (68.29% identity, 74.53% similarity) |

TABLE 1-continued

| Summary of SEQ ID NOs, Gene Class, and Variants thereof | | | | | | | | |
|---|---|---|---|---|---|---|---|---|
| APG ID | Seq ID | Modified Seq ID(s) | CryBP1 Seq ID | Split-Cry C-terminus Seq ID | Gene Class | % Identity | % Similarity | Homologs |
| | | | | | | | | US_9328356_B2-10 (68.29% identity, 74.25% similarity) |
| APG04959.0 | 229 | | | | MTX | 45, 50, 55, 60, 65, 70, 75, 80, 85, 90, 91, 92, 93, 94, 95, 96, 97, 98, 99, 100 | 60, 65, 70, 75, 80, 85, 90, 91, 92, 93, 94, 95, 96, 97, 98, 99, 100 | CA_2516349-9 (41.99% identity, 55.1% similarity)<br>APG04010.0 (41.74% identity, 54.82% similarity)<br>CA_2516349-8 (41.72% identity, 54.83% similarity)<br>CA_2516349-7 (40.16% identity, 54.2% similarity)<br>APG00726.0 US_2017_0175134_A1-139 (37.93% identity, 50.62% similarity)<br>APG07972.0 (37.85% identity, 53.35% similarity)<br>CA_2516349-11 (37.0% identity, 49.47% similarity)<br>US_9567381_B2-249 (36.97% identity, 52.8% similarity)<br>US_2016_0345590_A1-2 (36.58% identity, 52.34% similarity)<br>BAE79727.1 (36.45% identity, 51.94% similarity) |
| APG04966.0 | 230 | 231 | | | Bin | 85, 90, 91, 92, 93, 94, 95, 96, 97, 98, 99, 100 | 93, 94, 95, 96, 97, 98, 99, 100 | WP_002114997.1 (89.74% identity, 93.33% similarity)<br>WP_070128649.1 (87.69% identity, 91.28% similarity)<br>WP_098058849.1 (87.44% identity, 93.33% similarity)<br>WP_078212086.1 (86.92% identity, 93.08% similarity)<br>WP_097833300.1 (86.67% identity, 93.08% similarity)<br>WP_098166690.1 (86.15% identity, 92.82% similarity)<br>WP_098488891.1 (86.15% identity, 92.56% similarity)<br>WP_098665095.1 (85.9% identity, 92.31% similarity)<br>WP_001258160.1 (83.85% identity, 92.31% similarity)<br>CA_2844913-10 (83.63% identity, 92.07% similarity) |
| APG04977.0 | 232 | | | | MTX | 75, 80, 85, 90, 91, 92, 93, 94, 95, 96, 97, 98, 99, 100 | 85, 90, 91, 92, 93, 94, 95, 96, 97, 98, 99, 100 | APG03738.0 (74.45% identity, 86.13% similarity)<br>APG02471.0 (72.1% identity, 81.52% similarity)<br>APG04111.0 (63.92% identity, 74.23% |

TABLE 1-continued

Summary of SEQ ID NOs, Gene Class, and Variants thereof

| APG ID | Seq ID | Modified Seq ID(s) | CryBP1 Seq ID | Split-Cry C-terminus Seq ID | Gene Class | % Identity | % Similarity | Homologs |
|---|---|---|---|---|---|---|---|---|
| | | | | | | | | similarity)<br>APG00236.0 US_2016_0355842_A1-32 (47.12% identity, 65.42% similarity)<br>APG02633.0 (33.33% identity, 50.88% similarity)<br>APG02714.0 (30.46% identity, 49.01% similarity)<br>APG05793.0 (27.43% identity, 46.18% similarity) |
| APG05073.0 | 233 | 234, 235 | | | Cry | 50, 55, 60, 65, 70, 75, 80, 85, 90, 91, 92, 93, 94, 95, 96, 97, 98, 99, 100 | 60, 65, 70, 75, 80, 85, 90, 91, 92, 93, 94, 95, 96, 97, 98, 99, 100 | APG02071.0 (45.78% identity, 58.49% similarity)<br>US_5281530-3 (45.63% identity, 57.19% similarity)<br>CA_2595901-11 (45.59% identity, 57.16% similarity)<br>CA_2595901-11 (45.59% identity, 57.16% similarity)<br>US_5281530-4 (45.52% identity, 57.16% similarity)<br>US_5281530-4 (45.52% identity, 57.16% similarity)<br>US_9567381_B2-434 (45.4% identity, 55.37% similarity)<br>US_9567381_B2-434 (45.4% identity, 55.37% similarity)<br>WP_097983832.1 (45.33% identity, 55.09% similarity)<br>WP_097983832.1 (45.33% identity, 55.09% similarity)<br>CA_2595901-12 (45.33% identity, 55.02% similarity)<br>CA_2595901-12 (45.33% identity, 55.02% similarity) |
| APG05078.0 | 236 | | | | Cry34 | 5, 10, 15, 20, 25, 30, 35, 40, 45, 50, 55, 60, 65, 70, 75, 80, 85, 90, 91, 92, 93, 94, 95, 96, 97, 98, 99, 100 | 5, 10, 15, 20, 25, 30, 35, 40, 45, 50, 55, 60, 65, 70, 75, 80, 85, 90, 91, 92, 93, 94, 95, 96, 97, 98, 99, 100 | APG01380.0 (96.52% identity, 98.26% similarity)<br>WP_077106733.1 (92.17% identity, 93.91% similarity)<br>WP_103583963.1 (92.17% identity, 93.91% similarity) |
| APG05095.0 | 237 | 238 | | | Cry | 45, 50, 55, 60, 65, 70, 75, 80, 85, 90, 91, 92, 93, 94, 95, 96, 97, 98, 99, 100 | 60, 65, 70, 75, 80, 85, 90, 91, 92, 93, 94, 95, 96, 97, 98, 99, 100 | CA_2844913-178 (43.05% identity, 57.84% similarity)<br>APG00043.0 US_2016_0304898_A1-69 (27.91% identity, 42.51% similarity)<br>WP_098638318.1 (26.85% identity, 43.85% similarity)<br>APG00446.0 US_2016_0366881_A1-68 |

TABLE 1-continued

| Summary of SEQ ID NOs, Gene Class, and Variants thereof | | | | | | | | |
|---|---|---|---|---|---|---|---|---|
| APG ID | Seq ID | Modified Seq ID(s) | CryBP1 Seq ID | Split-Cry C-terminus Seq ID | Gene Class | % Identity | % Similarity | Homologs |
| | | | | | | | | (26.47% identity, 43.57% similarity)<br>APG00396.0 US_2016_0311864_A1-163 (26.01% identity, 37.58% similarity)<br>WP_098783217.1 (26.01% identity, 37.58% similarity)<br>APG00250.0 US_2016_0355842_A1-37 (25.79% identity, 41.5% similarity)<br>WP_098376017.1 (25.61% identity, 41.31% similarity)<br>APG00053.0 US_2016_0304898_A1-83 (25.42% identity, 41.31% similarity)<br>WP_044306828.1 (25.42% identity, 41.31% similarity)<br>WP_097891105.1 (25.42% identity, 41.12% similarity) |
| APG05115.0 | 239 | | | | MAC PF | 85, 90, 91, 92, 93, 94, 95, 96, 97, 98, 99, 100 | 90, 91, 92, 93, 94, 95, 96, 97, 98, 99, 100 | WO_2017_192560-379 (81.62% identity, 88.34% similarity)<br>APG02912.0 (78.9% identity, 86.0% similarity)<br>WO_2017_192560-154 (78.26% identity, 86.76% similarity)<br>WO_2017_192560-118 (77.67% identity, 86.17% similarity)<br>WO_2017_192560-155 (77.47% identity, 86.17% similarity)<br>WO_2017_192560-162 (77.47% identity, 85.77% similarity)<br>WO_2017_192560-179 (77.12% identity, 86.19% similarity)<br>WO_2017_192560-136 (77.12% identity, 85.8% similarity)<br>WO_2017_192560-114 (77.12% identity, 85.4% similarity)<br>WO_2017_192560-121 (77.08% identity, 85.57% similarity) |
| APG05149.0 | 240 | 241 | | | MTX | 99, 100 | 99, 100 | APG07049.0 (98.08% identity, 98.72% similarity)<br>APG02921.0 (93.59% identity, 96.79% similarity)<br>WP_097787431.1 (93.59% identity, 96.79% similarity)<br>APG06989.0 (92.95% identity, 97.12% similarity)<br>WP_098218026.1 (92.95% identity, 97.12% similarity)<br>WP_098610169.1 (92.63% identity, 97.44% |

TABLE 1-continued

Summary of SEQ ID NOs, Gene Class, and Variants thereof

| APG ID | Seq ID | Modified Seq ID(s) | CryBP1 Seq ID | Split-Cry C-terminus Seq ID | Gene Class | % Identity | % Similarity | Homologs |
|---|---|---|---|---|---|---|---|---|
| | | | | | | | | similarity)<br>APG08990.0 (91.67% identity, 96.15% similarity)<br>WP_097849229.1 (91.03% identity, 94.23% similarity)<br>APG01536.0 (90.71% identity, 94.55% similarity)<br>APG04226.0 (89.42% identity, 93.27% similarity) |
| APG05279.0 | 242 | 243, 244 | | | Cry | 35, 40, 45, 50, 55, 60, 65, 70, 75, 80, 85, 90, 91, 92, 93, 94, 95, 96, 97, 98, 99, 100 | 55, 60, 65, 70, 75, 80, 85, 90, 91, 92, 93, 94, 95, 96, 97, 98, 99, 100 | APG03909.0 (40.56% identity, 57.52% similarity)<br>APG02037.0 (34.48% identity, 52.41% similarity)<br>APG01146.0 (34.03% identity, 52.26% similarity)<br>APG03045.0 (33.22% identity, 50.16% similarity)<br>APG05915.0 (33.17% identity, 47.97% similarity)<br>WP_098783120.1 (29.84% identity, 45.9% similarity)<br>CA_2844913-152 (25.67% identity, 41.42% similarity)<br>CA_2844913-151 (25.51% identity, 41.42% similarity)<br>APG00615.0 US_2016_0366881_A1-119 (25.16% identity, 37.66% similarity) |
| APG05300.0 | 245 | | | | MTX | 93, 94, 95, 96, 97, 98, 99, 100 | 96, 97, 98, 99, 100 | APG04375.0 (92.25% identity, 94.83% similarity)<br>WP_098222386.1 (91.7% identity, 95.47% similarity)<br>APG04793.0 (91.39% identity, 94.76% similarity)<br>WP_087969959.1 (91.32% identity, 95.09% similarity)<br>APG07676.0 (90.64% identity, 95.51% similarity)<br>WP_098908549.1 (90.57% identity, 95.47% similarity)<br>WP_098162508.1 (90.19% identity, 95.09% similarity)<br>APG03686.0 (89.89% identity, 94.76% similarity)<br>WP_088080923.1 (89.43% identity, 93.96% similarity) |

TABLE 1-continued

| Summary of SEQ ID NOs, Gene Class, and Variants thereof | | | | | | | | |
|---|---|---|---|---|---|---|---|---|
| APG ID | Seq ID | Modified Seq ID(s) | CryBP1 Seq ID | Split-Cry C-terminus Seq ID | Gene Class | % Identity | % Similarity | Homologs |
| | | | | | | | | WP_098290465.1 (88.68% identity, 94.34% similarity) |
| APG05346.0 | 246 | 247 | | | MTX | 93, 94, 95, 96, 97, 98, 99, 100 | 96, 97, 98, 99, 100 | WP_098111055.1 (93.39% identity, 96.56% similarity)<br>CA_2844913-120 (92.59% identity, 95.5% similarity)<br>APG00202.0 US_2016_0304898_A1-195 (89.59% identity, 92.64% similarity)<br>APG02475.0 (88.04% identity, 92.62% similarity)<br>APG04431.0 (85.75% identity, 90.84% similarity)<br>APG00208.0 US_2016_0304898_A1-201 (85.06% identity, 89.37% similarity)<br>APG01443.0 (84.72% identity, 91.19% similarity)<br>APG07094.0 (81.58% identity, 89.47% similarity)<br>APG00352.0 US_2016_0366881_A1-29 (81.58% identity, 89.21% similarity)<br>WP_000715637.1 (75.79% identity, 84.74% similarity) |
| APG05388.0 | 248 | | | | MTX | 91, 92, 93, 94, 95, 96, 97, 98, 99, 100 | 96, 97, 98, 99, 100 | US_7214788_B2-2 (90.67% identity, 95.52% similarity)<br>AQM56933.1 (88.06% identity, 94.03% similarity)<br>US_9328356_B2-30 (86.57% identity, 93.28% similarity)<br>CA_2267665-3 (75.75% identity, 84.33% similarity)<br>US_7214788_B2-10 (61.36% identity, 64.65% similarity)<br>US_7214788_B2-6 (61.36% identity, 64.65% similarity)<br>US_7214788_B2-33 (60.75% identity, 64.0% similarity)<br>US_7214788_B2-8 (60.75% identity, 64.0% similarity)<br>US_7214788_B2-14 (60.5% identity, 63.75% similarity)<br>US_7214788_B2-16 (51.38% identity, 56.89% similarity) |
| APG05408.0 | 249 | 250 | | | Cry34 | 40, 45, 50, 55, 60, 65, 70, 75, 80, 85, 90, 91, 92, 93, 94, 95, 96, 97, 98, 99, 100 | 55, 60, 65, 70, 75, 80, 85, 90, 91, 92, 93, 94, 95, 96, 97, 98, 99, 100 | WP_098933161.1 (99.33% identity, 100.0% similarity)<br>APG03204.0 (38.86% identity, 50.86% similarity) |

TABLE 1-continued

| Summary of SEQ ID NOs, Gene Class, and Variants thereof | | | | | | | | |
|---|---|---|---|---|---|---|---|---|
| APG ID | Seq ID | Modified Seq ID(s) | CryBP1 Seq ID | Split-Cry C-terminus Seq ID | Gene Class | % Identity | % Similarity | Homologs |
| APG05414.0 | 251 | 252 | | | MTX | 75, 80, 85, 90, 91, 92, 93, 94, 95, 96, 97, 98, 99, 100 | 80, 85, 90, 91, 92, 93, 94, 95, 96, 97, 98, 99, 100 | US_8461415_B2-37 (73.86% identity, 77.41% similarity)<br>US_8461421_B2-79 (59.2% identity, 68.16% similarity)<br>WP_086387329.1 (58.93% identity, 69.13% similarity)<br>WP_065486138.1 (36.27% identity, 50.93% similarity)<br>WP_065487080.1 (36.0% identity, 50.67% similarity)<br>APG00228.0 US_2016_0355842_A1-31 (35.65% identity, 45.93% similarity)<br>APG00966.0 US_2016_0355842_A1-195 (35.34% identity, 52.05% similarity)<br>WP_098976737.1 (35.34% identity, 52.05% similarity)<br>APG00438.0 US_2016_0366881_A1-63 (33.66% identity, 48.51% similarity)<br>WP_078401253.1 (33.53% identity, 51.63% similarity) |
| APG05429.0 | 253 | 254, 255 | | | MTX | 92, 93, 94, 95, 96, 97, 98, 99, 100 | 93, 94, 95, 96, 97, 98, 99, 100 | WP_078404344.1 (96.87% identity, 97.65% similarity)<br>OPA24196.1 (93.99% identity, 94.26% similarity)<br>APG04807.0 (91.12% identity, 92.43% similarity)<br>APG08307.0 (48.98% identity, 62.76% similarity)<br>APG09864.0 (31.66% identity, 48.29% similarity)<br>APG02256.0 (30.62% identity, 47.85% similarity)<br>APG07058.0 (30.46% identity, 47.0% similarity)<br>WP_078404291.1 (30.46% identity, 47.0% similarity)<br>APG03055.0 (25.12% identity, 43.35% similarity) |
| APG05431.0 | 256 | 257 | | | MTX | 85, 90, 91, 92, 93, 94, 95, 96, 97, 98, 99, 100 | 92, 93, 94, 95, 96, 97, 98, 99, 100 | WP_098882546.1 (93.11% identity, 95.08% similarity)<br>WP_098814109.1 (85.62% identity, 93.79% similarity)<br>APG08085.0 (84.74% identity, 91.56% similarity)<br>WP_098090730.1 (84.74% identity, 91.56% similarity)<br>APG01155.0 (84.42% identity, 91.56% |

TABLE 1-continued

| Summary of SEQ ID NOs, Gene Class, and Variants thereof | | | | | | | | |
|---|---|---|---|---|---|---|---|---|
| APG ID | Seq ID | Modified Seq ID(s) | CryBP1 Seq ID | Split-Cry C-terminus Seq ID | Gene Class | % Identity | % Similarity | Homologs |
| | | | | | | | | similarity) APG00743.0 (84.04% identity, 91.86% similarity) WP_098096847.1 (84.04% identity, 91.86% similarity) WP_098813802.1 (84.04% identity, 91.21% similarity) WP_098643289.1 (83.99% identity, 92.48% similarity) WP_097849502.1 (83.71% identity, 91.21% similarity) |
| APG05471.0 | 258 | | | | MAC PF | 30, 35, 40, 45, 50, 55, 60, 65, 70, 75, 80, 85, 90, 91, 92, 93, 94, 95, 96, 97, 98, 99, 100 | 45, 50, 55, 60, 65, 70, 75, 80, 85, 90, 91, 92, 93, 94, 95, 96, 97, 98, 99, 100 | WP_090462870.1 (44.86% identity, 57.01% similarity) WP_090462867.1 (44.38% identity, 58.75% similarity) APG08370.0 (42.52% identity, 57.3% similarity) WP_076377347.1 (41.65% identity, 55.83% similarity) WP_076375462.1 (33.07% identity, 49.61% similarity) WP_091163039.1 (32.29% identity, 46.06% similarity) WP_078670461.1 (32.16% identity, 47.13% similarity) SKA29206.1 (31.61% identity, 46.4% similarity) WP_100340242.1 (31.35% identity, 46.94% similarity) WP_062550478.1 (29.63% identity, 47.59% similarity) |
| APG05481.0 | 259 | 260, 261 | | | MTX | 90, 91, 92, 93, 94, 95, 96, 97, 98, 99, 100 | 94, 95, 96, 97, 98, 99, 100 | APG05341.0 (86.91% identity, 93.19% similarity) APG00324.0 US_2016_0355842_A1-61 (71.5% identity, 80.83% similarity) APG01281.0 (61.44% identity, 70.69% similarity) APG00253.0 US_2016_0355842_A1-39 (47.51% identity, 60.89% similarity) APG00020.0 US_2016_0304898_A1-33 (46.46% identity, 60.37% similarity) WP_098539891.1 (46.46% identity, 60.37% similarity) APG00322.0 US_2016_0355842_A1-59 (46.37% identity, 62.18% similarity) APG01508.0 (46.19% identity, 60.37% |

TABLE 1-continued

| Summary of SEQ ID NOs, Gene Class, and Variants thereof | | | | | | | | |
|---|---|---|---|---|---|---|---|---|
| APG ID | Seq ID | Modified Seq ID(s) | CryBP1 Seq ID | Split-Cry C-terminus Seq ID | Gene Class | % Identity | % Similarity | Homologs |
| | | | | | | | | similarity)<br>WP_098322759.1 (46.19% identity, 60.37% similarity)<br>APG00764.0 US_2016_0355842_A1-168 (46.13% identity, 61.86% similarity) |
| APG05492.0 | 262 | | | | MTX | 90, 91, 92, 93, 94, 95, 96, 97, 98, 99, 100 | 95, 96, 97, 98, 99, 100 | WP_065397681.1 (99.64% identity, 100.0% similarity)<br>APG03604.0 (88.53% identity, 94.62% similarity)<br>WP_089734181.1 (86.74% identity, 93.91% similarity)<br>WP_086572501.1 (38.31% identity, 56.17% similarity)<br>WP_100573349.1 (37.54% identity, 52.55% similarity)<br>WP_067347886.1 (36.39% identity, 50.0% similarity)<br>WP_053730552.1 (36.04% identity, 53.45% similarity)<br>WP_039633689.1 (34.97% identity, 49.13% similarity)<br>WP_071966410.1 (34.71% identity, 51.47% similarity)<br>WP_102926521.1 (34.68% identity, 49.13% similarity) |
| APG05508.0 | 263 | 264 | | | Cry | 80, 85, 90, 91, 92, 93, 94, 95, 96, 97, 98, 99, 100 | 90, 91, 92, 93, 94, 95, 96, 97, 98, 99, 100 | WP_098018669.1 (76.34% identity, 86.88% similarity)<br>APG00030.0 US_2016_0304898_A1-50 (76.29% identity, 86.8% similarity)<br>APG01313.0 (74.9% identity, 86.26% similarity)<br>US_8461415_B2-14 (74.67% identity, 84.86% similarity)<br>US_8461415_B2-42 (74.56% identity, 84.86% similarity)<br>WP_097862021.1 (74.56% identity, 84.76% similarity)<br>WP_098329961.1 (74.56% identity, 84.76% similarity)<br>WP_098283907.1 (74.46% identity, 84.76% similarity)<br>WP_098980505.1 (74.46% identity, 84.65% similarity)<br>WP_097919094.1 (74.46% identity, 84.55% similarity) |

TABLE 1-continued

| Summary of SEQ ID NOs, Gene Class, and Variants thereof | | | | | | | | |
|---|---|---|---|---|---|---|---|---|
| APG ID | Seq ID | Modified Seq ID(s) | CryBP1 Seq ID | Split-Cry C-terminus Seq ID | Gene Class | % Identity | % Similarity | Homologs |
| APG05538.0 | 265 | 266, 267 | | | Cry | 70, 75, 80, 85, 90, 91, 92, 93, 94, 95, 96, 97, 98, 99, 100 | 80, 85, 90, 91, 92, 93, 94, 95, 96, 97, 98, 99, 100 | APG09282.0 (67.52% identity, 76.85% similarity)<br>APG02533.0 (63.01% identity, 73.67% similarity)<br>APG00787.0 US_2017_0175134_A1-156 (60.49% identity, 67.13% similarity)<br>APG00471.0 US_2016_0366881_A1-85 (58.19% identity, 71.29% similarity)<br>APG01860.0 (57.65% identity, 63.19% similarity)<br>APG09630.0 (50.52% identity, 60.86% similarity)<br>KXH80331.1 (49.93% identity, 57.96% similarity)<br>WP_098395829.1 (49.24% identity, 60.49% similarity)<br>WP_082770008.1 (48.81% identity, 56.64% similarity)<br>APG05689.0 (47.8% identity, 59.91% similarity) |
| APG05636.0 | 268 | | | | MTX | 98, 99, 100 | 100 | APG02554.0 (97.98% identity, 99.33% similarity)<br>APG09682.0 (96.3% identity, 98.65% similarity)<br>APG00201.0 US_2016_0304898_A1-193 (81.25% identity, 87.83% similarity)<br>WP_098866878.1 (81.25% identity, 87.83% similarity)<br>APG00847.0 US_2016_0304898_A1-223 (80.92% identity, 87.83% similarity)<br>APG07639.0 (80.81% identity, 88.55% similarity)<br>APG03379.0 (80.54% identity, 88.26% similarity)<br>APG08241.0 (80.47% identity, 88.55% similarity)<br>APG02279.0 (80.07% identity, 87.25% similarity)<br>WP_102956800.1 (79.93% identity, 86.84% similarity) |
| APG05643.0 | 269 | 270 | | 271 | Cry | 65, 70, 75, 80, 85, 90, 91, 92, 93, 94, 95, 96, 97, 98, 99, 100 | 75, 80, 85, 90, 91, 92, 93, 94, 95, 96, 97, 98, 99, 100 | US_9567381_B2-447 (63.64% identity, 70.1% similarity)<br>APG00123.0 US_2016_0304898_A1-146 (45.83% identity, 57.61% similarity)<br>WP_098213628.1 (45.83% identity, 57.61% similarity)<br>APG00136.0 US_2016_0177333_A1-75 |

TABLE 1-continued

| Summary of SEQ ID NOs, Gene Class, and Variants thereof | | | | | | | | |
|---|---|---|---|---|---|---|---|---|
| APG ID | Seq ID | Modified Seq ID(s) | CryBP1 Seq ID | Split-Cry C-terminus Seq ID | Gene Class | % Identity | % Similarity | Homologs |
| | | | | | | | | (26.34% identity, 38.35% similarity)<br>WP_097984025.1 (26.34% identity, 38.35% similarity)<br>APG00721.0 US_2017_0175134_A1-133 (26.08% identity, 38.36% similarity) |
| APG05662.0 | 272 | | | | Cyt | 93, 94, 95, 96, 97, 98, 99, 100 | 97, 98, 99, 100 | WP_076855475.1 (93.06% identity, 97.69% similarity)<br>WP_088326113.1 (93.06% identity, 97.22% similarity)<br>WP_098190289.1 (92.59% identity, 97.22% similarity)<br>CA_2844913-98 (92.59% identity, 96.76% similarity)<br>WP_098524519.1 (92.13% identity, 96.76% similarity)<br>APG03959.0 (91.67% identity, 95.83% similarity)<br>APG00394.0 US_2016_0366881_A1-48 (85.32% identity, 92.66% similarity)<br>WP_097961786.1 (29.86% identity, 55.66% similarity)<br>WP_063538656.1 (29.41% identity, 54.75% similarity)<br>WP_061667230.1 (28.51% identity, 55.2% similarity)<br>WP_098300708.1 (28.51% identity, 55.2% similarity) |
| APG05725.0 | 273 | 274 | | | Cry | 50, 55, 60, 65, 70, 75, 80, 85, 90, 91, 92, 93, 94, 95, 96, 97, 98, 99, 100 | 55, 60, 65, 70, 75, 80, 85, 90, 91, 92, 93, 94, 95, 96, 97, 98, 99, 100 | CA_2844913-184 (47.48% identity, 54.7% similarity)<br>APG09826.0 (38.39% identity, 52.98% similarity)<br>APG06774.0 (37.79% identity, 49.01% similarity)<br>US_8461415_B2-45 (35.36% identity, 47.49% similarity)<br>WP_097891157.1 (35.36% identity, 47.49% similarity)<br>APG03573.0 (35.23% identity, 48.01% similarity)<br>WP_098349415.1 (34.84% identity, 47.14% similarity)<br>APG04280.0 (34.76% identity, 52.23% similarity)<br>APG00424.0 US_2016_0366881_A1-52 (34.61% identity, 45.74% similarity) |

TABLE 1-continued

| Summary of SEQ ID NOs, Gene Class, and Variants thereof | | | | | | | | |
|---|---|---|---|---|---|---|---|---|
| APG ID | Seq ID | Modified Seq ID(s) | CryBP1 Seq ID | Split-Cry C-terminus Seq ID | Gene Class | % Identity | % Similarity | Homologs |
| | | | | | | | | WP_060852738.1 (34.61% identity, 45.74% similarity) |
| APG05734.0 | 275 | 276, 277, 278, 279 | | | Cry | 90, 91, 92, 93, 94, 95, 96, 97, 98, 99, 100 | 94, 95, 96, 97, 98, 99, 100 | WP_097832796.1 (89.41% identity, 92.66% similarity)<br>ETT82181.1 (89.29% identity, 93.02% similarity)<br>WP_098519790.1 (89.29% identity, 92.54% similarity)<br>US_9567381_B2-455 (88.93% identity, 93.02% similarity)<br>WP_016093954.1 (88.81% identity, 92.54% similarity)<br>WP_033729515.1 (88.81% identity, 92.54% similarity)<br>APG01446.0 (88.74% identity, 92.57% similarity)<br>WP_002147758.1 (88.45% identity, 92.54% similarity)<br>AGU12794.1 (88.45% identity, 92.3% similarity)<br>APG00705.0 US_2017_0175134_A1-120 (88.04% identity, 92.51% similarity) |
| APG05793.0 | 280 | | | | MTX | 65, 70, 75, 80, 85, 90, 91, 92, 93, 94, 95, 96, 97, 98, 99, 100 | 75, 80, 85, 90, 91, 92, 93, 94, 95, 96, 97, 98, 99, 100 | APG02714.0 (83.68% identity, 84.03% similarity)<br>APG06768.0 (62.76% identity, 73.1% similarity)<br>APG02633.0 (37.1% identity, 54.42% similarity)<br>APG04111.0 (29.93% identity, 47.28% similarity)<br>APG04977.0 (27.43% identity, 46.18% similarity)<br>APG00236.0 US_2016_0355842_A1-32 (26.6% identity, 47.47% similarity)<br>APG06578.0 (25.96% identity, 37.82% similarity) |
| APG05834.0 | 281 | 282 | | | MTX | 65, 70, 75, 80, 85, 90, 91, 92, 93, 94, 95, 96, 97, 98, 99, 100 | 75, 80, 85, 90, 91, 92, 93, 94, 95, 96, 97, 98, 99, 100 | APG04103.0 (61.99% identity, 75.15% similarity)<br>APG00585.0 US_2016_0366881_A1-116 (60.41% identity, 73.61% similarity)<br>WP_104030950.1 (60.41% identity, 73.31% similarity)<br>WP_099327316.1 (60.41% identity, 72.73% similarity)<br>WP_104150403.1 (60.18% identity, 71.09% similarity)<br>WP_094701865.1 (60.12% identity, 73.61% |

TABLE 1-continued

Summary of SEQ ID NOs, Gene Class, and Variants thereof

| APG ID | Seq ID | Modified Seq ID(s) | CryBP1 Seq ID | Split-Cry C-terminus Seq ID | Gene Class | % Identity | % Similarity | Homologs |
|---|---|---|---|---|---|---|---|---|
| | | | | | | | | similarity)<br>APG02401.0 (60.12% identity, 73.31% similarity)<br>WP_018673409.1 (60.12% identity, 73.31% similarity)<br>WP_104064947.1 (60.12% identity, 73.31% similarity)<br>APG06560.0 (59.59% identity, 71.39% similarity)<br>APG00851.0 US_2016_0311864_A1-222 (59.59% identity, 70.5% similarity)<br>WP_061663532.1 (59.59% identity, 70.5% similarity) |
| APG05878.0 | 283 | | | | Cry | 70, 75, 80, 85, 90, 91, 92, 93, 94, 95, 96, 97, 98, 99, 100 | 85, 90, 91, 92, 93, 94, 95, 96, 97, 98, 99, 100 | APG00603.0 US_2016_0311864_A1-198 (69.75% identity, 83.74% similarity)<br>WP_097981477.1 (69.75% identity, 83.74% similarity)<br>WP_098887934.1 (69.55% identity, 83.54% similarity)<br>APG01084.0 (67.28% identity, 84.16% similarity)<br>APG08526.0 (67.28% identity, 83.13% similarity)<br>WP_098867980.1 (66.87% identity, 80.86% similarity)<br>WP_098505564.1 (56.17% identity, 68.93% similarity)<br>APG01112.0 US_2017_0175134_A1-204 (55.14% identity, 68.93% similarity)<br>WP_097891153.1 (33.4% identity, 49.9% similarity)<br>WP_044306756.1 (33.2% identity, 49.71% similarity)<br>WP_098353196.1 (33.2% identity, 49.51% similarity) |
| APG05907.0 | 284 | 285 | | | Bin | 85, 90, 91, 92, 93, 94, 95, 96, 97, 98, 99, 100 | 90, 91, 92, 93, 94, 95, 96, 97, 98, 99, 100 | APG01153.0 (82.93% identity, 88.29% similarity)<br>APG00095.0 US_2016_0177333_A1-52 (68.28% identity, 77.24% similarity)<br>APG00700.0 US_2016_0311864_A1-207 (68.04% identity, 77.48% similarity)<br>APG00750.0 US_2016_0366881_A1-132 (32.76% identity, 47.54% similarity)<br>APG00629.0 US_2016_0366881_A1-126 (31.72% identity, 46.9% similarity)<br>APG07432.0 (30.41% identity, 42.88% |

TABLE 1-continued

Summary of SEQ ID NOs, Gene Class, and Variants thereof

| APG ID | Seq ID | Modified Seq ID(s) | CryBP1 Seq ID | Split-Cry C-terminus Seq ID | Gene Class | % Identity | % Similarity | Homologs |
|---|---|---|---|---|---|---|---|---|
| | | | | | | | | similarity)<br>APG08101.0 (29.9% identity, 44.27% similarity)<br>APG00474.0 US_2016_0366881_A1-89 (29.23% identity, 42.23% similarity)<br>APG06401.0 (29.16% identity, 44.15% similarity)<br>US_9567381_B2-398 (28.28% identity, 40.61% similarity) |
| APG05917.0 | 286 | | | | Bin | 90, 91, 92, 93, 94, 95, 96, 97, 98, 99, 100 | 94, 95, 96, 97, 98, 99, 100 | APG09153.0 (88.67% identity, 93.35% similarity)<br>APG08195.0 (82.6% identity, 88.97% similarity)<br>APG07868.0 (82.35% identity, 87.99% similarity)<br>APG00727.0 US_2016_0311864_A1-210 (81.46% identity, 87.07% similarity)<br>APG00178.0 US_2016_0311864_A1-54 (81.37% identity, 87.75% similarity)<br>APG06237.0 (81.13% identity, 89.46% similarity)<br>APG04627.0 (80.64% identity, 87.5% similarity)<br>APG00315.0 US_2016_0311864_A1-137 (77.45% identity, 85.29% similarity)<br>APG06559.0 (76.04% identity, 85.57% similarity)<br>WP_098771878.1 (35.47% identity, 40.89% similarity) |
| APG05920.0 | 287 | 288 | | | Cry | 30, 35, 40, 45, 50, 55, 60, 65, 70, 75, 80, 85, 90, 91, 92, 93, 94, 95, 96, 97, 98, 99, 100 | 45, 50, 55, 60, 65, 70, 75, 80, 85, 90, 91, 92, 93, 94, 95, 96, 97, 98, 99, 100 | WP_098396645.1 (76.71% identity, 85.1% similarity)<br>APG06420.0 (29.91% identity, 43.59% similarity)<br>APG00239.0 US_2016_0311864_A1-91 (28.75% identity, 42.35% similarity)<br>APG01803.0 (27.44% identity, 38.72% similarity)<br>APG00375.0 US_2016_0311864_A1-152 (26.36% identity, 38.1% similarity)<br>WP_098805991.1 (26.36% identity, 38.1% similarity)<br>APG00564.0 US_2016_0355842_A1-128 (26.15% identity, 40.83% similarity)<br>US_8318900_B2-91 (25.54% identity, 36.62% similarity) |

TABLE 1-continued

| Summary of SEQ ID NOs, Gene Class, and Variants thereof | | | | | | | | |
|---|---|---|---|---|---|---|---|---|
| APG ID | Seq ID | Modified Seq ID(s) | CryBP1 Seq ID | Split-Cry C-terminus Seq ID | Gene Class | % Identity | % Similarity | Homologs |
| APG05946.0 | 289 | | | | Bin | 65, 70, 75, 80, 85, 90, 91, 92, 93, 94, 95, 96, 97, 98, 99, 100 | 75, 80, 85, 90, 91, 92, 93, 94, 95, 96, 97, 98, 99, 100 | US_8829279_B2-4 (64.61% identity, 73.7% similarity)<br>WP_098689320.1 (58.54% identity, 66.4% similarity)<br>WP_098478562.1 (57.99% identity, 65.58% similarity)<br>APG00231.0 US_2016_0311864_A1-86 (57.91% identity, 65.68% similarity)<br>APG00568.0 US_2016_0311864_A1-391 (57.91% identity, 65.68% similarity)<br>WP_050845516.1 (57.72% identity, 66.12% similarity)<br>APG00377.0 US_2016_0311864_A1-154 (57.64% identity, 65.68% similarity)<br>AEX56523.1 (57.45% identity, 66.12% similarity)<br>WP_098830366.1 (57.45% identity, 65.31% similarity)<br>WP_098639761.1 (57.45% identity, 65.04% similarity) |
| APG05955.0 | 290 | | | | Bin | 40, 45, 50, 55, 60, 65, 70, 75, 80, 85, 90, 91, 92, 93, 94, 95, 96, 97, 98, 99, 100 | 60, 65, 70, 75, 80, 85, 90, 91, 92, 93, 94, 95, 96, 97, 98, 99, 100 | APG03361.0 (64.06% identity, 75.59% similarity)<br>APG09146.0 (39.73% identity, 55.19% similarity)<br>US_8461415_B2-29 (39.43% identity, 53.21% similarity)<br>WP_016099737.1 (36.46% identity, 50.54% similarity)<br>US_8461415_B2-44 (32.17% identity, 45.77% similarity)<br>APG06401.0 (29.44% identity, 43.09% similarity)<br>APG07310.0 (29.09% identity, 39.5% similarity)<br>WP_098826686.1 (29.0% identity, 43.95% similarity)<br>APG00075.0 US_2016_0177333_A1-40 (28.85% identity, 43.72% similarity)<br>APG08101.0 (28.67% identity, 42.83% similarity) |
| APG05992.0 | 291 | | | | MTX | 85, 90, 91, 92, 93, 94, 95, 96, 97, 98, 99, 100 | 91, 92, 93, 94, 95, 96, 97, 98, 99, 100 | APG08917.0 (81.62% identity, 90.81% similarity)<br>APG01706.0 (61.01% identity, 75.45% similarity)<br>APG05984.0 (59.78% identity, 73.55% similarity)<br>APG07780.0 (58.27% identity, 71.94% |

TABLE 1-continued

| Summary of SEQ ID NOs, Gene Class, and Variants thereof | | | | | | | | |
|---|---|---|---|---|---|---|---|---|
| APG ID | Seq ID | Modified Seq ID(s) | CryBP1 Seq ID | Split-Cry C-terminus Seq ID | Gene Class | % Identity | % Similarity | Homologs |
| | | | | | | | | similarity)<br>APG08576.0 (57.76% identity, 71.12% similarity)<br>APG05943.0 (56.46% identity, 69.39% similarity)<br>APG01093.0 (55.6% identity, 70.76% similarity)<br>APG09439.0 (52.88% identity, 69.06% similarity)<br>APG03587.0 (51.97% identity, 68.1% similarity)<br>APG01273.0 (51.94% identity, 70.67% similarity) |
| APG06027.0 | 292 | 293 | | | Bin | 85, 90, 91, 92, 93, 94, 95, 96, 97, 98, 99, 100 | 90, 91, 92, 93, 94, 95, 96, 97, 98, 99, 100 | APG07511.0 (81.32% identity, 88.95% similarity)<br>WP_098772949.1 (80.78% identity, 87.53% similarity)<br>APG00230.0 US_2016_0311864_A1-85 (80.57% identity, 87.31% similarity)<br>APG00413.0 US_2016_0311864_A1-174 (77.89% identity, 86.32% similarity)<br>APG06920.0 (77.14% identity, 87.27% similarity)<br>KEZ80012.1 (77.11% identity, 86.05% similarity)<br>APG05717.0 (76.58% identity, 85.79% similarity)<br>US_9321814_B2-3 (76.58% identity, 84.74% similarity)<br>US_9321814_B2-2 (76.38% identity, 84.51% similarity)<br>WP_098876539.1 (76.32% identity, 84.47% similarity) |
| APG06049.0 | 294 | 295 | | | MTX | 85, 90, 91, 92, 93, 94, 95, 96, 97, 98, 99, 100 | 91, 92, 93, 94, 95, 96, 97, 98, 99, 100 | APG06319.0 (84.2% identity, 91.01% similarity)<br>APG00483.0 US_2016_0355842_A1-104 (84.2% identity, 90.19% similarity)<br>APG06851.0 (80.38% identity, 90.74% similarity)<br>APG00421.0 US_2016_0355842_A1-86 (79.29% identity, 89.37% similarity)<br>WP_063226258.1 (76.16% identity, 87.95% similarity)<br>APG00995.0 US_2016_0355842_A1-200 (69.38% identity, 80.49% similarity)<br>APG00414.0 US_2016_0355842_A1-81 |

TABLE 1-continued

Summary of SEQ ID NOs, Gene Class, and Variants thereof

| APG ID | Seq ID | Modified Seq ID(s) | CryBP1 Seq ID | Split-Cry C-terminus Seq ID | Gene Class | % Identity | % Similarity | Homologs |
|---|---|---|---|---|---|---|---|---|
| | | | | | | | | (68.29% identity, 80.22% similarity)<br>APG00593.0 US_2016_0355842_A1-136 (68.29% identity, 79.95% similarity)<br>WP_097899326.1 (68.29% identity, 79.95% similarity)<br>APG00560.0 US_2016_0355842_A1-125 (65.85% identity, 79.4% similarity)<br>WP_098991345.1 (65.85% identity, 79.4% similarity) |
| APG06079.0 | 296 | 297 | | | Cry | 91, 92, 93, 94, 95, 96, 97, 98, 99, 100 | 94, 95, 96, 97, 98, 99, 100 | APG00041.0 US_2016_0304898_A1-64 (90.21% identity, 93.43% similarity)<br>WP_098583123.1 (90.21% identity, 93.43% similarity)<br>APG00145.0 US_2016_0304898_A1-163 (86.98% identity, 89.93% similarity)<br>WP_098772031.1 (86.98% identity, 89.93% similarity)<br>AEH76822.1 (65.14% identity, 75.0% similarity)<br>US_8461421_B2-84 (64.76% identity, 74.55% similarity)<br>EJR94916.1 (64.5% identity, 76.25% similarity)<br>WP_080029306.1 (64.11% identity, 75.79% similarity)<br>AQM56942.1 (60.59% identity, 67.0% similarity)<br>US_8461421_B2-184 (60.12% identity, 67.07% similarity) |
| APG06195.0 | 298 | | | | MTX | 97, 98, 99, 100 | 98, 99, 100 | APG06465.0 (96.39% identity, 97.38% similarity)<br>APG04483.0 (96.39% identity, 97.05% similarity)<br>WP_098908548.1 (96.39% identity, 97.05% similarity)<br>APG00696.0 US_2016_0355842_A1-160 (96.07% identity, 97.05% similarity)<br>WP_098222384.1 (96.07% identity, 97.05% similarity)<br>WP_098778568.1 (96.07% identity, 97.05% similarity)<br>WP_098162507.1 (96.07% identity, 96.72% similarity)<br>WP_088080922.1 (95.41% identity, 97.05% similarity)<br>APG01882.0 (95.1% identity, 96.41% |

TABLE 1-continued

Summary of SEQ ID NOs, Gene Class, and Variants thereof

| APG ID | Seq ID | Modified Seq ID(s) | CryBP1 Seq ID | Split-Cry C-terminus Seq ID | Gene Class | % Identity | % Similarity | Homologs |
|---|---|---|---|---|---|---|---|---|
| | | | | | | | | similarity)<br>WP_098290464.1 (95.1% identity, 96.41% similarity)<br>APG01265.0 (95.08% identity, 97.05% similarity)<br>APG02105.0 (95.08% identity, 96.07% similarity)<br>APG08138.0 (93.77% identity, 96.07% similarity)<br>APG03715.0 (91.56% identity, 92.5% similarity)<br>WP_087969960.1 (90.6% identity, 92.16% similarity) |
| APG06213.0 | 299 | 300, 301 | | | Cry | 85, 90, 91, 92, 93, 94, 95, 96, 97, 98, 99, 100 | 90, 91, 92, 93, 94, 95, 96, 97, 98, 99, 100 | APG06606.0 (96.84% identity, 98.59% similarity)<br>APG02110.0 (95.78% identity, 97.89% similarity)<br>APG07811.0 (95.08% identity, 97.19% similarity)<br>APG04108.0 (83.28% identity, 87.46% similarity)<br>APG00235.0 US_2016_0311864_A1-89 (81.77% identity, 88.37% similarity)<br>WP_050845493.1 (64.63% identity, 75.34% similarity)<br>APG08681.0 (54.79% identity, 65.93% similarity)<br>WP_048536324.1 (54.79% identity, 65.93% similarity)<br>APG00702.0 US_2017_0175134_A1-115 (38.1% identity, 50.79% similarity)<br>APG00702.0 US_2017_0175134_A1-115 (38.1% identity, 50.79% similarity) |
| APG06235.0 | 302 | | | | Vip3 | 93, 94, 95, 96, 97, 98, 99, 100 | 96, 97, 98, 99, 100 | APG00181.0 US_2016_0355842_A1-16 (92.25% identity, 95.32% similarity)<br>APG00038.0 US_2016_0355842_A1-1 (89.95% identity, 93.9% similarity)<br>APG09221.0 (89.75% identity, 93.53% similarity)<br>APG00675.0 US_2017_0175134_A1-97 (61.35% identity, 75.53% similarity)<br>APG00131.0 US_2016_0311864_A1-30 (60.53% identity, 76.28% similarity)<br>WP_098631820.1 (60.53% identity, 76.28% similarity)<br>APG07054.0 (51.4% identity, 67.83% |

TABLE 1-continued

Summary of SEQ ID NOs, Gene Class, and Variants thereof

| APG ID | Seq ID | Modified Seq ID(s) | CryBP1 Seq ID | Split-Cry C-terminus Seq ID | Gene Class | % Identity | % Similarity | Homologs |
|---|---|---|---|---|---|---|---|---|
| | | | | | | | | similarity)<br>APG00207.0 US_2016_0311864_A1-70 (46.38% identity, 64.31% similarity)<br>WP_098685831.1 (46.38% identity, 64.31% similarity)<br>AAY27873.1 (36.7% identity, 55.77% similarity) |
| APG06283.0 | 303 | | | | MTX | 70, 75, 80, 85, 90, 91, 92, 93, 94, 95, 96, 97, 98, 99, 100 | 80, 85, 90, 91, 92, 93, 94, 95, 96, 97, 98, 99, 100 | WP_098069633.1 (66.67% identity, 79.33% similarity)<br>WP_098099018.1 (66.58% identity, 79.18% similarity)<br>WP_098087707.1 (66.58% identity, 78.92% similarity)<br>WP_099010057.1 (66.32% identity, 78.92% similarity)<br>APG01797.0 (65.89% identity, 78.81% similarity)<br>APG03217.0 (65.57% identity, 77.97% similarity)<br>APG08029.0 (65.14% identity, 77.86% similarity)<br>APG04119.0 (64.25% identity, 78.24% similarity)<br>APG00932.0 (61.42% identity, 76.4% similarity)<br>APG02206.0 (61.19% identity, 75.12% similarity) |
| APG06304.0 | 304 | 305 | | | MTX | 55, 60, 65, 70, 75, 80, 85, 90, 91, 92, 93, 94, 95, 96, 97, 98, 99, 100 | 75, 80, 85, 90, 91, 92, 93, 94, 95, 96, 97, 98, 99, 100 | APG07609.0 (66.46% identity, 70.19% similarity)<br>APG08693.0 (54.63% identity, 73.15% similarity)<br>OUB07579.1 (54.63% identity, 73.15% similarity)<br>APG01808.0 (46.3% identity, 61.64% similarity)<br>APG00505.0 US_2016_0366881_A1-101 (42.51% identity, 58.68% similarity)<br>OUB07573.1 (42.51% identity, 58.68% similarity)<br>WP_098652068.1 (41.81% identity, 59.36% similarity)<br>APG00858.0 (41.69% identity, 58.91% similarity)<br>APG03543.0 (41.62% identity, 58.98% similarity)<br>US_8318900_B2-75 (41.52% identity, |

TABLE 1-continued

Summary of SEQ ID NOs, Gene Class, and Variants thereof

| APG ID | Seq ID | Modified Seq ID(s) | CryBP1 Seq ID | Split-Cry C-terminus Seq ID | Gene Class | % Identity | % Similarity | Homologs |
|---|---|---|---|---|---|---|---|---|
| | | | | | | | | 59.06% similarity)<br>WP_098179785.1 (41.52% identity, 59.06% similarity) |
| APG06319.0 | 306 | 307 | | | MTX | 92, 93, 94, 95, 96, 97, 98, 99, 100 | 96, 97, 98, 99, 100 | APG00483.0 US_2016_0355842_A1-104 (91.53% identity, 95.08% similarity)<br>APG00421.0 US_2016_0355842_A1-86 (86.89% identity, 94.54% similarity)<br>APG06851.0 (86.61% identity, 95.08% similarity)<br>APG06049.0 (84.2% identity, 91.01% similarity)<br>WP_063226258.1 (74.93% identity, 84.47% similarity)<br>APG00995.0 US_2016_0355842_A1-200 (69.35% identity, 81.18% similarity)<br>APG00593.0 US_2016_0355842_A1-136 (68.55% identity, 80.91% similarity)<br>WP_097899326.1 (68.55% identity, 80.91% similarity)<br>APG00414.0 US_2016_0355842_A1-81 (68.46% identity, 80.86% similarity)<br>APG04455.0 (65.42% identity, 76.94% similarity) |
| APG06331.0 | 308 | 309 | | | Bin | 94, 95, 96, 97, 98, 99, 100 | 97, 98, 99, 100 | APG07911.0 (93.03% identity, 96.02% similarity)<br>APG04176.0 (91.04% identity, 93.53% similarity)<br>APG04568.0 (90.8% identity, 94.28% similarity)<br>APG05715.0 (90.55% identity, 93.03% similarity)<br>CA_2844913-146 (89.43% identity, 93.12% similarity)<br>APG02445.0 (89.05% identity, 92.54% similarity)<br>WP_098807694.1 (89.05% identity, 92.54% similarity)<br>APG08004.0 (89.05% identity, 92.29% similarity)<br>WP_070144216.1 (85.82% identity, 91.04% similarity)<br>APG09027.0 (85.32% identity, 91.79% similarity) |
| APG06350.0 | 310 | 311 | | | MTX | 5, 10, 15, 20, 25, 30, 35, 40, 45, 50, 55, 60, 65, 70, 75, 80, | 5, 10, 15, 20, 25, 30, 35, 40, 45, 50, 55, 60, 65, 70, 75, 80, 85, | CEL21287.1 (61.85% identity, 74.11% similarity)<br>WP_042194387.1 (59.67% identity, 70.84% |

TABLE 1-continued

Summary of SEQ ID NOs, Gene Class, and Variants thereof

| APG ID | Seq ID | Modified Seq ID(s) | CryBP1 Seq ID | Split-Cry C-terminus Seq ID | Gene Class | % Identity | % Similarity | Homologs |
|---|---|---|---|---|---|---|---|---|
| | | | | | | 85, 90, 91, 92, 93, 94, 95, 96, 97, 98, 99, 100 | 90, 91, 92, 93, 94, 95, 96, 97, 98, 99, 100 | similarity)<br>WP_083472203.1 (57.82% identity, 68.17% similarity)<br>ALG11962.1 (57.8% identity, 68.01% similarity)<br>WP_083752681.1 (57.03% identity, 68.17% similarity)<br>ONI90142.1 (56.6% identity, 67.39% similarity)<br>WP_042191061.1 (55.91% identity, 67.72% similarity)<br>AHH99199.1 (52.72% identity, 65.76% similarity)<br>WP_037915008.1 (47.17% identity, 62.26% similarity)<br>WP_081789577.1 (44.03% identity, 54.65% similarity) |
| APG06378.0 | 312 | | | | Vip | 70, 75, 80, 85, 90, 91, 92, 93, 94, 95, 96, 97, 98, 99, 100 | 80, 85, 90, 91, 92, 93, 94, 95, 96, 97, 98, 99, 100 | US_2016_0339078_A1-28394 (68.57% identity, 77.14% similarity)<br>US_2016_0339078_A1-28394 (68.57% identity, 77.14% similarity)<br>US_2016_0339078_A1-28394 (68.57% identity, 77.14% similarity)<br>EOO61631.1 (62.08% identity, 68.05% similarity)<br>EOO61631.1 (62.08% identity, 68.05% similarity)<br>EOO61631.1 (62.08% identity, 68.05% similarity)<br>EOO61631.1 (62.08% identity, 68.05% similarity)<br>EJR89704.1 (40.84% identity, 48.67% similarity)<br>EJR89704.1 (40.84% identity, 48.67% similarity)<br>EJR89704.1 (40.84% identity, 48.67% similarity)<br>EJR89704.1 (40.84% identity, 48.67% similarity)<br>EJR89704.1 (40.84% identity, 48.67% similarity)<br>EJR89704.1 (40.84% identity, 48.67% similarity)<br>EJR89704.1 (40.84% identity, 48.67% similarity) |

TABLE 1-continued

Summary of SEQ ID NOs, Gene Class, and Variants thereof

| APG ID | Seq ID | Modified Seq ID(s) | CryBP1 Seq ID | Split-Cry C-terminus Seq ID | Gene Class | % Identity | % Similarity | Homologs |
|---|---|---|---|---|---|---|---|---|
| APG06424.0 | 313 | | | | Cry | 60, 65, 70, 75, 80, 85, 90, 91, 92, 93, 94, 95, 96, 97, 98, 99, 100 | 65, 70, 75, 80, 85, 90, 91, 92, 93, 94, 95, 96, 97, 98, 99, 100 | APG08171.0 (92.19% identity, 96.21% similarity) APG09835.0 (91.76% identity, 94.88% similarity) APG08468.0 (91.31% identity, 95.1% similarity) APG08852.0 (90.42% identity, 94.43% similarity) OPA11477.1 (90.42% identity, 94.43% similarity) APG00184.0 US_2016_0355842_A1-19 (59.82% identity, 64.51% similarity) WP_044306772.1 (59.82% identity, 64.51% similarity) WP_098816555.1 (59.6% identity, 64.29% similarity) WP_097891175.1 (59.38% identity, 64.29% similarity) WP_098217793.1 (59.38% identity, 64.29% similarity) |
| APG06479.0 | 314 | 315 | | | MTX | 98, 99, 100 | 99, 100 | APG09726.0 (97.2% identity, 98.6% similarity) APG02659.0 (50.13% identity, 59.79% similarity) APG02511.0 (47.37% identity, 61.32% similarity) JP_2016_516397-59 (46.67% identity, 56.0% similarity) ANS51604.1 (46.13% identity, 55.47% similarity) PGY60284.1 (45.94% identity, 46.22% similarity) WP_078401252.1 (45.73% identity, 61.71% similarity) WP_098213667.1 (45.16% identity, 58.06% similarity) WP_098487632.1 (45.16% identity, 58.06% similarity) JP_2016_516397-60 (45.07% identity, 54.4% similarity) |
| APG06480.0 | 316 | 317 | | | MTX | 85, 90, 91, 92, 93, 94, 95, 96, 97, 98, 99, 100 | 85, 90, 91, 92, 93, 94, 95, 96, 97, 98, 99, 100 | APG00718.0 US_2017_0175134_A1-132 (82.72% identity, 83.57% similarity) APG00860.0 US_2016_0355842_A1-180 (46.67% identity, 62.78% similarity) US_8318900_B2-77 (36.74% identity, 53.59% similarity) APG04021.0 (36.46% identity, 51.74% |

TABLE 1-continued

Summary of SEQ ID NOs, Gene Class, and Variants thereof

| APG ID | Seq ID | Modified Seq ID(s) | CryBP1 Seq ID | Split-Cry C-terminus Seq ID | Gene Class | % Identity | % Similarity | Homologs |
|---|---|---|---|---|---|---|---|---|
| | | | | | | | | similarity)<br>APG04586.0 (36.39% identity, 52.5% similarity)<br>APG04750.0 (35.81% identity, 53.58% similarity)<br>APG00586.0 US_2016_0355842_A1-135 (35.71% identity, 52.91% similarity)<br>APG09100.0 (35.71% identity, 51.06% similarity)<br>APG03324.0 (35.54% identity, 53.85% similarity)<br>APG08768.0 (35.22% identity, 52.42% similarity) |
| APG06493.0 | 318 | 319 | | | Cry | 95, 96, 97, 98, 99, 100 | 97, 98, 99, 100 | APG00142.0 US_2016_0304898_A1-162 (94.83% identity, 96.33% similarity) |
| APG06496.0 | 320 | | | | Cyt | 45, 50, 55, 60, 65, 70, 75, 80, 85, 90, 91, 92, 93, 94, 95, 96, 97, 98, 99, 100 | 65, 70, 75, 80, 85, 90, 91, 92, 93, 94, 95, 96, 97, 98, 99, 100 | US_9567381_B2-1427 (40.39% identity, 60.78% similarity)<br>US_9567381_B2-1429 (40.39% identity, 60.78% similarity)<br>WO_2017_199078-15 (40.39% identity, 60.78% similarity)<br>APG09181.0 (40.08% identity, 63.97% similarity)<br>ABV22504.1 (40.0% identity, 60.39% similarity)<br>AFA52539.1 (40.0% identity, 60.39% similarity)<br>AGT15589.1 (40.0% identity, 60.39% similarity)<br>US_9567381_B2-522 (40.0% identity, 60.39% similarity)<br>WO_2017_199078-16 (40.0% identity, 60.39% similarity)<br>WO_2017_199078-18 (40.0% identity, 60.39% similarity)<br>WO_2017_199078-4 (40.0% identity, 60.39% similarity)<br>WO_2017_199078-6 (40.0% identity, 60.39% similarity)<br>WP_043938803.1 (40.0% identity, 60.39% similarity) |
| APG06559.0 | 321 | | | | Bin | 90, 91, 92, 93, 94, 95, 96, 97, 98, 99, 100 | 94, 95, 96, 97, 98, 99, 100 | APG00315.0 US_2016_0311864_A1-137 (88.45% identity, 91.89% similarity)<br>APG07868.0 (87.22% identity, 92.14% similarity)<br>APG08195.0 (86.98% identity, 93.12% |

TABLE 1-continued

Summary of SEQ ID NOs, Gene Class, and Variants thereof

| APG ID | Seq ID | Modified Seq ID(s) | CryBP1 Seq ID | Split-Cry C-terminus Seq ID | Gene Class | % Identity | % Similarity | Homologs |
|---|---|---|---|---|---|---|---|---|
| | | | | | | | | similarity) APG04627.0 (86.49% identity, 92.87% similarity) APG00178.0 US_2016_0311864_A1-54 (85.96% identity, 91.87% similarity) APG06237.0 (85.5% identity, 92.63% similarity) APG00727.0 US_2016_0311864_A1-210 (84.03% identity, 90.42% similarity) APG05917.0 (76.04% identity, 85.57% similarity) APG09153.0 (74.02% identity, 84.56% similarity) WP_098771878.1 (34.98% identity, 40.64% similarity) |
| APG06576.0 | 322 | 323 | | | Cry | 75, 80, 85, 90, 91, 92, 93, 94, 95, 96, 97, 98, 99, 100 | 80, 85, 90, 91, 92, 93, 94, 95, 96, 97, 98, 99, 100 | APG00089.0 US_2016_0304898_A1-118 (70.02% identity, 79.34% similarity) WP_098905641.1 (70.02% identity, 79.34% similarity) US_9695440_B2-8 (53.26% identity, 63.58% similarity) US_9695440_B2-9 (53.16% identity, 63.29% similarity) US_9695440_B2-6 (53.14% identity, 63.69% similarity) US_9567381_B2-327 (51.75% identity, 64.11% similarity) JP_2002_335967-2 (50.59% identity, 62.69% similarity) US_8461421_B2-99 (50.11% identity, 61.85% similarity) US_8759619_B2-25 (49.62% identity, 60.53% similarity) WP_098722307.1 (49.62% identity, 60.53% similarity) WP_098733730.1 (49.62% identity, 60.53% similarity) |
| APG06578.0 | 324 | | | | MTX | 40, 45, 50, 55, 60, 65, 70, 75, 80, 85, 90, 91, 92, 93, 94, 95, 96, 97, 98, 99, 100 | 55, 60, 65, 70, 75, 80, 85, 90, 91, 92, 93, 94, 95, 96, 97, 98, 99, 100 | APG02166.0 (44.26% identity, 60.98% similarity) APG09957.0 (39.63% identity, 53.25% similarity) APG02633.0 (34.83% identity, 52.07% similarity) APG06768.0 (31.58% identity, 46.75% similarity) APG00236.0 US_2016_0355842_A1-32 |

TABLE 1-continued

| Summary of SEQ ID NOs, Gene Class, and Variants thereof | | | | | | | | |
|---|---|---|---|---|---|---|---|---|
| APG ID | Seq ID | Modified Seq ID(s) | CryBP1 Seq ID | Split-Cry C-terminus Seq ID | Gene Class | % Identity | % Similarity | Homologs |
| | | | | | | | | (31.21% identity, 49.04% similarity)<br>APG02714.0 (29.69% identity, 44.06% similarity)<br>APG05793.0 (25.96% identity, 37.82% similarity) |
| APG06606.0 | 325 | 326, 327 | | | Cry | 85, 90, 91, 92, 93, 94, 95, 96, 97, 98, 99, 100 | 90, 91, 92, 93, 94, 95, 96, 97, 98, 99, 100 | APG06213.0 (96.84% identity, 98.59% similarity)<br>APG02110.0 (95.08% identity, 97.19% similarity)<br>APG07811.0 (95.08% identity, 96.84% similarity)<br>APG04108.0 (81.36% identity, 86.59% similarity)<br>APG00235.0 US_2016_0311864_A1-89 (80.9% identity, 87.85% similarity)<br>WP_050845493.1 (63.44% identity, 75.51% similarity)<br>APG08681.0 (54.39% identity, 65.36% similarity)<br>WP_048536324.1 (54.39% identity, 65.36% similarity)<br>APG00702.0 US_2017_0175134_A1-115 (37.52% identity, 50.56% similarity)<br>APG00702.0 US_2017_0175134_A1-115 (37.52% identity, 50.56% similarity) |
| APG06677.0 | 328 | 329 | | | Cry | 75, 80, 85, 90, 91, 92, 93, 94, 95, 96, 97, 98, 99, 100 | 80, 85, 90, 91, 92, 93, 94, 95, 96, 97, 98, 99, 100 | WP_061663292.1 (89.04% identity, 89.61% similarity)<br>CA_2516349-42 (72.6% identity, 76.09% similarity)<br>CA_2682227-77 (72.6% identity, 76.09% similarity)<br>CA_2682227-78 (72.6% identity, 76.09% similarity)<br>US_5424410_A-29 (72.51% identity, 76.09% similarity)<br>EP_2728007-44 (63.31% identity, 70.25% similarity)<br>US_9567381_B2-472 (61.92% identity, 69.37% similarity)<br>US_9447153_B1-404 (61.87% identity, 71.21% similarity)<br>US_9447153_B1-377 (61.18% identity, 70.43% similarity)<br>US_9447153_B1-375 (61.13% identity, 70.36% similarity) |

TABLE 1-continued

Summary of SEQ ID NOs, Gene Class, and Variants thereof

| APG ID | Seq ID | Modified Seq ID(s) | CryBP1 Seq ID | Split-Cry C-terminus Seq ID | Gene Class | % Identity | % Similarity | Homologs |
|---|---|---|---|---|---|---|---|---|
| APG06697.0 | 330 | 331, 332 | | | Bin | 80, 85, 90, 91, 92, 93, 94, 95, 96, 97, 98, 99, 100 | 90, 91, 92, 93, 94, 95, 96, 97, 98, 99, 100 | WP_098063843.1 (90.3% identity, 90.3% similarity)<br>WP_000839920.1 (90.07% identity, 90.07% similarity)<br>WP_097861094.1 (89.84% identity, 90.07% similarity)<br>APG00336.0 US_2016_0366881_A1-19 (78.64% identity, 85.23% similarity)<br>APG00262.0 US_2016_0311864_A1-101 (76.8% identity, 83.33% similarity)<br>APG00223.0 US_2016_0311864_A1-82 (75.86% identity, 85.06% similarity)<br>APG00242.0 US_2016_0311864_A1-93 (75.63% identity, 84.83% similarity)<br>APG00454.0 US_2016_0311864_A1-179 (75.17% identity, 84.83% similarity)<br>APG00335.0 US_2016_0366881_A1-18 (74.71% identity, 84.37% similarity)<br>APG00118.0 US_2016_0311864_A1-28 (74.31% identity, 84.17% similarity) |
| APG06705.0 | 333 | 334, 335 | | | Cry | 90, 91, 92, 93, 94, 95, 96, 97, 98, 99, 100 | 91, 92, 93, 94, 95, 96, 97, 98, 99, 100 | APG05711.0 (86.6% identity, 90.41% similarity)<br>APG00182.0 US_2016_0355842_A1-17 (67.84% identity, 76.86% similarity)<br>CUB55361.1 (35.14% identity, 51.21% similarity)<br>WP_078401802.1 (34.54% identity, 48.38% similarity)<br>APG08067.0 (27.42% identity, 41.79% similarity)<br>APG05519.0 (26.71% identity, 41.28% similarity)<br>APG00097.0 US_2016_0177333_A1-53 (25.91% identity, 39.25% similarity)<br>APG00048.0 US_2016_0177333_A1-22 (25.64% identity, 38.25% similarity)<br>APG00950.0 US_2016_0355842_A1-192 (25.57% identity, 41.06% similarity)<br>APG00101.0 US_2016_0177333_A1-57 (25.47% identity, 41.16% similarity) |
| APG06718.0 | 336 | | | | Cyt | 30, 35, 40, 45, 50, 55, 60, 65, 70, 75, 80, 85, 90, 91, 92, 93, 94, 95, 96, 97, 98, 99, 100 | 50, 55, 60, 65, 70, 75, 80, 85, 90, 91, 92, 93, 94, 95, 96, 97, 98, 99, 100 | APG06496.0 (33.84% identity, 50.57% similarity)<br>APG09181.0 (28.85% identity, 49.62% similarity)<br>US_9567381_B2-1430 (26.97% identity, 48.69% similarity) |

TABLE 1-continued

| Summary of SEQ ID NOs, Gene Class, and Variants thereof | | | | | | | | |
|---|---|---|---|---|---|---|---|---|
| APG ID | Seq ID | Modified Seq ID(s) | CryBP1 Seq ID | Split-Cry C-terminus Seq ID | Gene Class | % Identity | % Similarity | Homologs |
| APG06738.0 | 337 | 338 | | | MTX | 55, 60, 65, 70, 75, 80, 85, 90, 91, 92, 93, 94, 95, 96, 97, 98, 99, 100 | 65, 70, 75, 80, 85, 90, 91, 92, 93, 94, 95, 96, 97, 98, 99, 100 | WP_088071735.1 (26.97% identity, 48.69% similarity)<br>JP_2003_284568-4 (51.82% identity, 64.24% similarity)<br>US_8461421_B2-103 (50.3% identity, 63.69% similarity)<br>ANN35811.1 (49.09% identity, 62.12% similarity)<br>2D42_A (45.45% identity, 56.06% similarity)<br>US_2015_0047076_A1-6 (31.52% identity, 49.09% similarity)<br>US_2015_0047076_A1-8 (30.9% identity, 46.94% similarity)<br>US_2015_0047076_A1-10 (30.21% identity, 45.16% similarity)<br>US_2015_0047076_A1-2 (30.0% identity, 45.76% similarity)<br>US_2015_0047076_A1-4 (29.85% identity, 45.97% similarity)<br>US_9567381_B2-384 (29.82% identity, 46.08% similarity) |
| APG06774.0 | 339 | | | | Cry | 40, 45, 50, 55, 60, 65, 70, 75, 80, 85, 90, 91, 92, 93, 94, 95, 96, 97, 98, 99, 100 | 55, 60, 65, 70, 75, 80, 85, 90, 91, 92, 93, 94, 95, 96, 97, 98, 99, 100 | APG05725.0 (37.79% identity, 49.01% similarity)<br>WP_017762581.1 (35.62% identity, 50.64% similarity)<br>APG05278.0 (35.58% identity, 53.96% similarity)<br>APG05402.0 (35.5% identity, 53.17% similarity)<br>APG03741.0 (35.26% identity, 50.32% similarity)<br>APG04175.0 (35.23% identity, 50.0% similarity)<br>WP_044306759.1 (35.2% identity, 51.97% similarity)<br>WP_098394433.1 (35.2% identity, 51.97% similarity)<br>US_8461415_B2-45 (35.2% identity, 51.81% similarity)<br>WP_097891157.1 (35.03% identity, 51.81% similarity) |
| APG06791.0 | 340 | 341 | | | MTX | 60, 65, 70, 75, 80, 85, 90, 91, 92, 93, 94, 95, 96, 97, 98, 99, 100 | 75, 80, 85, 90, 91, 92, 93, 94, 95, 96, 97, 98, 99, 100 | APG00594.0 US_2016_0355842_A1-137 (55.49% identity, 70.33% similarity)<br>WP_097795410.1 (55.49% identity, 70.33% similarity)<br>APG00154.0 US_2016_0355842_A1-5 |

TABLE 1-continued

| Summary of SEQ ID NOs, Gene Class, and Variants thereof | | | | | | | | |
|---|---|---|---|---|---|---|---|---|
| APG ID | Seq ID | Modified Seq ID(s) | CryBP1 Seq ID | Split-Cry C-terminus Seq ID | Gene Class | % Identity | % Similarity | Homologs |
| | | | | | | | | (55.22% identity, 70.33% similarity)<br>WP_090920591.1 (54.67% identity, 70.33% similarity)<br>APG06049.0 (54.45% identity, 67.28% similarity)<br>APG00483.0 US_2016_0355842_A1-104 (53.97% identity, 67.46% similarity)<br>APG06319.0 (53.79% identity, 67.1% similarity)<br>APG00486.0 US_2016_0355842_A1-107 (53.3% identity, 69.23% similarity)<br>APG00560.0 US_2016_0355842_A1-125 (52.79% identity, 66.84% similarity)<br>WP_098991345.1 (52.79% identity, 66.84% similarity) |
| APG06883.0 | 342 | 343 | | | Cry | 65, 70, 75, 80, 85, 90, 91, 92, 93, 94, 95, 96, 97, 98, 99, 100 | 70, 75, 80, 85, 90, 91, 92, 93, 94, 95, 96, 97, 98, 99, 100 | APG00471.0 US_2016_0366881_A1-85 (63.28% identity, 69.55% similarity)<br>APG00232.0 US_2016_0311864_A1-87 (51.22% identity, 61.84% similarity)<br>WP_098806888.1 (51.22% identity, 61.84% similarity)<br>APG02533.0 (49.02% identity, 60.15% similarity)<br>APG00787.0 US_2017_0175134_A1-156 (48.79% identity, 63.77% similarity)<br>APG09282.0 (45.2% identity, 60.37% similarity)<br>KXH80331.1 (44.54% identity, 57.85% similarity)<br>WP_098395829.1 (44.46% identity, 60.15% similarity)<br>APG07719.0 (44.26% identity, 58.97% similarity)<br>APG07057.0 (44.09% identity, 52.38% similarity) |
| APG06898.0 | 344 | 345 | | | Bin | 80, 85, 90, 91, 92, 93, 94, 95, 96, 97, 98, 99, 100 | 90, 91, 92, 93, 94, 95, 96, 97, 98, 99, 100 | WP_017154552.1 (78.74% identity, 86.61% similarity)<br>APG00596.0 US_2016_0311864_A1-196 (75.85% identity, 85.3% similarity)<br>APG06027.0 (73.49% identity, 83.73% similarity)<br>APG00741.0 US_2016_0311864_A1-213 (70.42% identity, 81.41% similarity)<br>APG00649.0 US_2017_0175134_A1-75 (70.05% identity, 80.73% similarity)<br>APG06920.0 (69.55% identity, 81.1% |

TABLE 1-continued

| Summary of SEQ ID NOs, Gene Class, and Variants thereof | | | | | | | | |
|---|---|---|---|---|---|---|---|---|
| APG ID | Seq ID | Modified Seq ID(s) | CryBP1 Seq ID | Split-Cry C-terminus Seq ID | Gene Class | % Identity | % Similarity | Homologs |
| | | | | | | | | similarity)<br>KEZ80012.1 (69.55% identity, 79.79% similarity)<br>APG07511.0 (69.03% identity, 79.53% similarity)<br>APG03279.0 (68.77% identity, 80.05% similarity)<br>APG05717.0 (68.77% identity, 79.79% similarity) |
| APG06937.0 | 346 | 347 | | | Cyt | 85, 90, 91, 92, 93, 94, 95, 96, 97, 98, 99, 100 | 90, 91, 92, 93, 94, 95, 96, 97, 98, 99, 100 | APG00128.0 US_2016_0304898_A1-157 (83.74% identity, 86.99% similarity)<br>WP_098207006.1 (83.74% identity, 86.99% similarity)<br>WP_016110459.1 (83.33% identity, 86.99% similarity)<br>APG02923.0 (82.93% identity, 86.59% similarity)<br>APG06385.0 (81.53% identity, 84.74% similarity)<br>WP_098682674.1 (66.4% identity, 79.76% similarity)<br>APG00126.0 US_2016_0304898_A1-153 (65.99% identity, 79.35% similarity)<br>WP_098207007.1 (65.99% identity, 79.35% similarity)<br>APG00437.0 US_2016_0366881_A1-62 (63.04% identity, 75.49% similarity)<br>WP_016110460.1 (60.96% identity, 76.1% similarity) |
| APG06954.0 | 348 | 349 | | | MTX | 5, 10, 15, 20, 25, 30, 35, 40, 45, 50, 55, 60, 65, 70, 75, 80, 85, 90, 91, 92, 93, 94, 95, 96, 97, 98, 99, 100 | 5, 10, 15, 20, 25, 30, 35, 40, 45, 50, 55, 60, 65, 70, 75, 80, 85, 90, 91, 92, 93, 94, 95, 96, 97, 98, 99, 100 | |
| APG07054.0 | 350 | | | | Vip3 | 55, 60, 65, 70, 75, 80, 85, 90, 91, 92, 93, 94, 95, 96, 97, 98, 99, 100 | 75, 80, 85, 90, 91, 92, 93, 94, 95, 96, 97, 98, 99, 100 | APG00675.0 US_2017_0175134_A1-97 (53.04% identity, 70.09% similarity)<br>APG00131.0 US_2016_0311864_A1-30 (52.53% identity, 69.11% similarity)<br>WP_098631820.1 (52.53% identity, 69.11% similarity)<br>APG06235.0 (51.4% identity, 67.83% similarity)<br>APG00038.0 US_2016_0355842_A1-1 (50.87% identity, 68.36% similarity)<br>APG00181.0 US_2016_0355842_A1-16 |

TABLE 1-continued

Summary of SEQ ID NOs, Gene Class, and Variants thereof

| APG ID | Seq ID | Modified Seq ID(s) | CryBP1 Seq ID | Split-Cry C-terminus Seq ID | Gene Class | % Identity | % Similarity | Homologs |
|---|---|---|---|---|---|---|---|---|
| | | | | | | | | (50.87% identity, 67.94% similarity)<br>APG09221.0 (50.61% identity, 67.54% similarity)<br>APG00207.0 US_2016_0311864_A1-70 (46.94% identity, 63.61% similarity)<br>WP_098685831.1 (46.94% identity, 63.61% similarity)<br>AAY27873.1 (38.77% identity, 56.17% similarity) |
| APG07057.0 | 351 | | | | Cry | 55, 60, 65, 70, 75, 80, 85, 90, 91, 92, 93, 94, 95, 96, 97, 98, 99, 100 | 65, 70, 75, 80, 85, 90, 91, 92, 93, 94, 95, 96, 97, 98, 99, 100 | APG00471.0 US_2016_0366881_A1-85 (54.65% identity, 62.68% similarity)<br>APG06883.0 (44.09% identity, 52.38% similarity)<br>APG00232.0 US_2016_0311864_A1-87 (43.02% identity, 51.8% similarity)<br>WP_098806888.1 (43.02% identity, 51.8% similarity)<br>APG05538.0 (41.96% identity, 53.79% similarity)<br>APG09282.0 (39.22% identity, 50.85% similarity)<br>APG02533.0 (36.91% identity, 49.17% similarity)<br>WP_061139797.1 (34.26% identity, 47.15% similarity)<br>APG07719.0 (32.8% identity, 44.69% similarity)<br>APG00457.0 US_2016_0355842_A1-98 (31.98% identity, 44.62% similarity)<br>WP_098376005.1 (31.98% identity, 44.62% similarity) |
| APG07094.0 | 352 | 353 | | | MTX | 96, 97, 98, 99, 100 | 98, 99, 100 | APG00352.0 US_2016_0366881_A1-29 (95.26% identity, 97.89% similarity)<br>WP_098111055.1 (82.63% identity, 89.47% similarity)<br>CA_2844913-120 (81.58% identity, 89.74% similarity)<br>APG05346.0 (81.58% identity, 89.47% similarity)<br>APG00202.0 US_2016_0304898_A1-195 (79.8% identity, 86.11% similarity)<br>APG00208.0 US_2016_0304898_A1-201 (79.04% identity, 86.36% similarity)<br>APG02475.0 (76.96% identity, 86.84% similarity)<br>APG01443.0 (75.77% identity, 86.86% |

TABLE 1-continued

Summary of SEQ ID NOs, Gene Class, and Variants thereof

| APG ID | Seq ID | Modified Seq ID(s) | CryBP1 Seq ID | Split-Cry C-terminus Seq ID | Gene Class | % Identity | % Similarity | Homologs |
|---|---|---|---|---|---|---|---|---|
| | | | | | | | | similarity)<br>APG04431.0 (74.68% identity, 85.06% similarity)<br>WP_000715637.1 (74.02% identity, 83.2% similarity) |
| APG07107.0 | 354 | 355 | | | MTX | 75, 80, 85, 90, 91, 92, 93, 94, 95, 96, 97, 98, 99, 100 | 85, 90, 91, 92, 93, 94, 95, 96, 97, 98, 99, 100 | WP_065212006.1 (91.1% identity, 95.55% similarity)<br>APG00633.0 US_2016_0355842_A1-148 (73.67% identity, 84.02% similarity)<br>WP_098866818.1 (73.67% identity, 84.02% similarity)<br>APG00552.0 US_2016_0366881_A1-110 (58.28% identity, 71.6% similarity)<br>WP_061885189.1 (53.25% identity, 68.05% similarity)<br>WP_088118891.1 (53.25% identity, 68.05% similarity)<br>APG08369.0 (51.6% identity, 68.22% similarity)<br>WP_016078640.1 (50.89% identity, 71.01% similarity)<br>APG00541.0 US_2016_0355842_A1-119 (49.7% identity, 66.86% similarity)<br>WP_097855808.1 (49.7% identity, 66.86% similarity)<br>WP_098581475.1 (49.7% identity, 66.86% similarity) |
| APG07137.0 | 356 | 357, 358 | | | MTX | 75, 80, 85, 90, 91, 92, 93, 94, 95, 96, 97, 98, 99, 100 | 85, 90, 91, 92, 93, 94, 95, 96, 97, 98, 99, 100 | WP_100797528.1 (79.62% identity, 87.58% similarity)<br>WP_036122586.1 (70.57% identity, 79.43% similarity)<br>KUF37510.1 (70.57% identity, 79.11% similarity)<br>WP_010859436.1 (70.45% identity, 77.31% similarity)<br>APG00010.0 US_2016_0177333_A1-8 (70.43% identity, 80.18% similarity)<br>WP_082673669.1 (70.43% identity, 80.18% similarity)<br>APG00489.0 US_2016_0177333_A1-123 (70.25% identity, 80.67% similarity)<br>APG00350.0 US_2016_0366881_A1-27 (65.61% identity, 78.66% similarity)<br>US_8318900_B2-74 (64.97% identity, 77.71% similarity) |

TABLE 1-continued

Summary of SEQ ID NOs, Gene Class, and Variants thereof

| APG ID | Seq ID | Modified Seq ID(s) | CryBP1 Seq ID | Split-Cry C-terminus Seq ID | Gene Class | % Identity | % Similarity | Homologs |
|---|---|---|---|---|---|---|---|---|
| | | | | | | | | US_8318900_B2-25 (64.65% identity, 77.71% similarity) |
| APG07162.0 | 359 | | | | Cry | 98, 99, 100 | 99, 100 | APG00062.0 US_2016_0177333_A1-29 (97.28% identity, 98.34% similarity)<br>WP_074651312.1 (93.8% identity, 97.28% similarity)<br>APG02438.0 (68.32% identity, 79.27% similarity)<br>WP_098349012.1 (60.54% identity, 74.4% similarity)<br>WP_098515340.1 (60.39% identity, 74.4% similarity)<br>WP_098675605.1 (60.39% identity, 74.4% similarity)<br>WP_097920476.1 (60.24% identity, 74.4% similarity)<br>WP_098563827.1 (60.24% identity, 74.4% similarity)<br>WP_098236459.1 (60.09% identity, 74.25% similarity)<br>WP_064532221.1 (59.94% identity, 73.95% similarity) |
| APG07176.0 | 360 | | | | MTX | 35, 40, 45, 50, 55, 60, 65, 70, 75, 80, 85, 90, 91, 92, 93, 94, 95, 96, 97, 98, 99, 100 | 55, 60, 65, 70, 75, 80, 85, 90, 91, 92, 93, 94, 95, 96, 97, 98, 99, 100 | APG08495.0 (39.66% identity, 61.36% similarity)<br>APG07983.0 (33.9% identity, 52.4% similarity)<br>APG02088.0 (31.43% identity, 51.43% similarity)<br>APG09675.0 (31.25% identity, 50.94% similarity)<br>APG07732.0 (29.56% identity, 46.23% similarity)<br>APG02633.0 (28.04% identity, 50.68% similarity) |
| APG07249.0 | 361 | 362, 363 | | | MTX | 45, 50, 55, 60, 65, 70, 75, 80, 85, 90, 91, 92, 93, 94, 95, 96, 97, 98, 99, 100 | 60, 65, 70, 75, 80, 85, 90, 91, 92, 93, 94, 95, 96, 97, 98, 99, 100 | APG01163.0 (60.92% identity, 73.85% similarity)<br>APG00580.0 US_2016_0355842_A1-132 (43.63% identity, 59.77% similarity)<br>WP_098146720.1 (43.63% identity, 59.77% similarity)<br>US_8461415_B2-38 (42.41% identity, 54.71% similarity)<br>APG00560.0 US_2016_0355842_A1-125 (41.45% identity, 56.48% similarity)<br>WP_098991345.1 (41.45% identity, 56.48% similarity)<br>APG00269.0 US_2016_0355842_A1-46 |

TABLE 1-continued

Summary of SEQ ID NOs, Gene Class, and Variants thereof

| APG ID | Seq ID | Modified Seq ID(s) | CryBP1 Seq ID | Split-Cry C-terminus Seq ID | Gene Class | % Identity | % Similarity | Homologs |
|---|---|---|---|---|---|---|---|---|
| | | | | | | | | (41.28% identity, 56.15% similarity)<br>WP_097904769.1 (41.28% identity, 56.15% similarity)<br>APG00414.0 US_2016_0355842_A1-81 (41.19% identity, 56.22% similarity)<br>APG00995.0 US_2016_0355842_A1-200 (41.19% identity, 56.22% similarity) |
| APG07257.0 | 364 | | 365 | | Bin | 40, 45, 50, 55, 60, 65, 70, 75, 80, 85, 90, 91, 92, 93, 94, 95, 96, 97, 98, 99, 100 | 55, 60, 65, 70, 75, 80, 85, 90, 91, 92, 93, 94, 95, 96, 97, 98, 99, 100 | WP_082180198.1 (44.47% identity, 49.69% similarity)<br>EJQ98132.1 (41.01% identity, 42.71% similarity)<br>APG00315.0 US_2016_0311864_A1-137 (35.85% identity, 51.15% similarity)<br>APG09153.0 (34.44% identity, 49.59% similarity)<br>APG04627.0 (34.3% identity, 49.17% similarity)<br>APG05917.0 (34.23% identity, 48.76% similarity)<br>APG00178.0 US_2016_0311864_A1-54 (34.17% identity, 50.0% similarity)<br>APG06237.0 (33.95% identity, 49.48% similarity)<br>APG08195.0 (33.88% identity, 49.79% similarity)<br>APG00727.0 US_2016_0311864_A1-210 (32.66% identity, 47.46% similarity) |
| APG07307.0 | 366 | 367 | | | Cry34 | 5, 10, 15, 20, 25, 30, 35, 40, 45, 50, 55, 60, 65, 70, 75, 80, 85, 90, 91, 92, 93, 94, 95, 96, 97, 98, 99, 100 | 5, 10, 15, 20, 25, 30, 35, 40, 45, 50, 55, 60, 65, 70, 75, 80, 85, 90, 91, 92, 93, 94, 95, 96, 97, 98, 99, 100 | WP_057916440.1 (73.89% identity, 73.89% similarity)<br>WP_057972564.1 (72.22% identity, 72.78% similarity)<br>WP_051884290.1 (55.0% identity, 62.22% similarity)<br>ALN65243.1 (31.67% identity, 32.78% similarity) |
| APG07310.0 | 368 | | | | Bin | 45, 50, 55, 60, 65, 70, 75, 80, 85, 90, 91, 92, 93, 94, 95, 96, 97, 98, 99, 100 | 60, 65, 70, 75, 80, 85, 90, 91, 92, 93, 94, 95, 96, 97, 98, 99, 100 | APG03778.0 (43.49% identity, 55.28% similarity)<br>US_6555655_B1-14 (43.32% identity, 57.58% similarity)<br>APG06401.0 (35.2% identity, 47.11% similarity)<br>US_6555655_B1-13 (35.12% identity, 46.68% similarity)<br>US_7692068_B2-2 (34.24% identity, 49.18% similarity)<br>WP_098826686.1 (34.14% identity, 47.14% |

TABLE 1-continued

Summary of SEQ ID NOs, Gene Class, and Variants thereof

| APG ID | Seq ID | Modified Seq ID(s) | CryBP1 Seq ID | Split-Cry C-terminus Seq ID | Gene Class | % Identity | % Similarity | Homologs |
|---|---|---|---|---|---|---|---|---|
| | | | | | | | | similarity)<br>APG00075.0 US_2016_0177333_A1-40 (33.97% identity, 46.9% similarity)<br>APG00063.0 US_2016_0304898_A1-95 (33.15% identity, 46.89% similarity)<br>APG00706.0 US_2017_0175134_A1-126 (32.44% identity, 48.21% similarity)<br>APG00750.0 US_2016_0366881_A1-132 (32.34% identity, 47.21% similarity) |
| APG07318.0 | 369 | 370 | | | Vip4 | 75, 80, 85, 90, 91, 92, 93, 94, 95, 96, 97, 98, 99, 100 | 85, 90, 91, 92, 93, 94, 95, 96, 97, 98, 99, 100 | APG04365.0 (74.78% identity, 82.68% similarity)<br>CA_2992084-2 (47.35% identity, 58.94% similarity)<br>APG09293.0 (44.82% identity, 57.77% similarity)<br>WP_087876282.1 (44.53% identity, 57.54% similarity)<br>WP_088113050.1 (44.38% identity, 57.21% similarity)<br>US_2016_0339078_A1-28464 (44.19% identity, 56.9% similarity)<br>US_2016_0339078_A1-29674 (43.82% identity, 58.14% similarity)<br>APG09984.0 (43.8% identity, 56.5% similarity)<br>WP_098779744.1 (43.8% identity, 56.5% similarity)<br>APG04069.0 (43.76% identity, 55.25% similarity) |
| APG07322.0 | 371 | 372, 373 | | 374 | Cry | 80, 85, 90, 91, 92, 93, 94, 95, 96, 97, 98, 99, 100 | 85, 90, 91, 92, 93, 94, 95, 96, 97, 98, 99, 100 | APG08378.0 (100.0% identity, 100.0% similarity)<br>CA_2516349-51 (76.93% identity, 84.67% similarity)<br>US_9567381_B2-373 (69.57% identity, 78.73% similarity)<br>US_8044266_B2-3 (67.7% identity, 77.43% similarity)<br>CA_2516349-14 (67.56% identity, 77.43% similarity)<br>CA_2516349-16 (67.28% identity, 77.01% similarity)<br>US_9567381_B2-374 (66.03% identity, 75.78% similarity)<br>APG00204.0 US_2016_0177333_A1-89 (65.14% identity, 75.04% similarity)<br>WP_098223478.1 (64.84% identity, 74.74% |

TABLE 1-continued

| Summary of SEQ ID NOs, Gene Class, and Variants thereof | | | | | | | | |
|---|---|---|---|---|---|---|---|---|
| APG ID | Seq ID | Modified Seq ID(s) | CryBP1 Seq ID | Split-Cry C-terminus Seq ID | Gene Class | % Identity | % Similarity | Homologs |
| | | | | | | | | similarity)<br>APG00695.0 US_2017_0175134_A1-109 (63.2% identity, 74.48% similarity) |
| APG07432.0 | 375 | 376 | | | Bin | 80, 85, 90, 91, 92, 93, 94, 95, 96, 97, 98, 99, 100 | 90, 91, 92, 93, 94, 95, 96, 97, 98, 99, 100 | APG08101.0 (79.52% identity, 86.08% similarity)<br>APG00075.0 US_2016_0177333_A1-40 (57.23% identity, 71.29% similarity)<br>WP_098826686.1 (56.64% identity, 70.7% similarity)<br>APG06401.0 (52.48% identity, 64.16% similarity)<br>US_7692068_B2-2 (42.17% identity, 55.32% similarity)<br>APG00750.0 US_2016_0366881_A1-132 (40.47% identity, 55.01% similarity)<br>APG00063.0 US_2016_0304898_A1-95 (37.92% identity, 53.09% similarity)<br>US_9567381_B2-394 (37.5% identity, 51.56% similarity)<br>APG00734.0 US_2016_0366881_A1-131 (36.8% identity, 49.63% similarity)<br>US_9567381_B2-398 (36.65% identity, 52.05% similarity) |
| APG07463.0 | 377 | | | | MTX | 35, 40, 45, 50, 55, 60, 65, 70, 75, 80, 85, 90, 91, 92, 93, 94, 95, 96, 97, 98, 99, 100 | 55, 60, 65, 70, 75, 80, 85, 90, 91, 92, 93, 94, 95, 96, 97, 98, 99, 100 | WP_073006288.1 (44.25% identity, 65.16% similarity)<br>APG08577.0 (36.49% identity, 54.04% similarity)<br>WP_073006284.1 (35.92% identity, 59.86% similarity)<br>SHH89794.1 (35.91% identity, 56.04% similarity)<br>WP_073008904.1 (33.99% identity, 51.82% similarity)<br>WP_084723762.1 (33.44% identity, 52.68% similarity)<br>APG04978.0 (32.62% identity, 52.48% similarity)<br>APG02115.0 (31.4% identity, 52.22% similarity) |
| APG07467.0 | 378 | 379 | | | MTX | 96, 97, 98, 99, 100 | 99, 100 | APG01949.0 (95.71% identity, 97.85% similarity)<br>APG05337.0 (95.09% identity, 98.47% similarity)<br>WP_050845726.1 (95.09% identity, 98.47% similarity)<br>WP_000823322.1 (94.79% identity, 98.16% |

TABLE 1-continued

Summary of SEQ ID NOs, Gene Class, and Variants thereof

| APG ID | Seq ID | Modified Seq ID(s) | CryBP1 Seq ID | Split-Cry C-terminus Seq ID | Gene Class | % Identity | % Similarity | Homologs |
|---|---|---|---|---|---|---|---|---|
| | | | | | | | | similarity)<br>WP_086397429.1 (94.17% identity, 98.16% similarity)<br>APG07936.0 (93.87% identity, 96.63% similarity)<br>APG02293.0 (93.56% identity, 98.47% similarity)<br>WP_098222113.1 (93.56% identity, 98.47% similarity)<br>WP_016084062.1 (92.64% identity, 97.24% similarity)<br>APG04806.0 (92.64% identity, 96.63% similarity)<br>APG04251.0 (92.33% identity, 96.93% similarity)<br>WP_016085044.1 (92.33% identity, 96.93% similarity)<br>WP_016084449.1 (92.33% identity, 96.63% similarity)<br>WP_016085279.1 (91.41% identity, 95.71% similarity)<br>WP_016084436.1 (90.8% identity, 95.4% similarity)<br>WP_016083901.1 (90.49% identity, 95.71% similarity) |
| APG07487.0 | 380 | | | | MTX | 90, 91, 92, 93, 94, 95, 96, 97, 98, 99, 100 | 91, 92, 93, 94, 95, 96, 97, 98, 99, 100 | APG00224.0 US_2016_0355842_A1-28 (86.65% identity, 90.91% similarity)<br>APG03760.0 (73.46% identity, 79.89% similarity)<br>WP_098584415.1 (73.46% identity, 79.89% similarity)<br>APG08240.0 (72.73% identity, 80.4% similarity)<br>APG05634.0 (61.19% identity, 73.09% similarity)<br>WP_098775686.1 (61.19% identity, 73.09% similarity)<br>APG00609.0 US_2017_0175134_A1-57 (60.62% identity, 71.39% similarity)<br>US_8829279_B2-37 (59.33% identity, 72.98% similarity)<br>US_8318900_B2-63 (59.17% identity, 72.5% similarity)<br>APG05506.0 (56.79% identity, 71.47% similarity) |

TABLE 1-continued

Summary of SEQ ID NOs, Gene Class, and Variants thereof

| APG ID | Seq ID | Modified Seq ID(s) | CryBP1 Seq ID | Split-Cry C-terminus Seq ID | Gene Class | % Identity | % Similarity | Homologs |
|---|---|---|---|---|---|---|---|---|
| APG07511.0 | 381 | 382 | | | Bin | 90, 91, 92, 93, 94, 95, 96, 97, 98, 99, 100 | 96, 97, 98, 99, 100 | APG05717.0 (89.87% identity, 95.47% similarity)<br>APG09069.0 (87.73% identity, 93.33% similarity)<br>APG00230.0 US_2016_0311864_A1-85 (86.24% identity, 92.33% similarity)<br>WP_098772949.1 (86.24% identity, 92.06% similarity)<br>APG00413.0 US_2016_0311864_A1-174 (82.71% identity, 91.22% similarity)<br>APG06920.0 (82.28% identity, 89.95% similarity)<br>US_9321814_B2-2 (81.96% identity, 89.39% similarity)<br>US_9321814_B2-3 (81.7% identity, 89.12% similarity)<br>WP_098876539.1 (81.43% identity, 88.86% similarity)<br>APG06027.0 (81.32% identity, 88.95% similarity) |
| APG07564.0 | 383 | 384 | | | Cry | 90, 91, 92, 93, 94, 95, 96, 97, 98, 99, 100 | 91, 92, 93, 94, 95, 96, 97, 98, 99, 100 | APG00083.0 US_2016_0304898_A1-111 (88.38% identity, 90.12% similarity)<br>APG00083.0 US_2016_0304898_A1-111 (88.38% identity, 90.12% similarity)<br>WP_098213625.1 (88.38% identity, 90.12% similarity)<br>WP_098213625.1 (88.38% identity, 90.12% similarity)<br>APG02071.0 (43.16% identity, 57.62% similarity)<br>APG02071.0 (43.16% identity, 57.62% similarity)<br>CA_2595901-13 (39.69% identity, 54.27% similarity)<br>CA_2595901-13 (39.69% identity, 54.27% similarity)<br>WP_103655243.1 (39.48% identity, 54.88% similarity)<br>US_2011_0239334_A1-80 (39.31% identity, 55.93% similarity) |
| APG07609.0 | 385 | 386 | | | MTX | 45, 50, 55, 60, 65, 70, 75, 80, 85, 90, 91, 92, 93, 94, 95, 96, 97, 98, 99, 100 | 55, 60, 65, 70, 75, 80, 85, 90, 91, 92, 93, 94, 95, 96, 97, 98, 99, 100 | APG06304.0 (66.46% identity, 70.19% similarity)<br>APG08693.0 (41.38% identity, 54.55% similarity)<br>OUB07579.1 (41.38% identity, 54.55% similarity)<br>APG01808.0 (34.82% identity, 45.13% |

TABLE 1-continued

| Summary of SEQ ID NOs, Gene Class, and Variants thereof | | | | | | | | |
|---|---|---|---|---|---|---|---|---|
| APG ID | Seq ID | Modified Seq ID(s) | CryBP1 Seq ID | Split-Cry C-terminus Seq ID | Gene Class | % Identity | % Similarity | Homologs |
| | | | | | | | | similarity)<br>OUB27300.1 (30.86% identity, 43.62% similarity)<br>APG00364.0 US_2016_0366881_A1-35 (30.56% identity, 43.62% similarity)<br>WP_098652068.1 (29.29% identity, 43.79% similarity)<br>US_8318900_B2-75 (28.99% identity, 43.49% similarity)<br>WP_098179785.1 (28.99% identity, 43.49% similarity)<br>APG04781.0 (28.0% identity, 42.29% similarity) |
| APG07636.0 | 387 | 388 | | | Cry | 65, 70, 75, 80, 85, 90, 91, 92, 93, 94, 95, 96, 97, 98, 99, 100 | 75, 80, 85, 90, 91, 92, 93, 94, 95, 96, 97, 98, 99, 100 | APG01288.0 (60.31% identity, 70.57% similarity)<br>WP_098214356.1 (60.31% identity, 70.57% similarity)<br>US_2011_0239334_A1-84 (58.53% identity, 65.54% similarity)<br>US_2011_0239334_A1-82 (58.14% identity, 65.14% similarity)<br>APG00801.0 US_2017_0175134_A1-160 (55.3% identity, 67.06% similarity)<br>APG00099.0 US_2016_0177333_A1-55 (54.73% identity, 66.31% similarity)<br>WP_098487817.1 (54.73% identity, 66.31% similarity)<br>APG00784.0 US_2017_0175134_A1-148 (54.35% identity, 65.82% similarity)<br>US_2012_0110706_A1-22 (52.74% identity, 59.52% similarity)<br>APG02221.0 (52.3% identity, 66.81% similarity) |
| APG07664.0 | 389 | 390 | | | Cry34 | 50, 55, 60, 65, 70, 75, 80, 85, 90, 91, 92, 93, 94, 95, 96, 97, 98, 99, 100 | 60, 65, 70, 75, 80, 85, 90, 91, 92, 93, 94, 95, 96, 97, 98, 99, 100 | WP_081083112.1 (49.19% identity, 66.94% similarity)<br>WP_081056378.1 (49.19% identity, 66.13% similarity)<br>WP_085040093.1 (46.77% identity, 59.68% similarity)<br>WP_034193354.1 (45.97% identity, 59.68% similarity)<br>WP_089445918.1 (45.97% identity, 57.26% similarity)<br>APG07643.0 (45.6% identity, 59.2% similarity)<br>WP_015876201.1 (45.16% identity, 61.29% |

TABLE 1-continued

| Summary of SEQ ID NOs, Gene Class, and Variants thereof | | | | | | | | |
|---|---|---|---|---|---|---|---|---|
| APG ID | Seq ID | Modified Seq ID(s) | CryBP1 Seq ID | Split-Cry C-terminus Seq ID | Gene Class | % Identity | % Similarity | Homologs |
| | | | | | | | | similarity)<br>WP_059574313.1 (45.16% identity, 58.06% similarity)<br>WP_060965848.1 (45.16% identity, 58.06% similarity)<br>WP_035977960.1 (41.48% identity, 57.04% similarity) |
| APG07665.0 | 391 | 392 | | | Cry | 80, 85, 90, 91, 92, 93, 94, 95, 96, 97, 98, 99, 100 | 85, 90, 91, 92, 93, 94, 95, 96, 97, 98, 99, 100 | US_7919272_B2-23 (77.86% identity, 84.33% similarity)<br>WP_103591151.1 (77.46% identity, 83.85% similarity)<br>US_7919272_B2-13 (75.89% identity, 81.78% similarity)<br>CA_2753918-13 (75.71% identity, 81.59% similarity)<br>WP_103591619.1 (75.5% identity, 81.3% similarity)<br>APG00786.0 US_2017_0175134_A1-153 (71.34% identity, 77.7% similarity)<br>APG04827.0 (69.45% identity, 76.77% similarity)<br>APG00662.0 US_2017_0175134_A1-84 (67.72% identity, 75.89% similarity)<br>APG00079.0 US_2016_0177333_A1-43 (67.2% identity, 76.04% similarity)<br>WP_016084057.1 (64.74% identity, 73.6% similarity)<br>WP_016084447.1 (64.74% identity, 73.6% similarity)<br>WP_016085042.1 (64.74% identity, 73.6% similarity) |
| APG07732.0 | 393 | | | | MTX | 50, 55, 60, 65, 70, 75, 80, 85, 90, 91, 92, 93, 94, 95, 96, 97, 98, 99, 100 | 65, 70, 75, 80, 85, 90, 91, 92, 93, 94, 95, 96, 97, 98, 99, 100 | APG02592.0 (45.49% identity, 66.32% similarity)<br>APG05918.0 (45.12% identity, 60.27% similarity)<br>APG02088.0 (44.94% identity, 61.08% similarity)<br>APG09675.0 (43.23% identity, 60.32% similarity)<br>APG07824.0 (42.63% identity, 61.13% similarity)<br>APG09455.0 (40.69% identity, 54.89% similarity)<br>APG06880.0 (40.06% identity, 55.05% similarity)<br>APG00598.0 US_2016_0355842_A1-140 |

TABLE 1-continued

Summary of SEQ ID NOs, Gene Class, and Variants thereof

| APG ID | Seq ID | Modified Seq ID(s) | CryBP1 Seq ID | Split-Cry C-terminus Seq ID | Gene Class | % Identity | % Similarity | Homologs |
|---|---|---|---|---|---|---|---|---|
| | | | | | | | | (39.24% identity, 58.54% similarity) APG08495.0 (33.97% identity, 47.62% similarity) APG02633.0 (31.85% identity, 53.08% similarity) |
| APG07753.0 | 394 | 395 | | | MTX | 55, 60, 65, 70, 75, 80, 85, 90, 91, 92, 93, 94, 95, 96, 97, 98, 99, 100 | 70, 75, 80, 85, 90, 91, 92, 93, 94, 95, 96, 97, 98, 99, 100 | WP_072335847.1 (66.37% identity, 77.98% similarity) APG09460.0 (50.0% identity, 66.47% similarity) APG00416.0 US_2016_0355842_A1-82 (47.6% identity, 64.97% similarity) WP_098425282.1 (47.6% identity, 64.97% similarity) APG05956.0 (47.31% identity, 65.27% similarity) APG00793.0 US_2016_0355842_A1-170 (47.04% identity, 64.23% similarity) APG07606.0 (44.5% identity, 59.52% similarity) APG05239.0 (42.03% identity, 59.13% similarity) APG02970.0 (42.03% identity, 57.68% similarity) APG01367.0 (41.83% identity, 60.46% similarity) |
| APG07798.0 | 396 | 397 | | | Cry | 5, 10, 15, 20, 25, 30, 35, 40, 45, 50, 55, 60, 65, 70, 75, 80, 85, 90, 91, 92, 93, 94, 95, 96, 97, 98, 99, 100 | 5, 10, 15, 20, 25, 30, 35, 40, 45, 50, 55, 60, 65, 70, 75, 80, 85, 90, 91, 92, 93, 94, 95, 96, 97, 98, 99, 100 | OPA04743.1 (100.0% identity, 100.0% similarity) |
| APG07810.0 | 398 | | | | Cry | 45, 50, 55, 60, 65, 70, 75, 80, 85, 90, 91, 92, 93, 94, 95, 96, 97, 98, 99, 100 | 65, 70, 75, 80, 85, 90, 91, 92, 93, 94, 95, 96, 97, 98, 99, 100 | WO_2014_102697-1 (44.53% identity, 60.73% similarity) WO_2014_102697-2 (44.03% identity, 59.86% similarity) WO_2014_102697-60 (44.03% identity, 59.86% similarity) WO_2014_102697-3 (43.37% identity, 59.2% similarity) WO_2014_102697-61 (43.37% identity, 59.2% similarity) WP_016098322.1 (42.48% identity, 56.52% similarity) APG00543.0 US_2017_0175134_A1-31 (41.61% identity, 56.49% similarity) APG08642.0 (40.15% identity, 53.45% |

TABLE 1-continued

| Summary of SEQ ID NOs, Gene Class, and Variants thereof | | | | | | | | |
|---|---|---|---|---|---|---|---|---|
| APG ID | Seq ID | Modified Seq ID(s) | CryBP1 Seq ID | Split-Cry C-terminus Seq ID | Gene Class | % Identity | % Similarity | Homologs |
| | | | | | | | | similarity)<br>AGV55018.1 (39.64% identity, 53.53% similarity)<br>US_9567381_B2-246 (38.79% identity, 51.6% similarity) |
| APG07811.0 | 399 | 400, 401 | | | Cry | 85, 90, 91, 92, 93, 94, 95, 96, 97, 98, 99, 100 | 90, 91, 92, 93, 94, 95, 96, 97, 98, 99, 100 | APG02110.0 (95.61% identity, 97.54% similarity)<br>APG06213.0 (95.08% identity, 97.19% similarity)<br>APG06606.0 (95.08% identity, 96.84% similarity)<br>APG00235.0 US_2016_0311864_A1-89 (83.51% identity, 88.89% similarity)<br>APG04108.0 (82.93% identity, 87.63% similarity)<br>WP_050845493.1 (64.12% identity, 75.51% similarity)<br>APG08681.0 (55.96% identity, 66.14% similarity)<br>WP_048536324.1 (55.96% identity, 66.14% similarity)<br>APG00702.0 US_2017_0175134_A1-115 (38.89% identity, 51.75% similarity)<br>APG00401.0 US_2016_0311864_A1-168 (33.93% identity, 44.69% similarity)<br>APG00401.0 US_2016_0311864_A1-168 (33.93% identity, 44.69% similarity) |
| APG07945.0 | 402 | 403 | 404 | | Cry | 65, 70, 75, 80, 85, 90, 91, 92, 93, 94, 95, 96, 97, 98, 99, 100 | 80, 85, 90, 91, 92, 93, 94, 95, 96, 97, 98, 99, 100 | US_2016_0122399_A1-2 (64.49% identity, 74.9% similarity)<br>US_2016_0122399_A1-1 (64.41% identity, 74.83% similarity)<br>US_8318900_B2-81 (64.22% identity, 75.36% similarity)<br>US_2016_0122399_A1-4 (64.18% identity, 74.75% similarity)<br>WP_099010013.1 (62.59% identity, 74.05% similarity)<br>US_8759619_B2-27 (61.39% identity, 72.41% similarity)<br>APG05370.0 (61.01% identity, 72.28% similarity)<br>US_8318900_B2-82 (59.07% identity, 71.35% similarity)<br>APG00974.0 (59.03% identity, 69.83% similarity) |

TABLE 1-continued

Summary of SEQ ID NOs, Gene Class, and Variants thereof

| APG ID | Seq ID | Modified Seq ID(s) | CryBP1 Seq ID | Split-Cry C-terminus Seq ID | Gene Class | % Identity | % Similarity | Homologs |
|---|---|---|---|---|---|---|---|---|
| | | | | | | | | APG06739.0 (58.77% identity, 70.5% similarity) |
| APG07969.0 | 405 | 406 | | | MTX | 40, 45, 50, 55, 60, 65, 70, 75, 80, 85, 90, 91, 92, 93, 94, 95, 96, 97, 98, 99, 100 | 60, 65, 70, 75, 80, 85, 90, 91, 92, 93, 94, 95, 96, 97, 98, 99, 100 | APG08547.0 (39.17% identity, 56.97% similarity)<br>APG02990.0 (39.13% identity, 57.1% similarity)<br>APG05787.0 (38.95% identity, 53.78% similarity)<br>APG00371.0 US__2016__0355842__A1-72 (34.59% identity, 52.91% similarity)<br>APG01148.0 (34.08% identity, 49.58% similarity)<br>APG03638.0 (33.05% identity, 49.72% similarity)<br>OOR71217.1 (33.05% identity, 49.72% similarity)<br>APG08605.0 (32.77% identity, 49.72% similarity)<br>APG04182.0 (32.71% identity, 50.27% similarity)<br>APG06273.0 (32.47% identity, 49.43% similarity) |
| APG08004.0 | 407 | 408 | | | Bin | 96, 97, 98, 99, 100 | 98, 99, 100 | APG05715.0 (95.21% identity, 97.48% similarity)<br>APG02445.0 (94.46% identity, 96.73% similarity)<br>WP__098807694.1 (94.46% identity, 96.73% similarity)<br>APG04176.0 (93.97% identity, 95.98% similarity)<br>APG04568.0 (91.73% identity, 94.74% similarity)<br>APG06331.0 (89.05% identity, 92.29% similarity)<br>WP__070144216.1 (88.44% identity, 93.72% similarity)<br>APG07911.0 (87.56% identity, 91.04% similarity)<br>APG00212.0 US__2016__0311864__A1-75 (86.86% identity, 91.24% similarity)<br>APG00806.0 US__2017__0175134__A1-167 (86.43% identity, 92.71% similarity) |
| APG08021.0 | 409 | 410 | | | Cry | 70, 75, 80, 85, 90, 91, 92, 93, 94, 95, 96, 97, 98, 99, 100 | 85, 90, 91, 92, 93, 94, 95, 96, 97, 98, 99, 100 | WO__2017__146899-16 (68.29% identity, 78.52% similarity)<br>WO__2017__146899-21 (68.29% identity, 78.52% similarity)<br>AGV55017.1 (68.24% identity, 79.86% |

TABLE 1-continued

Summary of SEQ ID NOs, Gene Class, and Variants thereof

| APG ID | Seq ID | Modified Seq ID(s) | CryBP1 Seq ID | Split-Cry C-terminus Seq ID | Gene Class | % Identity | % Similarity | Homologs |
|---|---|---|---|---|---|---|---|---|
| | | | | | | | | similarity)<br>WO_2017_146899-26 (68.11% identity, 80.0% similarity)<br>APG07037.0 (66.36% identity, 75.75% similarity)<br>US_9567381_B2-232 (64.33% identity, 76.09% similarity)<br>WP_016098327.1 (63.93% identity, 75.5% similarity)<br>OUB62847.1 (63.19% identity, 76.11% similarity)<br>US_9567381_B2-233 (62.27% identity, 75.33% similarity)<br>US_8461415_B2-30 (62.05% identity, 74.74% similarity) |
| APG08081.0 | 411 | 412, 413 | | | PI-PLC | 55, 60, 65, 70, 75, 80, 85, 90, 91, 92, 93, 94, 95, 96, 97, 98, 99, 100 | 70, 75, 80, 85, 90, 91, 92, 93, 94, 95, 96, 97, 98, 99, 100 | WP_000836979.1 (67.27% identity, 80.03% similarity)<br>WP_087876328.1 (67.18% identity, 79.69% similarity)<br>WP_016084067.1 (66.9% identity, 80.19% similarity)<br>WP_098633270.1 (52.96% identity, 69.22% similarity)<br>APG00078.0 US_2016_0366881_A1-1 (52.87% identity, 69.29% similarity)<br>WP_078178666.1 (52.75% identity, 68.99% similarity)<br>WP_063549551.1 (51.75% identity, 68.41% similarity)<br>WP_098342656.1 (51.01% identity, 67.65% similarity)<br>OUB31138.1 (50.68% identity, 65.71% similarity)<br>APG00732.0 US_2016_0311864_A1-212 (50.14% identity, 56.78% similarity) |
| APG08171.0 | 414 | | | | Cry | 65, 70, 75, 80, 85, 90, 91, 92, 93, 94, 95, 96, 97, 98, 99, 100 | 70, 75, 80, 85, 90, 91, 92, 93, 94, 95, 96, 97, 98, 99, 100 | APG09835.0 (92.2% identity, 94.43% similarity)<br>APG06424.0 (92.19% identity, 96.21% similarity)<br>APG08468.0 (91.31% identity, 94.88% similarity)<br>APG08852.0 (90.42% identity, 93.99% similarity)<br>OPA11477.1 (90.42% identity, 93.99% similarity)<br>APG00184.0 US_2016_0355842_A1-19 |

TABLE 1-continued

Summary of SEQ ID NOs, Gene Class, and Variants thereof

| APG ID | Seq ID | Modified Seq ID(s) | CryBP1 Seq ID | Split-Cry C-terminus Seq ID | Gene Class | % Identity | % Similarity | Homologs |
|---|---|---|---|---|---|---|---|---|
| | | | | | | | | (63.17% identity, 65.62% similarity)<br>WP_044306772.1 (63.17% identity, 65.62% similarity)<br>WP_098816555.1 (62.95% identity, 65.4% similarity)<br>WP_097891175.1 (62.72% identity, 65.4% similarity)<br>WP_098217793.1 (62.72% identity, 65.4% similarity) |
| APG08193.0 | 415 | 416 | | | Bin | 70, 75, 80, 85, 90, 91, 92, 93, 94, 95, 96, 97, 98, 99, 100 | 80, 85, 90, 91, 92, 93, 94, 95, 96, 97, 98, 99, 100 | WP_002114997.1 (71.25% identity, 79.9% similarity)<br>APG04966.0 (70.23% identity, 81.17% similarity)<br>WP_103458386.1 (69.9% identity, 77.81% similarity)<br>WP_070128649.1 (69.72% identity, 78.37% similarity)<br>WP_002191947.1 (68.22% identity, 77.0% similarity)<br>WP_002166959.1 (67.96% identity, 77.0% similarity)<br>APG00988.0 US_2017_0175134_A1-194 (67.61% identity, 78.41% similarity)<br>APG07247.0 (67.18% identity, 79.9% similarity)<br>WP_103458366.1 (67.18% identity, 79.9% similarity)<br>APG00331.0 US_2016_0366881_A1-15 (66.16% identity, 75.57% similarity) |
| APG08207.0 | 417 | 418, 419 | | | MTX | 60, 65, 70, 75, 80, 85, 90, 91, 92, 93, 94, 95, 96, 97, 98, 99, 100 | 65, 70, 75, 80, 85, 90, 91, 92, 93, 94, 95, 96, 97, 98, 99, 100 | APG04182.0 (56.18% identity, 63.99% similarity)<br>APG02990.0 (27.96% identity, 41.94% similarity)<br>APG07969.0 (27.71% identity, 40.91% similarity)<br>APG09091.0 (27.55% identity, 39.69% similarity)<br>APG05787.0 (27.53% identity, 41.08% similarity)<br>APG03553.0 (26.78% identity, 37.83% similarity)<br>APG01197.0 (26.57% identity, 38.19% similarity)<br>US_2017_0137842_A1-2 (26.19% identity, 40.21% similarity)<br>APG08547.0 (26.12% identity, 40.69% |

TABLE 1-continued

Summary of SEQ ID NOs, Gene Class, and Variants thereof

| APG ID | Seq ID | Modified Seq ID(s) | CryBP1 Seq ID | Split-Cry C-terminus Seq ID | Gene Class | % Identity | % Similarity | Homologs |
|---|---|---|---|---|---|---|---|---|
| | | | | | | | | similarity)<br>US_8829279_B2-11 (26.02% identity, 39.75% similarity) |
| APG08240.0 | 420 | | | | MTX | 85, 90, 91, 92, 93, 94, 95, 96, 97, 98, 99, 100 | 90, 91, 92, 93, 94, 95, 96, 97, 98, 99, 100 | APG03760.0 (80.23% identity, 86.16% similarity)<br>WP_098584415.1 (80.23% identity, 86.16% similarity)<br>APG00224.0 US_2016_0355842_A1-28 (76.14% identity, 84.09% similarity)<br>APG07487.0 (72.73% identity, 80.4% similarity)<br>US_8318900_B2-63 (67.61% identity, 80.0% similarity)<br>APG05634.0 (67.52% identity, 77.78% similarity)<br>WP_098775686.1 (67.52% identity, 77.78% similarity)<br>APG05506.0 (67.04% identity, 79.05% similarity)<br>APG00609.0 US_2017_0175134_A1-57 (64.57% identity, 76.57% similarity)<br>US_8829279_B2-37 (62.98% identity, 74.86% similarity) |
| APG08316.0 | 421 | | | | MTX | 5, 10, 15, 20, 25, 30, 35, 40, 45, 50, 55, 60, 65, 70, 75, 80, 85, 90, 91, 92, 93, 94, 95, 96, 97, 98, 99, 100 | 5, 10, 15, 20, 25, 30, 35, 40, 45, 50, 55, 60, 65, 70, 75, 80, 85, 90, 91, 92, 93, 94, 95, 96, 97, 98, 99, 100 | |
| APG08335.0 | 422 | 423 | | | MTX | 30, 35, 40, 45, 50, 55, 60, 65, 70, 75, 80, 85, 90, 91, 92, 93, 94, 95, 96, 97, 98, 99, 100 | 50, 55, 60, 65, 70, 75, 80, 85, 90, 91, 92, 93, 94, 95, 96, 97, 98, 99, 100 | WP_084812867.1 (73.54% identity, 80.16% similarity)<br>WP_098398583.1 (30.99% identity, 47.89% similarity)<br>CA_2844913-63 (29.41% identity, 47.9% similarity)<br>CA_2844913-64 (29.41% identity, 47.9% similarity) |
| APG08339.0 | 424 | 425 | | | MTX | 94, 95, 96, 97, 98, 99, 100 | 97, 98, 99, 100 | US_7919272_B2-22 (93.18% identity, 96.75% similarity)<br>WP_000730235.1 (92.53% identity, 96.75% similarity)<br>WP_078203893.1 (87.66% identity, 93.51% similarity)<br>CA_2844913-62 (65.85% identity, 75.38% similarity) |

TABLE 1-continued

Summary of SEQ ID NOs, Gene Class, and Variants thereof

| APG ID | Seq ID | Modified Seq ID(s) | CryBP1 Seq ID | Split-Cry C-terminus Seq ID | Gene Class | % Identity | % Similarity | Homologs |
|---|---|---|---|---|---|---|---|---|
| APG08370.0 | 426 | 427 | | | MAC PF | 5, 10, 15, 20, 25, 30, 35, 40, 45, 50, 55, 60, 65, 70, 75, 80, 85, 90, 91, 92, 93, 94, 95, 96, 97, 98, 99, 100 | 5, 10, 15, 20, 25, 30, 35, 40, 45, 50, 55, 60, 65, 70, 75, 80, 85, 90, 91, 92, 93, 94, 95, 96, 97, 98, 99, 100 | WP_090462867.1 (58.52% identity, 75.57% similarity)<br>WP_076377347.1 (55.85% identity, 71.89% similarity)<br>WP_090462870.1 (48.56% identity, 60.83% similarity)<br>APG05471.0 (42.52% identity, 57.3% similarity)<br>WP_008510716.1 (35.37% identity, 53.68% similarity)<br>WP_090503345.1 (30.2% identity, 43.0% similarity)<br>WP_062550478.1 (28.47% identity, 43.22% similarity)<br>WP_074492263.1 (27.29% identity, 42.71% similarity)<br>WP_078670461.1 (26.7% identity, 41.5% similarity)<br>SKA29206.1 (26.37% identity, 41.27% similarity) |
| APG08378.0 | 428 | 429 | | 430 | Cry | 80, 85, 90, 91, 92, 93, 94, 95, 96, 97, 98, 99, 100 | 85, 90, 91, 92, 93, 94, 95, 96, 97, 98, 99, 100 | APG07322.0 (100.0% identity, 100.0% similarity)<br>CA_2516349-51 (76.93% identity, 84.67% similarity)<br>US_9567381_B2-373 (69.57% identity, 78.73% similarity)<br>US_8044266_B2-3 (67.7% identity, 77.43% similarity)<br>CA_2516349-14 (67.56% identity, 77.43% similarity)<br>CA_2516349-16 (67.28% identity, 77.01% similarity)<br>US_9567381_B2-374 (66.03% identity, 75.78% similarity)<br>APG00204.0 US_2016_0177333_A1-89 (65.14% identity, 75.04% similarity)<br>WP_098223478.1 (64.84% identity, 74.74% similarity)<br>APG00695.0 US_2017_0175134_A1-109 (63.2% identity, 74.48% similarity) |
| APG08427.0 | 431 | 432 | | | Bin | 50, 55, 60, 65, 70, 75, 80, 85, 90, 91, 92, 93, 94, 95, 96, 97, 98, 99, 100 | 70, 75, 80, 85, 90, 91, 92, 93, 94, 95, 96, 97, 98, 99, 100 | WP_051903189.1 (54.19% identity, 74.42% similarity)<br>PIB64337.1 (53.56% identity, 71.95% similarity)<br>WP_071482605.1 (51.81% identity, 71.27% similarity)<br>WP_070996161.1 (51.71% identity, 69.48% |

TABLE 1-continued

| Summary of SEQ ID NOs, Gene Class, and Variants thereof | | | | | | | | |
|---|---|---|---|---|---|---|---|---|
| APG ID | Seq ID | Modified Seq ID(s) | CryBP1 Seq ID | Split-Cry C-terminus Seq ID | Gene Class | % Identity | % Similarity | Homologs |
| | | | | | | | | similarity)<br>WP_081041771.1 (51.71% identity, 69.48% similarity)<br>WP_065950078.1 (48.55% identity, 66.22% similarity)<br>WP_078835606.1 (48.49% identity, 69.37% similarity)<br>WP_101219829.1 (48.32% identity, 66.0% similarity)<br>APG00780.0 US_2016_0355842_A1-169 (48.1% identity, 66.0% similarity)<br>WP_060754610.1 (45.25% identity, 60.26% similarity) |
| APG08468.0 | 433 | | | | Cry | 60, 65, 70, 75, 80, 85, 90, 91, 92, 93, 94, 95, 96, 97, 98, 99, 100 | 65, 70, 75, 80, 85, 90, 91, 92, 93, 94, 95, 96, 97, 98, 99, 100 | APG08852.0 (96.88% identity, 98.44% similarity)<br>APG09835.0 (96.88% identity, 98.44% similarity)<br>OPA11477.1 (96.88% identity, 98.44% similarity)<br>APG06424.0 (91.31% identity, 95.1% similarity)<br>APG08171.0 (91.31% identity, 94.88% similarity)<br>APG00184.0 US_2016_0355842_A1-19 (59.02% identity, 63.47% similarity)<br>WP_044306772.1 (59.02% identity, 63.47% similarity)<br>WP_098816555.1 (58.8% identity, 63.25% similarity)<br>WP_097891175.1 (58.57% identity, 63.25% similarity)<br>WP_098217793.1 (58.57% identity, 63.25% similarity) |
| APG08495.0 | 434 | | | | MTX | 40, 45, 50, 55, 60, 65, 70, 75, 80, 85, 90, 91, 92, 93, 94, 95, 96, 97, 98, 99, 100 | 60, 65, 70, 75, 80, 85, 90, 91, 92, 93, 94, 95, 96, 97, 98, 99, 100 | APG07176.0 (39.06% identity, 60.94% similarity)<br>APG09675.0 (37.34% identity, 53.48% similarity)<br>APG07983.0 (35.23% identity, 55.7% similarity) |
| APG08526.0 | 435 | | | | Cry | 80, 85, 90, 91, 92, 93, 94, 95, 96, 97, 98, 99, 100 | 90, 91, 92, 93, 94, 95, 96, 97, 98, 99, 100 | APG00603.0 US_2016_0311864_A1-198 (77.16% identity, 87.45% similarity)<br>WP_097981477.1 (77.16% identity, 87.45% similarity)<br>WP_098887934.1 (76.95% identity, 87.24% similarity)<br>APG01084.0 (75.93% identity, 88.27% |

TABLE 1-continued

Summary of SEQ ID NOs, Gene Class, and Variants thereof

| APG ID | Seq ID | Modified Seq ID(s) | CryBP1 Seq ID | Split-Cry C-terminus Seq ID | Gene Class | % Identity | % Similarity | Homologs |
|---|---|---|---|---|---|---|---|---|
| | | | | | | | | similarity)<br>WP_098867980.1 (74.49% identity, 84.57% similarity)<br>APG05878.0 (67.28% identity, 83.13% similarity)<br>WP_098505564.1 (61.93% identity, 71.19% similarity)<br>APG01112.0 US_2017_0175134_A1-204 (61.32% identity, 70.16% similarity)<br>WP_097891119.1 (33.33% identity, 36.42% similarity)<br>APG00404.0 US_2016_0311864_A1-169 (30.91% identity, 48.73% similarity) |
| APG08576.0 | 436 | | | | MTX | 90, 91, 92, 93, 94, 95, 96, 97, 98, 99, 100 | 94, 95, 96, 97, 98, 99, 100 | APG07780.0 (87.41% identity, 93.17% similarity)<br>APG05984.0 (86.64% identity, 93.14% similarity)<br>APG05943.0 (75.59% identity, 83.39% similarity)<br>APG09439.0 (74.82% identity, 85.61% similarity)<br>APG03587.0 (73.84% identity, 84.95% similarity)<br>APG01093.0 (72.56% identity, 83.39% similarity)<br>APG01273.0 (70.67% identity, 81.27% similarity)<br>APG08917.0 (62.82% identity, 72.92% similarity)<br>APG05992.0 (57.76% identity, 71.12% similarity)<br>APG01706.0 (56.83% identity, 68.71% similarity) |
| APG08577.0 | 437 | | | | MTX | 45, 50, 55, 60, 65, 70, 75, 80, 85, 90, 91, 92, 93, 94, 95, 96, 97, 98, 99, 100 | 65, 70, 75, 80, 85, 90, 91, 92, 93, 94, 95, 96, 97, 98, 99, 100 | APG04978.0 (43.32% identity, 60.65% similarity)<br>APG02115.0 (42.81% identity, 62.23% similarity)<br>APG07463.0 (36.49% identity, 54.04% similarity)<br>WP_073006288.1 (36.36% identity, 55.64% similarity)<br>SHH89794.1 (35.25% identity, 54.68% similarity)<br>WP_084723762.1 (32.44% identity, 50.84% similarity)<br>WP_073006284.1 (32.38% identity, 53.74% |

TABLE 1-continued

| Summary of SEQ ID NOs, Gene Class, and Variants thereof | | | | | | | | |
|---|---|---|---|---|---|---|---|---|
| APG ID | Seq ID | Modified Seq ID(s) | CryBP1 Seq ID | Split-Cry C-terminus Seq ID | Gene Class | % Identity | % Similarity | Homologs |
| | | | | | | | | similarity)<br>WP_073008904.1 (30.24% identity, 49.14% similarity) |
| APG08624.0 | 438 | 439 | | | Bin | 55, 60, 65, 70, 75, 80, 85, 90, 91, 92, 93, 94, 95, 96, 97, 98, 99, 100 | 70, 75, 80, 85, 90, 91, 92, 93, 94, 95, 96, 97, 98, 99, 100 | WP_064675442.1 (58.69% identity, 71.78% similarity)<br>WP_095192304.1 (57.73% identity, 71.82% similarity)<br>KKX69741.1 (56.95% identity, 69.7% similarity)<br>WP_082240515.1 (56.95% identity, 69.48% similarity)<br>PAM83583.1 (56.92% identity, 69.42% similarity)<br>WP_046815282.1 (56.72% identity, 69.25% similarity)<br>WP_093227613.1 (56.49% identity, 72.21% similarity)<br>WP_077044189.1 (55.36% identity, 68.97% similarity)<br>WP_025110931.1 (52.38% identity, 68.4% similarity)<br>WP_102650854.1 (52.14% identity, 67.31% similarity) |
| APG08625.0 | 440 | 441 | | | MTX | 90, 91, 92, 93, 94, 95, 96, 97, 98, 99, 100 | 92, 93, 94, 95, 96, 97, 98, 99, 100 | APG04479.0 (89.74% identity, 91.5% similarity)<br>WP_061885189.1 (33.89% identity, 48.46% similarity)<br>WP_088118891.1 (33.89% identity, 48.46% similarity)<br>APG08369.0 (33.04% identity, 51.19% similarity)<br>WP_077997354.1 (32.11% identity, 49.01% similarity)<br>APG00146.0 US_2016_0304898_A1-166 (31.3% identity, 49.86% similarity)<br>WP_098582510.1 (31.3% identity, 49.86% similarity)<br>APG00552.0 US_2016_0366881_A1-110 (31.3% identity, 47.37% similarity)<br>APG03377.0 (30.97% identity, 49.15% similarity)<br>APG02315.0 (30.37% identity, 45.85% similarity) |
| APG08639.0 | 442 | | | | MTX | 60, 65, 70, 75, 80, 85, 90, 91, 92, 93, 94, 95, 96, 97, 98, 99, | 80, 85, 90, 91, 92, 93, 94, 95, 96, 97, 98, 99, 100 | APG02277.0 (59.78% identity, 76.09% similarity)<br>WP_098733797.1 (51.09% identity, 70.65% |

TABLE 1-continued

| Summary of SEQ ID NOs, Gene Class, and Variants thereof | | | | | | | | |
|---|---|---|---|---|---|---|---|---|
| APG ID | Seq ID | Modified Seq ID(s) | CryBP1 Seq ID | Split-Cry C-terminus Seq ID | Gene Class | % Identity | % Similarity | Homologs |
| | | | | | | 100 | | similarity)<br>WP_098069632.1 (50.72% identity, 70.29% similarity)<br>WP_098643607.1 (50.72% identity, 69.93% similarity)<br>US_8461421_B2-74 (50.53% identity, 69.4% similarity)<br>APG00091.0 US_2016_0304898_A1-120 (50.18% identity, 69.4% similarity)<br>APG03249.0 (49.82% identity, 68.68% similarity)<br>APG03891.0 (49.64% identity, 68.84% similarity)<br>WP_098652092.1 (49.64% identity, 68.84% similarity)<br>WP_098099019.1 (48.91% identity, 68.84% similarity)<br>APG00850.0 US_2016_0355842_A1-178 (48.91% identity, 68.12% similarity)<br>WP_098208340.1 (48.91% identity, 68.12% similarity) |
| APG08642.0 | 443 | 444, 445 | | | Cry | 85, 90, 91, 92, 93, 94, 95, 96, 97, 98, 99 100 | 90, 91, 92, 93, 94, 95, 96, 97, 98, 99, 100 | APG00543.0 US_2017_0175134_A1-31 (80.49% identity, 85.85% similarity)<br>AGV55018.1 (80.17% identity, 85.9% similarity)<br>WP_016098322.1 (77.06% identity, 83.25% similarity)<br>US_9567381_B2-246 (75.51% identity, 83.95% similarity)<br>APG07810.0 (40.15% identity, 53.45% similarity)<br>WO_2014_102697-2 (37.46% identity, 50.06% similarity)<br>WO_2014_102697-60 (37.46% identity, 50.06% similarity)<br>WO_2014_102697-1 (37.11% identity, 49.64% similarity)<br>WO_2014_102697-3 (36.95% identity, 49.59% similarity)<br>WO_2014_102697-61 (36.95% identity, 49.59% similarity) |
| APG08757.0 | 446 | 447 | | | MTX | 85, 90, 91, 92, 93, 94, 95, 96, 97, 98, 99, 100 | 91, 92, 93, 94, 95, 96, 97, 98, 99, 100 | APG04021.0 (81.43% identity, 90.86% similarity)<br>APG09100.0 (81.14% identity, 89.71% similarity)<br>US_8318900_B2-77 (47.09% identity, |

TABLE 1-continued

Summary of SEQ ID NOs, Gene Class, and Variants thereof

| APG ID | Seq ID | Modified Seq ID(s) | CryBP1 Seq ID | Split-Cry C-terminus Seq ID | Gene Class | % Identity | % Similarity | Homologs |
|---|---|---|---|---|---|---|---|---|
| | | | | | | | | 62.05% similarity)<br>APG04586.0 (46.81% identity, 61.77% similarity)<br>APG06820.0 (42.36% identity, 59.25% similarity)<br>APG06480.0 (34.13% identity, 49.74% similarity)<br>APG00718.0 US_2017_0175134_A1-132 (33.89% identity, 48.33% similarity)<br>APG00860.0 US_2016_0355842_A1-180 (33.8% identity, 52.63% similarity)<br>APG00586.0 US_2016_0355842_A1-135 (32.97% identity, 53.68% similarity)<br>APG00420.0 US_2016_0355842_A1-85 (32.61% identity, 53.53% similarity) |
| APG08765.0 | 448 | | 449 | | Cry | 40, 45, 50, 55, 60, 65, 70, 75, 80, 85, 90, 91, 92, 93, 94, 95, 96, 97, 98, 99, 100 | 55, 60, 65, 70, 75, 80, 85, 90, 91, 92, 93, 94, 95, 96, 97, 98, 99, 100 | AIW52619.1 (37.1% identity, 51.08% similarity)<br>US_9567381_B2-424 (36.96% identity, 51.08% similarity)<br>US_8461421_B2-120 (36.79% identity, 51.87% similarity)<br>APG00864.0 US_2017_0175134_A1-174 (36.76% identity, 51.34% similarity)<br>APG00664.0 US_2017_0175134_A1-89 (35.62% identity, 49.22% similarity)<br>US_8318900_B2-83 (34.93% identity, 49.73% similarity)<br>APG03124.0 (34.78% identity, 48.58% similarity)<br>APG04010.0 (34.69% identity, 48.28% similarity)<br>ABW89734.1 (34.64% identity, 50.07% similarity)<br>CA_2516349-43 (34.51% identity, 50.34% similarity)<br>US_9567381_B2-34 (34.51% identity, 50.34% similarity)<br>WP_043939395.1 (34.51% identity, 50.2% similarity)<br>APG07972.0 (34.51% identity, 50.0% similarity) |
| APG08791.0 | 450 | 451, 452 | | | MTX | 94, 95, 96, 97, 98, 99, 100 | 96, 97, 98, 99, 100 | APG06381.0 (93.19% identity, 95.05% similarity)<br>WP_098783206.1 (89.47% identity, 91.33% similarity) |

TABLE 1-continued

| Summary of SEQ ID NOs, Gene Class, and Variants thereof | | | | | | | | |
|---|---|---|---|---|---|---|---|---|
| APG ID | Seq ID | Modified Seq ID(s) | CryBP1 Seq ID | Split-Cry C-terminus Seq ID | Gene Class | % Identity | % Similarity | Homologs |
| APG08812.0 | 453 | | | | MTX | 35, 40, 45, 50, 55, 60, 65, 70, 75, 80, 85, 90, 91, 92, 93, 94, 95, 96, 97, 98, 99, 100 | 55, 60, 65, 70, 75, 80, 85, 90, 91, 92, 93, 94, 95, 96, 97, 98, 99, 100 | PCJ04527.1 (33.9% identity, 55.93% similarity)<br>WP_015268242.1 (31.88% identity, 53.02% similarity)<br>PQJ72467.1 (31.72% identity, 54.14% similarity)<br>WP_056615748.1 (31.16% identity, 51.03% similarity)<br>WP_096527538.1 (31.06% identity, 53.58% similarity)<br>WP_038918640.1 (30.95% identity, 53.06% similarity)<br>APG05045.0 (30.72% identity, 49.02% similarity)<br>WP_011306610.1 (30.0% identity, 55.0% similarity)<br>WP_048041904.1 (29.51% identity, 52.46% similarity)<br>US_9879277_B2-24 (29.35% identity, 52.22% similarity) |
| APG08823.0 | 454 | | | | MTX | 65, 70, 75, 80, 85, 90, 91, 92, 93, 94, 95, 96, 97, 98, 99, 100 | 75, 80, 85, 90, 91, 92, 93, 94, 95, 96, 97, 98, 99, 100 | WP_002193629.1 (64.21% identity, 74.58% similarity)<br>APG01051.0 (64.0% identity, 73.67% similarity)<br>WP_103458389.1 (61.69% identity, 71.1% similarity)<br>APG00871.0 (59.03% identity, 72.58% similarity)<br>APG00755.0 US_2016_0355842_A1-166 (58.58% identity, 70.87% similarity)<br>WP_098711954.1 (58.58% identity, 70.87% similarity)<br>APG02980.0 (56.33% identity, 66.87% similarity)<br>APG00402.0 US_2016_0355842_A1-77 (54.33% identity, 71.67% similarity)<br>APG00583.0 US_2016_0366881_A1-114 (42.15% identity, 59.69% similarity)<br>APG06065.0 (31.29% identity, 49.68% similarity) |
| APG08852.0 | 455 | | | | Cry | 60, 65, 70, 75, 80, 85, 90, 91, 92, 93, 94, 95, 96, 97, 98, 99, 100 | 65, 70, 75, 80, 85, 90, 91, 92, 93, 94, 95, 96, 97, 98, 99, 100 | OPA11477.1 (100.0% identity, 100.0% similarity)<br>APG08468.0 (96.88% identity, 98.44% similarity)<br>APG09835.0 (96.44% identity, 98.22% similarity)<br>APG06424.0 (90.42% identity, 94.43% |

TABLE 1-continued

| Summary of SEQ ID NOs, Gene Class, and Variants thereof | | | | | | | | |
|---|---|---|---|---|---|---|---|---|
| APG ID | Seq ID | Modified Seq ID(s) | CryBP1 Seq ID | Split-Cry C-terminus Seq ID | Gene Class | % Identity | % Similarity | Homologs |
| | | | | | | | | similarity) APG08171.0 (90.42% identity, 93.99% similarity) APG00184.0 US_2016_0355842_A1-19 (58.35% identity, 63.03% similarity) WP_044306772.1 (58.35% identity, 63.03% similarity) WP_098816555.1 (58.13% identity, 62.81% similarity) WP_097891175.1 (57.91% identity, 62.81% similarity) WP_098217793.1 (57.91% identity, 62.81% similarity) |
| APG08912.0 | 456 | 457, 458 | | | MTX | 90, 91, 92, 93, 94, 95, 96, 97, 98, 99, 100 | 94, 95, 96, 97, 98, 99, 100 | APG03861.0 (88.25% identity, 93.37% similarity) WP_103623145.1 (88.25% identity, 93.37% similarity) APG07783.0 (87.65% identity, 92.77% similarity) APG03506.0 (83.63% identity, 88.99% similarity) APG09901.0 (81.44% identity, 88.92% similarity) APG00545.0 US_2016_0355842_A1-122 (32.47% identity, 47.7% similarity) APG00276.0 US_2016_0355842_A1-47 (32.27% identity, 48.55% similarity) APG08369.0 (31.92% identity, 44.92% similarity) APG00362.0 US_2016_0366881_A1-33 (30.56% identity, 45.28% similarity) WP_079562232.1 (29.89% identity, 45.53% similarity) APG00552.0 US_2016_0366881_A1-110 (29.89% identity, 43.58% similarity) |
| APG09027.0 | 459 | 460 | | | Bin | 90, 91, 92, 93, 94, 95, 96, 97, 98, 99, 100 | 92, 93, 94, 95, 96, 97, 98, 99, 100 | APG06331.0 (85.32% identity, 91.79% similarity) APG04176.0 (85.07% identity, 91.29% similarity) APG07911.0 (84.58% identity, 90.8% similarity) APG00306.0 US_2016_0366881_A1-3 (83.82% identity, 88.97% similarity) APG00600.0 US_2016_0311864_A1-197 (83.74% identity, 88.92% similarity) WP_099012321.1 (83.74% identity, 88.92% |

TABLE 1-continued

Summary of SEQ ID NOs, Gene Class, and Variants thereof

| APG ID | Seq ID | Modified Seq ID(s) | CryBP1 Seq ID | Split-Cry C-terminus Seq ID | Gene Class | % Identity | % Similarity | Homologs |
|---|---|---|---|---|---|---|---|---|
| | | | | | | | | similarity)<br>APG08004.0 (82.09% identity, 88.56% similarity)<br>APG05715.0 (81.59% identity, 89.3% similarity)<br>APG02445.0 (81.59% identity, 88.81% similarity)<br>WP_098807694.1 (81.59% identity, 88.81% similarity) |
| APG09028.0 | 461 | 462 | | | Cry | 50, 55, 60, 65, 70, 75, 80, 85, 90, 91, 92, 93, 94, 95, 96, 97, 98, 99, 100 | 55, 60, 65, 70, 75, 80, 85, 90, 91, 92, 93, 94, 95, 96, 97, 98, 99, 100 | WP_095156798.1 (48.22% identity, 58.31% similarity)<br>APG09441.0 (45.64% identity, 54.5% similarity)<br>APG01679.0 (31.25% identity, 43.48% similarity)<br>WP_048536362.1 (31.25% identity, 43.48% similarity)<br>APG03986.0 (30.11% identity, 43.46% similarity)<br>APG00702.0 US_2017_0175134_A1-115 (30.0% identity, 43.38% similarity)<br>APG00787.0 US_2017_0175134_A1-156 (29.63% identity, 42.11% similarity)<br>APG02533.0 (29.27% identity, 39.24% similarity)<br>APG00372.0 US_2016_0311864_A1-150 (29.17% identity, 39.41% similarity)<br>APG08243.0 (29.09% identity, 41.12% similarity) |
| APG09048.0 | 463 | 464 | | | MTX | 90, 91, 92, 93, 94, 95, 96, 97, 98, 99, 100 | 92, 93, 94, 95, 96, 97, 98, 99, 100 | WP_068985586.1 (87.61% identity, 91.45% similarity)<br>APG09392.0 (87.32% identity, 91.15% similarity)<br>APG02862.0 (87.02% identity, 91.15% similarity)<br>APG07381.0 (86.14% identity, 90.86% similarity)<br>APG01874.0 (84.14% identity, 87.82% similarity)<br>APG00417.0 US_2016_0355842_A1-83 (76.61% identity, 84.8% similarity)<br>WP_090695735.1 (76.02% identity, 84.21% similarity)<br>WP_071745741.1 (75.73% identity, 83.92% similarity)<br>APG00667.0 US_2016_0355842_A1-155 |

TABLE 1-continued

| Summary of SEQ ID NOs, Gene Class, and Variants thereof | | | | | | | | |
|---|---|---|---|---|---|---|---|---|
| APG ID | Seq ID | Modified Seq ID(s) | CryBP1 Seq ID | Split-Cry C-terminus Seq ID | Gene Class | % Identity | % Similarity | Homologs |
| | | | | | | | | (61.66% identity, 74.85% similarity)<br>WP_098018654.1 (61.66% identity, 74.85% similarity) |
| APG09152.0 | 465 | 466 | | | MTX | 80, 85, 90, 91, 92, 93, 94, 95, 96, 97, 98, 99, 100 | 90, 91, 92, 93, 94, 95, 96, 97, 98, 99, 100 | APG09904.0 (78.93% identity, 89.64% similarity)<br>APG00850.0 US_2016_0355842_A1-178 (76.79% identity, 87.86% similarity)<br>WP_098208340.1 (76.79% identity, 87.86% similarity)<br>WP_098683229.1 (76.43% identity, 87.5% similarity)<br>WP_098785528.1 (76.07% identity, 87.5% similarity)<br>APG00021.0 US_2016_0304898_A1-35 (70.0% identity, 84.29% similarity)<br>APG00601.0 US_2016_0355842_A1-141 (69.64% identity, 83.93% similarity)<br>APG03249.0 (69.64% identity, 83.57% similarity)<br>APG03891.0 (69.29% identity, 83.57% similarity)<br>WP_098634134.1 (69.29% identity, 83.21% similarity) |
| APG09158.0 | 467 | 468 | | | MTX | 45, 50, 55, 60, 65, 70, 75, 80, 85, 90, 91, 92, 93, 94, 95, 96, 97, 98, 99, 100 | 60, 65, 70, 75, 80, 85, 90, 91, 92, 93, 94, 95, 96, 97, 98, 99, 100 | WP_103655156.1 (45.4% identity, 60.34% similarity)<br>APG05653.0 (44.31% identity, 59.18% similarity)<br>WP_098873359.1 (41.57% identity, 58.43% similarity)<br>WP_098257700.1 (41.57% identity, 58.14% similarity)<br>WP_097908332.1 (40.71% identity, 56.64% similarity)<br>APG05385.0 (38.97% identity, 57.88% similarity)<br>US_8461415_B2-32 (37.13% identity, 53.51% similarity)<br>WP_091737463.1 (36.9% identity, 52.39% similarity)<br>WP_086397082.1 (36.67% identity, 56.67% similarity)<br>APG06364.0 (36.28% identity, 57.62% similarity) |
| APG09181.0 | 469 | | | | Cyt | 35, 40, 45, 50, 55, 60, 65, 70, 75, 80, 85, 90, 91, 92, 93, 94, | 55, 60, 65, 70, 75, 80, 85, 90, 91, 92, 93, 94, 95, 96, 97, 98, | APG06496.0 (40.08% identity, 63.97% similarity)<br>US_9567381_B2-1430 (31.27% identity, |

TABLE 1-continued

Summary of SEQ ID NOs, Gene Class, and Variants thereof

| APG ID | Seq ID | Modified Seq ID(s) | CryBP1 Seq ID | Split-Cry C-terminus Seq ID | Gene Class | % Identity | % Similarity | Homologs |
|---|---|---|---|---|---|---|---|---|
| | | | | | | 95, 96, 97, 98, 99, 100 | 99, 100 | 51.35% similarity)<br>WP_088071735.1 (31.27% identity, 51.35% similarity)<br>APG02790.0 (30.27% identity, 46.94% similarity)<br>AJW76686.1 (29.56% identity, 48.54% similarity)<br>AGT15589.1 (29.46% identity, 51.16% similarity)<br>US_9567381_B2-1427 (29.46% identity, 51.16% similarity)<br>US_9567381_B2-1429 (29.46% identity, 51.16% similarity)<br>WO_2017_199078-6 (29.46% identity, 51.16% similarity)<br>WP_043938803.1 (29.46% identity, 51.16% similarity)<br>ABV22504.1 (29.46% identity, 50.78% similarity)<br>AFA52539.1 (29.46% identity, 50.78% similarity) |
| APG09201.0 | 470 | | | | Cyt | 5, 10, 15, 20, 25, 30, 35, 40, 45, 50, 55, 60, 65, 70, 75, 80, 85, 90, 91, 92, 93, 94, 95, 96, 97, 98, 99, 100 | 5, 10, 15, 20, 25, 30, 35, 40, 45, 50, 55, 60, 65, 70, 75, 80, 85, 90, 91, 92, 93, 94, 95, 96, 97, 98, 99, 100 | |
| APG09210.0 | 471 | | | | Cry | 55, 60, 65, 70, 75, 80, 85, 90, 91, 92, 93, 94, 95, 96, 97, 98, 99, 100 | 60, 65, 70, 75, 80, 85, 90, 91, 92, 93, 94, 95, 96, 97, 98, 99, 100 | APG00275.0 US_2016_0311864_A1-111 (53.24% identity, 54.05% similarity)<br>WP_098376074.1 (52.97% identity, 54.05% similarity)<br>APG05139.0 (50.87% identity, 58.19% similarity)<br>US_8318900_B2-90 (49.3% identity, 55.92% similarity)<br>WP_044307627.1 (41.53% identity, 42.86% similarity)<br>WP_098816511.1 (41.31% identity, 42.58% similarity)<br>WP_098285136.1 (40.7% identity, 41.53% similarity)<br>WP_097891341.1 (39.44% identity, 40.46% similarity)<br>WP_098639056.1 (39.19% identity, 40.2% similarity) |

TABLE 1-continued

| Summary of SEQ ID NOs, Gene Class, and Variants thereof | | | | | | | | |
|---|---|---|---|---|---|---|---|---|
| APG ID | Seq ID | Modified Seq ID(s) | CryBP1 Seq ID | Split-Cry C-terminus Seq ID | Gene Class | % Identity | % Similarity | Homologs |
| | | | | | | | | WP_044307626.1 (38.93% identity, 40.2% similarity) |
| APG09221.0 | 472 | | | | Vip3 | 97, 98, 99, 100 | 99, 100 | APG00038.0 US_2016_0355842_A1-1 (96.22% identity, 98.02% similarity)<br>APG06235.0 (89.75% identity, 93.53% similarity)<br>APG00181.0 US_2016_0355842_A1-16 (89.57% identity, 94.06% similarity)<br>APG00675.0 US_2017_0175134_A1-97 (60.49% identity, 74.83% similarity)<br>APG00131.0 US_2016_0311864_A1-30 (59.54% identity, 75.62% similarity)<br>WP_098631820.1 (59.54% identity, 75.62% similarity)<br>APG07054.0 (50.61% identity, 67.54% similarity)<br>APG00207.0 US_2016_0311864_A1-70 (45.22% identity, 62.8% similarity)<br>WP_098685831.1 (45.22% identity, 62.8% similarity)<br>AAK97481.1 (34.25% identity, 50.22% similarity) |
| APG09238.0 | 473 | 474, 475 | | | Vip4 | 98, 99, 100 | 99, 100 | APG01474.0 (97.94% identity, 98.66% similarity)<br>APG02585.0 (97.75% identity, 98.57% similarity)<br>APG00766.0 (55.57% identity, 71.15% similarity)<br>APG07032.0 (54.16% identity, 70.79% similarity)<br>APG04069.0 (53.74% identity, 69.23% similarity)<br>CA_2844913-129 (53.29% identity, 68.9% similarity)<br>CA_2844913-130 (53.29% identity, 68.9% similarity)<br>APG04672.0 (53.12% identity, 67.4% similarity)<br>APG02031.0 (53.01% identity, 67.37% similarity)<br>WP_016123960.1 (52.91% identity, 67.17% similarity) |
| APG09266.0 | 476 | 477 | | | Bin | 85, 90, 91, 92, 93, 94, 95, 96, 97, 98, 99, 100 | 90, 91, 92, 93, 94, 95, 96, 97, 98, 99, 100 | APG00413.0 US_2016_0311864_A1-174 (83.68% identity, 88.68% similarity)<br>APG05717.0 (82.37% identity, 87.89% similarity)<br>APG06920.0 (82.15% identity, 86.88% |

TABLE 1-continued

Summary of SEQ ID NOs, Gene Class, and Variants thereof

| APG ID | Seq ID | Modified Seq ID(s) | CryBP1 Seq ID | Split-Cry C-terminus Seq ID | Gene Class | % Identity | % Similarity | Homologs |
|---|---|---|---|---|---|---|---|---|
| | | | | | | | | similarity)<br>APG09069.0 (80.53% identity, 86.58% similarity)<br>US_9321814_B2-2 (80.26% identity, 88.42% similarity)<br>US_9321814_B2-3 (80.0% identity, 88.16% similarity)<br>WP_098876539.1 (79.74% identity, 87.89% similarity)<br>WP_017154552.1 (79.0% identity, 88.19% similarity)<br>US_9321814_B2-4 (78.42% identity, 86.58% similarity)<br>KEZ80012.1 (78.42% identity, 85.26% similarity) |
| APG09289.0 | 478 | 479, 480 | | | Cry | 35, 40, 45, 50, 55, 60, 65, 70, 75, 80, 85, 90, 91, 92, 93, 94, 95, 96, 97, 98, 99, 100 | 50, 55, 60, 65, 70, 75, 80, 85, 90, 91, 92, 93, 94, 95, 96, 97, 98, 99, 100 | APG02309.0 (65.9% identity, 75.48% similarity)<br>APG02309.0 (65.9% identity, 75.48% similarity)<br>CA_2595901-10 (32.11% identity, 45.96% similarity)<br>CA_2595901-10 (32.11% identity, 45.96% similarity)<br>CA_2595901-10 (32.11% identity, 45.96% similarity)<br>US_5281530-4 (31.46% identity, 44.71% similarity)<br>US_5281530-4 (31.46% identity, 44.71% similarity)<br>US_5281530-4 (31.46% identity, 44.71% similarity)<br>CA_2595901-11 (31.37% identity, 44.78% similarity)<br>CA_2595901-11 (31.37% identity, 44.78% similarity)<br>CA_2595901-11 (31.37% identity, 44.78% similarity)<br>US_5281530-3 (31.37% identity, 44.78% similarity)<br>US_5281530-3 (31.37% identity, 44.78% similarity)<br>US_5281530-3 (31.37% identity, 44.78% similarity) |
| APG09323.0 | 481 | 482 | | | Bin | 93, 94, 95, 96, 97, 98, 99, 100 | 97, 98, 99, 100 | APG00132.0 US_2016_0311864_A1-31 (92.01% identity, 94.67% similarity)<br>APG00249.0 US_2016_0311864_A1-96 |

TABLE 1-continued

Summary of SEQ ID NOs, Gene Class, and Variants thereof

| APG ID | Seq ID | Modified Seq ID(s) | CryBP1 Seq ID | Split-Cry C-terminus Seq ID | Gene Class | % Identity | % Similarity | Homologs |
|---|---|---|---|---|---|---|---|---|
| | | | | | | | | (91.57% identity, 96.14% similarity)<br>APG00709.0 (89.86% identity, 94.93% similarity)<br>WP_098431222.1 (89.64% identity, 94.22% similarity)<br>APG00459.0 US_2016_0311864_A1-181 (87.29% identity, 91.61% similarity)<br>WP_098625308.1 (87.29% identity, 91.61% similarity)<br>APG00065.0 US_2016_0177333_A1-31 (79.0% identity, 84.49% similarity)<br>WP_097786723.1 (77.33% identity, 82.82% similarity)<br>APG00229.0 US_2016_0311864_A1-84 (75.0% identity, 82.62% similarity)<br>APG00407.0 US_2016_0311864_A1-170 (74.46% identity, 83.13% similarity)<br>WP_098589502.1 (74.46% identity, 83.13% similarity) |
| APG09412.0 | 483 | 484 | | | MTX | 65, 70, 75, 80, 85, 90, 91, 92, 93, 94, 95, 96, 97, 98, 99, 100 | 80, 85, 90, 91, 92, 93, 94, 95, 96, 97, 98, 99, 100 | APG00466.0 US_2016_0366881_A1-80 (64.09% identity, 78.95% similarity)<br>WP_086405659.1 (64.09% identity, 78.95% similarity)<br>WP_036654376.1 (42.04% identity, 57.06% similarity)<br>ETK27180.1 (40.84% identity, 55.26% similarity)<br>WP_061885189.1 (40.76% identity, 57.48% similarity)<br>APG03377.0 (40.54% identity, 59.46% similarity)<br>WP_088118891.1 (40.47% identity, 57.48% similarity)<br>WP_077997354.1 (40.36% identity, 60.53% similarity)<br>AVF26040.1 (40.36% identity, 60.24% similarity)<br>APG04746.0 (39.34% identity, 56.46% similarity) |
| APG09415.0 | 485 | 486 | | | MTX | 75, 80, 85, 90, 91, 92, 93, 94, 95, 96, 97, 98, 99, 100 | 90, 91, 92, 93, 94, 95, 96, 97, 98, 99, 100 | WP_098157467.1 (100.0% identity, 100.0% similarity)<br>WP_097969898.1 (99.68% identity, 100.0% similarity)<br>WP_071744311.1 (99.68% identity, 99.68% similarity)<br>WP_098786706.1 (99.05% identity, 99.68% |

TABLE 1-continued

| Summary of SEQ ID NOs, Gene Class, and Variants thereof | | | | | | | | |
|---|---|---|---|---|---|---|---|---|
| APG ID | Seq ID | Modified Seq ID(s) | CryBP1 Seq ID | Split-Cry C-terminus Seq ID | Gene Class | % Identity | % Similarity | Homologs |
| APG09416.0 | 487 | | | | MTX | 93, 94, 95, 96, 97, 98, 99, 100 | 96, 97, 98, 99, 100 | similarity)<br>WP_070143005.1 (99.05% identity, 99.37% similarity)<br>WP_098425855.1 (98.42% identity, 99.37% similarity)<br>WP_025147991.1 (98.11% identity, 99.68% similarity)<br>WP_098304287.1 (96.85% identity, 98.74% similarity)<br>WP_001079819.1 (96.23% identity, 98.11% similarity)<br>WP_098431274.1 (95.91% identity, 98.11% similarity)<br>APG04316.0 (92.74% identity, 96.21% similarity)<br>APG00749.0 (92.36% identity, 95.35% similarity)<br>APG02638.0 (89.97% identity, 94.98% similarity)<br>APG03379.0 (86.96% identity, 93.65% similarity)<br>APG08088.0 (80.46% identity, 89.4% similarity)<br>APG00155.0 US_2016_0311864_A1-40 (80.27% identity, 86.62% similarity)<br>APG01127.0 (80.0% identity, 86.33% similarity)<br>APG07655.0 (79.93% identity, 86.96% similarity)<br>APG03504.0 (79.93% identity, 86.62% similarity)<br>APG09682.0 (79.8% identity, 86.09% similarity)<br>APG08241.0 (79.26% identity, 86.29% similarity)<br>APG07639.0 (79.26% identity, 84.95% similarity) |
| APG09430.0 | 488 | 489 | | | Cry | 90, 91, 92, 93, 94, 95, 96, 97, 98, 99, 100 | 93, 94, 95, 96, 97, 98, 99, 100 | APG00149.0 US_2016_0304898_A1-172 (89.91% identity, 92.92% similarity)<br>WP_098326418.1 (89.91% identity, 92.92% similarity)<br>WP_098902198.1 (40.03% identity, 56.23% similarity)<br>APG00066.0 US_2016_0177333_A1-33 (39.11% identity, 54.94% similarity)<br>APG00081.0 US_2016_0304898_A1-105 |

TABLE 1-continued

| Summary of SEQ ID NOs, Gene Class, and Variants thereof | | | | | | | | |
|---|---|---|---|---|---|---|---|---|
| APG ID | Seq ID | Modified Seq ID(s) | CryBP1 Seq ID | Split-Cry C-terminus Seq ID | Gene Class | % Identity | % Similarity | Homologs |
| | | | | | | | | (38.9% identity, 56.41% similarity)<br>APG07810.0 (33.62% identity, 49.29% similarity)<br>WO_2014_102697-1 (32.11% identity, 49.93% similarity)<br>WO_2014_102697-2 (32.03% identity, 50.21% similarity)<br>WO_2014_102697-60 (32.03% identity, 50.21% similarity)<br>APG01434.0 (31.64% identity, 46.35% similarity) |
| APG09439.0 | 490 | | | | MTX | 80, 85, 90, 91, 92, 93, 94, 95, 96, 97, 98, 99, 100 | 90, 91, 92, 93, 94, 95, 96, 97, 98, 99, 100 | APG03587.0 (92.83% identity, 96.42% similarity)<br>APG07780.0 (77.34% identity, 86.69% similarity)<br>APG05984.0 (77.34% identity, 86.33% similarity)<br>APG08576.0 (74.82% identity, 85.61% similarity)<br>APG01093.0 (72.3% identity, 82.37% similarity)<br>APG05943.0 (68.58% identity, 79.73% similarity)<br>APG01273.0 (67.61% identity, 77.82% similarity)<br>APG08917.0 (58.27% identity, 70.86% similarity)<br>APG05992.0 (52.88% identity, 69.06% similarity)<br>APG01706.0 (51.25% identity, 64.87% similarity) |
| APG09465.0 | 491 | 492 | | | Bin | 90, 91, 92, 93, 94, 95, 96, 97, 98, 99, 100 | 95, 96, 97, 98, 99, 100 | APG02955.0 (89.67% identity, 94.96% similarity)<br>APG07877.0 (88.92% identity, 93.95% similarity)<br>APG09977.0 (80.9% identity, 84.92% similarity)<br>APG00243.0 US_2016_0311864_A1-94 (78.64% identity, 83.92% similarity)<br>WP_074651503.1 (77.0% identity, 82.5% similarity)<br>WP_097786723.1 (76.0% identity, 85.0% similarity)<br>APG04176.0 (75.38% identity, 83.67% similarity)<br>APG02445.0 (74.62% identity, 83.17% |

TABLE 1-continued

| Summary of SEQ ID NOs, Gene Class, and Variants thereof | | | | | | | | |
|---|---|---|---|---|---|---|---|---|
| APG ID | Seq ID | Modified Seq ID(s) | CryBP1 Seq ID | Split-Cry C-terminus Seq ID | Gene Class | % Identity | % Similarity | Homologs |
| | | | | | | | | similarity)<br>WP_098807694.1 (74.62% identity, 83.17% similarity)<br>APG08004.0 (74.62% identity, 82.41% similarity) |
| APG09511.0 | 493 | 494 | | | Cry | 99, 100 | 99, 100 | APG07866.0 (98.05% identity, 98.7% similarity)<br>APG07224.0 (53.47% identity, 62.1% similarity)<br>APG05103.0 (53.23% identity, 63.54% similarity)<br>APG00457.0 US_2016_0355842_A1-98 (42.83% identity, 56.22% similarity)<br>WP_044307385.1 (42.83% identity, 56.22% similarity)<br>WP_098376005.1 (42.83% identity, 56.22% similarity)<br>APG09895.0 (40.12% identity, 56.08% similarity)<br>CA_2844913-200 (36.42% identity, 49.47% similarity)<br>APG00348.0 US_2016_0366881_A1-26 (36.3% identity, 49.5% similarity)<br>APG00348.0 US_2016_0366881_A1-26 (36.3% identity, 49.5% similarity) |
| APG09548.0 | 495 | 496 | | 497 | Cry | 45, 50, 55, 60, 65, 70, 75, 80, 85, 90, 91, 92, 93, 94, 95, 96, 97, 98, 99, 100 | 55, 60, 65, 70, 75, 80, 85, 90, 91, 92, 93, 94, 95, 96, 97, 98, 99, 100 | APG00123.0 US_2016_0304898_A1-146 (43.62% identity, 54.0% similarity)<br>WP_098213628.1 (43.62% identity, 54.0% similarity)<br>APG00721.0 US_2017_0175134_A1-133 (37.1% identity, 49.22% similarity)<br>APG00136.0 US_2016_0177333_A1-75 (36.33% identity, 48.81% similarity)<br>WP_097984025.1 (36.33% identity, 48.81% similarity)<br>APG08350.0 (26.14% identity, 40.46% similarity)<br>APG06056.0 (25.21% identity, 41.21% similarity) |
| APG09675.0 | 498 | | | | MTX | 65, 70, 75, 80, 85, 90, 91, 92, 93, 94, 95, 96, 97, 98, 99, 100 | 80, 85, 90, 91, 92, 93, 94, 95, 96, 97, 98, 99, 100 | APG02088.0 (63.79% identity, 79.73% similarity)<br>APG07824.0 (63.64% identity, 79.46% similarity)<br>APG07732.0 (43.23% identity, 60.32% similarity)<br>APG08495.0 (37.34% identity, 53.48% |

TABLE 1-continued

Summary of SEQ ID NOs, Gene Class, and Variants thereof

| APG ID | Seq ID | Modified Seq ID(s) | CryBP1 Seq ID | Split-Cry C-terminus Seq ID | Gene Class | % Identity | % Similarity | Homologs |
|---|---|---|---|---|---|---|---|---|
| | | | | | | | | similarity)<br>APG00598.0 US_2016_0355842_A1-140 (36.28% identity, 51.52% similarity)<br>APG05918.0 (34.82% identity, 54.63% similarity)<br>APG06880.0 (31.5% identity, 46.82% similarity)<br>APG02592.0 (31.33% identity, 50.32% similarity)<br>APG00236.0 US_2016_0355842_A1-32 (31.31% identity, 51.76% similarity)<br>APG07176.0 (31.25% identity, 50.94% similarity) |
| APG09773.0 | 499 | | | | Cry | 70, 75, 80, 85, 90, 91, 92, 93, 94, 95, 96, 97, 98, 99, 100 | 80, 85, 90, 91, 92, 93, 94, 95, 96, 97, 98, 99, 100 | APG01165.0 (95.13% identity, 96.43% similarity)<br>APG00296.0 US_2016_0355842_A1-52 (66.77% identity, 77.38% similarity)<br>WP_098926211.1 (66.77% identity, 77.38% similarity)<br>APG07033.0 (65.16% identity, 75.43% similarity)<br>APG03264.0 (58.54% identity, 71.99% similarity)<br>APG06221.0 (52.32% identity, 69.44% similarity)<br>APG00553.0 US_2016_0355842_A1-124 (50.72% identity, 68.32% similarity)<br>WP_098926212.1 (50.72% identity, 68.32% similarity)<br>APG04454.0 (50.39% identity, 67.09% similarity)<br>APG09727.0 (50.16% identity, 67.68% similarity) |
| APG09812.0 | 500 | | | | Cry | 97, 98, 99, 100 | 98, 99, 100 | WP_103108858.1 (96.99% identity, 98.15% similarity)<br>APG03438.0 (96.05% identity, 97.67% similarity)<br>APG09824.0 (95.81% identity, 97.44% similarity)<br>APG09936.0 (95.81% identity, 96.51% similarity)<br>APG04458.0 (94.42% identity, 96.51% similarity)<br>KNB72291.1 (94.42% identity, 96.51% similarity)<br>APG05978.0 (94.29% identity, 95.21% |

TABLE 1-continued

| Summary of SEQ ID NOs, Gene Class, and Variants thereof | | | | | | | | |
|---|---|---|---|---|---|---|---|---|
| APG ID | Seq ID | Modified Seq ID(s) | CryBP1 Seq ID | Split-Cry C-terminus Seq ID | Gene Class | % Identity | % Similarity | Homologs |
| | | | | | | | | similarity) APG04141.0 (93.72% identity, 96.51% similarity) WP_084765780.1 (92.71% identity, 94.53% similarity) WP_093871939.1 (37.53% identity, 58.43% similarity) |
| APG09814.0 | 501 | | | | Cry | 80, 85, 90, 91, 92, 93, 94, 95, 96, 97, 98, 99, 100 | 85, 90, 91, 92, 93, 94, 95, 96, 97, 98, 99, 100 | APG00965.0 (76.53% identity, 84.11% similarity) WP_001087511.1 (73.51% identity, 82.68% similarity) WP_097842690.1 (73.22% identity, 82.82% similarity) CA_2844913-12 (73.07% identity, 82.68% similarity) WP_098209375.1 (73.07% identity, 82.68% similarity) APG07954.0 (71.78% identity, 80.32% similarity) WP_098377949.1 (71.78% identity, 80.32% similarity) WP_098381669.1 (71.78% identity, 80.17% similarity) EEM92570.1 (70.6% identity, 78.6% similarity) APG00152.0 US_2016_0311864_A1-36 (65.56% identity, 78.15% similarity) |
| APG09826.0 | 502 | 503 | | | Cry | 85, 90, 91, 92, 93, 94, 95, 96, 97, 98, 99, 100 | 90, 91, 92, 93, 94, 95, 96, 97, 98, 99, 100 | APG00424.0 US_2016_0366881_A1-52 (82.76% identity, 85.66% similarity) WP_060852738.1 (82.76% identity, 85.66% similarity) APG03573.0 (82.0% identity, 86.1% similarity) WP_098349415.1 (81.93% identity, 85.15% similarity) APG00329.0 US_2016_0355842_A1-62 (79.65% identity, 82.78% similarity) WP_017762581.1 (77.93% identity, 81.32% similarity) APG07069.0 (76.74% identity, 83.01% similarity) WP_097891157.1 (75.49% identity, 82.47% similarity) US_8461415_B2-45 (75.31% identity, 82.29% similarity) |

TABLE 1-continued

| Summary of SEQ ID NOs, Gene Class, and Variants thereof | | | | | | | | |
|---|---|---|---|---|---|---|---|---|
| APG ID | Seq ID | Modified Seq ID(s) | CryBP1 Seq ID | Split-Cry C-terminus Seq ID | Gene Class | % Identity | % Similarity | Homologs |
| | | | | | | | | WP_044306759.1 (75.13% identity, 82.11% similarity) |
| APG09835.0 | 504 | | | | Cry | 60, 65, 70, 75, 80, 85, 90, 91, 92, 93, 94, 95, 96, 97, 98, 99, 100 | 65, 70, 75, 80, 85, 90, 91, 92, 93, 94, 95, 96, 97, 98, 99, 100 | APG08468.0 (96.88% identity, 98.44% similarity)<br>APG08852.0 (96.44% identity, 98.22% similarity)<br>OPA11477.1 (96.44% identity, 98.22% similarity)<br>APG08171.0 (92.2% identity, 94.43% similarity)<br>APG06424.0 (91.76% identity, 94.88% similarity)<br>APG00184.0 US_2016_0355842_A1-19 (59.24% identity, 63.03% similarity)<br>WP_044306772.1 (59.24% identity, 63.03% similarity)<br>WP_098816555.1 (59.02% identity, 62.81% similarity)<br>WP_097891175.1 (58.8% identity, 62.81% similarity)<br>WP_098217793.1 (58.8% identity, 62.81% similarity) |
| APG09895.0 | 505 | 506 | | | Cry | 65, 70, 75, 80, 85, 90, 91, 92, 93, 94, 95, 96, 97, 98, 99, 100 | 75, 80, 85, 90, 91, 92, 93, 94, 95, 96, 97, 98, 99, 100 | APG03986.0 (60.19% identity, 71.18% similarity)<br>APG00471.0 US_2016_0366881_A1-85 (47.7% identity, 58.22% similarity)<br>APG05538.0 (44.92% identity, 58.31% similarity)<br>APG00702.0 US_2017_0175134_A1-115 (40.28% identity, 58.32% similarity)<br>APG09511.0 (40.12% identity, 56.08% similarity)<br>APG07866.0 (40.06% identity, 55.5% similarity)<br>APG06995.0 (39.32% identity, 52.23% similarity)<br>APG05091.0 (38.96% identity, 52.15% similarity)<br>APG00401.0 US_2016_0311864_A1-168 (38.44% identity, 53.29% similarity)<br>APG00457.0 US_2016_0355842_A1-98 (37.42% identity, 54.04% similarity)<br>WP_044307385.1 (37.42% identity, 54.04% similarity)<br>WP_098376005.1 (37.42% identity, 54.04% similarity) |

TABLE 1-continued

| Summary of SEQ ID NOs, Gene Class, and Variants thereof | | | | | | | | |
|---|---|---|---|---|---|---|---|---|
| APG ID | Seq ID | Modified Seq ID(s) | CryBP1 Seq ID | Split-Cry C-terminus Seq ID | Gene Class | % Identity | % Similarity | Homologs |
| APG09901.0 | 507 | 508, 509 | | | MTX | 90, 91, 92, 93, 94, 95, 96, 97, 98, 99, 100 | 93, 94, 95, 96, 97, 98, 99, 100 | APG03506.0 (88.39% identity, 92.26% similarity)<br>WP_103623145.1 (83.83% identity, 89.22% similarity)<br>APG03861.0 (83.23% identity, 89.22% similarity)<br>APG07783.0 (83.23% identity, 88.92% similarity)<br>APG08912.0 (81.44% identity, 88.92% similarity)<br>APG00276.0 US_2016_0355842_A1-47 (32.86% identity, 46.29% similarity)<br>APG08369.0 (30.34% identity, 45.79% similarity)<br>APG00545.0 US_2016_0355842_A1-122 (30.0% identity, 44.0% similarity)<br>WP_061885189.1 (29.97% identity, 45.66% similarity)<br>WP_088118891.1 (29.69% identity, 45.66% similarity) |
| APG09903.0 | 510 | 511 | | | Cry | 30, 35, 40, 45, 50, 55, 60, 65, 70, 75, 80, 85, 90, 91, 92, 93, 94, 95, 96, 97, 98, 99, 100 | 45, 50, 55, 60, 65, 70, 75, 80, 85, 90, 91, 92, 93, 94, 95, 96, 97, 98, 99, 100 | APG02986.0 (29.07% identity, 44.84% similarity)<br>US_8461421_B2-198 (26.74% identity, 40.52% similarity)<br>US_8461421_B2-204 (26.48% identity, 41.23% similarity)<br>US_8461421_B2-180 (26.01% identity, 40.32% similarity)<br>US_8461421_B2-200 (25.27% identity, 38.62% similarity) |
| APG10001.0 | 512 | 513, 514 | | | MTX | 91, 92, 93, 94, 95, 96, 97, 98, 99, 100 | 93, 94, 95, 96, 97, 98, 99, 100 | OJG59749.1 (93.79% identity, 94.08% similarity)<br>WP_086334647.1 (92.01% identity, 92.01% similarity)<br>WP_071867270.1 (91.72% identity, 92.01% similarity)<br>WP_074798963.1 (91.42% identity, 91.72% similarity)<br>APG07672.0 (90.83% identity, 92.6% similarity)<br>WP_077151343.1 (89.94% identity, 91.42% similarity)<br>WP_062805258.1 (89.64% identity, 91.12% similarity)<br>WP_010735505.1 (89.35% identity, 91.12% similarity)<br>WP_023519628.1 (89.35% identity, 91.12% |

TABLE 1-continued

| Summary of SEQ ID NOs, Gene Class, and Variants thereof | | | | | | | | |
|---|---|---|---|---|---|---|---|---|
| APG ID | Seq ID | Modified Seq ID(s) | CryBP1 Seq ID | Split-Cry C-terminus Seq ID | Gene Class | % Identity | % Similarity | Homologs |
| | | | | | | | | similarity)<br>WP_019722830.1 (79.59% identity, 87.57% similarity) |
| APG01902.0 | 515 | 516 | | | Cry | 98, 99, 100 | 99, 100 | WP_103108858.1 (99.31% identity, 99.54% similarity)<br>APG09824.0 (97.67% identity, 98.84% similarity)<br>APG09812.0 (97.21% identity, 98.6% similarity)<br>APG02996.0 (97.21% identity, 98.14% similarity)<br>APG06717.0 (96.98% identity, 98.37% similarity)<br>APG03098.0 (96.74% identity, 98.37% similarity)<br>APG03438.0 (96.74% identity, 98.37% similarity)<br>APG04619.0 (96.05% identity, 97.91% similarity)<br>APG09936.0 (96.05% identity, 97.21% similarity)<br>APG05978.0 (95.21% identity, 96.12% similarity)<br>APG04458.0 (94.65% identity, 97.21% similarity)<br>KNB72291.1 (94.65% identity, 97.21% similarity)<br>APG04141.0 (93.49% identity, 96.51% similarity)<br>WP_084765780.1 (92.94% identity, 95.22% similarity)<br>APG04517.0 (91.2% identity, 94.44% similarity) |
| APG02996.0 | 517 | 518 | | | Cry | 97, 98, 99, 100 | 98, 99, 100 | APG09812.0 (97.91% identity, 98.84% similarity)<br>APG04619.0 (97.44% identity, 98.37% similarity)<br>APG01902.0 (97.21% identity, 98.14% similarity)<br>WP_103108858.1 (96.99% identity, 97.69% similarity)<br>APG03098.0 (96.74% identity, 97.91% similarity)<br>APG03438.0 (96.74% identity, 97.91% similarity)<br>APG06717.0 (96.28% identity, 97.67% |

TABLE 1-continued

| Summary of SEQ ID NOs, Gene Class, and Variants thereof | | | | | | | | |
|---|---|---|---|---|---|---|---|---|
| APG ID | Seq ID | Modified Seq ID(s) | CryBP1 Seq ID | Split-Cry C-terminus Seq ID | Gene Class | % Identity | % Similarity | Homologs |
| | | | | | | | | similarity)<br>APG09824.0 (96.28% identity, 97.44% similarity)<br>APG09936.0 (95.58% identity, 96.28% similarity)<br>APG05978.0 (94.75% identity, 95.21% similarity)<br>APG04458.0 (94.42% identity, 96.51% similarity)<br>KNB72291.1 (94.42% identity, 96.51% similarity)<br>APG04141.0 (93.49% identity, 96.28% similarity)<br>WP_084765780.1 (92.71% identity, 94.53% similarity)<br>APG04517.0 (91.67% identity, 94.44% similarity) |
| APG03098.0 | 519 | 520 | | | Cry | 98, 99, 100 | 100 | APG04619.0 (99.3% identity, 99.53% similarity)<br>APG09824.0 (97.67% identity, 99.07% similarity)<br>APG06717.0 (97.67% identity, 98.84% similarity)<br>APG03438.0 (97.44% identity, 98.84% similarity)<br>APG01902.0 (96.74% identity, 98.37% similarity)<br>APG02996.0 (96.74% identity, 97.91% similarity)<br>WP_103108858.1 (96.53% identity, 97.92% similarity)<br>APG05978.0 (96.35% identity, 97.03% similarity)<br>APG09812.0 (96.28% identity, 97.91% similarity)<br>APG09936.0 (95.12% identity, 96.74% similarity)<br>KNB72291.1 (94.88% identity, 97.21% similarity)<br>APG04458.0 (94.65% identity, 97.21% similarity)<br>APG04141.0 (93.49% identity, 96.98% similarity)<br>WP_084765780.1 (93.17% identity, 95.22% similarity) |

TABLE 1-continued

Summary of SEQ ID NOs, Gene Class, and Variants thereof

| APG ID | Seq ID | Modified Seq ID(s) | CryBP1 Seq ID | Split-Cry C-terminus Seq ID | Gene Class | % Identity | % Similarity | Homologs |
|---|---|---|---|---|---|---|---|---|
| | | | | | | | | APG04517.0 (91.2% identity, 94.91% similarity) |
| APG04517.0 | 521 | | | | Cry | 92, 93, 94, 95, 96, 97, 98, 99, 100 | 96, 97, 98, 99, 100 | APG04141.0 (92.34% identity, 95.59% similarity)<br>KNB72291.1 (91.88% identity, 94.9% similarity)<br>APG09824.0 (91.67% identity, 95.37% similarity)<br>APG03438.0 (91.67% identity, 94.91% similarity)<br>WP_103108858.1 (91.67% identity, 94.68% similarity)<br>APG02996.0 (91.67% identity, 94.44% similarity)<br>APG04458.0 (91.65% identity, 94.66% similarity)<br>APG06717.0 (91.44% identity, 95.14% similarity)<br>APG09812.0 (91.44% identity, 94.21% similarity)<br>APG03098.0 (91.2% identity, 94.91% similarity)<br>APG01902.0 (91.2% identity, 94.44% similarity)<br>APG09936.0 (91.18% identity, 93.27% similarity)<br>WP_084765780.1 (90.87% identity, 93.61% similarity)<br>APG04619.0 (90.74% identity, 94.68% similarity)<br>APG05978.0 (90.41% identity, 93.61% similarity) |
| APG04619.0 | 522 | 523 | | | Cry | 98, 99, 100 | 99, 100 | APG03098.0 (99.3% identity, 99.53% similarity)<br>APG02996.0 (97.44% identity, 98.37% similarity)<br>APG03438.0 (97.21% identity, 98.84% similarity)<br>APG09824.0 (96.98% identity, 98.6% similarity)<br>APG06717.0 (96.98% identity, 98.37% similarity)<br>APG01902.0 (96.05% identity, 97.91% similarity)<br>WP_103108858.1 (95.83% identity, 97.45% similarity)<br>APG09812.0 (95.81% identity, 97.67% |

TABLE 1-continued

| Summary of SEQ ID NOs, Gene Class, and Variants thereof | | | | | | | | |
|---|---|---|---|---|---|---|---|---|
| APG ID | Seq ID | Modified Seq ID(s) | CryBP1 Seq ID | Split-Cry C-terminus Seq ID | Gene Class | % Identity | % Similarity | Homologs |
| | | | | | | | | similarity) APG05978.0 (95.66% identity, 96.58% similarity) APG09936.0 (94.65% identity, 96.51% similarity) KNB72291.1 (94.42% identity, 96.98% similarity) APG04458.0 (94.19% identity, 96.98% similarity) APG04141.0 (93.02% identity, 96.74% similarity) WP_084765780.1 (92.71% identity, 94.99% similarity) APG04517.0 (90.74% identity, 94.68% similarity) |
| APG06717.0 | 524 | 525 | | | Cry | 97, 98, 99, 100 | 100 | APG03098.0 (97.67% identity, 98.84% similarity) APG03438.0 (96.98% identity, 99.07% similarity) APG01902.0 (96.98% identity, 98.37% similarity) APG04619.0 (96.98% identity, 98.37% similarity) WP_103108858.1 (96.76% identity, 97.92% similarity) APG09824.0 (96.74% identity, 98.84% similarity) APG02996.0 (96.28% identity, 97.67% similarity) APG09812.0 (95.81% identity, 97.67% similarity) APG05978.0 (95.43% identity, 96.8% similarity) KNB72291.1 (95.12% identity, 97.91% similarity) APG09936.0 (95.12% identity, 96.98% similarity) APG04458.0 (94.88% identity, 97.67% similarity) APG04141.0 (93.49% identity, 97.21% similarity) WP_084765780.1 (93.39% identity, 95.9% similarity) APG04517.0 (91.44% identity, 95.14% similarity) |

i. Classes of Pesticidal Proteins

The pesticidal proteins provided herein and the nucleotide sequences encoding them are useful in methods for impacting pests. That is, the compositions and methods of the invention find use in agriculture for controlling or killing pests, including pests of many crop plants. The pesticidal proteins provided herein are toxin proteins from bacteria and exhibit activity against certain pests. The pesticidal proteins are from several classes of toxins including Cry, Cyt, BIN, Mtx toxins. See, for example, Table 1 for the specific protein classifications of the various SEQ ID NOs provided herein. In addition, reference is made throughout this disclosure to Pfam database entries. The Pfam database is a database of protein families, each represented by multiple sequence alignments and a profile hidden Markov model. Finn et al. (2014) *Nucl. Acid Res.* Database Issue 42:D222-D230.

*Bacillus thuringiensis* (Bt) is a gram-positive bacterium that produces insecticidal proteins as crystal inclusions during its sporulation phase of growth. The proteinaceous inclusions of *Bacillus thuringiensis* (Bt) are called crystal proteins or 6-endotoxins (or Cry proteins), which are toxic to members of the class Insecta and other invertebrates. Similarly, Cyt proteins are parasporal inclusion proteins from Bt that exhibits hemolytic (Cytolitic) activity or has obvious sequence similarity to a known Cyt protein. These toxins are highly specific to their target organism, are innocuous to humans, vertebrates, and plants.

The structure of the Cry toxins reveals five conserved amino acid blocks, concentrated mainly in the center of the domain or at the junction between the domains. The Cry toxin consists of three domains, each with a specific function. Domain I is a seven α-helix bundle in which a central helix is completely surrounded by six outer helices. This domain is implicated in channel formation in the membrane. Domain II appears as a triangular column of three anti-parallel β-sheets, which are similar to antigen-binding regions of immunoglobulins. Domain III contains anti-parallel β-strands in a β sandwich form. The N-terminal part of the toxin protein is responsible for its toxicity and specificity and contains five conserved regions. The C-terminal part is usually highly conserved and probably responsible for crystal formation. See, for example, U.S. Pat. No. 8,878,007.

Strains of *B. thuringiensis* show a wide range of specificity against different insect orders (Lepidoptera, Diptera, Coleoptera, Hymenoptera, Homoptera, Phthiraptera or Mallophaga, and Acari) and other invertebrates (Nemathelminthes, Platyhelminthes, and Sarocomastebrates). The cry proteins have been classified into groups based on toxicity to various insect and invertebrate groups. Generally, Cry I demonstrates toxicity to lepidopterans, Cry II to lepidopterans and dipterans, CryIII to coleopterans, Cry IV to dipterans, and Cry V and Cry VI to nematodes. New Cry proteins can be identified and assigned to a Cry group based on amino acid identity. See, for example, Bravo, A. (1997) *J. of Bacteriol.* 179:2793-2801; Bravo et al. (2013) *Microb. Biotechnol.* 6:17-26, herein incorporated by reference.

Over 750 different cry gene sequences have been classified into 73 groups (Cry1-Cry73), with new members of this gene family continuing to be discovered (Crickmore et al. (2014) www.btnomenclature.info/). The cry gene family consists of several phylogentically non-related protein families that may have different modes of action: the family of three-domain Cry toxins, the family of mosquitocidal Cry toxins, the family of the binary-like toxins, and the Cyt family of toxins (Bravo et al., 2005). Some Bt strains produce additional insecticidal toxins, the VIP toxins. See, also, Cohen et al. (2011) *J. Mol. Biol.* 413:4-814; Crickmore et al. (2014) *Bacillus thuringiensis* toxin nomenclature, found on the world wide web at lifesci.sussex.ac.uk/home/Neil_Crickmore/Bt/; Crickmore et al. (1988) *Microbiol. Mol. Biol. Rev.* 62: 807-813; Gill et al. (1992) *Ann. Rev. Entomol.* 37: 807-636; Goldbert et al. (1997) *Appl. Environ. Microbiol.* 63:2716-2712; Knowles et al. (1992) *Proc. R. Soc. Ser. B.* 248: 1-7; Koni et al. (1994) *Microbiology* 140: 1869-1880; Lailak et al. (2013) *Biochem. Biophys. Res. Commun.* 435: 216-221; Lopez-Diaz et al. (2013) *Environ. Microbiol.* 15: 3030-3039; Perez et al. (2007) *Cell. Microbiol.* 9: 2931-2937; Promdonkoy et al. (2003) *Biochem. J.* 374: 255-259; Rigden (2009) *FEBS Lett.* 583: 1555-1560; Schnepf et al. (1998) *Microbiol. Mol. Biol. Rev.* 62: 775-806; Soberon et al. (2013) *Peptides* 41: 87-93; Thiery et al. (1998) *J. Am. Mosq. Control Assoc.* 14: 472-476; Thomas et al. (1983) *FEBS Lett.* 154: 362-368; Wirth et al. (1997) *Proc. Natl. Acad. Sci. U.S.A.* 94: 10536-10540; Wirth et al (2005) *Appl. Environ. Microbiol.* 71: 185-189; and, Zhang et al. (2006) *Biosci. Biotechnol. Biochem.* 70: 2199-2204; each of which is herein incorporated by reference in their entirety.

Cyt designates a parasporal crystal inclusion protein from *Bacillus thuringiensis* with cytolytic activity, or a protein with sequence similarity to a known Cyt protein. (Crickmore et al. (1998) *Microbiol. Mol. Biol. Rev.* 62: 807-813). The gene is denoted by cyt. These proteins are different in structure and activity from Cry proteins (Gill et al. (1992) *Annu. Rev. Entomol.* 37: 615-636). The Cyt toxins were first discovered in *B. thuringiensis* subspecies *israelensis* (Goldberg et al. (1977) *Mosq. News.* 37: 355-358). There are 3 Cyt toxin families including 11 holotype toxins in the current nomenclature (Crickmore et al. (2014) *Bacillus thuringiensis* toxin nomenclature found on the world wide web at lifesci.sussex.ac.uk/home/Neil_Crickmore/Bt/). The majority of the *B. thuringiensis* isolates with cyt genes show activity against dipteran insects (particularly mosquitoes and black flies), but there are also cyt genes that have been described in *B. thuringiensis* strains targeting lepidopteran or coleopteran insects (Guerchicoff et al. (1997) *Appl. Environ. Microbiol.* 63: 2716-2721).

The structure of Cyt2A, solved by X-ray crystallography, shows a single domain where two outer layers of α-helix wrap around a mixed β-sheet. Further available crystal structures of Cyt toxins support a conserved α-β structural model with two α-helix hairpins flanking a β-sheet core containing seven to eight β-strands. (Cohen et al. (2011) *J. Mol. Biol.* 413: 80 4-814) Mutagenic studies identified β-sheet residues as critical for toxicity, while mutations in the helical domains did not affect toxicity (Adang et al.; Diversity of *Bacillus thuringiensis* Crystal Toxins and Mechanism of Action. In: T. S. Dhadialla and S. S. Gill, eds, *Advances in Insect Physiology*, Vol. 47, Oxford: Academic Press, 2014, pp. 39-87.) The representative domain of the Cyt toxin is a 8-endotoxin, Bac_thur_toxin (Pfam PF01338).

There are multiple proposed models for the mode of action of Cyt toxins, and it is still an area of active investigation. Some Cyt proteins (Cyt1A) have been shown to require the presence of accessory proteins for crystallization. Cyt1A and Cyt2A protoxins are processed by digestive proteases at the same sites in the N- and C-termini to a stable toxin core. Cyt toxins then interact with non-saturated membrane lipids, such as phosphatidylcholine, phosphatidylethanolamine, and sphingomyelin. For Cyt toxins, pore-formation and detergent-like membrane disruption have been proposed as non-exclusive mechanisms; and it is generally accepted that both may occur depending on toxin concentration, with lower concentrations favoring oligomeric pores and higher concentrations leading to membrane breaks. (Butko (2003) *Appl. Environ. Microbiol.* 69: 2415-2422) In the pore-formation model, the Cyt toxin binds to the cell membrane, inducing the formation of cation-selective channels in the membrane vesicles leading to colloid-osmotic lysis of the cell. (Knowles et al. (1989) FEBS Lett. 244: 259-262; Knowles et al. (1992) Proc. R. Soc. Ser. B. 248: 1-7 and Promdonkoy et al. (2003) *Biochem. J.* 374: 255-259). In the detergent model, there is a nonspecific aggregation of the toxin on the surface of the lipid bilayer leading to membrane disassembly and cell death. (Butko (2003) supra; Manceva et al. (2005) *Biochem.* 44: 589-597).

Multiple studies have shown synergistic activity between Cyt toxins and other *B. thuringiensis* toxins, particularly the Cry, Bin, and Mtx toxins. This synergism has even been shown to overcome an insect's resistance to the other toxin. (Wirth 1997, Wirth 2005, Thiery 1998, Zhang 2006) The Cyt synergistic effect for Cry toxins is proposed to involve Cyt1A binding to domain II of Cry toxins in solution or on the membrane plane to promote formation of a Cry toxin pre-pore oligomer. Formation of this oligomer is independent of the Cyt oligomerization, binding or insertion. (Lailak 2013, Perez 2007, Lopez-Diaz 2013)

A number of pesticidal proteins unrelated to the Cry proteins are produced by some strains of *B. thuringiensis* and *B. cereus* during vegetative growth (Estruch et al. (1996) *Proc Natl Acad Sci USA* 93:5389-5394; Warren et al. (1994) WO 94/21795). These vegetative insecticidal proteins, or Vips, do not form parasporal crystal proteins and are apparently secreted from the cell. The Vips are presently excluded from the Cry protein nomenclature because they are not crystal-forming proteins. The term VIP is a misnomer in the sense that some *B. thuringiensis* Cry proteins are also produced during vegetative growth as well as during the stationary and sporulation phases, most notably Cry3Aa. The location of the Yip genes in the *B. thuringiensis* genome has been reported to reside on large plasmids that also encode cry genes (Mesrati et al. (2005) *FEMS Microbiol. Lett.* 244(2):353-8). A web-site for the nomenclature of Bt toxins can be found on the world wide web at lifesci.sussex.ac.uk with the path "/home/Neil_Crickmore/Bt/" and at: "btnomenclature.info/". See also, Schnepf et al. (1998) *Microbiol. Mol. Biol. Rev.* 62(3):775-806. Such references are herein incorporated by reference.

Vip genes can be classified into 4 categories. Some Vip genes form binary two-component protein complexes; an "A" component is usually the "active" portion, and a "B" component is usually the "binding" portion. (Pfam pfam.xfam.org/family/PF03495). The Vip1 and Vip4 proteins generally contain binary toxin B protein domains. Vip2 proteins generally contain binary toxin A protein domains.

The Vip1 and Vip2 proteins are the two components of a binary toxin that exhibits toxicity to coleopterans. Vip1Aa1 and Vip2Aa1 are very active against corn rootworms, particularly *Diabrotica virgifera* and *Diabrotica longicornis* (Han et al. (1999) Nat. Struct. Biol. 6:932-936; Warren G W (1997) "Vegetative insecticidal proteins: novel proteins for control of corn pests" In: Carozzi N B, Koziel M (eds) *Advances in insect control, the role of transgenic plants*; Taylor & Francis Ltd, London, pp 109-21). The membrane-binding 95 kDa Vip1 multimer provides a pathway for the 52 kDa vip2 ADP-ribosylase to enter the cytoplasm of target western corn rootworm cells (Warren (1997) supra). The NAD-dependent ADP-ribosyltransferase Vip2 likely modifies monomeric actin at Arg177 to block polymerization, leading to loss of the actin cytoskeleton and eventual cell death due to the rapid subunit ex-change within actin filaments in vivo (Carlier M. F. (1990) *Adv. Biophys.* 26:51-73).

Like Cry toxins, activated Vip3A toxins are pore-forming proteins capable of making stable ion channels in the membrane (Lee et al. (2003) *Appl. Environ. Microbiol.* 69:4648-4657). Vip3 proteins are active against several major lepidopteran pests (Rang et al. (2005) *Appl. Environ. Microbiol.* 71(10):6276-6281; Bhalla et al. (2005) *FEMS Microbiol. Lett.* 243:467-472; Estruch et al. (1998) WO 9844137; Estruch et al. (1996) *Proc Natl Acad Sci USA* 93:5389-5394; Selvapandiyan et al. (2001) *Appl. Environ Microbiol.* 67:5855-5858; Yu et al. (1997) *Appl. Environ Microbiol.* 63:532-536). Vip3A is active against *Agrotis ipsilon, Spodoptera frugiperda, Spodoptera exigua, Heliothis virescens*, and *Helicoverpa zea* (Warren et al. (1996) WO 96/10083; Estruch et al. (1996) *Proc Natl Acad Sci USA* 93:5389-5394). Like Cry toxins, Vip3A proteins must be activated by proteases prior to recognition at the surface of the midgut epithelium of specific membrane proteins different from those recognized by Cry toxins.

The MTX family of toxin proteins is characterized by the presence of a conserved domain, ETX_MTX2 (pfam 03318). Members of this family share sequence homology with the mosquitocidal toxins Mtx2 and Mtx3 from *Bacillus sphaericus*, as well as with the epsilon toxin ETX from *Clostridium perfringens* (Cole et al. (2004) *Nat. Struct. Mol. Biol.* 11: 797-8; Thanabalu et al. (1996) Gene 170:85-9). The MTX-like proteins are structurally distinct from the three-domain Cry toxins, as they have an elongated and predominately β-sheet-based structure. However, similar to the three-domain toxins, the MTX-like proteins are thought to form pores in the membranes of target cells (Adang et al. (2014) supra). Unlike the three-domain Cry proteins, the MTX-like proteins are much smaller in length, ranging from 267 amino acids (Cry23) to 340 amino acids (Cry15A).

The protein family of MTX-like toxins is a relatively small class compared to the three-domain Cry family (Crickmore et al. (2014) supra; Adang et al. (2014) supra). The members of the MTX-like toxin family include Cry15, Cry23, Cry33, Cry38, Cry45, Cry46, Cry51, Cry60A, Cry60B, and Cry64. This family exhibits a range of insecticidal activity, including activity against insect pests of the Lepidopteran and Coleopteran orders. Some members of this family may form binary partnerships with other proteins, which may or may not be required for insecticidal activity.

Cry15 is a 34 kDA protein that was identified in *Bacillus thuringiensis* serovar thompsoni HD542; it occurs naturally in a crystal together with an unrelated protein of approximately 40 kDa. The gene encoding Cry15 and its partner protein are arranged together in an operon. Cry15 alone has been shown to have activity against lepidopteran insect pests including *Manduca sexta, Cydia pomonella*, and *Pieris rapae*, with the presence of the 40 kDA protein having been shown to increase activity of Cry15 only against *C. pomonella* (Brown K. and Whiteley H. (1992) *J. Bacteriol.* 174:549-557; Naimov et al. (2008) *Appl. Environ. Microbiol.* 74:7145-7151). Further studies are needed to elucidate the function of the partner protein of Cry15. Similarly, Cry23 is a 29 kDA protein that has been shown to have activity against the coleopteran pests *Tribolium castaneum* and *Popillia japonica* together with its partner protein Cry37 (Donovan et al. (2000) U.S. Pat. No. 6,063,756).

New members of the MTX-like family are continuing to be identified. An ETX_MTX toxin gene was recently identified in the genome of *Bacillus thuringiensis* serovar tolworthi strain Na205-3. This strain was found to be toxic against the lepidpoteran pest *Helicoverpa armigera*, and it also contained homologs of Cry1, Cry11, Vip1, Vip2, and Vip3 (Palma et al. (2014) *Genome Announc.* 2(2): e00187-14. Published online Mar. 13, 2014 at doi: 10.1128/genomeA.00187-14; PMCID: PMC3953196). Because the MTX-like proteins have a unique domain structure relative to the three-domain Cry proteins, they are believed to possess a unique mode of action, thereby making them a valuable tool in insect control and the fight against insect resistance. Bacterial cells produce large numbers of toxins with diverse specificity against host and non-host organisms. Large families of binary toxins have been identified in numerous bacterial families, including toxins that have activity against insect pests. (Poopathi and Abidha (2010) *J. Physiol. Path.* 1(3): 22-38). Lysinibacillus *sphaericus* (Ls), formerly *Bacillus sphaericus*, (Ahmed et al. (2007) *Int. J. Syst. Evol. Microbiol.* 57:1117-1125) is well-known as an insect biocontrol strain. Ls produces several insecticidal proteins, including the highly potent binary complex BinA/BinB. This binary complex forms a parasporal crystal in Ls cells and has strong and specific activity against dipteran insects, specifically mosquitos. In some areas, insect resistance to existing Ls mosquitocidal strains has been reported. The discovery of new binary toxins with different target specificity or the ability to overcome insect resistance is of significant interest.

The Ls binary insecticidal protein complex contains two major polypeptides, a 42 kDa polypeptide and a 51 kDa polypepdide, designated BinA and BinB, respectively (Ahmed et al. (2007) supra). The two polypeptides act synergistically to confer toxicity to their targets. Mode of action involves binding of the proteins to receptors in the larval midgut. In some cases, the proteins are modified by protease digestion in the larval gut to produce activated forms. The BinB component is thought to be involved in binding, while the BinA component confers toxicity (Nielsen-LeRoux et al. (2001) *Appl. Environ. Microbiol.* 67(11):5049-5054). When cloned and expressed separately, the BinA component is toxic to mosquito larvae, while the BinB component is not. However, co-administration of the proteins markedly increases toxicity (Nielsen-LeRoux et al. (2001) supra).

A small number of Bin protein homologs have been described from bacterial sources. Priest et al. (1997) *Appl. Environ. Microbiol.* 63(4):1195-1198 describe a hybridization effort to identify new Ls strains, although most of the genes they identified encoded proteins identical to the known BinA/BinB proteins. The BinA protein contains a defined conserved domain known as the Toxin 10 superfamily domain. This toxin domain was originally defined by its presence in BinA and BinB. The two proteins both have the domain, although the sequence similarity between BinA and BinB is limited in this region (<40%). The Cry49Aa protein, which also has insecticidal activity, also has this domain (described below).

The Cry48Aa/Cry49Aa binary toxin of Ls has the ability to kill *Culex quinquefasciatus* mosquito larvae. These proteins are in a protein structural class that has some similarity to the Cry protein complex of *Bacillus thuringiensis* (Bt), a well-known insecticidal protein family. The Cry34/Cry35 binary toxin of Bt is also known to kill insects, including Western corn rootworm, a significant pest of corn. Cry34, of which several variants have been identified, is a small (14 kDa) polypeptide, while Cry35 (also encoded by several variants) is a 44 kDa polypeptide. These proteins have some sequence homology with the BinA/BinB protein group and are thought to be evolutionarily related (Ellis et al. (2002) *Appl. Environ. Microbiol.* 68(3):1137-1145).

Phosphoinositide phospholipase C proteins (PI-PLC; also phosphotidylinositol phospholipase C) are members of the broader group of phospholipase C proteins. Many of these proteins play important roles in signal transduction as part of normal cell physiology. Several important bacterial toxins also contain domains with similarity to these proteins (Titball, R. W. (1993) *Microbiological Reviews.* 57(2):347-366). Importantly, these proteins are implicated in signal amplification during intoxication of insect cells by Bt Cry proteins (Valaitis, A. P. (2008) *Insect Biochemistry and Molecular Biology.* 38: 611-618).

The PI-PLC toxin class occurs in *Bacillus* isolates, commonly seen in co-occurrence with homologs to other described toxin classes, such as Binary Toxins. This class of sequences has homology to phosphatidylinositol phosphodiesterases (also referred to as phosphatidylinositol-specific phospholipase C-PI-PLC). The crystal structure and its active site were solved for *B. cereus* PI-PLC by Heinz et al (Heinz, et. al., (1995) The EMBO Journal. 14(16): 3855-3863). The roles of the *B. cereus* PI-PLC active site amino acid residues in catalysis and substrate binding were investigated by Gässier et al using site-directed mutagenesis, kinetics, and crystal structure analysis (Gässier, et. al., (1997) Biochemistry. 36(42): 12802-13).

These PI-PLC toxin proteins contain a PLC-like phosphodiesterase, TIM beta/alpha-barrel domain (IPRO17946) and/or a Phospholipase C, phosphatidylinositol-specific, X domain (IPR000909) (also referred to as the PI-PLC X-box domain). We have also seen proteins with these domains in combination with other typical *Bacillus* protein toxin domains. This list includes most commonly a lectin domain (IPR000772), a sugar-binding domain that can be present in one or more copies and is thought to bind cell membranes, as well as the Insecticidal crystal toxin (IPR008872) (also referred to as Toxin10 or P42), which is the defining domain of the Binary Toxin.

Previously, toxins of this PI-PLC class were defined in U.S. Pat. No. 8,318,900 B2 SEQ ID NOs: 30 (DNA) and 79 (amino acid), in U.S. Patent Publication No. 20110263488A1 SEQ ID NOs: 8 (DNA) and 9 (amino acid), and in U.S. Pat. No. 8,461,421B2 SEQ ID NOs: 3 (DNA) and 63 (amino acid).

Provided herein are pesticidal proteins from these classes of toxins. The pesticidal proteins are classified by their structure, homology to known toxins and/or their pesticidal specificity.

ii. Variants and Fragments of Pesticidal Proteins and Polynucleotides Encoding the Same Pesticidal proteins or polypeptides of the invention include those set forth in SEQ ID NOs: 1, 2, 3, 4, 5, 6, 7, 8, 9, 10, 11, 12, 13, 14, 15, 16, 17, 18, 19, 20, 21, 22, 23, 24, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, and/or 525, and fragments and variants thereof. By "pesticidal toxin" or "pesticidal protein" or "pesticidal polypeptide" is intended a toxin or protein or polypeptide that has activity against one or more pests, including, insects, fungi, nematodes, and the like such that the pest is killed or controlled.

An "isolated" or "purified" polypeptide or protein, or biologically active portion thereof, is substantially or essentially free from components that normally accompany or interact with the polypeptide or protein as found in its naturally occurring environment. Thus, an isolated or purified polypeptide or protein is substantially free of other cellular material, or culture medium when produced by recombinant techniques, or substantially free of chemical precursors or other chemicals when chemically synthesized. A protein that is substantially free of cellular material includes preparations of protein having less than about 30%, 20%, 10%, 5%, or 1% (by dry weight) of contaminating protein. When the protein of the invention or biologically active portion thereof is recombinantly produced, optimally culture medium represents less than about 30%, 20%, 10%, 5%, or 1% (by dry weight) of chemical precursors or non-protein-of-interest chemicals.

The term "fragment" refers to a portion of a polypeptide sequence of the invention. "Fragments" or "biologically active portions" include polypeptides comprising a sufficient number of contiguous amino acid residues to retain the biological activity, i.e., have pesticidal activity. Fragments of the pesticidal proteins include those that are shorter than the full-length sequences, either due to the use of an alternate downstream start site, or due to processing that produces a shorter protein having pesticidal activity. Processing may occur in the organism the protein is expressed in, or in the pest after ingestion of the protein. Examples of fragments of the proteins can be found in Table 1. A biologically active portion of a pesticidal protein can be a polypeptide that is, for example, 10, 25, 50, 100, 150, 200, 250 or more amino acids in length of any one of SEQ ID NO: 1, 2, 3, 4, 5, 6, 7, 8, 9, 10, 11, 12, 13, 14, 15, 16, 17, 18, 19, 20, 21, 22, 23, 24, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, and/or 525. Such biologically active portions can be prepared by recombinant techniques and evaluated for pesticidal activity. As used here, a fragment comprises at least 8 contiguous amino acids of SEQ ID NOs: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, and/or 525.

Bacterial genes, including those encoding the pesticidal proteins disclosed herein, quite often possess multiple methionine initiation codons in proximity to the start of the open reading frame. Often, translation initiation at one or more of these start codons will lead to generation of a functional protein. These start codons can include ATG codons. However, bacteria such as *Bacillus* sp. also recognize the codon GTG as a start codon, and proteins that initiate translation at GTG codons contain a methionine at the first amino acid. On rare occasions, translation in bacterial systems can initiate at a TTG codon, though in this event the TTG encodes a methionine. Furthermore, it is not often determined a priori which of these codons are used naturally in the bacterium. Thus, it is understood that use of one of the alternate methionine codons may also lead to generation of pesticidal proteins. These pesticidal proteins are encompassed in the present invention and may be used in the methods disclosed herein. It will be understood that, when expressed in plants, it will be necessary to alter the alternate start codon to ATG for proper translation.

In various embodiments the pesticidal proteins provided herein include amino acid sequences deduced from the full-length nucleotide sequences and amino acid sequences that are shorter than the full-length sequences due to the use of an alternate downstream start site. Thus, the nucleotide sequence of the invention and/or vectors, host cells, and plants comprising the nucleotide sequence of the invention (and methods of making and using the nucleotide sequence of the invention) may comprise a nucleotide sequence encoding an alternate start site.

It is recognized that modifications may be made to the pesticidal polypeptides provided herein creating variant proteins. Changes designed by man may be introduced through the application of site-directed mutagenesis techniques. Alternatively, native, as yet-unknown or as yet unidentified polynucleotides and/or polypeptides structurally and/or functionally-related to the sequences disclosed herein may also be identified that fall within the scope of the present invention. Conservative amino acid substitutions may be made in nonconserved regions that do not alter the function of the pesticidal proteins. Alternatively, modifications may be made that improve the activity of the toxin. Modification of Cry toxins by domain III swapping has resulted in some cases in hybrid toxins with improved toxicities against certain insect species. Thus, domain III swapping could be an effective strategy to improve toxicity of Cry toxins or to create novel hybrid toxins with toxicity against pests that show no susceptibility to the parental Cry toxins. Site-directed mutagenesis of domain II loop sequences may result in new toxins with increased insecticidal activity. Domain II loop regions are key binding regions of initial Cry toxins that are suitable targets for the mutagenesis and selection of Cry toxins with improved insecticidal properties. Domain I of the Cry toxin may be modified to introduce protease cleavage sites to improve activity against certain pests. Strategies for shuffling the three different domains among large numbers of cry genes and high through output bioassay screening methods may provide novel Cry toxins with improved or novel toxicities.

As indicated, fragments and variants of the polypeptides disclosed herein will retain pesticidal activity. Pesticidal activity comprises the ability of the composition to achieve an observable effect diminishing the occurrence or an activity of the target pest, including for example, bringing about death of at least one pest, or a noticeable reduction in pest growth, feeding, or normal physiological development. Such decreases in numbers, pest growth, feeding or normal development can comprise any statistically significant decrease, including, for example a decrease of about 5%, 10%, 15%, 20%, 25%, 30%, 35%, 40%, 45%, 50%, 55%, 60%, 65%, 70%, 75%, 85%, 90%, 95% or greater. The pesticidal activity against one or more of the various pests provided herein, including, for example, pesticidal activity against Coleoptera, Diptera, Hymenoptera, Lepidoptera, Mallophaga, Homoptera, Hemiptera, Orthroptera, Nematodes, Thysanoptera, Dermaptera, Isoptera, Anoplura, Siphonaptera, Trichoptera, etc., or any other pest described herein. It is recognized that the pesticidal activity may be different or improved relative to the activity of the native protein, or it may be unchanged, so long as pesticidal activity is retained. Methods for measuring pesticidal activity are provided elsewhere herein. See also, Czapla and Lang (1990) *J. Econ. Entomol.* 83:2480-2485; Andrews et al. (1988) *Biochem. J.* 252:199-206; Marrone et al. (1985) *J. of Economic Entomology* 78:290-293; and U.S. Pat. No. 5,743,477, all of which are herein incorporated by reference in their entirety.

By "variants" is intended polypeptides having an amino acid sequence that is at least about 60%, about 65%, about 70%, about 75%, about 80%, about 85%, about 86%, about 87%, about 88%, about 89%, about 90%, about 91%, about 92%, about 93%, about 94%, about 95%, about 96%, about 97%, about 98% or about 99% identical to the amino acid sequence of any of SEQ ID NOs: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, and/or 525, and retain pesticidal activity. Note, Table 1 provides non-limiting examples of variant polypeptides (and polynucleotide encoding the same) for each of SEQ ID NOs: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, and/or 525. A biologically active variant of a pesticidal polypeptide of the invention may differ by as few as about 1-15 amino acid residues, as few as about 1-10, such as about 6-10, as few as 5, as few as 4, as few as 3, as few as 2, or as few as 1 amino acid residue. In specific embodiments, the polypeptides can comprise an N-terminal or a C-terminal truncation, which can comprise at least a deletion of 10, 15, 20, 25, 30, 35, 40, 45, 50 amino acids or more from either the N or C terminal of the polypeptide.

Table 2 provides protein domains found in SEQ ID NOs: 1-525 based on PFAM data. Both the domain description and the positions within a given SEQ ID NO are provided in Table 2. In specific embodiments, the active variant comprising any one of SEQ ID NOs: 1-525 can comprise at least 70%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% sequence identity to any one of SEQ ID NOs: 1-525 and further comprises at least one of the conserved domains set forth in Table 2. For example, in one embodiment, the active variant will comprise at least 70%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% sequence identity to SEQ ID NO:1, and further comprises the native amino acids at positions 267-329.

TABLE 2

Summary of PFAM domains in each of SEQ ID NOs: 1-525

| APG ID | Seq ID | Modification Type | Accession | Description | Start | Stop |
|---|---|---|---|---|---|---|
| APG00751.0 | 1 | | PF03945 | delta endotoxin, N-terminal domain | 134 | 244 |
| | | | PF03945 | delta endotoxin, N-terminal domain | 267 | 329 |
| | | | PF00555 | delta endotoxin | 337 | 517 |
| | | | PF03944 | delta endotoxin | 549 | 690 |
| APG00751.1 | 2 | 3' Truncation | PF03945 | delta endotoxin, N-terminal domain | 133 | 244 |
| | | | PF03945 | delta endotoxin, N-terminal domain | 267 | 329 |
| | | | PF00555 | delta endotoxin | 337 | 517 |
| | | | PF03944 | delta endotoxin | 549 | 690 |
| APG00751 CryBP1 (APG04508.0) | 3 | | no PFAM domains | | | |
| APG00831.0 | 4 | | PF03945 | delta endotoxin, N-terminal domain | 90 | 303 |
| | | | PF00555 | delta endotoxin | 311 | 524 |
| | | | PF03944 | delta endotoxin | 534 | 674 |

TABLE 2-continued

Summary of PFAM domains in each of SEQ ID NOs: 1-525

| APG ID | Seq ID | Modification Type | Accession | Description | Start | Stop |
|---|---|---|---|---|---|---|
| APG00831.1 | 5 | Alternate start | PF03945 | delta endotoxin, N-terminal domain | 84 | 297 |
| | | | PF00555 | delta endotoxin | 305 | 518 |
| | | | PF03944 | delta endotoxin | 528 | 668 |
| APG00831.2 | 6 | Alternate start and 3' Truncation | PF03945 | delta endotoxin, N-terminal domain | 84 | 297 |
| | | | PF00555 | delta endotoxin | 305 | 397 |
| | | | PF03944 | delta endotoxin | 528 | 668 |
| APG00832.0 | 7 | | PF03945 | delta endotoxin, N-terminal domain | 103 | 291 |
| | | | PF00555 | delta endotoxin | 309 | 506 |
| | | | PF03944 | delta endotoxin | 523 | 665 |
| APG00832.1 | 8 | 3' Truncation | PF03945 | delta endotoxin, N-terminal domain | 103 | 291 |
| | | | PF00555 | delta endotoxin | 309 | 506 |
| | | | PF03944 | delta endotoxin | 523 | 663 |
| APG00832 CryBP1 (APG04850.0) | 9 | | no PFAM domains | | | |
| APG00842.0 | 10 | | PF03318 | Clostridium epsilon toxin ETX/Bacillus mosquitocidal toxin MTX2 | 113 | 256 |
| APG00842.1 | 11 | Alternate start | PF03318 | Clostridium epsilon toxin ETX/Bacillus mosquitocidal toxin MTX2 | 96 | 239 |
| APG00887.0 | 12 | | PF03318 | Clostridium epsilon toxin ETX/Bacillus mosquitocidal toxin MTX2 | 130 | 319 |
| APG00887.1 | 13 | Alternate start | PF03318 | Clostridium epsilon toxin ETX/Bacillus mosquitocidal toxin MTX2 | 114 | 303 |
| APG00961.0 | 14 | | PF03945 | delta endotoxin, N-terminal domain | 67 | 263 |
| | | | PF00555 | delta endotoxin | 271 | 494 |
| | | | PF03944 | delta endotoxin | 505 | 639 |
| APG00961.1 | 15 | Alternate start | PF03945 | delta endotoxin, N-terminal domain | 67 | 263 |
| | | | PF00555 | delta endotoxin | 271 | 494 |
| | | | PF03944 | delta endotoxin | 505 | 639 |
| APG00973.0 | 16 | | no PFAM domains | | | |
| APG00973.1 | 17 | Alternate start | no PFAM domains | | | |
| APG00973.2 | 18 | Alternate start | no PFAM domains | | | |
| APG01038.0 | 19 | | PF03318 | Clostridium epsilon toxin ETX/Bacillus mosquitocidal toxin MTX2 | 84 | 189 |
| APG01038.1 | 20 | Signal peptide removed | PF03318 | Clostridium epsilon toxin ETX/Bacillus mosquitocidal toxin MTX2 | 58 | 161 |
| APG01063.0 | 21 | | PF14200 | Ricin-type beta-trefoil lectin domain-like | 33 | 109 |
| | | | PF05431 | Insecticidal Crystal Toxin, P42 | 241 | 401 |
| APG01063.1 | 22 | Signal peptide removed | PF14200 | Ricin-type beta-trefoil lectin domain-like | 6 | 82 |
| | | | PF05431 | Insecticidal Crystal Toxin, P42 | 214 | 374 |
| APG01092.0 | 23 | | PF03945 | delta endotoxin, N-terminal domain | 243 | 338 |
| | | | PF03944 | delta endotoxin | 544 | 681 |
| APG01092.1 | 24 | 3' Truncation | PF03945 | delta endotoxin, N-terminal domain | 243 | 338 |
| | | | PF03944 | delta endotoxin | 544 | 680 |
| APG01102.0 | 25 | | PF03944 | delta endotoxin | 563 | 721 |
| APG01102.1 | 26 | 3' Truncation | PF03944 | delta endotoxin | 563 | 721 |
| APG01102 | 27 | | no PFAM | | | |

TABLE 2-continued

| Summary of PFAM domains in each of SEQ ID NOs: 1-525 | | | | | | |
|---|---|---|---|---|---|---|
| APG ID | Seq ID | Modification Type | Accession | Description | Start | Stop |
| SplitCry (APG01056.0) | | | domains | | | |
| APG01127.0 | 28 | | PF03318 | Clostridium epsilon toxin ETX/Bacillus mosquitocidal toxin MTX2 | 44 | 249 |
| APG01141.0 | 29 | | PF14200 | Ricin-type beta-trefoil lectin domain-like | 36 | 109 |
| | | | PF05431 | Insecticidal Crystal Toxin, P42 | 181 | 336 |
| APG01141.1 | 30 | Alternate start | PF14200 | Ricin-type beta-trefoil lectin domain-like | 36 | 109 |
| | | | PF05431 | Insecticidal Crystal Toxin, P42 | 181 | 336 |
| APG01163.0 | 31 | | PF03318 | Clostridium epsilon toxin ETX/Bacillus mosquitocidal toxin MTX2 | 123 | 215 |
| APG01163.1 | 32 | Signal peptide removed | PF03318 | Clostridium epsilon toxin ETX/Bacillus mosquitocidal toxin MTX2 | 94 | 186 |
| APG01165.0 | 33 | | PF03945 | delta endotoxin, N-terminal domain | 54 | 127 |
| | | | PF03945 | delta endotoxin, N-terminal domain | 212 | 287 |
| APG01165.1 | 34 | Alternate start | PF03945 | delta endotoxin, N-terminal domain | 52 | 125 |
| | | | PF03945 | delta endotoxin, N-terminal domain | 210 | 285 |
| APG01201.0 | 35 | | PF03318 | Clostridium epsilon toxin ETX/Bacillus mosquitocidal toxin MTX2 | 131 | 322 |
| APG01201.1 | 36 | Signal peptide removed | PF03318 | Clostridium epsilon toxin ETX/Bacillus mosquitocidal toxin MTX2 | 104 | 295 |
| APG01281.0 | 37 | | PF03318 | Clostridium epsilon toxin ETX/Bacillus mosquitocidal toxin MTX2 | 136 | 244 |
| APG01281.1 | 38 | Signal peptide removed | PF03318 | Clostridium epsilon toxin ETX/Bacillus mosquitocidal toxin MTX2 | 107 | 215 |
| APG01352.0 | 39 | | PF05431 | Insecticidal Crystal Toxin, P42 | 206 | 372 |
| APG01352.1 | 40 | Signal peptide removed | PF05431 | Insecticidal Crystal Toxin, P42 | 179 | 345 |
| APG01380.0 | 41 | | no PFAM domains | | | |
| APG01385.0 | 42 | | PF03318 | Clostridium epsilon toxin ETX/Bacillus mosquitocidal toxin MTX2 | 33 | 274 |
| APG01396.0 | 43 | | PF03318 | Clostridium epsilon toxin ETX/Bacillus mosquitocidal toxin MTX2 | 51 | 285 |
| APG01396.1 | 44 | Alternate start | PF03318 | Clostridium epsilon toxin ETX/Bacillus mosquitocidal toxin MTX2 | 29 | 263 |
| APG01434.0 | 45 | | PF03945 | delta endotoxin, N-terminal domain | 115 | 302 |
| | | | PF00555 | delta endotoxin | 315 | 485 |
| | | | PF03944 | delta endotoxin | 498 | 636 |
| APG01434.1 | 46 | Alternate start | PF03945 | delta endotoxin, N-terminal domain | 112 | 299 |
| | | | PF00555 | delta endotoxin | 312 | 482 |
| | | | PF03944 | delta endotoxin | 495 | 633 |
| APG01434.2 | 47 | Alternate start and 3' | PF03945 | delta endotoxin, N-terminal domain | 112 | 299 |

TABLE 2-continued

| Summary of PFAM domains in each of SEQ ID NOs: 1-525 | | | | | | |
|---|---|---|---|---|---|---|
| APG ID | Seq ID | Modification Type | Accession | Description | Start | Stop |
| | | Truncation | PF00555 | delta endotoxin | 312 | 482 |
| | | | PF03944 | delta endotoxin | 495 | 632 |
| APG01434 SplitCry (APG03109.0) | 48 | | no PFAM domains | | | |
| APG01455.0 | 49 | | no PFAM domains | | | |
| APG01516.0 | 50 | | PF03318 | Clostridium epsilon toxin ETX/Bacillus mosquitocidal toxin MTX2 | 129 | 241 |
| APG01516.1 | 51 | Signal peptide removed | PF03318 | Clostridium epsilon toxin ETX/Bacillus mosquitocidal toxin MTX2 | 93 | 205 |
| APG01549.0 | 52 | | PF03318 | Clostridium epsilon toxin ETX/Bacillus mosquitocidal toxin MTX2 | 62 | 270 |
| APG01617.0 | 53 | | PF03318 | Clostridium epsilon toxin ETX/Bacillus mosquitocidal toxin MTX2 | 103 | 313 |
| APG01617.1 | 54 | Signal peptide removed | PF03318 | Clostridium epsilon toxin ETX/Bacillus mosquitocidal toxin MTX2 | 72 | 282 |
| APG01681.0 | 55 | | PF14200 | Ricin-type beta-trefoil lectin domain-like | 80 | 141 |
| | | | PF05431 | Insecticidal Crystal Toxin, P42 | 240 | 404 |
| APG01681.1 | 56 | Alternate start | PF14200 | Ricin-type beta-trefoil lectin domain-like | 64 | 125 |
| | | | PF05431 | Insecticidal Crystal Toxin, P42 | 224 | 388 |
| APG01681 CryBP1 (APG08871.0) | 57 | | no PFAM domains | | | |
| APG01686.0 | 58 | | PF03945 | delta endotoxin, N-terminal domain | 244 | 338 |
| | | | PF03944 | delta endotoxin | 544 | 679 |
| APG01686.1 | 59 | 3' Truncation | PF03945 | delta endotoxin, N-terminal domain | 244 | 338 |
| | | | PF03944 | delta endotoxin | 544 | 678 |
| APG01710.0 | 60 | | PF03945 | delta endotoxin, N-terminal domain | 123 | 330 |
| APG01710.1 | 61 | Alternate start | PF03945 | delta endotoxin, N-terminal domain | 54 | 261 |
| APG01788.0 | 62 | | PF03945 | delta endotoxin, N-terminal domain | 106 | 323 |
| | | | PF03944 | delta endotoxin | 383 | 510 |
| APG01788.1 | 63 | 3' Truncation | PF03945 | delta endotoxin, N-terminal domain | 106 | 323 |
| | | | PF03944 | delta endotoxin | 383 | 510 |
| APG01803.0 | 64 | | PF01473 | Putative cell wall binding repeat | 411 | 427 |
| | | | PF01473 | Putative cell wall binding repeat | 439 | 452 |
| APG01803.1 | 65 | Signal peptide removed | PF01473 | Putative cell wall binding repeat | 373 | 389 |
| | | | PF01473 | Putative cell wall binding repeat | 401 | 414 |
| APG01810.0 | 66 | | PF14200 | Ricin-type beta-trefoil lectin domain-like | 32 | 99 |
| | | | PF05431 | Insecticidal Crystal Toxin, P42 | 223 | 383 |
| APG01810.1 | 67 | Signal peptide removed | PF14200 | Ricin-type beta-trefoil lectin domain-like | 5 | 72 |
| | | | PF05431 | Insecticidal Crystal Toxin, P42 | 196 | 356 |
| APG01817.0 | 68 | | PF03945 | delta endotoxin, N-terminal domain | 89 | 292 |
| | | | PF00555 | delta endotoxin | 302 | 509 |
| | | | PF03944 | delta endotoxin | 520 | 666 |

TABLE 2-continued

Summary of PFAM domains in each of SEQ ID NOs: 1-525

| APG ID | Seq ID | Modification Type | Accession | Description | Start | Stop |
|---|---|---|---|---|---|---|
| APG01819.0 | 69 | | PF03945 | delta endotoxin, N-terminal domain | 113 | 310 |
| | | | PF01473 | Putative cell wall binding repeat | 388 | 405 |
| | | | PF01473 | Putative cell wall binding repeat | 408 | 424 |
| APG01819.1 | 70 | Signal peptide removed | PF03945 | delta endotoxin, N-terminal domain | 71 | 267 |
| | | | PF01473 | Putative cell wall binding repeat | 346 | 363 |
| | | | PF01473 | Putative cell wall binding repeat | 366 | 382 |
| APG01860.0 | 71 | | PF03945 | delta endotoxin, N-terminal domain | 116 | 316 |
| APG01860.1 | 72 | Signal peptide removed | PF03945 | delta endotoxin, N-terminal domain | 78 | 278 |
| APG01967.0 | 73 | | PF03318 | Clostridium epsilon toxin ETX/Bacillus mosquitocidal toxin MTX2 | 48 | 258 |
| APG01967.1 | 74 | Alternate start | PF03318 | Clostridium epsilon toxin ETX/Bacillus mosquitocidal toxin MTX2 | 44 | 255 |
| APG02071.0 | 75 | | PF03945 | delta endotoxin, N-terminal domain | 95 | 305 |
| | | | PF03944 | delta endotoxin | 505 | 643 |
| APG02071.1 | 76 | Alternate start and 3' Truncation | PF03945 | delta endotoxin, N-terminal domain | 82 | 292 |
| | | | PF03944 | delta endotoxin | 492 | 630 |
| APG02105.0 | 77 | | PF03318 | Clostridium epsilon toxin ETX/Bacillus mosquitocidal toxin MTX2 | 45 | 280 |
| APG02110.0 | 78 | | PF03945 | delta endotoxin, N-terminal domain | 143 | 323 |
| | | | PF14200 | Ricin-type beta-trefoil lectin domain-like | 464 | 549 |
| APG02110.1 | 79 | Alternate start | PF03945 | delta endotoxin, N-terminal domain | 120 | 293 |
| | | | PF14200 | Ricin-type beta-trefoil lectin domain-like | 441 | 526 |
| APG02115.0 | 80 | | PF03318 | Clostridium epsilon toxin ETX/Bacillus mosquitocidal toxin MTX2 | 34 | 189 |
| APG02143.0 | 81 | | PF03318 | Clostridium epsilon toxin ETX/Bacillus mosquitocidal toxin MTX2 | 32 | 278 |
| APG02166.0 | 82 | | PF03318 | Clostridium epsilon toxin ETX/Bacillus mosquitocidal toxin MTX2 | 59 | 224 |
| APG02206.0 | 83 | | no PFAM domains | | | |
| APG02206.1 | 84 | Alternate start | no PFAM domains | | | |
| APG02206 SplitCry (APG07749.0) | 85 | | PF07029 | CryBP1 protein | 40 | 146 |
| APG02221.0 | 86 | | PF03945 | delta endotoxin, N-terminal domain | 225 | 334 |
| | | | PF03944 | delta endotoxin | 562 | 699 |
| APG02221.1 | 87 | 3' Truncation | PF03945 | delta endotoxin, N-terminal domain | 225 | 334 |
| | | | PF03944 | delta endotoxin | 562 | 699 |
| APG02256.0 | 88 | | PF03318 | Clostridium epsilon toxin ETX/Bacillus mosquitocidal toxin MTX2 | 68 | 209 |

TABLE 2-continued

Summary of PFAM domains in each of SEQ ID NOs: 1-525

| APG ID | Seq ID | Modification Type | Accession | Description | Start | Stop |
|---|---|---|---|---|---|---|
| APG02256.1 | 89 | Signal peptide removed | PF03318 | Clostridium epsilon toxin ETX/Bacillus mosquitocidal toxin MTX2 | 40 | 181 |
| APG02309.0 | 90 | | PF03945 | delta endotoxin, N-terminal domain | 87 | 304 |
| | | | PF03944 | delta endotoxin | 525 | 648 |
| APG02309.1 | 91 | Alternate start | PF03945 | delta endotoxin, N-terminal domain | 83 | 300 |
| | | | PF03944 | delta endotoxin | 521 | 644 |
| APG02309.2 | 92 | Alternate start and 3' Truncation | PF03945 | delta endotoxin, N-terminal domain | 83 | 300 |
| | | | PF03944 | delta endotoxin | 521 | 643 |
| APG02315.0 | 93 | | PF03318 | Clostridium epsilon toxin ETX/Bacillus mosquitocidal toxin MTX2 | 81 | 289 |
| APG02315.1 | 94 | Signal peptide removed | PF03318 | Clostridium epsilon toxin ETX/Bacillus mosquitocidal toxin MTX2 | 58 | 266 |
| APG02319.0 | 95 | | no PFAM domains | | | |
| APG02380.0 | 96 | | PF12495 | Vegetative insecticide protein 3A N terminal | 14 | 190 |
| | | | PF02018 | Carbohydrate binding domain | 538 | 654 |
| APG02380.1 | 97 | Alternate start | PF12495 | Vegetative insecticide protein 3A N terminal | 12 | 188 |
| | | | PF02018 | Carbohydrate binding domain | 536 | 652 |
| APG02451.0 | 98 | | PF03318 | Clostridium epsilon toxin ETX/Bacillus mosquitocidal toxin MTX2 | 39 | 274 |
| APG02451.1 | 99 | Alternate start | PF03318 | Clostridium epsilon toxin ETX/Bacillus mosquitocidal toxin MTX2 | 33 | 268 |
| APG02475.0 | 100 | | PF03318 | Clostridium epsilon toxin ETX/Bacillus mosquitocidal toxin MTX2 | 179 | 373 |
| APG02475.1 | 101 | Alternate start | PF03318 | Clostridium epsilon toxin ETX/Bacillus mosquitocidal toxin MTX2 | 164 | 358 |
| APG02475.2 | 102 | Signal peptide removed | PF03318 | Clostridium epsilon toxin ETX/Bacillus mosquitocidal toxin MTX2 | 134 | 328 |
| APG02506.0 | 103 | | PF03945 | delta endotoxin, N-terminal domain | 130 | 317 |
| | | | PF01473 | Putative cell wall binding repeat | 465 | 476 |
| | | | PF01473 | Putative cell wall binding repeat | 550 | 560 |
| APG02506.1 | 104 | Signal peptide removed | PF03945 | delta endotoxin, N-terminal domain | 92 | 279 |
| | | | PF01473 | Putative cell wall binding repeat | 427 | 438 |
| | | | PF01473 | Putative cell wall binding repeat | 512 | 522 |
| APG02511.0 | 105 | | no PFAM domains | | | |
| APG02511.1 | 106 | Alternate start | no PFAM domains | | | |
| APG02511.2 | 107 | Signal peptide removed | no PFAM domains | | | |
| APG02587.0 | 108 | | PF00555 | delta endotoxin | 320 | 515 |
| | | | PF03944 | delta endotoxin | 537 | 679 |
| APG02587.1 | 109 | 3' Truncation | PF03945 | delta endotoxin, N-terminal domain | 74 | 310 |

TABLE 2-continued

Summary of PFAM domains in each of SEQ ID NOs: 1-525

| APG ID | Seq ID | Modification Type | Accession | Description | Start | Stop |
|---|---|---|---|---|---|---|
| | | | PF00555 | delta endotoxin | 320 | 515 |
| | | | PF03944 | delta endotoxin | 537 | 679 |
| APG02592.0 | 110 | | PF03318 | Clostridium epsilon toxin ETX/Bacillus mosquitocidal toxin MTX2 | 53 | 267 |
| APG02656.0 | 111 | | no PFAM domains | | | |
| APG02656.1 | 112 | Alternate start | no PFAM domains | | | |
| APG02659.0 | 113 | | no PFAM domains | | | |
| APG02659.1 | 114 | Signal peptide removed | no PFAM domains | | | |
| APG02671.0 | 115 | | PF01338 | Bacillus thuringiensis toxin | 39 | 254 |
| APG02671.1 | 116 | Alternate start | PF01338 | Bacillus thuringiensis toxin | 23 | 238 |
| APG02676.0 | 117 | | no PFAM domains | | | |
| APG02706.0 | 118 | | PF03945 | delta endotoxin, N-terminal domain | 73 | 293 |
| | | | PF03944 | delta endotoxin | 517 | 656 |
| APG02706.1 | 119 | Alternate | PF03945 | delta endotoxin, N-terminal domain | 73 | 293 |
| | | start | PF03944 | delta endotoxin | 517 | 656 |
| APG02706.2 | 120 | Alternate start and 3' | PF03945 | delta endotoxin, N-terminal domain | 73 | 293 |
| | | Truncation | PF03944 | delta endotoxin | 517 | 656 |
| APG02706.3 | 121 | Alternate start | PF03945 | delta endotoxin, N-terminal domain | 64 | 284 |
| | | | PF03944 | delta endotoxin | 508 | 647 |
| APG02706.4 | 122 | Alternate start and 3' | PF03945 | delta endotoxin, N-terminal domain | 64 | 284 |
| | | Truncation | PF03944 | delta endotoxin | 508 | 647 |
| APG02706.5 | 123 | Alternate start | PF03945 | delta endotoxin, N-terminal domain | 16 | 226 |
| | | | PF03944 | delta endotoxin | 450 | 589 |
| APG02706.6 | 124 | Alternate start and 3' | PF03945 | delta endotoxin, N-terminal domain | 16 | 226 |
| | | Truncation | PF03944 | delta endotoxin | 450 | 589 |
| APG02714.0 | 125 | | PF03318 | Clostridium epsilon toxin ETX/Bacillus mosquitocidal toxin MTX2 | 60 | 206 |
| APG02718.0 | 126 | | PF06101 | Vacuolar protein sorting-associated protein 62 | 13 | 234 |
| | | | PF05431 | Insecticidal Crystal Toxin, P42 | 267 | 408 |
| APG02718.1 | 127 | Alternate start | PF06101 | Vacuolar protein sorting-associated protein 62 | 3 | 221 |
| | | | PF05431 | Insecticidal Crystal Toxin, P42 | 254 | 395 |
| APG02767.0 | 128 | | PF12495 | Vegetative insecticide protein 3A N terminal | 16 | 187 |
| | | | PF02018 | Carbohydrate binding domain | 547 | 659 |
| APG02767.1 | 129 | Alternate start | PF12495 | Vegetative insecticide protein 3A N terminal | 14 | 185 |
| | | | PF02018 | Carbohydrate binding domain | 545 | 657 |
| APG02941.0 | 130 | | no PFAM domains | | | |
| APG02947.0 | 131 | | PF03945 | delta endotoxin, N-terminal domain | 89 | 302 |
| | | | PF00555 | delta endotoxin | 310 | 520 |
| | | | PF03944 | delta endotoxin | 531 | 659 |
| | | | PF14200 | Ricin-type beta-trefoil lectin domain-like | 700 | 789 |
| APG02947.1 | 132 | Alternate start | PF03945 | delta endotoxin, N-terminal domain | 73 | 286 |
| | | | PF00555 | delta endotoxin | 294 | 504 |

TABLE 2-continued

Summary of PFAM domains in each of SEQ ID NOs: 1-525

| APG ID | Seq ID | Modification Type | Accession | Description | Start | Stop |
|---|---|---|---|---|---|---|
| | | | PF03944 | delta endotoxin | 515 | 643 |
| | | | PF14200 | Ricin-type beta-trefoil lectin domain-like | 684 | 773 |
| APG02947.2 | 133 | Alternate start and 3' Truncation | PF03945 | delta endotoxin, N-terminal domain | 73 | 286 |
| | | | PF00555 | delta endotoxin | 294 | 504 |
| | | | PF03944 | delta endotoxin | 515 | 643 |
| APG02956.0 | 134 | | PF03318 | Clostridium epsilon toxin ETX/Bacillus mosquitocidal toxin MTX2 | 70 | 270 |
| APG02986.0 | 135 | | PF03945 | delta endotoxin, N-terminal domain | 70 | 245 |
| | | | PF00555 | delta endotoxin | 342 | 547 |
| | | | PF03944 | delta endotoxin | 557 | 691 |
| APG03018.0 | 136 | | PF03945 | delta endotoxin, N-terminal domain | 113 | 297 |
| | | | PF00555 | delta endotoxin | 311 | 484 |
| | | | PF03944 | delta endotoxin | 495 | 636 |
| APG03018.1 | 137 | Alternate start | PF03945 | delta endotoxin, N-terminal domain | 110 | 294 |
| | | | PF00555 | delta endotoxin | 308 | 481 |
| | | | PF03944 | delta endotoxin | 492 | 633 |
| APG03018.2 | 138 | Alternate start and 3' Truncation | PF03945 | delta endotoxin, N-terminal domain | 110 | 294 |
| | | | PF00555 | delta endotoxin | 308 | 481 |
| | | | PF03944 | delta endotoxin | 492 | 632 |
| APG03018 SplitCry (APG08753.0) | 139 | | no PFAM domains | | | |
| APG03054.0 | 140 | | PF03945 | delta endotoxin, N-terminal domain | 87 | 287 |
| | | | PF00555 | delta endotoxin | 295 | 511 |
| | | | PF03944 | delta endotoxin | 521 | 658 |
| APG03056.0 | 141 | | PF03945 | delta endotoxin, N-terminal domain | 82 | 290 |
| | | | PF00555 | delta endotoxin | 299 | 504 |
| | | | PF03944 | delta endotoxin | 515 | 650 |
| APG03056.1 | 142 | 3' Truncation | PF03945 | delta endotoxin, N-terminal domain | 82 | 290 |
| | | | PF00555 | delta endotoxin | 299 | 504 |
| | | | PF03944 | delta endotoxin | 515 | 649 |
| APG03056 CryBP1 (APG02727.0) | 143 | | no PFAM domains | | | |
| APG03182.0 | 144 | | no PFAM domains | | | |
| APG03182.1 | 145 | Alternate start | no PFAM domains | | | |
| APG03182.2 | 146 | Signal peptide removed | no PFAM domains | | | |
| APG03218.0 | 147 | | PF03318 | Clostridium epsilon toxin ETX/Bacillus mosquitocidal toxin MTX2 | 121 | 312 |
| APG03218.1 | 148 | Signal peptide removed | PF03318 | Clostridium epsilon toxin ETX/Bacillus mosquitocidal toxin MTX2 | 95 | 286 |
| APG03247.0 | 149 | | PF03945 | delta endotoxin, N-terminal domain | 124 | 329 |
| | | | PF03944 | delta endotoxin | 519 | 662 |
| APG03247.1 | 150 | Alternate start and 3' Truncation | PF03945 | delta endotoxin, N-terminal domain | 107 | 312 |
| | | | PF03944 | delta endotoxin | 502 | 645 |
| APG03361.0 | 151 | | PF05431 | Insecticidal Crystal Toxin, P42 | 300 | 468 |
| APG03392.0 | 152 | | PF03945 | delta endotoxin, N-terminal domain | 122 | 306 |
| | | | PF01473 | Putative cell wall binding repeat | 437 | 449 |
| APG03392.1 | 153 | Signal peptide | PF03945 | delta endotoxin, N-terminal domain | 84 | 268 |

TABLE 2-continued

| Summary of PFAM domains in each of SEQ ID NOs: 1-525 | | | | | | |
|---|---|---|---|---|---|---|
| APG ID | Seq ID | Modification Type | Accession | Description | Start | Stop |
| | | removed | PF01473 | Putative cell wall binding repeat | 399 | 411 |
| APG03415.0 | 154 | | PF03318 | Clostridium epsilon toxin ETX/Bacillus mosquitocidal toxin MTX2 | 40 | 282 |
| APG03504.0 | 155 | | PF03318 | Clostridium epsilon toxin ETX/Bacillus mosquitocidal toxin MTX2 | 45 | 248 |
| APG03505.0 | 156 | | PF03945 | delta endotoxin, N-terminal domain | 78 | 299 |
| | | | PF03944 | delta endotoxin | 490 | 648 |
| APG03505.1 | 157 | Alternate start | PF03945 | delta endotoxin, N-terminal domain | 75 | 296 |
| | | | PF03944 | delta endotoxin | 487 | 645 |
| APG03505.2 | 158 | Alternate start and 3' | PF03945 | delta endotoxin, N-terminal domain | 75 | 296 |
| | | Truncation | PF03944 | delta endotoxin | 487 | 645 |
| APG03505.3 | 159 | Alternate start | PF03945 | delta endotoxin, N-terminal domain | 36 | 257 |
| | | | PF03944 | delta endotoxin | 448 | 606 |
| APG03505.4 | 160 | Alternate start and 3' | PF03945 | delta endotoxin, N-terminal domain | 36 | 257 |
| | | Truncation | PF03944 | delta endotoxin | 448 | 606 |
| APG03505.5 | 161 | Alternate start | PF03945 | delta endotoxin, N-terminal domain | 17 | 238 |
| | | | PF03944 | delta endotoxin | 429 | 587 |
| APG03505.6 | 162 | Alternate start and 3' | PF03945 | delta endotoxin, N-terminal domain | 17 | 238 |
| | | Truncation | PF03944 | delta endotoxin | 429 | 587 |
| APG03527.0 | 163 | | PF03318 | Clostridium epsilon toxin ETX/Bacillus mosquitocidal toxin MTX2 | 61 | 251 |
| APG03527.1 | 164 | Alternate start | PF03318 | Clostridium epsilon toxin ETX/Bacillus mosquitocidal toxin MTX2 | 58 | 248 |
| APG03584.0 | 165 | | no PFAM domains | | | |
| APG03584.1 | 166 | Signal peptide removed | no PFAM domains | | | |
| APG03587.0 | 167 | | no PFAM domains | | | |
| APG03674.0 | 168 | | PF01338 | Bacillus thuringiensis toxin | 5 | 192 |
| APG03674.1 | 169 | Alternate start | PF01338 | Bacillus thuringiensis toxin | 4 | 192 |
| APG03738.0 | 170 | | PF03318 | Clostridium epsilon toxin ETX/Bacillus mosquitocidal toxin MTX2 | 46 | 206 |
| APG03748.0 | 171 | | PF14200 | Ricin-type beta-trefoil lectin domain-like | 81 | 157 |
| | | | PF05431 | Insecticidal Crystal Toxin, P42 | 238 | 398 |
| APG03748.1 | 172 | Signal peptide | PF14200 | Ricin-type beta-trefoil lectin domain-like | 46 | 121 |
| | | removed | PF05431 | Insecticidal Crystal Toxin, P42 | 202 | 362 |
| APG03758.0 | 173 | | PF03318 | Clostridium epsilon toxin ETX/Bacillus mosquitocidal toxin MTX2 | 42 | 269 |
| | | | PF00388 | Phosphatidylinositol-specific phospholipase C, X domain | 358 | 469 |
| APG03778.0 | 174 | | PF05431 | Insecticidal Crystal Toxin, P42 | 312 | 475 |
| APG03789.0 | 175 | | PF05431 | Insecticidal Crystal Toxin, P42 | 223 | 377 |
| APG03826.0 | 176 | | PF03318 | Clostridium epsilon toxin ETX/Bacillus | 70 | 245 |

TABLE 2-continued

Summary of PFAM domains in each of SEQ ID NOs: 1-525

| APG ID | Seq ID | Modification Type | Accession | Description | Start | Stop |
|---|---|---|---|---|---|---|
| | | | | mosquitocidal toxin MTX2 | | |
| APG03887.0 | 177 | | no PFAM domains | | | |
| APG03893.0 | 178 | | PF03945 | delta endotoxin, N-terminal domain | 85 | 289 |
| | | | PF00555 | delta endotoxin | 299 | 503 |
| | | | PF03944 | delta endotoxin | 514 | 645 |
| APG03909.0 | 179 | | PF03945 | delta endotoxin, N-terminal domain | 158 | 307 |
| APG03909.1 | 180 | Alternate start | PF03945 | delta endotoxin, N-terminal domain | 125 | 274 |
| APG03959.0 | 181 | | PF01338 | Bacillus thuringiensis toxin | 4 | 205 |
| APG04009.0 | 182 | | no PFAM domains | | | |
| APG04019.0 | 183 | | PF05431 | Insecticidal Crystal Toxin, P42 | 89 | 254 |
| APG04019.1 | 184 | Alternate start | PF05431 | Insecticidal Crystal Toxin, P42 | 89 | 254 |
| APG04103.0 | 185 | | PF03318 | Clostridium epsilon toxin ETX/Bacillus mosquitocidal toxin MTX2 | 115 | 318 |
| APG04103.1 | 186 | Signal peptide removed | PF03318 | Clostridium epsilon toxin ETX/Bacillus mosquitocidal toxin MTX2 | 89 | 292 |
| APG04111.0 | 187 | | PF03318 | Clostridium epsilon toxin ETX/Bacillus mosquitocidal toxin MTX2 | 52 | 253 |
| APG04141.0 | 188 | | PF03945 | delta endotoxin, N-terminal domain | 19 | 172 |
| APG04162.0 | 189 | | no PFAM domains | | | |
| APG04162.1 | 190 | Signal peptide removed | no PFAM domains | | | |
| APG04208.0 | 191 | | PF14200 | Ricin-type beta-trefoil lectin domain-like | 31 | 101 |
| | | | PF05431 | Insecticidal Crystal Toxin, P42 | 239 | 397 |
| APG04208.1 | 192 | Signal peptide removed | PF14200 | Ricin-type beta-trefoil lectin domain-like | 5 | 73 |
| | | | PF05431 | Insecticidal Crystal Toxin, P42 | 212 | 370 |
| APG04302.0 | 193 | | PF14200 | Ricin-type beta-trefoil lectin domain-like | 35 | 91 |
| | | | PF05431 | Insecticidal Crystal Toxin, P42 | 197 | 358 |
| APG04316.0 | 194 | | no PFAM domains | | | |
| APG04316.1 | 195 | Signal peptide removed | no PFAM domains | | | |
| APG04323.0 | 196 | | no PFAM domains | | | |
| APG04360.0 | 197 | | PF01338 | Bacillus thuringiensis toxin | 19 | 202 |
| APG04439.0 | 198 | | no PFAM domains | | | |
| APG04439.1 | 199 | Alternate start | no PFAM domains | | | |
| APG04442.0 | 200 | | no PFAM domains | | | |
| APG04442.1 | 201 | Signal peptide removed | no PFAM domains | | | |
| APG04476.0 | 202 | | PF03945 | delta endotoxin, N-terminal domain | 78 | 308 |
| | | | PF00030 | Beta/Gamma crystallin | 745 | 824 |
| APG04476.1 | 203 | Alternate start | PF03945 | delta endotoxin, N-terminal domain | 64 | 294 |

TABLE 2-continued

Summary of PFAM domains in each of SEQ ID NOs: 1-525

| APG ID | Seq ID | Modification Type | Accession | Description | Start | Stop |
|---|---|---|---|---|---|---|
| | | | PF00030 | Beta/Gamma crystallin | 731 | 810 |
| APG04568.0 | 204 | | PF14200 | Ricin-type beta-trefoil lectin domain-like | 31 | 102 |
| | | | PF05431 | Insecticidal Crystal Toxin, P42 | 233 | 393 |
| APG04568.1 | 205 | Signal peptide removed | PF14200 | Ricin-type beta-trefoil lectin domain-like | 4 | 73 |
| | | | PF05431 | Insecticidal Crystal Toxin, P42 | 204 | 364 |
| APG04602.0 | 206 | | PF07691 | PA14 domain | 46 | 174 |
| | | | PF03495 | Clostridial binary toxin B/anthrax toxin PA Ca-binding domain | 213 | 288 |
| | | | PF17475 | Clostridial binary toxin B/anthrax toxin PA domain 2 | 291 | 500 |
| | | | PF17476 | Clostridial binary toxin B/anthrax toxin PA domain 3 | 519 | 607 |
| APG04602.1 | 207 | Signal peptide removed | PF07691 | PA14 domain | 17 | 145 |
| | | | PF03495 | Clostridial binary toxin B/anthrax toxin PA Ca-binding domain | 184 | 259 |
| | | | PF17475 | Clostridial binary toxin B/anthrax toxin PA domain 2 | 262 | 471 |
| | | | PF17476 | Clostridial binary toxin B/anthrax toxin PA domain 3 | 490 | 578 |
| APG04651.0 | 208 | | PF03945 | delta endotoxin, N-terminal domain | 76 | 279 |
| | | | PF00555 | delta endotoxin | 287 | 499 |
| | | | PF03944 | delta endotoxin | 509 | 646 |
| APG04683.0 | 209 | | no PFAM domains | | | |
| APG04683.1 | 210 | Alternate start | no PFAM domains | | | |
| APG04683.2 | 211 | Signal peptide removed | no PFAM domains | | | |
| APG04687.0 | 212 | | PF03318 | Clostridium epsilon toxin ETX/Bacillus mosquitocidal toxin MTX2 | 129 | 220 |
| APG04687.1 | 213 | Alternate start | PF03318 | Clostridium epsilon toxin ETX/Bacillus mosquitocidal toxin MTX2 | 127 | 219 |
| APG04687.2 | 214 | Signal peptide removed | PF03318 | Clostridium epsilon toxin ETX/Bacillus mosquitocidal toxin MTX2 | 98 | 189 |
| APG04692.0 | 215 | | PF03318 | Clostridium epsilon toxin ETX/Bacillus mosquitocidal toxin MTX2 | 108 | 265 |
| APG04692.1 | 216 | Alternate start | PF03318 | Clostridium epsilon toxin ETX/Bacillus mosquitocidal toxin MTX2 | 103 | 260 |
| APG04692.2 | 217 | Signal peptide removed | PF03318 | Clostridium epsilon toxin ETX/Bacillus mosquitocidal toxin MTX2 | 75 | 232 |
| APG04694.0 | 218 | | PF03945 | delta endotoxin, N-terminal domain | 92 | 263 |
| | | | PF00555 | delta endotoxin | 349 | 559 |
| | | | PF03944 | delta endotoxin | 569 | 698 |
| APG04694.1 | 219 | 3' Truncation | PF03945 | delta endotoxin, N-terminal domain | 92 | 263 |
| | | | PF00555 | delta endotoxin | 349 | 559 |
| | | | PF03944 | delta endotoxin | 569 | 698 |

TABLE 2-continued

Summary of PFAM domains in each of SEQ ID NOs: 1-525

| APG ID | Seq ID | Modification Type | Accession | Description | Start | Stop |
|---|---|---|---|---|---|---|
| APG04694 CryBP1 (APG06866.0) | 220 | | no PFAM domains | | | |
| APG04786.0 | 221 | | PF03945 | delta endotoxin, N-terminal domain | 83 | 267 |
| | | | PF00555 | delta endotoxin | 326 | 509 |
| | | | PF03944 | delta endotoxin | 520 | 650 |
| | | | PF14200 | Ricin-type beta-trefoil lectin domain-like | 697 | 784 |
| APG04786.1 | 222 | Alternate start | PF03945 | delta endotoxin, N-terminal domain | 81 | 265 |
| | | | PF00555 | delta endotoxin | 324 | 507 |
| | | | PF03944 | delta endotoxin | 518 | 648 |
| | | | PF14200 | Ricin-type beta-trefoil lectin domain-like | 695 | 782 |
| APG04786.2 | 223 | Alternate start and 3' Truncation | PF03945 | delta endotoxin, N-terminal domain | 81 | 265 |
| | | | PF00555 | delta endotoxin | 324 | 507 |
| | | | PF03944 | delta endotoxin | 518 | 648 |
| APG04794.0 | 224 | | no PFAM domains | | | |
| APG04821.0 | 225 | | PF03318 | Clostridium epsilon toxin ETX/Bacillus mosquitocidal toxin MTX2 | 44 | 281 |
| APG04821.1 | 226 | Alternate start | PF03318 | Clostridium epsilon toxin ETX/Bacillus mosquitocidal toxin MTX2 | 32 | 269 |
| APG04822.0 | 227 | | PF03318 | Clostridium epsilon toxin ETX/Bacillus mosquitocidal toxin MTX2 | 84 | 319 |
| APG04822.1 | 228 | Signal peptide removed | PF03318 | Clostridium epsilon toxin ETX/Bacillus mosquitocidal toxin MTX2 | 71 | 306 |
| APG04959.0 | 229 | | PF03945 | delta endotoxin, N-terminal domain | 118 | 300 |
| | | | PF00555 | delta endotoxin | 310 | 507 |
| | | | PF03944 | delta endotoxin | 518 | 659 |
| APG04966.0 | 230 | | PF14200 | Ricin-type beta-trefoil lectin domain-like | 72 | 153 |
| | | | PF05431 | Insecticidal Crystal Toxin, P42 | 224 | 385 |
| APG04966.1 | 231 | Signal peptide removed | PF14200 | Ricin-type beta-trefoil lectin domain-like | 44 | 126 |
| | | | PF05431 | Insecticidal Crystal Toxin, P42 | 196 | 357 |
| APG04977.0 | 232 | | PF03318 | Clostridium epsilon toxin ETX/Bacillus mosquitocidal toxin MTX2 | 50 | 241 |
| APG05073.0 | 233 | | PF03945 | delta endotoxin, N-terminal domain | 89 | 302 |
| | | | PF03944 | delta endotoxin | 523 | 669 |
| APG05073.1 | 234 | Signal peptide removed | PF03945 | delta endotoxin, N-terminal domain | 53 | 266 |
| | | | PF03944 | delta endotoxin | 487 | 633 |
| APG05073.2 | 235 | Signal peptide removed and 3' Truncation | PF03945 | delta endotoxin, N-terminal domain | 53 | 266 |
| | | | PF03944 | delta endotoxin | 487 | 633 |
| APG05078.0 | 236 | | no PFAM domains | | | |
| APG05095.0 | 237 | | PF03945 | delta endotoxin, N-terminal domain | 90 | 267 |
| APG05095.1 | 238 | Alternate start | PF03945 | delta endotoxin, N-terminal domain | 90 | 267 |
| APG05115.0 | 239 | | PF01823 | MAC/Perforin domain | 143 | 335 |
| APG05149.0 | 240 | | no PFAM domains | | | |
| APG05149.1 | 241 | Signal peptide removed | no PFAM domains | | | |

TABLE 2-continued

| Summary of PFAM domains in each of SEQ ID NOs: 1-525 | | | | | | |
|---|---|---|---|---|---|---|
| APG ID | Seq ID | Modification Type | Accession | Description | Start | Stop |
| APG05279.0 | 242 | | PF03945 | delta endotoxin, N-terminal domain | 152 | 301 |
| APG05279.1 | 243 | Alternate start | PF03945 | delta endotoxin, N-terminal domain | 126 | 275 |
| APG05279.2 | 244 | Signal peptide removed | PF03945 | delta endotoxin, N-terminal domain | 85 | 234 |
| APG05300.0 | 245 | | no PFAM domains | | | |
| APG05346.0 | 246 | | PF03318 | Clostridium epsilon toxin ETX/Bacillus mosquitocidal toxin MTX2 | 164 | 357 |
| APG05346.1 | 247 | Signal peptide removed | PF03318 | Clostridium epsilon toxin ETX/Bacillus mosquitocidal toxin MTX2 | 134 | 328 |
| APG05388.0 | 248 | | PF03318 | Clostridium epsilon toxin ETX/Bacillus mosquitocidal toxin MTX2 | 24 | 239 |
| APG05408.0 | 249 | | no PFAM domains | | | |
| APG05408.1 | 250 | Alternate start | no PFAM domains | | | |
| APG05414.0 | 251 | | PF03318 | Clostridium epsilon toxin ETX/Bacillus mosquitocidal toxin MTX2 | 75 | 211 |
| APG05414.1 | 252 | Alternate start | PF03318 | Clostridium epsilon toxin ETX/Bacillus mosquitocidal toxin MTX2 | 75 | 211 |
| APG05429.0 | 253 | | PF03318 | Clostridium epsilon toxin ETX/Bacillus mosquitocidal toxin MTX2 | 91 | 229 |
| APG05429.1 | 254 | Alternate start | PF03318 | Clostridium epsilon toxin ETX/Bacillus mosquitocidal toxin MTX2 | 74 | 213 |
| APG05429.2 | 255 | Signal peptide removed | PF03318 | Clostridium epsilon toxin ETX/Bacillus mosquitocidal toxin MTX2 | 42 | 181 |
| APG05431.0 | 256 | | no PFAM domains | | | |
| APG05431.1 | 257 | Signal peptide removed | no PFAM domains | | | |
| APG05471.0 | 258 | | PF01823 | MAC/Perforin domain | 135 | 332 |
| APG05481.0 | 259 | | PF03318 | Clostridium epsilon toxin ETX/Bacillus mosquitocidal toxin MTX2 | 153 | 314 |
| APG05481.1 | 260 | Alternate start | PF03318 | Clostridium epsilon toxin ETX/Bacillus mosquitocidal toxin MTX2 | 140 | 301 |
| APG05481.2 | 261 | Signal peptide removed | PF03318 | Clostridium epsilon toxin ETX/Bacillus mosquitocidal toxin MTX2 | 111 | 272 |
| APG05492.0 | 262 | | PF03318 | Clostridium epsilon toxin ETX/Bacillus mosquitocidal toxin MTX2 | 47 | 257 |
| APG05508.0 | 263 | | PF03945 | delta endotoxin, N-terminal domain | 67 | 297 |
| | | | PF00030 | Beta/Gamma crystallin | 735 | 812 |
| | | | PF14200 | Ricin-type beta-trefoil lectin domain-like | 900 | 943 |
| APG05508.1 | 264 | Alternate start | PF03945 | delta endotoxin, N-terminal domain | 64 | 294 |

TABLE 2-continued

| Summary of PFAM domains in each of SEQ ID NOs: 1-525 | | | | | | |
|---|---|---|---|---|---|---|
| APG ID | Seq ID | Modification Type | Accession | Description | Start | Stop |
| | | | PF00030 | Beta/Gamma crystallin | 732 | 809 |
| | | | PF14200 | Ricin-type beta-trefoil lectin domain-like | 897 | 940 |
| APG05538.0 | 265 | | PF03945 | delta endotoxin, N-terminal domain | 118 | 290 |
| | | | PF14200 | Ricin-type beta-trefoil lectin domain-like | 502 | 586 |
| APG05538.1 | 266 | Alternate start | PF03945 | delta endotoxin, N-terminal domain | 116 | 288 |
| | | | PF14200 | Ricin-type beta-trefoil lectin domain-like | 500 | 584 |
| APG05538.2 | 267 | Signal peptide removed | PF03945 | delta endotoxin, N-terminal domain | 78 | 250 |
| | | | PF14200 | Ricin-type beta-trefoil lectin domain-like | 462 | 546 |
| APG05636.0 | 268 | | PF03318 | Clostridium epsilon toxin ETX/Bacillus mosquitocidal toxin MTX2 | 46 | 248 |
| APG05643.0 | 269 | | PF03944 | delta endotoxin | 596 | 734 |
| APG05643.1 | 270 | Alternate start and 3' Truncation | PF03944 | delta endotoxin | 596 | 734 |
| APG05643 SplitCry (APG08971.0) | 271 | | no PFAM domains | | | |
| APG05662.0 | 272 | | PF01338 | Bacillus thuringiensis toxin | 4 | 207 |
| APG05725.0 | 273 | | PF03945 | delta endotoxin, N-terminal domain | 49 | 243 |
| | | | PF01473 | Putative cell wall binding repeat | 360 | 374 |
| APG05725.1 | 274 | Alternate start | PF03945 | delta endotoxin, N-terminal domain | 49 | 243 |
| | | | PF01473 | Putative cell wall binding repeat | 360 | 374 |
| APG05734.0 | 275 | | PF03945 | delta endotoxin, N-terminal domain | 124 | 354 |
| | | | PF03944 | delta endotoxin | 550 | 686 |
| APG05734.1 | 276 | Alternate start | PF03945 | delta endotoxin, N-terminal domain | 103 | 333 |
| | | | PF03944 | delta endotoxin | 529 | 665 |
| APG05734.2 | 277 | Signal peptide removed | PF03945 | delta endotoxin, N-terminal domain | 73 | 303 |
| | | | PF03944 | delta endotoxin | 499 | 635 |
| APG05734.3 | 278 | Alternate start and 3' Truncation | PF03945 | delta endotoxin, N-terminal domain | 103 | 333 |
| | | | PF03944 | delta endotoxin | 529 | 665 |
| APG05734.4 | 279 | Signal peptide removed and 3' Truncation | PF03945 | delta endotoxin, N-terminal domain | 73 | 303 |
| | | | PF03944 | delta endotoxin | 499 | 635 |
| APG05793.0 | 280 | | PF03318 | Clostridium epsilon toxin ETX/Bacillus mosquitocidal toxin MTX2 | 16 | 161 |
| APG05834.0 | 281 | | PF03318 | Clostridium epsilon toxin ETX/Bacillus mosquitocidal toxin MTX2 | 103 | 321 |
| APG05834.1 | 282 | Signal peptide removed | PF03318 | Clostridium epsilon toxin ETX/Bacillus mosquitocidal toxin MTX2 | 70 | 288 |
| APG05878.0 | 283 | | PF03945 | delta endotoxin, N-terminal domain | 79 | 254 |
| APG05907.0 | 284 | | PF05431 | Insecticidal Crystal Toxin, P42 | 245 | 406 |
| APG05907.1 | 285 | Alternate start | PF05431 | Insecticidal Crystal Toxin, P42 | 216 | 377 |
| APG05917.0 | 286 | | PF05431 | Insecticidal Crystal Toxin, P42 | 217 | 378 |
| APG05920.0 | 287 | | no PFAM domains | | | |

TABLE 2-continued

Summary of PFAM domains in each of SEQ ID NOs: 1-525

| APG ID | Seq ID | Modification Type | Accession | Description | Start | Stop |
|---|---|---|---|---|---|---|
| APG05920.1 | 288 | Signal peptide removed | no PFAM domains | | | |
| APG05946.0 | 289 | | PF14200 | Ricin-type beta-trefoil lectin domain-like | 6 | 53 |
| | | | PF05431 | Insecticidal Crystal Toxin, P42 | 90 | 252 |
| APG05955.0 | 290 | | PF05431 | Insecticidal Crystal Toxin, P42 | 330 | 495 |
| APG05992.0 | 291 | | no PFAM domains | | | |
| APG06027.0 | 292 | | PF14200 | Ricin-type beta-trefoil lectin domain-like | 41 | 101 |
| | | | PF05431 | Insecticidal Crystal Toxin, P42 | 212 | 372 |
| APG06027.1 | 293 | Alternate start | PF14200 | Ricin-type beta-trefoil lectin domain-like | 41 | 101 |
| | | | PF05431 | Insecticidal Crystal Toxin, P42 | 212 | 372 |
| APG06049.0 | 294 | | PF03318 | Clostridium epsilon toxin ETX/Bacillus mosquitocidal toxin MTX2 | 144 | 341 |
| APG06049.1 | 295 | Signal peptide removed | PF03318 | Clostridium epsilon toxin ETX/Bacillus mosquitocidal toxin MTX2 | 114 | 312 |
| APG06079.0 | 296 | | PF03945 | delta endotoxin, N-terminal domain | 86 | 312 |
| | | | PF00555 | delta endotoxin | 322 | 485 |
| | | | PF03944 | delta endotoxin | 518 | 656 |
| | | | PF05588 | Clostridium botulinum HA-17 domain | 668 | 752 |
| APG06079.1 | 297 | 3' Truncation | PF03945 | delta endotoxin, N-terminal domain | 86 | 312 |
| | | | PF00555 | delta endotoxin | 322 | 485 |
| | | | PF03944 | delta endotoxin | 518 | 656 |
| APG06195.0 | 298 | | PF03318 | Clostridium epsilon toxin ETX/Bacillus mosquitocidal toxin MTX2 | 65 | 280 |
| APG06213.0 | 299 | | PF03945 | delta endotoxin, N-terminal domain | 143 | 322 |
| | | | PF14200 | Ricin-type beta-trefoil lectin domain-like | 464 | 549 |
| APG06213.1 | 300 | Alternate start | PF03945 | delta endotoxin, N-terminal domain | 120 | 299 |
| | | | PF14200 | Ricin-type beta-trefoil lectin domain-like | 441 | 526 |
| APG06213.2 | 301 | Signal peptide removed | PF03945 | delta endotoxin, N-terminal domain | 84 | 263 |
| | | | PF14200 | Ricin-type beta-trefoil lectin domain-like | 405 | 490 |
| APG06235.0 | 302 | | PF12495 | Vegetative insecticide protein 3A N terminal | 10 | 185 |
| APG06283.0 | 303 | | no PFAM domains | | | |
| APG06304.0 | 304 | | no PFAM domains | | | |
| APG06304.1 | 305 | Signal peptide removed | no PFAM domains | | | |
| APG06319.0 | 306 | | PF03318 | Clostridium epsilon toxin ETX/Bacillus mosquitocidal toxin MTX2 | 143 | 341 |
| APG06319.1 | 307 | Signal peptide removed | PF03318 | Clostridium epsilon toxin ETX/Bacillus mosquitocidal toxin MTX2 | 114 | 312 |
| APG06331.0 | 308 | | PF14200 | Ricin-type beta-trefoil lectin domain-like | 31 | 101 |
| | | | PF05431 | Insecticidal Crystal Toxin, P42 | 236 | 396 |

TABLE 2-continued

| Summary of PFAM domains in each of SEQ ID NOs: 1-525 | | | | | | |
|---|---|---|---|---|---|---|
| APG ID | Seq ID | Modification Type | Accession | Description | Start | Stop |
| APG06331.1 | 309 | Signal peptide removed | PF14200 | Ricin-type beta-trefoil lectin domain-like | 5 | 74 |
| | | | PF05431 | Insecticidal Crystal Toxin, P42 | 209 | 369 |
| APG06350.0 | 310 | | PF00652 | Ricin-type beta-trefoil lectin domain | 52 | 180 |
| APG06350.1 | 311 | Signal peptide removed | PF00652 | Ricin-type beta-trefoil lectin domain | 17 | 145 |
| APG06378.0 | 312 | | PF02018 | Carbohydrate binding domain | 562 | 679 |
| | | | PF03496 | ADP-ribosyltransferase exoenzyme | 937 | 1130 |
| APG06424.0 | 313 | | PF03945 | delta endotoxin, N-terminal domain | 60 | 237 |
| APG06479.0 | 314 | | no PFAM domains | | | |
| APG06479.1 | 315 | Signal peptide removed | no PFAM domains | | | |
| APG06480.0 | 316 | | PF03318 | Clostridium epsilon toxin ETX/Bacillus mosquitocidal toxin MTX2 | 128 | 316 |
| APG06480.1 | 317 | Alternate start | PF03318 | Clostridium epsilon toxin ETX/Bacillus mosquitocidal toxin MTX2 | 80 | 268 |
| APG06493.0 | 318 | | PF03945 | delta endotoxin, N-terminal domain | 148 | 334 |
| APG06493.1 | 319 | Alternate start | PF03945 | delta endotoxin, N-terminal domain | 82 | 268 |
| APG06496.0 | 320 | | PF01338 | Bacillus thuringiensis toxin | 22 | 244 |
| APG06559.0 | 321 | | PF14200 | Ricin-type beta-trefoil lectin domain-like | 81 | 161 |
| | | | PF05431 | Insecticidal Crystal Toxin, P42 | 215 | 378 |
| APG06576.0 | 322 | | PF03945 | delta endotoxin, N-terminal domain | 90 | 271 |
| | | | PF00555 | delta endotoxin | 329 | 413 |
| | | | PF03944 | delta endotoxin | 505 | 639 |
| APG06576.1 | 323 | 3' Truncation | PF03945 | delta endotoxin, N-terminal domain | 90 | 271 |
| | | | PF00555 | delta endotoxin | 329 | 413 |
| | | | PF03944 | delta endotoxin | 505 | 638 |
| APG06578.0 | 324 | | PF03318 | Clostridium epsilon toxin ETX/Bacillus mosquitocidal toxin MTX2 | 63 | 240 |
| APG06606.0 | 325 | | PF03945 | delta endotoxin, N-terminal domain | 143 | 315 |
| | | | PF14200 | Ricin-type beta-trefoil lectin domain-like | 464 | 549 |
| APG06606.1 | 326 | Alternate start | PF03945 | delta endotoxin, N-terminal domain | 120 | 292 |
| | | | PF14200 | Ricin-type beta-trefoil lectin domain-like | 441 | 526 |
| APG06606.2 | 327 | Signal peptide removed | PF03945 | delta endotoxin, N-terminal domain | 84 | 256 |
| | | | PF14200 | Ricin-type beta-trefoil lectin domain-like | 405 | 490 |
| APG06677.0 | 328 | | PF03945 | delta endotoxin, N-terminal domain | 3 | 87 |
| | | | PF00555 | delta endotoxin | 95 | 313 |
| | | | PF03944 | delta endotoxin | 323 | 461 |
| APG06677.1 | 329 | Alternate start and 3' Truncation | PF03945 | delta endotoxin, N-terminal domain | 3 | 87 |
| | | | PF00555 | delta endotoxin | 95 | 313 |
| | | | PF03944 | delta endotoxin | 323 | 461 |
| APG06697.0 | 330 | | PF14200 | Ricin-type beta-trefoil lectin domain-like | 76 | 149 |
| | | | PF05431 | Insecticidal Crystal Toxin, P42 | 269 | 428 |

TABLE 2-continued

Summary of PFAM domains in each of SEQ ID NOs: 1-525

| APG ID | Seq ID | Modification Type | Accession | Description | Start | Stop |
|---|---|---|---|---|---|---|
| APG06697.1 | 331 | Alternate start | PF14200 | Ricin-type beta-trefoil lectin domain-like | 34 | 107 |
| | | | PF05431 | Insecticidal Crystal Toxin, P42 | 227 | 386 |
| APG06697.2 | 332 | Signal peptide removed | PF14200 | Ricin-type beta-trefoil lectin domain-like | 71 | 133 |
| | | | PF05431 | Insecticidal Crystal Toxin, P42 | 199 | 358 |
| APG06705.0 | 333 | | PF03945 | delta endotoxin, N-terminal domain | 100 | 314 |
| | | | PF03944 | delta endotoxin | 518 | 648 |
| APG06705.1 | 334 | Alternate start | PF03945 | delta endotoxin, N-terminal domain | 84 | 298 |
| | | | PF03944 | delta endotoxin | 502 | 632 |
| APG06705.2 | 335 | Alternate start and 3' Truncation | PF03945 | delta endotoxin, N-terminal domain | 84 | 298 |
| | | | PF03944 | delta endotoxin | 502 | 631 |
| APG06718.0 | 336 | | PF01338 | Bacillus thuringiensis toxin | 33 | 254 |
| APG06738.0 | 337 | | PF03318 | Clostridium epsilon toxin ETX/Bacillus mosquitocidal toxin MTX2 | 105 | 293 |
| APG06738.1 | 338 | Alternate start | PF03318 | Clostridium epsilon toxin ETX/Bacillus mosquitocidal toxin MTX2 | 64 | 252 |
| APG06774.0 | 339 | | PF03945 | delta endotoxin, N-terminal domain | 125 | 311 |
| APG06791.0 | 340 | | PF03318 | Clostridium epsilon toxin ETX/Bacillus mosquitocidal toxin MTX2 | 138 | 247 |
| APG06791.1 | 341 | Signal peptide removed | PF03318 | Clostridium epsilon toxin ETX/Bacillus mosquitocidal toxin MTX2 | 104 | 200 |
| APG06883.0 | 342 | | PF03945 | delta endotoxin, N-terminal domain | 118 | 282 |
| | | | PF01473 | Putative cell wall binding repeat | 505 | 517 |
| | | | PF01473 | Putative cell wall binding repeat | 538 | 553 |
| APG06883.1 | 343 | Signal peptide removed | PF03945 | delta endotoxin, N-terminal domain | 80 | 244 |
| | | | PF01473 | Putative cell wall binding repeat | 467 | 479 |
| | | | PF01473 | Putative cell wall binding repeat | 500 | 515 |
| APG06898.0 | 344 | | PF14200 | Ricin-type beta-trefoil lectin domain-like | 47 | 100 |
| | | | PF05431 | Insecticidal Crystal Toxin, P42 | 215 | 379 |
| APG06898.1 | 345 | Alternate start | PF14200 | Ricin-type beta-trefoil lectin domain-like | 47 | 100 |
| | | | PF05431 | Insecticidal Crystal Toxin, P42 | 215 | 379 |
| APG06937.0 | 346 | | PF01338 | Bacillus thuringiensis toxin | 25 | 234 |
| APG06937.1 | 347 | Alternate start | PF01338 | Bacillus thuringiensis toxin | 19 | 228 |
| APG06954.0 | 348 | | PF03318 | Clostridium epsilon toxin ETX/Bacillus mosquitocidal toxin MTX2 | 106 | 281 |
| APG06954.1 | 349 | Alternate start | PF03318 | Clostridium epsilon toxin ETX/Bacillus mosquitocidal toxin MTX2 | 102 | 277 |
| APG07054.0 | 350 | | PF12495 | Vegetative insecticide protein 3A N terminal | 11 | 189 |
| APG07057.0 | 351 | | PF03945 | delta endotoxin, N-terminal domain | 4 | 167 |
| | | | PF14200 | Ricin-type beta-trefoil lectin domain-like | 404 | 493 |

TABLE 2-continued

| Summary of PFAM domains in each of SEQ ID NOs: 1-525 | | | | | | |
|---|---|---|---|---|---|---|
| APG ID | Seq ID | Modification Type | Accession | Description | Start | Stop |
| APG07094.0 | 352 | | PF03318 | Clostridium epsilon toxin ETX/Bacillus mosquitocidal toxin MTX2 | 165 | 332 |
| APG07094.1 | 353 | Signal peptide removed | PF03318 | Clostridium epsilon toxin ETX/Bacillus mosquitocidal toxin MTX2 | 134 | 301 |
| APG07107.0 | 354 | | PF03318 | Clostridium epsilon toxin ETX/Bacillus mosquitocidal toxin MTX2 | 98 | 314 |
| APG07107.1 | 355 | Signal peptide removed | PF03318 | Clostridium epsilon toxin ETX/Bacillus mosquitocidal toxin MTX2 | 65 | 281 |
| APG07137.0 | 356 | | PF03318 | Clostridium epsilon toxin ETX/Bacillus mosquitocidal toxin MTX2 | 88 | 287 |
| APG07137.1 | 357 | Alternate start | PF03318 | Clostridium epsilon toxin ETX/Bacillus mosquitocidal toxin MTX2 | 72 | 271 |
| APG07137.2 | 358 | Signal peptide removed | PF03318 | Clostridium epsilon toxin ETX/Bacillus mosquitocidal toxin MTX2 | 45 | 244 |
| APG07162.0 | 359 | | PF03945 | delta endotoxin, N-terminal domain | 82 | 272 |
| | | | PF03944 | delta endotoxin | 518 | 649 |
| APG07176.0 | 360 | | PF03318 | Clostridium epsilon toxin ETX/Bacillus mosquitocidal toxin MTX2 | 57 | 268 |
| APG07249.0 | 361 | | PF03318 | Clostridium epsilon toxin ETX/Bacillus mosquitocidal toxin MTX2 | 133 | 227 |
| APG07249.1 | 362 | Alternate start | PF03318 | Clostridium epsilon toxin ETX/Bacillus mosquitocidal toxin MTX2 | 121 | 215 |
| APG07249.2 | 363 | Signal peptide removed | PF03318 | Clostridium epsilon toxin ETX/Bacillus mosquitocidal toxin MTX2 | 92 | 186 |
| APG07257.0 | 364 | | PF05431 | Insecticidal Crystal Toxin, P42 | 276 | 439 |
| APG07257 CryBP1 (APG02145.0) | 365 | | no PFAM domains | | | |
| APG07307.0 | 366 | | no PFAM domains | | | |
| APG07307.1 | 367 | Alternate start | no PFAM domains | | | |
| APG07310.0 | 368 | | PF05431 | Insecticidal Crystal Toxin, P42 | 301 | 463 |
| APG07318.0 | 369 | | PF07691 | PA14 domain | 67 | 164 |
| | | | PF03495 | Clostridial binary toxin B/anthrax toxin PA Ca-binding domain | 240 | 315 |
| | | | PF17475 | Clostridial binary toxin B/anthrax toxin PA domain 2 | 318 | 492 |
| | | | PF17476 | Clostridial binary toxin B/anthrax toxin PA domain 3 | 539 | 639 |
| APG07318.1 | 370 | Alternate start | PF07691 | PA14 domain | 64 | 161 |
| | | | PF03495 | Clostridial binary toxin B/anthrax toxin PA Ca-binding domain | 237 | 312 |
| | | | PF17475 | Clostridial binary toxin B/anthrax toxin PA domain 2 | 315 | 489 |

TABLE 2-continued

Summary of PFAM domains in each of SEQ ID NOs: 1-525

| APG ID | Seq ID | Modification Type | Accession | Description | Start | Stop |
|---|---|---|---|---|---|---|
| | | | PF17476 | Clostridial binary toxin B/anthrax toxin PA domain 3 | 536 | 636 |
| APG07322.0 | 371 | | PF03945 | delta endotoxin, N-terminal domain | 100 | 301 |
| | | | PF00555 | delta endotoxin | 309 | 504 |
| | | | PF03944 | delta endotoxin | 516 | 644 |
| APG07322.1 | 372 | Alternate start | PF03945 | delta endotoxin, N-terminal domain | 97 | 298 |
| | | | PF00555 | delta endotoxin | 306 | 501 |
| | | | PF03944 | delta endotoxin | 513 | 641 |
| APG07322.2 | 373 | Alternate start and 3' Truncation | PF03945 | delta endotoxin, N-terminal domain | 97 | 298 |
| | | | PF00555 | delta endotoxin | 306 | 501 |
| | | | PF03944 | delta endotoxin | 513 | 640 |
| APG07322 SplitCry (APG07435.0) | 374 | | no PFAM domains | | | |
| APG07432.0 | 375 | | PF05431 | Insecticidal Crystal Toxin, P42 | 287 | 449 |
| APG07432.1 | 376 | Alternate start | PF05431 | Insecticidal Crystal Toxin, P42 | 284 | 446 |
| APG07463.0 | 377 | | PF03318 | Clostridium epsilon toxin ETX/Bacillus mosquitocidal toxin MTX2 | 35 | 163 |
| APG07467.0 | 378 | | no PFAM domains | | | |
| APG07467.1 | 379 | Signal peptide removed | no PFAM domains | | | |
| APG07487.0 | 380 | | PF03318 | Clostridium epsilon toxin ETX/Bacillus mosquitocidal toxin MTX2 | 85 | 316 |
| APG07511.0 | 381 | | PF14200 | Ricin-type beta-trefoil lectin domain-like | 38 | 97 |
| | | | PF14200 | Ricin-type beta-trefoil lectin domain-like | 118 | 179 |
| | | | PF05431 | Insecticidal Crystal Toxin, P42 | 208 | 368 |
| APG07511.1 | 382 | Alternate start | PF14200 | Ricin-type beta-trefoil lectin domain-like | 37 | 96 |
| | | | PF14200 | Ricin-type beta-trefoil lectin domain-like | 117 | 178 |
| | | | PF05431 | Insecticidal Crystal Toxin, P42 | 207 | 367 |
| APG07564.0 | 383 | | PF03945 | delta endotoxin, N-terminal domain | 80 | 294 |
| | | | PF03944 | delta endotoxin | 495 | 630 |
| APG07564.1 | 384 | 3' Truncation | PF03945 | delta endotoxin, N-terminal domain | 80 | 294 |
| | | | PF03944 | delta endotoxin | 495 | 630 |
| APG07609.0 | 385 | | no PFAM domains | | | |
| APG07609.1 | 386 | Signal peptide removed | no PFAM domains | | | |
| APG07636.0 | 387 | | PF03945 | delta endotoxin, N-terminal domain | 230 | 327 |
| | | | PF03944 | delta endotoxin | 550 | 688 |
| APG07636.1 | 388 | 3' Truncation | PF03945 | delta endotoxin, N-terminal domain | 230 | 327 |
| | | | PF03944 | delta endotoxin | 550 | 687 |
| APG07664.0 | 389 | | no PFAM domains | | | |
| APG07664.1 | 390 | Alternate start | no PFAM domains | | | |
| APG07665.0 | 391 | | PF03945 | delta endotoxin, N-terminal domain | 85 | 284 |
| | | | PF00555 | delta endotoxin | 293 | 502 |
| | | | PF03944 | delta endotoxin | 512 | 654 |
| APG07665.1 | 392 | Alternate start and 3' | PF03945 | delta endotoxin, N-terminal domain | 79 | 278 |

TABLE 2-continued

| Summary of PFAM domains in each of SEQ ID NOs: 1-525 | | | | | | |
|---|---|---|---|---|---|---|
| APG ID | Seq ID | Modification Type | Accession | Description | Start | Stop |
| | | Truncation | PF00555 | delta endotoxin | 287 | 496 |
| | | | PF03944 | delta endotoxin | 506 | 648 |
| APG07732.0 | 393 | | PF03318 | Clostridium epsilon toxin ETX/Bacillus mosquitocidal toxin MTX2 | 55 | 263 |
| APG07753.0 | 394 | | PF03318 | Clostridium epsilon toxin ETX/Bacillus mosquitocidal toxin MTX2 | 117 | 306 |
| APG07753.1 | 395 | Signal peptide removed | PF03318 | Clostridium epsilon toxin ETX/Bacillus mosquitocidal toxin MTX2 | 85 | 275 |
| APG07798.0 | 396 | | PF03945 | delta endotoxin, N-terminal domain | 63 | 299 |
| | | | PF09259 | Fungal immunomodulatory protein Fve | 999 | 1085 |
| APG07798.1 | 397 | 3' Truncation | PF03945 | delta endotoxin, N-terminal domain | 63 | 299 |
| APG07810.0 | 398 | | PF03945 | delta endotoxin, N-terminal domain | 89 | 294 |
| | | | PF00555 | delta endotoxin | 306 | 480 |
| | | | PF03944 | delta endotoxin | 501 | 663 |
| APG07811.0 | 399 | | PF03945 | delta endotoxin, N-terminal domain | 140 | 316 |
| | | | PF14200 | Ricin-type beta-trefoil lectin domain-like | 464 | 549 |
| APG07811.1 | 400 | Alternate start | PF03945 | delta endotoxin, N-terminal domain | 117 | 299 |
| | | | PF14200 | Ricin-type beta-trefoil lectin domain-like | 441 | 526 |
| APG07811.2 | 401 | Signal peptide removed | PF03945 | delta endotoxin, N-terminal domain | 79 | 255 |
| | | | PF14200 | Ricin-type beta-trefoil lectin domain-like | 403 | 488 |
| APG07945.0 | 402 | | PF03945 | delta endotoxin, N-terminal domain | 115 | 297 |
| | | | PF00555 | delta endotoxin | 305 | 524 |
| | | | PF03944 | delta endotoxin | 534 | 671 |
| APG07945.1 | 403 | 3' Truncation | PF03945 | delta endotoxin, N-terminal domain | 115 | 297 |
| | | | PF00555 | delta endotoxin | 305 | 524 |
| | | | PF03944 | delta endotoxin | 534 | 671 |
| APG07945 CryBP1 (APG04357.0) | 404 | | PF07029 | CryBP1 protein | 46 | 152 |
| APG07969.0 | 405 | | PF03318 | Clostridium epsilon toxin ETX/Bacillus mosquitocidal toxin MTX2 | 94 | 244 |
| APG07969.1 | 406 | Signal peptide removed | PF03318 | Clostridium epsilon toxin ETX/Bacillus mosquitocidal toxin MTX2 | 72 | 223 |
| APG08004.0 | 407 | | PF14200 | Ricin-type beta-trefoil lectin domain-like | 32 | 102 |
| | | | PF14200 | Ricin-type beta-trefoil lectin domain-like | 111 | 148 |
| | | | PF05431 | Insecticidal Crystal Toxin, P42 | 231 | 391 |
| APG08004.1 | 408 | Signal peptide removed | PF14200 | Ricin-type beta-trefoil lectin domain-like | 5 | 75 |
| | | | PF14200 | Ricin-type beta-trefoil lectin domain-like | 84 | 121 |
| | | | PF05431 | Insecticidal Crystal Toxin, P42 | 204 | 364 |
| APG08021.0 | 409 | | PF03945 | delta endotoxin, N-terminal domain | 99 | 277 |
| | | | PF00555 | delta endotoxin | 285 | 476 |
| | | | PF03944 | delta endotoxin | 487 | 623 |
| APG08021.1 | 410 | 3' Truncation | PF03945 | delta endotoxin, N-terminal domain | 99 | 277 |

TABLE 2-continued

Summary of PFAM domains in each of SEQ ID NOs: 1-525

| APG ID | Seq ID | Modification Type | Accession | Description | Start | Stop |
|---|---|---|---|---|---|---|
| | | | PF00555 | delta endotoxin | 285 | 476 |
| | | | PF03944 | delta endotoxin | 487 | 622 |
| APG08081.0 | 411 | | PF00388 | Phosphatidylinositol-specific phospholipase C, X domain | 94 | 208 |
| | | | PF14200 | Ricin-type beta-trefoil lectin domain-like | 553 | 619 |
| APG08081.1 | 412 | Signal peptide removed | PF00388 | Phosphatidylinositol-specific phospholipase C, X domain | 58 | 172 |
| | | | PF14200 | Ricin-type beta-trefoil lectin domain-like | 517 | 583 |
| APG08081.2 | 413 | Signal peptide removed and 3' Truncation | PF00388 | Phosphatidylinositol-specific phospholipase C, X domain | 57 | 172 |
| APG08171.0 | 414 | | PF03945 | delta endotoxin, N-terminal domain | 60 | 239 |
| | | | PF01473 | Putative cell wall binding repeat | 316 | 327 |
| APG08193.0 | 415 | | PF14200 | Ricin-type beta-trefoil lectin domain-like | 70 | 139 |
| | | | PF05431 | Insecticidal Crystal Toxin, P42 | 213 | 376 |
| APG08193.1 | 416 | Signal peptide removed | PF14200 | Ricin-type beta-trefoil lectin domain-like | 43 | 112 |
| | | | PF05431 | Insecticidal Crystal Toxin, P42 | 186 | 349 |
| APG08207.0 | 417 | | PF03318 | Clostridium epsilon toxin ETX/Bacillus mosquitocidal toxin MTX2 | 241 | 357 |
| APG08207.1 | 418 | Alternate start | PF03318 | Clostridium epsilon toxin ETX/Bacillus mosquitocidal toxin MTX2 | 219 | 326 |
| APG08207.2 | 419 | Signal peptide removed | PF03318 | Clostridium epsilon toxin ETX/Bacillus mosquitocidal toxin MTX2 | 191 | 301 |
| APG08240.0 | 420 | | PF03318 | Clostridium epsilon toxin ETX/Bacillus mosquitocidal toxin MTX2 | 101 | 322 |
| APG08316.0 | 421 | | PF03318 | Clostridium epsilon toxin ETX/Bacillus mosquitocidal toxin MTX2 | 5 | 62 |
| APG08335.0 | 422 | | PF03318 | Clostridium epsilon toxin ETX/Bacillus mosquitocidal toxin MTX2 | 107 | 307 |
| APG08335.1 | 423 | Signal peptide removed | PF03318 | Clostridium epsilon toxin ETX/Bacillus mosquitocidal toxin MTX2 | 82 | 282 |
| APG08339.0 | 424 | | PF03318 | Clostridium epsilon toxin ETX/Bacillus mosquitocidal toxin MTX2 | 79 | 292 |
| APG08339.1 | 425 | Signal peptide removed | PF03318 | Clostridium epsilon toxin ETX/Bacillus mosquitocidal toxin MTX2 | 50 | 263 |
| APG08370.0 | 426 | | PF01823 | MAC/Perforin domain | 144 | 342 |
| | | | PF01453 | D-mannose binding lectin | 388 | 463 |
| APG08370.1 | 427 | Signal peptide removed | PF01823 | MAC/Perforin domain | 118 | 316 |
| | | | PF01453 | D-mannose binding lectin | 362 | 437 |
| APG08378.0 | 428 | | PF03945 | delta endotoxin, N-terminal domain | 100 | 301 |
| | | | PF00555 | delta endotoxin | 309 | 504 |
| | | | PF03944 | delta endotoxin | 516 | 644 |

TABLE 2-continued

Summary of PFAM domains in each of SEQ ID NOs: 1-525

| APG ID | Seq ID | Modification Type | Accession | Description | Start | Stop |
|---|---|---|---|---|---|---|
| APG08378.1 | 429 | Alternate start | PF03945 | delta endotoxin, N-terminal domain | 97 | 298 |
| | | | PF00555 | delta endotoxin | 306 | 501 |
| | | | PF03944 | delta endotoxin | 513 | 641 |
| APG08378 SplitCry (APG08000.0) | 430 | | no PFAM domains | | | |
| APG08427.0 | 431 | | PF06101 | Vacuolar protein sorting-associated protein 62 | 22 | 194 |
| APG08427.1 | 432 | Alternate start | PF06101 | Vacuolar protein sorting-associated protein 62 | 14 | 186 |
| APG08468.0 | 433 | | PF03945 | delta endotoxin, N-terminal domain | 60 | 238 |
| | | | PF01473 | Putative cell wall binding repeat | 316 | 327 |
| APG08495.0 | 434 | | PF03318 | Clostridium epsilon toxin ETX/Bacillus mosquitocidal toxin MTX2 | 60 | 271 |
| APG08526.0 | 435 | | PF03945 | delta endotoxin, N-terminal domain | 77 | 263 |
| APG08576.0 | 436 | | no PFAM domains | | | |
| APG08577.0 | 437 | | PF03318 | Clostridium epsilon toxin ETX/Bacillus mosquitocidal toxin MTX2 | 41 | 253 |
| APG08624.0 | 438 | | PF06101 | Vacuolar protein sorting-associated protein 62 | 18 | 205 |
| APG08624.1 | 439 | Alternate start | PF06101 | Vacuolar protein sorting-associated protein 62 | 16 | 203 |
| APG08625.0 | 440 | | PF03318 | Clostridium epsilon toxin ETX/Bacillus mosquitocidal toxin MTX2 | 84 | 296 |
| APG08625.1 | 441 | Signal peptide removed | PF03318 | Clostridium epsilon toxin ETX/Bacillus mosquitocidal toxin MTX2 | 56 | 268 |
| APG08639.0 | 442 | | PF03318 | Clostridium epsilon toxin ETX/Bacillus mosquitocidal toxin MTX2 | 55 | 248 |
| APG08642.0 | 443 | | PF03945 | delta endotoxin, N-terminal domain | 101 | 308 |
| | | | PF00555 | delta endotoxin | 321 | 505 |
| | | | PF03944 | delta endotoxin | 529 | 687 |
| APG08642.1 | 444 | Alternate start | PF03945 | delta endotoxin, N-terminal domain | 94 | 301 |
| | | | PF00555 | delta endotoxin | 314 | 498 |
| | | | PF03944 | delta endotoxin | 522 | 680 |
| APG08642.2 | 445 | Alternate start and 3' Truncation | PF03945 | delta endotoxin, N-terminal domain | 94 | 301 |
| | | | PF00555 | delta endotoxin | 314 | 498 |
| | | | PF03944 | delta endotoxin | 522 | 680 |
| APG08757.0 | 446 | | PF03318 | Clostridium epsilon toxin ETX/Bacillus mosquitocidal toxin MTX2 | 134 | 333 |
| APG08757.1 | 447 | Signal peptide removed | PF03318 | Clostridium epsilon toxin ETX/Bacillus mosquitocidal toxin MTX2 | 107 | 306 |
| APG08765.0 | 448 | | PF03945 | delta endotoxin, N-terminal domain | 127 | 301 |
| | | | PF00555 | delta endotoxin | 310 | 506 |
| | | | PF03944 | delta endotoxin | 516 | 670 |
| APG08765 CryBP1 (APG07717.0) | 449 | | no PFAM domains | | | |

TABLE 2-continued

| Summary of PFAM domains in each of SEQ ID NOs: 1-525 | | | | | | |
|---|---|---|---|---|---|---|
| APG ID | Seq ID | Modification Type | Accession | Description | Start | Stop |
| APG08791.0 | 450 | | no PFAM domains | | | |
| APG08791.1 | 451 | Alternate start | no PFAM domains | | | |
| APG08791.2 | 452 | Signal peptide removed | no PFAM domains | | | |
| APG08812.0 | 453 | | no PFAM domains | | | |
| APG08823.0 | 454 | | PF03318 | Clostridium epsilon toxin ETX/Bacillus mosquitocidal toxin MTX2 | 71 | 267 |
| APG08852.0 | 455 | | PF03945 | delta endotoxin, N-terminal domain | 59 | 238 |
| APG08912.0 | 456 | | PF03318 | Clostridium epsilon toxin ETX/Bacillus mosquitocidal toxin MTX2 | 96 | 315 |
| APG08912.1 | 457 | Alternate start | PF03318 | Clostridium epsilon toxin ETX/Bacillus mosquitocidal toxin MTX2 | 93 | 312 |
| APG08912.2 | 458 | Signal peptide removed | PF03318 | Clostridium epsilon toxin ETX/Bacillus mosquitocidal toxin MTX2 | 65 | 284 |
| APG09027.0 | 459 | | PF14200 | Ricin-type beta-trefoil lectin domain-like | 32 | 101 |
| | | | PF05431 | Insecticidal Crystal Toxin, P42 | 236 | 396 |
| APG09027.1 | 460 | Signal peptide removed | PF14200 | Ricin-type beta-trefoil lectin domain-like | 4 | 72 |
| | | | PF05431 | Insecticidal Crystal Toxin, P42 | 207 | 367 |
| APG09028.0 | 461 | | PF03945 | delta endotoxin, N-terminal domain | 114 | 329 |
| | | | PF01473 | Putative cell wall binding repeat | 341 | 353 |
| | | | PF01473 | Putative cell wall binding repeat | 360 | 371 |
| | | | PF01473 | Putative cell wall binding repeat | 387 | 398 |
| | | | PF01473 | Putative cell wall binding repeat | 471 | 484 |
| | | | PF01473 | Putative cell wall binding repeat | 522 | 536 |
| | | | PF02839 | Carbohydrate binding domain | 636 | 661 |
| APG09028.1 | 462 | Signal peptide removed | PF03945 | delta endotoxin, N-terminal domain | 76 | 291 |
| | | | PF01473 | Putative cell wall binding repeat | 303 | 315 |
| | | | PF01473 | Putative cell wall binding repeat | 322 | 333 |
| | | | PF01473 | Putative cell wall binding repeat | 349 | 360 |
| | | | PF01473 | Putative cell wall binding repeat | 433 | 446 |
| | | | PF01473 | Putative cell wall binding repeat | 484 | 498 |
| | | | PF02839 | Carbohydrate binding domain | 598 | 623 |
| APG09048.0 | 463 | | PF03318 | Clostridium epsilon toxin ETX/Bacillus mosquitocidal toxin MTX2 | 73 | 276 |
| APG09048.1 | 464 | Signal peptide removed | PF03318 | Clostridium epsilon toxin ETX/Bacillus mosquitocidal toxin MTX2 | 55 | 258 |
| APG09152.0 | 465 | | PF03318 | Clostridium epsilon toxin ETX/Bacillus mosquitocidal toxin MTX2 | 54 | 250 |

TABLE 2-continued

| Summary of PFAM domains in each of SEQ ID NOs: 1-525 | | | | | | |
|---|---|---|---|---|---|---|
| APG ID | Seq ID | Modification Type | Accession | Description | Start | Stop |
| APG09152.1 | 466 | Alternate start | PF03318 | Clostridium epsilon toxin ETX/Bacillus mosquitocidal toxin MTX2 | 49 | 245 |
| APG09158.0 | 467 | | no PFAM domains | | | |
| APG09158.1 | 468 | Signal peptide removed | no PFAM domains | | | |
| APG09181.0 | 469 | | PF01338 | Bacillus thuringiensis toxin | 22 | 243 |
| APG09201.0 | 470 | | PF01338 | Bacillus thuringiensis toxin | 17 | 255 |
| APG09210.0 | 471 | | PF03945 | delta endotoxin, N-terminal domain | 91 | 274 |
| APG09221.0 | 472 | | PF12495 | Vegetative insecticide protein 3A N terminal | 10 | 185 |
| APG09238.0 | 473 | | PF07691 | PA14 domain | 52 | 178 |
| | | | PF03495 | Clostridial binary toxin B/anthrax toxin PA Ca-binding domain | 220 | 295 |
| | | | PF17475 | Clostridial binary toxin B/anthrax toxin PA domain 2 | 300 | 492 |
| | | | PF17476 | Clostridial binary toxin B/anthrax toxin PA domain 3 | 528 | 614 |
| APG09238.1 | 474 | Alternate start | PF07691 | PA14 domain | 50 | 176 |
| | | | PF03495 | Clostridial binary toxin B/anthrax toxin PA Ca-binding domain | 218 | 293 |
| | | | PF17475 | Clostridial binary toxin B/anthrax toxin PA domain 2 | 298 | 490 |
| | | | PF17476 | Clostridial binary toxin B/anthrax toxin PA domain 3 | 526 | 612 |
| APG09238.2 | 475 | Signal peptide removed | PF07691 | PA14 domain | 26 | 152 |
| | | | PF03495 | Clostridial binary toxin B/anthrax toxin PA Ca-binding domain | 194 | 269 |
| | | | PF17475 | Clostridial binary toxin B/anthrax toxin PA domain 2 | 274 | 466 |
| | | | PF17476 | Clostridial binary toxin B/anthrax toxin PA domain 3 | 502 | 588 |
| APG09266.0 | 476 | | PF14200 | Ricin-type beta-trefoil lectin domain-like | 42 | 102 |
| | | | PF05431 | Insecticidal Crystal Toxin, P42 | 214 | 374 |
| APG09266.1 | 477 | Alternate start | PF14200 | Ricin-type beta-trefoil lectin domain-like | 41 | 101 |
| | | | PF05431 | Insecticidal Crystal Toxin, P42 | 213 | 373 |
| APG09289.0 | 478 | | PF03945 | delta endotoxin, N-terminal domain | 85 | 304 |
| | | | PF03944 | delta endotoxin | 527 | 647 |
| APG09289.1 | 479 | Alternate start | PF03945 | delta endotoxin, N-terminal domain | 81 | 300 |
| | | | PF03944 | delta endotoxin | 523 | 643 |
| APG09289.2 | 480 | Alternate start and 3' Truncation | PF03945 | delta endotoxin, N-terminal domain | 81 | 300 |
| | | | PF03944 | delta endotoxin | 523 | 642 |
| APG09323.0 | 481 | | PF14200 | Ricin-type beta-trefoil lectin domain-like | 41 | 116 |
| | | | PF05431 | Insecticidal Crystal Toxin, P42 | 247 | 407 |
| APG09323.1 | 482 | Alternate start | PF14200 | Ricin-type beta-trefoil lectin domain-like | 32 | 107 |
| | | | PF05431 | Insecticidal Crystal Toxin, P42 | 238 | 398 |
| APG09412.0 | 483 | | PF03318 | Clostridium epsilon toxin ETX/Bacillus | 92 | 295 |

TABLE 2-continued

| Summary of PFAM domains in each of SEQ ID NOs: 1-525 | | | | | | |
|---|---|---|---|---|---|---|
| APG ID | Seq ID | Modification Type | Accession | Description | Start | Stop |
| | | | | mosquitocidal toxin MTX2 | | |
| APG09412.1 | 484 | Signal peptide removed | PF03318 | Clostridium epsilon toxin ETX/Bacillus mosquitocidal toxin MTX2 | 60 | 263 |
| APG09415.0 | 485 | | no PFAM domains | | | |
| APG09415.1 | 486 | Signal peptide removed | no PFAM domains | | | |
| APG09416.0 | 487 | | PF03318 | Clostridium epsilon toxin ETX/Bacillus mosquitocidal toxin MTX2 | 47 | 250 |
| APG09430.0 | 488 | | PF03945 | delta endotoxin, N-terminal domain | 109 | 299 |
| | | | PF00555 | delta endotoxin | 311 | 483 |
| | | | PF03944 | delta endotoxin | 494 | 660 |
| APG09430.1 | 489 | 3' Truncation | PF03945 | delta endotoxin, N-terminal domain | 109 | 299 |
| | | | PF00555 | delta endotoxin | 311 | 483 |
| | | | PF03944 | delta endotoxin | 494 | 659 |
| APG09439.0 | 490 | | no PFAM domains | | | |
| APG09465.0 | 491 | | PF14200 | Ricin-type beta-trefoil lectin domain-like | 72 | 151 |
| | | | PF05431 | Insecticidal Crystal Toxin, P42 | 231 | 390 |
| APG09465.1 | 492 | Signal peptide removed | PF14200 | Ricin-type beta-trefoil lectin domain-like | 45 | 124 |
| | | | PF05431 | Insecticidal Crystal Toxin, P42 | 204 | 363 |
| APG09511.0 | 493 | | PF03945 | delta endotoxin, N-terminal domain | 144 | 311 |
| | | | PF14200 | Ricin-type beta-trefoil lectin domain-like | 553 | 595 |
| APG09511.1 | 494 | Signal peptide removed | PF03945 | delta endotoxin, N-terminal domain | 108 | 276 |
| | | | PF14200 | Ricin-type beta-trefoil lectin domain-like | 517 | 559 |
| APG09548.0 | 495 | | PF03945 | delta endotoxin, N-terminal domain | 86 | 265 |
| | | | PF00555 | delta endotoxin | 358 | 567 |
| | | | PF03944 | delta endotoxin | 579 | 711 |
| APG09548.1 | 496 | 3' Truncation | PF03945 | delta endotoxin, N-terminal domain | 86 | 265 |
| | | | PF00555 | delta endotoxin | 358 | 567 |
| | | | PF03944 | delta endotoxin | 579 | 710 |
| APG09548 SplitCry (APG01177.0) | 497 | | no PFAM domains | | | |
| APG09675.0 | 498 | | PF03318 | Clostridium epsilon toxin ETX/Bacillus mosquitocidal toxin MTX2 | 58 | 279 |
| APG09773.0 | 499 | | PF03945 | delta endotoxin, N-terminal domain | 54 | 127 |
| | | | PF03945 | delta endotoxin, N-terminal domain | 218 | 293 |
| APG09812.0 | 500 | | PF03945 | delta endotoxin, N-terminal domain | 21 | 172 |
| APG09814.0 | 501 | | PF03945 | delta endotoxin, N-terminal domain | 86 | 290 |
| | | | PF00555 | delta endotoxin | 298 | 517 |
| | | | PF03944 | delta endotoxin | 527 | 683 |
| APG09826.0 | 502 | | PF03945 | delta endotoxin, N-terminal domain | 74 | 258 |
| APG09826.1 | 503 | Alternate start | PF03945 | delta endotoxin, N-terminal domain | 28 | 212 |
| APG09835.0 | 504 | | PF03945 | delta endotoxin, N-terminal domain | 60 | 239 |
| | | | PF01473 | Putative cell wall binding repeat | 316 | 327 |

TABLE 2-continued

| Summary of PFAM domains in each of SEQ ID NOs: 1-525 | | | | | | |
|---|---|---|---|---|---|---|
| APG ID | Seq ID | Modification Type | Accession | Description | Start | Stop |
| APG09895.0 | 505 | | PF03945 | delta endotoxin, N-terminal domain | 128 | 311 |
| | | | PF14200 | Ricin-type beta-trefoil lectin domain-like | 519 | 605 |
| APG09895.1 | 506 | Signal peptide removed | PF03945 | delta endotoxin, N-terminal domain | 94 | 277 |
| | | | PF14200 | Ricin-type beta-trefoil lectin domain-like | 485 | 571 |
| APG09901.0 | 507 | | PF03318 | Clostridium epsilon toxin ETX/Bacillus mosquitocidal toxin MTX2 | 96 | 273 |
| APG09901.1 | 508 | Alternate start | PF03318 | Clostridium epsilon toxin ETX/Bacillus mosquitocidal toxin MTX2 | 93 | 270 |
| APG09901.2 | 509 | Signal peptide removed | PF03318 | Clostridium epsilon toxin ETX/Bacillus mosquitocidal toxin MTX2 | 65 | 242 |
| APG09903.0 | 510 | | PF03945 | delta endotoxin, N-terminal domain | 65 | 234 |
| | | | PF00555 | delta endotoxin | 375 | 559 |
| | | | PF03944 | delta endotoxin | 607 | 735 |
| APG09903.1 | 511 | Alternate start | PF03945 | delta endotoxin, N-terminal domain | 65 | 234 |
| | | | PF00555 | delta endotoxin | 375 | 559 |
| | | | PF03944 | delta endotoxin | 607 | 735 |
| APG10001.0 | 512 | | PF03318 | Clostridium epsilon toxin ETX/Bacillus mosquitocidal toxin MTX2 | 112 | 317 |
| APG10001.1 | 513 | Alternate start | PF03318 | Clostridium epsilon toxin ETX/Bacillus mosquitocidal toxin MTX2 | 92 | 297 |
| APG10001.2 | 514 | Signal peptide removed | PF03318 | Clostridium epsilon toxin ETX/Bacillus mosquitocidal toxin MTX2 | 58 | 263 |
| APG01902.0 | 515 | | PF03945 | delta endotoxin, N-terminal domain | 21 | 172 |
| APG01902.1 | 516 | Alternate start | PF03945 | delta endotoxin, N-terminal domain | 21 | 172 |
| APG02996.0 | 517 | | PF03945 | delta endotoxin, N-terminal domain | 22 | 172 |
| APG02996.1 | 518 | Alternate start | PF03945 | delta endotoxin, N-terminal domain | 22 | 172 |
| APG03098.0 | 519 | | PF03945 | delta endotoxin, N-terminal domain | 21 | 172 |
| APG03098.1 | 520 | Alternate start | PF03945 | delta endotoxin, N-terminal domain | 21 | 172 |
| APG04517.0 | 521 | | PF03945 | delta endotoxin, N-terminal domain | 20 | 174 |
| APG04619.0 | 522 | | PF03945 | delta endotoxin, N-terminal domain | 21 | 172 |
| APG04619.1 | 523 | Alternate start | PF03945 | delta endotoxin, N-terminal domain | 21 | 172 |
| APG06717.0 | 524 | | PF03945 | delta endotoxin, N-terminal domain | 21 | 172 |
| APG06717.1 | 525 | Alternate start | PF03945 | delta endotoxin, N-terminal domain | 21 | 172 |

Recombinant or synthetic nucleic acids encoding the pesticidal polypeptides disclosed herein are also provided. Of particular interest are nucleic acid sequences that have been designed for expression in a plant of interest. That is, the nucleic acid sequence can be optimized for increased expression in a host plant. A pesticidal protein of the invention can be back-translated to produce a nucleic acid comprising codons optimized for expression in a particular host, for example, a crop plant. In another embodiment, the polynucleotides encoding the polypeptides provided herein may be optimized for increased expression in the transformed plant. That is, the polynucleotides can be synthesized using plant-preferred codons for improved expression. See, for example, Campbell and Gowri (1990) *Plant Physiol.* 92:1-11 for a discussion of host-preferred codon usage. Methods are available in the art for synthesizing plant-preferred genes. See, for example, U.S. Pat. Nos. 5,380,831, and 5,436,391, and Murray et al. (1989) *Nucleic*

*Acids Res.* 17:477-498, herein incorporated by reference. Expression of such a coding sequence by the transformed plant (e.g., dicot or monocot) will result in the production of a pesticidal polypeptide and confer increased resistance in the plant to a pest. Recombinant and synthetic nucleic acid molecules encoding the pesticidal proteins of the invention do not include the naturally occurring bacterial sequence encoding the protein.

A "recombinant polynucleotide" or "recombinant nucleic acid" comprises a combination of two or more chemically linked nucleic acid segments which are not found directly joined in nature. By "directly joined" is intended the two nucleic acid segments are immediately adjacent and joined to one another by a chemical linkage. In specific embodiments, the recombinant polynucleotide comprises a polynucleotide of interest or a variant or fragment thereof such that an additional chemically linked nucleic acid segment is located either 5', 3' or internal to the polynucleotide of interest. Alternatively, the chemically-linked nucleic acid segment of the recombinant polynucleotide can be formed by deletion of a sequence. The additional chemically linked nucleic acid segment or the sequence deleted to join the linked nucleic acid segments can be of any length, including for example, 1, 2, 3, 4, 5, 6, 7, 8, 9, 10, 15, 20 or greater nucleotides. Various methods for making such recombinant polynucleotides include chemical synthesis or by the manipulation of isolated segments of polynucleotides by genetic engineering techniques. In specific embodiments, the recombinant polynucleotide can comprise a recombinant DNA sequence or a recombinant RNA sequence. A "fragment of a recombinant polynucleotide or nucleic acid" comprises at least one of a combination of two or more chemically linked amino acid segments which are not found directly joined in nature.

Fragments of a polynucleotide (RNA or DNA) may encode protein fragments that retain activity. In specific embodiments, a fragment of a recombinant polynucleotide or a recombinant polynucleotide construct comprises at least one junction of the two or more chemically linked or operably linked nucleic acid segments which are not found directly joined in nature. A fragment of a polynucleotide that encodes a biologically active portion of a polypeptide that retains pesticidal activity will encode at least 25, 30, 40, 50, 70, 75, 80, 90, 100, 110, 120, 125, 130, 140, 150, 160, 170, 175, 180, contiguous amino acids, or up to the total number of amino acids present in a full-length polypeptide as set forth in SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, and/or 525. In specific embodiments, such polypeptide fragments are active fragment, and in still other embodiments, the polypeptide fragment comprises a recombinant polypeptide fragment. As used herein a fragment of a recombinant polypeptide comprises at least one of a combination of two or more chemically linked amino acid segments which are not found directly joined in nature.

By "variants" is intended to mean substantially similar sequences. For polynucleotides, a variant comprises a deletion and/or addition of one or more nucleotides at one or more internal sites within the native polynucleotide and/or a substitution of one or more nucleotides at one or more sites in the native polynucleotide. As used herein, a "native" polynucleotide or polypeptide comprises a naturally occurring nucleotide sequence or amino acid sequence, respectively.

Variants of a particular polynucleotide of the invention (i.e., the reference polynucleotide) can also be evaluated by comparison of the percent sequence identity between the polypeptide encoded by a variant polynucleotide and the polypeptide encoded by the reference polynucleotide. Thus, for example, an isolated polynucleotide that encodes a polypeptide with a given percent sequence identity to the polypeptide of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, and/or 525 are disclosed. Percent sequence identity between any two polypeptides can be calculated using sequence alignment programs and parameters described elsewhere herein. Where any given pair of polynucleotides of the invention is evaluated by comparison of the percent sequence identity shared by the two polypeptides they encode, the percent sequence identity between the two encoded polypeptides is at least about 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98%, 99% or more sequence identity to SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, and/or 525. In other embodiments, the variant of the polynucleotide provided herein differs from the native sequence by at least 1, 2, 3, 4, 5, 6, 7, 8, 9, 10 or more nucleotides.

Variant polynucleotide and proteins also encompass sequences and proteins derived from a mutagenic and recombinogenic procedure such as DNA shuffling. With such a procedure, one or more different pesticidal protein disclosed herein (SEQ ID NO: 1-525) is manipulated to create a new pesticidal protein possessing the desired properties. In this manner, libraries of recombinant polynucleotides are generated from a population of related sequence polynucleotides comprising sequence regions that have substantial sequence identity and can be homologously recombined in vitro or in vivo. For example, using this approach, sequence motifs encoding a domain of interest may be shuffled between the pesticidial sequences provided herein and other known pesticidial genes to obtain a new gene coding for a protein with an improved property of interest, such as an increased K m in the case of an enzyme. Strategies for such DNA shuffling are known in the art. See, for example, Stemmer (1994) *Proc. Natl. Acad. Sci. USA* 91:10747-10751; Stemmer (1994) *Nature* 370:389-391; Crameri et al. (1997) *Nature Biotech.* 15:436-438; Moore et al. (1997) *J. Mol. Biol.* 272:336-347; Zhang et al. (1997) *Proc. Natl. Acad. Sci. USA* 94:4504-4509; Crameri et al. (1998) *Nature* 391:288-291; and U.S. Pat. Nos. 5,605,793 and 5,837,458. A "shuffled" nucleic acid is a nucleic acid produced by a shuffling procedure such as any shuffling procedure set forth herein. Shuffled nucleic acids are produced by recombining (physically or virtually) two or more nucleic acids (or character strings), for example in an artificial, and optionally recursive, fashion. Generally, one or more screening steps are used in shuffling processes to identify nucleic acids of interest; this screening step can be performed before or after any recombination step. In some (but not all) shuffling embodiments, it is desirable to perform multiple rounds of recombination prior to selection to increase the diversity of the pool to be screened. The overall process of recombination and selection are optionally repeated recursively. Depending on context, shuffling can refer to an overall process of recombination and selection, or, alternately, can simply refer to the recombinational portions of the overall process.

In one embodiment, a method of obtaining a polynucleotide that encodes an improved polypeptide comprising pesticidal activity is provided, wherein the improved polypeptide has at least one improved property over any one of SEQ ID NOs: 1-525. Such methods can comprises (a) recombining a plurality of parental polynucleotides to produce a library of recombinant polynucleotides encoding recombinant pesticidal polypeptides; (b) screening the library to identify a recombinant polynucleotide that encodes an improved recombinant pesticidal polypeptide that has an enhanced property improved over the parental polynucleotide; (c) recovering the recombinant polynucleotide that encodes the improved recombinant pesticidal polypeptide identified in (b); and, (d) repeating steps (a), (b) and (c) using the recombinant polynucleotide recovered in step (c) as one of the plurality of parental polynucleotides in repeated step (a).

iii. Sequence Comparisons

As used herein, the term "identity" or "percent identity" when used with respect to a particular pair of aligned amino acid sequences, refers to the percent amino acid sequence identity that is obtained by counting the number of identical matches in the alignment and dividing such number of identical matches by the length of the aligned sequences. As used herein, the term "similarity" or "percent similarity" when used with respect to a particular pair of aligned amino acid sequences, refers to the sum of the scores that are obtained from a scoring matrix for each amino acid pair in the alignment divided by the length of the aligned sequences.

Unless otherwise stated, identity and similarity will be calculated by the Needleman-Wunsch global alignment and scoring algorithms (Needleman and Wunsch (1970) *J. Mol. Biol.* 48(3):443-453) as implemented by the "needle" program, distributed as part of the EMBOSS software package (Rice, P. Longden, I. and Bleasby, A., EMBOSS: The European Molecular Biology Open Software Suite, 2000, *Trends in Genetics* 16, (6) pp 276-277, versions 6.3.1 available from EMBnet at embnet.org/resource/emboss and emboss.sourceforge.net, among other sources) using default gap penalties and scoring matrices (EBLOSUM62 for protein and EDNAFULL for DNA). Equivalent programs may also be used. By "equivalent program" is intended any sequence comparison program that, for any two sequences in question, generates an alignment having identical nucleotide residue matches and an identical percent sequence identity when compared to the corresponding alignment generated by needle from EMBOSS version 6.3.1.

Additional mathematical algorithms are known in the art and can be utilized for the comparison of two sequences. See, for example, the algorithm of Karlin and Altschul (1990) Proc. Natl. Acad. Sci. USA 87:2264, modified as in Karlin and Altschul (1993) Proc. Natl. Acad. Sci. USA 90:5873-5877. Such an algorithm is incorporated into the BLAST programs of Altschul et al. (1990) J. Mol. Biol. 215:403. BLAST nucleotide searches can be performed with the BLASTN program (nucleotide query searched against nucleotide sequences) to obtain nucleotide sequences homologous to pesticidal-like nucleic acid molecules of the invention, or with the BLASTX program (translated nucleotide query searched against protein sequences) to obtain protein sequences homologous to pesticidal nucleic acid molecules of the invention. BLAST protein searches can be performed with the BLASTP program (protein query searched against protein sequences) to obtain amino acid sequences homologous to pesticidal protein molecules of the invention, or with the TBLASTN program (protein query searched against translated nucleotide sequences) to obtain nucleotide sequences homologous to pesticidal protein molecules of the invention. To obtain gapped alignments for comparison purposes, Gapped BLAST (in BLAST 2.0) can be utilized as described in Altschul et al. (1997) *Nucleic Acids Res.* 25:3389. Alternatively, PSI-Blast can be used to perform an iterated search that detects distant relationships between molecules. See Altschul et al. (1997) supra. When utilizing BLAST, Gapped BLAST, and PSI-Blast programs, the default parameters of the respective programs (e.g., BLASTX and BLASTN) can be used. Alignment may also be performed manually by inspection.

Two sequences are "optimally aligned" when they are aligned for similarity scoring using a defined amino acid substitution matrix (e.g., BLOSUM62), gap existence penalty and gap extension penalty so as to arrive at the highest score possible for that pair of sequences. Amino acid substitution matrices and their use in quantifying the similarity between two sequences are well-known in the art and described, e.g., in Dayhoff et al. (1978) "A model of evolutionary change in proteins." In "Atlas of Protein Sequence and Structure," Vol. 5, Suppl. 3 (ed. M. O. Dayhoff), pp. 345-352. Natl. Biomed. Res. Found., Washington, D.C. and Henikoff et al. (1992) Proc. Natl. Acad. Sci. USA 89:10915-10919. The BLOSUM62 matrix is often used as a default scoring substitution matrix in sequence alignment protocols. The gap existence penalty is imposed for the introduction of a single amino acid gap in one of the aligned sequences, and the gap extension penalty is imposed for each additional empty amino acid position inserted into an already opened gap. The alignment is defined by the amino acids positions of each sequence at which the alignment begins and ends, and optionally by the insertion of a gap or multiple gaps in one or both sequences, so as to arrive at the highest possible score. While optimal alignment and scoring can be accomplished manually, the process is facilitated by the use of a computer-implemented alignment algorithm, e.g., gapped BLAST 2.0, described in Altschul et al. (1997) *Nucleic Acids Res.* 25:3389-3402, and made available to the public at the National Center for Biotechnology Information Website (www.ncbi.nlm.nih.gov). Optimal alignments, including multiple alignments, can be prepared using, e.g., PSI-BLAST, available through www.ncbi.nlm.nih.gov and described by Altschul et al. (1997) *Nucleic Acids Res.* 25:3389-3402.

With respect to an amino acid sequence that is optimally aligned with a reference sequence, an amino acid residue "corresponds to" the position in the reference sequence with which the residue is paired in the alignment. The "position" is denoted by a number that sequentially identifies each amino acid in the reference sequence based on its position relative to the N-terminus. For example, in SEQ ID NO: 1 position 1 is V, position 2 is F, position 3 is L, etc. When a test sequence is optimally aligned with SEQ ID NO: 1, a residue in the test sequence that aligns with the L at position 3 is said to "correspond to position 3" of SEQ ID NO: 1. Owing to deletions, insertion, truncations, fusions, etc., that must be taken into account when determining an optimal alignment, in general the amino acid residue number in a test sequence as determined by simply counting from the N-terminal will not necessarily be the same as the number of its corresponding position in the reference sequence. For example, in a case where there is a deletion in an aligned test sequence, there will be no amino acid that corresponds to a position in the reference sequence at the site of deletion. Where there is an insertion in an aligned reference sequence, that insertion will not correspond to any amino acid position in the reference sequence. In the case of truncations or fusions there can be stretches of amino acids in either the reference or aligned sequence that do not correspond to any amino acid in the corresponding sequence.

iv. Antibodies

Antibodies to the polypeptides of the present invention, or to variants or fragments thereof, are also encompassed. Methods for producing antibodies are well known in the art (see, for example, Harlow and Lane (1988) Antibodies: A Laboratory Manual, Cold Spring Harbor Laboratory, Cold Spring Harbor, N.Y.; and U.S. Pat. No. 4,196,265). These antibodies can be used in kits for the detection and isolation of toxin polypeptides. Thus, this disclosure provides kits comprising antibodies that specifically bind to the polypeptides described herein, including, for example, polypeptides having the sequence of SEQ ID NOs: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, and/or 525.

II. Pests

The compositions and methods provided herein are useful against a variety of pests. "Pests" includes but is not limited to, insects, fungi, bacteria, nematodes, acarids, protozoan pathogens, animal-parasitic liver flukes, and the like. Pests of particular interest are insect pests, particularly insect pests that cause significant damage to agricultural plants. Insect pests include insects selected from the orders Coleoptera, Diptera, Hymenoptera, Lepidoptera, Mallophaga, Homoptera, Hemiptera, Orthroptera, Thysanoptera, Dermaptera, Isoptera, Anoplura, Siphonaptera, Trichoptera, or nematodes. In non-limiting embodiments, the insect pest comprises Western corn rootworm, *Diabrotica virgifera virgifera*; Fall armyworm, *Spodoptera frugiperda*; Colorado potato beetle, *Leptinotarsa decemlineata*; Corn earworm, *Helicoverpa zea* (in North America same species attacks cotton and called cotton bollworm); European corn borer, *Ostrinia nubilalis*; Black cutworm, *Agrotis ipsilon*; Diamondback moth, *Plutella xylostella*; Velvetbean caterpillar, *Anticarsia gemmatalis*; Southwestern corn borer, *Diatraea grandiosella*; Cotton bollworm, *Helicoverpa armigera* (found other than USA in rest of the world); Southern green stink bug, *Nezara viridula*; Green stink bug, *Chinavia halaris*; Brown marmorated stink bug, *Halyomorpha halys*; and Brown stink bug, *Euschistus servus, Euschistus heros* (Neotropical brown stink bug OR soy stink bug); *Piezodorus guildinii* (red-banded stink bug); *Dichelops melacanthus* (no common name) and/or *Dichelops furcatus* (no common name); an aphid, such as a soybean aphid. In other embodiments, the pest comprises a nematode including, but not limited to, *Meloidogyne hapla* (Northern root-knot nematode); *Meloidogyne enterolobii, Meloidogyne arenaria* (peanut root-knot nematode); and *Meloidogyne javanica.*

The term "insect pests" as used herein refers to insects and other similar pests such as, for example, those of the order Acari including, but not limited to, mites and ticks. Insect pests of the present invention include, but are not limited to, insects of the order Lepidoptera, e.g. *Achoroia grisella, Acleris gloverana, Acleris variana, Adoxophyes orana, Agrotis ipsilon, Alabama argillacea, Alsophila pometaria, Amyelois transitella, Anagasta kuehniella, Anarsia lineatella, Anisota senatoria, Antheraea pernyi, Anticarsia gemmatalis, Archips* sp., Argyrotaenia sp., *Athetis mindara, Bombyx mori, Bucculatrix thurberiella, Cadra cautella, Choristoneura* sp., *Cochylls hospes, Colias eurytheme, Corcyra cephalonica, Cydia latiferreanus, Cydia pomonella, Datana integerrima, Dendrolimus sibericus, Desmiafeneralis, Diaphania hyalinata, Diaphania nitidalis, Diatraea grandiosella, Diatraea saccharalis, Ennomos subsignaria, Eoreuma loftini, Esphestia elutella, Erannis tilaria, Estigmene acrea, Eulia salubricola, Eupocoellia ambiguella, Eupoecilia ambiguella, Euproctis chrysorrhoea, Euxoa messoria, Galleria mellonella, Grapholita molesta, Harrisina americana, Helicoverpa subflexa, Helicoverpa zea, Heliothis virescens, Hemileuca oliviae, Homoeosoma electellum, Hyphantia cunea, Keiferia lycopersicella, Lambdina fiscellaria fiscellaria, Lambdina fiscellaria lugubrosa, Leucoma salicis, Lobesia botrana, Loxostege sticticalis, Lymantria dispar, Macalla thyrisalis, Malacosoma* sp., *Mamestra brassicae, Mamestra configurata, Manduca quinquemaculata, Manduca sexta, Maruca testulalis, Melanchra picta, Operophtera brumata, Orgyia* sp., *Ostrinia nubilalis, Paleacrita vernata, Papilio cresphontes, Pectinophora gossypiella, Phryganidia californica, Phyllonorycter blancardella, Pieris napi, Pieris rapae, Plathypena scabra, Platynota flouendana, Platynota stultana, Platyptilia carduidactyla, Plodia interpunctella, Plutella xylostella, Pontia protodice, Pseudaletia unipuncta, Pseudoplasia includens, Sabulodes aegrotata, Schizura concinna, Sitotroga cerealella, Spilonta ocellana, Spodoptera* sp., *Thaurnstopoea pityocampa, Tinsola bisselliella, Trichoplusia hi, Udea rubigalis, Xylomyges curiails*, and *Yponomeuta padella.*

Insect pests also include insects selected from the orders Diptera, Hymenoptera, Lepidoptera, Mallophaga, Homoptera, Hemiptera, Orthroptera, Thysanoptera, Dermaptera, Isoptera, Anoplura, Siphonaptera, Trichoptera, Coleoptera. Insect pests of the invention for the major crops include, but are not limited to: Maize: *Ostrinia nubilalis*, European corn borer; *Agrotis ipsilon*, black cutworm; *Helicoverpa zeae*, corn earworm; *Spodoptera frugiperda*, fall armyworm; *Diatraea grandiosella*, southwestern corn borer; *Elasmopalpus lignosellus*, lesser cornstalk borer; *Diatraea* saccharalis, surgarcane borer; western corn rootworm, e.g., *Diabrotica virgifera virgifera*; northern corn rootworm, e.g., *Diabrotica longicomis barberi*; southern corn rootworm, e.g., *Diabrotica undecimpunctata howardi*; Melanotus spp., wireworms; *Cyclocephala borealis*, northern masked chafer (white grub); *Cyclocephala immaculata*, southern masked chafer (white grub); *Popillia japonica*, Japanese beetle; *Chaetocnema pulicaria*, corn flea beetle; *Sphenophorus maidis*, maize billbug; *Rhopalosiphum maidis*, corn leaf aphid; *Anuraphis maidiradicis*, corn root aphid; *Euschistus heros* (Neotropical brown stink bug OR soy stink bug); *Piezodorus guildinii* (red-banded stink bug); *Dichelops melacanthus* (no common name); *Dichelops furcatus* (no common name); *Blissus leucopterus leucopterus*, chinch bug; *Melanoplus femurrubrum*, redlegged grasshopper; *Melanoplus sanguinipes*, migratory grasshopper; *Hylemya platura*, seedcorn maggot; *Agromyza parvicornis*, corn blotch leafminer; *Anaphothrips obscrurus*, grass thrips; *Solenopsis milesta*, thief ant; *Tetranychus urticae*, two spotted spider mite; Sorghum: *Chilo partellus*, sorghum borer; *Spodoptera frugiperda*, fall armyworm; *Helicoverpa zea*, corn earworm; *Elasmopalpus lignosellus*, leser cornstalk borer; *Feltia subterranea*, granulate cutworm; *Phyllophaga crinita*, white grub; *Eleodes*, Conoderus, and Aeolus spp., wireworms; *Oulema melanopus*, cereal leaf beetle; *Chaetocnema pulicaria*, corn flea beetle; *Sphenophorus maidis*, maize billbug; *Rhopalosiphum maidis*; corn leaf aphid; *Sipha flava*, yellow sugarcane aphid; chinch bug, e.g., *Blissus leucopterus leucopterus; Contarinia sorghicola*, sorghum midge; *Tetranychus cinnabarinus*, carmine spider mite; *Tetranychus urticae*, two-spotted spider mite; Wheat: *Pseudaletia unipunctata*, army worm; *Spodoptera frugiperda*, fall armyworm; *Elasmopalpus lignosellus*, lesser cornstalk borer; *Agrotis orthogonia*, pale western cutworm; *Elasmopalpus lignosellus*, lesser cornstalk borer; *Oulema melanopus*, cereal leaf beetle; *Hypera punctata*, clover leaf weevil; southern corn rootworm, e.g., *Diabrotica undecimpunctata howardi*; Russian wheat aphid; *Schizaphis graminum*, greenbug; *Macrosiphum avenae*, English grain aphid; *Melanoplus femurrubrum*, redlegged grasshopper; *Melanoplus differentialis*, differential grasshopper; *Melanoplus sanguinipes*, migratory grasshopper; *Mayetiola destructor*, Hessian fly; *Sitodiplosis mosellana*, wheat midge; *Meromyza americana*, wheat stem maggot; *Hylemya coarctata*, wheat bulb fly; *Frankliniella fusca*, tobacco *thrips; Cephus cinctus*, wheat stem sawfly; *Aceria tulipae*, wheat curl mite; Sunflower: *Cylindrocupturus adspersus*, sunflower stem weevil; *Smicronyx fulus*, red sunflower seed weevil; *Smicronyx sordidus*, gray sunflower seed weevil; *Suleima helianthana*, sunflower bud moth; *Homoeosoma electellum*, sunflower moth; *Zygogramma exclamationis*, sunflower beetle; *Bothyrus gibbosus*, carrot beetle; *Neolasioptera murtfeldtiana*, sunflower seed midge; Cotton: *Heliothis virescens*, tobacco budworm; *Helicoverpa zea*, cotton bollworm; *Spodoptera exigua*, beet armyworm; *Pectinophora gossypiella*, pink bollworm; boll weevil, e.g., *Anthonomus grandis; Aphis gossypii*, cotton aphid; *Pseudatomoscelis seriatus*, cotton fleahopper; *Trialeurodes abutilonea*, bandedwinged whitefly; *Lygus lineolaris*, tarnished plant bug; *Melanoplus femurrubrum*, redlegged grasshopper; *Melanoplus differentialis*, differential grasshopper; *Thrips tabaci*, onion *thrips; Franklinkiella fusca*, tobacco thrips; *Tetranychus cinnabarinus*, carmine spider mite; *Tetranychus urticae*, two-spotted spider mite; Rice: *Diatraea saccharalis*, sugarcane borer; *Spodoptera frugiperda*, fall armyworm; *Helicoverpa zea*, corn earworm; *Colaspis brunnea*, grape *colaspis; Lissorhoptrus oryzophilus*, rice water weevil; *Sitophilus oryzae*, rice weevil; *Nephotettix nigropictus*, rice leafhoper; chinch bug, e.g., *Blissus leucopterus leucopterus; Acrosternum hilare*, green stink bug; Soybean: *Pseudoplusia includens*, soybean looper; *Anticarsia gemmatalis*, velvetbean caterpillar; *Plathypena scabra*, green cloverworm; *Ostrinia nubilalis*, European corn borer; *Agrotis ipsilon*, black cutworm; *Spodoptera exigua*, beet armyworm; *Heliothis virescens*, tobacco budworm; *Helicoverpa zea*, cotton bollworm; *Epilachna varivestis*, Mexican bean beetle; *Myzus persicae*, green peach aphid; *Empoasca fabae*, potato leafhopper; *Acrosternum hilare*, green stink bug; *Melanoplus femurrubrum*, redlegged grasshopper; *Melanoplus differentialis*, differential grasshopper; *Hylemya platura*, seedcorn maggot; *Sericothrips variabilis*, soybean thrips; *Thrips tabaci*, onion thrips; *Tetranychus turkestani*, strawberry spider mite; *Tetranychus urticae*, two-spotted spider mite; Barley: *Ostrinia nubilalis*, European corn borer; *Agrotis ipsilon*, black cutworm; *Schizaphis graminum*, greenbug; chinch bug, e.g., *Blissus leucopterus leucopterus; Acrosternum hilare*, green stink bug; *Euschistus servus*, brown stink bug; *Jylemya platura*, seedcorn maggot; *Mayetiola destructor*, Hessian fly; *Petrobia latens*, brown wheat mite; Oil Seed Rape: *Vrevicoryne brassicae*, cabbage aphid; *Phyllotreta cruciferae*, crucifer flea beetle; *Phyllotreta striolata*, striped flea beetle; *Phyllotreta nemorum*, striped turnip flea beetle; *Meligethes aeneus*, rapeseed beetle; and the pollen beetles *Meligethes rufimanus, Meligethes nigrescens, Meligethes canadianus*, and *Meligethes viridescens*; Potato: *Leptinotarsa decemlineata*, Colorado potato beetle.

The methods and compositions provided herein may be effective against Hemiptera such *as Lygus hesperus, Lygus lineolaris, Lygus pratensis, Lygus rugulipennis Popp, Lygus pabulinus, Calocoris norvegicus, Orthops compestris, Plesiocoris rugicollis, Cyrtopeltis modestus, Cyrtopeltis notatus, Spanagonicus albofasciatus, Diaphnocoris chlorinonis, Labopidicola allii, Pseudatomoscelis seriatus, Adelphocoris rapidus, Poecilocapsus lineatus, Blissus leucopterus, Nysius ericae, Nysius raphanus, Euschistus servus, Nezara viridula, Eurygaster, Coreidae, Pyrrhocoridae, Tinidae, Blostomatidae, Reduviidae, and Cimicidae*. Pests of interest also include *Araecerus fasciculatus*, coffee bean weevil; *Acanthoscelides obtectus*, bean weevil; *Bruchus rufmanus*, broadbean weevil; *Bruchus pisorum*, pea weevil; *Zabrotes subfasciatus*, Mexican bean weevil; *Diabrotica balteata*, banded cucumber beetle; *Cerotoma trifurcata*, bean leaf beetle; *Diabrotica virgifera*, Mexican corn rootworm; *Epitrix cucumeris*, potato flea beetle; *Chaetocnema confinis*, sweet potato flea beetle; *Hypera postica*, alfalfa weevil; *Anthonomus quadrigibbus*, apple curculio; *Sternechus paludatus*, bean stalk weevil; *Hypera brunnipennis*, Egyptian alfalfa weevil; *Sitophilus granaries*, granary weevil; *Craponius inaequalis*, grape curculio; *Sitophilus zeamais*, maize weevil; *Conotrachelus nenuphar*, plum curculio; *Euscepes postfaciatus*, West Indian sweet potato weevil; *Maladera castanea*, Asiatic garden beetle; *Rhizotrogus majalis*, European chafer; *Macrodactylus subspinosus*, rose chafer; *Tribolium confusum*, confused flour beetle; *Tenebrio obscurus*, dark mealworm; *Tribolium castaneum*, red flour beetle; *Tenebrio molitor*, yellow mealworm.

Nematodes include parasitic nematodes such as root-knot, cyst, and lesion nematodes, including *Heterodera* spp., *Meloidogyne* spp., and *Globodera* spp.; particularly members of the cyst nematodes, including, but not limited to, *Heterodera glycines* (soybean cyst nematode); *Heterodera schachtii* (beet cyst nematode); *Heterodera avenae* (cereal cyst nematode); and *Globodera rostochiensis* and *Globodera pailida* (potato cyst nematodes). Lesion nematodes include *Pratylenchus* spp.

Insect pests may be tested for pesticidal activity of compositions of the invention in early developmental stages, e.g., as larvae or other immature forms. The insects may be reared in total darkness at from about 20° C. to about 30° C. and from about 30% to about 70% relative humidity. Bioassays may be performed as described in Czapla and Lang (1990) *J. Econ. Entomol.* 83 (6): 2480-2485. See, also the experimental section herein.

III. Expression Cassettes

Polynucleotides encoding the pesticidal proteins provided herein can be provided in expression cassettes for expression in an organism of interest. The cassette will include 5' and 3' regulatory sequences operably linked to a polynucleotide encoding a pesticidal polypeptide provided herein that allows for expression of the polynucleotide. The cassette may additionally contain at least one additional gene or genetic element to be cotransformed into the organism. Where additional genes or elements are included, the components are operably linked. Alternatively, the additional gene(s) or element(s) can be provided on multiple expression cassettes. Such an expression cassette is provided with a plurality of restriction sites and/or recombination sites for insertion of the polynucleotides to be under the transcriptional regulation of the regulatory regions. The expression cassette may additionally contain a selectable marker gene.

The expression cassette will include in the 5'-3' direction of transcription, a transcriptional and translational initiation region (i.e., a promoter), a pesticidal polynucleotide of the invention, and a transcriptional and translational termination region (i.e., termination region) functional in the organism of interest, i.e., a plant or bacteria. The promoters of the invention are capable of directing or driving expression of a coding sequence in a host cell. The regulatory regions (i.e., promoters, transcriptional regulatory regions, and translational termination regions) may be endogenous or heterologous to the host cell or to each other. As used herein, "heterologous" in reference to a sequence is a sequence that originates from a foreign species, or, if from the same species, is substantially modified from its native form in composition and/or genomic locus by deliberate human intervention. As used herein, a chimeric gene comprises a coding sequence operably linked to a transcription initiation region that is heterologous to the coding sequence.

Convenient termination regions are available from the Ti-plasmid of *A. tumefaciens*, such as the octopine synthase and nopaline synthase termination regions. See also Guerineau et al. (1991) *Mol. Gen. Genet.* 262:141-144; Proudfoot (1991) *Cell* 64:671-674; Sanfacon et al. (1991) *Genes Dev.* 5:141-149; Mogen et al. (1990) *Plant Cell* 2:1261-1272; Munroe et al. (1990) *Gene* 91:151-158; Ballas et al. (1989) *Nucleic Acids Res.* 17:7891-7903; and Joshi et al. (1987) *Nucleic Acids Res.* 15:9627-9639.

Additional regulatory signals include, but are not limited to, transcriptional initiation start sites, operators, activators, enhancers, other regulatory elements, ribosomal binding sites, an initiation codon, termination signals, and the like. See, for example, U.S. Pat. Nos. 5,039,523 and 4,853,331; EPO 0480762A2; Sambrook et al. (1992) Molecular Cloning: A Laboratory Manual, ed. Maniatis et al. (Cold Spring Harbor Laboratory Press, Cold Spring Harbor, N.Y.), hereinafter "Sambrook 11"; Davis et al., eds. (1980) Advanced Bacterial Genetics (Cold Spring Harbor Laboratory Press), Cold Spring Harbor, N.Y., and the references cited therein.

In preparing the expression cassette, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g., transitions and transversions, may be involved.

A number of promoters can be used in the practice of the invention. The promoters can be selected based on the desired outcome. The nucleic acids can be combined with constitutive, inducible, tissue-preferred, or other promoters for expression in the organism of interest. See, for example, promoters set forth in WO 99/43838 and in U.S. Pat. Nos. 8,575,425; 7,790,846; 8,147,856; 8,586832; 7,772,369; 7,534,939; 6,072,050; 5,659,026; 5,608,149; 5,608,144; 5,604,121; 5,569,597; 5,466,785; 5,399,680; 5,608,142; and 6,177,611; herein incorporated by reference.

For expression in plants, constitutive promoters also include CaMV 35S promoter (Odell et al. (1985) *Nature* 313:810-812); rice actin (McElroy et al. (1990) *Plant Cell* 2:163-171); ubiquitin (Christensen et al. (1989) *Plant Mol. Biol.* 12:619-632 and Christensen et al. (1992) *Plant Mol. Biol.* 18:675-689); pEMU (Last et al. (1991) *Theor. Appl. Genet.* 81:581-588); MAS (Velten et al. (1984) EMBO J. 3:2723-2730). Inducible promoters include those that drive expression of pathogenesis-related proteins (PR proteins), which are induced following infection by a pathogen. See, for example, Redolfi et al. (1983) *Neth. J. Plant Pathol.* 89:245-254; Uknes et al. (1992) *Plant Cell* 4:645-656; and Van Loon (1985) *Plant Mol. Virol.* 4:111-116; and WO 99/43819, herein incorporated by reference. Promoters that are expressed locally at or near the site of pathogen infection may also be used (Marineau et al. (1987) *Plant Mol. Biol.* 9:335-342; Matton et al. (1989) *Molecular Plant-Microbe Interactions* 2:325-331; Somsisch et al. (1986) *Proc. Natl. Acad. Sci. USA* 83:2427-2430; Somsisch et al. (1988) *Mol. Gen. Genet.* 2:93-98; and Yang (1996) *Proc. Natl. Acad. Sci. USA* 93:14972-14977; Chen et al. (1996) *Plant J.* 10:955-966; Zhang et al. (1994) *Proc. Natl. Acad. Sci. USA* 91:2507-2511; Warner et al. (1993) *Plant J.* 3:191-201; Siebertz et al. (1989) *Plant Cell* 1:961-968; Cordero et al. (1992) *Physiol. Mol. Plant Path.* 41:189-200; U.S. Pat. No. 5,570,386 (nematode-inducible); and the references cited therein).

Wound-inducible promoters may be used in the constructions of the invention. Such wound-inducible promoters include pin II promoter (Ryan (1990) *Ann. Rev. Phytopath.* 28:425-449; Duan et al. (1996) *Nature Biotechnology* 14:494-498); wun1 and wun2 (U.S. Pat. No. 5,428,148); win1 and win2 (Stanford et al. (1989) *Mol. Gen. Genet.* 215:200-208); systemin (McGurl et al. (1992) *Science* 225: 1570-1573); WIP1 (Rohmeier et al. (1993) *Plant Mol. Biol.* 22:783-792; Eckelkamp et al. (1993) *FEBS Letters* 323:73-76); MPI gene (Corderok et al. (1994) *Plant J.* 6(2):141-150); and the like, herein incorporated by reference.

Tissue-preferred promoters for use in the invention include those set forth in Yamamoto et al. (1997) Plant J. 12(2):255-265; Kawamata et al. (1997) *Plant Cell Physiol.* 38(7):792-803; Hansen et al. (1997) *Mol. Gen Genet.* 254 (3):337-343; Russell et al. (1997) *Transgenic Res.* 6(2):157-168; Rinehart et al. (1996) *Plant Physiol.* 112(3):1331-1341; Van Camp et al. (1996) *Plant Physiol.* 112(2):525-535; Canevascini et al. (1996) *Plant Physiol.* 112(2):513-524; Yamamoto et al. (1994) *Plant Cell Physiol.* Lam (1994) *Results Probl. Cell Differ.* 20:181-196; Orozco et al. (1993) *Plant Mol Biol.* 23(6):1129-1138; Matsuoka et al. (1993) *Proc Natl. Acad. Sci. USA* 90(2):9586-9590; and Guevara-Garcia et al. (1993) Plant J. 4(3):495-505.

Leaf-preferred promoters include those set forth in Yamamoto et al. (1997) *Plant J.* 12(2):255-265; Kwon et al. (1994) *Plant Physiol.* 105:357-67; Yamamoto et al. (1994) *Plant Cell Physiol.* 35(5):773-778; Gotor et al. (1993) *Plant J.* 3:509-18; Orozco et al. (1993) *Plant Mol. Biol.* 23(6): 1129-1138; and Matsuoka et al. (1993) *Proc. Natl. Acad. Sci. USA* 90(20):9586-9590.

Root-preferred promoters are known and include those in Hire et al. (1992) *Plant Mol. Biol.* 20(2):207-218 (soybean root-specific glutamine synthetase gene); Keller and Baumgartner (1991) *Plant Cell* 3(10):1051-1061 (root-specific control element); Sanger et al. (1990) *Plant Mol. Biol.*

14(3):433-443 (mannopine synthase (MAS) gene of *Agrobacterium tumefaciens*); and Miao et al. (1991) *Plant Cell* 3(1):11-22 (cytosolic glutamine synthetase (GS)); Bogusz et al. (1990) *Plant Cell* 2(7):633-641; Leach and Aoyagi (1991) *Plant Science* (Limerick) 79(1):69-76 (rolC and rolD); Teeri et al. (1989) *EMBO J.* 8(2):343-350; Kuster et al. (1995) *Plant Mol. Biol.* 29(4):759-772 (the VfENOD-GRP3 gene promoter); and, Capana et al. (1994) *Plant Mol. Biol.* 25(4):681-691 (rolB promoter). See also U.S. Pat. Nos. 5,837,876; 5,750,386; 5,633,363; 5,401,836; 5,110,732; and 5,023,179.

"Seed-preferred" promoters include both "seed-specific" promoters (those promoters active during seed development such as promoters of seed storage proteins) as well as "seed-germinating" promoters (those promoters active during seed germination). See Thompson et al. (1989) *BioEssays* 10:108. Seed-preferred promoters include, but are not limited to, Ciml (cytokinin-induced message); cZ19B1 (maize 19 kDa zein); milps (myo-inositol-1-phosphate synthase) (see WO 00/11177 and U.S. Pat. No. 6,225,529). Gamma-zein is an endosperm-specific promoter. Globulin 1 (Glb-1) is a representative embryo-specific promoter. For dicots, seed-specific promoters include, but are not limited to, bean β-phaseolin, napin, β-conglycinin, soybean lectin, cruciferin, and the like. For monocots, seed-specific promoters include, but are not limited to, maize 15 kDa zein, 22 kDa zein, 27 kDa zein, gamma-zein, waxy, shrunken 1, shrunken 2, Globulin 1, etc. See also WO 00/12733, where seed-preferred promoters from end1 and end2 genes are disclosed.

For expression in a bacterial host, promoters that function in bacteria are well-known in the art. Such promoters include any of the known crystal protein gene promoters, including the promoters of any of the pesticidal proteins of the invention, and promoters specific for *B. thuringiensis* sigma factors. Alternatively, mutagenized or recombinant crystal protein-encoding gene promoters may be recombinantly engineered and used to promote expression of the novel gene segments disclosed herein.

The expression cassette can also comprise a selectable marker gene for the selection of transformed cells. Selectable marker genes are utilized for the selection of transformed cells or tissues. Marker genes include genes encoding antibiotic resistance, such as those encoding neomycin phosphotransferase II (NEO) and hygromycin phosphotransferase (HPT), as well as genes conferring resistance to herbicidal compounds, such as glufosinate ammonium, bromoxynil, imidazolinones, and 2,4-dichlorophenoxyacetate (2,4-D). Additional selectable markers are known and any can be used. See, for example, U.S. Provisional application 62/094,697, filed on Dec. 19, 2014, and U.S. Provisional Application 62/189,505, filed Jul. 7, 2015, both of which are herein incorporated by reference in their entirety, which discloses glufosinate resistance sequences that can be employed as selectable markers. See, for example, PCT/US2015/066648, filed on Dec. 18, 2015, herein incorporated by reference in its entirety, which discloses glufosinate resistance sequences that can be employed as selectable markers.

IV. Methods, Host Cells and Plant Cells

As indicated, DNA constructs comprising nucleotide sequences encoding the pesticidal proteins or active variants or fragment thereof can be used to transform plants of interest or other organisms of interest. Methods for transformation involve introducing a nucleotide construct into a plant. By "introducing" is intended to introduce the nucleotide construct to the plant or other host cell in such a manner that the construct gains access to the interior of a cell of the plant or host cell. The methods of the invention do not require a particular method for introducing a nucleotide construct to a plant or host cell, only that the nucleotide construct gains access to the interior of at least one cell of the plant or the host organism. Methods for introducing nucleotide constructs into plants and other host cells are known in the art including, but not limited to, stable transformation methods, transient transformation methods, and virus-mediated methods.

The methods result in a transformed organisms, such as a plant, including whole plants, as well as plant organs (e.g., leaves, stems, roots, etc.), seeds, plant cells, propagules, embryos and progeny of the same. Plant cells can be differentiated or undifferentiated (e.g. callus, suspension culture cells, protoplasts, leaf cells, root cells, phloem cells, pollen).

"Transgenic plants" or "transformed plants" or "stably transformed" plants or cells or tissues refers to plants that have incorporated or integrated a polynucleotide encoding at least one pesticidal polypeptide of the invention. It is recognized that other exogenous or endogenous nucleic acid sequences or DNA fragments may also be incorporated into the plant cell. *Agrobacterium*- and biolistic-mediated transformation remain the two predominantly employed approaches. However, transformation may be performed by infection, transfection, microinjection, electroporation, microprojection, biolistics or particle bombardment, electroporation, silica/carbon fibers, ultrasound mediated, PEG mediated, calcium phosphate co-precipitation, polycation DMSO technique, DEAE dextran procedure, Agro and viral mediated (Caulimoriviruses, Geminiviruses, RNA plant viruses), liposome mediated and the like.

Transformation protocols as well as protocols for introducing polypeptides or polynucleotide sequences into plants may vary depending on the type of plant or plant cell, i.e., monocot or dicot, targeted for transformation. Methods for transformation are known in the art and include those set forth in U.S. Pat. Nos. 8,575,425; 7,692,068; 8,802,934; 7,541,517; each of which is herein incorporated by reference. See, also, Rakoczy-Trojanowska, M. (2002) *Cell Mol Biol Lett.* 7:849-858; Jones et al. (2005) *Plant Methods* 1:5; Rivera et al. (2012) *Physics of Life Reviews* 9:308-345; Bartlett et al. (2008) *Plant Methods* 4:1-12; Bates, G. W. (1999) *Methods in Molecular Biology* 111:359-366; Binns and Thomashow (1988) *Annual Reviews in Microbiology* 42:575-606; Christou, P. (1992) *The Plant Journal* 2:275-281; Christou, P. (1995) *Euphytica* 58:13-27 Tzfira et al. (2004) *TRENDS in Genetics* 20:375-383; Yao et al. (2006) *Journal of Experimental Botany* 57:3737-3746; Zupan and Zambryski (1995) *Plant Physiology* 107:1041-1047; Jones et al. (2005) *Plant Methods* 1:5;

Transformation may result in stable or transient incorporation of the nucleic acid into the cell. "Stable transformation" is intended to mean that the nucleotide construct introduced into a host cell integrates into the genome of the host cell and is capable of being inherited by the progeny thereof. "Transient transformation" is intended to mean that a polynucleotide is introduced into the host cell and does not integrate into the genome of the host cell.

Methods for transformation of chloroplasts are known in the art. See, for example, Svab et al. (1990) Proc. Nail. Acad. Sci. USA 87:8526-8530; Svab and Maliga (1993) Proc. Natl. Acad. Sci. USA 90:913-917; Svab and Maliga (1993) EMBO J. 12:601-606. The method relies on particle gun delivery of DNA containing a selectable marker and targeting of the DNA to the plastid genome through homologous recombination. Additionally, plastid transformation can be accomplished by transactivation of a silent plastid-borne transgene by tissue-preferred expression of a nuclear-encoded and plastid-directed RNA polymerase. Such a system has been reported in McBride et al. (1994) Proc. Natl. Acad. Sci. USA 91:7301-7305.

The cells that have been transformed may be grown into plants in accordance with conventional ways. See, for example, McCormick et al. (1986) Plant Cell Reports 5:81-84. These plants may then be grown, and either pollinated with the same transformed strain or different strains, and the resulting hybrid having constitutive expression of the desired phenotypic characteristic identified. Two or more generations may be grown to ensure that expression of the desired phenotypic characteristic is stably maintained and inherited and then seeds harvested to ensure expression of the desired phenotypic characteristic has been achieved. In this manner, the present invention provides transformed seed (also referred to as "transgenic seed") having a nucleotide construct of the invention, for example, an expression cassette of the invention, stably incorporated into their genome.

In specific embodiments, the sequences provide herein can be targeted to specific cite within the genome of the host cell or plant cell. Such methods include, but are not limited to, meganucleases designed against the plant genomic sequence of interest (D'Halluin et al. 2013 *Plant Biotechnol J*); CRISPR-Cas9, TALENs, and other technologies for precise editing of genomes (Feng, et al. Cell Research 23:1229-1232, 2013, Podevin, et al. *Trends Biotechnology*, online publication, 2013, Wei et al., *J Gen Genomics,* 2013, Zhang et al (2013) WO 2013/026740); Cre-lox site-specific recombination (Dale et al. (1995) *Plant J* 7:649-659; Lyznik, et al. (2007) *Transgenic Plant J* 1: 1-9; FLP-FRT recombination (Li et al. (2009) *Plant Physiol* 151:1087-1095); Bxb1-mediated integration (Yau et al. *Plant J* (2011) 701: 147-166); zinc-finger mediated integration (Wright et al. (2005) *Plant J* 44:693-705); Cai et al. (2009) *Plant Mol Biol* 69:699-709); and homologous recombination (Lieberman-Lazarovich and Levy (2011) *Methods Mol Biol* 701: 51-65); Puchta (2002) *Plant Mol Biol* 48:173-182).

The sequence provided herein may be used for transformation of any plant species, including, but not limited to, monocots and dicots. Examples of plants of interest include, but are not limited to, corn (maize), sorghum, wheat, sunflower, tomato, crucifers, peppers, potato, cotton, rice, soybean, sugarbeet, sugarcane, tobacco, barley, and oilseed rape, Brassica sp., alfalfa, rye, millet, safflower, peanuts, sweet potato, cassaya, coffee, coconut, pineapple, citrus trees, cocoa, tea, banana, avocado, fig, guava, mango, olive, papaya, cashew, macadamia, almond, oats, vegetables, ornamentals, and conifers.

Vegetables include, but are not limited to, tomatoes, lettuce, green beans, lima beans, peas, and members of the genus Curcumis such as cucumber, cantaloupe, and musk melon. Ornamentals include, but are not limited to, azalea, hydrangea, hibiscus, roses, tulips, daffodils, petunias, carnation, poinsettia, and chrysanthemum. Preferably, plants of the present invention are crop plants (for example, maize, sorghum, wheat, sunflower, tomato, crucifers, peppers, potato, cotton, rice, soybean, sugarbeet, sugarcane, tobacco, barley, oilseed rape, etc.).

As used herein, the term plant includes plant cells, plant protoplasts, plant cell tissue cultures from which plants can be regenerated, plant calli, plant clumps, and plant cells that are intact in plants or parts of plants such as embryos, pollen, ovules, seeds, leaves, flowers, branches, fruit, kernels, ears, cobs, husks, stalks, roots, root tips, anthers, and the like. Grain is intended to mean the mature seed produced by commercial growers for purposes other than growing or reproducing the species. Progeny, variants, and mutants of the regenerated plants are also included within the scope of the invention, provided that these parts comprise the introduced polynucleotides. Further provided is a processed plant product or byproduct that retains the sequences disclosed herein, including for example, soymeal.

In another embodiment, the genes encoding the pesticidal proteins can be used to transform insect pathogenic organisms. Such organisms include baculoviruses, fungi, protozoa, bacteria, and nematodes. Microorganism hosts that are known to occupy the "phytosphere" (phylloplane, phyllosphere, rhizosphere, and/or rhizoplana) of one or more crops of interest may be selected. These microorganisms are selected so as to be capable of successfully competing in the particular environment with the wild-type microorganisms, provide for stable maintenance and expression of the gene expressing the pesticidal protein, and desirably, provide for improved protection of the pesticide from environmental degradation and inactivation.

Such microorganisms include archaea, bacteria, algae, and fungi. Of particular interest are microorganisms such as bacteria, e.g., *Bacillus, Pseudomonas, Erwinia, Serratia, Klebsiella, Xanthomonas, Streptomyces, Rhizobium, Rhodopseudomonas, Methylius, Agrobacterium, Acetobacter, Lactobacillus, Arthrobacter, Azotobacter, Leuconostoc*, and *Alcaligenes*. Fungi include yeast, e.g., *Saccharomyces, Cryptococcus, Kluyveromyces, Sporobolomyces, Rhodotorula*, and *Aureobasidium*. Of particular interest are such phytosphere bacterial species as *Pseudomonas syringae, Pseudomonas aeruginosa, Pseudomonas fluorescens, Serratia marcescens, Acetobacter xylinum, Agrobacteria, Rhodopseudomonas spheroides, Xanthomonas campestris, Rhizobium melioti, Alcaligenes entrophus, Clavibacter xyli* and *Azotobacter vinlandir* and phytosphere yeast species such as *Rhodotorula rubra, R. glutinis, R. marina, R. aurantiaca, Cryptococcus albidus, C. diffluens, C. laurentii, Saccharomyces rosei, S. pretoriensis, S. cerevisiae, Sporobolomyces rosues, S. odorus, Kluyveromyces veronae, Aureobasidium pollulans, Bacillus thuringiensis, Escherichia coli, Bacillus subtilis*, and the like.

Illustrative prokaryotes, both Gram-negative and gram-positive, include Enterobacteriaceae, such as *Escherichia, Erwinia, Shigella, Salmonella*, and *Proteus*; Bacillaceae; Rhizobiceae, such as *Rhizobium*; Spirillaceae, such as photobacterium, *Zymomonas, Serratia, Aeromonas, Vibrio, Desulfovibrio*, Spirillum; Lactobacillaceae; Pseudomonadaceae, such as *Pseudomonas* and *Acetobacter*; Azotobacteraceae and Nitrobacteraceae. Fungi include Phycomycetes and Ascomycetes, e.g., yeast, such as *Saccharomyces* and *Schizosaccharomyces*; and Basidiomycetes yeast, such as *Rhodotorula, Aureobasidium*, Sporobolomyces, and the like.

Genes encoding pesticidal proteins can be introduced by means of electrotransformation, PEG induced transformation, heat shock, transduction, conjugation, and the like. Specifically, genes encoding the pesticidal proteins can be cloned into a shuttle vector, for example, pHT3101 (Lerecius et al. (1989) *FEMS Microbiol. Letts.* 60: 211-218. The shuttle vector pHT3101 containing the coding sequence for the particular pesticidal protein gene can, for example, be transformed into the root-colonizing *Bacillus* by means of electroporation (Lerecius et al. (1989) *FEMS Microbiol. Letts.* 60: 211-218).

Expression systems can be designed so that pesticidal proteins are secreted outside the cytoplasm of gram-negative bacteria by fusing an appropriate signal peptide to the amino-terminal end of the pesticidal protein. Signal peptides recognized by *E. coli* include the OmpA protein (Ghrayeb et al. (1984) EMBO J, 3: 2437-2442).

Pesticidal proteins and active variants thereof can be fermented in a bacterial host and the resulting bacteria processed and used as a microbial spray in the same manner that *Bacillus thuringiensis* strains have been used as insecticidal sprays. In the case of a pesticidal protein(s) that is secreted from *Bacillus*, the secretion signal is removed or mutated using procedures known in the art. Such mutations and/or deletions prevent secretion of the pesticidal protein(s) into the growth medium during the fermentation process. The pesticidal proteins are retained within the cell, and the cells are then processed to yield the encapsulated pesticidal proteins.

Alternatively, the pesticidal proteins are produced by introducing heterologous genes into a cellular host. Expression of the heterologous gene results, directly or indirectly, in the intracellular production and maintenance of the pesticide. These cells are then treated under conditions that prolong the activity of the toxin produced in the cell when the cell is applied to the environment of target pest(s). The resulting product retains the toxicity of the toxin. These naturally encapsulated pesticidal proteins may then be formulated in accordance with conventional techniques for application to the environment hosting a target pest, e.g., soil, water, and foliage of plants. See, for example U.S. Pat. No. 6,468,523 and U.S. Publication No. 20050138685, and the references cited therein. In the present invention, a transformed microorganism (which includes whole organisms, cells, spore(s), pesticidal protein(s), pesticidal component(s), pest-impacting component(s), mutant(s), living or dead cells and cell components, including mixtures of living and dead cells and cell components, and including broken cells and cell components) or an isolated pesticidal protein can be formulated with an acceptable carrier into a pesticidal or agricultural composition(s) that is, for example, a suspension, a solution, an emulsion, a dusting powder, a dispersible granule, a wettable powder, and an emulsifiable concentrate, an aerosol, an impregnated granule, an adjuvant, a coatable paste, and also encapsulations in, for example, polymer substances.

Agricultural compositions may comprise a polypeptide, a recombinogenic polypeptide or a variant or fragment thereof, as disclosed herein. The agricultural composition disclosed herein may be applied to the environment of a plant or an area of cultivation, or applied to the plant, plant part, plant cell, or seed.

Such compositions disclosed above may be obtained by the addition of a surface-active agent, an inert carrier, a preservative, a humectant, a feeding stimulant, an attractant, an encapsulating agent, a binder, an emulsifier, a dye, a UV protectant, a buffer, a flow agent or fertilizers, micronutrient donors, or other preparations that influence plant growth. One or more agrochemicals including, but not limited to, herbicides, insecticides, fungicides, bactericides, nematicides, molluscicides, acaracides, plant growth regulators, harvest aids, and fertilizers, can be combined with carriers, surfactants or adjuvants customarily employed in the art of formulation or other components to facilitate product handling and application for particular target pests. Suitable carriers and adjuvants can be solid or liquid and correspond to the substances ordinarily employed in formulation technology, e.g., natural or regenerated mineral substances, solvents, dispersants, wetting agents, tackifiers, binders, or fertilizers. The active ingredients of the present invention are normally applied in the form of compositions and can be applied to the crop area, plant, or seed to be treated. For example, the compositions of the present invention may be applied to grain in preparation for or during storage in a grain bin or silo, etc. The compositions of the present invention may be applied simultaneously or in succession with other compounds. Methods of applying an active ingredient of the present invention or an agrochemical composition of the present invention that contains at least one of the pesticidal proteins produced by the bacterial strains of the present invention include, but are not limited to, foliar application, seed coating, and soil application. The number of applications and the rate of application depend on the intensity of infestation by the corresponding pest.

Suitable surface-active agents include, but are not limited to, anionic compounds such as a carboxylate of, for example, a metal; a carboxylate of a long chain fatty acid; an N-acylsarcosinate; mono or di-esters of phosphoric acid with fatty alcohol ethoxylates or salts of such esters; fatty alcohol sulfates such as sodium dodecyl sulfate, sodium octadecyl sulfate or sodium cetyl sulfate; ethoxylated fatty alcohol sulfates; ethoxylated alkylphenol sulfates; lignin sulfonates; petroleum sulfonates; alkyl aryl sulfonates such as alkyl-benzene sulfonates or lower alkylnaphtalene sulfonates, e.g., butyl-naphthalene sulfonate; salts of sulfonated naphthalene-formaldehyde condensates; salts of sulfonated phenol-formaldehyde condensates; more complex sulfonates such as the amide sulfonates, e.g., the sulfonated condensation product of oleic acid and N-methyl taurine; or the dialkyl sulfosuccinates, e.g., the sodium sulfonate of dioctyl succinate. Non-ionic agents include condensation products of fatty acid esters, fatty alcohols, fatty acid amides or fatty-alkyl- or alkenyl-substituted phenols with ethylene oxide, fatty esters of polyhydric alcohol ethers, e.g., sorbitan fatty acid esters, condensation products of such esters with ethylene oxide, e.g., polyoxyethylene sorbitar fatty acid esters, block copolymers of ethylene oxide and propylene oxide, acetylenic glycols such as 2,4,7,9-tetraethyl-5-decyn-4,7-diol, or ethoxylated acetylenic glycols. Examples of a cationic surface-active agent include, for instance, an aliphatic mono-, di-, or polyamine such as an acetate, naphthenate or oleate; or oxygen-containing amine such as an amine oxide of polyoxyethylene alkylamine; an amide-linked amine prepared by the condensation of a carboxylic acid with a di- or polyamine; or a quaternary ammonium salt.

Examples of inert materials include but are not limited to inorganic minerals such as kaolin, phyllosilicates, carbonates, sulfates, phosphates, or botanical materials such as cork, powdered corncobs, peanut hulls, rice hulls, and walnut shells.

The compositions of the present invention can be in a suitable form for direct application or as a concentrate of primary composition that requires dilution with a suitable quantity of water or other diluant before application. The pesticidal concentration will vary depending upon the nature of the particular formulation, specifically, whether it is a concentrate or to be used directly. The composition contains 1 to 98% of a solid or liquid inert carrier, and 0 to 50% or 0.1 to 50% of a surfactant. These compositions will be administered at the labeled rate for the commercial product, for example, about 0.01 lb-5.0 lb. per acre when in dry form and at about 0.01 pts.-10 pts. per acre when in liquid form.

In a further embodiment, the compositions, as well as the transformed microorganisms and pesticidal proteins, provided herein can be treated prior to formulation to prolong the pesticidal activity when applied to the environment of a target pest as long as the pretreatment is not deleterious to the pesticidal activity. Such treatment can be by chemical and/or physical means as long as the treatment does not deleteriously affect the properties of the composition(s). Examples of chemical reagents include but are not limited to halogenating agents; aldehydes such as formaldehyde and glutaraldehyde; anti-infectives, such as zephiran chloride; alcohols, such as isopropanol and ethanol; and histological fixatives, such as Bouin's fixative and Helly's fixative (see, for example, Humason (1967) *Animal Tissue Techniques* (W.H. Freeman and Co.).

In one aspect, pests may be killed or reduced in numbers in a given area by application of the pesticidal proteins provided herein to the area. Alternatively, the pesticidal proteins may be prophylactically applied to an environmental area to prevent infestation by a susceptible pest. Preferably the pest ingests, or is contacted with, a pesticidally-effective amount of the polypeptide. By "pesticidally-effective amount" is intended an amount of the pesticide that is able to bring about death to at least one pest, or to noticeably reduce pest growth, feeding, or normal physiological development. This amount will vary depending on such factors as, for example, the specific target pests to be controlled, the specific environment, location, plant, crop, or agricultural site to be treated, the environmental conditions, and the method, rate, concentration, stability, and quantity of application of the pesticidally-effective polypeptide composition. The formulations or compositions may also vary with respect to climatic conditions, environmental considerations, and/or frequency of application and/or severity of pest infestation.

The active ingredients are normally applied in the form of compositions and can be applied to the crop area, plant, or seed to be treated. Methods are therefore provided for providing to a plant, plant cell, seed, plant part or an area of cultivation, an effective amount of the agricultural composition comprising the polypeptide, recombinogenic polypeptide or an active variant or fragment thereof. By "effective amount" is intended an amount of a protein or composition has pesticidal activity that is sufficient to kill or control the pest or result in a noticeable reduction in pest growth, feeding, or normal physiological development. Such decreases in numbers, pest growth, feeding or normal development can comprise any statistically significant decrease, including, for example a decrease of about 5%, 10%, 15%, 20%, 25%, 30%, 35%, 40%, 45%, 50%, 55%, 60%, 65%, 70%, 75%, 85%, 90%, 95% or greater.

For example, the compositions may be applied to grain in preparation for or during storage in a grain bin or silo, etc. The compositions may be applied simultaneously or in succession with other compounds. Methods of applying an active ingredient or an agrochemical composition comprising at least one of the polypeptides, recombinogenic polypeptides or variants or fragments thereof as disclosed herein, include but are not limited to, foliar application, seed coating, and soil application.

Methods for increasing plant yield are provided. The methods comprise providing a plant or plant cell expressing a polynucleotide encoding the pesticidal polypeptide sequence disclosed herein and growing the plant or a seed thereof in a field infested with (or susceptible to infestation by) a pest against which said polypeptide has pesticidal activity. In some embodiments, the polypeptide has pesticidal activity against a lepidopteran, coleopteran, dipteran, hemipteran, or nematode pest, and said field is infested with a lepidopteran, hemipteran, coleopteran, dipteran, or nematode pest. As defined herein, the "yield" of the plant refers to the quality and/or quantity of biomass produced by the plant. By "biomass" is intended any measured plant product. An increase in biomass production is any improvement in the yield of the measured plant product. Increasing plant yield has several commercial applications. For example, increasing plant leaf biomass may increase the yield of leafy vegetables for human or animal consumption. Additionally, increasing leaf biomass can be used to increase production of plant-derived pharmaceutical or industrial products. An increase in yield can comprise any statistically significant increase including, but not limited to, at least a 1% increase, at least a 3% increase, at least a 5% increase, at least a 10% increase, at least a 20% increase, at least a 30%, at least a 50%, at least a 70%, at least a 100% or a greater increase in yield compared to a plant not expressing the pesticidal sequence. In specific methods, plant yield is increased as a result of improved pest resistance of a plant expressing a pesticidal protein disclosed herein. Expression of the pesticidal protein results in a reduced ability of a pest to infest or feed.

The plants can also be treated with one or more chemical compositions, including one or more herbicide, insecticides, or fungicides.

Non-limiting embodiments include:

1. An isolated polypeptide having insecticidal activity, comprising (a) a polypeptide comprising an amino acid sequence selected from the group consisting of sequences set forth in SEQ ID NO: 1, 2, 3, 4, 5, 6, 7, 8, 9, 10, 11, 12, 13, 14, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, and/or 525; or (b) a polypeptide comprising an amino acid sequence having at least the percent sequence identity set forth in Table 1 to an amino acid sequence selected from the group consisting of sequences set forth in SEQ ID NOs: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, and/or 525.

2. The polypeptide of embodiment 1, wherein said polypeptide comprises the amino acid sequence set forth in SEQ ID NO: 1, 2, 3, 4, 5, 6, 7, 8, 9, 10, 11, 12, 13, 14, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, and/or 525.

3. A composition comprising the polypeptide of embodiments 1 or 2.

4. The polypeptide of embodiment 2, further comprising heterologous amino acid sequences.

5. A recombinant nucleic acid molecule that encodes the polypeptide of embodiment 1, wherein said recombinant nucleic acid molecule is not the naturally occurring sequence encoding said polypeptide.

6. The recombinant nucleic acid of embodiment 5, wherein said nucleic acid molecule is a synthetic sequence that has been designed for expression in a plant.

7. The recombinant nucleic acid molecule of embodiment 6, wherein said nucleic acid molecule is operably linked to a promoter capable of directing expression in a plant cell.

8. The recombinant nucleic acid molecule of embodiment 5, wherein said nucleic acid molecule is operably linked to a promoter capable of directing expression in a bacteria.

9. A host cell that contains the recombinant nucleic acid molecule of embodiment 8.

10. The host cell of embodiment 9, wherein said host cell is a bacterial host cell.

11. A DNA construct comprising a promoter that drives expression in a plant cell operably linked to a recombinant nucleic acid molecule comprising (a) a nucleotide sequence that encodes a polypeptide comprising the amino acid sequence of any one of SEQ ID NOs: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, and/or 525; or, (b) a nucleotide sequence that encodes a polypeptide comprising an amino acid sequence having at least the percent sequence identity set forth in Table 1 to an amino acid sequence selected from the group consisting of sequences set forth in SEQ ID NOs: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, and/or 525.

12. The DNA construct of embodiment 11, wherein said nucleotide sequence is a synthetic DNA sequence that has been designed for expression in a plant.

13. A vector comprising the DNA construct of embodiment 11.

14. A host cell that contains the DNA construct of any one of embodiments 11-13.

15. The host cell of embodiment 14, wherein the host cell is a plant cell.

16. A transgenic plant comprising the host cell of embodiment 15.

17. A composition comprising the host cell of embodiment 10.

18. The composition of embodiment 17, wherein said composition is selected from the group consisting of a powder, dust, pellet, granule, spray, emulsion, colloid, and solution.

19. The composition of embodiment 17, wherein said composition comprises from about 1% to about 99% by weight of said polypeptide.

20. A method for controlling a pest population comprising contacting said population with a pesticidal-effective amount of the composition of embodiment 17.

21. A method for killing a pest population comprising contacting said population with a pesticidal-effective amount of the composition of embodiment 17.

22. A method for producing a polypeptide with pesticidal activity, comprising culturing the host cell of embodiment 9 under conditions in which the nucleic acid molecule encoding the polypeptide is expressed.

23. A plant having stably incorporated into its genome a DNA construct comprising a nucleotide sequence that encodes a protein having pesticidal activity, wherein said nucleotide sequence comprise (a) a nucleotide sequence that encodes a polypeptide comprising the amino acid sequence of any one of SEQ ID NOs: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, and/or 525; or, (b) a nucleotide sequence that encodes a polypeptide comprising an amino acid sequence having at least the percent sequence identity set forth in Table 1 to an amino acid sequence selected from the group consisting of sequences set forth in SEQ ID NOs: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, and/or 525.

24. A transgenic seed of the plant of embodiment 23.

25. A method for protecting a plant from an insect pest, comprising expressing in a plant or cell thereof a nucleotide sequence that encodes a pesticidal polypeptide, wherein said nucleotide sequence comprising (a) a nucleotide sequence that encodes a polypeptide comprising the amino acid sequence of any one of SEQ ID NOs: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, and/or 525; or, (b) a nucleotide sequence that encodes a polypeptide comprising an amino acid sequence having at least the percent sequence identity set forth in Table 1 to an amino acid sequence selected from the group consisting of sequences set forth in SEQ ID NOs: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, and/or 525.

26. The method of embodiment 25, wherein said plant produces a pesticidal polypeptide having pesticidal against a lepidopteran or coleopteran pest.

27. A method for increasing yield in a plant comprising growing in a field a plant or seed thereof having stably incorporated into its genome a DNA construct comprising a promoter that drives expression in a plant operably linked to a nucleotide sequence that encodes a pesticidal polypeptide, wherein said nucleotide sequence comprises (a) a nucleotide sequence that encodes a polypeptide comprising the amino acid sequence of any one of SEQ ID NOs: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, and/or 525; or, (b) a nucleotide sequence that encodes a polypeptide comprising an amino acid sequence having at least the percent sequence identity set forth in Table 1 to an amino acid sequence selected from the group consisting of sequences set forth in SEQ ID NOs: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, and/or 525.

28. A method of obtaining a polynucleotide that encodes an improved polypeptide comprising pesticidal activity is provided, wherein the improved polypeptide has at least one improved property over any one of SEQ ID NOs: 1, 2, 3, 4, 5, 6, 7, 8, 9, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, and/or 525 comprising:

(a) recombining a plurality of parental polynucleotides comprising SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, and/or 525, or an active variant or fragment thereof to produce a library of recombinant polynucleotides encoding recombinant pesticidal polypeptides;

(b) screening the library to identify a recombinant polynucleotide that encodes an improved recombinant pesticidal polypeptide that has an enhanced property improved over the parental polynucleotide;

(c) recovering the recombinant polynucleotide that encodes the improved recombinant pesticidal polypeptide identified in (b); and, (d) repeating steps (a), (b) and (c) using the recombinant polynucleotide recovered in step (c) as one of the plurality of parental polynucleotides in repeated step (a).

The following examples are offered by way of illustration and not by way of limitation.

EXPERIMENTAL

Example 1: Discovery of Novel Genes by Sequencing and DNA Analysis

Microbial cultures were grown in liquid culture in standard laboratory media. Cultures were grown to saturation (16 to 24 hours) before DNA preparation. DNA was extracted from bacterial cells by detergent lysis, followed by binding to a silica matrix and washing with an ethanol buffer. Purified DNA was eluted from the silica matrix with a mildly alkaline aqueous buffer.

DNA for sequencing was tested for purity and concentration by spectrophotometry. Sequencing libraries were prepared using the Nextera XT library preparation kit according to the manufacturer's protocol. Sequence data was generated on a HiSeq 2000 according to the Illumina HiSeq 2000 System User Guide protocol. Sequencing reads were assembled into draft genomes using the CLC Bio Assembly Cell software package. Following assembly, gene calls were made by several methods and resulting gene sequences were interrogated to identify novel homologs of pesticidal genes. Novel genes were identified by BLAST, by domain composition, and by pairwise alignment versus a target set of pesticidal genes. A summary of such sequences is set forth in Table 1.

Genes identified in the homology search were amplified from bacterial DNA by PCR and cloned into bacterial expression vectors containing fused in-frame purification tags. Cloned genes were expressed in *E. coli* and purified by column chromatography. Purified proteins were assessed in insect diet bioassay studies to identify active proteins.

Example 2. Heterologous Expression in *E. Coli*

Each open reading frame set forth in SEQ ID NOs: 1-525 is cloned into an *E. coli* expression vector containing a maltose binding protein (pMBP). The expression vector is transformed into BL21*RIPL. An LB culture supplemented with carbenicillin is inoculated with a single colony and grown overnight at 37° C. using 0.5% of the overnight culture, a fresh culture is inoculated and grown to logarithmic phase at 37° C. The culture is induced using 250 mM IPTG for 18 hours at 16° C. The cells are pelleted and resuspended in 10 mM Tris pH7.4 and 150 mM NaCl supplemented with protease inhibitors. The protein expression is evaluated by SDS-PAGE.

Example 3. Pesticidal Activity Against Coleopteran and Lepidopteran

Methods

Protein Expression: Each sequence set forth in SEQ ID NOs: 1-525 is expressed in *E. coli* as described in Example 2. 400 mL of LB is inoculated and grown to an OD600 of 0.6. The culture is induced with 0.25 mM IPTG overnight at 16° C. The cells are spun down and the cell pellet is resuspend in 5 mL of buffer. The resuspension is sonicated for 2 min on ice.

Bioassay: Fall army worm (FAW), corn ear worm (CEW), European corn borer (ECB) southwestern corn borer (SWCB), velvetbean caterpillar (VBC) and diamond backed moth (DBM) eggs are purchased from a commercial insectary (Benzon Research Inc., Carlisle, PA). The FAW, CEW, ECB, VBC and BCW eggs are incubated to the point that eclosion would occur within 12 hrs of the assay setup. SWCB and DBM are introduced to the assay as neonate larvae. Assays are carried out in 24-well trays containing multispecies lepidopteran diet (SOUTHLAND PRODUCTS INCORPORATED, Lake Village, AR). Samples of the sonicated lysate are applied to the surface of the diet (diet overlay) and allowed to evaporate and soak into the diet. 100 of sonicated lysate is added to the diet surface and dried. The bioassay plates are sealed with a plate sealing film vented with pin holes. The plates are incubated at 26° C. at 65% RH on a 16:8 day:night cycle in a Percival for 5 days. The assays are assessed for level of mortality, growth inhibition and feeding inhibition.

For the western corn rootworm bioassay, the protein construct/lysate is evaluated in an insect bioassay by dispensing 60 μl volume on the top surface of diet in wells of 24-well plate (Cellstar, 24-well, Greiner Bio One) and allowed to dry. Each well contains 500 μl diet (Marrone et al., 1985). Fifteen to twenty neonate larvae are introduced in each well using a fine tip paint brush and the plate is covered with membrane (Viewseal, Greiner Bio One). The bioassay is stored at ambient temperature and scored for mortality, and/or growth/feeding inhibition at day 4.

For Colorado Potato Beetle (CPB) a cork bore size No. 8 leaf disk is excised from potato leaf and is dipped in the protein construct/lysate until thoroughly wet and placed on top of filter disk (Millipore, glass fiber filter, 13 mm). Sixty μl $dH_2O$ is added to each filter disk and placed in each well of 24-well plate (Cellstar, 24-well, Greiner Bio One). The leaf disk is allowed to dry and five to seven first instar larvae are introduced in each well using a fine tip paint brush. The plate is covered with membrane (Viewseal, Greiner Bio One) and small hole is punctured in each well of the membrane. The construct is evaluated with four replicates, and scored for mortality and leaf damage on day 3.

TABLE 3

| APG | Seq ID | VBC | FAW | CEW | BCW | ECB | SWCB | CPB | DBM | WCRW |
|---|---|---|---|---|---|---|---|---|---|---|
| APG00751.1 | 2 | SS | — | — | NT | NT | NT | NT | NT | — |
| APG00831.2 | 6 | — | — | — | NT | NT | NT | NT | NT | — |
| APG00832.1 | 8 | NT | — | — | NT | NT | NT | NT | NT | — |
| APG00842.1 | 11 | NT | — | SS | NT | NT | NT | NT | NT | — |
| APG00887.1 | 13 | NT | M, S | — | NT | NT | NT | NT | NT | — |
| APG00961.1 | 15 | NT | — | — | NT | NT | NT | NT | NT | — |
| APG00973.2 | 18 | — | — | — | NT | NT | NT | NT | NT | — |
| APG01038.1 | 20 | — | — | — | NT | NT | NT | NT | NT | — |
| APG01063.1 | 22 | NT | S | — | NT | NT | NT | NT | NT | — |
| APG01092.1 | 24 | — | — | — | NT | NT | NT | NT | NT | — |

TABLE 3-continued

| APG | Seq ID | VBC | FAW | CEW | BCW | ECB | SWCB | CPB | DBM | WCRW |
|---|---|---|---|---|---|---|---|---|---|---|
| APG01102.1 | 26 | — | — | — | NT | NT | NT | NT | NT | — |
| APG01127.0 | 28 | NT | — | — | NT | NT | NT | NT | NT | — |
| APG01141.1 | 30 | NT | M, S | M, S | NT | NT | NT | NT | NT | — |
| APG01163.1 | 32 | — | — | — | NT | NT | NT | NT | NT | 100 |
| APG01165.1 | 34 | — | — | — | NT | NT | NT | NT | NT | — |
| APG01201.1 | 36 | — | — | — | NT | NT | NT | NT | NT | — |
| APG01281.1 | 38 | — | — | — | NT | NT | NT | NT | NT | — |
| APG01385.0 | 42 | NT | — | — | NT | NT | NT | NT | NT | — |
| APG01396.1 | 44 | — | — | — | NT | NT | NT | NT | NT | — |
| APG01434.2 | 47 | — | — | — | NT | NT | NT | NT | NT | — |
| APG01455.0 | 49 | — | — | — | NT | NT | NT | NT | NT | — |
| APG01516.1 | 51 | NT | — | — | NT | NT | NT | NT | NT | — |
| APG01549.0 | 52 | SS | — | — | NT | NT | NT | NT | NT | — |
| APG01617.1 | 54 | — | — | — | NT | NT | NT | NT | NT | — |
| APG01681.1 | 56 | — | — | — | NT | NT | NT | NT | NT | 100 |
| APG01686.1 | 59 | — | — | — | NT | NT | NT | NT | NT | — |
| APG01710.1 | 61 | — | — | — | NT | NT | NT | NT | NT | — |
| APG01788.1 | 63 | SS | SS | — | NT | NT | NT | NT | NT | — |
| APG01803.1 | 65 | NT | — | — | NT | NT | NT | NT | NT | — |
| APG01810.1 | 67 | NT | — | — | NT | NT | NT | NT | NT | — |
| APG01817.0 | 68 | NT | — | — | NT | NT | NT | NT | NT | — |
| APG01819.1 | 70 | — | — | — | NT | NT | NT | NT | NT | — |
| APG01860.1 | 72 | NT | — | — | NT | NT | NT | NT | NT | — |
| APG01967.1 | 74 | NT | | — | NT | NT | NT | NT | NT | — |
| APG02071.1 | 76 | NT | — | — | NT | NT | NT | NT | NT | — |
| APG02105.0 | 77 | NT | — | — | NT | NT | NT | NT | NT | — |
| APG02110.1 | 79 | — | — | — | NT | NT | NT | NT | NT | — |
| APG02115.0 | 80 | SS | — | — | NT | NT | NT | NT | NT | — |
| APG02143.0 | 81 | — | — | — | NT | NT | NT | NT | NT | — |
| APG02166.0 | 82 | NT | — | — | NT | NT | NT | NT | NT | — |
| APG02206.1 | 84 | — | — | — | NT | NT | NT | NT | NT | — |
| APG02221.1 | 87 | — | — | — | NT | NT | NT | NT | NT | — |
| APG02256.0 | 88 | NT | — | — | NT | NT | NT | NT | NT | — |
| APG02256.1 | 89 | NT | — | — | NT | NT | NT | NT | NT | — |
| APG02309.2 | 92 | NT | — | — | NT | NT | NT | NT | NT | — |
| APG02315.1 | 94 | NT | — | — | NT | NT | NT | NT | NT | — |
| APG02319.0 | 95 | — | — | — | NT | NT | NT | NT | NT | — |
| APG02380.1 | 97 | NT | | — | NT | NT | NT | NT | NT | — |
| APG02451.1 | 99 | — | — | — | NT | NT | NT | NT | NT | 84 |
| APG02475.2 | 102 | — | — | — | NT | NT | NT | NT | NT | — |
| APG02506.1 | 104 | — | — | — | NT | NT | NT | NT | NT | — |
| APG02511.2 | 107 | NT | — | — | NT | NT | NT | NT | NT | — |
| APG02587.1 | 109 | NT | — | — | NT | NT | NT | NT | NT | — |
| APG02592.0 | 110 | NT | — | — | NT | NT | NT | NT | NT | — |
| APG02656.1 | 112 | NT | — | — | NT | NT | NT | NT | NT | — |
| APG02659.1 | 114 | NT | — | — | NT | NT | NT | NT | NT | — |
| APG02671.1 | 116 | — | — | — | NT | NT | NT | NT | NT | — |
| APG02676.0 | 117 | NT | — | — | NT | NT | NT | NT | NT | — |
| APG02706.2 | 120 | — | — | — | NT | NT | NT | NT | NT | — |
| APG02706.6 | 124 | — | — | — | NT | NT | NT | NT | NT | — |
| APG02714.0 | 125 | — | — | — | NT | NT | NT | NT | NT | 93 |
| APG02718.1 | 127 | NT | — | — | NT | NT | NT | NT | NT | — |
| APG02767.1 | 129 | NT | — | — | NT | NT | NT | NT | NT | — |
| APG02941.0 | 130 | — | — | — | NT | NT | NT | NT | NT | — |
| APG02947.2 | 133 | — | — | — | NT | NT | NT | NT | NT | — |
| APG02956.0 | 134 | NT | — | — | NT | NT | NT | NT | NT | — |
| APG02986.0 | 135 | NT | — | — | NT | NT | NT | NT | NT | — |
| APG03018.2 | 138 | — | — | — | NT | NT | NT | NT | NT | — |
| APG03054.0 | 140 | NT | — | — | NT | NT | NT | NT | NT | — |
| APG03056.1 | 142 | NT | — | — | NT | NT | NT | NT | NT | — |
| APG03182.2 | 146 | NT | — | — | NT | NT | NT | NT | NT | — |
| APG03218.1 | 148 | — | — | — | NT | NT | NT | NT | NT | — |
| APG03247.1 | 150 | NT | — | — | NT | NT | NT | NT | NT | — |
| APG03361.0 | 151 | NT | — | — | NT | NT | NT | NT | NT | — |
| APG03392.1 | 153 | NT | — | — | NT | NT | NT | NT | NT | — |
| APG03415.0 | 154 | — | — | — | NT | NT | NT | NT | NT | 86 |
| APG03504.0 | 155 | — | — | — | NT | NT | NT | NT | NT | 100 |
| APG03505.2 | 158 | — | — | — | NT | NT | NT | NT | NT | — |
| APG03505.4 | 160 | — | — | — | NT | NT | NT | NT | NT | — |
| APG03505.6 | 162 | — | — | — | NT | NT | NT | NT | NT | — |
| APG03527.1 | 164 | — | — | — | NT | NT | NT | NT | NT | 62 |
| APG03584.0 | 165 | NT | — | — | NT | NT | NT | NT | NT | — |
| APG03584.1 | 166 | NT | — | — | NT | NT | NT | NT | NT | — |
| APG03587.0 | 167 | — | — | — | NT | NT | NT | NT | NT | — |
| APG03674.1 | 169 | — | — | — | NT | NT | NT | NT | NT | — |
| APG03738.0 | 170 | NT | — | — | NT | NT | NT | NT | NT | — |
| APG03758.0 | 173 | NT | — | — | NT | NT | NT | NT | NT | — |
| APG03778.0 | 174 | NT | — | — | NT | NT | NT | NT | NT | — |

TABLE 3-continued

| APG | Seq ID | VBC | FAW | CEW | BCW | ECB | SWCB | CPB | DBM | WCRW |
|---|---|---|---|---|---|---|---|---|---|---|
| APG03789.0 | 175 | NT | — | — | NT | NT | NT | NT | NT | — |
| APG03826.0 | 176 | NT | — | — | NT | NT | NT | NT | NT | — |
| APG03887.0 | 177 | SS | — | — | NT | NT | NT | NT | NT | — |
| APG03893.0 | 178 | — | — | — | NT | NT | NT | NT | NT | — |
| APG03909.1 | 180 | NT | — | — | NT | NT | NT | NT | NT | — |
| APG03959.0 | 181 | NT | — | — | NT | NT | NT | NT | NT | — |
| APG04009.0 | 182 | NT | S | — | NT | NT | NT | NT | NT | — |
| APG04019.1 | 184 | — | — | — | NT | NT | NT | NT | NT | — |
| APG04103.1 | 186 | NT | S | — | NT | NT | NT | NT | NT | — |
| APG04111.0 | 187 | — | — | — | NT | NT | NT | NT | NT | — |
| APG04141.0 | 188 | NT | — | — | NT | NT | NT | NT | NT | — |
| APG04162.1 | 190 | NT | — | — | NT | NT | NT | NT | NT | — |
| APG04302.0 | 193 | NT | — | — | NT | NT | NT | NT | NT | — |
| APG04316.1 | 195 | NT | — | — | NT | NT | NT | NT | NT | — |
| APG04323.0 | 196 | NT | — | — | NT | NT | NT | NT | NT | — |
| APG04360.0 | 197 | — | — | — | NT | NT | NT | NT | NT | — |
| APG04439.1 | 199 | NT | — | — | NT | NT | NT | NT | NT | — |
| APG04442.1 | 201 | NT | — | — | NT | NT | NT | NT | NT | — |
| APG04476.1 | 203 | — | — | — | NT | NT | NT | NT | NT | — |
| APG04568.1 | 205 | — | — | — | NT | NT | NT | NT | NT | — |
| APG04602.1 | 207 | — | — | — | NT | NT | NT | NT | NT | — |
| APG04651.0 | 208 | — | — | — | NT | NT | NT | NT | NT | — |
| APG04683.2 | 211 | NT | M, S | — | NT | NT | NT | NT | NT | 83 |
| APG04687.2 | 214 | NT | — | — | NT | NT | NT | NT | NT | — |
| APG04692.2 | 217 | — | — | — | NT | NT | NT | NT | NT | — |
| APG04694.1 | 219 | — | — | — | NT | NT | NT | NT | NT | — |
| APG06866.0 | 220 | — | SS | — | NT | NT | NT | NT | NT | — |
| APG04786.2 | 223 | NT | — | — | NT | NT | NT | NT | NT | — |
| APG04794.0 | 224 | — | — | — | NT | NT | NT | NT | NT | — |
| APG04821.1 | 226 | NT | — | — | NT | NT | NT | NT | NT | — |
| APG04822.1 | 228 | — | — | — | NT | NT | NT | NT | NT | — |
| APG04959.0 | 229 | NT | — | — | NT | NT | NT | NT | NT | — |
| APG04966.1 | 231 | NT | — | — | NT | NT | NT | NT | NT | — |
| APG04977.0 | 232 | — | — | — | NT | NT | NT | NT | NT | — |
| APG05073.2 | 235 | — | — | — | NT | NT | NT | NT | NT | — |
| APG05078.0 | 236 | NT | — | — | NT | NT | NT | NT | NT | — |
| APG05095.1 | 238 | — | — | — | NT | NT | NT | NT | NT | — |
| APG05149.1 | 241 | — | — | — | NT | NT | NT | NT | NT | — |
| APG05279.2 | 244 | — | — | — | NT | NT | NT | NT | NT | — |
| APG05300.0 | 245 | NT | — | — | NT | NT | NT | NT | NT | — |
| APG05346.1 | 247 | NT | — | — | NT | NT | NT | NT | NT | — |
| APG05388.0 | 248 | NT | — | — | NT | NT | NT | NT | NT | — |
| APG05408.1 | 250 | NT | — | — | NT | NT | NT | NT | NT | — |
| APG05414.1 | 252 | NT | SS | SS | NT | NT | NT | NT | NT | — |
| APG05429.1 | 254 | NT | — | — | NT | NT | NT | NT | NT | — |
| APG05429.2 | 255 | NT | — | — | NT | NT | NT | NT | NT | — |
| APG05431.1 | 257 | — | — | — | NT | NT | NT | NT | NT | 100 |
| APG05471.0 | 258 | NT | — | — | NT | NT | NT | NT | NT | — |
| APG05481.2 | 261 | — | — | — | NT | NT | NT | NT | NT | — |
| APG05492.0 | 262 | NT | — | — | NT | NT | NT | NT | NT | 100 |
| APG05508.1 | 264 | — | — | — | NT | NT | NT | NT | NT | — |
| APG05538.2 | 267 | — | — | — | NT | NT | NT | NT | NT | — |
| APG05636.0 | 268 | NT | — | — | NT | NT | NT | NT | NT | — |
| APG05643.1 | 270 | NT | — | — | NT | NT | NT | NT | NT | — |
| APG05662.0 | 272 | NT | — | — | NT | NT | NT | NT | NT | — |
| APG05725.1 | 274 | — | — | — | NT | NT | NT | NT | NT | — |
| APG05734.4 | 279 | — | — | — | NT | NT | NT | NT | NT | — |
| APG05793.0 | 280 | — | — | — | NT | NT | NT | NT | NT | — |
| APG05834.1 | 282 | NT | — | — | NT | NT | NT | NT | NT | — |
| APG05878.0 | 283 | — | — | — | NT | NT | NT | NT | NT | — |
| APG05907.1 | 285 | NT | — | — | NT | NT | NT | NT | NT | — |
| APG05917.0 | 286 | NT | — | — | NT | NT | NT | NT | NT | — |
| APG05920.1 | 288 | NT | — | — | NT | NT | NT | NT | NT | — |
| APG05946.0 | 289 | NT | — | — | NT | NT | NT | NT | NT | — |
| APG05955.0 | 290 | NT | — | — | NT | NT | NT | NT | NT | — |
| APG05992.0 | 291 | — | — | — | NT | NT | NT | NT | NT | — |
| APG06027.1 | 293 | NT | — | — | NT | NT | NT | NT | NT | — |
| APG06049.1 | 295 | NT | — | — | NT | NT | NT | NT | NT | — |
| APG06079.1 | 297 | NT | — | — | NT | NT | NT | NT | NT | — |
| APG06195.0 | 298 | NT | M, S | — | NT | NT | NT | NT | NT | — |
| APG06213.1 | 300 | NT | — | — | NT | NT | NT | NT | NT | — |
| APG06213.2 | 301 | NT | — | — | NT | NT | NT | NT | NT | — |
| APG06235.0 | 302 | NT | — | — | NT | NT | NT | NT | NT | — |
| APG06283.0 | 303 | NT | S | — | NT | NT | NT | NT | NT | — |
| APG06304.1 | 305 | NT | — | — | NT | NT | NT | NT | NT | — |
| APG06319.1 | 307 | NT | — | — | NT | NT | NT | NT | NT | — |
| APG06331.1 | 309 | NT | — | — | NT | NT | NT | NT | NT | — |
| APG06424.0 | 313 | NT | — | — | NT | NT | NT | NT | NT | — |

TABLE 3-continued

| APG | Seq ID | VBC | FAW | CEW | BCW | ECB | SWCB | CPB | DBM | WCRW |
|---|---|---|---|---|---|---|---|---|---|---|
| APG06479.1 | 315 | NT | — | — | NT | NT | NT | NT | NT | — |
| APG06480.1 | 317 | — | — | — | NT | NT | NT | NT | NT | — |
| APG06493.1 | 319 | NT | — | — | NT | NT | NT | NT | NT | — |
| APG06496.0 | 320 | NT | | — | NT | NT | NT | NT | NT | — |
| APG06576.1 | 323 | — | — | — | NT | NT | NT | NT | NT | — |
| APG06578.0 | 324 | NT | S | — | NT | NT | NT | NT | NT | — |
| APG06606.1 | 326 | — | — | — | NT | NT | NT | NT | NT | — |
| APG06606.2 | 327 | — | — | — | NT | NT | NT | NT | NT | — |
| APG06677.1 | 329 | NT | — | — | NT | NT | NT | NT | NT | — |
| APG06697.2 | 332 | NT | — | — | NT | NT | NT | NT | NT | — |
| APG06705.2 | 335 | — | — | — | NT | NT | NT | NT | NT | — |
| APG06718.0 | 336 | NT | — | — | NT | NT | NT | NT | NT | — |
| APG06738.1 | 338 | — | — | — | NT | NT | NT | NT | NT | — |
| APG06774.0 | 339 | NT | — | — | NT | NT | NT | NT | NT | — |
| APG06791.1 | 341 | NT | — | — | NT | NT | NT | NT | NT | — |
| APG06883.1 | 343 | NT | — | — | NT | NT | NT | NT | NT | — |
| APG06898.1 | 345 | NT | — | — | NT | NT | NT | NT | NT | — |
| APG06937.1 | 347 | — | — | — | NT | NT | NT | NT | NT | — |
| APG06954.1 | 349 | NT | — | — | NT | NT | NT | NT | NT | — |
| APG07054.0 | 350 | NT | HM, S | — | NT | NT | NT | NT | NT | — |
| APG07057.0 | 351 | NT | — | — | NT | NT | NT | NT | NT | — |
| APG07094.1 | 353 | NT | — | — | NT | NT | NT | NT | NT | — |
| APG07107.1 | 355 | — | — | — | NT | NT | NT | NT | NT | — |
| APG07137.2 | 358 | NT | S | — | NT | NT | NT | NT | NT | — |
| APG07162.0 | 359 | NT | — | — | NT | NT | NT | NT | NT | — |
| APG07176.0 | 360 | NT | — | — | NT | NT | NT | NT | NT | — |
| APG07249.2 | 363 | — | — | — | NT | NT | NT | NT | NT | — |
| APG07257.0 | 364 | — | — | — | NT | NT | NT | NT | NT | — |
| APG07307.1 | 367 | NT | — | — | NT | NT | NT | NT | NT | — |
| APG07310.0 | 368 | — | — | — | NT | NT | NT | NT | NT | — |
| APG07318.1 | 370 | — | — | — | NT | NT | NT | NT | NT | — |
| APG07322.2 | 373 | — | — | — | NT | NT | NT | NT | NT | — |
| APG07432.1 | 376 | NT | — | — | NT | NT | NT | NT | NT | — |
| APG07463.0 | 377 | — | — | — | NT | NT | NT | NT | NT | — |
| APG07467.1 | 379 | — | — | — | NT | NT | NT | NT | NT | — |
| APG07487.0 | 380 | — | — | — | NT | NT | NT | NT | NT | — |
| APG07511.1 | 382 | NT | — | — | NT | NT | NT | NT | NT | — |
| APG07564.1 | 384 | NT | — | — | NT | NT | NT | NT | NT | — |
| APG07609.1 | 386 | — | — | — | NT | NT | NT | NT | NT | — |
| APG07636.0 | 387 | NT | — | — | NT | NT | NT | NT | NT | — |
| APG07636.1 | 388 | NT | — | — | NT | NT | NT | NT | NT | — |
| APG07664.1 | 390 | NT | M, S | — | NT | NT | NT | NT | NT | — |
| APG07665.1 | 392 | NT | — | — | NT | NT | NT | NT | NT | — |
| APG07732.0 | 393 | NT | — | — | NT | NT | NT | NT | NT | — |
| APG07753.1 | 395 | NT | — | — | NT | NT | NT | NT | NT | — |
| APG07798.1 | 397 | NT | — | — | NT | NT | NT | NT | NT | — |
| APG07810.0 | 398 | — | — | — | NT | NT | NT | NT | NT | — |
| APG07811.1 | 400 | NT | — | — | NT | NT | NT | NT | NT | — |
| APG07811.2 | 401 | NT | — | — | NT | NT | NT | NT | NT | — |
| APG07945.1 | 403 | — | — | — | NT | NT | NT | NT | NT | — |
| APG07969.1 | 406 | NT | — | — | NT | NT | NT | NT | NT | — |
| APG08021.1 | 410 | — | — | — | NT | NT | NT | NT | NT | — |
| APG08081.2 | 413 | NT | — | — | NT | NT | NT | NT | NT | — |
| APG08171.0 | 414 | NT | — | — | NT | NT | NT | NT | NT | — |
| APG08193.1 | 416 | — | — | — | NT | NT | NT | NT | NT | — |
| APG08207.2 | 419 | — | — | — | NT | NT | NT | NT | NT | — |
| APG08240.0 | 420 | — | — | — | NT | NT | NT | NT | NT | — |
| APG08316.0 | 421 | — | — | — | NT | NT | NT | NT | NT | — |
| APG08335.1 | 423 | NT | — | — | NT | NT | NT | NT | NT | — |
| APG08339.1 | 425 | NT | — | — | NT | NT | NT | NT | NT | — |
| APG08370.1 | 427 | — | SS | — | NT | NT | NT | NT | NT | 100 |
| APG08378.1 | 429 | NT | — | — | NT | NT | NT | NT | NT | — |
| APG08427.1 | 432 | NT | — | — | NT | NT | NT | NT | NT | — |
| APG08468.0 | 433 | NT | — | — | NT | NT | NT | NT | NT | — |
| APG08495.0 | 434 | — | — | — | NT | NT | NT | NT | NT | — |
| APG08526.0 | 435 | NT | — | — | NT | NT | NT | NT | NT | — |
| APG08576.0 | 436 | NT | — | — | NT | NT | NT | NT | NT | — |
| APG08577.0 | 437 | NT | — | — | NT | NT | NT | NT | NT | — |
| APG08624.1 | 439 | NT | — | — | NT | NT | NT | NT | NT | — |
| APG08625.1 | 441 | NT | — | — | NT | NT | NT | NT | NT | — |
| APG08639.0 | 442 | NT | S | SS | NT | NT | NT | NT | NT | — |
| APG08642.2 | 445 | — | — | — | NT | NT | NT | NT | NT | — |
| APG08757.1 | 447 | NT | — | — | NT | NT | NT | NT | NT | — |
| APG08765.0 | 448 | — | — | — | NT | NT | NT | NT | NT | — |
| APG08791.2 | 452 | — | — | — | NT | NT | NT | NT | NT | — |
| APG08812.0 | 453 | NT | — | — | NT | NT | NT | NT | NT | — |
| APG08823.0 | 454 | NT | — | — | NT | NT | NT | NT | NT | — |
| APG08852.0 | 455 | NT | — | — | NT | NT | NT | NT | NT | — |

TABLE 3-continued

| APG | Seq ID | VBC | FAW | CEW | BCW | ECB | SWCB | CPB | DBM | WCRW |
|---|---|---|---|---|---|---|---|---|---|---|
| APG08912.1 | 457 | NT | — | — | NT | NT | NT | NT | NT | — |
| APG08912.2 | 458 | NT | — | — | NT | NT | NT | NT | NT | — |
| APG09027.1 | 460 | — | — | — | NT | NT | NT | NT | NT | 84 |
| APG09028.1 | 462 | NT | — | — | NT | NT | NT | NT | NT | — |
| APG09048.1 | 464 | NT | | — | NT | NT | NT | NT | NT | — |
| APG09152.1 | 466 | — | — | — | NT | NT | NT | NT | NT | — |
| APG09158.1 | 468 | NT | — | — | NT | NT | NT | NT | NT | — |
| APG09181.0 | 469 | NT | SS | SS | NT | NT | NT | NT | NT | — |
| APG09201.0 | 470 | NT | SS | — | NT | NT | NT | NT | NT | — |
| APG09210.0 | 471 | — | — | — | NT | NT | NT | NT | NT | — |
| APG09221.0 | 472 | NT | — | — | NT | NT | NT | NT | NT | — |
| APG09238.2 | 475 | — | — | — | NT | NT | NT | NT | NT | — |
| APG09266.1 | 477 | NT | SS | SS | NT | NT | NT | NT | NT | — |
| APG09289.2 | 480 | SS | HM, S | — | NT | NT | NT | NT | NT | 100 |
| APG09323.1 | 482 | NT | — | — | NT | NT | NT | NT | NT | — |
| APG09412.1 | 484 | NT | — | — | NT | NT | NT | NT | NT | — |
| APG09416.0 | 487 | NT | — | — | NT | NT | NT | NT | NT | — |
| APG09430.1 | 489 | NT | — | — | NT | NT | NT | NT | NT | — |
| APG09439.0 | 490 | NT | — | — | NT | NT | NT | NT | NT | — |
| APG09465.1 | 492 | NT | S | — | NT | NT | NT | NT | NT | — |
| APG09511.1 | 494 | NT | — | — | NT | NT | NT | NT | NT | — |
| APG09548.1 | 496 | — | — | — | NT | NT | NT | NT | NT | — |
| APG09675.0 | 498 | NT | S | — | NT | NT | NT | NT | NT | — |
| APG09773.0 | 499 | NT | — | — | NT | NT | NT | NT | NT | — |
| APG09812.0 | 500 | NT | — | — | NT | NT | NT | NT | NT | — |
| APG09814.0 | 501 | NT | — | — | NT | NT | NT | NT | NT | — |
| APG09826.1 | 503 | NT | — | — | NT | NT | NT | NT | NT | — |
| APG09835.0 | 504 | — | — | — | NT | NT | NT | NT | NT | — |
| APG09895.1 | 506 | — | — | — | NT | NT | NT | NT | NT | — |
| APG09901.1 | 508 | NT | — | — | NT | NT | NT | NT | NT | — |
| APG09901.2 | 509 | NT | — | — | NT | NT | NT | NT | NT | — |
| APG09903.1 | 511 | — | — | — | NT | NT | NT | NT | NT | — |
| APG10001.2 | 514 | — | — | — | NT | NT | NT | NT | NT | — |
| APG01902.1 | 516 | — | — | — | NT | NT | NT | NT | NT | — |
| APG02996.1 | 518 | — | — | — | NT | NT | NT | NT | NT | — |
| APG03098.1 | 520 | — | — | — | NT | NT | NT | NT | NT | — |
| APG04517.0 | 521 | — | — | — | NT | NT | NT | NT | NT | — |
| APG04619.1 | 523 | — | — | — | NT | NT | NT | NT | NT | — |
| APG06717.1 | 525 | — | — | — | NT | NT | NT | NT | NT | — |

NT: Not tested

Example 4. Pesticidal Activity Against Hemipteran

Protein Expression: Each of the sequences set forth in SEQ ID NOs: 1-525 is expressed in *E. coli* as described in Example 2. 400 mL of LB is inoculated and grown to an OD600 of 0.6. The culture is induced with 0.25 mM IPTG overnight at 16° C. The cells are spun down and the cell pellet is re-suspended in 5 mL of buffer. The resuspension is sonicated for 2 min on ice. Mortality is scored for each sample.

Second instar southern green stink bug (SGSB) are obtained from a commercial insectary (Benzon Research Inc., Carlisle, PA). A 50% v/v ratio of sonicated lysate sample to 20% sucrose is employed in the bioassay. Stretched parafilm is used as a feeding membrane to expose the SGSB to the diet/sample mixture. The plates are incubated at 25° C.:21° C., 16:8 day:night cycle at 65% RH for 5 days. Mortality is scored for each sample.

Soybean Aphids (SBA) are originally obtained from Michigan State University before maintenance in a colony on soybean plants at the AgBiome laboratory. Six adult aphids are added to each well of a 24 well plate. Protein extracts are provided in liquid artificial diet at a rate of 25% and are sealed with an artificial membrane through which the aphids are able to feed on the diet/sample mixture. The plates are held in an incubator at 26° C., 60% relative humidity, 16:8 day:night cycle for 4-5 days. The SBA test uses a combination of mortality, reproduction and feeding to acquire a Combined score which is recorded on day 4 and day 5 following the initiation of the assay. To have an active sample, the combined score must be below 1.5 (scale: 0-3).

For the *Lygus hesperus* (LH) bioassay, *Lygus hesperus* are originally obtained from Ova the Hill Insectary before maintenance in a colony at the AgBiome laboratory. A 3:1 v/v ratio of protein fractions to 40% sucrose is employed in the bioassay (final concentration of sample is 10% sucrose). The sample is loaded into capillary tubes with 4 holes drilled for access to the sample. A total of six tubes containing 25 μl of sample are assayed on a total of 10 second instar *Lygus hesperus*. The tubes are held in small petri dishes and incubated at a 25° C.:21° C., 16:8 day:night cycle at 65% relative humidity for 8 days. Percent mortality is recorded on days 6 and 8. Positive activity in the assay is considered mortality above 50%.

TABLE 4

| APG | Seq ID | SGSB | SBA | LH |
|---|---|---|---|---|
| APG00751.1 | 2 | NT | NT | NT |
| APG00831.2 | 6 | NT | NT | – |
| APG00832.1 | 8 | NT | NT | – |
| APG00842.1 | 11 | NT | NT | – |
| APG00887.1 | 13 | NT | NT | – |
| APG00961.1 | 15 | NT | NT | – |
| APG00973.2 | 18 | NT | NT | – |
| APG01038.1 | 20 | NT | NT | NT |
| APG01063.1 | 22 | NT | NT | NT |
| APG01092.1 | 24 | NT | NT | NT |
| APG01102.1 | 26 | NT | NT | – |

TABLE 4-continued

| APG | Seq ID | SGSB | SBA | LH |
|---|---|---|---|---|
| APG01127.0 | 28 | NT | NT | – |
| APG01141.1 | 30 | NT | NT | NT |
| APG01163.1 | 32 | NT | NT | NT |
| APG01165.1 | 34 | NT | NT | – |
| APG01201.1 | 36 | NT | NT | – |
| APG01281.1 | 38 | NT | NT | NT |
| APG01385.0 | 42 | NT | NT | – |
| APG01396.1 | 44 | NT | NT | – |
| APG01434.2 | 47 | NT | NT | – |
| APG01455.0 | 49 | NT | NT | – |
| APG01516.1 | 51 | NT | NT | – |
| APG01549.0 | 52 | NT | NT | NT |
| APG01617.1 | 54 | NT | NT | – |
| APG01681.1 | 56 | NT | NT | – |
| APG01686.1 | 59 | NT | NT | – |
| APG01710.1 | 61 | NT | NT | – |
| APG01788.1 | 63 | NT | NT | NT |
| APG01803.1 | 65 | NT | NT | – |
| APG01810.1 | 67 | NT | NT | NT |
| APG01817.0 | 68 | NT | NT | NT |
| APG01819.1 | 70 | NT | NT | NT |
| APG01860.1 | 72 | NT | NT | NT |
| APG01967.1 | 74 | NT | NT | NT |
| APG02071.1 | 76 | NT | NT | + |
| APG02105.0 | 77 | NT | NT | – |
| APG02110.1 | 79 | NT | NT | NT |
| APG02115.0 | 80 | NT | NT | + |
| APG02143.0 | 81 | NT | NT | – |
| APG02166.0 | 82 | NT | NT | NT |
| APG02206.1 | 84 | NT | NT | – |
| APG02221.1 | 87 | NT | NT | NT |
| APG02256.0 | 88 | NT | NT | – |
| APG02256.1 | 89 | NT | NT | – |
| APG02309.2 | 92 | NT | NT | NT |
| APG02315.1 | 94 | NT | NT | – |
| APG02319.0 | 95 | NT | NT | – |
| APG02380.1 | 97 | NT | NT | NT |
| APG02451.1 | 99 | NT | NT | NT |
| APG02475.2 | 102 | NT | NT | – |
| APG02506.1 | 104 | NT | NT | – |
| APG02511.2 | 107 | NT | NT | NT |
| APG02587.1 | 109 | NT | NT | – |
| APG02592.0 | 110 | NT | NT | NT |
| APG02656.1 | 112 | NT | NT | – |
| APG02659.1 | 114 | NT | NT | NT |
| APG02671.1 | 116 | NT | NT | – |
| APG02676.0 | 117 | NT | NT | – |
| APG02706.2 | 120 | NT | NT | – |
| APG02706.6 | 124 | NT | NT | – |
| APG02714.0 | 125 | NT | NT | – |
| APG02718.1 | 127 | NT | NT | – |
| APG02767.1 | 129 | NT | NT | – |
| APG02941.0 | 130 | NT | NT | – |
| APG02947.2 | 133 | NT | NT | NT |
| APG02956.0 | 134 | NT | NT | – |
| APG02986.0 | 135 | NT | NT | – |
| APG03018.2 | 138 | NT | NT | – |
| APG03054.0 | 140 | NT | NT | – |
| APG03056.1 | 142 | NT | NT | – |
| APG03182.2 | 146 | NT | NT | – |
| APG03218.1 | 148 | NT | NT | – |
| APG03247.1 | 150 | NT | NT | – |
| APG03361.0 | 151 | NT | NT | – |
| APG03392.1 | 153 | NT | NT | NT |
| APG03415.0 | 154 | NT | NT | NT |
| APG03504.0 | 155 | NT | NT | NT |
| APG03505.2 | 158 | NT | NT | – |
| APG03505.4 | 160 | NT | NT | – |
| APG03505.6 | 162 | NT | NT | – |
| APG03527.1 | 164 | NT | NT | – |
| APG03584.0 | 165 | NT | NT | – |
| APG03584.1 | 166 | NT | NT | – |
| APG03587.0 | 167 | NT | NT | – |
| APG03674.1 | 169 | NT | NT | – |
| APG03738.0 | 170 | NT | NT | NT |
| APG03758.0 | 173 | NT | NT | NT |
| APG03778.0 | 174 | NT | NT | – |
| APG03789.0 | 175 | NT | NT | + |

TABLE 4-continued

| APG | Seq ID | SGSB | SBA | LH |
|---|---|---|---|---|
| APG03826.0 | 176 | NT | NT | NT |
| APG03887.0 | 177 | NT | NT | NT |
| APG03893.0 | 178 | NT | NT | – |
| APG03909.1 | 180 | NT | NT | – |
| APG03959.0 | 181 | NT | NT | – |
| APG04009.0 | 182 | NT | NT | NT |
| APG04019.1 | 184 | NT | NT | – |
| APG04103.1 | 186 | NT | NT | – |
| APG04111.0 | 187 | NT | NT | – |
| APG04141.0 | 188 | NT | NT | NT |
| APG04162.1 | 190 | NT | NT | NT |
| APG04302.0 | 193 | NT | NT | – |
| APG04316.1 | 195 | NT | NT | NT |
| APG04323.0 | 196 | NT | NT | NT |
| APG04360.0 | 197 | NT | NT | – |
| APG04439.1 | 199 | NT | NT | – |
| APG04442.1 | 201 | NT | NT | – |
| APG04476.1 | 203 | NT | NT | – |
| APG04568.1 | 205 | NT | NT | – |
| APG04602.1 | 207 | NT | NT | NT |
| APG04651.0 | 208 | NT | NT | – |
| APG04683.2 | 211 | NT | NT | NT |
| APG04687.2 | 214 | NT | NT | – |
| APG04692.2 | 217 | NT | NT | NT |
| APG04694.1 | 219 | NT | NT | NT |
| APG06866.0 | 220 | NT | NT | NT |
| APG04786.2 | 223 | NT | NT | – |
| APG04794.0 | 224 | NT | NT | – |
| APG04821.1 | 226 | NT | NT | – |
| APG04822.1 | 228 | NT | NT | – |
| APG04959.0 | 229 | NT | NT | – |
| APG04966.1 | 231 | NT | NT | – |
| APG04977.0 | 232 | NT | NT | – |
| APG05073.2 | 235 | NT | NT | – |
| APG05078.0 | 236 | NT | NT | NT |
| APG05095.1 | 238 | NT | NT | NT |
| APG05149.1 | 241 | NT | NT | NT |
| APG05279.2 | 244 | NT | NT | NT |
| APG05300.0 | 245 | NT | NT | – |
| APG05346.1 | 247 | NT | NT | NT |
| APG05388.0 | 248 | NT | NT | – |
| APG05408.1 | 250 | NT | NT | NT |
| APG05414.1 | 252 | NT | NT | NT |
| APG05429.1 | 254 | NT | NT | – |
| APG05429.2 | 255 | NT | NT | – |
| APG05431.1 | 257 | NT | NT | NT |
| APG05471.0 | 258 | NT | NT | NT |
| APG05481.2 | 261 | NT | NT | – |
| APG05492.0 | 262 | NT | NT | NT |
| APG05508.1 | 264 | NT | NT | NT |
| APG05538.2 | 267 | NT | NT | NT |
| APG05636.0 | 268 | NT | NT | – |
| APG05643.1 | 270 | NT | NT | – |
| APG05662.0 | 272 | NT | NT | – |
| APG05725.1 | 274 | NT | NT | NT |
| APG05734.4 | 279 | NT | NT | NT |
| APG05793.0 | 280 | NT | NT | – |
| APG05834.1 | 282 | NT | NT | + |
| APG05878.0 | 283 | NT | NT | – |
| APG05907.1 | 285 | NT | NT | – |
| APG05917.0 | 286 | NT | NT | – |
| APG05920.1 | 288 | NT | NT | – |
| APG05946.0 | 289 | NT | NT | – |
| APG05955.0 | 290 | NT | NT | – |
| APG05992.0 | 291 | NT | NT | – |
| APG06027.1 | 293 | NT | NT | NT |
| APG06049.1 | 295 | NT | NT | – |
| APG06079.1 | 297 | NT | NT | NT |
| APG06195.0 | 298 | NT | NT | NT |
| APG06213.1 | 300 | NT | NT | NT |
| APG06213.2 | 301 | NT | NT | NT |
| APG06235.0 | 302 | NT | NT | – |
| APG06283.0 | 303 | NT | NT | NT |
| APG06304.1 | 305 | NT | NT | NT |
| APG06319.1 | 307 | NT | NT | – |
| APG06331.1 | 309 | NT | NT | – |
| APG06424.0 | 313 | NT | NT | NT |
| APG06479.1 | 315 | NT | NT | – |

TABLE 4-continued

| APG | Seq ID | SGSB | SBA | LH |
|---|---|---|---|---|
| APG06480.1 | 317 | NT | NT | NT |
| APG06493.1 | 319 | NT | NT | – |
| APG06496.0 | 320 | NT | NT | NT |
| APG06576.1 | 323 | NT | NT | – |
| APG06578.0 | 324 | NT | NT | NT |
| APG06606.1 | 326 | NT | NT | – |
| APG06606.2 | 327 | NT | NT | – |
| APG06677.1 | 329 | NT | NT | – |
| APG06697.2 | 332 | NT | NT | + |
| APG06705.2 | 335 | NT | NT | – |
| APG06718.0 | 336 | NT | NT | NT |
| APG06738.1 | 338 | NT | NT | – |
| APG06774.0 | 339 | NT | NT | + |
| APG06791.1 | 341 | NT | NT | – |
| APG06883.1 | 343 | NT | NT | – |
| APG06898.1 | 345 | NT | NT | – |
| APG06937.1 | 347 | NT | NT | – |
| APG06954.1 | 349 | NT | NT | – |
| APG07054.0 | 350 | NT | NT | NT |
| APG07057.0 | 351 | NT | NT | – |
| APG07094.1 | 353 | NT | NT | NT |
| APG07107.1 | 355 | NT | NT | NT |
| APG07137.2 | 358 | NT | NT | – |
| APG07162.0 | 359 | NT | NT | – |
| APG07176.0 | 360 | NT | NT | NT |
| APG07249.2 | 363 | NT | NT | NT |
| APG07257.0 | 364 | NT | NT | |
| APG07307.1 | 367 | NT | NT | NT |
| APG07310.0 | 368 | NT | NT | NT |
| APG07318.1 | 370 | NT | NT | NT |
| APG07322.2 | 373 | NT | NT | NT |
| APG07432.1 | 376 | NT | NT | NT |
| APG07463.0 | 377 | NT | NT | NT |
| APG07467.1 | 379 | NT | NT | – |
| APG07487.0 | 380 | NT | NT | – |
| APG07511.1 | 382 | NT | NT | – |
| APG07564.1 | 384 | NT | NT | NT |
| APG07609.1 | 386 | NT | NT | – |
| APG07636.0 | 387 | NT | NT | – |
| APG07636.1 | 388 | NT | NT | – |
| APG07664.1 | 390 | NT | NT | NT |
| APG07665.1 | 392 | NT | NT | – |
| APG07732.0 | 393 | NT | NT | NT |
| APG07753.1 | 395 | NT | NT | NT |
| APG07798.1 | 397 | NT | NT | – |
| APG07810.0 | 398 | NT | NT | – |
| APG07811.1 | 400 | NT | NT | NT |
| APG07811.2 | 401 | NT | NT | NT |
| APG07945.1 | 403 | NT | NT | – |
| APG07969.1 | 406 | NT | NT | NT |
| APG08021.1 | 410 | NT | NT | NT |
| APG08081.2 | 413 | NT | NT | NT |
| APG08171.0 | 414 | NT | NT | NT |
| APG08193.1 | 416 | NT | NT | – |
| APG08207.2 | 419 | NT | NT | – |
| APG08240.0 | 420 | NT | NT | – |
| APG08316.0 | 421 | NT | NT | NT |
| APG08335.1 | 423 | NT | NT | – |
| APG08339.1 | 425 | NT | NT | NT |
| APG08370.1 | 427 | NT | NT | NT |
| APG08378.1 | 429 | NT | NT | – |
| APG08427.1 | 432 | NT | NT | – |
| APG08468.0 | 433 | NT | NT | NT |
| APG08495.0 | 434 | NT | NT | – |
| APG08526.0 | 435 | NT | NT | NT |
| APG08576.0 | 436 | NT | NT | NT |
| APG08577.0 | 437 | NT | NT | NT |
| APG08624.1 | 439 | NT | NT | – |
| APG08625.1 | 441 | NT | NT | – |
| APG08639.0 | 442 | NT | NT | NT |
| APG08642.2 | 445 | NT | NT | – |
| APG08757.1 | 447 | NT | NT | – |
| APG08765.0 | 448 | NT | NT | – |
| APG08791.2 | 452 | NT | NT | NT |
| APG08812.0 | 453 | NT | NT | NT |
| APG08823.0 | 454 | NT | NT | NT |
| APG08852.0 | 455 | NT | NT | – |
| APG08912.1 | 457 | NT | NT | NT |

TABLE 4-continued

| APG | Seq ID | SGSB | SBA | LH |
|---|---|---|---|---|
| APG08912.2 | 458 | NT | NT | NT |
| APG09027.1 | 460 | NT | NT | – |
| APG09028.1 | 462 | NT | NT | – |
| APG09048.1 | 464 | NT | NT | NT |
| APG09152.1 | 466 | NT | NT | – |
| APG09158.1 | 468 | NT | NT | NT |
| APG09181.0 | 469 | NT | NT | NT |
| APG09201.0 | 470 | NT | NT | – |
| APG09210.0 | 471 | NT | NT | – |
| APG09221.0 | 472 | NT | NT | – |
| APG09238.2 | 475 | NT | NT | NT |
| APG09266.1 | 477 | NT | NT | NT |
| APG09289.2 | 480 | NT | NT | NT |
| APG09323.1 | 482 | NT | NT | NT |
| APG09412.1 | 484 | NT | NT | NT |
| APG09416.0 | 487 | NT | NT | – |
| APG09430.1 | 489 | NT | NT | – |
| APG09439.0 | 490 | NT | NT | NT |
| APG09465.1 | 492 | NT | NT | NT |
| APG09511.1 | 494 | NT | NT | – |
| APG09548.1 | 496 | NT | NT | – |
| APG09675.0 | 498 | NT | NT | NT |
| APG09773.0 | 499 | NT | NT | NT |
| APG09812.0 | 500 | NT | NT | NT |
| APG09814.0 | 501 | NT | NT | – |
| APG09826.1 | 503 | NT | NT | NT |
| APG09835.0 | 504 | NT | NT | – |
| APG09895.1 | 506 | NT | NT | NT |
| APG09901.1 | 508 | NT | NT | NT |
| APG09901.2 | 509 | NT | NT | NT |
| APG09903.1 | 511 | NT | NT | – |
| APG10001.2 | 514 | NT | NT | – |
| APG01902.1 | 516 | NT | NT | – |
| APG02996.1 | 518 | NT | NT | – |
| APG03098.1 | 520 | NT | NT | – |
| APG04517.0 | 521 | NT | NT | – |
| APG04619.1 | 523 | NT | NT | – |
| APG06717.1 | 525 | NT | NT | + |

NT: Not tested

Example 5. Transformation of Soybean

DNA constructs comprising each of SEQ ID NOs: 1-525 or active variants or fragments thereof operably linked to a promoter active in a plant are cloned into transformation vectors and introduced into *Agrobacterium* as described in U.S. Provisional Application No. 62/094,782, filed Dec. 19, 2015, herein incorporated by reference in its entirety.

Four days prior to inoculation, several loops of *Agrobacterium* are streaked to a fresh plate of YEP* medium supplemented with the appropriate antibiotics** (spectinomycin, chloramphenicol and kanamycin). Bacteria are grown for two days in the dark at 28° C. After two days, several loops of bacteria are transferred to 3 ml of YEP liquid medium with antibiotics in a 125 ml Erlenmeyer flask. Flasks are placed on a rotary shaker at 250 RPM at 28° C. overnight. One day before inoculation, 2-3 ml of the overnight culture were transferred to 125 ml of YEP with antibiotics in a 500 ml Erlenmeyer flask. Flasks are placed on a rotary shaker at 250 RPM at 28° C. overnight.

Prior to inoculation, the OD of the bacterial culture is checked at OD 620. An OD of 0.8-1.0 indicates that the culture is in log phase. The culture is centrifuged at 4000 RPM for 10 minutes in Oakridge tubes. The supernatant is discarded and the pellet is re-suspended in a volume of Soybean Infection Medium (SI) to achieve the desired OD. The cultures are held with periodic mixing until needed for inoculation.

Two or three days prior to inoculation, soybean seeds are surface sterilized using chlorine gas. In a fume hood, a petri dish with seeds is place in a bell jar with the lid off. 1.75 ml of 12 N HCl is slowly added to 100 ml of bleach in a 250 ml Erlenmeyer flask inside the bell jar. The lid is immediately placed on top of the bell jar. Seeds are allowed to sterilize for 14-16 hours (overnight). The top is removed from the bell jar and the lid of the petri dish is replaced. The petri dish with the surface sterilized is then opened in a laminar flow for around 30 minutes to disperse any remaining chlorine gas.

Seeds are imbibed with either sterile DI water or soybean infection medium (SI) for 1-2 days. Twenty to 30 seeds are covered with liquid in a 100×25 mm petri dish and incubated in the dark at 24° C. After imbibition, non-germinating seeds are discarded.

Cotyledonary explants are processed on a sterile paper plate with sterile filter paper dampened using SI medium employing the methods of U.S. Pat. No. 7,473,822, herein incorporated by reference.

Typically, 16-20 cotyledons are inoculated per treatment. The SI medium used for holding the explants is discarded and replaced with 25 ml of *Agrobacterium* culture (OD 620=0.8-20). After all explants are submerged, the inoculation is carried out for 30 minutes with periodic swirling of the dish. After 30 minutes, the *Agrobacterium* culture is removed.

Co-cultivation plates are prepared by overlaying one piece of sterile paper onto Soybean Co-cultivation Medium (SCC). Without blotting, the inoculated cotyledons are cultured adaxial side down on the filter paper. Around 20 explants can be cultured on each plate. The plates are sealed with Parafilm and cultured at 24° C. and around 120 μmoles m-2s-1 (in a Percival incubator) for 4-5 days.

After co-cultivation, the cotyledons are washed 3 times in 25 ml of Soybean Wash Medium with 200 mg/l of cefotaxime and timentin. The cotyledons are blotted on sterile filter paper and then transferred to Soybean Shoot Induction Medium (SSI). The nodal end of the explant is depressed slightly into the medium with distal end kept above the surface at about 45 deg. No more than 10 explants are cultured on each plate. The plates are wrapped with Micropore tape and cultured in the Percival at 24° C. and around 120 μmoles m-2s-1.

The explants are transferred to fresh SSI medium after 14 days. Emerging shoots from the shoot apex and cotyledonary node are discarded. Shoot induction is continued for another 14 days under the same conditions.

After 4 weeks of shoot induction, the cotyledon is separated from the nodal end and a parallel cut is made underneath the area of shoot induction (shoot pad). The area of the parallel cut is placed on Soybean Shoot Elongation Medium (SSE) and the explants cultured in the Percival at 24° C. and around 120 umoles m-2s-1. This step is repeated every two weeks for up to 8 weeks as long as shoots continue to elongate.

When shoots reach a length of 2-3 cm, they are transferred to Soybean Rooting Medium (SR) in a Plantcon vessel and incubated under the same conditions for 2 weeks or until roots reach a length of around 3-4 cm. After this, plants are transferred to soil.

Note, all media mentioned for soybean transformation are found in Paz et al. (2010) *Agrobacterium*-mediated transformation of soybean and recovery of transgenic soybean plants; Plant Transformation Facility of Iowa State University, which is herein incorporated by reference in its entirety. (See, agron-www.agron.iastate.edu/ptf/protocol/Soybean.pdf.)

Example 6. Transformation of Maize

Maize ears are best collected 8-12 days after pollination. Embryos are isolated from the ears, and those embryos 0.8-1.5 mm in size are preferred for use in transformation. Embryos are plated scutellum side-up on a suitable incubation media, such as DN62A5S media (3.98 g/L N6 Salts; 1 mL/L (of 1000.times. Stock) N6 Vitamins; 800 mg/L L-Asparagine; 100 mg/L Myo-inositol; 1.4 g/L L-Proline; 100 mg/L Casamino acids; 50 g/L sucrose; 1 mL/L (of 1 mg/mL Stock) 2,4-D). However, media and salts other than DN62A5S are suitable and are known in the art. Embryos are incubated overnight at 25° C. in the dark. However, it is not necessary per se to incubate the embryos overnight.

The resulting explants are transferred to mesh squares (30-40 per plate), transferred onto osmotic media for about 30-45 minutes, then transferred to a beaming plate (see, for example, PCT Publication No. WO/0138514 and U.S. Pat. No. 5,240,842). DNA constructs designed to express the GRG proteins of the present invention in plant cells are accelerated into plant tissue using an aerosol beam accelerator, using conditions essentially as described in PCT Publication No. WO/0138514. After beaming, embryos are incubated for about 30 min on osmotic media, and placed onto incubation media overnight at 25° C. in the dark. To avoid unduly damaging beamed explants, they are incubated for at least 24 hours prior to transfer to recovery media. Embryos are then spread onto recovery period media, for about 5 days, 25° C. in the dark, then transferred to a selection media. Explants are incubated in selection media for up to eight weeks, depending on the nature and characteristics of the particular selection utilized. After the selection period, the resulting callus is transferred to embryo maturation media, until the formation of mature somatic embryos is observed. The resulting mature somatic embryos are then placed under low light, and the process of regeneration is initiated by methods known in the art. The resulting shoots are allowed to root on rooting media, and the resulting plants are transferred to nursery pots and propagated as transgenic plants.

Example 7. Pesticidal Activity Against Nematodes

*Heterodera glycine's* (Soybean Cyst Nematode) in-vitro assay.

Soybean Cyst Nematodes are dispensed into a 96 well assay plate with a total volume of 100 uls and 100 J2 per well. The protein of interest as set forth in any one of SEQ ID NOs: 1-525 is dispensed into the wells and held at room temperature for assessment. Finally the 96 well plate containing the SCN J2 is analyzed for motility. Data is reported as % inhibition as compared to the controls. Hits are defined as greater or equal to 70% inhibition.

*Heterodera Glycine's* (Soybean Cyst Nematode) On-Plant Assay

Soybean plants expressing one or more of SEQ ID NOs: 1-525 are generated as described elsewhere herein. A 3-week-old soybean cutting is inoculated with 5000 SCN eggs per plant. This infection is held for 70 days and then harvested for counting of SCN cyst that has developed on the plant. Data is reported as % inhibition as compared to the controls. Hits are defined as greater or equal to 90% inhibition.

*Meloidogyne incognita* (Root-Knot Nematode) In-Vitro Assay

Root-Knot Nematodes are dispensed into a 96 well assay plate with a total volume of 100 μls and 100 J2 per well. The protein of interest comprising any one of SEQ ID NOs: 1-525 is dispensed into the wells and held at room temperature for assessment. Finally the 96 well plate containing the RKN J2 is analyzed for motility. Data is reported as % inhibition as compared to the controls. Hits are defined as greater or equal to 70% inhibition.

*Meloidogyne incognita* (Root-Knot Nematode) On-Plant Assay

Soybean plants expressing one or more of SEQ ID NOs: 1-525 are generated as described elsewhere herein. A 3-week-old soybean is inoculated with 5000 RKN eggs per plant. This infection is held for 70 days and then harvested for counting of RKN eggs that have developed in the plant. Data is reported as % inhibition as compared to the controls. Hits are defined as greater or equal to 90% inhibition.

Example 8. Additional Assays for Pesticidal Activity

The various polypeptides set forth in SEQ ID NOs: 1-525 can be tested to act as a pesticide upon a pest in a number of ways. One such method is to perform a feeding assay. In such a feeding assay, one exposes the pest to a sample containing either compounds to be tested or control samples. Often this is performed by placing the material to be tested, or a suitable dilution of such material, onto a material that the pest will ingest, such as an artificial diet. The material to be tested may be composed of a liquid, solid, or slurry. The material to be tested may be placed upon the surface and then allowed to dry. Alternatively, the material to be tested may be mixed with a molten artificial diet, and then dispensed into the assay chamber. The assay chamber may be, for example, a cup, a dish, or a well of a microtiter plate.

Assays for sucking pests (for example aphids) may involve separating the test material from the insect by a partition, ideally a portion that can be pierced by the sucking mouth parts of the sucking insect, to allow ingestion of the test material. Often the test material is mixed with a feeding stimulant, such as sucrose, to promote ingestion of the test compound.

Other types of assays can include microinjection of the test material into the mouth, or gut of the pest, as well as development of transgenic plants, followed by test of the ability of the pest to feed upon the transgenic plant. Plant testing may involve isolation of the plant parts normally consumed, for example, small cages attached to a leaf, or isolation of entire plants in cages containing insects.

Other methods and approaches to assay pests are known in the art, and can be found, for example in Robertson and Preisler, eds. (1992) Pesticide bioassays with arthropods, CRC, Boca Raton, Fla. Alternatively, assays are commonly described in the journals Arthropod Management Tests and Journal of Economic Entomology or by discussion with members of the Entomological Society of America (ESA). Any one of SEQ ID NOs: 1-525 can be expressed and employed in an assay as set forth in Examples 3 and 4, herein.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

That which is claimed is:

1. A polypeptide comprising:

(a) an amino acid sequence having at least 96% sequence identity to the amino acid sequence set forth in SEQ ID NO: 186 or 185, wherein the polypeptide has pesticidal activity, and wherein the polypeptide further comprises a chemically linked heterologous amino acid sequence; or (b) the amino acid sequence set forth in SEQ ID NO: 186 or 185, wherein the polypeptide further comprises a chemically linked heterologous amino acid sequence.

2. A recombinant nucleic acid molecule encoding a polypeptide comprising:

(a) an amino acid sequence having at least 96% sequence identity to the amino acid sequence set forth in SEQ ID NO: 186 or 185, wherein the polypeptide has pesticidal activity, and wherein the recombinant nucleic acid molecule is operably linked to a heterologous promoter; or (b) the amino acid sequence set forth in SEQ ID NO: 186 or 185, wherein the recombinant nucleic acid molecule is operably linked to a heterologous promoter.

3. The nucleic acid of claim 2, wherein said nucleic acid molecule is a synthetic sequence designed for expression in a plant.

4. A host cell comprising the nucleic acid molecule of claim 2.

5. A DNA construct comprising a heterologous promoter operably linked to a nucleotide sequence that encodes a polypeptide comprising:

(a) an amino acid sequence having at least 96% sequence identity to the amino acid sequence set forth in SEQ ID NO: 186 or 185, wherein the polypeptide has pesticidal activity; or (b) the amino acid sequence set forth in SEQ ID NO: 186 or 185.

6. The DNA construct of claim 5, wherein the promoter drives expression in a plant cell or a bacterial cell.

7. The DNA construct of claim 5, wherein said nucleotide sequence is a synthetic DNA sequence designed for expression in a plant.

8. A vector comprising the DNA construct of claim 5.

9. A host cell comprising the DNA construct of claim 5.

10. A formulation comprising the polypeptide of claim 1.

11. A method for controlling a pest population, the method comprising contacting said pest population with a pesticidal-effective amount of the formulation of claim 10.

12. A method for producing a polypeptide with pesticidal activity, the method comprising culturing the host cell of claim 9 under conditions in which the nucleic acid molecule encoding the polypeptide is expressed.

13. A plant having stably incorporated into its genome a DNA construct comprising the nucleic acid molecule of claim 2.

14. A transgenic seed of the plant of claim 13, wherein said seed has stably incorporated into its genome the DNA construct.

15. The plant of claim 13, wherein the plant is a monocot or a dicot.

16. The plant of claim 15, wherein (a) the monocot plant is corn, sorghum, wheat, rice, sugarcane, barley, oats, rye, millet, coconut, pineapple or banana; or (b) the dicot plant is sunflower, tomato, crucifers, peppers, potato, cotton, soybean, sugarbeet, tobacco, oilseed rape, sweet potato, alfalfa, safflower, peanuts, cassava, coffee, cocoa, cucumber, lettuce, olive, peas, or tea.

17. A method for protecting a plant from an insect pest, the method comprising expressing in a plant or cell thereof the nucleic acid molecule of claim 2.

18. The method of claim 17, wherein protecting said plant comprises controlling insect pest damage to said plant.

19. A method for increasing yield in a plant, the method comprising growing in a field a plant or seed thereof having stably incorporated into its genome a DNA construct comprising a promoter that drives expression in a plant operably linked to the nucleic acid molecule of claim 2.

* * * * *

SEQUENCE LISTING

```
Sequence total quantity: 525
SEQ ID NO: 1           moltype = AA  length = 1196
FEATURE                Location/Qualifiers
source                 1..1196
                       mol_type = protein
                       organism = Bacillus sp.
SEQUENCE: 1
MYSNNKNNND YEIIDSYASP YPPNRNNEYS KYPYRNNPNQ PIANTNYKDW LNMCQKNQIY  60
DGSPESFASA DTIAAVSAGI IVTGTMLGAF TSPLGAAIII SFGTLLPILW SPEETKREAI  120
WQAFTTIGNR PYDSVVDQNI VNLLYDTIKG LQGPIHEYDR LFNDWKATRK PNVAGELLRT  180
FTNVHLNLQG QLQGTLSGQY KLQMLPGYAQ VANWHLNLLQ QASVYYDEWV RDSRKPAEIY  240
SEEYINPSNE LQTCLNTCAS SNGTGNSTYY KCSLKCYIKE YTNYCIKTYN DGLNTLKNIP  300
NVTWNIFNTY RREITLTVLD LVALFPNYDS DNYPIGVQTE LTREIYTDAL ESPESKLNLT  360
DKEYYFTREP HLFSYLDALD LFTRESIIAR EAYFLFGVRN TISFLGPTNP SVSQYYMPKD  420
INVNELKLTG IFKFKKDVNS LYQTTKIILD IEINFINIYQ MIFYLNNSNT SFEFTPPGPA  480
PILLEKKTLQ IPSKLDPTGN SRPSHVLSYI KISQEPFFLG VLGTRGVQTC FAWVPAFIDL  540
SNTIHEKIIT SIPAVKAYQI SNNSFVVKGP GFTGGDLIVL QNSIDFELIF PRDYLISYDV  600
RVRYASSTGN LLIVLSGGRT PLSAIFQNTM NRQTPEDLNF TDFKYEDFQY VTFPGPFLSR  660
QPGTKQIISL LGLTTRPAEN LWIDKIEFIP RTPQYLEILE KEKIENLQQE INDIFIDSQK  720
QFIKSETTDY EIDHMATTIE TISEECYLQE KMVLLDKIKY AKQQSQSRNV LQNGDFQDLT  780
GWHTNNDITI QTGDPSFKEY ALHMPGARTT EMNDTIFRTS LYQKIEESKL KPYTRYIIRG  840
FVKNSKDLEI YIRRYHQEMH TIINIPDDTT YMNRNEQTKH TTNQNSVYPT IPSRQSISQY  900
SCDCESNTLP IICQDSPAFS FTIDVGNLDF HANPGMQLLF KISNPGGYAT MGNLEVIEER  960
SLTEEEINSI KHQEQKWNET KEKQQKETEH MYSQAQQAIQ SLFINNNMLQ LETNMLDIDR  1020
ANNLIDQIPD IYNTWFPQEP DFNYNRYTDL KQQISQAYTL YQHRNLIQNG DFKNGTTNWS  1080
TSPAATVQQI DNTSILLIPN WSTQVSQQIQ LQPNHRYILR VMAKKEGRGN GYVTISDCDK  1140
QIETLSFTES DSYTNQMEYV TKTIYLTPHT NQVRIDIGET EGTFKISSIE LICSHS      1196

SEQ ID NO: 2           moltype = AA  length = 691
FEATURE                Location/Qualifiers
REGION                 1..691
                       note = Description of Artificial Sequence: Synthetic
                        polypeptide
```

```
source                  1..691
                        mol_type = protein
                        organism = synthetic construct
SEQUENCE: 2
MYSNNKNNND YEIIDSYASP YPPNRNNEYS KYPYRNNPNQ PIANTNYKDW LNMCQKNQIY  60
DGSPESFASA DTIAAVSAGI IVTGTMLGAF TSPLGAAIII SFGTLLPILW SPEETKREAI  120
WQAFTTIGNR PYDSVVDQNI VNLLYDTIKG LQGPIHEYDR LFNDWKATRK PNVAGELLRT  180
FTNVHLNLQG QLQGTLSGQY KLQMLPGYAQ VANWHLNLLQ QASVYYDEWV RDSRKPAEIY  240
SEEYINPSNE LQTCLNTCAS SNGTGNSTYY KCSLKCYIKE YTNYCIKTYN DGLNTLKNIP  300
NVTWNIFNTY RREITLTVLD LVALFPNYDS DNYPIGVQTE LTREIYTDAL ESPESKLNLT  360
DKEYYFTREP HLFSYLDALD LFTRESIIAR EAYFLFGVRN TISFLGPTNP SVSQYYMPKD  420
INVNELKLTG IFKFKKDVNS LYQTTKIILD IEINFINIYQ MIFYLNNSNT SFEFTPPGPA  480
PILLEKKTLQ IPSKLDPTGN SRPSHVLSYI KISQEPFFLG VLGTRGVQTC FAWVPAFIDL  540
SNTIHEKIIT SIPAVKAYQI SNNSFVVKGP GFTGGDLIVL QNSIDFELIF PRDYLISYDV  600
RVRYASSTGN LLIVLSGGRT PLSAIFQNTM NRQTPEDLNF TDFKYEDFQY VTFPGPFLSR  660
QPGTKQIISL LGLTTRPAEN LWIDKIEFIP R                               691

SEQ ID NO: 3            moltype = AA  length = 223
FEATURE                 Location/Qualifiers
source                  1..223
                        mol_type = protein
                        organism = Bacillus sp.
SEQUENCE: 3
MSTSIYLFFS HKNKKKTCYM TKTKREIYLV KGGKTLIMEH NYSHQNRNVH ESQQIPTYPS  60
HLDVHHDTHP NEKNHTLPFS VILTLPKGFH IHKQMDPKLV YDVSYLSMTK EICKKSIEVD  120
NCGYVDVDLH VLKIKGCLSF LLNLCIEPIH TRKMCFTNHK DNFVFLSARD TLYVDHVLKY  180
SVDTLPYYVI DEDHIQVRNL EINMLDHSYE IAKISGEFYF EYE                  223

SEQ ID NO: 4            moltype = AA  length = 803
FEATURE                 Location/Qualifiers
source                  1..803
                        mol_type = protein
                        organism = Bacillus sp.
SEQUENCE: 4
MIGGQFMNQY YQNNEMEVLD VGVGRSRYPY AQNPGFELQS MNYKDWMNMC TSNESGELFN  60
SVRNGVIIAT AISSYVLSVS FPIASAAVGI ISVLLPLMWP EEAGDPGSTQ AQFTWDQLMR  120
AVEGIVNESI SNLVRDQAIK TLAKLQSSIK DYQQKVCNLK NSSPDDPSYE QYKAAVRRDF  180
NDAEDQAKLA IIDLKASGYE ILLLASYVEA ANLHLLLLRD VVQHGESWGF SALEVQQYYS  240
NTSSIGNPGM LQLLAIYTEY CVKWYNSGLQ KQWNTNNWNT FNDFRRDMTV MVLDVVSFWP  300
TYDPKYYPLP TKSQLTRTLY TSLIKGKAVP TSINDLENYL VAPPSLFRWL REIDFYLAKP  360
TTPEPKYLTG MKEFYQYTLS SNIEDSGLQG SSTSDVSSLT VPTPTSQDDI WSIIGTYDPF  420
SSAGGYIGGF KFRLTKSADQ DIIIAGDIGT KNYLGFPCKP SNLYACDPCD PNGSCTAGIT  480
DAANPCNTVD LYSHRCSHMG SYFGNYAIKS LCYASFGWTH VSADANNLLD TEKITQIPAV  540
KAYNIMAAYG VIKGSGSTGG DLVKLFNGSQ PGQMELNVTV PKGSEISYRV RIRYACDVTS  600
NVYVSAGGST AWFNANSTTT NMSNLTYNDF GYLETVLFRN VVPEYDRETT VQIYAQGYTT  660
GSFIVDKVEF IPTTESLTAY EAKQNLENAR KAVNALFTNE MKNSLQVDVT DYDVDQAANK  720
VDCLSDDMFL KEKMMLRDQV KHAKRLSQAR NLLNYGDFKS QNWSDENGWR VSNNVTVQSN  780
YPISKGRYLN MPEARSIDFS NKM                                        803

SEQ ID NO: 5            moltype = AA  length = 797
FEATURE                 Location/Qualifiers
REGION                  1..797
                        note = Description of Artificial Sequence: Synthetic
                         polypeptide
source                  1..797
                        mol_type = protein
                        organism = synthetic construct
SEQUENCE: 5
MNQYYQNNEM EVLDVGVGRS RYPYAQNPGF ELQSMNYKDW MNMCTSNESG ELFNSVRNGV  60
IIATAISSYV LSVSFPIASA AVGIISVLLP LMWPEEAGDP GSTQAQFTWD QLMRAVEGIV  120
NESISNLVRD QAIKTLAKLQ SSIKDYQQKV CNLKNSSPDD PSYEQYKAAV RRDFNDAEDQ  180
AKLAIIDLKA SGYEILLLAS YVEAANLHLL LLRDVVQHGE SWGFSALEVQ QYYSNTSSIG  240
NPGMLQLLAI YTEYCVKWYN SGLQKQWNTN NWNTFNDFRR DMTVMVLDVV SFWPTYDPKY  300
YPLPTKSQLT RTLYTSLIKG KAVPTSINDL ENYLVAPPSL FRWLREIDFY LAKPTTPEPK  360
YLTGMKEFYQ YTLSSNIEDS GLQGSSTSDV SSLTVPTPTS QDDIWSIIGT YDPFSSAGGY  420
IGGFKFRLTK SADQDIIIAG DIGTKNYLGF PCKPSNLYAC DPCDPNGSCT AGITDAANPC  480
NTVDLYSHRC SHMGSYFGNY AIKSLCYASF GWTHVSADAN NLLDTEKITQ IPAVKAYNIM  540
AAYGVIKGSG STGGDLVKLF NGSQPGQMEL NVTVPKGSEI SYRVRIRYAC DVTSNVYVSA  600
GGSTAWFNAN STTTNMSNLT YNDFGYLETV LFRNVVPEYD RETTVQIYAQ GYTTGSFIVD  660
KVEFIPTTES LTAYEAKQNL ENARKAVNAL FTNEMKNSLQ VDVTDYDVDQ AANKVDCLSD  720
DMFLKEKMML RDQVKHAKRL SQARNLLNYG DFKSQNWSDE NGWRVSNNVT VQSNYPISKG  780
RYLNMPEARS IDFSNKM                                               797

SEQ ID NO: 6            moltype = AA  length = 668
FEATURE                 Location/Qualifiers
REGION                  1..668
                        note = Description of Artificial Sequence: Synthetic
                         polypeptide
source                  1..668
```

```
                        mol_type = protein
                        organism = synthetic construct
SEQUENCE: 6
MNQYYQNNEM EVLDVGVGRS RYPYAQNPGF ELQSMNYKDW MNMCTSNESG ELFNSVRNGV  60
IIATAISSYV LSVSFPIASA AVGIISVLLP LMWPEEAGDP GSTQAQFTWD QLMRAVEGIV  120
NESISNLVRD QAIKTLAKLQ SSIKDYQQKV CNLKNSSPDD PSYEQYKAAV RRDFNDAEDQ  180
AKLAIIDLKA SGYEILLLAS YVEAANLHLL LLRDVVQHGE SWGFSALEVQ QYYSNTSSIG  240
NPGMLQLLAI YTEYCVKWYN SGLQKQWNTN NWNTFNDFRR DMTVMVLDVV SFWPTYDPKY  300
YPLPTKSQLT RTLYTSLIKG KAVPTSINDL ENYLVAPPSL FRWLREIDFY LAKPTTPEPK  360
YLTGMKEFYQ YTLSSNIEDS GLQGSSTSDV SSLTVPTPTS QDDIWSIIGT YDPFSSAGGY  420
IGGFKFRLTK SADQDIIIAG DIGTKNYLGF PCKPSNLYAC DPCDPNGSCT AGITDAANPC  480
NTVDLYSHRC SHMGSYFGNY AIKSLCYASF GWTHVSADAN NLLDTEKITQ IPAVKAYNIM  540
AAYGVIKGSG STGGDLVKLF NGSQPGQMEL NVTVPKGSEI SYRVRIRYAC DVTSNVYVSA  600
GGSTAWFNAN STTTNMSNLT YNDFGYLETV LFRNVVPEYD RETTVQIYAQ GYTTGSFIVD  660
KVEFIPTT                                                          668

SEQ ID NO: 7            moltype = AA  length = 670
FEATURE                 Location/Qualifiers
source                  1..670
                        mol_type = protein
                        organism = Bacillus sp.
SEQUENCE: 7
MNSYNNNEYE IIDSHASLYP PNRNNDHSRY PYTNNPNHPM QNTNYKDVFN VKPANYYACQ  60
LPPSMDWSKI ITTSLNIIGT LLGGVEGATG ASILTVNNIL PFYWPSNNST VWEDFIRQGN  120
TALPTQDITE AVKSIVIGKI NGLYDSFKAY QIALENWKYN KNEQNRDAVK FRFEYAVREI  180
SSALAGEISL TNYEVLLLPT YTQAALLHLI LLYEGISYEK EWNLARNAGD LYRQELDMAI  240
KTHINYCEKW YQNGLNTIRN SPGVTWYAYN TYRREYTISV LHIMSTFLTF DLKKYPINKE  300
RIIREITEKI YTTLPEVTNI YPINNIQEIE NSLIPPLDFV TWLRNLRLHT LIDTAASGAN  360
NQNVLSGLAN SYNYTLGNLI NGNTYGIATN VYKDIQLSSS IAIFSNLINS YSAAYNIQVP  420
YLGIKSMKFR TIDLNTKRVI SSNLEYDSNG KSQQVCELEN PLPLKTKNYP TEQDYNYTLS  480
FMTIPKFITH FNYSLIYAQT WTHKSVNPAN SVQSRDRLGN YLVTQIPAVK ANLKSTLYQP  540
NAPHNIQVIQ GPGHTGGPLV KFGNYNDYIK ITCKFVDNAS YYIRIRYASS NGGFLNITLN  600
NKIVDLQLYP TNFNPNTNTV KYENFSYVTT SNNYSVTANT YSELYLKFMG SSPIVIDQIE  660
FIPANIINNF                                                        670

SEQ ID NO: 8            moltype = AA  length = 664
FEATURE                 Location/Qualifiers
REGION                  1..664
                        note = Description of Artificial Sequence: Synthetic
                         polypeptide
source                  1..664
                        mol_type = protein
                        organism = synthetic construct
SEQUENCE: 8
MNSYNNNEYE IIDSHASLYP PNRNNDHSRY PYTNNPNHPM QNTNYKDVFN VKPANYYACQ  60
LPPSMDWSKI ITTSLNIIGT LLGGVEGATG ASILTVNNIL PFYWPSNNST VWEDFIRQGN  120
TALPTQDITE AVKSIVIGKI NGLYDSFKAY QIALENWKYN KNEQNRDAVK FRFEYAVREI  180
SSALAGEISL TNYEVLLLPT YTQAALLHLI LLYEGISYEK EWNLARNAGD LYRQELDMAI  240
KTHINYCEKW YQNGLNTIRN SPGVTWYAYN TYRREYTISV LHIMSTFLTF DLKKYPINKE  300
RIIREITEKI YTTLPEVTNI YPINNIQEIE NSLIPPLDFV TWLRNLRLHT LIDTAASGAN  360
NQNVLSGLAN SYNYTLGNLI NGNTYGIATN VYKDIQLSSS IAIFSNLINS YSAAYNIQVP  420
YLGIKSMKFR TIDLNTKRVI SSNLEYDSNG KSQQVCELEN PLPLKTKNYP TEQDYNYTLS  480
FMTIPKFITH FNYSLIYAQT WTHKSVNPAN SVQSRDRLGN YLVTQIPAVK ANLKSTLYQP  540
NAPHNIQVIQ GPGHTGGPLV KFGNYNDYIK ITCKFVDNAS YYIRIRYASS NGGFLNITLN  600
NKIVDLQLYP TNFNPNTNTV KYENFSYVTT SNNYSVTANT YSELYLKFMG SSPIVIDQIE  660
FIPA                                                              664

SEQ ID NO: 9            moltype = AA  length = 206
FEATURE                 Location/Qualifiers
source                  1..206
                        mol_type = protein
                        organism = Bacillus sp.
SEQUENCE: 9
MYLYKGGEPI SMENKHSHPN SDYPNHNEYE SESQPSLSYS HPSSHLHQHT LHPNDKNHIL  60
PFSVILNLPK GFHIQKQIHP KLVYDLSYLS MSKEICKKSI EVDNCGYVDV DLHVLKIKGC  120
LSFLLNVCME PIHKQKMCST DHKDDFIFLC AQDTLYVDHI LKYSIDTLPY YVIDEEHIHV  180
RKLEIEMLEP SHGIVKISGE FYFEYE                                      206

SEQ ID NO: 10           moltype = AA  length = 304
FEATURE                 Location/Qualifiers
source                  1..304
                        mol_type = protein
                        organism = Acinetobacter sp.
SEQUENCE: 10
VILYGFNKTY LNKWRKTMSV KHLDKLYLRS LLTDFWKKEL NTNKDPANGK WYEKGAQNDG  60
GLYGDVSDAD DVEIIFHQDQ AKLEKNQVTI IHSDFDNSKS NIGTEFSTEL SDTCTLAKTH  120
TTTKSHTIKF GLGYEVKAKA GIVFVDVSET IKVNFEYQYA TSKTESTTES SSQTIKQTIK  180
CIVPAGKIYR ASLVCTKQRL LIPFTALIAF KGTTGTWFES RVDNHYHWIS SIGHAFQQIN  240
AKKLAGNDSE RFTVRGIEDK GMMDNSQQFD FKIIISDITD LVNLGNVEKL IEKEENFVEL  300
```

```
VELA                                                          304

SEQ ID NO: 11          moltype = AA  length = 287
FEATURE                Location/Qualifiers
REGION                 1..287
                       note = Description of Artificial Sequence: Synthetic
                        polypeptide
source                 1..287
                       mol_type = protein
                       organism = synthetic construct
SEQUENCE: 11
MSVKHLDKLY LRSLLTDFWK KELNTNKDPA NGKWYEKGAQ NDGGLYGDVS DADDVEIIFH  60
QDQAKLEKNQ VTIIHSDFDN SKSNIGTEFS TELSDTCTLA KTHTTTKSHT IKFGLGYEVK  120
AKAGIVFVDV SETIKVNFEY QYATSKTEST TESSSQTIKQ TIKCIVPAGK IYRASLVCTK  180
QRLLIPFTAL IAFKGTTGTW FESRVDNHYH WISSIGHAFQ QINAKKLAGN DSERFTVRGI  240
EDKGMMDNSQ QFDFKIIISD ITDLVNLGNV EKLIEKEENF VELVELA               287

SEQ ID NO: 12          moltype = AA  length = 346
FEATURE                Location/Qualifiers
REGION                 1..346
                       note = Description of Unknown: Organism from environmental
                        sample
source                 1..346
                       mol_type = protein
                       organism = unidentified
SEQUENCE: 12
MLQCNIKKPK QGRLLKMKQY KKLAMAIPLT GMLCGGGMPT DTNKSFAASF EQQQNYKGYD  60
NIQDPYRVDL SSRILGALSA RDHEEYGISD VDKFNAKWDW QFQYVDGQIN TNATVDSYTD  120
SGEIELLNYR NATNVNQNHQ TVEKTVKTTE NFTYSNAVGA KLGLEVEANV GVEVPFVAKG  180
GLTVTAKTEF SYNHTSSNAV TKETMYKFPS QTIVCQAGYI TRYVGKVQRA NFSGTFSGKA  240
VATGNLEIYV INSKGERVFK TISIYDIYKY TKDDMPLHNG VELDDQKKRA IIPWDIESSY  300
TGQGGHNATV NVTVTPINNQ GAARTMPLRN YLEKVNDGTL DEFMKK                346

SEQ ID NO: 13          moltype = AA  length = 330
FEATURE                Location/Qualifiers
REGION                 1..330
                       note = Description of Artificial Sequence: Synthetic
                        polypeptide
source                 1..330
                       mol_type = protein
                       organism = synthetic construct
SEQUENCE: 13
MKQYKKLAMA IPLTGMLCGG GMPTDTNKSF AASFEQQQNY KGYDNIQDPY RVDLSSRILG  60
ALSARDHEEY GISDVDKFNA KWDWQFQYVD GQINTNATVD SYTDSGEIEL LNYRNATNVN  120
QNHQTVEKTV KTTENFTYSN AVGAKLGLEV EANVGVEVPF VAKGGLTVTA KTEFSYNHTS  180
SNAVTKETMY KFPSQTIVCQ AGYITRYVGK VQRANFSGTF SGKAVATGNL EIYVINSKGE  240
RVFKTISIYD IYKYTKDDMP LHNGVELDDQ KKRAIIPWDI ESSYTGQGGH NATVNVTVTP  300
INNQGAARTM PLRNYLEKVN DGTLDEFMKK                                  330

SEQ ID NO: 14          moltype = AA  length = 648
FEATURE                Location/Qualifiers
source                 1..648
                       mol_type = protein
                       organism = Bacillus sp.
SEQUENCE: 14
LTNDLETDLH NMNYKDFLRM SEEHNAGFIA NPEVFASTQD SIKIGMNIVG KTLGFLGVPF  60
IRSIIKFYTV MIDLLWPSSG GKNSWEMFME RMEELINQKI TEYARKKALA ELEGLGANFA  120
LYLVALEEWQ ENPNSSRITR DVRTRFEILD SLFTQFIPSF KVSDYEVPLL TIYAHAANLH  180
LLLLKDASIF GEEWGLSTTT INNYYKRQIN LTAQYSDHCV KWYNTGLDRL KGSNAESWLK  240
YHHFRREMTL MVLDIVALYP NYDTRLYPIQ TAAQLTREVY SDPLGYNPTD PENSGFGIPW  300
TRLGFHNFAQ IENDVIRPPH LFSILKSVEI GTIKGTLALN NKEYINYWNG HSLKYIYTNN  360
LENYESKHGN PNTSEKNQFD LMDRDIYKID STAACLANHY TYLYGGVKAD FLMVKRDSST  420
TTAYSYSKTH TALPSRIQNY DSENELPQET TDQPNYQAYN HRLSHITSYS FKNIGNSNGQ  480
FGNLPVFVWT HRSANFDNFI FLDKITQLPL TKSYEIADNV TIVNSDYVGG SLLKVNRSML  540
KNNMVNSIRF SLPESKRYIA RVRYASTGDG YMGMTGISSD TYFNATIKEE SDLKYDSFRY  600
LTLGTISASL NSSYSLYLPT PHGEKYTIYI DTIELIPVDE TYEVEKNF              648

SEQ ID NO: 15          moltype = AA  length = 648
FEATURE                Location/Qualifiers
REGION                 1..648
                       note = Description of Artificial Sequence: Synthetic
                        polypeptide
source                 1..648
                       mol_type = protein
                       organism = synthetic construct
SEQUENCE: 15
MTNDLETDLH NMNYKDFLRM SEEHNAGFIA NPEVFASTQD SIKIGMNIVG KTLGFLGVPF  60
IRSIIKFYTV MIDLLWPSSG GKNSWEMFME RMEELINQKI TEYARKKALA ELEGLGANFA  120
LYLVALEEWQ ENPNSSRITR DVRTRFEILD SLFTQFIPSF KVSDYEVPLL TIYAHAANLH  180
```

```
LLLLKDASIF GEEWGLSTTT INNYYKRQIN LTAQYSDHCV KWYNTGLDRL KGSNAESWLK  240
YHHFRREMTL MVLDIVALYP NYDTRLYPIQ TAAQLTREVY SDPLGYNPTD PENSGFGIPW  300
TRLGFHNFAQ IENDVIRPPH LFSILKSVEI GTIKGTLALN NKEYINYWNG HSLKYIYTNN  360
LENYESKHGN PNTSEKNQFD LMDRDIYKID STAACLANHY TYLYGGVKAD FLMVKRDSST  420
TTAYSYSKTH TALPSRIQNY DSENELPQET TDQPNYQAYN HRLSHITSYS FKNIGNSNGQ  480
FGNLPVFVWT HRSANFDNFI FLDKITQLPL TKSYEIADNV TIVNSDYVGG SLLKVNRSML  540
KNNMVNSIRF SLPESKRYIA RVRYASTGDG YMGMTGISSD TYFNATIKEE SDLKYDSFRY  600
LTLGTISASL NSSYSLYLPT PHGEKYTIYI DTIELIPVDE TYEVEKNF              648

SEQ ID NO: 16          moltype = AA  length = 363
FEATURE                Location/Qualifiers
source                 1..363
                       mol_type = protein
                       organism = Bacillus sp.
SEQUENCE: 16
MGGRMIMAIE ITDVISLFGE YAQMWSNQQG GGHSRISLVL PGYESYALSR SKAETKYYPP  60
TNQTETAVAI SSNTYTNTGK HPKEICLTLE GETDNWAKFV ASVGASEGGK RLLDIDMPTD  120
VPAFLVNQSA ISLPLGDDTL TISERQTWAV NHPFTIRPRF KVKATLMVKK RNWKRCFDIK  180
HTLSGYIGVI TSQPINGKFM SLHHVARILE RYDSPYFEVN GEKVTIFANG MLTASYALEP  240
YIHIVAESLD IPGLVEEYDI YNPQTDQNVI PFEPSQPIIA GSVSQEEVVT MGSSNETVMS  300
APSNYSVPTY QTVPMSSSNE TAMTTGSEIC SRESTRKERC GCLSCMAASS NYPTQSDNMY  360
TDF                                                               363

SEQ ID NO: 17          moltype = AA  length = 359
FEATURE                Location/Qualifiers
REGION                 1..359
                       note = Description of Artificial Sequence: Synthetic
                        polypeptide
source                 1..359
                       mol_type = protein
                       organism = synthetic construct
SEQUENCE: 17
MIMAIEITDV ISLFGEYAQM WSNQQGGGHS RISLVLPGYE SYALSRSKAE TKYYPPTNQT  60
ETAVAISSNT YTNTGKHPKE ICLTLEGETD NWAKFVASVG ASEGGKRLLD IDMPTDVPAF  120
LVNQSAISLP LGDDTLTISE RQTWAVNHPF TIRPRFKVKA TLMVKKRNWK RCFDIKHTLS  180
GYIGVITSQP INGKFMSLHH VARILERYDS PYFEVNGEKV TIFANGMLTA SYALEPYIHI  240
VAESLDIPGL VEEYDIYNPQ TDQNVIPFEP SQPIIAGSVS QEEVVTMGSS NETVMSAPSN  300
YSVPTYQTVP MSSSNETAMT TGSEICSRES TRKERCGCLS CMAASSNYPT QSDNMYTDF   359

SEQ ID NO: 18          moltype = AA  length = 357
FEATURE                Location/Qualifiers
REGION                 1..357
                       note = Description of Artificial Sequence: Synthetic
                        polypeptide
source                 1..357
                       mol_type = protein
                       organism = synthetic construct
SEQUENCE: 18
MAIEITDVIS LFGEYAQMWS NQQGGGHSRI SLVLPGYESY ALSRSKAETK YYPPTNQTET  60
AVAISSNTYT NTGKHPKEIC LTLEGETDNW AKFVASVGAS EGGKRLLDID MPTDVPAFLV  120
NQSAISLPLG DDTLTISERQ TWAVNHPFTI RPRFKVKATL MVKKRNWKRC FDIKHTLSGY  180
IGVITSQPIN GKFMSLHHVA RILERYDSPY FEVNGEKVTI FANGMLTASY ALEPYIHIVA  240
ESLDIPGLVE EYDIYNPQTD QNVIPFEPSQ PIIAGSVSQE EVVTMGSSNE TVMSAPSNYS  300
VPTYQTVPMS SSNETAMTTG SEICSRESTR KERCGCLSCM AASSNYPTQS DNMYTDF     357

SEQ ID NO: 19          moltype = AA  length = 312
FEATURE                Location/Qualifiers
source                 1..312
                       mol_type = protein
                       organism = Bacillus sp.
SEQUENCE: 19
MKFKTLATTG LALTLGLACV GTTTTPAHAA TTSVANPDIE NHKDLYSSHD MLKFVPFSTT  60
GYKITSQSKD LKSIDFAIND NSGNPDSSAR KSPIKSYSRT DSLTLNASTE FSVGTEISAS  120
AKLPGIADVT EKMTAGFKIS TGISHTSSET KTLTYGGDEI LAKPHEIVRV DYYLEQLNTS  180
GTMNTGTRIT DIGDNLQIQI NTDDGEGYFD VYNPGHATGE DVYKSFKRME EINKKHPIST  240
AQKKNGEFWL QIPKGHLSDF FFIDDVAKTV STAGAQAGFD GISGTGLTIK TSVIDPTTNK  300
IKSVKTKTMK LQ                                                     312

SEQ ID NO: 20          moltype = AA  length = 284
FEATURE                Location/Qualifiers
REGION                 1..284
                       note = Description of Artificial Sequence: Synthetic
                        polypeptide
source                 1..284
                       mol_type = protein
                       organism = synthetic construct
SEQUENCE: 20
MATTSVANPD IENHKDLYSS HDMLKFVPFS TTGYKITSQS KDLKSIDFAI NDNSGNPDSS  60
ARKSPIKSYS RTDSLTLNAS TEFSVGTEIS ASAKLPGIAD VTEKMTAGFK ISTGISHTSS  120
```

```
ETKTLTYGGD EILAKPHEIV RVDYYLEQLN TSGTMNTGTR ITDIGDNLQI QINTDDGEGY  180
FDVYNPGHAT GEDVYKSFKR MEEINKKHPI STAQKKNGEF WLQIPKGHLS DFFFIDDVAK  240
TVSTAGAQAG FDGISGTGLT IKTSVIDPTT NKIKSVKTKT MKLQ                  284

SEQ ID NO: 21          moltype = AA  length = 407
FEATURE                Location/Qualifiers
source                 1..407
                       mol_type = protein
                       organism = Bacillus sp.
SEQUENCE: 21
MKFLSKKAMT GLMVGAMSLS IWAPASEAAT LENNRYYSIH LKDNPNKIWD VSRASLDNDR  60
AILLWDPSTV GDNEQFVFFP LDNGKYAIVN KNSGKTVTIG SGWINDGADQ TLNNEGLKQQ  120
SWTGSDAEQW YLRGQGGNAY EIVNQGYQKV ASYAWANAVG GLEYVDLDEA NPSDSDRVFL  180
ISNNPFGWEK DPFEGMPPQF KTEYGTFSLP QLPAVGTRPN APDYNTGAGP NQQLPQTSNS  240
VVVGASLIPC IMVKDSQVSD YTKIHNSPYY TLVKEEYWDK AGSTTLTPGA SQSIAFKTGM  300
SSTDQQKMTE TLSMKIGADF GLKYGNQTAA LKAEITKTIQ TETSTSTSEI TEDTVTNTFT  360
GEVGKTSDYT LYQLATKYTL KRADGSTVSG SWTVKNNKVT VLRKNSY                407

SEQ ID NO: 22          moltype = AA  length = 380
FEATURE                Location/Qualifiers
REGION                 1..380
                       note = Description of Artificial Sequence: Synthetic
                        polypeptide
source                 1..380
                       mol_type = protein
                       organism = synthetic construct
SEQUENCE: 22
MATLENNRYY SIHLKDNPNK IWDVSRASLD NDRAILLWDP STVGDNEQFV FFPLDNGKYA  60
IVNKNSGKTV TIGSGWINDG ADQTLNNEGL KQQSWTGSDA EQWYLRGQGG NAYEIVNQGY  120
QKVASYAWAN AVGGLEYVDL DEANPSDSDR VFLISNNPFG WEKDPFEGMP PQFKTEYGTF  180
SLPQLPAVGT RPNAPDYNTG AGPNQQLPQT SNSVVVGASL IPCIMVKDSQ VSDYTKIHNS  240
PYYTLVKEEY WDKAGSTTLT PGASQSIAFK TGMSSTDQQK MTETLSMKIG ADFGLKYGNQ  300
TAALKAEITK TIQTETSTST SEITEDTVTN TFTGEVGKTS DYTLYQLATK YTLKRADGST  360
VSGSWTVKNN KVTVLRKNSY                                              380

SEQ ID NO: 23          moltype = AA  length = 1284
FEATURE                Location/Qualifiers
source                 1..1284
                       mol_type = protein
                       organism = Bacillus sp.
SEQUENCE: 23
MDQDSMLPSA FSSPTMSIPY NVLSSSAYNT LSYNNLMTFQ DIIELFKRIY AATGDIPAGS  60
IKQVWDGAQK DNWLDIIHGV LGLGAFAIPE LAPAVPIITR LIDFIYPKLF GATEPNPPSV  120
WDQISTKVQN LVDQQINANE KATLLAKFSG LNNIVENFRN AVNVATCNGR EPGFLNDSTD  180
TTNETSCGSA YATNSDDCTP YGNTIENEAV RATFIATNTF FIGVLPEFNK ATAASSTGDA  240
RVNYINLSLP LFTTAASLHL LLIQSAVDSG LKWGFSQAQV NDYHVDLRTR IKEYTAIIRN  300
TFNEGLALTQ GNYNRQQIYI ANITTECFDV AALWPTYDRF DYVNPGQTKI EQTRVLYSGL  360
ISSVLPGFNA GDQIPDDSVR HYIGELTKVD FSIWSTTLEK FFNGMQNTLT TPSGTSTVYP  420
YGSYPYINSG NTTYSGGVSI TRENPATGVA IWNARYNAIR TSQADFYFAD GTTKSIGSLV  480
TDIPPNPPYY GGAVVALFNN KLEFVYPFNH GDPLQGFSAG FVFANLFPEN IVGTIDPDSN  540
TPVITGIPAE KSSSSTGFDK VIERINGASA MRSVLSPSGS SASYRINIVT AGPYKIRARL  600
SSPTDSATLA LFKDGSQLAR ILLPNTTNTA NAQKGLQGDY GVYMLVDIVS TIALQSGISN  660
FEVRVNGANV CIDRIEFIPL NAEESNYPPQ FNEDFNLLSD QFKTLWRGET IHTVNAIDGY  720
LNTPQAIPIV VVHGITIQFW NDTNHLTQYD KSARSNPNGV AHYPYITPFH FDGFSIPEGF  780
TEIRIQQIEQ APSVGHISGS VGIGTRTTFL TPADLEEVTN VVQGLFISPG ANALAPSVTD  840
YIIDQAFLKV QALSDELFAT EKAQLRQQVN AAKRLSQSNN LIVGSTFENT SNWALGQDAR  900
VVAGDDVFPG GYLVLQPSMY PIARPSYAYQ KVAESKLKAN TRYIVTGFIR SAHDLEIRVS  960
RYGGEIQDEI EIPYTDALPL TPGSLPNCCL PPVCPPCEKE PIDSHIFAYR IDVGALQPEA  1020
NLGIELAFKL LSPDGLAQLS NIEIKEERPL TDGEIRKVQQ REKTWKQIYA QQQQTVNQQI  1080
QQVHTQLAAL YIGPQQTQLK PNVQYEDIKS IRIPDIPAVY NCYIPQIPGQ NNNVFAALVA  1140
AKTTALSLYP QNYIKNGYFE QGLQDWQVEG TVTVQPTDYE QWMLQLTSWD SLASQILLLP  1200
PSEQDIEYRL RVTAKGVGSI QVKDGEEHEQ ITFTNRQEGW QTKELTFFAD KDTNIKQIII  1260
QENGAEFFVK TIEVFVPPVP LTGA                                         1284

SEQ ID NO: 24          moltype = AA  length = 680
FEATURE                Location/Qualifiers
REGION                 1..680
                       note = Description of Artificial Sequence: Synthetic
                        polypeptide
source                 1..680
                       mol_type = protein
                       organism = synthetic construct
SEQUENCE: 24
MDQDSMLPSA FSSPTMSIPY NVLSSSAYNT LSYNNLMTFQ DIIELFKRIY AATGDIPAGS  60
IKQVWDGAQK DNWLDIIHGV LGLGAFAIPE LAPAVPIITR LIDFIYPKLF GATEPNPPSV  120
WDQISTKVQN LVDQQINANE KATLLAKFSG LNNIVENFRN AVNVATCNGR EPGFLNDSTD  180
TTNETSCGSA YATNSDDCTP YGNTIENEAV RATFIATNTF FIGVLPEFNK ATAASSTGDA  240
RVNYINLSLP LFTTAASLHL LLIQSAVDSG LKWGFSQAQV NDYHVDLRTR IKEYTAIIRN  300
TFNEGLALTQ GNYNRQQIYI ANITTECFDV AALWPTYDRF DYVNPGQTKI EQTRVLYSGL  360
```

```
ISSVLPGFNA GDQIPDDSVR HYIGELTKVD FSIWSTTLEK FFNGMQNTLT TPSGTSTVYP  420
YGSYPYINSG NTTYSGGVSI TRENPATGVA IWNARYNAIR TSQADFYFAD GTTKSIGSLV  480
TDIPPNPPYY GGAVVALFNN KLEFVYPFNH GDPLQGFSAG FVFANLFPEN IVGTIDPDSN  540
TPVITGIPAE KSSSSTGFDK VIERINGASA MRSVLSPSGS SASYRINIVT AGPYKIRARL  600
SSPTDSATLA LFKDGSQLAR ILLPNTTNTA NAQKGLQGDY GVYMLVDIVS TIALQSGISN  660
FEVRVNGANV CIDRIEFIPL                                              680

SEQ ID NO: 25           moltype = AA  length = 866
FEATURE                 Location/Qualifiers
source                  1..866
                        mol_type = protein
                        organism = Bacillus sp.
SEQUENCE: 25
MNLLQTLQAQ PIIPYNVLAN PSIGNADAQP GSLGDLIASL KEAWVEFQKT GSDKLLQTVF  60
QNGFSAASGG SFNYLAVLQA VIGVLGTVLG AEIPGVAVAA PILSMVIGWI WPSKKKDETQ  120
QLIDLIDAEI QKQLNKALSE QDKNTWTGYL NAIFQISQDA ARAVVDAQFT GNDGDTNRQP  180
RQPGTSDYEN VYNHLLATTG SLIVALSQMI NGNFDTLAIP YFVIGATVQL STYQSFIQFA  240
NKWLPIVYPD YQTVGTPGYT QHQNLVNAKT DMRIAIQANT QKVFNAFKAG MPSLGSNKYS  300
INDYNVYVRG MVLNGLDTLA TWPSMYPDDY PSQTDLEQTR VIFSDMVGQD QTSDGNVTIK  360
NILDGNSLTQ HGSIDLNSIS YFPGDISGGT LGTYVSSSRC YTFGIELDYL NNNGGTNIFQ  420
YSDAAGIKDF CYSVFGPLPT WVNAQNQNTR YVNAASLVVE NITSYGCNGN YNSNSCYMPG  480
AQSSCSPCPP GRTCTNGSSW TTSCNGPLPG QKINVLYPFT QPQHNKDQEG FLGLLASHVP  540
YDLSPQNVFG TVDSDTGNII GKGFPAEKGY WSNGGDRPIP NSNRAREWVN GANAVKVEYG  600
AFLAMKATNM TAGTYHVRVR YANPSNQPMS MWQEIWVGNQ KLQGGAWTFP STSDDNVANN  660
FPHQVYVTGQ QGNYVIQDIT WPNGGNAGDP LTLPSGEIMI KLSGQNAGDS IYVDRIEFIP  720
VPAPISTGAN LDYTINSRLP NWSVNNNPPM SAFPTIWVAS SGTAGTNATI SVENLTLNID  780
TDAPPVISLL AKTGLGDESD QSNWQWMCDT SGTTSLYDGL TYTFNPTNSD SCFNKPFTAI  840
KLVGNTSNHR VVVGGHLSGT VSIQNS                                       866

SEQ ID NO: 26           moltype = AA  length = 721
FEATURE                 Location/Qualifiers
REGION                  1..721
                        note = Description of Artificial Sequence: Synthetic
                         polypeptide
source                  1..721
                        mol_type = protein
                        organism = synthetic construct
SEQUENCE: 26
MNLLQTLQAQ PIIPYNVLAN PSIGNADAQP GSLGDLIASL KEAWVEFQKT GSDKLLQTVF  60
QNGFSAASGG SFNYLAVLQA VIGVLGTVLG AEIPGVAVAA PILSMVIGWI WPSKKKDETQ  120
QLIDLIDAEI QKQLNKALSE QDKNTWTGYL NAIFQISQDA ARAVVDAQFT GNDGDTNRQP  180
RQPGTSDYEN VYNHLLATTG SLIVALSQMI NGNFDTLAIP YFVIGATVQL STYQSFIQFA  240
NKWLPIVYPD YQTVGTPGYT QHQNLVNAKT DMRIAIQANT QKVFNAFKAG MPSLGSNKYS  300
INDYNVYVRG MVLNGLDTLA TWPSMYPDDY PSQTDLEQTR VIFSDMVGQD QTSDGNVTIK  360
NILDGNSLTQ HGSIDLNSIS YFPGDISGGT LGTYVSSSRC YTFGIELDYL NNNGGTNIFQ  420
YSDAAGIKDF CYSVFGPLPT WVNAQNQNTR YVNAASLVVE NITSYGCNGN YNSNSCYMPG  480
AQSSCSPCPP GRTCTNGSSW TTSCNGPLPG QKINVLYPFT QPQHNKDQEG FLGLLASHVP  540
YDLSPQNVFG TVDSDTGNII GKGFPAEKGY WSNGGDRPIP NSNRAREWVN GANAVKVEYG  600
AFLAMKATNM TAGTYHVRVR YANPSNQPMS MWQEIWVGNQ KLQGGAWTFP STSDDNVANN  660
FPHQVYVTGQ QGNYVIQDIT WPNGGNAGDP LTLPSGEIMI KLSGQNAGDS IYVDRIEFIP  720
V                                                                  721

SEQ ID NO: 27           moltype = AA  length = 532
FEATURE                 Location/Qualifiers
source                  1..532
                        mol_type = protein
                        organism = Bacillus sp.
SEQUENCE: 27
MAVNTNQISS AVTTSNDVAQ TRTMVQGLFS ADNPTQLAPG VTDYWIDYVH QQVQSLPNTF  60
AVEKRELSTR VNQAKRLSKS KNVLMSSSFQ GSGWQLGRKV FISPGDLQYA GRQLVLPPSS  120
LVYPSYAYQT VPESALKPYT RYYLSVFVLQ ADSLHIVASR YGNEVSQVVN VGYSTSMPTS  180
ADGVLNSPHF FQYPIDVGAV HSDANLGITV SFTVPTNGFA KISQVSLTEG RPLTAAEARR  240
VQNQDEQWLQ PYLAQQAQMQ ASLQSATNQL NAIYGSTSWS GTIGPNVTYT DLANLTLLQP  300
TPSQPGSLTN LPIQDPYAGQ KATISQAAQR AWMQLQARNI VQNGLFLQRG QNWITEGTVS  360
FPQGDNNKSV LTLSDWDATV SQMISLPVHT GYTEYRVRVR AKGQGTISIV PPGDAKRMLF  420
FNQPAFTTQE FYFYPDASTA QVNLIIQSEG VEFTVDWVEI QEMKFTEEPL SANEQNAAHT  480
VGMTKPVGHP ETFMMASNPS MGSQMTNSSS NSYNCQCGQS SDNSNSGCNC SH          532

SEQ ID NO: 28           moltype = AA  length = 297
FEATURE                 Location/Qualifiers
source                  1..297
                        mol_type = protein
                        organism = Bacillus sp.
SEQUENCE: 28
MAIVDLDAYL TALAKKVFPI PQMIKGVITS ELSIKNAESY GFEIKNSKPQ GTMFMGESVL  60
KNDTNETQLI HSDSFTKTIT DSVTLSVTNG ITTGVNISIG GKVFGMGVDT SMSFEVSTST  120
TREQTSTEGV AYTVPSQTVS VPARKTYYVY TALQRSQLEG SIRLRADLSG DFHVKLELAG  180
GMEGTINLGN IYEYIKTNQL LHPLPSGISL NHNNKSVHFE GIAELIYGTG TKFNVTITDK  240
PSSQGTQEHT TIDDKTGLGT YEIQLDGKKL GFDLNDLKDK TEPEVFEKLK ELQNEIV     297
```

```
SEQ ID NO: 29          moltype = AA  length = 351
FEATURE                Location/Qualifiers
REGION                 1..351
                       note = Description of Unknown: Organism from environmental
                        sample
source                 1..351
                       mol_type = protein
                       organism = unidentified
SEQUENCE: 29
LVVSGLKAND RLVWDIYGEK RDDAFPVLLY QSRQSDNQLF LFFELDNGKY AIVNYNSGKC  60
IYFGNTLYGP NILAGQTKWT GADSQQWYLR SVDPSHNQYE IVNQGLGKVA SYGKVGEPTA  120
PPVVDPDDSK PSDPDRVFGI NPTTRYPITL PTLPAVGTRP AVPDYFSSPY DNMPATSASQ  180
IVGASLIPCI MVNDSQQEDY TKIQNSPYYK LIKEEYWEQT YSLVLAPSQK RSYSYVTGTS  240
SVDQTRMTNT LNIEIGADFG LKFNNVTSNI SGKITKTIQT EVSSTNQQSV SETKSDEISN  300
GTSNYTIGFT QYQLVTKYTL YRMDGTAVSN PFISKNDKIA VTRSRSQLAT G           351

SEQ ID NO: 30          moltype = AA  length = 351
FEATURE                Location/Qualifiers
REGION                 1..351
                       note = Description of Artificial Sequence: Synthetic
                        polypeptide
source                 1..351
                       mol_type = protein
                       organism = synthetic construct
SEQUENCE: 30
MVVSGLKAND RLVWDIYGEK RDDAFPVLLY QSRQSDNQLF LFFELDNGKY AIVNYNSGKC  60
IYFGNTLYGP NILAGQTKWT GADSQQWYLR SVDPSHNQYE IVNQGLGKVA SYGKVGEPTA  120
PPVVDPDDSK PSDPDRVFGI NPTTRYPITL PTLPAVGTRP AVPDYFSSPY DNMPATSASQ  180
IVGASLIPCI MVNDSQQEDY TKIQNSPYYK LIKEEYWEQT YSLVLAPSQK RSYSYVTGTS  240
SVDQTRMTNT LNIEIGADFG LKFNNVTSNI SGKITKTIQT EVSSTNQQSV SETKSDEISN  300
GTSNYTIGFT QYQLVTKYTL YRMDGTAVSN PFISKNDKIA VTRSRSQLAT G           351

SEQ ID NO: 31          moltype = AA  length = 336
FEATURE                Location/Qualifiers
source                 1..336
                       mol_type = protein
                       organism = Bacillus sp.
SEQUENCE: 31
MKRYKKILVI APLACMLSIG VLNSQNTAHA ASAGSSAQMS KLREGETFNF AQLQADIQDR  60
ALAAAIHLNK DPNNTVKSVN IGGDLDASKM HYGSISIDNT VNVDAHVDSY KDLGQTNLVT  120
INNNDGTVAQ QANTPETTIK QTETSSYSNT EGIKLGASAT LKLDVKVPFV ADGGASVTTS  180
TEFNYAHGDT QTSTKETDIT FKSQPVVAAP GGTTTYYGST KTANFSGMFH GSKAPIEQLD  240
LSYSEAGTGS GGNAPNISGE RLYAIFKYGD KPVPDYLTLD DTNKRVLINH DTDFKVTGQG  300
GFYTDITVKF VPKDHNKTPQ TMPYAEYAEK LRSKTL                           336

SEQ ID NO: 32          moltype = AA  length = 307
FEATURE                Location/Qualifiers
REGION                 1..307
                       note = Description of Artificial Sequence: Synthetic
                        polypeptide
source                 1..307
                       mol_type = protein
                       organism = synthetic construct
SEQUENCE: 32
MASAGSSAQM SKLREGETFN FAQLQADIQD RALAAAIHLN KDPNNTVKSV NIGGDLDASK  60
MHYGSISIDN TVNVDAHVDS YKDLGQTNLV TINNNDGTVA QQANTPETTI KQTETSSYSN  120
TEGIKLGASA TLKLDVKVPF VADGGASVTT STEFNYAHGD TQTSTKETDI TFKSQPVVAA  180
PGGTTTYYGS TKTANFSGMF HGSKAPIEQL DLSYSEAGTG SGGNAPNISG ERLYAIFKYG  240
DKPVPDYLTL DDTNKRVLIN HDTDFKVTGQ GGFYTDITVK FVPKDHNKTP QTMPYAEYAE  300
KLRSKTL                                                           307

SEQ ID NO: 33          moltype = AA  length = 610
FEATURE                Location/Qualifiers
source                 1..610
                       mol_type = protein
                       organism = Bacillus sp.
SEQUENCE: 33
MFMPNIDQIL QDLPKATSAS NYKISLTAVE KVVPNIIKGV NERNINNAAK ALAVYGTSLI  60
PYAGVLISPL ISLLWPELGG SKTLQQMRKE ISDEIDTKIK DSFKTYDETL LKKQIKPFFQ  120
RIQQFEELIN GTTGIKYKGI DDSAYSDHSA YSDHSAYSVY SDMSSNILSP DDYYAEGTSD  180
QTARSEALDI NSKFNEIISS CTKDPSGLLV DMDIWELPIY VLLATAHLQF LYFITINGKK  240
EKSEKIQFDA NTLETYFSKP LKQKIVEYRD YIERTYKKGY QQFESKMGAL ANGNSDRERL  300
QYLKNQIDFY KYHNGPHTSD SGLVKKYEDT LKKYENLITE RDKYLELTIN TKTFNMAVPG  360
TWNPTWQNAY DEDPTVHKYR WLNDNNHFYY LDPTKDGRIK FGWFLDLNEK WYYFNPVRED  420
IDHNPLFAQG EMLADTSSVI NSTRYYFNAD GSCKDPFSRE SVGRLILREG TYRIELDNNS  480
FLAISKEKLT THHVPYNVVA AFSENSADLS QKWTAKFDSK KEAYQFVNQD NNWVLAWNKT  540
EKHYDQMLIG APNEHKDEHY WILSSTSDGR FYAKNFADQN SNLYLSYAPQ SSVYLSVLPR  600
GSAARLKFVN                                                        610
```

```
SEQ ID NO: 34           moltype = AA  length = 608
FEATURE                 Location/Qualifiers
REGION                  1..608
                        note = Description of Artificial Sequence: Synthetic
                         polypeptide
source                  1..608
                        mol_type = protein
                        organism = synthetic construct
SEQUENCE: 34
MPNIDQILQD LPKATSASNY KISLTAVEKV VPNIIKGVNE RNINNAAKAL AVYGTSLIPY  60
AGVLISPLIS LLWPELGGSK TLQQMRKEIS DEIDTKIKDS FKTYDETLLK KQIKPFFQRI  120
QQFEELINGT TGIKYKGIDD SAYSDHSAYS DHSAYSVYSD MSSNILSPDD YYAEGTSDQT  180
ARSEALDINS KFNEIISSCT KDPSGLLVDM DIWELPIYVL LATAHLQFLY FITINGKKEK  240
SEKIQFDANT LETYFSKPLK QKIVEYRDYI ERTYKKGYQQ FESKMGALAN GNSDRERLQY  300
LKNQIDFYKY HNGPHTSDSG LVKKYEDTLK KYENLITERD KYLELTINTK TFNMAVPGTW  360
NPTWQNAYDE DPTVHKYRWL NDNNHFYYLD PTKDGRIKFG WFLDLNEKWY YFNPVREDID  420
HNPLFAQGEM LADTSSVINS TRYYFNADGS CKDPFSRESV GRLILREGTY RIELDNNSFL  480
AISKEKLTTH HVPYNVVAAF SENSADLSQK WTAKFDSKKE AYQFVNQDNN WVLAWNKTEK  540
HYDQMLIGAP NEHKDEHYWI LSSTSDGRFY AKNFADQNSN LYLSYAPQSS VYLSVLPRGS  600
AARLKFVN                                                          608

SEQ ID NO: 35           moltype = AA  length = 350
FEATURE                 Location/Qualifiers
source                  1..350
                        mol_type = protein
                        organism = Bacillus sp.
SEQUENCE: 35
MNIIKIKKMA PLAVLSTAIL VFPTYSFAAE QPTGQTIPYA HKQSIVGQTS QVAISDAAMK  60
DDMVKRLAAP YKDKNDVVSK GVRGLIKSSV DQWTPQYTNA SNDISISDAK LGEYVPKEIV  120
LGSVTNDDPY NTETQQFVTE SQTESTTESF TYTTSDSQKF GFGLDTKIKV GLPFGMGDAE  180
TTLKTSTEFS FTQTSSNTTS HTKSTTYPSQ VIKAAPGYKT TLLAFFAEAN YSGTMNIDGK  240
LSNLNELFPL VTVVELSNLD NKKLYQIYKD TSSTIPLPAG VTLDDANQVV KFNTDIPYNG  300
RAGSYSDAKF TTVKIESLDG KEKVIMPLKQ YQNSKVRKEI LQKNGININQ            350

SEQ ID NO: 36           moltype = AA  length = 323
FEATURE                 Location/Qualifiers
REGION                  1..323
                        note = Description of Artificial Sequence: Synthetic
                         polypeptide
source                  1..323
                        mol_type = protein
                        organism = synthetic construct
SEQUENCE: 36
MAEQPTGQTI PYAHKQSIVG QTSQVAISDA AMKDDMVKRL AAPYKDKNDV VSKGVRGLIK  60
SSVDQWTPQY TNASNDISIS DAKLGEYVPK EIVLGSVTND DPYNTETQQF VTESQTESTT  120
ESFTYTTSDS QKFGFGLDTK IKVGLPFGMG DAETTLKTST EFSFTQTSSN TTSHTKSTTY  180
PSQVIKAAPG YKTTLLAFFA EANYSGTMNI DGKLSNLNEL FPLVTVVELS NLDNKKLYQI  240
YKDTSSTIPL PAGVTLDDAN QVVKFNTDIP YNGRAGSYSD AKFTTVKIES LDGKEKVIMP  300
LKQYQNSKVR KEILQKNGIN INQ                                         323

SEQ ID NO: 37           moltype = AA  length = 366
FEATURE                 Location/Qualifiers
source                  1..366
                        mol_type = protein
                        organism = Bacillus sp.
SEQUENCE: 37
MKKYKKILLI APLACIVSTG VFTLLNGAQA ATNPQTATSQ QPVDVYNQDT VATQENLIQT  60
LHLRLRYGIE HSPELRKKFK IADDEQIKID FGEIKDGYIY PQLEKLEAVL SGTSFSANPT  120
AITLEDDGLV NVVSYNNQSG ITQTLATPEV TKSYSRTIST TNQFGMKIGF EASTKLKVGL  180
PGIVAGEIGL KASSEYSMGL TVGQSVTTTD TLAFKSQTVQ AAAKGTTDYF YRVKKAKFSG  240
TYKADAFLKD GLILKLPIVK KNDMDNVIHT EEVTLTAADL YTIYKTANFA PLPPYMKFDD  300
QSKKVIVNTE FNYEGEGGFY TQAQVTFTPN VTAQGPDSTT PGSLYTPQAK TMTYEEYVKA  360
IQAKKI                                                            366

SEQ ID NO: 38           moltype = AA  length = 337
FEATURE                 Location/Qualifiers
REGION                  1..337
                        note = Description of Artificial Sequence: Synthetic
                         polypeptide
source                  1..337
                        mol_type = protein
                        organism = synthetic construct
SEQUENCE: 38
MATNPQTATS QQPVDVYNQD TVATQENLIQ TLHLRLRYGI EHSPELRKKF KIADDEQIKI  60
DFGEIKDGYI YPQLEKLEAV LSGTSFSANP TAITLEDDGL VNVVSYNNQS GITQTLATPE  120
VTKSYSRTIS TTNQFGMKIG FEASTKLKVG LPGIVAGEIG LKASSEYSMG LTVGQSVTTT  180
DTLAFKSQTV QAAAKGTTDY FYRVKKAKFS GTYKADAFLK DGLILKLPIV KKNDMDNVIH  240
TEEVTLTAAD LYTIYKTANF APLPPYMKFD DQSKKVIVNT EFNYEGEGGF YTQAQVTFTP  300
```

```
NVTAQGPDST TPGSLYTPQA KTMTYEEYVK AIQAKKI                    337

SEQ ID NO: 39          moltype = AA  length = 384
FEATURE                Location/Qualifiers
source                 1..384
                       mol_type = protein
                       organism = Bacillus sp.
SEQUENCE: 39
MKIKNLIIKI LFLLSLTIIW NYSGTVLAET VNKSTFYQIE NVRYKTTIFS EDIGGQAKEI  60
LLFLGAPSQE NNQQYIFYPL DNNYYAIVNK ETGNAITSSE IKYSRGPSFV DRPWGTIHNQ  120
RQKFQLLSEG TGSYILRNQY DGKVLEGTNI ELVLQSNFTK SNNQYWHLKP LSSIKNVPEL  180
INTEILPEIP KYASYNDTLP EKTKSVVTGS TIIPAIMVTD NNWSNSTKIK NSPYYRLIKQ  240
QYWKRIADHS FAPNTTYTAT YTTGMSSEDV TSMTNTTGIS IKADLGVSFD GSTSALATTF  300
TKELALTHST TTKEIQEEKV EVKIENPSKE NNFAWSKYAL ATEYSLERID GSKVGNSWMV  360
VDKNVTRDST WPSGFTPRTT IQNT                                  384

SEQ ID NO: 40          moltype = AA  length = 357
FEATURE                Location/Qualifiers
REGION                 1..357
                       note = Description of Artificial Sequence: Synthetic
                        polypeptide
source                 1..357
                       mol_type = protein
                       organism = synthetic construct
SEQUENCE: 40
METVNKSTFY QIENVRYKTT IFSEDIGGQA KEILLFLGAP SQENNQQYIF YPLDNNYYAI  60
VNKETGNAIT SSEIKYSRGP SFVDRPWGTI HNQRQKFQLL SEGTGSYILR NQYDGKVLEG  120
TNIELVLQSN FTKSNNQYWH LKPLSSIKNV PELINTEILP EIPKYASYND TLPEKTKSVV  180
TGSTIIPAIM VTDNNWSNST KIKNSPYYRL IKQQYWKRIA DHSFAPNTTY TATYTTGMSS  240
EDVTSMTNTT GISIKADLGV SFDGSTSALA TTFTKELALT HSTTTKEIQE EKVEVKIENP  300
SKENNFAWSK YALATEYSLE RIDGSKVGNS WMVVDKNVTR DSTWPSGFTP RTTIQNT     357

SEQ ID NO: 41          moltype = AA  length = 115
FEATURE                Location/Qualifiers
source                 1..115
                       mol_type = protein
                       organism = Rhizobium sp.
SEQUENCE: 41
MSAARSTVWT ITNATDSDWS LTSSTLNHGV WASNPPQTIK AGATASLTAE SNGLATGDEG  60
TVVYSFSGGS VSFYFDNPFL GSDDYKSTVP PGYDQTSNQQ TGNTQVLTTR VFKTS       115

SEQ ID NO: 42          moltype = AA  length = 297
FEATURE                Location/Qualifiers
source                 1..297
                       mol_type = protein
                       organism = Bacillus sp.
SEQUENCE: 42
MSILDMRTIA EQYARYWYEP QAVPGSVTNF QMYEGVLYED VATPTQTNFK VTPALARTAV  60
QTLKNGTDVP QNQTVKFSET KTLTTKTTTT EGIKNTESTK TSTKFSAGFK VDWFNAGMDF  120
TIEVTSTGEY SYTTSMEQSF SNSSLWEVTQ PVTVPPHSTV RAILYIYEAT FNVNYDLNTK  180
IRGTKTSPIP SYYKYFSIQY RRKSDNSLRT VWFDAANLYD TKWPAKPSSF VGREVGGYYP  240
LYYKGKGVST VATGLYTEVE FIQSPLPGYA GETKIWKTGP ILAPSDKKLT LDCSGQY     297

SEQ ID NO: 43          moltype = AA  length = 315
FEATURE                Location/Qualifiers
source                 1..315
                       mol_type = protein
                       organism = Bacillus sp.
SEQUENCE: 43
MAEIQHLDYY LGGLPVVELG WGMGNLTCDE VKSSINSLLQ GTPASGENGV NLTGNVNVTN  60
QSVTILDDLN TIATIVPQYV YDNYFENRTS TEKTYQTISF EQDVQTAIST TVTHGFQIGG  120
KIGAEVKGGV SIPFLADAGV TVNVEISGQY NFSSATTETT TTSQKLIIPS QSGNTPPGYT  180
TRVQIMLAKV NIPDAAVHFS GSMSGTVKLT GADPFQDYDL YSAVKLIEDS CPNSIVGGST  240
GLTLNNSNKS VDFSGSGYFS GSVTSYNFYV KLTESKNDDS SQENIKWYSI RPKVLTQSII  300
KHRFPSNLSI NNCSC                                            315

SEQ ID NO: 44          moltype = AA  length = 293
FEATURE                Location/Qualifiers
REGION                 1..293
                       note = Description of Artificial Sequence: Synthetic
                        polypeptide
source                 1..293
                       mol_type = protein
                       organism = synthetic construct
SEQUENCE: 44
MGNLTCDEVK SSINSLLQGT PASGENGVNL TGNVNVTNQS VTILDDLNTI ATIVPQYVYD  60
NYFENRTSTE KTYQTISFEQ DVQTAISTTV THGFQIGGKI GAEVKGGVSI PFLADAGVTV  120
NVEISGQYNF SSATTETTTT SQKLIIPSQS GNTPPGYTTR VQIMLAKVNI PDAAVHFSGS  180
MSGTVKLTGA DPFQDYDLYS AVKLIEDSCP NSIVGGSTGL TLNNSNKSVD FSGSGYFSGS  240
```

```
VTSYNFYVKL TESKNDDSSQ ENIKWYSIRP KVLTQSIIKH RFPSNLSINN CSC        293

SEQ ID NO: 45          moltype = AA  length = 661
FEATURE                Location/Qualifiers
source                 1..661
                       mol_type = protein
                       organism = Bacillus sp.
SEQUENCE: 45
VKNMNSYQNK NEYEILDTSP NSSTMSTRYP RYPLAKNPQI SMQNTNYKDW INMCTNNTLI  60
PIEPLDLTWQ NALVSVFGIA SAVAALLAAP ITGGTSIAAG AAIIANILPL TFPANDESVP  120
NKLMDATQEL LGPLEEYTRN RANSELLSLS SQLEAFKGLF DYWLANRQNP SATNSVSARF  180
TAIHNNFIGA MALFKIPGYE ALLLPVYAQA ARLHLLHLRD GITYANEWQL ADPTNVTYSG  240
DYHYSEFQRY SAQYADHCEL VVNNQLNKIQ NTPNKTWKDY NEYRRKMILS VFDIVAEFST  300
FDPILYKGAI NREILTRKIY TDPVNFTPGS SIANDENKYT VPPSRVNQLV ASTLFTNVRS  360
AQYAGFIGNI NRYLSLSGGE PFEGPVIGKS VDDKVVAGVP TTESIYEVGV NGYPNDYPRN  420
IGLRWGSLTA FQNYYAGSQY NLGGITRVSM PPKNNAPINN TNFTHRLSDI ILPGNSGSSF  480
AWTHVEINPT GNYLSTNQIN LIAGTKASES PTIKKGPGFI GGDLLTADWR TGNIISPSYQ  540
LRLKFPGTRT SFRVRVRYGA NSSGSMQFTF GATASSQMVY PATGYNTTNT KYNQFRTIEF  600
FTPLEITTDG KLILVLYNTN SAPTFVIDRL ELIPMTGLPT EYNEPQKLET AKKAVTDLFT  660
N                                                                 661

SEQ ID NO: 46          moltype = AA  length = 658
FEATURE                Location/Qualifiers
REGION                 1..658
                       note = Description of Artificial Sequence: Synthetic
                        polypeptide
source                 1..658
                       mol_type = protein
                       organism = synthetic construct
SEQUENCE: 46
MNSYQNKNEY EILDTSPNSS TMSTRYPRYP LAKNPQISMQ NTNYKDWINM CTNNTLIPIE  60
PLDLTWQNAL VSVFGIASAV AALLAAPITG GTSIAAGAAI IANILPLTFP ANDESVPNKL  120
MDATQELLGP LEEYTRNRAN SELLSLSSQL EAFKGLFDYW LANRQNPSAT NSVSARFTAI  180
HNNFIGAMAL FKIPGYEALL LPVYAQAARL HLLHLRDGIT YANEWQLADP TNVTYSGDYH  240
YSEFQRYSAQ YADHCELVVN NQLNKIQNTP NKTWKDYNEY RRKMILSVFD IVAEFSTFDP  300
ILYKGAINRE ILTRKIYTDP VNFTPGSSIA NDENKYTVPP SRVNQLVAST LFTNVRSAQY  360
AGFIGNINRY LSLSGGEPFE GPVIGKSVDD KVVAGVPTTE SIYEVGVNGY PNDYPRNIGL  420
RWGSLTAFQN YYAGSQYNLG GITRVSMPPK NNAPINNTNF THRLSDIILP GNSGSSFAWT  480
HVEINPTGNY LSTNQINLIA GTKASESPTI KKGPGFIGGD LLTADWRTGN IISPSYQLRL  540
KFPGTRTSFR VRVRYGANSS GSMQFTFGAT ASSQMVYPAT GYNTTNTKYN QFRTIEFFTP  600
LEITTDGKLI LVLYNTNSAP TFVIDRLELI PMTGLPTEYN EPQKLETAKK AVTDLFTN    658

SEQ ID NO: 47          moltype = AA  length = 632
FEATURE                Location/Qualifiers
REGION                 1..632
                       note = Description of Artificial Sequence: Synthetic
                        polypeptide
source                 1..632
                       mol_type = protein
                       organism = synthetic construct
SEQUENCE: 47
MNSYQNKNEY EILDTSPNSS TMSTRYPRYP LAKNPQISMQ NTNYKDWINM CTNNTLIPIE  60
PLDLTWQNAL VSVFGIASAV AALLAAPITG GTSIAAGAAI IANILPLTFP ANDESVPNKL  120
MDATQELLGP LEEYTRNRAN SELLSLSSQL EAFKGLFDYW LANRQNPSAT NSVSARFTAI  180
HNNFIGAMAL FKIPGYEALL LPVYAQAARL HLLHLRDGIT YANEWQLADP TNVTYSGDYH  240
YSEFQRYSAQ YADHCELVVN NQLNKIQNTP NKTWKDYNEY RRKMILSVFD IVAEFSTFDP  300
ILYKGAINRE ILTRKIYTDP VNFTPGSSIA NDENKYTVPP SRVNQLVAST LFTNVRSAQY  360
AGFIGNINRY LSLSGGEPFE GPVIGKSVDD KVVAGVPTTE SIYEVGVNGY PNDYPRNIGL  420
RWGSLTAFQN YYAGSQYNLG GITRVSMPPK NNAPINNTNF THRLSDIILP GNSGSSFAWT  480
HVEINPTGNY LSTNQINLIA GTKASESPTI KKGPGFIGGD LLTADWRTGN IISPSYQLRL  540
KFPGTRTSFR VRVRYGANSS GSMQFTFGAT ASSQMVYPAT GYNTTNTKYN QFRTIEFFTP  600
LEITTDGKLI LVLYNTNSAP TFVIDRLELI PM                               632

SEQ ID NO: 48          moltype = AA  length = 565
FEATURE                Location/Qualifiers
source                 1..565
                       mol_type = protein
                       organism = Bacillus sp.
SEQUENCE: 48
VNHMYINTMK NTLKIETTDY EIDQAAISIE CVSNEQNSQE KMILWDEIKQ AKQLSQSRNL  60
LYNGDFEDAS NGWKTSYTIE IRKNSPIFKG QYLHMFGARD VLGEVFPTYV YQKIDESKLK  120
PYTRYRVRGF VGSSKDLKLV VTRYGKEIDA IMDVPDDLAY MQPNPSCGDY RCDSSSKSMM  180
SQGYPTSVTD GYASDMYACP SDRVKKHVKC HDRHPFDFHI DTGELDTNTN LGMLVLFKIS  240
HPNGYATLGN LEVIEEGPLT DEALEHVKQK EKKWNRHIEK ARMETQQAYD PAKQAVDALF  300
TSVQELHYHT TLNHIKNADQ LVQSIPYVNH AWLPDAPSMN YDLYQGLNAR IMQAYNLYDA  360
RNVITNGDFT QGLHGWHTTG NAAVQQMDGA SVLVLSNWSA GVSQNLHAQD HHGYVLRVIA  420
KKEGTGKGYV TMMDCNGKQE TLTFTSCEEG YMTKTVEVFP ESDRVRIEIG ETEGTFYIDS  480
IELLCMKGYT SNYNQNTGNM YEQSYNGNYN QNTSDVYHQG YTNNYNKDSS SMYNQNYTNN  540
DDQHSGCTCN KGHNPGCTCN QRYNR                                       565
```

```
SEQ ID NO: 49           moltype = AA  length = 126
FEATURE                 Location/Qualifiers
source                  1..126
                        mol_type = protein
                        organism = Bacillus sp.
SEQUENCE: 49
MTVYNVTFTI KFYNDGEWGG PEPYGKIYAY LQNPDHNFVI WSQDNWGGDT PEKSSHTQTI  60
KISSPTGGPI NQMCFYGDVK EYDVGNADDV LAYPSQKVCS TPGTTIRLNG DEKGSYIQIS  120
YSLAPA                                                             126

SEQ ID NO: 50           moltype = AA  length = 359
FEATURE                 Location/Qualifiers
source                  1..359
                        mol_type = protein
                        organism = Bacillus sp.
SEQUENCE: 50
MQRRMMMKKS YKKLLMVAPL ACTLATGIAA VPHAALAASP VADIQMNQKF SDQEPAVFSE  60
AQFKQDIADR AVAAITNQPN VFGAISTTNV QFKDETINYG GYTNSGSVDT DATVDHYTDA  120
GHVELLSYRN ETPVNQNFNT PEKTVKSSET FSYSNQEGVK LGVASETKVK ASIPFIGEGE  180
ETVKVSSEFS YNHTSTNSVT NEETNTFKSQ PVVCIPGYTT QFVGTVQNAV FSGSFTGTTA  240
VNGDIKFTAK VGPLEVFPFD TATHADASNK GHAIYNVFKY SGKPLPSYVH LDDVNRRVLI  300
DNVKSTYEGV GGHYSRVVVK VFPNTRSNEG AITMPYAEYM QKVQDGTLQQ ELEQHFKEA   359

SEQ ID NO: 51           moltype = AA  length = 323
FEATURE                 Location/Qualifiers
REGION                  1..323
                        note = Description of Artificial Sequence: Synthetic
                         polypeptide
source                  1..323
                        mol_type = protein
                        organism = synthetic construct
SEQUENCE: 51
MASPVADIQM NQKFSDQEPA VFSEAQFKQD IADRAVAAIT NQPNVFGAIS TTNVQFKDET  60
INYGGYTNSG SVDTDATVDH YTDAGHVELL SYRNETPVNQ NFNTPEKTVK SSETFSYSNQ  120
EGVKLGVASE TKVKASIPFI GEGEETVKVS SEFSYNHTST NSVTNEETNT FKSQPVVCIP  180
GYTTQFVGTV QNAVFSGSFT GTTAVNGDIK FTAKVGPLEV FPFDTATHAD ASNKGHAIYN  240
VFKYSGKPLP SYVHLDDVNR RVLIDNVKST YEGVGGHYSR VVVKVFPNTR SNEGAITMPY  300
AEYMQKVQDG TLQQELEQHF KEA                                          323

SEQ ID NO: 52           moltype = AA  length = 314
FEATURE                 Location/Qualifiers
source                  1..314
                        mol_type = protein
                        organism = Bacillus sp.
SEQUENCE: 52
MSITNLELAT INYMKWYATN FLQANPTTFY NEGIYPYQVS NLKLSPKWKD FSVIPFENEI  60
ITQVIENPTN QTQHKSIEFR ELTSENIEYR INEGFKLYNG IRSTFPLSID VEFMISDGLH  120
QSIKIPFDIE FISHSTKVEK NNIKKKWELR QSINIPAYKR LITSLIIMGC KIIIPIQFSA  180
NITGTYSYQD KNNWFSSLSF REHNNLETSA IFCASNLSQT TWPDKPKVFV SPGRNGSLNL  240
KGEAEVTYEP GLYTMIKYEQ LSLKEYSNEN NIWYSDQVIL RDGRMIILPN FDILTGHSSC  300
IEVATINNST QRFY                                                    314

SEQ ID NO: 53           moltype = AA  length = 328
FEATURE                 Location/Qualifiers
source                  1..328
                        mol_type = protein
                        organism = Bacillus sp.
SEQUENCE: 53
MKYKKASLKK SVALAIATTT GIVLTSLTPT YAATNGIDEI SQITKLNAQE YQIDSSNQSN  60
RSQFNTFNFK AVDLYRFFNL KGTVAFKPHA NTTFEFRDAQ VKDVGSPKIE GESSLFVGRN  120
ILRNSSDREQ ELTTSEFSKT YANAVSTSVT HGAEVGAEIS STFGIPLIGN TEVTLSASYN  180
FSKTGTQEHS EEHTYVASPQ TVSVPAHSAV EVEVKLKTMD ISGDVELSAV GYGAIRNVQF  240
VTLSGPDIYK DVTAREFLDT RRKYEQIGKQ LYPELYNAPI KDNGNGTFTL NGKGKYKATY  300
GSTFEVTVKD IKTGKILETK NIPAHILE                                     328

SEQ ID NO: 54           moltype = AA  length = 297
FEATURE                 Location/Qualifiers
REGION                  1..297
                        note = Description of Artificial Sequence: Synthetic
                         polypeptide
source                  1..297
                        mol_type = protein
                        organism = synthetic construct
SEQUENCE: 54
MATNGIDEIS QITKLNAQEY QIDSSNQSNR SQFNTFNFKA VDLYRFFNLK GTVAFKPHAN  60
TTFEFRDAQV KDVGSPKIEG ESSLFVGRNI LRNSSDREQE LTTSEFSKTY ANAVSTSVTH  120
GAEVGAEISS TFGIPLIGNT EVTLSASYNF SKTGTQEHSE EHTYVASPQT VSVPAHSAVE  180
VEVKLKTMDI SGDVELSAVG YGAIRNVQFV TLSGPDIYKD VTAREFLDTR RKYEQIGKQL  240
```

```
YPELYNAPIK DNGNGTFTLN GKGKYKATYG STFEVTVKDI KTGKILETKN IPAHILE     297

SEQ ID NO: 55          moltype = AA  length = 429
FEATURE                Location/Qualifiers
source                 1..429
                       mol_type = protein
                       organism = Bacillus sp.
SEQUENCE: 55
LSFYIRNIIL KECGCYMANG NNNNTYNSGN TENNGYMNDN MYNTGSTNNN PYTSASLENN  60
RTISPKPAKP LLNLDKFAFY SINTFSPGKC VDIKNWSTAN DAEAIQYTYG NQINQKFMVI  120
PLDDGSTILA AKHSGKVLDQ KYNSRIIQYD FNNYDNQKFY LGNNNHIVSK YNGESFDVKD  180
AASGNGAVIA TYPTHSWNNQ KFYFMHRESI PIQFPATTTL PPAPTFTSLT QQLPDSTSPV  240
IVSYTTIPYL LVQDPTYTHQ QRIGFSPYYL LIKKQYWRKE SQRILAPRDE YEFTVKYGMS  300
TTEQESMEQT TSITIGADFG FQFKALSAGI STQITDELKV SKSRSSTQLK EETHRYFYTN  360
PFDSRMARAE YIRVDEFQLK RMNGTQVSMS WTVEDKNHTS VTTYIEGSGR SIPAEEDKAA  420
QLPSGLFMN                                                          429

SEQ ID NO: 56          moltype = AA  length = 413
FEATURE                Location/Qualifiers
REGION                 1..413
                       note = Description of Artificial Sequence: Synthetic
                        polypeptide
source                 1..413
                       mol_type = protein
                       organism = synthetic construct
SEQUENCE: 56
MANGNNNNTY NSGNTENNGY MNDNMYNTGS TNNNPYTSAS LENNRTISPK PAKPLLNLDK  60
FAFYSINTFS PGKCVDIKNW STANDAEAIQ YTYGNQINQK FMVIPLDDGS TILAAKHSGK  120
VLDQKYNSRI IQYDFNNYDN QKFYLGNNNH IVSKYNGESF DVKDAASGNG AVIATYPTHS  180
WNNQKFYFMH RESIPIQFPA TTTLPPAPTF TSLTQQLPDS TSPVIVSYTT IPYLLVQDPT  240
YTHQQRIGFS PYYLLIKKQY WRKESQRILA PRDEYEFTVK YGMSTTEQES MEQTTSITIG  300
ADFGFQFKAL SAGISTQITD ELKVSKSRSS TQLKEETHRY FYTNPFDSRM ARAEYIRVDE  360
FQLKRMNGTQ VSMSWTVEDK NHTSVTTYIE GSGRSIPAEE DKAAQLPSGL FMN         413

SEQ ID NO: 57          moltype = AA  length = 189
FEATURE                Location/Qualifiers
source                 1..189
                       mol_type = protein
                       organism = Bacillus sp.
SEQUENCE: 57
MPFEEDVPYS PTGAYSNQTP VRSEYAEGAE SLGDTLVTNY EVPFCCMISL PHGFQYEGRK  60
QPKLVYDTSC LTLAHEMSKR SVTVDNIGTL DIDLQVLKIK GCLTLFLNVP IVPIHSEYIC  120
TSHRDMPALY TGYQEAIKVD HIVKCSMGRL PYYVLDCEHM KVCDLQIHPV QEPHCPVVKV  180
SGRFEFLYT                                                          189

SEQ ID NO: 58          moltype = AA  length = 1265
FEATURE                Location/Qualifiers
source                 1..1265
                       mol_type = protein
                       organism = Bacillus sp.
SEQUENCE: 58
MDQDSITPSI SSSLPGGIPY NVLSSSGYNA LSYNNLMTIQ DIIEFFKKIY AETGDIPAGS  60
IKQIWDGGQK DNWLDIIHGM LGLGAFAIPE LAVAVPIITR LIDFIYPKLF GATESDPPSV  120
WDQISEQVQN LIGQQINAQE KANLLAKFSG LNSTVTDFRN KIDTATCNGP EPGFLNNSTS  180
TTNENNCGSA YATNSEDCIP YGNAIETEAV RSTFISTNTF FIGILPEFNK AAPTSSTGEA  240
RFEYINLSLP LFTMAASLHL LLIQSAIDSG LKWGFTQAQI NAYHVSLRTN IKDYTAIIRN  300
TFNEGLSLIQ GDYNREQLYI ANITTQCFDI SALWPTYDRF DYVNPGETKI EQTRVLYSPL  360
VPSILPGFNA SPQVPPDSVR NYIGELTRVD FSIWSTTLET FLNGMQNTLT TPGGTTKTDP  420
YGSYSNINSG NTRYRGGVSI TRENPVTAVG IWNAKYNAIR TSEAAFYMAD GSTQVIGSLV  480
YDSPPNQAYY GGVAGAPFNN KVEYIYPFNN GDPLQGFSAG FVRAKVFPEN IVGTIDPDSN  540
TPVITGIPAE KCSSITGFDK VLERINGASA IRSVLSPSGS SASYRVNVVT AGSYTIRVRV  600
ATSGEGNSFT FGGDAIAQTQ IILPNTQATA TPQKGLQGDY GVYMLVNVGT VELKSGLQTF  660
TLSVSGATTL IDRIEFIPPN ITIDPNTFNE DFKGLQPNET RWIWSGPTAA GVNVSGYLYP  720
PATNTPGGIS IQFWQDDTLV RTLPASAQSF AFHHIPFSYP NQAIGAFNKI GIKGTSSLPI  780
DGHIEGNVIG SQVMFTTQAD LDQVTAVVEA LSTPSALGVT DYMIDQAFLK VQALSDAVFA  840
AEKAQLRQQV NAAKRLSQSN NLIVGSTFEN TSNWALGQEA RVVAGDDVFP GGYLVLQPSM  900
YPTARPSYAY QKVAESKLKA NTRYIVTGFI RAAHDLEIWV SRYGGEILDE IEIPYTDALP  960
LTPGILPNCC LPPVCPPCEK ESIDSHTFSY RIDVGALQPE ANLGIELAFK LLSPDGLAQL  1020
SNIEIKEERP LTDGEIRKVQ QREKAWKQVY AQQQQTANQQ IQQVQTQLAA LYTGPQQTQL  1080
KPTVQYQDIT SIKIPDIPAV YNCYIPQIPG QNNDAFFALL AKKTQALSLY PRNYIKNGYF  1140
EQGLQDWQIE GTVTVQPTDY EQWMLQLTSW DSVASQTLVL PLSEQDIEYR LRVTAKGVGT  1200
IQVKDGEEYE QIAFTNKQGG WQTKELTFYA DKDTNIKQIV IQENGAEFFV KTIEVFVPLA  1260
PLTEA                                                              1265

SEQ ID NO: 59          moltype = AA  length = 679
FEATURE                Location/Qualifiers
REGION                 1..679
                       note = Description of Artificial Sequence: Synthetic
                        polypeptide
```

```
source                  1..679
                        mol_type = protein
                        organism = synthetic construct
SEQUENCE: 59
MDQDSITPSI SSSLPGGIPY NVLSSSGYNA LSYNNLMTIQ DIIEFFKKIY AETGDIPAGS  60
IKQIWDGGQK DNWLDIIHGM LGLGAFAIPE LAVAVPIITR LIDFIYPKLF GATESDPPSV  120
WDQISEQVQN LIGQQINAQE KANLLAKFSG LNSTVTDFRN KIDTATCNGP EPGFLNNSTS  180
TTNENNCGSA YATNSEDCIP YGNAIETEAV RSTFISTNTF FIGILPEFNK AAPTSSTGEA  240
RFEYINLSLP LFTMAASLHL LLIQSAIDSG LKWGFTQAQI NAYHVSLRTN IKDYTAIIRN  300
TFNEGLSLIQ GDYNREQLYI ANITTQCFDI SALWPTYDRF DYVNPGETKI EQTRVLYSPL  360
VPSILPGFNA SPQVPPDSVR NYIGELTRVD FSIWSTTLET FLNGMQNTLT TPGGTTKTDP  420
YGSYSNINSG NTRYRGGVSI TRENPVTAVG IWNAKYNAIR TSEAAFYMAD GSTQVIGSLV  480
YDSPPNQAYY GGVAGAPFNN KVEYIYPFNN GDPLQGFSAG FVRAKVFPEN IVGTIDPDSN  540
TPVITGIPAE KCSSITGFDK VLERINGASA IRSVLSPSGS SASYRVNVVT AGSYTIRVRV  600
ATSGEGNSFT FGGDAIAQTQ IILPNTQATA TPQKGLQGDY GVYMLVNVGT VELKSGLQTF  660
TLSVSGATTL IDRIEFIPP                                               679

SEQ ID NO: 60           moltype = AA  length = 718
FEATURE                 Location/Qualifiers
source                  1..718
                        mol_type = protein
                        organism = Bacillus sp.
SEQUENCE: 60
MFYNNGQFVR SSGNREANPH VDNDCSCSEN HNDLLLQKTN FPLDSITDTE KLYASSLLIE  60
NGGDFQPQAL DSSTYETIQN NENSQIGIKD ITCVWDKWGE NRQRFSEPTV RIDPVSGAIG  120
SFLLKKIGGI IATKLINGIY GILFPTPAPI TLEQILDAVS ELLNQRLDTD NYRRVHLELE  180
GLQASSKAFI ETVEAYEQKI YNDPLYAETH VDEIRNAMNT FHTLCVNRMP QFRLPGYQIL  240
LLPLYAQAAN IHIGFLKDVL DNQTKWGLST ADVKLYTNRF LDVVGTYSTY CNTTYHTDFI  300
RQFSEDIKRP LDYRTFMILN VLDYVSLWSM LRFNKLEILT STPLYEYGRA TPSGIIPKYS  360
YSFWDNLNRL FQGFPNRILE RVVSQNKYIY TSRPNILNYV NRSYGITTYY SGNKSFKVGY  420
NTFSFCNGND RCEYYTNSIN AKNLKEASQI SNLYTHSQGW PNVSITVRDW HDMRYKDGTR  480
EEATIASDSF SRNWVSYPER TIQSIIGLPP SMPNEHINII DGPQNRVQSD GVIAANITAF  540
QRKAAKTYAV SNGTIRHPFT AGKGLAISPL EYISTYNIAS AAKREFYIVQ RYGNNGDALR  600
IPNPRSFGSN FHGLLYHVFN PYGSPFSLDV YLKVSAPNST VLGVYLNGVG GKKEISTGTD  660
NDGVTDNNSK SKIVKFLSGY NLKPGNVELL LLNEGNADLF VENIFVVPTG STFISRIN    718

SEQ ID NO: 61           moltype = AA  length = 649
FEATURE                 Location/Qualifiers
REGION                  1..649
                        note = Description of Artificial Sequence: Synthetic
                         polypeptide
source                  1..649
                        mol_type = protein
                        organism = synthetic construct
SEQUENCE: 61
MDSSTYETIQ NNENSQIGIK DITCVWDKWG ENRQRFSEPT VRIDPVSGAI GSFLLKKIGG  60
IIATKLINGI YGILFPTPAP ITLEQILDAV SELLNQRLDT DNYRRVHLEL EGLQASSKAF  120
IETVEAYEQK IYNDPLYAET HVDEIRNAMN TFHTLCVNRM PQFRLPGYQI LLLPLYAQAA  180
NIHIGFLKDV LDNQTKWGLS TADVKLYTNR FLDVVGTYST YCNTTYHTDF IRQFSEDIKR  240
PLDYRTFMIL NVLDYVSLWS MLRFNKLEIL TSTPLYEYGR ATPSGIIPKY SYSFWDNLNR  300
LFQGFPNRIL ERVVSQNKYI YTSRPNILNY VNRSYGITTY YSGNKSFKVG YNTFSFCNGN  360
DRCEYYTNSI NAKNLKEASQ ISNLYTHSQG WPNVSITVRD WHDMRYKDGT REEATIASDS  420
FSRNWVSYPE RTIQSIIGLP PSMPNEHINI IDGPQNRVQS DGVIAANITA FQRKAAKTYA  480
VSNGTIRHPF TAGKGLAISP LEYISTYNIA SAAKREFYIV QRYGNNGDAL RIPNPRSFGS  540
NFHGLLYHVF NPYGSPFSLD VYLKVSAPNS TVLGVYLNGV GGKKEISTGT DNDGVTDNNS  600
KSKIVKFLSG YNLKPGNVEL LLLNEGNADL FVENIFVVPT GSTFISRIN              649

SEQ ID NO: 62           moltype = AA  length = 1017
FEATURE                 Location/Qualifiers
source                  1..1017
                        mol_type = protein
                        organism = Bacillus sp.
SEQUENCE: 62
MDNLSHIYPF ALYNKIQPFR IKNEIKLDKF NKTLKDIQCA WNQYSKDGLV TSQRRAIHNA  60
WNMLNEKTLN FLDLLKGLLG LGGAMGYLSQ SYTGESQDCY IIPMQNFILE ILWPQLLDSS  120
ITTDVWEILK DRAEVMMEIK IRDNEWLEIN RIATLLQSSL LDLKESIQEA VYQPLSYHNT  180
NVRAQHNFIP YNNAELNAQI RKKLDAALNQ FELYIYDFKK TNSRLIELPF FCLTATLHLI  240
TLQSKAQFGV RWGFDLEVVI QTMRTLRATI TKYKKYAQML LKEEKGIYEL FFSNTTIHQS  300
NNSVLKFLLT ECVNHISMWT TFDVIQYPFY TIIESALIRN TPIVPPLSPI TIEALDFDMR  360
VPIIKSISVE TCVTTGEKIA GSIVGEYAIK LSYGGQIIELP FTNLTDSKYQ IRYRFSNCTK  420
TNNIRSEIGS WTSISKIEWT LSNTDSKILE LQDEQELHKI FPEIKFNSNF QYNISNENII  480
EYLPVGNHVL KITNTGLTDI IIDRIEFMPI LSNDNSKVLL KEKKDLQCVT EEVIKLFTNP  540
SYTELKGSVT DYQINQVVMR VDSLSFDRFG IEKNFLRRLV NIAKQLSTSR NLLGDGNFER  600
LDSWLLGREV RSISNYHLYK GKHLLLLPPK TSSSYAYQKI DESTLKMNTR YIISGCISRC  660
KHLEIIISRY EKEVQTILST SNQESLLKDE QTYCTIHSTQ CLVCNEQKKN PHFFKYSIDV  720
GCLYEKMNLG IEIGFRIVKP DGFAEISNVE VREDGPLSEI ETTLCKCGKR HAIRRKKRIF  780
EPPKNLTIIK RLQRKEQQWQ KRVDKERRDI IEQIQPIILQ INALYQNEDW NGFIRPNITY  840
QHVQEIELPT LPKQKHWFME DRTGELYFIT ERLQQALSQA VEQVEERNLL ENGNFRKNLT  900
NWITNGNISI IPLQNGGGVQ LLGWDKSISQ CIHNLDFTTR QKYIVRACGK GNGTVIIQHG  960
```

```
NTIQLIVFDV NYFSTKEECF TLKDKDIEIL VQSEETEFTI KYIEFFKLPE ENPKQLY     1017

SEQ ID NO: 63          moltype = AA  length = 510
FEATURE                Location/Qualifiers
REGION                 1..510
                       note = Description of Artificial Sequence: Synthetic
                        polypeptide
source                 1..510
                       mol_type = protein
                       organism = synthetic construct
SEQUENCE: 63
MDNLSHIYPF ALYNKIQPFR IKNEIKLDKF NKTLKDIQCA WNQYSKDGLV TSQRRAIHNA  60
WNMLNEKTLN FLDLLKGLLG LGGAMGYLSQ SYTGESQDCY IIPMQNFILE ILWPQLLDSS  120
ITTDVWEILK DRAEVMMEIK IRDNEWLEIN RIATLLQSSL LDLKESIQEA VYQPLSYHNT  180
NVRAQHNFIP YNNAELNAQI RKKLDAALNQ FELYIYDFKK TNSRLIELPF FCLTATLHLI  240
TLQSKAQFGV RWGFDLEVVI QTMRTLRATI TKYKKYAQML LKEEKGIYEL FFSNTTIHQS  300
NNSVLKFLLT ECVNHISMWT TFDVIQYPFY TIIESALIRN TPIVPPLSPI TIEALDFDMR  360
VPIIKSISVE TCVTTGEKIA GSIVGEYAIK LSYGQIIELP FTNLTDSKYQ IRYRFSNCTK  420
TNNIRSEIGS WTSISKIEWT LSNTDSKILE LQDEQELHKI FPEIKFNSNF QYNISNENII  480
EYLPVGNHVL KITNTGLTDI IIDRIEFMPI                                   510

SEQ ID NO: 64          moltype = AA  length = 563
FEATURE                Location/Qualifiers
source                 1..563
                       mol_type = protein
                       organism = Bacillus sp.
SEQUENCE: 64
MKYKDRKNAK RKYKQALLAT VATMTLGVST LGSTASVFAA EETGETTVQA GGVLQPAEPL  60
PEQQPQMAVP TQDIINHSAE LLKTFTDVFA KSKEYPKGLS EAKISTIKTT LDSMKSLPDI  120
IKSANNGNYD KATKDIVKAM LAFAPYGTWV TPLLDIMYPE ASTSGDNLMN QVEKKISTAI  180
QGYFNGELKI NLSEATRLMK NFETTLAHPA SIQSSISEDA KKADDAFVKL RDSAAHDGLE  240
EEGLPIYTGA AVAHLLFLKS LMLQTSNKTS LIPGSLNRID PGTMETRFAE NNYKDYLEAY  300
KTHINKYAQQ HIDTVKQKLR DIAKEQGVDS SYINLDTFKD IMGKEYTEAA KAAKRYPGDR  360
GSIDFSFNQK IAKRDALSQA IDEGCTLLAE LKTYINDTVN NAGFNTIAYG TGWKEINGKT  420
YYFGEAGDKT KVDNGTMATG WQTIKGKTYY FGAPGDGTEV DNWTMATSIH RIDGKYYSFD  480
KDGVCANPEG AKTGGTTPTW FGNDYKGFIS GKGDGADTFA GHIAQNTKTW INGTTSLNGH  540
PVHEGNYEFD KDGVCINFNE LNK                                          563

SEQ ID NO: 65          moltype = AA  length = 525
FEATURE                Location/Qualifiers
REGION                 1..525
                       note = Description of Artificial Sequence: Synthetic
                        polypeptide
source                 1..525
                       mol_type = protein
                       organism = synthetic construct
SEQUENCE: 65
MAEETGETTV QAGGVLQPAE PLPEQQPQMA VPTQDIINHS AELLKTFTDV FAKSKEYPKG  60
LSEAKISTIK TTLDSMKSLP DIIKSANNGN YDKATKDIVK AMLAFAPYGT WVTPLLDIMY  120
PEASTSGDNL MNQVEKKIST AIQGYFNGEL KINLSEATRL MKNFETTLAH PASIQSSISE  180
DAKKADDAFV KLRDSAAHDG LEEEGLPIYT GAAVAHLLFL KSLMLQTSNK TSLIPGSLNR  240
IDPGTMETRF AENNYKDYLE AYKTHINKYA QQHIDTVKQK LRDIAKEQGV DSSYINLDTF  300
KDIMGKEYTE AAKAAKRYPG DRGSIDFSFN QKIAKRDALS QAIDEGCTLL AELKTYINDT  360
VNNAGFNTIA YGTGWKEING KTYYFGEAGD KTKVDNGTMA TGWQTIKGKT YYFGAPGDGT  420
EVDNWTMATS IHRIDGKYYS FDKDGVCANP EGAKTGGTTP TWFGNDYKGF ISGKGDGADT  480
FAGHIAQNTK TWINGTTSLN GHPVHEGNYE FDKDGVCINF NELNK                  525

SEQ ID NO: 66          moltype = AA  length = 388
FEATURE                Location/Qualifiers
source                 1..388
                       mol_type = protein
                       organism = Bacillus sp.
SEQUENCE: 66
MKFVSKQVMT GLMVGAMGLS IWAPASQAAV PENNRYYTIN LKANQKLVWD VANESNDKDR  60
AILLYDGKRG DNEQFVFFQL DGGTYAIVNK NSGKPVTIGS AAWYGDYSYP GLIRGTDVLQ  120
QQSWTGAPAE QWYLRDKGSN NYEVVNQGNG RVASYAGVSM TGGWIQYVDL DESNPSDSDR  180
VFNIANSPSG LSLPTLPATG TRPTAPNYTG GSDQQLPRTS DSVVIGASLI PCIMVNDSQA  240
SEYTKIHNSP YYVLVKEEYW EQTFSKVIQP GLSESYSYKT GISSVDQQKM TDTLSIQVGA  300
DLGLKFGDKT AALKAQITKT LQTEVSTTNT QASEETITQT ATGEPGKATG YTQYQLATKY  360
TLKRQDGSTV SDPWVVKNNR ITVTRKSS                                     388

SEQ ID NO: 67          moltype = AA  length = 361
FEATURE                Location/Qualifiers
REGION                 1..361
                       note = Description of Artificial Sequence: Synthetic
                        polypeptide
source                 1..361
                       mol_type = protein
                       organism = synthetic construct
```

```
SEQUENCE: 67
MAVPENNRYY TINLKANQKL VWDVANESND KDRAILLYDG KRGDNEQFVF FQLDGGTYAI  60
VNKNSGKPVT IGSAAWYGDY SYPGLIRGTD VLQQQSWTGA PAEQWYLRDK GSNNYEVVNQ  120
GNGRVASYAG VSMTGGWIQY VDLDESNPSD SDRVFNIANS PSGLSLPTLP ATGTRPTAPN  180
YTGGSDQQLP RTSDSVVIGA SLIPCIMVND SQASEYTKIH NSPYYVLVKE EYWEQTFSKV  240
IQPGLSESYS YKTGISSVDQ QKMTDTLSIQ VGADLGLKFG DKTAALKAQI TKTLQTEVST  300
TNTQASEETI TQTATGEPGK ATGYTQYQLA TKYTLKRQDG STVSDPWVVK NNRITVTRKS  360
S                                                                  361

SEQ ID NO: 68          moltype = AA  length = 1168
FEATURE                Location/Qualifiers
source                 1..1168
                       mol_type = protein
                       organism = Bacillus sp.
SEQUENCE: 68
MKVRLLMNKN YLSKSQDLTQ ISEIIGYDPI HPLVNPKNHI ESLRVNRNEL RTLPEGFASS  60
TESAITNTLN IISILLDASG HPAAARVLGV ITGIIGILWP GGSQKPWEEF MAAVETLVDE  120
KITEAFKSEA ISKLNGLADL YTVYLSELEL WLEHPHDPSI IQSVRTRFLD LDSEFISSIP  180
QFAVSGFEVQ FLPVYAHAAN LHLLLLRDLS YYGNDWGLQQ AEIDNFYNRQ INNIQKYTDH  240
CVEWYERGLQ DVYNSFSSTN INEDGGLPWT HYNRYRREMT IYVLDLIATF PTNDWKKYHL  300
ETNVELSREI YTDPLGYEDN DTENITDVDW YSEGVSFSTI ENLHGPRLVE WLNKVYIKTD  360
YFSAGSDESY CWASHTIYSS FTDSNEEHSR SYGSPENVEG TQTISFYPAE IYKVVSTVGS  420
ERNATYDNYV NSANKFYGVT PTNELKRFDY IMPNDYDQKV LYSDNQLPLE TDTPKYGEYS  480
HRLSNITIAP LNSDDFGLVP ILGWTHTSLK RENRIYPDKI TQIPAVKSFS TEGTWERVAA  540
GPGFTGGNVT QATNTVISGI NTTDLVKIRV RIDSTASSKQ YRVRLRYASN QDFSHAHFYT  600
GTGANETTFS LKKTTDFPFA NYNSFGYVEI PRVLKFSSGS EIINVYVYPE NGLNVQVDKI  660
EFIPVDDSYE DRVTLEKAQK AVNTLFTVGR NALQTDVTDY KVDQVSILVD CVSEELYPNE  720
KKELQNLVKY AKRLSISRNL LLDPNFTSIN APKIRGWHGS QGIIVGNGNY IFKGPYVHLQ  780
GTNDAQYPTY LYQKIDESKL KEYIRYKLRG FIESSQDLEV YVIRYDAKRE TLDVSNNLSS  840
DDTPANACGG PNRCIEQQYL DDNPTLECSS IQDGILFDSH SFSLNIDTGS IDYNENVGIW  900
VVFKISTLEG YAKLGNVEVI EDGPLVGEAL ARVKRQETKW RNKLAQLRTE TQAIYTRAKQ  960
SLDNLFIDAQ DAHLKIGTPF AAIVAAREAV QSIREVYMPW LSVVAGVNYP IFTELNLRVR  1020
RAIQLYDLRN VVRNGRFRNG LSNWNVTSDV EVQEENGNNL LVLSGWDAQV LQQVTVFQNR  1080
GYILRVTARK EGLGEGYVTI TDEQGNTDQL TFNACENIDA SSTFVSTGYI TKELEFFPDT  1140
DQVQLEIGET EGIFKVESVE LFLMEDLC                                    1168

SEQ ID NO: 69          moltype = AA  length = 546
FEATURE                Location/Qualifiers
source                 1..546
                       mol_type = protein
                       organism = Bacillus sp.
SEQUENCE: 69
MKYKNRIQAK NRYKKALLAT AAALTLGVGT VGSFSAVPTA IYAEETTSSN KVWSLNDDGD  60
LIFNNTFNLG NPKAIGKEAA KVSGTNFLKL VSNPNITADE AKNIMRDLTL GVTQLIPYGG  120
SFVSSIIAFA WPPAGKGELE LLMERVAKMI DEKIEFYDGS TLKRKYETLR LHLQKVENAL  180
NGAKAPLPSV YYTSTDTTMT AALQDLNNEF EGLLSECKKE GFKEAELPLY TTIATAHLSF  240
LKFMKANGTS HPQIGITEKN LNDFYYADQL DKLSEVYSDY INTTFNSAQE KFLKKINSII  300
KGDNASYQQM LTYGKSYKEI IDKVLNVEID LEYQQAKSIG NLSRDYIASH PGDIRKQIME  360
VRDELNDFDN LTMSSPAWKV IKDSFASKWE KDNQGAWYYR DLNGVALTGW FKSADNNWYY  420
LDPNKGGAAA ANTTLTLDDR KYDFNENGTC MTPSGYTSNS IEELLKITKS GNYIVINADN  480
LLFKSNINSA MVKVSKNGSM LFMTGVKKGG YTANTATFSP TDVVKVEVQV DNNFVKVFEG  540
PFSSIN                                                            546

SEQ ID NO: 70          moltype = AA  length = 504
FEATURE                Location/Qualifiers
REGION                 1..504
                       note = Description of Artificial Sequence: Synthetic
                        polypeptide
source                 1..504
                       mol_type = protein
                       organism = synthetic construct
SEQUENCE: 70
MEETTSSNKV WSLNDDGDLI FNNTFNLGNP KAIGKEAAKV SGTNFLKLVS NPNITADEAK  60
NIMRDLTLGV TQLIPYGGSF VSSIIAFAWP PAGKGELELL MERVAKMIDE KIEFYDGSTL  120
KRKYETLRLH LQKVENALNG AKAPLPSVYY TSTDTTMTAA LQDLNNEFEG LLSECKKEGF  180
KEAELPLYTT IATAHLSFLK FMKANGTSHP QIGITEKNLN DFYYADQLDK LSEVYSDYIN  240
TTFNSAQEKF LKKINSIIKG DNASYQQMLT YGKSYKEIID KVLNVEIDLE YQQAKSIGNL  300
SRDYIASHPG DIRKQIMEVR DELNDFDNLT MSSPAWKVIK DSFASKWEKD NQGAWYYRDL  360
NGVALTGWFK SADNNWYYLD PNKGGAAAAN TTLTLDDRKY DFNENGTCMT PSGYTSNSIE  420
ELLKITKSGN YIVINADNLL FKSNINSAMV KVSKNGSMLF MTGVKKGGYT ANTATFSPTD  480
VVKVEVQVDN NFVKVFEGPF SSIN                                        504

SEQ ID NO: 71          moltype = AA  length = 467
FEATURE                Location/Qualifiers
source                 1..467
                       mol_type = protein
                       organism = Bacillus sp.
SEQUENCE: 71
MKYKNRAHAK RKYKQAILAT VATMTLGVST LGSTNSVFAA ENTVSAQQAS SASATDGPVF  60
```

```
KRESNGAITV LKDKLFNIET LKAIGSLGGD TLKQAWADSK VEGGNFNNTF RTLTMGSAAL  120
IPYGGVVISP LIGLLWPEDT TDAKNRLENL MKDIAKQTNA QIGSYDLETL GQKLEKLYKD  180
LKEFEQIMNP TSRKLASSPS VGDEAAAIRS KAEFIHDDFK NLISESQKPS YKEAEFPIFM  240
IAATAHLNFL QYMELHGKDP KINYDDKGLK LTFLDPQKQA RKDYLDYANK FAKPALDDSN  300
KSVINIQDLV RKRNEASNSF ERSLRTTAIN LVIQGVSQNL EKTLNKSINN VAFKQVLGIK  360
SEWTLDQNGR TFYYDLKGEM QTGWKEISTS FATRLEVESN NAGNMFSKQW LKDQGLSYSR  420
YYFSLEKTAT FEKGEMYRDT TQTLPDGKTY KFDKDGKCLN PDGGEEK                467

SEQ ID NO: 72           moltype = AA  length = 429
FEATURE                 Location/Qualifiers
REGION                  1..429
                        note = Description of Artificial Sequence: Synthetic
                         polypeptide
source                  1..429
                        mol_type = protein
                        organism = synthetic construct
SEQUENCE: 72
MAENTVSAQQ ASSASATDGP VFKRESNGAI TVLKDKLFNI ETLKAIGSLG GDTLKQAWAD  60
SKVEGGNFNN TFRTLTMGSA ALIPYGGVVI SPLIGLLWPE DTTDAKNRLE NLMKDIAKQT  120
NAQIGSYDLE TLGQKLEKLY KDLKEFEQIM NPTSRKLASS PSVGDEAAAI RSKAEFIHDD  180
FKNLISESQK PSYKEAEFPI FMIAATAHLN FLQYMELHGK DPKINYDDKG LKLTFLDPQK  240
QARKDYLDYA NKFAKPALDD SNKSVINIQD LVRKRNEASN SFERSLRTTA INLVIQGVSQ  300
NLEKTLNKSI NNVAFKQVLG IKSEWTLDQN GRTFYYDLKG EMQTGWKEIS TSFATRLEVE  360
SNNAGNMFSK QWLKDQGLSY SRYYFSLEKT ATFEKGEMYR DTTQTLPDGK TYKFDKDGKC  420
LNPDGGEEK                                                          429

SEQ ID NO: 73           moltype = AA  length = 283
FEATURE                 Location/Qualifiers
REGION                  1..283
                        note = Description of Unknown: Organism from environmental
                         sample
source                  1..283
                        mol_type = protein
                        organism = unidentified
SEQUENCE: 73
VDCMAILDLK KVAEDNWKNW CKLAKVDFQR VIMSNVDGSN PVRLYNYNMS VPNPIVTDNP  60
TNSAMAKGTT PNPTSQPIVR TVTFNETLTD SQSTTTEHGI TAGASVTVKS EAGILFAKVG  120
VEATLSFEYN WSTSTTKTTE TSRSWTDSVQ ITIPPGYVTE HTFIVQTGPF NKNVVLECDI  180
TGTTTCVYRF PNTSQDRYTG DNAGMISEAL RAMGVPNITY PDFGIAHFTG SGSLIGRMGL  240
QSFVNVVERP LSGRSGQVRE YQIPLTGRSG LDIPIFDPVV SRQ                    283

SEQ ID NO: 74           moltype = AA  length = 280
FEATURE                 Location/Qualifiers
REGION                  1..280
                        note = Description of Artificial Sequence: Synthetic
                         polypeptide
source                  1..280
                        mol_type = protein
                        organism = synthetic construct
SEQUENCE: 74
MAILDLKKVA EDNWKNWCKL AKVDFQRVIM SNVDGSNPVR LYNYNMSVPN PIVTDNPTNS  60
AMAKGTTPNP TSQPIVRTVT FNETLTDSQS TTTEHGITAG ASVTVKSEAG ILFAKVGVEA  120
TLSFEYNWST STTKTTETSR SWTDSVQITI PPGYVTEHTF IVQTGPFNKN VVLECDITGT  180
TTCVYRFPNT SQDRYTGDNA GMISEALRAM GVPNITYPDF GIAHFTGSGS LIGRMGLQSF  240
VNVVERPLSG RSGQVREYQI PLTGRSGLDI PIFDPVVSRQ                        280

SEQ ID NO: 75           moltype = AA  length = 1251
FEATURE                 Location/Qualifiers
REGION                  1..1251
                        note = Description of Unknown: Organism from environmental
                         sample
source                  1..1251
                        mol_type = protein
                        organism = unidentified
SEQUENCE: 75
LCLFILSTRR SDRMATLNEL YPVPYNVLSP AAYNKYNVLI STSNSDQVDD ILQQIKDIYG  60
KTGSIPQKLI EQIYGYYNTG KFDYLALTKN LVSLVGLIPE VAPVVPFVNQ FIDLVWPKVF  120
GGPKPPPSIF EQLKPQIQAL VDDAIYKQHL QDLDDAAKGF QNVVHEYYNA VDHLKNYPND  180
SGALKTLHEA IGLVRAFFVN TIPAFQRAGI VAMPYIAQMT TIHLMILRTA ILSGSKWGVT  240
PGDKDTYLTQ FKESIIEQSN WVYDTLKPKL FPDNQGSGLN WNDRSDLIKN ITLTSLDLVA  300
LWPTLHPVNY PMETNIEFTR TITSHHFTPS ESPGNMIFPE LFYLGELSQL QLSLYKNEDG  360
WMQYFDRLQN IIIDSAGQEH TYNFNSGTPY IPGTWLNPFP SNPPRMINQV NYYNAVYGRA  420
RESSFSVGYI DGGTGGVSTG HNVNSDNAHY FEVKDVAPAQ HKLNYVYAPD EGLSDFANVY  480
IPVNTPAVNI IGDIDSDTKQ PIAQIKGFPF EKNSYNNGTV VREWLNGANV IKLSPGQSIG  540
IPITNITQQN YQVRCRYASN GPNDIFFNLD TGGANPIFQT VSFESTSDSG VGVRGEQGTY  600
VVKSIPTDDN SVTVNLPVKT FTVHLTNNGS SDLFLDRIEF MPIVSDTGDS DSVNINSTFS  660
VPANQPKMVW SDDTKTYNFV DLMVEAMVGD VDLVFYKDNN VISRKHFQED YFSMPVPLKT  720
SLAPFNKLVI ENTDGDEDAE SEVDITGTLS NSSTRNMLFT NPQDLSNVIT QVNALFASSA  780
QDALATSVSD YWIEQVVLKV DALSNDLFGK EKKALRKLVN TAKRLSKVRN LLVGGNFDNF  840
```

```
DAWYRGRNVV RVSDHELFKS DHVLLPPPAL YPSYIFQKVE ESKLKPNTRY TVSGFIAHAE  900
DLEIVISRYG QEIQKVVQVP YGEAFPLTSG AASSCCIPRS TRDGKPADPH LFSYSIDVGA  960
LDLEANPGIE IGLRIVKPTG MARVSNLEVR EERPLKASEM RKVQRAARDW RKVYDKERAD  1020
VTALLQPVLN QINALYVNGN WNGAIRSGIT YRDLESIILP ELSTLRHWFM SDRLGEQGAV  1080
LERFQEALNR AYTQLEGSTL LHNGHFTSDI TNWTVEGDAH QTILSDGKRV LRLPDWSSSA  1140
SQTIEIENFD PDQEYQLNVH AKGEGSVTLQ HGETGENVDV HVHNTNSFTT SISEPMTLET  1200
NQVTVEITSE DGEFLVDHIA LVAVPAEGTT SNMNPSMNTA ITPNWNMNRN Q           1251

SEQ ID NO: 76          moltype = AA  length = 631
FEATURE                Location/Qualifiers
REGION                 1..631
                       note = Description of Artificial Sequence: Synthetic
                        polypeptide
source                 1..631
                       mol_type = protein
                       organism = synthetic construct
SEQUENCE: 76
MATLNELYPV PYNVLSPAAY NKYNVLISTS NSDQVDDILQ QIKDIYGKTG SIPQKLIEQI  60
YGYYNTGKFD YLALTKNLVS LVGLIPEVAP VVPFVNQFID LVWPKVFGGP KPPPSIFEQL  120
KPQIQALVDD AIYKQHLQDL DDAAKGFQNV VHEYYNAVDH LKNYPNDSGA LKTLHEAIGL  180
VRAFFVNTIP AFQRAGIVAM PYIAQMTTIH LMILRTAILS GSKWGVTPGD KDTYLTQFKE  240
SIIEQSNWVY DTLKPKLFPD NQGSGLNWND RSDLIKNITL TSLDLVALWP TLHPVNYPME  300
TNIEFTRTIT SHHFTPSESP GNMIFPELFY LGELSQLQLS LYKNEDGWMQ YFDRLQNIII  360
DSAGQEHTYN FNSGTPYIPG TWLNPFPSNP PRMINQVNYY NAVYGRARES SFSVGYIDGG  420
TGGVSTGHNV NSDNAHYFEV KDVAPAQHKL NYVYAPDEGL SDFANVYIPV NTPAVNIIGD  480
IDSDTKQPIA QIKGFPFEKN SYNNGTVVRE WLNGANVIKL SPGQSIGIPI TNITQQNYQV  540
RCRYASNGPN DIFFNLDTGG ANPIFQTVSF ESTSDSGVGV RGEQGTYVVK SIPTDDNSVT  600
VNLPVKTFTV HLTNNGSSDL FLDRIEFMPI V                                631

SEQ ID NO: 77          moltype = AA  length = 305
FEATURE                Location/Qualifiers
source                 1..305
                       mol_type = protein
                       organism = Bacillus sp.
SEQUENCE: 77
MTVVDFNQLI TEYAQSLASS PGNQGVTFTG QYGYIEVGDP SGAPPFTVSN VVATPDTTTY  60
NFSPGSSVFS SSQVVQNSSD TPITQDLTLG QAVQDSNSTS TTNGLSTNYS ITTKSTFTIK  120
FGVTDGNSIS EEIDATFGQT FNFSTTDSNT QTDSQNWTET TSFTVPPYSQ MTVLYTVLGG  180
NYSINTTLTC ELQGCIWFTL NYPGIGDVKE IVDIYFVIEN AGLNGSYPPP GPTGTPFSIS  240
QPGEVAFFGG TGEFTGTQGI QSIVTATSSP LPGYPGQTTT STTPLTSINS DGTVTPASSP  300
IPIYS                                                             305

SEQ ID NO: 78          moltype = AA  length = 569
FEATURE                Location/Qualifiers
source                 1..569
                       mol_type = protein
                       organism = Bacillus sp.
SEQUENCE: 78
MLQCPCTMKP IYSINNTTRK DDLMKYKDRK DAQRKYKQAI LTTVATMTLG VSTLGPTVSA  60
FAAEGDNISV ISSLETQTEN TKLSESNFVD KVKAKIDVLN SEKDKLKPVG KFMGTTILEL  120
IKYANKGPEQ MNDTLRAITM ASIEVIPYGG MFIAPLIGAI WPQTNGINSQ LNALREDLTK  180
LVTNEIDNEQ LNFLNAEFKT LINLQTDLEH AINADNSQNA DENTKNQRGA WANGIEQSFR  240
RLLDHTSSDK HKITNLPIYT KVALAHLLFL DSLNNKAVSS KMNITQQSLK ELYTKDGVKT  300
LANDYVLHIM KTFYDAPQIK KIKQVPEFHF NPDDAENQIK DLKDRLSKVK VQYKEWKDGV  360
MSAGGFGMVP NKEYEFNIAI LEDAISSYEF VEKLYNATVG DPMIKELIKD SGNQEIKELA  420
KDSSEVFVAD TTYKIVYSKA NKVVDFGERG IELPLIWYDH SGKNQRWEFK YDADKKAYQI  480
INRADGRILA YNTTPNADDT ALVTENQHKP EHYWILEDAG AGNVLLVNYA NKNKVLDVYD  540
EKTEDGSRVY VRDKLNDSNA QKFKLVISF                                   569

SEQ ID NO: 79          moltype = AA  length = 546
FEATURE                Location/Qualifiers
REGION                 1..546
                       note = Description of Artificial Sequence: Synthetic
                        polypeptide
source                 1..546
                       mol_type = protein
                       organism = synthetic construct
SEQUENCE: 79
MKYKDRKDAQ RKYKQAILTT VATMTLGVST LGPTVSAFAA EGDNISVISS LETQTENTKL  60
SESNFVDKVK AKIDVLNSEK DKLKPVGKFM GTTILELIKY ANKGPEQMND TLRAITMASI  120
EVIPYGGMFI APLIGAIWPQ TNGINSQLNA LREDLTKLVT NEIDNEQLNF LNAEFKTLIN  180
LQTDLEHAIN ADNSQNADEN TKNQRGAWAN GIEQSFRRLL DHTSSDKHKI TNLPIYTKVA  240
LAHLLFLDSL NNKAVSSKMN ITQQSLKELY TKDGVKTLAN DYVLHIMKTF YDAPQIKKIK  300
QVPEFHFNPD DAENQIKDLK DRLSKVKVQY KEWKDGVMSA GGFGMVPNKE YEFNIAILED  360
AISSYEFVEK LYNATVGDPM IKELIKDSGN QEIKELAKDS SEVFVADTTY KIVYSKANKV  420
VDFGERGIEL PLIWYDHSGK NQRWEFKYDA DKKAYQIINR ADGRILAYNT TPNADDTALV  480
TENQHKPEHY WILEDAGAGN VLLVNYANKN KVLDVYDEKT EDGSRVYVRD KLNDSNAQKF  540
KLVISF                                                            546
```

```
SEQ ID NO: 80          moltype = AA  length = 266
FEATURE                Location/Qualifiers
source                 1..266
                       mol_type = protein
                       organism = Bacillus sp.
SEQUENCE: 80
MAILNLREIL QKAADADTYA GRGAGILNPD VKVSSTVLDI PSTGLVVNTP GTSISYKETY  60
ENRTNQDSQP QTIKFKRETQ NTFSTKTTQG FEFGTGVEVS ASTDIFFASV ETKVSTSFKY  120
NTSTENTIES SETITWEREF PIIIPKKSKT VITYLIRFGG PFTQEINFWA TVTGTFMKEF  180
TLIPTPIGQL IGTLRDQNPN LTINLGPQME GEDPFTRLRF QGTLQINGTI GIDAYGTQED  240
FPLANNPALP ASRTFPLQLA PRTLIF                                     266

SEQ ID NO: 81          moltype = AA  length = 327
FEATURE                Location/Qualifiers
source                 1..327
                       mol_type = protein
                       organism = Bacillus sp.
SEQUENCE: 81
MPIFDFKQKM EEFAADYVKA LGGYQAHNIQ LSYQIQNVSA VPSGSTNINV IPRLARTSVQ  60
NAINNTSVTQ TQTLTFSETT TETDSSTTTH GSKFSTTVSS TSKFSANLKF NEVGTSTEKT  120
IGVSVTGEYN FSNSQTKTVT KGRNWNLTQP VVIPPRTSLT CTLLVYDSPF SVPINLNCNI  180
VGTTKVSSPG VETRNFLGTF DYRKVNDSNT YRYYLPPNSI MQRNWPGKPP EFVGYTTTNS  240
RDDTLIFRGQ GIEEVATGLY STVRFDESPL PGYQGEKRTY YSPAQLVNED NIISSESMNI  300
PIINPFSNTN DFSVVNPITN SLNDFPV                                    327

SEQ ID NO: 82          moltype = AA  length = 283
FEATURE                Location/Qualifiers
source                 1..283
                       mol_type = protein
                       organism = Bacillus sp.
SEQUENCE: 82
MALLNLNDVL SNYVSLLGTP FSNPNNWTSP QFADGPTRSG IQQNSLSITG TSNIDTTPIA  60
ITGIGENMTV YQIINNLDSN IPSTKAVKLE QKVTEGTETT LTQGVETDIK ADASISGVLD  120
FLTLGASASF TTKTSLTNSQ KTTNQKETTW AETTTVTVPA ATKATVYYTV TVGPFNIFVD  180
VDINMIGTVT YFYIIGTPLF PNQGPFVKWT SAPIDIKTIF QSQNVQYPGI SYPSTGGVNI  240
KGKVQLTGKF GLLTTTTMKT ESKNGATNTI PLGSTNQKQT FIF                  283

SEQ ID NO: 83          moltype = AA  length = 398
FEATURE                Location/Qualifiers
source                 1..398
                       mol_type = protein
                       organism = Bacillus sp.
SEQUENCE: 83
LMSKGRGLIM NSQNNINMSS KDIINIFSNY AKNWSQRENG GMSEISLVLP GFEEHALKPG  60
FPIRTNYDDI HEEEKIISLT TTTIENLYDV EQEEYIILSS DVEEWGKWKF TDVATIFGNH  120
VVEVDLPDDL VIPPLGSMGK IPIRLLNEEV KHSGLRTWSV KHPFKLNPRT RVTATLQVKQ  180
KEIKRDFYVE QDLTGYLGVI TEHLVDNSHM SLHQIKQILK CHYHPLIQVI DEGVTIKSKG  240
IFSSLISLEA RIHIKIENLD CPGMHEEYII YNPQTGKTTV LIKDSTRGPQ KRLVAVVSSA  300
PKPLSGQKYR SSGNFSIEAS TLPHGTYALQ WVVESSIPQS PSLHFGVAKD VSGGSDPTLL  360
AAVYSNDTTN IITDRNLYIG GPQSATAEFQ VYVYALYQ                         398

SEQ ID NO: 84          moltype = AA  length = 389
FEATURE                Location/Qualifiers
REGION                 1..389
                       note = Description of Artificial Sequence: Synthetic
                        polypeptide
source                 1..389
                       mol_type = protein
                       organism = synthetic construct
SEQUENCE: 84
MNSQNNINMS SKDIINIFSN YAKNWSQREN GGMSEISLVL PGFEEHALKP GFPIRTNYDD  60
IHEEEKIISL TTTTIENLYD VEQEEYIILS SDVEEWGKWK FTDVATIFGN HVVEVDLPDD  120
LVIPPLGSMG KIPIRLLNEE VKHSGLRTWS VKHPFKLNPR TRVTATLQVK QKEIKRDFYV  180
EQDLTGYLGV ITEHLVDNSH MSLHQIKQIL KCHYHPLIQV IDEGVTIKSK GIFSSLISLE  240
ARIHIKIENL DCPGMHEEYI IYNPQTGKTT VLIKDSTRGP QKRLVAVVSS APKPLSGQKY  300
RSSGNFSIEA STLPHGTYAL QWVVESSIPQ SPSLHFGVAK DVSGGSDPTL LAAVYSNDTT  360
NIITDRNLYI GGPQSATAEF QVYVYALYQ                                  389

SEQ ID NO: 85          moltype = AA  length = 193
FEATURE                Location/Qualifiers
source                 1..193
                       mol_type = protein
                       organism = Bacillus sp.
SEQUENCE: 85
MDENGYKKGS FLHQNHEPLS FLPEELEHME SKPECCEEVN TKVPFCCMVQ VPHGFQYVPS  60
STPKIAYNLD CLSVVEETCR KTIQVEGCGP VEVKLNLLKV VGCIPYIANA TVEGECGKEC  120
EYDVNGRHHI SVCCSGSICI DNVLKCSTEC LPHYTINCHH VNISDFSVKS VCDQGCEMLQ  180
FTGMIEFKHI PYE                                                   193
```

```
SEQ ID NO: 86          moltype = AA  length = 914
FEATURE                Location/Qualifiers
source                 1..914
                       mol_type = protein
                       organism = Bacillus sp.
SEQUENCE: 86
MATLSELYPI NVLANPPAQL DDNSSSFMDI FNQLKDAYDE FSKTGAVDPL KQHLMIAWQA  60
YQTGTVDYLA LVKATISLVG LIPGAEAAVP FINMFVDLVF PTLFGASKAD PYVELFKQIM  120
QAVEKYVDQQ FVTFEISLLT NILEGLQAVI VNVQDAIQVA VCQGKTPSTA ESQDSTTDDS  180
CVTTPIPCIP CAANLDAVTR AFENADTMFD SSLPHFKNPE SNTNDTDNNG FHIKLIGVTL  240
PMYTMAATLQ LVMYQGYIQF MEKWNGLNSA TLNQTKAKLQ EKIRNYSQVV FDTYQKYLPP  300
LDTTHRDTLN KHLDYVRSMK LNVFDIAYMW PTLDSTHYET PITLERTRLV HSNIVGPMAV  360
SQEDLDNEGG YSRLTILPVS QQLPNVVDRP DPTITTTTPD LKDLITHSHY QPFRFKNAAF  420
HQTSKKSSVC LSDGIKQTLI VNDKEYTLTS GETSEYWSAE NVNAGYQTAF TGESAIYAES  480
QVMNGLDHAN LHPGGTCWFG NPTIDDSIPL STEKIQFIYM VTGDSAMPGD KGKRGAFSSH  540
VSNEVVPENI LNYDADNPSS QGFPAEKGTL HNAIGSLQYA EELLNGNNAI KLTYQQILQL  600
PITVVNTGFY NIRIRYASQK DITGYFRVNT PAGDLNQSSV TFINTSDTTN KMYVKGANGN  660
YMLLTVAEAI KFSSGQATVY IQNNSNDDLF LDRIEFIPLT PSQLPSPSTA NQFTFVGPYI  720
MLPQEEFTIW QTSQTCMYNP NSTLSFTIKG SGEFQVLDMN NNIIARRTEN QNNPTTETWN  780
LPQNVEKIRF VANNYVILRN IIGKINCQEP VKPCTLGGQT LVDRDYNTSG EQVLWSSTDP  840
MGNCTVDIVI DGDFISSIAT LQFQDNTGTV VRSIDFGPGE QTQTVSVAST TKIVLKPTTF  900
GQISGHLKIK VVTN                                                    914

SEQ ID NO: 87          moltype = AA  length = 699
FEATURE                Location/Qualifiers
REGION                 1..699
                       note = Description of Artificial Sequence: Synthetic
                        polypeptide
source                 1..699
                       mol_type = protein
                       organism = synthetic construct
SEQUENCE: 87
MATLSELYPI NVLANPPAQL DDNSSSFMDI FNQLKDAYDE FSKTGAVDPL KQHLMIAWQA  60
YQTGTVDYLA LVKATISLVG LIPGAEAAVP FINMFVDLVF PTLFGASKAD PYVELFKQIM  120
QAVEKYVDQQ FVTFEISLLT NILEGLQAVI VNVQDAIQVA VCQGKTPSTA ESQDSTTDDS  180
CVTTPIPCIP CAANLDAVTR AFENADTMFD SSLPHFKNPE SNTNDTDNNG FHIKLIGVTL  240
PMYTMAATLQ LVMYQGYIQF MEKWNGLNSA TLNQTKAKLQ EKIRNYSQVV FDTYQKYLPP  300
LDTTHRDTLN KHLDYVRSMK LNVFDIAYMW PTLDSTHYET PITLERTRLV HSNIVGPMAV  360
SQEDLDNEGG YSRLTILPVS QQLPNVVDRP DPTITTTTPD LKDLITHSHY QPFRFKNAAF  420
HQTSKKSSVC LSDGIKQTLI VNDKEYTLTS GETSEYWSAE NVNAGYQTAF TGESAIYAES  480
QVMNGLDHAN LHPGGTCWFG NPTIDDSIPL STEKIQFIYM VTGDSAMPGD KGKRGAFSSH  540
VSNEVVPENI LNYDADNPSS QGFPAEKGTL HNAIGSLQYA EELLNGNNAI KLTYQQILQL  600
PITVVNTGFY NIRIRYASQK DITGYFRVNT PAGDLNQSSV TFINTSDTTN KMYVKGANGN  660
YMLLTVAEAI KFSSGQATVY IQNNSNDDLF LDRIEFIPL                         699

SEQ ID NO: 88          moltype = AA  length = 376
FEATURE                Location/Qualifiers
source                 1..376
                       mol_type = protein
                       organism = Bacillus sp.
SEQUENCE: 88
MRKKTVTSVT ATIMSLGILG LGGTPSAYAL ENNPIYYTDF GQENNQISEQ YKKDTERFLS  60
GWFQYGNTAQ TIGKINDSKA SDEIIMAQNG TLDNTQGSTP QKFTTISESV KQIDSVTTTK  120
GLEGSFEAGL EASFESEQSI GVAKAKESLK ATMKVGMKKS ESQANTQTNE RMITIPSQNI  180
EVPAGKKYQI RYIVKKAEMS GELSQVKEIT RGTSNDGLIN SPRVSYAIDV SKPGTNAIDS  240
MYWEDIYNAT PYQFFNRLDE IKNKFIKGGP QQEFMDVYLQ RHNVGKDRVV FQIDGMDNQA  300
GNNDNGRYRM GEQGLLENIY LNHNLKKVYV NSENIPFTAS IGLDYVIQLV DITNGDDTLL  360
KETQPSTVGQ TAPKFK                                                  376

SEQ ID NO: 89          moltype = AA  length = 348
FEATURE                Location/Qualifiers
REGION                 1..348
                       note = Description of Artificial Sequence: Synthetic
                        polypeptide
source                 1..348
                       mol_type = protein
                       organism = synthetic construct
SEQUENCE: 89
MLENNPIYYT DFGQENNQIS EQYKKDTERF LSGWFQYGNT AQTIGKINDS KASDEIIMAQ  60
NGTLDNTQGS TPQKFTTISE SVKQIDSVTT TKGLEGSFEA GLEASFESEQ SIGVAKAKES  120
LKATMKVGMK KSESQANTQT NERMITIPSQ NIEVPAGKKY QIRYIVKKAE MSGELSQVKE  180
ITRGTSNDGL INSPRVSYAI DVSKPGTNAI DSMYWEDIYN ATPYQFFNRL DEIKNKFIKG  240
GPQQEFMDVY LQRHNVGKDR VVFQIDGMDN QAGNNDNGRY RMGEQGLLEN IYLNHNLKKV  300
YVNSENIPFT ASIGLDYVIQ LVDITNGDDT LLKETQPSTV GQTAPKFK               348

SEQ ID NO: 90          moltype = AA  length = 1376
FEATURE                Location/Qualifiers
source                 1..1376
                       mol_type = protein
```

```
                        organism = Bacillus sp.
SEQUENCE: 90
LVIYMPRLED LYPRSDAGFQ AIRLETEDST SESLLQNLKT GIEKGTYQQA IDTIFQNVSS  60
GTIDYVSFVD RTLRLAPMST PETGLFSPLV GLYFSGLNQI PTTRDIQSNV FQAMNPLIAD  120
ALDRPLTTDE LDHMNSEVSG LRAALIPYQT AMNQIQNVYG GFENATSAAR QAFVNAVENV  180
DAILADRLPS LLYTDPAQAM MGLPYFCGFA TMHLQLYKDI IMHGSTWNPD YYDAQVIGIK  240
KATLKKFIQL YAQEAYTGFT QGLSLLGGGN LKPSNTATFS QQKQYIQFLT INALDKVRLF  300
PTFDPDLYPY GLTTNIPTNH QFVSSILPGY CMPSSFPSDF DFPISDNGAI RKDPELVTIE  360
SDTSTDKTYG SPVFLQMVDR NGTVRKWGKE SGDQYSLPLI DNFDPLIGFG AAAAVRFDSN  420
GHPKYDLCSS DSIFGFQFLT ASGKLTTWEL VTLPADFMPW LRAPNGYKIR TLYPLYDSSK  480
PDTPFGGYVA VFSPINPTTL GFLAPDASGN LSVIGIPFES FGEQQGWVVP EWTTGSNVVQ  540
LPPGQTITVP IFNVLEGQYT MRVNYACNAN VDMLVNIETG TGNSVFSNTL SFFATNSNDF  600
PGKNGYYRNQ LITDTLDMGT FSITIDYIQL TNKGTSDIFL NRVEFIPAAS NTVQTGTFIA  660
QAFTIPNDTN SITIYEGNTV YNTIELSYAF QTESDSFPVE FQFFYKGLLV DTVMPTASVR  720
VTKQVPLRFD QIKLHSTTPL SGTHNVNVIA KLTFDSTIPN INVNTSVPSA QQSGLLASDF  780
NQAAKIWEAP PGIAVLQLTN LQVRITNDSL YKTVLIFAAD DLPLSGHGAP PAFFDSIWAF  840
ASPLIPSVPV GPSVPIHLQG DTELIDKRAS PLNRTSFHLE SSTILIDADE IVSKHTSLTK  900
QTDLNSITGQ VNALFTFSTH DTLASDISDY QIDQVVLKVD ALSDEVFGKE KKALRKLVNK  960
AKQLSKARNL LIGGSFDTLD AWQLGKNVVR REDGDLFKGE HLLLPPPTTL SPSYAYQKID  1020
EAKLKPYTRY TVSGFVAQGD PLEIVVSRYG KEIEKTLHVP YEEAHPITSE PTPNCCQSGT  1080
SSSCNGETPD SHFFHYSIDV GALQPEANLG ISLGLRIGET AENTLGLARI GNLEMREERP  1140
LTASEIRKVQ KVETKWKKAW EQERADVTAK LQPVIDQINA LYVNNDWNGL VRPHIVEADI  1200
HAITIPDLPK QRHWFMTDRE GEHRSITEQM QQALTRAMNL LESQNLIHNG SFTNELMNWT  1260
VEGGATIQLV SGENKALFLP HWDSSAAQNV QITNFDEDTE YTLRVRGKGK GKITIQHGTT  1320
GEQVETLVFS QKNMQKQELS YLTFETAEIE IKILSEDGGL TIDSIELIEM IEMTEM      1376

SEQ ID NO: 91           moltype = AA  length = 1372
FEATURE                 Location/Qualifiers
REGION                  1..1372
                        note = Description of Artificial Sequence: Synthetic
                         polypeptide
source                  1..1372
                        mol_type = protein
                        organism = synthetic construct
SEQUENCE: 91
MPRLEDLYPR SDAGFQAIRL ETEDSTSESL LQNLKTGIEK GTYQQAIDTI FQNVSSGTID  60
YVSFVDRTLR LAPMSTPETG LFSPLVGLYF SGLNQIPTTR DIQSNVFQAM NPLIADALDR  120
PLTTDELDHM NSEVSGLRAA LIPYQTAMNQ IQNVYGGFEN ATSAARQAFV NAVENVDAIL  180
ADRLPSLLYT DPAQAMMGLP YFCGFATMHL QLYKDIIMHG STWNPDYYDA QVIGIKKATL  240
KKFIQLYAQE AYTGFTQGLS LLGGGNLKPS NTATFSQQKQ YIQFLTINAL DKVRLFPTFD  300
PDLYPYGLTT NIPTNHQFVS SILPGYCMPS SFPSDFDFPI SDNGAIRKDP ELVTIESDTS  360
TDKTYGSPVF LQMVDRNGTV RKWGKESGDQ YSLPLIDNFD PLIGFGAAAA VRFDSNGHPK  420
YDLCSSDSIF GFQFLTASGK LTTWELVTLP ADFMPWLRAP NGYKIRTLYP LYDSSKPDTP  480
FGGYVAVFSP INPTTLGFLA PDASGNLSVI GIPFESFGEQ QGWVVPEWTT GSNVVQLPPG  540
QTITVPIFNV LEGQYTMRVN YACNANVDML VNIETGTGNS VFSNTLSFFA TNSNDFPGKN  600
GYYRNQLITD TLDMGTFSIT IDYIQLTNKG TSDIFLNRVE FIPAASNTVQ TGTFIAQAFT  660
IPNDTNSITI YEGNTVYNTI ELSYAFQTES DSFPVEFQFF YKGLLVDTVM PTASVRVTKQ  720
VPLRFDQIKL HSTTPLSGTH NVNVIAKLTF DSTIPNINVN TSVPSAQQSG LLASDFNQAA  780
KIWEAPPGIA VLQLTNLQVR ITNDSLYKTV LIFAADDLPL SGHGAPPAFF DSIWAFASPL  840
IPSVPVGPSV PIHLQGDTEL IDKRASPLNR TSFHLESSTI LIDADEIVSK HTSLTKQTDL  900
NSITGQVNAL FTFSTHDTLA SDISDYQIDQ VVLKVDALSD EVFGKEKKAL RKLVNKAKQL  960
SKARNLLIGG SFDTLDAWQL GKNVVRREDG DLFKGEHLLL PPPTTLSPSY AYQKIDEAKL  1020
KPYTRYTVSG FVAQGDPLEI VVSRYGKEIE KTLHVPYEEA HPITSEPTPN CCQSGTSSSC  1080
NGETPDSHFF HYSIDVGALQ PEANLGISLG LRIGETAENT LGLARIGNLE MREERPLTAS  1140
EIRKVQKVET KWKKAWEQER ADVTAKLQPV IDQINALYVN NDWNGLVRPH IVEADIHAIT  1200
IPDLPKQRHW FMTDREGEHR SITEQMQQAL TRAMNLLESQ NLIHNGSFTN ELMNWTVEGG  1260
ATIQLVSGEN KALFLPHWDS SAAQNVQITN FDEDTEYTLR VRGKGKGKIT IQHGTTGEQV  1320
ETLVFSQKNM QKQELSYLTF ETAEIEIKIL SEDGGLTIDS IELIEMIEMT EM          1372

SEQ ID NO: 92           moltype = AA  length = 644
FEATURE                 Location/Qualifiers
REGION                  1..644
                        note = Description of Artificial Sequence: Synthetic
                         polypeptide
source                  1..644
                        mol_type = protein
                        organism = synthetic construct
SEQUENCE: 92
MPRLEDLYPR SDAGFQAIRL ETEDSTSESL LQNLKTGIEK GTYQQAIDTI FQNVSSGTID  60
YVSFVDRTLR LAPMSTPETG LFSPLVGLYF SGLNQIPTTR DIQSNVFQAM NPLIADALDR  120
PLTTDELDHM NSEVSGLRAA LIPYQTAMNQ IQNVYGGFEN ATSAARQAFV NAVENVDAIL  180
ADRLPSLLYT DPAQAMMGLP YFCGFATMHL QLYKDIIMHG STWNPDYYDA QVIGIKKATL  240
KKFIQLYAQE AYTGFTQGLS LLGGGNLKPS NTATFSQQKQ YIQFLTINAL DKVRLFPTFD  300
PDLYPYGLTT NIPTNHQFVS SILPGYCMPS SFPSDFDFPI SDNGAIRKDP ELVTIESDTS  360
TDKTYGSPVF LQMVDRNGTV RKWGKESGDQ YSLPLIDNFD PLIGFGAAAA VRFDSNGHPK  420
YDLCSSDSIF GFQFLTASGK LTTWELVTLP ADFMPWLRAP NGYKIRTLYP LYDSSKPDTP  480
FGGYVAVFSP INPTTLGFLA PDASGNLSVI GIPFESFGEQ QGWVVPEWTT GSNVVQLPPG  540
QTITVPIFNV LEGQYTMRVN YACNANVDML VNIETGTGNS VFSNTLSFFA TNSNDFPGKN  600
GYYRNQLITD TLDMGTFSIT IDYIQLTNKG TSDIFLNRVE FIPA                  644
```

```
SEQ ID NO: 93          moltype = AA  length = 328
FEATURE                Location/Qualifiers
REGION                 1..328
                       note = Description of Unknown: Organism from environmental
                        sample
source                 1..328
                       mol_type = protein
                       organism = unidentified
SEQUENCE: 93
MKKISKNILG IAAIASMGIS FSIADPGLVS AAPSNSTENN IKKEIKSNTS IEDWSNPFYD  60
AGIIVGKNLD VPGIYAHTFT RFNSIKFEQY SVEADGSPTI TDSEALFVGK STLTNNTNND  120
QTLTTDSFSK TISNSVENST THGFSFGQTA SAKFNVPLVG ETGVELSTEY NFSNTNENRK  180
AESYTYTATP QTIKVPAHSA VEVIVNLNTA KINGNVKLLS LVDGRYDSKY NNMVGGSSGS  240
LTEIAARALQ YDKNLNLSVN GVESQDKVYV VGRGNYAAEY GTEFAVTVRP VAKPSTFAAK  300
SRSMVAENSK TTNEGYTYTV KPEVKKEQ                                    328

SEQ ID NO: 94          moltype = AA  length = 305
FEATURE                Location/Qualifiers
REGION                 1..305
                       note = Description of Artificial Sequence: Synthetic
                        polypeptide
source                 1..305
                       mol_type = protein
                       organism = synthetic construct
SEQUENCE: 94
MDPGLVSAAP SNSTENNIKK EIKSNTSIED WSNPFYDAGI IVGKNLDVPG IYAHTFTRFN  60
SIKFEQYSVE ADGSPTITDS EALFVGKSTL TNNTNNDQTL TTDSFSKTIS NSVENSTTHG  120
FSFGQTASAK FNVPLVGETG VELSTEYNFS NTNENRKAES YTYTATPQTI KVPAHSAVEV  180
IVNLNTAKIN GNVKLLSLVD GRYDSKYNNM VGGSSGSLTE IAARALQYDK NLNLSVNGVE  240
SQDKVYVVGR GNYAAEYGTE FAVTVRPVAK PSTFAAKSRS MVAENSKTTN EGYTYTVKPE  300
VKKEQ                                                             305

SEQ ID NO: 95          moltype = AA  length = 260
FEATURE                Location/Qualifiers
source                 1..260
                       mol_type = protein
                       organism = Bacillus sp.
SEQUENCE: 95
MDIQDVIELI NNYAHNWTEQ QGGTHSEIRL IDSRFANYAL KIEAAHTTYL DPTKQDMPDV  60
KLDTQVFTNT STQPKTFQFD MFGEYDTWQK WKIQEGATES GKRLFNIEPL YLSEDVSNPL  120
SLFLDETLTL SGKKAFSVEG RNFTVRPRFK VTATLMIKPK TSTRAFDVTH DATGYVELFT  180
TLASGDVQES LHNVGAIFQK YYSPYIEVNG GRVTFRNRGE YQSLDASDIY IHIFAESLDI  240
PGLTEEYNIY DLSNGAVLEL                                             260

SEQ ID NO: 96          moltype = AA  length = 789
FEATURE                Location/Qualifiers
REGION                 1..789
                       note = Description of Unknown: Organism from environmental
                        sample
source                 1..789
                       mol_type = protein
                       organism = unidentified
SEQUENCE: 96
MNMNKNNTKL SARALPSFID YFNGIYGFAT GIKDIMNMIF KTDTGGDLTL DEILKNQQLL  60
NDISGKLDGV NGSLNDLIAQ GNLNTELSKE ILKIANEQNQ VLNDVNNKLN AINTMLHIYL  120
PKITSMLSDV MKQNYALSLQ IEYLSKQLQE ISDKLDIINV NVLINSTLTE ITPAYQRIKY  180
VNEKFEELTF ATETTLKAKN DSSPADILDE LTELTELAKS VTKNDVDGFE FYLNTFHDVM  240
VGNNLFGRSA LKTASELIAK ENVKTSGSEV GNVYNFLIVL TALQAKAFLT LTTCRKLLGL  300
ADIDYTSIMN EHLNKEKEEF RVNILPTLSN TFSNPNYEKV KGSDEDAKMI VEAKPGYALV  360
GFEMSNDSIT VLKAYQAKLK QNYQVDKKSL SEIVYGDMDK LFCPNQSEQI YYTNNIEFPN  420
EYVITKITFT KKMNSLRYEA TANFYDPSTG GIDLNKTKVE SSEAEYSTLR ASNDGVYMPL  480
GIISETFLTP INGFGLVVDE NSRLVTLTCR SYLREILLTT DLSNKETKLI VPPNGFISNI  540
VENGNLEGEN LEPWKANNKN AYVDHIGGVN GTKVLYVHKD GEFSQFIGDK LKSKTEYVIK  600
YIVKGKAAIY LKNEKNGDYI YEETNNELED FQTVTKRFIT GTESSGVHLI FTSQNGEEVF  660
GGNFIILEIR PSEELLSPEL IKSDAWVGSQ GTWISGNSLN INSNVNGTFR QNLALESYST  720
YSMNFTVNGF GKVTVRNSRE VLFEKSYPQF SPKDISEKFT TAANNTGLYV ELSRSTSGGV  780
INFQNFSIK                                                         789

SEQ ID NO: 97          moltype = AA  length = 787
FEATURE                Location/Qualifiers
REGION                 1..787
                       note = Description of Artificial Sequence: Synthetic
                        polypeptide
source                 1..787
                       mol_type = protein
                       organism = synthetic construct
SEQUENCE: 97
MNKNNTKLSA RALPSFIDYF NGIYGFATGI KDIMNMIFKT DTGGDLTLDE ILKNQQLLND  60
```

```
ISGKLDGVNG SLNDLIAQGN LNTELSKEIL KIANEQNQVL NDVNNKLNAI NTMLHIYLPK  120
ITSMLSDVMK QNYALSLQIE YLSKQLQEIS DKLDIINVNV LINSTLTEIT PAYQRIKYVN  180
EKFEELTFAT ETTLKAKNDS SPADILDELT ELTELAKSVT KNDVDGFEFY LNTFHDVMVG  240
NNLFGRSALK TASELIAKEN VKTSGSEVGN VYNFLIVLTA LQAKAFLTLT TCRKLLGLAD  300
IDYTSIMNEH LNKEKEEFRV NILPTLSNTF SNPNYEKVKG SDEDAKMIVE AKPGYALVGF  360
EMSNDSITVL KAYQAKLKQN YQVDKKSLSE IVYGDMDKLF CPNQSEQIYY TNNIEFPNEY  420
VITKITFTKK MNSLRYEATA NFYDPSTGGI DLNKTKVESS EAEYSTLRAS NDGVYMPLGI  480
ISETFLTPIN GFGLVVDENS RLVTLTCRSY LREILLTTDL SNKETKLIVP PNGFISNIVE  540
NGNLEGENLE PWKANNKNAY VDHIGGVNGT KVLYVHKDGE FSQFIGDKLK SKTEYVIKYI  600
VKGKAAIYLK NEKNGDYIYE ETNNELEDFQ TVTKRFITGT ESSGVHLIFT SQNGEEVFGG  660
NFIILEIRPS EELLSPELIK SDAWVGSQGT WISGNSLNIN SNVNGTFRQN LALESYSTYS  720
MNFTVNGFGK VTVRNSREVL FEKSYPQFSP KDISEKFTTA ANNTGLYVEL SRSTSGGVIN  780
FQNFSIK                                                           787

SEQ ID NO: 98          moltype = AA  length = 293
FEATURE                Location/Qualifiers
source                 1..293
                       mol_type = protein
                       organism = Bacillus sp.
SEQUENCE: 98
LLGGETMIHD LKEDIINFTK WYAEKYYNAN PDTFHDEKVF DPSVSNTEVV PDKIEFDTTP  60
KLKNRVTDIL INDTSVSQSI TPKLSTRTVE TTSITTTEGY KIGAGVKYTS TMKLKLFLIG  120
EISNSIEIAV TSEYNHSTSE TQTNTTEKIW EYTRPVIVPP RTKVTATLEI YAGPVKVPVT  180
LRSTITGMGI ASTGYGYILG SVAYKDRGGK IWIDSWRSRS LYDFRSTWPG FKPVYVGTDG  240
EYGVKVQGTA QVELELGLYG VVTYKEEPLL GNDSNNSQTY CEIIPRQGLN TRI         293

SEQ ID NO: 99          moltype = AA  length = 287
FEATURE                Location/Qualifiers
REGION                 1..287
                       note = Description of Artificial Sequence: Synthetic
                        polypeptide
source                 1..287
                       mol_type = protein
                       organism = synthetic construct
SEQUENCE: 99
MIHDLKEDII NFTKWYAEKY YNANPDTFHD EKVFDPSVSN TEVVPDKIEF DTTPKLKNRV  60
TDILINDTSV SQSITPKLST RTVETTSITT TEGYKIGAGV KYTSTMKLKL FLIGEISNSI  120
EIAVTSEYNH STSETQTNTT EKIWEYTRPV IVPPRTKVTA TLEIYAGPVK VPVTLRSTIT  180
GMGIASTGYG YILGSVAYKD RGGKIWIDSW RSRSLYDFRS TWPGFKPVYV GTDGEYGVKV  240
QGTAQVELEL GLYGVVTYKE EPLLGNDSNN SQTYCEIIPR QGLNTRI                287

SEQ ID NO: 100         moltype = AA  length = 393
FEATURE                Location/Qualifiers
source                 1..393
                       mol_type = protein
                       organism = Bacillus sp.
SEQUENCE: 100
VVHSTTTTNE KEFSSMLRKN RIFFAGMTAL TIVGSGLTVS IPTAFANTQE NINPLQSVQG  60
QEFTDENGQV ISPGTFANIS PYWLIGDSNN ELYNFYNQVK QRIVDKKNKE QNMLKLDEYL  120
NDLWFVGAVS QLYETPNDHN KRLEASNLVR WYKNNNAAKP NFDILESKLD NVEPILDITE  180
PIGYFATDSE YTNNSPHRGE YLIPGWSNTT STTYTTTTTQ GFSIGANGDI KISLPFLDKL  240
GLTGTYNFSK SDSVTTTDST TLTIPVQTIQ VSPFSHSKTS FYFQTHQYRA KFDVTAKFKA  300
EVGRDAEYTR KRSAFYLLAK YNDYLPKGIV VENGGKLTLV GKGEISVPNH INGFKLVKET  360
KETPLSGEEG KTIKESYTKN PNTNKFNPEI KKT                               393

SEQ ID NO: 101         moltype = AA  length = 378
FEATURE                Location/Qualifiers
REGION                 1..378
                       note = Description of Artificial Sequence: Synthetic
                        polypeptide
source                 1..378
                       mol_type = protein
                       organism = synthetic construct
SEQUENCE: 101
MLRKNRIFFA GMTALTIVGS GLTVSIPTAF ANTQENINPL QSVQGQEFTD ENGQVISPGT  60
FANISPYWLI GDSNNELYNF YNQVKQRIVD KKNKEQNMLK LDEYLNDLWF VGAVSQLYET  120
PNDHNKRLEA SNLVRWYKNN NAAKPNFDIL ESKLDNVEPI LDITEPIGYF ATDSEYTNNS  180
PHRGEYLIPG WSNTTSTTYT TTTTQGFSIG ANGDIKISLP FLDKLGLTGT YNFSKSDSVT  240
TTDSTTLTIP VQTIQVSPFS HSKTSFYFQT HQYRAKFDVT AKFKAEVGRD AEYTRKRSAF  300
YLLAKYNDYL PKGIVVENGG KLTLVGKGEI SVPNHINGFK LVKETKETPL SGEEGKTIKE  360
SYTKNPNTNK FNPEIKKT                                                378

SEQ ID NO: 102         moltype = AA  length = 348
FEATURE                Location/Qualifiers
REGION                 1..348
                       note = Description of Artificial Sequence: Synthetic
                        polypeptide
source                 1..348
                       mol_type = protein
```

```
                         organism = synthetic construct
SEQUENCE: 102
MNTQENINPL QSVQGQEFTD ENGQVISPGT FANISPYWLI GDSNNELYNF YNQVKQRIVD  60
KKNKEQNMLK LDEYLNDLWF VGAVSQLYET PNDHNKRLEA SNLVRWYKNN NAAKPNFDIL  120
ESKLDNVEPI LDITEPIGYF ATDSEYTNNS PHRGEYLIPG WSNTTSTTYT TTTTQGFSIG  180
ANGDIKISLP FLDKLGLTGT YNFSKSDSVT TTDSTTLTIP VQTIQVSPFS HSKTSFYFQT  240
HQYRAKFDVT AKFKAEVGRD AEYTRKRSAF YLLAKYNDYL PKGIVVENGG KLTLVGKGEI  300
SVPNHINGFK LVKETKETPL SGEEGKTIKE SYTKNPNTNK FNPEIKKT              348

SEQ ID NO: 103           moltype = AA  length = 595
FEATURE                  Location/Qualifiers
source                   1..595
                         mol_type = protein
                         organism = Bacillus sp.
SEQUENCE: 103
MKYKNRTHAK RKYKQALLAT VATMTLGVST LGNASSAFAE AKTEAQQEQA TTDSLGAGGG  60
ATLEEQWKEM TKELGDHHSP SLNAKGAADL LSKGAFSFYK DAHSNKGNFN NTFRTLSMGI  120
SEYFPYGKLF ISPLIGLLWS ETVSDKNNQF ESLIQEMSSL MDKKIEEFDL STIKRQIVAL  180
KKEMQVFESL VNSQILTESF YSAGSPEESA RTKAEHLQAK FHELISLCQK DKLSEAELPL  240
YTKIANIHLL FLDFMDKNWN KSKLQIDQKS FNDLYANDIK NAAQTYAQHI HDTFVLSNQK  300
IDKKLSDIAK YGDHKATLEW LRNKWASLGN DLALKEKGKT GSSNRSLAKV KQEYDAFEKI  360
YDNYKNLLDK KNTYQASTVD DTGFHAALGK WKKEDKKWYF LNIHGDKQIG WVLSRNSNYY  420
YLNPEKTDIK NSAGVTFKPG EMVTGKIDIK GKTYFFKPET GEMITGWVQD GDKYYYVSHY  480
DGFKNLNDVA FKEGEFVTGW IQPPGGNTYY LSPTDGSKND AGVVFNKGEM MTGWVAVAHD  540
GKSTNTNPET YGGAWYYFDD KNNSNFQGTL GRMLHDEYVT TKDGTWWINE NGTKK       595

SEQ ID NO: 104           moltype = AA  length = 557
FEATURE                  Location/Qualifiers
REGION                   1..557
                         note = Description of Artificial Sequence: Synthetic
                          polypeptide
source                   1..557
                         mol_type = protein
                         organism = synthetic construct
SEQUENCE: 104
MEAKTEAQQE QATTDSLGAG GGATLEEQWK EMTKELGDHH SPSLNAKGAA DLLSKGAFSF  60
YKDAHSNKGN FNNTFRTLSM GISEYFPYGK LFISPLIGLL WSETVSDKNN QFESLIQEMS  120
SLMDKKIEEF DLSTIKRQIV ALKKEMQVFE SLVNSQILTE SFYSAGSPEE SARTKAEHLQ  180
AKFHELISLC QKDKLSEAEL PLYTKIANIH LLFLDFMDKN WNKSKLQIDQ KSFNDLYAND  240
IKNAAQTYAQ HIHDTFVLSN QKIDKKLSDI AKYGDHKATL EWLRNKWASL GNDLALKEKG  300
KTGSSNRSLA KVKQEYDAFE KIYDNYKNLL DKKNTYQAST VDDTGFHAAL GKWKKEDKKW  360
YFLNIHGDKQ IGWVLSRNSN YYYLNPEKTD IKNSAGVTFK PGEMVTGKID IKGKTYFFKP  420
ETGEMITGWV QDGDKYYYVS HYDGFKNLND VAFKEGEFVT GWIQPPGGNT YYLSPTDGSK  480
NDAGVVFNKG EMMTGWVAVA HDGKSTNTNP ETYGGAWYYF DDKNNSNFQG TLGRMLHDEY  540
VTTKDGTWWI NENGTKK                                                  557

SEQ ID NO: 105           moltype = AA  length = 340
FEATURE                  Location/Qualifiers
source                   1..340
                         mol_type = protein
                         organism = Bacillus sp.
SEQUENCE: 105
MHQKSNAWKG DFRMVYFKKT WKVTPIIVLS TSILFSPVCT FAAETSSSVQ ANSIASQGNV  60
IQGYLFKNGV KTPVYKKSGI SNKSMQLDAT PYPELSSNPN DPILEKGSSI TESGNIGSIL  120
YFSRAPFTIN DQNQNLYLEK SADNKKVTAG KYDPSTLQKT PEFSFSAESF SPENYQDFMS  180
FFDGTTVKRE TAFHKLGSGV VPKTGAYTFS QAVTSGLSTA DAIGGSLTLG YKISIKAGGG  240
VIPAETTNEF SSQLTASYNH TITVSNQVTN TQTLSNPKAP DTYQYDKYVG AVYQLCSKYT  300
VLPGSALSKE ISAGKAILAQ TAFSYDDSTL YLAVTPGAGS                        340

SEQ ID NO: 106           moltype = AA  length = 327
FEATURE                  Location/Qualifiers
REGION                   1..327
                         note = Description of Artificial Sequence: Synthetic
                          polypeptide
source                   1..327
                         mol_type = protein
                         organism = synthetic construct
SEQUENCE: 106
MVYFKKTWKV TPIIVLSTSI LFSPVCTFAA ETSSSVQANS IASQGNVIQG YLFKNGVKTP  60
VYKKSGISNK SMQLDATPYP ELSSNPNDPI LEKGSSITES GNIGSILYFS RAPFTINDQN  120
QNLYLEKSAD NKKVTAGKYD PSTLQKTPEF SFSAESFSPE NYQDFMSFFD GTTVKRETAF  180
HKLGSGVVPK TGAYTFSQAV TSGLSTADAI GGSLTLGYKI SIKAGGGVIP AETTNEFSSQ  240
LTASYNHTIT VSNQVTNTQT LSNPKAPDTY QYDKYVGAVY QLCSKYTVLP GSALSKEISA  300
GKAILAQTAF SYDDSTLYLA VTPGAGS                                      327

SEQ ID NO: 107           moltype = AA  length = 299
FEATURE                  Location/Qualifiers
REGION                   1..299
                         note = Description of Artificial Sequence: Synthetic
```

```
                         polypeptide
source                  1..299
                        mol_type = protein
                        organism = synthetic construct
SEQUENCE: 107
MAETSSSVQA NSIASQGNVI QGYLFKNGVK TPVYKKSGIS NKSMQLDATP YPELSSNPND  60
PILEKGSSIT ESGNIGSILY FSRAPFTIND QNQNLYLEKS ADNKKVTAGK YDPSTLQKTP  120
EFSFSAESFS PENYQDFMSF FDGTTVKRET AFHKLGSGVV PKTGAYTFSQ AVTSGLSTAD  180
AIGGSLTLGY KISIKAGGGV IPAETTNEFS SQLTASYNHT ITVSNQVTNT QTLSNPKAPD  240
TYQYDKYVGA VYQLCSKYTV LPGSALSKEI SAGKAILAQT AFSYDDSTLY LAVTPGAGS   299

SEQ ID NO: 108          moltype = AA  length = 1176
FEATURE                 Location/Qualifiers
REGION                  1..1176
                        note = Description of Unknown: Organism from environmental
                         sample
source                  1..1176
                        mol_type = protein
                        organism = unidentified
SEQUENCE: 108
MDCNLQSQQN IPYNVLAIPV SNVNSLTDTV EQLKKAWEAF QKTGSFSLTA LQQGFAASQG  60
GTFNYLALLQ SGISLAGSFV PGGTFVAPIV NMVIGWLWPH KNKKADTENL INLIDSEIQK  120
QLNKALLDQD KNDWTSYLES IFDSSNNLNG AIIDAQWSGT VNDTNRTLKQ PTESDYINVV  180
TNFIAADGDI SNNEHHIMNG NFNVAAAPYF VIGATARFAT MQSYIKFCSA WIDKVGLSDS  240
QLATQKANLD RTKQTMRNAI YNYTEQVMKT FKDPNNMPTI GNNKFSVDVY NVYIKGMTLN  300
VLDIVAIWPS LYPDDYTSQT ALEQTRVTFS NMVGQEEGTD GTLKIYNTFD SLSYQHNLIP  360
NNNVNLISYY NDELQNLQLG VYTPAKKGNG YAYPFGFILN YTNSKYKYGD SHDPESLGEL  420
FTLPAPIQQI NSATQKSIIL DGETINGIGA SLAGYCTTGC SPVEAPFSCT STANNYKESC  480
NPSDTNQKIN ALYPFTQTNV QGNTGKLGVL ASFVPYDLNP ENIFGELDPD TNNVILKGIP  540
AEKGYFPNNT RPTVVKEWIN GANAVLLDSG NTLFMTATNL TATQYKIRIR YANPNSNTQI  600
GVRITQNGSL IFNSNLTLYS TTDMNSTLPL NVYVTGENGN YTLLNLYSTT NVLSTGDITL  660
QLTGGDQKIF IDRIEFVPTM PVPGNTNNNP PYHGCAIAGT QQFCFGPPKF EQVSDLEKIA  720
TQVYMLFKSS PYEELALEVS SYQISQVALK VMALSDELFC EEKSLLRKLV NKAKQLLETS  780
NLLIGGNFET TQNWVLGTNA YINYDSFLFN GNYLSLQPAS GFFTSYAYQK IDESTLKPYT  840
RYKVSGFIGQ SNQVELIISR YGKEIDKILN VPYTGPLPIT ADASITCCAP EIGQCDAEQS  900
DSHFFNYSID VGALHPELNP GIEIGLKIVQ SNGYITISNL EIIEERPLTE MEIQAVNRKS  960
QKWEREKLLE CASISELLQP IINQIDSLFK DGNWYNDILP HVTYQDLKNI IIPDLPKLNH  1020
WFIEYLPGEY HEIEQKMKEA LKHAFTQLDE KNLIHNGHFT TNLINWQVEG NAQMKVLEND  1080
ALALQLFNWD SSASQSINIL EFDEDKAYKL RVYAQGSGTI QFGNCEDEAI QFNTNSFIYQ  1140
EKIIYFDTPS VNLHIQSEGS EFIVSSIDLI ELSDDQ                           1176

SEQ ID NO: 109          moltype = AA  length = 679
FEATURE                 Location/Qualifiers
REGION                  1..679
                        note = Description of Artificial Sequence: Synthetic
                         polypeptide
source                  1..679
                        mol_type = protein
                        organism = synthetic construct
SEQUENCE: 109
MDCNLQSQQN IPYNVLAIPV SNVNSLTDTV EQLKKAWEAF QKTGSFSLTA LQQGFAASQG  60
GTFNYLALLQ SGISLAGSFV PGGTFVAPIV NMVIGWLWPH KNKKADTENL INLIDSEIQK  120
QLNKALLDQD KNDWTSYLES IFDSSNNLNG AIIDAQWSGT VNDTNRTLKQ PTESDYINVV  180
TNFIAADGDI SNNEHHIMNG NFNVAAAPYF VIGATARFAT MQSYIKFCSA WIDKVGLSDS  240
QLATQKANLD RTKQTMRNAI YNYTEQVMKT FKDPNNMPTI GNNKFSVDVY NVYIKGMTLN  300
VLDIVAIWPS LYPDDYTSQT ALEQTRVTFS NMVGQEEGTD GTLKIYNTFD SLSYQHNLIP  360
NNNVNLISYY NDELQNLQLG VYTPAKKGNG YAYPFGFILN YTNSKYKYGD SHDPESLGEL  420
FTLPAPIQQI NSATQKSIIL DGETINGIGA SLAGYCTTGC SPVEAPFSCT STANNYKESC  480
NPSDTNQKIN ALYPFTQTNV QGNTGKLGVL ASFVPYDLNP ENIFGELDPD TNNVILKGIP  540
AEKGYFPNNT RPTVVKEWIN GANAVLLDSG NTLFMTATNL TATQYKIRIR YANPNSNTQI  600
GVRITQNGSL IFNSNLTLYS TTDMNSTLPL NVYVTGENGN YTLLNLYSTT NVLSTGDITL  660
QLTGGDQKIF IDRIEFVPT                                              679

SEQ ID NO: 110          moltype = AA  length = 287
FEATURE                 Location/Qualifiers
source                  1..287
                        mol_type = protein
                        organism = Bacillus sp.
SEQUENCE: 110
MAVNLDSIVS DYGNWLAPNF PLNQTSDIID TIFVPGTHIG NFTAYVGATV FSNNIKVTGQ  60
SNIVLNNAIP LTNTTTKFLK DSTFINNSPN TVPGKFTFSE STKNSISTTN TNALEFSVGS  120
ETTINGTFAG IGASQKISFT TKTSNSNSTT ITNEETKTWT DSFEPPIPPY TSARAVYDVK  180
LGHYEQTLDV DVIISGTVQY RITYYQPVIP GQRDGAFPLV PVAEIFKDRP GFTVLSDGTV  240
KYIGKVKLVA DIGLFTTMTY TETSLKNGAT SSPIILPGSK SNPTLIM                287

SEQ ID NO: 111          moltype = AA  length = 502
FEATURE                 Location/Qualifiers
REGION                  1..502
                        note = Description of Unknown: Organism from environmental
```

```
                          sample
source                   1..502
                         mol_type = protein
                         organism = unidentified
SEQUENCE: 111
MQRGRCSRFS MSSPPEIHRR DTGVVMQEAK ELDQVINVGF LFGIAKVHAD APQDYARQHM  60
LQYLASHGER AMEEEPLRKM IAPMAAIPMA APDTLPALRD SVQRQHAART ACVMQSVQRD  120
TPLLDGETLL EETFTYLNKP YNGARARSVV LLRSTNYGQL VYLFKDVVVD QEGRLLFIEP  180
VAKVLAQDAD LELFLDNPEE VLATIGSKLA GSLLSSLGGA IAKSLFEAVF PPGVPSYFDK  240
VYAEMKRIVG EELQQSLIDS VDGAIKSIQQ HLEDEYLPAK AERNLDVLED RKHLFALMQK  300
YESTYLSGPG GMLGTLMSDK YAKLGFSVFL IAASLQLALF QEMAVVDPGN LERDGTPRSP  360
LLSSYGRPET GTVAKAAAKY ADFAEKLWPK IVADRRAKVH LLAQTLCAPG DTCGGSCHHY  420
AWYVDDLVPG AAKLPTTWNT KVVEYRQADG DKHGNNPNKE LIANNFEVYK TQKVEELRKS  480
LGVPEKIVEV WRQLVKAPLK PA                                         502

SEQ ID NO: 112           moltype = AA  length = 477
FEATURE                  Location/Qualifiers
REGION                   1..477
                         note = Description of Artificial Sequence: Synthetic
                          polypeptide
source                   1..477
                         mol_type = protein
                         organism = synthetic construct
SEQUENCE: 112
MQEAKELDQV INVGFLFGIA KVHADAPQDY ARQHMLQYLA SHGERAMEEE PLRKMIAPMA  60
AIPMAAPDTL PALRDSVQRQ HAARTACVMQ SVQRDTPLLD GETLLEETFT YLNKPYNGAR  120
ARSVVLLRST NYGQLVYLFK DVVVDQEGRL LFIEPVAKVL AQDADLELFL DNPEEVLATI  180
GSKLAGSLLS SLGGAIAKSL FEAVFPPGVP SYFDKVYAEM KRIVGEELQQ SLIDSVDGAI  240
KSIQQHLEDE YLPAKAERNL DVLEDRKHLF ALMQKYESTY LSGPGGMLGT LMSDKYAKLG  300
FSVFLIAASL QLALFQEMAV VDPGNLERDG TPRSPLLSSY GRPETGTVAK AAAKYADFAE  360
KLWPKIVADR RAKVHLLAQT LCAPGDTCGG SCHHYAWYVD DLVPGAAKLP TTWNTKVVEY  420
RQADGDKHGN NPNKELIANN FEVYKTQKVE ELRKSLGVPE KIVEVWRQLV KAPLKPA     477

SEQ ID NO: 113           moltype = AA  length = 344
FEATURE                  Location/Qualifiers
source                   1..344
                         mol_type = protein
                         organism = Bacillus sp.
SEQUENCE: 113
MKCYKKIAAI APIAALSTSI LFSPVSTFAA ENKQLVSAPS NTVSQNNIRG YLIKNGIKTP  60
VYNNSDIGSR STQVNEAPYP ELSSNPNDPV PTKGSITSEN GKVGSVLYFS KLGVRVTNPM  120
VAGSGSSSTV KFDNAYLEKK DDGSIVVGTY DPSTLKRTPL SDQKFEYNTA LGMNYTFDED  180
LAKKYFANTT VKRETAFTKI GSGVVPKNGA YEFSQAVTSG LSTADAVGGA VTLGYKMGIK  240
EGGGVLPAEA TQEFSAQLTV SYNHTITVSS QVTNTQTLKN PKASDTYKYD KYVGAVYQLK  300
SSYTIVPGPE LKQAIANGDV VLAQNAFQYD DSTLYLAVTP GAGS                 344

SEQ ID NO: 114           moltype = AA  length = 316
FEATURE                  Location/Qualifiers
REGION                   1..316
                         note = Description of Artificial Sequence: Synthetic
                          polypeptide
source                   1..316
                         mol_type = protein
                         organism = synthetic construct
SEQUENCE: 114
MAENKQLVSA PSNTVSQNNI RGYLIKNGIK TPVYNNSDIG SRSTQVNEAP YPELSSNPND  60
PVPTKGSITS ENGKVGSVLY FSKLGVRVTN PMVAGSGSSS TVKFDNAYLE KKDDGSIVVG  120
TYDPSTLKRT PLSDQKFEYN TALGMNYTFD EDLAKKYFAN TTVKRETAFT KIGSGVVPKN  180
GAYEFSQAVT SGLSTADAVG GAVTLGYKMG IKEGGGVLPA EATQEFSAQL TVSYNHTITV  240
SSQVTNTQTL KNPKASDTYK YDKYVGAVYQ LKSSYTIVPG PELKQAIANG DVVLAQNAFQ  300
YDDSTLYLAV TPGAGS                                                316

SEQ ID NO: 115           moltype = AA  length = 286
FEATURE                  Location/Qualifiers
source                   1..286
                         mol_type = protein
                         organism = Bacillus sp.
SEQUENCE: 115
MDLKIECYLI KKERYFMNID TLNKNEIELN NVNQSVFGNF RQITLTLPAE EERNFTEIYQ  60
VEPQYLAQAL RLANAFQRAL DPEDLNFNFE RALHIANEIP NSAIVKTMNQ NVVHHTIQIS  120
VMIDQLKELI RTVLGFAISS PNFWNSVAAA ITSTFTNLNT QEDSAWIFWK NESSSNTTYY  180
YNILFSIQNA ETGGVMAVLP IAFEISVNLE KKRVLFLTIR DSARYEVRVK AITLAQALDR  240
NQRNSTDIFN MHKNNPYQAI ENRVLNEEMI NQLMHKPVSS SGIILP               286

SEQ ID NO: 116           moltype = AA  length = 270
FEATURE                  Location/Qualifiers
REGION                   1..270
                         note = Description of Artificial Sequence: Synthetic
                          polypeptide
```

```
source                  1..270
                        mol_type = protein
                        organism = synthetic construct
SEQUENCE: 116
MNIDTLNKNE IELNNVNQSV FGNFRQITLT LPAEEERNFT EIYQVEPQYL AQALRLANAF  60
QRALDPEDLN FNFERALHIA NEIPNSAIVK TMNQNVVHHT IQISVMIDQL KELIRTVLGF  120
AISSPNFWNS VAAAITSTFT NLNTQEDSAW IFWKNESSSN TTYYYNILFS IQNAETGGVM  180
AVLPIAFEIS VNLEKKRVLF LTIRDSARYE VRVKAITLAQ ALDRNQRNST DIFNMHKNNP  240
YQAIENRVLN EEMINQLMHK PVSSSGIILP                                  270

SEQ ID NO: 117          moltype = AA  length = 388
FEATURE                 Location/Qualifiers
REGION                  1..388
                        note = Description of Unknown: Organism from environmental
                         sample
source                  1..388
                        mol_type = protein
                        organism = unidentified
SEQUENCE: 117
MKVKQSIPFM VPSIIIIFTA YLTFSCFRRD TDPSDRLDDR GTIMELDAAK FPNVKKDSIE  60
KETYNNIRQL GDIEFFLQLE DSYFGKNTLQ TNGKGKELTL QSFTPDDNAQ LFYFKFSTDI  120
PYMIYSAREN TPIGIGSYKR NPNRYVLFNQ TSERTALFGF GWNLISNTDR NKYFLQNHDI  180
SDTSTINYVI STQSGELSVE KKNNTIGQQF NIVPNDEFII EDLQISTKGG EIIESKSIIL  240
KQGNVENNTT QEMKRNLPFS ESLISTNSFV ERMGGILITK TGSLDIETKL PKVILSGGVP  300
TFGHSEVTKL KYSTKSPVTT TFQLNSDITI PSRTILNYKV TVLQHSFRLK YTARCRGVKS  360
GKVINISGVY SGFDYSAPSL ETNTAPLK                                    388

SEQ ID NO: 118          moltype = AA  length = 1239
FEATURE                 Location/Qualifiers
source                  1..1239
                        mol_type = protein
                        organism = Bacillus sp.
SEQUENCE: 118
LGGWSFPKKL EDFSKSSKDI NDGWDAYKKT GIWDPTQKVL DQAVNVYLGK PVDYLALLKA  60
GVSLGGTLLS SAIPGVSILV PFVNMFLGMF WPREKKIDVM KALKEELERM MEQKIEDYDK  120
GVMAAKIQGA ESIMENLRDA IQVAICQGGG PKLAAVADSC TPYGNSTHNE EVRSRFANVD  180
DHFAGMIPEF QKQGFQEIEL SYFVTAANLH LLSLQGVVQL GLKWGYTQDQ VDNYSKKLRE  240
LIKTYTATVY NTFTQHLPKI DSTKKSTINK HLRYVTAMNI QCFDYVAQWP TLDPYDYPLD  300
TNLEATRVVF SDIVGPVEDK PDLNLNIIMD DSQTKSITEI ANITYTGKQM SSVQFHTTRD  360
DDSNTNGSEH CRTDGILQNY QTYNSPGSFT YGASSSYTDN PYHRYAGYGV QLSSPLAKIN  420
MSSQNAKYID YTFVTIDDHY AAGCSPIGAS SSSKNDDLEL QQIQWIYPVS AANPADVWGR  480
AGKLGFIAAH VPADLTPTTT IGHFDENTGI PYIEGVSVEK GTTTGQRVIE RINAANAIKL  540
LTGQTITLPF TNLIPQKYQI RYRVATKNTG SLNFQINSWS NSVPIANTET MATTQKGLKG  600
DQGFYIIFPE TKRDEDKKII PPTENVVSLT PGTQTLIIKN TGAAEVILDR IEFVPMPAPP  660
PVPTLPVNTS FSVGPGGQEI IWDGKGTTAS SAKLTINFTK SDSTGVGIQF LRGSHVIYSE  720
GFREGQSSIP YSHTSPTEFT AIALHKYFGS ESSDGSVTGS VDVYSTSQNF VKPEDLEQIM  780
QQVNALFTSS SYTELSPTIT DYWIDQMVMK VDALSDEVFG IEKKALRKLV SKAKHLSKQR  840
NLLVAGNLES LDEWFLGRNV IRRSGNDLFK GDHLLLPPPT RYSSYAYQKV DESKLKPYTR  900
YTVSGFVAQS EHLELVVSRY GKEIETILNV PYGEALPISA GNQSNCCKPA SCLCSACTGE  960
PDSHFFSYSI DVGALHQGLN PGIEFGLRIV KPNGLASVSN MEIREERPLT EREIQKMQRK  1020
EQKWKKAFDK ERAEISAILQ PVINQINAFY KNEDWSSDIL PPITYQDLHK VVLPELPKVR  1080
HWFMEDREGE HYGILRQLKQ ALDRVFTHLE EQNLIHNGSF TNGLTDWLVD GDAQITTLEN  1140
GNLALQLSTW YASASQSIDI SDFDEDKEYK LRVRGKGKGT ITIQHGEEME TMSFDKTGFY  1200
FQEQPFYFEE PSFQLQIQSE GNEFIVDSVE IIEVPEEDE                        1239

SEQ ID NO: 119          moltype = AA  length = 1239
FEATURE                 Location/Qualifiers
REGION                  1..1239
                        note = Description of Artificial Sequence: Synthetic
                         polypeptide
source                  1..1239
                        mol_type = protein
                        organism = synthetic construct
SEQUENCE: 119
MGGWSFPKKL EDFSKSSKDI NDGWDAYKKT GIWDPTQKVL DQAVNVYLGK PVDYLALLKA  60
GVSLGGTLLS SAIPGVSILV PFVNMFLGMF WPREKKIDVM KALKEELERM MEQKIEDYDK  120
GVMAAKIQGA ESIMENLRDA IQVAICQGGG PKLAAVADSC TPYGNSTHNE EVRSRFANVD  180
DHFAGMIPEF QKQGFQEIEL SYFVTAANLH LLSLQGVVQL GLKWGYTQDQ VDNYSKKLRE  240
LIKTYTATVY NTFTQHLPKI DSTKKSTINK HLRYVTAMNI QCFDYVAQWP TLDPYDYPLD  300
TNLEATRVVF SDIVGPVEDK PDLNLNIIMD DSQTKSITEI ANITYTGKQM SSVQFHTTRD  360
DDSNTNGSEH CRTDGILQNY QTYNSPGSFT YGASSSYTDN PYHRYAGYGV QLSSPLAKIN  420
MSSQNAKYID YTFVTIDDHY AAGCSPIGAS SSSKNDDLEL QQIQWIYPVS AANPADVWGR  480
AGKLGFIAAH VPADLTPTTT IGHFDENTGI PYIEGVSVEK GTTTGQRVIE RINAANAIKL  540
LTGQTITLPF TNLIPQKYQI RYRVATKNTG SLNFQINSWS NSVPIANTET MATTQKGLKG  600
DQGFYIIFPE TKRDEDKKII PPTENVVSLT PGTQTLIIKN TGAAEVILDR IEFVPMPAPP  660
PVPTLPVNTS FSVGPGGQEI IWDGKGTTAS SAKLTINFTK SDSTGVGIQF LRGSHVIYSE  720
GFREGQSSIP YSHTSPTEFT AIALHKYFGS ESSDGSVTGS VDVYSTSQNF VKPEDLEQIM  780
QQVNALFTSS SYTELSPTIT DYWIDQMVMK VDALSDEVFG IEKKALRKLV SKAKHLSKQR  840
NLLVAGNLES LDEWFLGRNV IRRSGNDLFK GDHLLLPPPT RYSSYAYQKV DESKLKPYTR  900
```

```
YTVSGFVAQS EHLELVVSRY GKEIETILNV PYGEALPISA GNQSNCCKPA SCLCSACTGE  960
PDSHFFSYSI DVGALHQGLN PGIEFGLRIV KPNGLASVSN MEIREERPLT EREIQKMQRK  1020
EQKWKKAFDK ERAEISAILQ PVINQINAFY KNEDWSSDIL PPITYQDLHK VVLPELPKVR  1080
HWFMEDREGE HYGILRQLKQ ALDRVFTHLE EQNLIHNGSF TNGLTDWLVD GDAQITTLEN  1140
GNLALQLSTW YASASQSIDI SDFDEDKEYK LRVRGKGKGT ITIQHGEEME TMSFDKTGFY  1200
FQEQPFYFEE PSFQLQIQSE GNEFIVDSVE IIEVPEEDE                        1239

SEQ ID NO: 120         moltype = AA  length = 657
FEATURE                Location/Qualifiers
REGION                 1..657
                       note = Description of Artificial Sequence: Synthetic
                        polypeptide
source                 1..657
                       mol_type = protein
                       organism = synthetic construct
SEQUENCE: 120
MGGWSFPKKL EDFSKSSKDI NDGWDAYKKT GIWDPTQKVL DQAVNVYLGK PVDYLALLKA  60
GVSLGGTLLS SAIPGVSILV PFVNMFLGMF WPREKKIDVM KALKEELERM MEQKIEDYDK  120
GVMAAKIQGA ESIMENLRDA IQVAICQGGG PKLAAVADSC TPYGNSTHNE EVRSRFANVD  180
DHFAGMIPEF QKQGFQEIEL SYFVTAANLH LLSLQGVVQL GLKWGYTQDQ VDNYSKKLRE  240
LIKTYTATVY NTFTQHLPKI DSTKKSTINK HLRYVTAMNI QCFDYVAQWP TLDPYDYPLD  300
TNLEATRVVF SDIVGPVEDK PDLNLNIIMD DSQTKSITEI ANITYTGKQM SSVQFHTTRD  360
DDSNTNGSEH CRTDGILQNY QTYNSPGSFT YGASSSYTDN PYHRYAGYGV QLSSPLAKIN  420
MSSQNAKYID YTFVTIDDHY AAGCSPIGAS SSSKNDDLEL QQIQWIYPVS AANPADVWGR  480
AGKLGFIAAH VPADLTPTTT IGHFDENTGI PYIEGVSVEK GTTTGQRVIE RINAANAIKL  540
LTGQTITLPF TNLIPQKYQI RYRVATKNTG SLNFQINSWS NSVPIANTET MATTQKGLKG  600
DQGFYIIFPE TKRDEDKKII PPTENVVSLT PGTQTLIIKN TGAAEVILDR IEFVPMP     657

SEQ ID NO: 121         moltype = AA  length = 1230
FEATURE                Location/Qualifiers
REGION                 1..1230
                       note = Description of Artificial Sequence: Synthetic
                        polypeptide
source                 1..1230
                       mol_type = protein
                       organism = synthetic construct
SEQUENCE: 121
MEDFSKSSKD INDGWDAYKK TGIWDPTQKV LDQAVNVYLG KPVDYLALLK AGVSLGGTLL  60
SSAIPGVSIL VPFVNMFLGM FWPREKKIDV MKALKEELER MMEQKIEDYD KGVMAAKIQG  120
AESIMENLRD AIQVAICQGG GPKLAAVADS CTPYGNSTHN EEVRSRFANV DDHFAGMIPE  180
FQKQGFQEIE LSYFVTAANL HLLSLQGVVQ LGLKWGYTQD QVDNYSKKLR ELIKTYTATV  240
YNTFTQHLPK IDSTKKSTIN KHLRYVTAMN IQCFDYVAQW PTLDPYDYPL DTNLEATRVV  300
FSDIVGPVED KPDLNLNIIM DDSQTKSITE IANITYTGKQ MSSVQFHTTR DDDSNTNGSE  360
HCRTDGILQN YQTYNSPGSF TYGASSSYTD NPYHRYAGYG VQLSSPLAKI NMSSQNAKYI  420
DYTFVTIDDH YAAGCSPIGA SSSSKNDDLE LQQIQWIYPV SAANPADVWG RAGKLGFIAA  480
HVPADLTPTT TIGHFDENTG IPYIEGVSVE KGTTTGQRVI ERINAANAIK LLTGQTITLP  540
FTNLIPQKYQ IRYRVATKNT GSLNFQINSW SNSVPIANTE TMATTQKGLK GDQGFYIIFP  600
ETKRDEDKKI IPPTENVVSL TPGTQTLIIK NTGAAEVILD RIEFVPMPAP PPVPTLPVNT  660
SFSVGPGGQE IIWDGKGTTA SSAKLTINFT KSDSTGVGIQ FLRGSHVIYS EGFREGQSSI  720
PYSHTSPTEF TAIALHKYFG SESSDGSVTG SVDVYSTSQN FVKPEDLEQI MQQVNALFTS  780
SSYTELSPTI TDYWIDQMVM KVDALSDEVF GIEKKALRKL VSKAKHLSKQ RNLLVAGNLE  840
SLDEWFLGRN VIRRSGNDLF KGDHLLLPPP TRYSSYAYQK VDESKLKPYT RYTVSGFVAQ  900
SEHLELVVSR YGKEIETILN VPYGEALPIS AGNQSNCCKP ASCLCSACTG EPDSHFFSYS  960
IDVGALHQGL NPGIEFGLRI VKPNGLASVS NMEIREERPL TEREIQKMQR KEQKWKKAFD  1020
KERAEISAIL QPVINQINAF YKNEDWSSDI LPPITYQDLH KVVLPELPKV RHWFMEDREG  1080
EHYGILRQLK QALDRVFTHL EEQNLIHNGS FTNGLTDWLV DGDAQITTLE NGNLALQLST  1140
WYASASQSID ISDFDEDKEY KLRVRGKGKG TITIQHGEEM ETMSFDKTGF YFQEQPFYFE  1200
EPSFQLQIQS EGNEFIVDSV EIIEVPEEDE                                  1230

SEQ ID NO: 122         moltype = AA  length = 648
FEATURE                Location/Qualifiers
REGION                 1..648
                       note = Description of Artificial Sequence: Synthetic
                        polypeptide
source                 1..648
                       mol_type = protein
                       organism = synthetic construct
SEQUENCE: 122
MEDFSKSSKD INDGWDAYKK TGIWDPTQKV LDQAVNVYLG KPVDYLALLK AGVSLGGTLL  60
SSAIPGVSIL VPFVNMFLGM FWPREKKIDV MKALKEELER MMEQKIEDYD KGVMAAKIQG  120
AESIMENLRD AIQVAICQGG GPKLAAVADS CTPYGNSTHN EEVRSRFANV DDHFAGMIPE  180
FQKQGFQEIE LSYFVTAANL HLLSLQGVVQ LGLKWGYTQD QVDNYSKKLR ELIKTYTATV  240
YNTFTQHLPK IDSTKKSTIN KHLRYVTAMN IQCFDYVAQW PTLDPYDYPL DTNLEATRVV  300
FSDIVGPVED KPDLNLNIIM DDSQTKSITE IANITYTGKQ MSSVQFHTTR DDDSNTNGSE  360
HCRTDGILQN YQTYNSPGSF TYGASSSYTD NPYHRYAGYG VQLSSPLAKI NMSSQNAKYI  420
DYTFVTIDDH YAAGCSPIGA SSSSKNDDLE LQQIQWIYPV SAANPADVWG RAGKLGFIAA  480
HVPADLTPTT TIGHFDENTG IPYIEGVSVE KGTTTGQRVI ERINAANAIK LLTGQTITLP  540
FTNLIPQKYQ IRYRVATKNT GSLNFQINSW SNSVPIANTE TMATTQKGLK GDQGFYIIFP  600
ETKRDEDKKI IPPTENVVSL TPGTQTLIIK NTGAAEVILD RIEFVPMP              648
```

```
SEQ ID NO: 123          moltype = AA  length = 1172
FEATURE                 Location/Qualifiers
REGION                  1..1172
                        note = Description of Artificial Sequence: Synthetic
                         polypeptide
source                  1..1172
                        mol_type = protein
                        organism = synthetic construct
SEQUENCE: 123
MLSSAIPGVS ILVPFVNMFL GMFWPREKKI DVMKALKEEL ERMMEQKIED YDKGVMAAKI  60
QGAESIMENL RDAIQVAICQ GGGPKLAAVA DSCTPYGNST HNEEVRSRFA NVDDHFAGMI  120
PEFQKQGFQE IELSYFVTAA NLHLLSLQGV VQLGLKWGYT QDQVDNYSKK LRELIKTYTA  180
TVYNTFTQHL PKIDSTKKST INKHLRYVTA MNIQCFDYVA QWPTLDPYDY PLDTNLEATR  240
VVFSDIVGPV EDKPDLNLNI IMDDSQTKSI TEIANITYTG KQMSSVQFHT TRDDDSNTNG  300
SEHCRTDGIL QNYQTYNSPG SFTYGASSSY TDNPYHRYAG YGVQLSSPLA KINMSSQNAK  360
YIDYTFVTID DHYAAGCSPI GASSSSKNDD LELQQIQWIY PVSAANPADV WGRAGKLGFI  420
AAHVPADLTP TTTIGHFDEN TGIPYIEGVS VEKGTTTGQR VIERINAANA IKLLTGQTIT  480
LPFTNLIPQK YQIRYRVATK NTGSLNFQIN SWSNSVPIAN TETMATTQKG LKGDQGFYII  540
FPETKRDEDK KIIPPTENVV SLTPGTQTLI IKNTGAAEVI LDRIEFVPMP APPPVPTLPV  600
NTSFSVGPGG QEIIWDGKGT TASSAKLTIN FTKSDSTGVG IQFLRGSHVI YSEGFREGQS  660
SIPYSHTSPT EFTAIALHKY FGSESSDGSV TGSVDVYSTS QNFVKPEDLE QIMQQVNALF  720
TSSSYTELSP TITDYWIDQM VMKVDALSDE VFGIEKKALR KLVSKAKHLS KQRNLLVAGN  780
LESLDEWFLG RNVIRRSGND LFKGDHLLLP PPTRYSSYAY QKVDESKLKP YTRYTVSGFV  840
AQSEHLELVV SRYGKEIETI LNVPYGEALP ISAGNQSNCC KPASCLCSAC TGEPDSHFFS  900
YSIDVGALHQ GLNPGIEFGL RIVKPNGLAS VSNMEIREER PLTEREIQKM QRKEQKWKKA  960
FDKERAEISA ILQPVINQIN AFYKNEDWSS DILPPITYQD LHKVVLPELP KVRHWFMEDR  1020
EGEHYGILRQ LKQALDRVFT HLEEQNLIHN GSFTNGLTDW LVDGDAQITT LENGNLALQL  1080
STWYASASQS IDISDFDEDK EYKLRVRGKG KGTITIQHGE EMETMSFDKT GFYFQEQPFY  1140
FEEPSFQLQI QSEGNEFIVD SVEIIEVPEE DE                              1172

SEQ ID NO: 124          moltype = AA  length = 590
FEATURE                 Location/Qualifiers
REGION                  1..590
                        note = Description of Artificial Sequence: Synthetic
                         polypeptide
source                  1..590
                        mol_type = protein
                        organism = synthetic construct
SEQUENCE: 124
MLSSAIPGVS ILVPFVNMFL GMFWPREKKI DVMKALKEEL ERMMEQKIED YDKGVMAAKI  60
QGAESIMENL RDAIQVAICQ GGGPKLAAVA DSCTPYGNST HNEEVRSRFA NVDDHFAGMI  120
PEFQKQGFQE IELSYFVTAA NLHLLSLQGV VQLGLKWGYT QDQVDNYSKK LRELIKTYTA  180
TVYNTFTQHL PKIDSTKKST INKHLRYVTA MNIQCFDYVA QWPTLDPYDY PLDTNLEATR  240
VVFSDIVGPV EDKPDLNLNI IMDDSQTKSI TEIANITYTG KQMSSVQFHT TRDDDSNTNG  300
SEHCRTDGIL QNYQTYNSPG SFTYGASSSY TDNPYHRYAG YGVQLSSPLA KINMSSQNAK  360
YIDYTFVTID DHYAAGCSPI GASSSSKNDD LELQQIQWIY PVSAANPADV WGRAGKLGFI  420
AAHVPADLTP TTTIGHFDEN TGIPYIEGVS VEKGTTTGQR VIERINAANA IKLLTGQTIT  480
LPFTNLIPQK YQIRYRVATK NTGSLNFQIN SWSNSVPIAN TETMATTQKG LKGDQGFYII  540
FPETKRDEDK KIIPPTENVV SLTPGTQTLI IKNTGAAEVI LDRIEFVPMP             590

SEQ ID NO: 125          moltype = AA  length = 288
FEATURE                 Location/Qualifiers
source                  1..288
                        mol_type = protein
                        organism = Bacillus sp.
SEQUENCE: 125
MAVLDLSRTI NDYFYSIFPS SLGRASVGFF QLREFYRADS LNIKGRMSLP DNIIPVSGSG  60
RTIVKTDSVL NASTDIPIEK TFSLKETTSD AVSTTRTQGV DTSIDIELNL GATIDFLNLG  120
AKTGFSTKTS LSNSKTISQT KERTWEENIK ITVPPQTKAT LMYTITTGPF DALIPVDFVI  180
SGSVTGYATW ASDTFSSMSI SQIEGIQPDL IRRRSETINI VNLFKNLNTP GFTFNGDSEA  240
IFRGEVRVQG ELGVQSSLQL TTVSLLGNGA PRVQNFPTTP TYNMVLFA             288

SEQ ID NO: 126          moltype = AA  length = 433
FEATURE                 Location/Qualifiers
REGION                  1..433
                        note = Description of Unknown: Organism from environmental
                         sample
source                  1..433
                        mol_type = protein
                        organism = unidentified
SEQUENCE: 126
VARHGRSTAE EVDMTSTTMA FGELELAFTD QLSWCWDDED TGGKHWVSFW HPTAPKGFLP  60
LGTVAIPAWG SANLNPKTGA KKIEDHVVAL CVRETGETRP GMGPALAPPV SYEKIWTDVG  120
TGGKYKGSLW RPIPPKGYVA LGCVAPKDTY EEPPLSAVTC VRADLTDHAK AHFVYSDKGT  180
GGKQDVSVWQ NNVPPAYVDN TSGDTRALIA ANTFTSHAAY SEPNSLPSMR VLCLPMPVKK  240
APWGAEPELA NRSRPAEKTS PVTANTLWVP FTAVNDKDRS VPWKLEHSPF YRIERKVSWE  300
LVDHVDNNTE SPAKLSRTIM TGVEKESADT FHITTGVSVN ATAGVSAGVA SASLSTTYSL  360
ELGFAHSSSL KELSSEAVTA EATVMPYTSM AAWVGSNTLQ VAREDGTLVG KPLPFRGKSI  420
```

-continued

```
RYDQYPDKAP SSK                                              433

SEQ ID NO: 127          moltype = AA  length = 420
FEATURE                 Location/Qualifiers
REGION                  1..420
                        note = Description of Artificial Sequence: Synthetic
                         polypeptide
source                  1..420
                        mol_type = protein
                        organism = synthetic construct
SEQUENCE: 127
MTSTTMAFGE LELAFTDQLS WCWDDEDTGG KHWVSFWHPT APKGFLPLGT VAIPAWGSAN  60
LNPKTGAKKI EDHVVALCVR ETGETRPGMG PALAPPVSYE KIWTDVGTGG KYKGSLWRPI  120
PPKGYVALGC VAPKDTYEEP PLSAVTCVRA DLTDHAKAHF VYSDKGTGGK QDVSVWQNNV  180
PPAYVDNTSG DTRALIAANT FTSHAAYSEP NSLPSMRVLC LPMPVKKAPW GAEPELANRS  240
RPAEKTSPVT ANTLWVPFTA VNDKDRSVPW KLEHSPFYRI ERKVSWELVD HVDNNTESPA  300
KLSRTIMTGV EKESADTFHI TTGVSVNATA GVSAGVASAS LSTTYSLELG FAHSSSLKEL  360
SSEAVTAEAT VMPYTSMAAW VGSNTLQVAR EDGTLVGKPL PFRGKSIRYD QYPDKAPSSK  420

SEQ ID NO: 128          moltype = AA  length = 956
FEATURE                 Location/Qualifiers
source                  1..956
                        mol_type = protein
                        organism = Bacillus sp.
SEQUENCE: 128
MIMQMVTKAM TPKLGALPDF IDDFNGIFGF MGNITDVMST IFGIDTGDSS IDDVLNNEEL  60
LQEMLDQMNT MQISIRDILE QQGISADIEK QILALTTDLA TSINTELGKI EGILNTYLPA  120
ISNMLSNIYE QTSVIDQKVD KLLALMTFAL KELDYIKDNV VLNSSIVEIT PHVEKLVYVN  180
KKFLSLTKGF LQGEDVSIDS MQEIQEWARS ILATDMNSFE FSVDTLHNII IGDNLYKRSA  240
LKTFSDVLLD DADQYGDFGT PLAKFYTFFS SLATLQINAY LCLTFARKVL GLSEIDYQVT  300
MQDRIEQQNQ MFVNLIQDKN YSNALEITGI YPMSVDWGDC KSTDLQADAG YALIGLEFFM  360
DNGIYKAKAY QGKIGKNFSV SADTVTEIIS DDLSTVFNDM TNDNPELYVV YPLSGELTGP  420
SNTIITRVGF GTKYDKTRES SVQAFAYVDA DFSPYDYISG TISKEGTQTV SLEGNDHKNR  480
CYSMWPMGLI GDLYMTPLKS LSLNVADTGT TLNMSGESYF STILSREYNT NFILFPYTNN  540
SSPIVENLIQ NGDFEDGDKY WEVVSGTAVI AEGEGVYGSN AMKISDVIKQ ELNLKPYTNY  600
ELTAYVKSKT NDKQRGRISI TYNNAEIAWT QQTFSTSYKQ IELKFRTGAD NQDFHVTFEN  660
LDNDYLLLDN IQLHGIPQTD NLIDCGDFGG YDIVTDDYKL LRDPYLWELD GGGTISHGFK  720
EGLFETDCLK ILESGGANQK VQLKANTNYI LTAYVKVDDP TTTAQIGCGS NQVPCNSTSY  780
TPVKLKFKTG EDPSTTESSV YCSNPNDSGT VWADNFVLYE APNLIRNGDF EQFDQSSWNF  840
SPSEGGRIYL QSGLGMSRSN AVVIHGENGK ISQKIPLKPF TKYRLTAYVK VSKGSIAHIG  900
YGDNTCACAV DDFRQARVDF TTGANPMQSD DAIYLDSYAS AYTVADNFEL YELDQI      956

SEQ ID NO: 129          moltype = AA  length = 954
FEATURE                 Location/Qualifiers
REGION                  1..954
                        note = Description of Artificial Sequence: Synthetic
                         polypeptide
source                  1..954
                        mol_type = protein
                        organism = synthetic construct
SEQUENCE: 129
MQMVTKAMTP KLGALPDFID DFNGIFGFMG NITDVMSTIF GIDTGDSSID DVLNNEELLQ  60
EMLDQMNTMQ ISIRDILEQQ GISADIEKQI LALTTDLATS INTELGKIEG ILNTYLPAIS  120
NMLSNIYEQT SVIDQKVDKL LALMTFALKE LDYIKDNVVL NSSIVEITPH VEKLVYVNKK  180
FLSLTKGFLQ GEDVSIDSMQ EIQEWARSIL ATDMNSFEFS VDTLHNIIIG DNLYKRSALK  240
TFSDVLLDDA DQYGDFGTPL AKFYTFFSSL ATLQINAYLC LTFARKVLGL SEIDYQVTMQ  300
DRIEQQNQMF VNLIQDKNYS NALEITGIYP MSVDWGDCKS TDLQADAGYA LIGLEFFMDN  360
GIYKAKAYQG KIGKNFSVSA DTVTEIISDD LSTVFNDMTN DNPELYVVYP LSGELTGPSN  420
TIITRVGFGT KYDKTRESSV QAFAYVDADF SPYDYISGTI SKEGTQTVSL EGNDHKNRCY  480
SMWPMGLIGD LYMTPLKSLS LNVADTGTTL NMSGESYFST ILSREYNTNF ILFPYTNNSS  540
PIVENLIQNG DFEDGDKYWE VVSGTAVIAE GEGVYGSNAM KISDVIKQEL NLKPYTNYEL  600
TAYVKSKTND KQRGRISITY NNAEIAWTQQ TFSTSYKQIE LKFRTGADNQ DFHVTFENLD  660
NDYLLLDNIQ LHGIPQTDNL IDCGDFGGYD IVTDDYKLLR DPYLWELDGG GTISHGFKEG  720
LFETDCLKIL ESGGANQKVQ LKANTNYILT AYVKVDDPTT TAQIGCGSNQ VPCNSTSYTP  780
VKLKFKTGED PSTTESSVYC SNPNDSGTVW ADNFVLYEAP NLIRNGDFEQ FDQSSWNFSP  840
SEGGRIYLQS GLGMSRSNAV VIHGENGKIS QKIPLKPFTK YRLTAYVKVS KGSIAHIGYG  900
DNTCACAVDD FRQARVDFTT GANPMQSDDA IYLDSYASAY TVADNFELYE LDQI        954

SEQ ID NO: 130          moltype = AA  length = 307
FEATURE                 Location/Qualifiers
source                  1..307
                        mol_type = protein
                        organism = Bacillus sp.
SEQUENCE: 130
MVRVYPDFDK MVWEAAQKWS EANGLLFQTL SYADPLTNAD TISLHVNFTD IGCPEEFVEL  60
EKIRIPKAFA NNAEQQQKEI WEDIVYVEKQ FTWENEYEFV LPGQSFLTIP RIPMSVHEEI  120
HPGFLVNLFG RNQRFDTKLR EQRSLRAEVF LEPSSSAAIQ LKVEKQHISQ LYQIELSIQG  180
CIIVTTQNRD GQQHEHYVGL IDLMPFFHSH TNFSWEGQAL IFREKGKFTG ILSRAIRVYV  240
TQTLYHDGKT LEYEIPLLRT SSARQPMAPT LSNATIPSQP SITMNSTSCG CPTCMSTKSN  300
```

```
ENVYTNQ                                                             307

SEQ ID NO: 131          moltype = AA  length = 804
FEATURE                 Location/Qualifiers
source                  1..804
                        mol_type = protein
                        organism = Bacillus sp.
SEQUENCE: 131
LCTIAIKNKN YMRDKKMNSN QNKNEYEILN TSGNSVNTLT RYPFANDPDS SVLSSCQRSG  60
PGNWINILGN AVSQAVSNSQ DILSLLRQPS LSGIISMAFS LLNRMTGSNG RSISELSMCD  120
LLAIIDLRVN QSVLDAGVAD FNGSLVVYRN YLEALQRWNN NPNSATAEDV RTRFRNSDTT  180
FDFILTRGSL TNGGSLARNN AQILLLPSFA NAAYFHLLLL RDANVYGDNW GLFRDTPNIN  240
YKSKLLDLIR LYTNYCTHWY NQGLNELRNR GNNATAWLEF HRFRRDMTLM VLDIVASFSN  300
FDITRYPRAT DIQLSRVIYT DPIGFVNRSD PSAGRTWFSF HNQANFSALE SGIPIPSFSQ  360
FLDSMRISTG PLSLPASPNI HRAGVWYGNQ NNFNGSSSQT FGEVTNENQT ISGLNIFRID  420
SQAVNLNNTT FGVSRAEFYH DTSQGSQRSI YQGFVDTSGP STAVAQNIQT FFPGENSNIP  480
TPHDYTHILS RSTNLTGGLR QVASGRRSSL VLHGWTHKSL SRQNRVEPNR ITQVPAVKVS  540
TDSNCTVIAG PGFTGGDVVR INSNGSVSYN ITPANQQVVI RLRYACQGIA SLRMTFGNGS  600
SQVIPLVSTT ASINNLQYEN FSFVTGPNSV NFLSAGTSVT IQNISTNSNV VLDRVELVPE  660
LPEPPIIPGE YQIVTAINNS SVLDLNSGTR VTLWSNSRGA HQIWSFVYDH QRNAYVIRNV  720
SNPSLVLTWD FTSSNNIVFA APFSPGRDEQ YWIAESFQNG FVLGNLRNRN MVLDVSGGST  780
SNGTNIIAYP RHNGNAQRFF IRRP                                          804

SEQ ID NO: 132          moltype = AA  length = 788
FEATURE                 Location/Qualifiers
REGION                  1..788
                        note = Description of Artificial Sequence: Synthetic
                         polypeptide
source                  1..788
                        mol_type = protein
                        organism = synthetic construct
SEQUENCE: 132
MNSNQNKNEY EILNTSGNSV NTLTRYPFAN DPDSSVLSSC QRSGPGNWIN ILGNAVSQAV  60
SNSQDILSLL RQPSLSGIIS MAFSLLNRMT GSNGRSISEL SMCDLLAIID LRVNQSVLDA  120
GVADFNGSLV VYRNYLEALQ RWNNNPNSAT AEDVRTRFRN SDTTFDFILT RGSLTNGGSL  180
ARNNAQILLL PSFANAAYFH LLLLRDANVY GDNWGLFRDT PNINYKSKLL DLIRLYTNYC  240
THWYNQGLNE LRNRGNNATA WLEFHRFRRD MTLMVLDIVA SFSNFDITRY PRATDIQLSR  300
VIYTDPIGFV NRSDPSAGRT WFSFHNQANF SALESGIPIP SFSQFLDSMR ISTGPLSLPA  360
SPNIHRAGVW YGNQNNFNGS SSQTFGEVTN ENQTISGLNI FRIDSQAVNL NNTTFGVSRA  420
EFYHDTSQGS QRSIYQGFVD TSGPSTAVAQ NIQTFFPGEN SNIPTPHDYT HILSRSTNLT  480
GGLRQVASGR RSSLVLHGWT HKSLSRQNRV EPNRITQVPA VKVSTDSNCT VIAGPGFTGG  540
DVVRINSNGS VSYNITPANQ QVVIRLRYAC QGIASLRMTF GNGSSQVIPL VSTTASINNL  600
QYENFSFVTG PNSVNFLSAG TSVTIQNIST NSNVVLDRVE LVPELPEPPI IPGEYQIVTA  660
INNSSVLDLN SGTRVTLWSN SRGAHQIWSF VYDHQRNAYV IRNVSNPSLV LTWDFTSSNN  720
IVFAAPFSPG RDEQYWIAES FQNGFVLGNL RNRNMVLDVS GGSTSNGTNI IAYPRHNGNA  780
QRFFIRRP                                                            788

SEQ ID NO: 133          moltype = AA  length = 644
FEATURE                 Location/Qualifiers
REGION                  1..644
                        note = Description of Artificial Sequence: Synthetic
                         polypeptide
source                  1..644
                        mol_type = protein
                        organism = synthetic construct
SEQUENCE: 133
MNSNQNKNEY EILNTSGNSV NTLTRYPFAN DPDSSVLSSC QRSGPGNWIN ILGNAVSQAV  60
SNSQDILSLL RQPSLSGIIS MAFSLLNRMT GSNGRSISEL SMCDLLAIID LRVNQSVLDA  120
GVADFNGSLV VYRNYLEALQ RWNNNPNSAT AEDVRTRFRN SDTTFDFILT RGSLTNGGSL  180
ARNNAQILLL PSFANAAYFH LLLLRDANVY GDNWGLFRDT PNINYKSKLL DLIRLYTNYC  240
THWYNQGLNE LRNRGNNATA WLEFHRFRRD MTLMVLDIVA SFSNFDITRY PRATDIQLSR  300
VIYTDPIGFV NRSDPSAGRT WFSFHNQANF SALESGIPIP SFSQFLDSMR ISTGPLSLPA  360
SPNIHRAGVW YGNQNNFNGS SSQTFGEVTN ENQTISGLNI FRIDSQAVNL NNTTFGVSRA  420
EFYHDTSQGS QRSIYQGFVD TSGPSTAVAQ NIQTFFPGEN SNIPTPHDYT HILSRSTNLT  480
GGLRQVASGR RSSLVLHGWT HKSLSRQNRV EPNRITQVPA VKVSTDSNCT VIAGPGFTGG  540
DVVRINSNGS VSYNITPANQ QVVIRLRYAC QGIASLRMTF GNGSSQVIPL VSTTASINNL  600
QYENFSFVTG PNSVNFLSAG TSVTIQNIST NSNVVLDRVE LVPE                    644

SEQ ID NO: 134          moltype = AA  length = 292
FEATURE                 Location/Qualifiers
source                  1..292
                        mol_type = protein
                        organism = Bacillus sp.
SEQUENCE: 134
MTIIQLDQYF QFLAEGDLAF NYYEIPWISA QLDSVYGRLV KGESLQLSKL DLSNVRLHDV  60
TVDVSEIDLE NNLTLFIDEK NTFENRGYIS NEIYYTSIVS EAVTNSVKTT NTTGYKFGEK  120
LTVSSKFKAK VPIVDVEGEY SVGFELSFEQ NISSAVEEFD GRTITITVPS QPVTVRPRTR  180
KLVSVQLFRL DSPSIITSTS GYATGSIPVA SGRNNLYDAL SRINTTCPQK YVNRDDHLRL  240
DSNRKALCFQ GAGTATVSAV SLDFRIVTRE EDLDTGDIIS VNNKVKRASI QV           292
```

```
SEQ ID NO: 135          moltype = AA  length = 701
FEATURE                 Location/Qualifiers
REGION                  1..701
                        note = Description of Unknown: Organism from environmental
                         sample
source                  1..701
                        mol_type = protein
                        organism = unidentified
SEQUENCE: 135
MNQNDNNNKS EILDPKGREC QQKYPFAEAP DVMNPCMEKA YTRGQSADIS NATNTTTAVT  60
SQLLSLKSPL LSVAGGIIKV LIKILWPTGT QQEWGSFMNA VEQLINVKLD TLVRNEAIAK  120
LEGLKEVLGV YVDKITIYTD DPSEAHAQSL KNQADITNNI FVSSMPSFKI RDYEIQLLTV  180
YAQAANLYLA FLRDIVKFGA EWGFTPTEIA NYHKSMKERT EEYTNYCVET YNKGLEKAKT  240
LNATLCDLNT YPWVHYNQGW REEEKPNCSS QQINDYDPQL NECLEKENPN KADFRWSIGE  300
YQKLEDWNLY NAYRRDMTIM ILDVVSLWPT YDPVLYPTSF GVKSELTREL YTDIRGTTYR  360
SDESQNKLTV IEGRMIPPPQ LFRWLSSLNF HLRKVGTDPN DNWTYGEIAT GLQSTVQKTL  420
ATPEVLPLDG TTGTHTKTLN PLDYADGITW IDTQQWFEPR WFQFWSGGYS TVWKSHGTFG  480
SIEEKNPFWA AGPTRYIYDK TNRSSQIPVH RLSWITYEPV RENAPFVWPQ YKQLGAVALG  540
WTHQSVDLNS TIVSDKITSI PAVKAFRIVG PTNVIKGPGS TGGDLVELLP NGTLDISVVL  600
STQATDRNYK LRIRYASRGI STLFVKQTHS IFSNGNYYTI NQTTTNDQLT YSTFRYLEKG  660
DLNTINPKIS LHLKNTGNSA IIIDKFEFIP YTPTPEPEPP Q                      701

SEQ ID NO: 136          moltype = AA  length = 661
FEATURE                 Location/Qualifiers
source                  1..661
                        mol_type = protein
                        organism = Bacillus sp.
SEQUENCE: 136
VKKMNSYENK NEYEILDASP NNSNMSNRYP RYPLAKDPYT PMRNTNYKEW LAMCANNNQV  60
PIDPLDNTWA GVMSALFASA AAIAGLMSAV PVFSVVATGT ALAAALTPIL FPSTGPDVST  120
QLMSNTEALL KRELDTYVRS RADSEFQALE AQREFFKSAF DYWRLYPTNS NAIATVAARF  180
HTVNGAFVTA MRLFRTAGYE ALLLPVYAQA ARLHLLHLRD GVLFANEWGL AKPDPGDLHD  240
QEFNKYAAEY ADYCESTYNT ELNRIKTAPG KTWLDYNQYR RIMTIAVLDI AAKFSILNPR  300
IYRLPLQEEI LTRKIYTDPV NFSPGLSIAD DENRYTVPPS YVKQLVGATL YTNVASAQNA  360
GFIGNKNRYL RISDGDPFDG PLIGNSVYEN RIASIPTNET VYEVGVNGIQ NDYPRSIGLR  420
WGLSTAFQNS YAGGTTNLGS LTRVSMPTKD NASINNTNLT HRLSDIILPG NKGSSFAWTH  480
VEVDPTGNYL STTKINLIPG TKISKLPNSY QITKGPGFIG GDLIKFTSGS GYVYKFKFKS  540
SGSSANFRIR IRYAGAGSGS SSDGLVFFRL GNYQSPDTRW GHTGFSYTNP KYNQFKVLEL  600
LGTAENITAN DLEIIVWTGL STTDFYLDRL ELIPMTGIST EYNESQELET AKKAVTDLFT  660
N                                                                  661

SEQ ID NO: 137          moltype = AA  length = 658
FEATURE                 Location/Qualifiers
REGION                  1..658
                        note = Description of Artificial Sequence: Synthetic
                         polypeptide
source                  1..658
                        mol_type = protein
                        organism = synthetic construct
SEQUENCE: 137
MNSYENKNEY EILDASPNNS NMSNRYPRYP LAKDPYTPMR NTNYKEWLAM CANNNQVPID  60
PLDNTWAGVM SALFASAAAI AGLMSAVPVF SVVATGTALA AALTPILFPS TGPDVSTQLM  120
SNTEALLKRE LDTYVRSRAD SEFQALEAQR EFFKSAFDYW RLYPTNSNAI ATVAARFHTV  180
NGAFVTAMRL FRTAGYEALL LPVYAQAARL HLLHLRDGVL FANEWGLAKP DPGDLHDQEF  240
NKYAAEYADY CESTYNTELN RIKTAPGKTW LDYNQYRRIM TIAVLDIAAK FSILNPRIYR  300
LPLQEEILTR KIYTDPVNFS PGLSIADDEN RYTVPPSYVK QLVGATLYTN VASAQNAGFI  360
GNKNRYLRIS DGDPFDGPLI GNSVYENRIA SIPTNETVYE VGVNGIQNDY PRSIGLRWGL  420
STAFQNSYAG GTTNLGSLTR VSMPTKDNAS INNTNLTHRL SDIILPGNKG SSFAWTHVEV  480
DPTGNYLSTT KINLIPGTKI SKLPNSYQIT KGPGFIGGDL IKFTSGSGYV YKFKFKSSGS  540
SANFRIRIRY AGAGSGSSSD GLVFFRLGNY QSPDTRWGHT GFSYTNPKYN QFKVLELLGT  600
AENITANDLE IIVWTGLSTT DFYLDRLELI PMTGISTEYN ESQELETAKK AVTDLFTN    658

SEQ ID NO: 138          moltype = AA  length = 632
FEATURE                 Location/Qualifiers
REGION                  1..632
                        note = Description of Artificial Sequence: Synthetic
                         polypeptide
source                  1..632
                        mol_type = protein
                        organism = synthetic construct
SEQUENCE: 138
MNSYENKNEY EILDASPNNS NMSNRYPRYP LAKDPYTPMR NTNYKEWLAM CANNNQVPID  60
PLDNTWAGVM SALFASAAAI AGLMSAVPVF SVVATGTALA AALTPILFPS TGPDVSTQLM  120
SNTEALLKRE LDTYVRSRAD SEFQALEAQR EFFKSAFDYW RLYPTNSNAI ATVAARFHTV  180
NGAFVTAMRL FRTAGYEALL LPVYAQAARL HLLHLRDGVL FANEWGLAKP DPGDLHDQEF  240
NKYAAEYADY CESTYNTELN RIKTAPGKTW LDYNQYRRIM TIAVLDIAAK FSILNPRIYR  300
LPLQEEILTR KIYTDPVNFS PGLSIADDEN RYTVPPSYVK QLVGATLYTN VASAQNAGFI  360
GNKNRYLRIS DGDPFDGPLI GNSVYENRIA SIPTNETVYE VGVNGIQNDY PRSIGLRWGL  420
```

```
STAFQNSYAG GTTNLGSLTR VSMPTKDNAS INNTNLTHRL SDIILPGNKG SSFAWTHVEV  480
DPTGNYLSTT KINLIPGTKI SKLPNSYQIT KGPGFIGGDL IKFTSGSGYV YKFKFKSSGS  540
SANFRIRIRY AGAGSGSSSD GLVFFRLGNY QSPDTRWGHT GFSYTNPKYN QFKVLELLGT  600
AENITANDLE IIVWTGLSTT DFYLDRLELI PM                               632

SEQ ID NO: 139         moltype = AA  length = 562
FEATURE                Location/Qualifiers
source                 1..562
                       mol_type = protein
                       organism = Bacillus sp.
SEQUENCE: 139
VNHMYTNTTK STLKIETTDY EIDQAAISIE CMSDEQTPQE KMMLWDEVKQ AKQLSWSRNL  60
LYNGDFEDAS NGWKTSYTIE IRKNSPIFKG QYLHMFGARD VLGEVFPTYV YQKIDESKLK  120
PYTRYRVRGF VGSSKDLNLV VTRYGKEIDA IMDVPDDLAS MQPNPSCGDY RCESASQYVS  180
QGTPNADGYA SEMYACPSDR VKKHVKCHDR HPFDFHIDTG ELDINTNVGI WVLFKISNPD  240
GYATLGNLEV IEEGPLTGEA LTHAKQKEKK WNQHMEKVRI ETQQAYDPAK QAVDALFTNA  300
QGEELHYHIT LDHIQNAHQL VQSIPYVHHA WLPDAPGMNY DVYQGVNARI MQAYNLYDAR  360
NVITNGDFTQ GLTGWHAEGK AMVQQMNGAS VLVLSNWSAG VSQNLHIQEH HGYVLRVIAK  420
KEGPGKGYVT MMDCNGKQET LKFTSCEEGY MTKTVEVFPE SDRIRIEMGE TEGTFYVDSI  480
ELICMKGYNH NQNTGTMYEQ SYNGNYNQNT SDVYHQGYTN NYNQVSSSMY NQNYTNNDDL  540
HSGCTCNQGH NSGCTCNQGY NR                                          562

SEQ ID NO: 140         moltype = AA  length = 659
FEATURE                Location/Qualifiers
REGION                 1..659
                       note = Description of Unknown: Organism from environmental
                        sample
source                 1..659
                       mol_type = protein
                       organism = unidentified
SEQUENCE: 140
MNSNSNNNSN NNENNTTGTL VVPSLSTTSV KHPLANNPIT SEQNIDYKDF FNSSAEPYLS  60
PQDGVNIGID IVGGILNFLG VPGIGIIAEF YKFTIGKLWP SNNSNEIWET FMKQMEELID  120
KKIAEHIKKE AISKLEGLQE GLIGYINALE AYQRDTKNFQ AKSLVKDRFV SLDMIFKTTM  180
PQLAIKDSEA LLLPIYAQAA NLHLYLIKDA QIFGEEWGME QKDIQLLYKE QLEATGKYIN  240
HCLKWYTIER DRLDKSETSK GWLIYLRFRR EMTLVVLDLI SLFPYYDTRT YPIPTKVQLT  300
REVYTTPIGY NPEKANGWCR PWTNISNDEL SFRKLERDCI RPAHLFEILK SIEITTIHQS  360
IDSSGKGYLK YWSGHSLKYT NVNSSTTSKA DYGYLNSSEK DTFNLVDEDI VSIASRAVCL  420
ANFYVSYYGV PFANFLKLKR DHSMVYNTIY TKSHSALPGN IQAYNSTDEL PLETGPMHNH  480
RLSHITFMSH RTAQLNNVTF PVYSWTHLSA DINNTIYPDK ITQIPLVKAH TKDSSTGVDG  540
GTGFTGGDLL YRNTPGVVAQ LKVTVNSPLS QRYKVRVRYC STTKMRIFIT VSGQRTYATT  600
VDKTRETNET FKFESYNFGT IDTPFTFSKK VDTVTVGVDT FNSSNAKVYI DKVEFIPVK   659

SEQ ID NO: 141         moltype = AA  length = 1148
FEATURE                Location/Qualifiers
source                 1..1148
                       mol_type = protein
                       organism = Bacillus sp.
SEQUENCE: 141
MNSNDNNNYE IIDSNASPYS PNRNNEYSRY PYAHNPDQPL QNTNYKDWLN NCQGNQQYIN  60
TANVQKTITT SLNITAAILG ASPLAPIGAG LAIGAIVIDL LWPDNTPNQW IAMMDRASEI  120
TIEAVTQAVR NTALSTLEGL KRLYKDYETD FNNWQKYKNN DSNGYYRNRV ENQFNILNSH  180
FIHDMAFFAP VGANQKVALL PVYAQTANLH LYLLNHGLIY SNEWSGTIIN KTEIHTNLTK  240
YTKEYTNHCI DWYNYGLNQI KNTSLIQIKT YHREMTIKVL DIIALFPSYD FIIYPTNPKM  300
ELTREIYTDP LTLSFNPKTS DDLAVVNYNL TRVPNLFTWL GGFTFYIDNK DIYFQNKLVG  360
HEYLYSYTNN IIANNRSIYY GKKINNPEIT DIAFNLTQRI FLVNTEHFEL PEISDRNLTI  420
KEILFRYEEN ERGGAKSLHI NAASSNQVKK VNQNFYLPSI KTGGYPDYND FNHRLSSMLT  480
HISNPINNST FHPIYIFGWT HSSVNFNNTV FKNQITQIPA VKAFRLGINS TVEKGPGHTG  540
GDLVFLQQHM MLNVTFPQDM NQPYRVRVRY SVNRATSLSL TIGNSSEVQQ IVGTTPSINS  600
TNLKYEHFQY VTFPTIIQPL TGQTQLVTLL TIQNSLVKLY IDKIEFIPVT SQYLETSEKE  660
KVETIQQRMN DVFLDPQHQS LQTKVTDYEI DQLASEIETL SDEWYPQEKM MLLDEIKHAK  720
QLSLARNILQ NGDFKNWIGW TTINDSTIQT GNPIFKGNTL HMPRARTTEI NNTVFPTYVY  780
QKIDESKLKP YTRYRVRGFI ESSKNLEVYI TRYNQEIHTM MNVLDDVIYR NSYEQTNSIL  840
QSSTTSNDSC HCDATQMSSV CQDPQAFSFF IDTGDLHGNE NLGISILFKI SDPDGYATLG  900
NLEVIEDQPL NEEDSKHIKE TEKVWNQTKE NQQKETEQIY SQAQQAVNNL FSNNQMLQIE  960
TTMADIIKAD SLIDTIPYVY NKWIPTEPGM NYQLYTDLKN QISQAYSFYD RRNIMKNGSF  1020
TNSLTHWQAS PDAYVEQMDT TSVLVLPNWS TQVSQQIQVQ QNHRYLLRVI AKKEGNGTGT  1080
IHISDCSNQV KTLVFHGSDN INQNMWENDM EYLTKTTIIT PHTNQVRIDI GETEGTFKIS  1140
SVEFICTN                                                          1148

SEQ ID NO: 142         moltype = AA  length = 649
FEATURE                Location/Qualifiers
REGION                 1..649
                       note = Description of Artificial Sequence: Synthetic
                        polypeptide
source                 1..649
                       mol_type = protein
                       organism = synthetic construct
SEQUENCE: 142
```

```
MNSNDNNNYE IIDSNASPYS PNRNNEYSRY PYAHNPDQPL QNTNYKDWLN NCQGNQQYIN  60
TANVQKTITT SLNITAAILG ASPLAPIGAG LAIGAIVIDL LWPDNTPNQW IAMMDRASEI  120
TIEAVTQAVR NTALSTLEGL KRLYKDYETD FNNWQKYKNN DSNGYYRNRV ENQFNILNSH  180
FIHDMAFFAP VGANQKVALL PVYAQTANLH LYLLNHGLIY SNEWSGTIIN KTEIHTNLTK  240
YTKEYTNHCI DWYNYGLNQI KNTSLIQIKT YHREMTIKVL DIIALFPSYD FIIYPTNPKM  300
ELTREIYTDP LTLSFNPKTS DDLAVVNYNL TRVPNLFTWL GGFTFYIDNK DIYFQNKLVG  360
HEYLYSYTNN IIANNRSIYY GKKINNPEIT DIAFNLTQRI FLVNTEHFEL PEISDRNLTI  420
KEILFRYEEN ERGGAKSLHI NAASSNQVKK VNQNFYLPSI KTGGYPDYND FNHRLSSMLT  480
HISNPINNST FHPIYIFGWT HSSVNFNNTV FKNQITQIPA VKAFRLGINS TVEKGPGHTG  540
GDLVFLQQHM MLNVTFPQDM NQPYRVRVRY SVNRATSLSL TIGNSSEVQQ IVGTTPSINS  600
TNLKYEHFQY VTFPTIIQPL TGQTQLVTLL TIQNSLVKLY IDKIEFIPV             649

SEQ ID NO: 143         moltype = AA  length = 185
FEATURE                Location/Qualifiers
source                 1..185
                       mol_type = protein
                       organism = Bacillus sp.
SEQUENCE: 143
MENNHPKHPI HEPQQAPSFP THPSHLQQTT YPNEKNHILP FSIIINLPKG FHIQKQRDPK  60
LVYDLSYLSM SKEICKKSIE VDNCGYVDVD LHVLKIKGCL SFLLNVCIEP IHKQKMCSTD  120
HKDDTIFLCA QDTLYVDHVL KYSVGKLPYY VINEEHVQVR KLEIQMLEGS HHTAKISGEF  180
YFEYE                                                             185

SEQ ID NO: 144         moltype = AA  length = 408
FEATURE                Location/Qualifiers
source                 1..408
                       mol_type = protein
                       organism = Bacillus sp.
SEQUENCE: 144
VKTKKWLHTI PSICLLSSAI LSFPTSSSAA FDLEHCHNRM YIQKCVEQTD PGVNNTTQRM  60
YETISGLLET DDLQEQTNFD GFHWYTSWYD FIRLNYLILP SQNKEILDQL NTIQKGNVDL  120
KQILKILNGY HHSTNTITDV STLQLSNMMV DKYIDVPEAD PESDQYLEIS TKLINDSYST  180
SLVKKTQPVT RTVKSSKQLT VTHGLNTGIR TESKAAFDVG IPLIGEVEGS IAFEYRVNHE  240
YKSASATMDK FIYSVSTPIE EIPLGPRTAA IITAKLSTPV YKTKLLSNTR IKGFYTDQVN  300
NTPTWLQLGI YNKFKIISQY NQQIWEKLKF LGFDLDDQTK EVIFTGVIDL KVNKVPGSIF  360
ESRTQIYELD ANGEINYNKP VGAPHMEVGD VEEIGSSQNT KQLVLRKR               408

SEQ ID NO: 145         moltype = AA  length = 408
FEATURE                Location/Qualifiers
REGION                 1..408
                       note = Description of Artificial Sequence: Synthetic
                        polypeptide
source                 1..408
                       mol_type = protein
                       organism = synthetic construct
SEQUENCE: 145
MKTKKWLHTI PSICLLSSAI LSFPTSSSAA FDLEHCHNRM YIQKCVEQTD PGVNNTTQRM  60
YETISGLLET DDLQEQTNFD GFHWYTSWYD FIRLNYLILP SQNKEILDQL NTIQKGNVDL  120
KQILKILNGY HHSTNTITDV STLQLSNMMV DKYIDVPEAD PESDQYLEIS TKLINDSYST  180
SLVKKTQPVT RTVKSSKQLT VTHGLNTGIR TESKAAFDVG IPLIGEVEGS IAFEYRVNHE  240
YKSASATMDK FIYSVSTPIE EIPLGPRTAA IITAKLSTPV YKTKLLSNTR IKGFYTDQVN  300
NTPTWLQLGI YNKFKIISQY NQQIWEKLKF LGFDLDDQTK EVIFTGVIDL KVNKVPGSIF  360
ESRTQIYELD ANGEINYNKP VGAPHMEVGD VEEIGSSQNT KQLVLRKR               408

SEQ ID NO: 146         moltype = AA  length = 380
FEATURE                Location/Qualifiers
REGION                 1..380
                       note = Description of Artificial Sequence: Synthetic
                        polypeptide
source                 1..380
                       mol_type = protein
                       organism = synthetic construct
SEQUENCE: 146
MAFDLEHCHN RMYIQKCVEQ TDPGVNNTTQ RMYETISGLL ETDDLQEQTN FDGFHWYTSW  60
YDFIRLNYLI LPSQNKEILD QLNTIQKGNV DLKQILKILN GYHHSTNTIT DVSTLQLSNM  120
MVDKYIDVPE ADPESDQYLE ISTKLINDSY STSLVKKTQP VTRTVKSSKQ LTVTHGLNTG  180
IRTESKAAFD VGIPLIGEVE GSIAFEYRVN HEYKSASATM DKFIYSVSTP IEEIPLGPRT  240
AAIITAKLST PVYKTKLLSN TRIKGFYTDQ VNNTPTWLQL GIYNKFKIIS QYNQQIWEKL  300
KFLGFDLDDQ TKEVIFTGVI DLKVNKVPGS IFESRTQIYE LDANGEINYN KPVGAPHMEV  360
GDVEEIGSSQ NTKQLVLRKR                                             380

SEQ ID NO: 147         moltype = AA  length = 341
FEATURE                Location/Qualifiers
source                 1..341
                       mol_type = protein
                       organism = Bacillus sp.
SEQUENCE: 147
MKSSKKKILP ISLLSTAILL SPLQAFAKIG QQASNIKVQN VNVKSSKLSV VDEKTMKDDL  60
VKRMNNLVDE YNENRSKDQA SKAKIKNLDG WAPEYTNADG YIDLPNPNIG PTNVKNVELG  120
```

```
TIVNEDPKET QVLNTPSTIE SVTESFTYTD STSEKFSFGL DTKVKVGLPF DMGSAEETIK  180
TSSEFMFTQT SSNTTSNTKS VTYPSQQIKA APGYKTTLVA SVAETSFSGM MDIHGKLMNL  240
NKIDSEISKQ EDVYQIYKKT SSTIPLPTGV SLDDANHIVT FDISIPYSGV GGHLSNAKFT  300
SVKIESFDGK KKVIMPLKDY QNPSVRQEIA KRKGIVLTIS E                      341

SEQ ID NO: 148         moltype = AA  length = 315
FEATURE                Location/Qualifiers
REGION                 1..315
                       note = Description of Artificial Sequence: Synthetic
                        polypeptide
source                 1..315
                       mol_type = protein
                       organism = synthetic construct
SEQUENCE: 148
MKIGQQASNI KVQNVNVKSS KLSVVDEKTM KDDLVKRMNN LVDEYNENRS KDQASKAKIK  60
NLDGWAPEYT NADGYIDLPN PNIGPTNVKN VELGTIVNED PKETQVLNTP STIESVTESF  120
TYTDSTSEKF SFGLDTKVKV GLPFDMGSAE ETIKTSSEFM FTQTSSNTTS NTKSVTYPSQ  180
QIKAAPGYKT TLVASVAETS FSGMMDIHGK LMNLNKIDSE ISKQEDVYQI YKKTSSTIPL  240
PTGVSLDDAN HIVTFDISIP YSGVGGHLSN AKFTSVKIES FDGKKKVIMP LKDYQNPSVR  300
QEIAKRKGIV LTISE                                                   315

SEQ ID NO: 149         moltype = AA  length = 771
FEATURE                Location/Qualifiers
REGION                 1..771
                       note = Description of Unknown: Organism from environmental
                        sample
source                 1..771
                       mol_type = protein
                       organism = unidentified
SEQUENCE: 149
LYMRSHFVYF PREIVIRMQR TQLYEYTSKN VKIRKLIGVV FIYPKRGNHA MQEKNLLSTG  60
PYNTLSTSAY QQLNNLANKA DGFDWEQLLK DVWNDVYHGQ ITQDYLQIAT DNNIDYRALV  120
TTILSYASSY VPFVGPVIGF FIPIIDLIWP PSQPDLFDIL RQQIQDLINQ ALTTDTLNKL  180
QALLQGWKNE LDALATEVKN LTDPKTSTIG STVNTIHLQF VHDIPQFTLK DYAAYALPLY  240
VQAATMHLGL LKEAISKQTD WGISDSDKTN FLTYLKQWIV KHSENVYTLF ATGLQNIKDD  300
ESSQISTDDF IYTSTLYGFD IATLWPTFDK WPTNDSPEVY PTQTDIEQTR FLFSDLVGRF  360
DWRGYPSAGD PSTYLYGNFP GELTQISTRT WDRVDQIQQV LNRGYNQSQT YTYGGSGGAA  420
NDPINISSDN PLIGVTPRVM SPYVGIMMDF ADGTSITNGG SYGYDKMVVA PENHKVHFVF  480
PWTDELGGQD AVINAFVFKN LHPENVIGQS DPTTGVVTIK GIPAEKGYME DGSSLNVVQE  540
RLNGTNAVQL PLGPSLVVPI TNKLAGQYHI RVRYANPSDS SIDIWQSVHA GNQTLQGGNF  600
TFPSTKNVQD QGYVPGQNGN YRLLTISLPD PISLPVGEID VRLGQYTSQT QGNLFIDRIE  660
FVQVQTHANL FSGPYYLYAP NGYPFSKTLW KGNTINSRIS IAGTANFSSE PAILQFYQDS  720
TLRKEIPIPG SGQNYNYPNT SIPNGFNKIV LHTNQSAGKG IRGTMQIFVI N            771

SEQ ID NO: 150         moltype = AA  length = 648
FEATURE                Location/Qualifiers
REGION                 1..648
                       note = Description of Artificial Sequence: Synthetic
                        polypeptide
source                 1..648
                       mol_type = protein
                       organism = synthetic construct
SEQUENCE: 150
MQRTQLYEYT SKNVKIRKLI GVVFIYPKRG NHAMQEKNLL STGPYNTLST SAYQQLNNLA  60
NKADGFDWEQ LLKDVWNDVY HGQITQDYLQ IATDNNIDYR ALVTTILSYA SSYVPFVGPV  120
IGFFIPIIDL IWPPSQPDLF DILRQQIQDL INQALTTDTL NKLQALLQGW KNELDALATE  180
VKNLTDPKTS TIGSTVNTIH LQFVHDIPQF TLKDYAAYAL PLYVQAATMH LGLLKEAISK  240
QTDWGISDSD KTNFLTYLKQ WIVKHSENVY TLFATGLQNI KDDESSQIST DDFIYTSTLY  300
GFDIATLWPT FDKWPTNDSP EVYPTQTDIE QTRFLFSDLV GRFDWRGYPS AGDPSTYLYG  360
NFPGELTQIS TRTWDRVDQI QQVLNRGYNQ SQTYTYGGSG GAANDPINIS SDNPLIGVTP  420
RVMSPYVGIM MDFADGTSIT NGGSYGYDKM VVAPENHKVH FVFPWTDELG GQDAVINAFV  480
FKNLHPENVI GQSDPTTGVV TIKGIPAEKG YMEDGSSLNV VQERLNGTNA VQLPLGPSLV  540
VPITNKLAGQ YHIRVRYANP SDSSIDIWQS VHAGNQTLQG GNFTFPSTKN VQDQGYVPGQ  600
NGNYRLLTIS LPDPISLPVG EIDVRLGQYT SQTQGNLFID RIEFVQVQ               648

SEQ ID NO: 151         moltype = AA  length = 477
FEATURE                Location/Qualifiers
source                 1..477
                       mol_type = protein
                       organism = Bacillus sp.
SEQUENCE: 151
MNGNGRHDGW NHNQNMESRQ MNQNHSGSCG CGCQQNQNEY NGTNNGSYSY QENSYASNQN  60
NQDMYMQNDM YGNHTYSNGS YYSTGYADTD DPLANLPDES KKFQRITNIS SGDKFVMEAS  120
NRPIGYYLDP VGTCSRQTEI ENTVTNGTAT PATQETRDTQ NFVFYNTDMK DTFIIANKGN  180
GRVLELVDTG ATDGTLASRA YNPNVLAQFY KRELVQGKTD QFYLITTLNN IEVGINNCHN  240
NPTAWQKYTA YPRDRFDNNA YKFLDKTDIV FPNDLKVYPQ QLPNPRPLTN IDDLGEEPSV  300
LQGKVLLPCI FVKDLSLSLN QQIKQSPYYI LEYTESWSKV FTNTLYPNGY ASWNEVIGIT  360
SGTQDSMRET IDISIGGNTT QAWGLLFGNK SAPFQSQISS GLSISKSFDS ELGSTSRVDY  420
IQNMDTKPIR YVKYLKKHEL KLKRLDGTQV LNGVWNIFSN EGIMKTYPDI NSSQYSY      477
```

```
SEQ ID NO: 152          moltype = AA  length = 489
FEATURE                 Location/Qualifiers
source                  1..489
                        mol_type = protein
                        organism = Bacillus sp.
SEQUENCE: 152
MKYKDRIQAK RNYKQTIFAA ATTLTLGVSA LAGPASAFAA EQKTADHTKT VQNQKQSQFK  60
VMAGDDSYID SLEKFKKNFS PTSKTGKFLD DLTKKGLGSL TKTANGGNIN YNNFFRDLTI  120
SSMDLIPYGG ALFSTFIALM WPMEQNSNIM DQLVEKFSKM VDEKIVDYDN GTLKQQAIAL  180
QDQLEQFDKL VNRIENKVTT YMSDREAAAT LALNLNTAFN NLLRNCQKDD QKVSELPLYT  240
QIATTHLVFL KYVVENGGKG TTLDFEKNAL QTFKDSLDNG TKEYSNHIQN VAREGLAKIS  300
NQKLGFVATN NEEYTQAMML GAQRTIQSLE QLPIRTPEQT RQLNNARSEL EAMKNGKKYV  360
LPTEVAKDIY DYRASTVDNL AFNTLISILK GNKHTGWVKE NGLFFYEKEG IRENSGWFRD  420
EDKRYYYLDP KDGHMVTGWI KDKEKWYYLI PNKYYNGAFK EGEMVYQISK ILIDGKEYEF  480
DGKGVCLNP                                                         489

SEQ ID NO: 153          moltype = AA  length = 451
FEATURE                 Location/Qualifiers
REGION                  1..451
                        note = Description of Artificial Sequence: Synthetic
                         polypeptide
source                  1..451
                        mol_type = protein
                        organism = synthetic construct
SEQUENCE: 153
MAEQKTADHT KTVQNQKQSQ FKVMAGDDSY IDSLEKFKKN FSPTSKTGKF LDDLTKKGLG  60
SLTKTANGGN INYNNFFRDL TISSMDLIPY GGALFSTFIA LMWPMEQNSN IMDQLVEKFS  120
KMVDEKIVDY DNGTLKQQAI ALQDQLEQFD KLVNRIENKV TTYMSDREAA ATLALNLNTA  180
FNNLLRNCQK DDQKVSELPL YTQIATTHLV FLKYVVENGG KGTTLDFEKN ALQTFKDSLD  240
NGTKEYSNHI QNVAREGLAK ISNQKLGFVA TNNEEYTQAM MLGAQRTIQS LEQLPIRTPE  300
QTRQLNNARS ELEAMKNGKK YVLPTEVAKD IYDYRASTVD NLAFNTLISI LKGNKHTGWV  360
KENGLFFYEK EGIRENSGWF RDEDKRYYYL DPKDGHMVTG WIKDKEKWYY LIPNKYYNGA  420
FKEGEMVYQI SKILIDGKEY EFDGKGVCLN P                                451

SEQ ID NO: 154          moltype = AA  length = 311
FEATURE                 Location/Qualifiers
source                  1..311
                        mol_type = protein
                        organism = Bacillus sp.
SEQUENCE: 154
MIITDIEQET RNYLNWFLNK KYPNNNLQFR GVSFFPFEVT DAIIRPKNTI FESVPVLKGT  60
AYRVVENHTS LPQSQTIKLS EKVIDTVTNT TTEGYKVGAG IKSSTKVSVN IKFLVSGGIE  120
QTFETSFNAE YNYSTTQSIT ETTESLWEVT EPVNVPPYKR VTASLQIMGA DIEVPMELTG  180
NLKGTQYYYD ELDTKRSFYR FAAGTYEYAP APGYWVGSIK DIPASDLADS NWPDRPSSFK  240
AKGVNDALYL EGAGISSLGT ALFSITKFEE TPLSGFEGET KTWYSPQIQL KDGTVIYVPN  300
INEVIENYRP L                                                      311

SEQ ID NO: 155          moltype = AA  length = 296
FEATURE                 Location/Qualifiers
source                  1..296
                        mol_type = protein
                        organism = Bacillus sp.
SEQUENCE: 155
MAIVDLDAYL FALVKKVFPF PQMLKGVLTS ELSIANAESY GFEIKNSKPQ GTMFMGESVL  60
ENDTSETQLI HSDSFTKTIT DSVTLSVTNG ITTGVNISIG GKVFGMGVET SMSFEVSTST  120
TREQTSTEGV AYTVPSQTVS VPARKTYYVY TALQRSQLEG SIRLRADLSG DLHVKIDVGG  180
AEGTMYIGNI YEYIKTHQLL HPLPSGISLN HNNKSIHFEG IAELIYGTGT KFNVTITDKP  240
SSQGTQEHTT IDAKTGLGTY EIQLDGKKLG FDLNDLKDKT EPEVFEKLKE LQNEIV      296

SEQ ID NO: 156          moltype = AA  length = 1236
FEATURE                 Location/Qualifiers
source                  1..1236
                        mol_type = protein
                        organism = Bacillus sp.
SEQUENCE: 156
MDDMTTLSDL YSLVPYNVLT TPNVLATNKE LLSETDALTK LYMDFQIGKI SAATFDALWS  60
LMTTGSYDWS SIVKLGWSLA TGAAPLLGIF SPIIDLIFPA LFGSKPSLFE QLKPQIEKLI  120
IDKLTDEEKN FLNQKTNDIQ SYLNDYQTAV SKISNPNATD SDFQSLHGTI DQTLSKIKGS  180
LSYYSNFDYP DDRKSIYTIL GLPYYTLMAT MYLTLLRDVI LNTEKWKITA ASSDSYHQQF  240
KENMNSFVRT IKQNYQTGFN YIKDKASKNV FKKSSEIILS FENQMIVNCF DYITIWPTLY  300
PDDYYTKKTN LQQTRLLFSP ILGRMPDSRS KWLHTSPYSW DNNTFTFDHY YIAELTHINT  360
HEWDRVDRID QTYLEGYQEE EHQYIDSYTG GGTPNKDASF TTDNPLAIMY PTQSGNYVNT  420
AIQWFDSRTI GGLTPYSGDP DPKAPDDHKV NFLYTVKDEL NGIDAWVNSW VPIYTTVPNI  480
IGNEMIPTTK GFPFEKGIID TDGAGGDKIY QPERLNGAMA INLQYNQIIK LPFTNTISGD  540
YIIRLRYASH SDINAFVHIQ PKNGNDMRST PLGNITLSNT QNFTIPNKNE YKPNQPQYTN  600
YIEGNAGKYA LYQFTQKISL TSGQYTFYIQ NNSNTDLFLD RIEFIPVNQS LNKILPDVTI  660
QDNNVSHDIW SDNENTGQSL SGTIQFGGAA TLNLTQVVLN YMDKNGKIVH SDVTPLSDLN  720
NHTFPIKVWN GSFNRISAYG QNLITNSWIE NGYIELTDLL LTIQTPQFTA PEDLEQITVQ  780
```

```
VNQLFTSSSQ TGLATTVTDY RIDQVVMKVD ALSDDEFGVE KKELRKLVNQ AKQLSKARNV  840
LVGGNFEKGH KWILSRKATM VANDELFKGD HLLLPPPTLY PSYAYQKIDE SKLKSNTRYT  900
VSGFIAQSEH LEVFVSRYGK EVYNMLDVPY EEVLPISSDE SPNCCKPTTC QCLSCDSSQP  960
DSHFFSYSID VGSVQTDVNL GIEFGLRIAK ANGFAKISNL EIKEDRPLTE KEIKKVQRKE  1020
QKWKKAFDQE QTELTITIQP TLNQINALYQ NEDWNSSLHP HVTYQHLSDV VIPTLPKQRH  1080
WFMKDREGEH YHIIQQFQQA LDRAFQQVEK QNLIHNGSFA NGLTDWTVTG DAQVTIHDED  1140
PVLELAHWDA SVSQIVEIMD FEEETEYKLR VRANGNGTVT IQHGEEKLEK MTFNTSSFTT  1200
QEQTFYFEGK AVDVHVQSEN NTFLVDSVEL IKIVEE                           1236

SEQ ID NO: 157         moltype = AA  length = 1233
FEATURE                Location/Qualifiers
REGION                 1..1233
                       note = Description of Artificial Sequence: Synthetic
                        polypeptide
source                 1..1233
                       mol_type = protein
                       organism = synthetic construct
SEQUENCE: 157
MTTLSDLYSL VPYNVLTTPN VLATNKELLS ETDALTKLYM DFQIGKISAA TFDALWSLMT  60
TGSYDWSSIV KLGWSLATGA APLLGIFSPI IDLIFPALFG SKPSLFEQLK PQIEKLIIDK  120
LTDEEKNFLN QKTNDIQSYL NDYQTAVSKI SNPNATDSDF QSLHGTIDQT LSKIKGSLSY  180
YSNFDYPDDR KSIYTILGLP YYTLMATMYL TLLRDVILNT EKWKITAASS DSYHQQFKEN  240
MNSFVRTIKQ NYQTGFNYIK DKASKNVFKK SSEIILSFEN QMIVNCFDYI TIWPTLYPDD  300
YYTKKTNLQQ TRLLFSPILG RMPDSRSKWL HTSPYSWDNN TFTFDHYYIA ELTHINTHEW  360
DRVDRIDQTY LEGYQEEEHQ YIDSYTGGGT PNKDASFTTD NPLAIMYPTQ SGNYVNTAIQ  420
WFDSRTIGGL TPYSGDPDPK APDDHKVNFL YTVKDELNGI DAWVNSWVPI YTTVPNIIGN  480
EMIPTTKGFP FEKGIIDTDG AGGDKIYQPE RLNGAMAINL QYNQIIKLPF TNTISGDYII  540
RLRYASHSDI NAFVHIQPKN GNDMRSTPLG NITLSNTQNF TIPNKNEYKP NQPQYTNYIE  600
GNAGKYALYQ FTQKISLTSG QYTFYIQNNS NTDLFLDRIE FIPVNQSLNK ILPDVTIQDN  660
NVSHDIWSDN ENTGQSLSGT IQFGGAATLN LTQVVLNYMD KNGKIVHSDV TPLSDLNNHT  720
FPIKVWNGSF NRISAYGQNL ITNSWIENGY IELTDLLLTI QTPQFTAPED LEQITVQVNQ  780
LFTSSSQTGL ATTVTDYRID QVVMKVDALS DDEFGVEKKE LRKLVNQAKQ LSKARNVLVG  840
GNFEKGHKWI LSRKATMVAN DELFKGDHLL LPPPTLYPSY AYQKIDESKL KSNTRYTVSG  900
FIAQSEHLEV FVSRYGKEVY NMLDVPYEEV LPISSDESPN CCKPTTCQCL SCDSSQPDSH  960
FFSYSIDVGS VQTDVNLGIE FGLRIAKANG FAKISNLEIK EDRPLTEKEI KKVQRKEQKW  1020
KKAFDQEQTE LTITIQPTLN QINALYQNED WNSSLHPHVT YQHLSDVVIP TLPKQRHWFM  1080
KDREGEHYHI IQQFQQALDR AFQQVEKQNL IHNGSFANGL TDWTVTGDAQ VTIHDEDPVL  1140
ELAHWDASVS QIVEIMDFEE ETEYKLRVRA NGNGTVTIQH GEEKLEKMTF NTSSFTTQEQ  1200
TFYFEGKAVD VHVQSENNTF LVDSVELIKI VEE                              1233

SEQ ID NO: 158         moltype = AA  length = 645
FEATURE                Location/Qualifiers
REGION                 1..645
                       note = Description of Artificial Sequence: Synthetic
                        polypeptide
source                 1..645
                       mol_type = protein
                       organism = synthetic construct
SEQUENCE: 158
MTTLSDLYSL VPYNVLTTPN VLATNKELLS ETDALTKLYM DFQIGKISAA TFDALWSLMT  60
TGSYDWSSIV KLGWSLATGA APLLGIFSPI IDLIFPALFG SKPSLFEQLK PQIEKLIIDK  120
LTDEEKNFLN QKTNDIQSYL NDYQTAVSKI SNPNATDSDF QSLHGTIDQT LSKIKGSLSY  180
YSNFDYPDDR KSIYTILGLP YYTLMATMYL TLLRDVILNT EKWKITAASS DSYHQQFKEN  240
MNSFVRTIKQ NYQTGFNYIK DKASKNVFKK SSEIILSFEN QMIVNCFDYI TIWPTLYPDD  300
YYTKKTNLQQ TRLLFSPILG RMPDSRSKWL HTSPYSWDNN TFTFDHYYIA ELTHINTHEW  360
DRVDRIDQTY LEGYQEEEHQ YIDSYTGGGT PNKDASFTTD NPLAIMYPTQ SGNYVNTAIQ  420
WFDSRTIGGL TPYSGDPDPK APDDHKVNFL YTVKDELNGI DAWVNSWVPI YTTVPNIIGN  480
EMIPTTKGFP FEKGIIDTDG AGGDKIYQPE RLNGAMAINL QYNQIIKLPF TNTISGDYII  540
RLRYASHSDI NAFVHIQPKN GNDMRSTPLG NITLSNTQNF TIPNKNEYKP NQPQYTNYIE  600
GNAGKYALYQ FTQKISLTSG QYTFYIQNNS NTDLFLDRIE FIPVN                  645

SEQ ID NO: 159         moltype = AA  length = 1194
FEATURE                Location/Qualifiers
REGION                 1..1194
                       note = Description of Artificial Sequence: Synthetic
                        polypeptide
source                 1..1194
                       mol_type = protein
                       organism = synthetic construct
SEQUENCE: 159
MDFQIGKISA ATFDALWSLM TTGSYDWSSI VKLGWSLATG AAPLLGIFSP IIDLIFPALF  60
GSKPSLFEQL KPQIEKLIID KLTDEEKNFL NQKTNDIQSY LNDYQTAVSK ISNPNATDSD  120
FQSLHGTIDQ TLSKIKGSLS YYSNFDYPDD RKSIYTILGL PYYTLMATMY LTLLRDVILN  180
TEKWKITAAS SDSYHQQFKE NMNSFVRTIK QNYQTGFNYI KDKASKNVFK KSSEIILSFE  240
NQMIVNCFDY ITIWPTLYPD DYYTKKTNLQ QTRLLFSPIL GRMPDSRSKW LHTSPYSWDN  300
NTFTFDHYYI AELTHINTHE WDRVDRIDQT YLEGYQEEEH QYIDSYTGGG TPNKDASFTT  360
DNPLAIMYPT QSGNYVNTAI QWFDSRTIGG LTPYSGDPDP KAPDDHKVNF LYTVKDELNG  420
IDAWVNSWVP IYTTVPNIIG NEMIPTTKGF PFEKGIIDTD GAGGDKIYQP ERLNGAMAIN  480
LQYNQIIKLP FTNTISGDYI IRLRYASHSD INAFVHIQPK NGNDMRSTPL GNITLSNTQN  540
```

```
FTIPNKNEYK PNQPQYTNYI EGNAGKYALY QFTQKISLTS GQYTFYIQNN SNTDLFLDRI  600
EFIPVNQSLN KILPDVTIQD NNVSHDIWSD NENTGQSLSG TIQFGGAATL NLTQVVLNYM  660
DKNGKIVHSD VTPLSDLNNH TFPIKVWNGS FNRISAYGQN LITNSWIENG YIELTDLLLT  720
IQTPQFTAPE DLEQITVQVN QLFTSSSQTG LATTVTDYRI DQVVMKVDAL SDDEFGVEKK  780
ELRKLVNQAK QLSKARNVLV GGNFEKGHKW ILSRKATMVA NDELFKGDHL LLPPPTLYPS  840
YAYQKIDESK LKSNTRYTVS GFIAQSEHLE VFVSRYGKEV YNMLDVPYEE VLPISSDESP  900
NCCKPTTCQC LSCDSSQPDS HFFSYSIDVG SVQTDVNLGI EFGLRIAKAN GFAKISNLEI  960
KEDRPLTEKE IKKVQRKEQK WKKAFDQEQT ELTITIQPTL NQINALYQNE DWNSSLHPHV  1020
TYQHLSDVVI PTLPKQRHWF MKDREGEHYH IIQQFQQALD RAFQQVEKQN LIHNGSFANG  1080
LTDWTVTGDA QVTIHDEDPV LELAHWDASV SQIVEIMDFE EETEYKLRVR ANGNGTVTIQ  1140
HGEEKLEKMT FNTSSFTTQE QTFYFEGKAV DVHVQSENNT FLVDSVELIK IVEE        1194

SEQ ID NO: 160          moltype = AA  length = 606
FEATURE                 Location/Qualifiers
REGION                  1..606
                        note = Description of Artificial Sequence: Synthetic
                         polypeptide
source                  1..606
                        mol_type = protein
                        organism = synthetic construct
SEQUENCE: 160
MDFQIGKISA ATFDALWSLM TTGSYDWSSI VKLGWSLATG AAPLLGIFSP IIDLIFPALF  60
GSKPSLFEQL KPQIEKLIID KLTDEEKNFL NQKTNDIQSY LNDYQTAVSK ISNPNATDSD  120
FQSLHGTIDQ TLSKIKGSLS YYSNFDYPDD RKSIYTILGL PYYTLMATMY LTLLRDVILN  180
TEKWKITAAS SDSYHQQFKE NMNSFVRTIK QNYQTGFNYI KDKASKNVFK KSSEIILSFE  240
NQMIVNCFDY ITIWPTLYPD DYYTKKTNLQ QTRLLFSPIL GRMPDSRSKW LHTSPYSWDN  300
NTFTFDHYYI AELTHINTHE WDRVDRIDQT YLEGYQEEEH QYIDSYTGGG TPNKDASFTT  360
DNPLAIMYPT QSGNYVNTAI QWFDSRTIGG LTPYSGDPDP KAPDDHKVNF LYTVKDELNG  420
IDAWVNSWVP IYTTVPNIIG NEMIPTTKGF PFEKGIIDTD GAGGDKIYQP ERLNGAMAIN  480
LQYNQIIKLP FTNTISGDYI IRLRYASHSD INAFVHIQPK NGNDMRSTPL GNITLSNTQN  540
FTIPNKNEYK PNQPQYTNYI EGNAGKYALY QFTQKISLTS GQYTFYIQNN SNTDLFLDRI  600
EFIPVN                                                            606

SEQ ID NO: 161          moltype = AA  length = 1175
FEATURE                 Location/Qualifiers
REGION                  1..1175
                        note = Description of Artificial Sequence: Synthetic
                         polypeptide
source                  1..1175
                        mol_type = protein
                        organism = synthetic construct
SEQUENCE: 161
MTTGSYDWSS IVKLGWSLAT GAAPLLGIFS PIIDLIFPAL FGSKPSLFEQ LKPQIEKLII  60
DKLTDEEKNF LNQKTNDIQS YLNDYQTAVS KISNPNATDS DFQSLHGTID QTLSKIKGSL  120
SYYSNFDYPD DRKSIYTILG LPYYTLMATM YLTLLRDVIL NTEKWKITAA SSDSYHQQFK  180
ENMNSFVRTI KQNYQTGFNY IKDKASKNVF KKSSEIILSF ENQMIVNCFD YITIWPTLYP  240
DDYYTKKTNL QQTRLLFSPI LGRMPDSRSK WLHTSPYSWD NNTFTFDHYY IAELTHINTH  300
EWDRVDRIDQ TYLEGYQEEE HQYIDSYTGG GTPNKDASFT TDNPLAIMYP TQSGNYVNTA  360
IQWFDSRTIG GLTPYSGDPD PKAPDDHKVN FLYTVKDELN GIDAWVNSWV PIYTTVPNII  420
GNEMIPTTKG FPFEKGIIDT DGAGGDKIYQ PERLNGAMAI NLQYNQIIKL PFTNTISGDY  480
IIRLRYASHS DINAFVHIQP KNGNDMRSTP LGNITLSNTQ NFTIPNKNEY KPNQPQYTNY  540
IEGNAGKYAL YQFTQKISLT SGQYTFYIQN NSNTDLFLDR IEFIPVNQSL NKILPDVTIQ  600
DNNVSHDIWS DNENTGQSLS GTIQFGGAAT LNLTQVVLNY MDKNGKIVHS DVTPLSDLNN  660
HTFPIKVWNG SFNRISAYGQ NLITNSWIEN GYIELTDLLL TIQTPQFTAP EDLEQITVQV  720
NQLFTSSSQT GLATTVTDYR IDQVVMKVDA LSDDEFGVEK KELRKLVNQA KQLSKARNVL  780
VGGNFEKGHK WILSRKATMV ANDELFKGDH LLLPPPTLYP SYAYQKIDES KLKSNTRYTV  840
SGFIAQSEHL EVFVSRYGKE VYNMLDVPYE EVLPISSDES PNCCKPTTCQ CLSCDSSQPD  900
SHFFSYSIDV GSVQTDVNLG IEFGLRIAKA NGFAKISNLE IKEDRPLTEK EIKKVQRKEQ  960
KWKKAFDQEQ TELTITIQPT LNQINALYQN EDWNSSLHPH VTYQHLSDVV IPTLPKQRHW  1020
FMKDREGEHY HIIQQFQQAL DRAFQQVEKQ NLIHNGSFAN GLTDWTVTGD AQVTIHDEDP  1080
VLELAHWDAS VSQIVEIMDF EEETEYKLRV RANGNGTVTI QHGEEKLEKM TFNTSSFTTQ  1140
EQTFYFEGKA VDVHVQSENN TFLVDSVELI KIVEE                            1175

SEQ ID NO: 162          moltype = AA  length = 587
FEATURE                 Location/Qualifiers
REGION                  1..587
                        note = Description of Artificial Sequence: Synthetic
                         polypeptide
source                  1..587
                        mol_type = protein
                        organism = synthetic construct
SEQUENCE: 162
MTTGSYDWSS IVKLGWSLAT GAAPLLGIFS PIIDLIFPAL FGSKPSLFEQ LKPQIEKLII  60
DKLTDEEKNF LNQKTNDIQS YLNDYQTAVS KISNPNATDS DFQSLHGTID QTLSKIKGSL  120
SYYSNFDYPD DRKSIYTILG LPYYTLMATM YLTLLRDVIL NTEKWKITAA SSDSYHQQFK  180
ENMNSFVRTI KQNYQTGFNY IKDKASKNVF KKSSEIILSF ENQMIVNCFD YITIWPTLYP  240
DDYYTKKTNL QQTRLLFSPI LGRMPDSRSK WLHTSPYSWD NNTFTFDHYY IAELTHINTH  300
EWDRVDRIDQ TYLEGYQEEE HQYIDSYTGG GTPNKDASFT TDNPLAIMYP TQSGNYVNTA  360
IQWFDSRTIG GLTPYSGDPD PKAPDDHKVN FLYTVKDELN GIDAWVNSWV PIYTTVPNII  420
```

```
GNEMIPTTKG FPFEKGIIDT DGAGGDKIYQ PERLNGAMAI NLQYNQIIKL PFTNTISGDY  480
IIRLRYASHS DINAFVHIQP KNGNDMRSTP LGNITLSNTQ NFTIPNKNEY KPNQPQYTNY  540
IEGNAGKYAL YQFTQKISLT SGQYTFYIQN NSNTDLFLDR IEFIPVN                587

SEQ ID NO: 163         moltype = AA  length = 276
FEATURE                Location/Qualifiers
source                 1..276
                       mol_type = protein
                       organism = Bacillus sp.
SEQUENCE: 163
VDCMAILDLR AVAENYWKKY CASRGYNYIR TDMPNVEISN FNMNILDPVI FATPGETALA  60
TGVTTNRTSR DVLRTLTFNE TQTDSQSTTT EHGITAGISV TARAEASILF ATVGIETTMS  120
LEYNYTNSKT YTKEVSRSWE DSTTITVPPG YETEYAFIIQ TGPFNKNVAL ECDITGLTTC  180
RYSHPQMPGY TFGESDYMSR ILGYEGIPNI SLIGSHDIAR FKGVGKLAGS MGLKSYIDLD  240
ERPLPGRSGQ TRRYQIPLTG RSGIDIPILD PVLSRQ                            276

SEQ ID NO: 164         moltype = AA  length = 273
FEATURE                Location/Qualifiers
REGION                 1..273
                       note = Description of Artificial Sequence: Synthetic
                        polypeptide
source                 1..273
                       mol_type = protein
                       organism = synthetic construct
SEQUENCE: 164
MAILDLRAVA ENYWKKYCAS RGYNYIRTDM PNVEISNFNM NILDPVIFAT PGETALATGV  60
TTNRTSRDVL RTLTFNETQT DSQSTTTEHG ITAGISVTAR AEASILFATV GIETTMSLEY  120
NYTNSKTYTK EVSRSWEDST TITVPPGYET EYAFIIQTGP FNKNVALECD ITGLTTCRYS  180
HPQMPGYTFG ESDYMSRILG YEGIPNISLI GSHDIARFKG VGKLAGSMGL KSYIDLDERP  240
LPGRSGQTRR YQIPLTGRSG IDIPILDPVL SRQ                               273

SEQ ID NO: 165         moltype = AA  length = 423
FEATURE                Location/Qualifiers
source                 1..423
                       mol_type = protein
                       organism = Bacillus sp.
SEQUENCE: 165
MRENHKVKYW KRKSTKLVPV CLLSTSFLFN ITDSAFAAER VDLYHTCGQA GMSWGNASKP  60
YNQTCVKQHD GEERTGKMYD TVAKLTNQDS FKEKTNWGEK VWQWSEERQE VNNNFIALGY  120
IITPSQEQGV LDKLNQISKD NVKLPDVLAA LNGLDTDHIE DFTKPTSISK LDISQMNVKR  180
MVQAEIDLNA PQSRRYTNEF INQTDHDQPG QLVSTTYKYI SSKTISDIQA INIGFKQGLK  240
MTIGASAQIP EVGGLTAQTE VSLEANESFG YTHSAQTFSS VEHAITTPST LYTIKPHTGL  300
VVTTELGTPT YKATLLGETR IKGIYTNFVN SYDIWVQQSI YLKFKLVESE NPIIWSKIQE  360
LGFSLDETTK EVIYKGSMNY TEHGLPATRW SVKTQEYQLT TKGTIDYMKP IGTPSIKEAK  420
CTI                                                                423

SEQ ID NO: 166         moltype = AA  length = 387
FEATURE                Location/Qualifiers
REGION                 1..387
                       note = Description of Artificial Sequence: Synthetic
                        polypeptide
source                 1..387
                       mol_type = protein
                       organism = synthetic construct
SEQUENCE: 166
MAERVDLYHT CGQAGMSWGN ASKPYNQTCV KQHDGEERTG KMYDTVAKLT NQDSFKEKTN  60
WGEKVWQWSE ERQEVNNNFI ALGYIITPSQ EQGVLDKLNQ ISKDNVKLPD VLAALNGLDT  120
DHIEDFTKPT SISKLDISQM NVKRMVQAEI DLNAPQSRRY TNEFINQTDH DQPGQLVSTT  180
YKYISSKTIS DIQAINIGFK QGLKMTIGAS AQIPEVGGLT AQTEVSLEAN ESFGYTHSAQ  240
TFSSVEHAIT TPSTLYTIKP HTGLVVTTEL GTPTYKATLL GETRIKGIYT NFVNSYDIWV  300
QQSIYLKFKL VESENPIIWS KIQELGFSLD ETTKEVIYKG SMNYTEHGLP ATRWSVKTQE  360
YQLTTKGTID YMKPIGTPSI KEAKCTI                                      387

SEQ ID NO: 167         moltype = AA  length = 279
FEATURE                Location/Qualifiers
source                 1..279
                       mol_type = protein
                       organism = Bacillus sp.
SEQUENCE: 167
IMANQRKNPL DLIEIFSTFA NNWSMQNQGC AGTLFLLPHD ATQQGLEVSS DFTAVYAAPV  60
EQKETISHSS FSFSNISNTF KEQQVLVNTT TDISEFWELT QSVCPGGNDF FTITTPALTD  120
VPGVPSQDPI QICDHETVTH SHSYTWNVNQ TISLPPRSTT TVTFQTTLKN VTRDFQFVFW  180
MTGNIGVTSM NPINSSTETY FPITQVLQWY SNDLLTLDFD FNKVTCLNKG IYKATYQVSP  240
QLLIETKSAD NAGITQNTVI DLNTGTTTLV NNSNGCCPA                         279

SEQ ID NO: 168         moltype = AA  length = 204
FEATURE                Location/Qualifiers
source                 1..204
                       mol_type = protein
```

```
                         organism = Bacillus sp.
SEQUENCE: 168
VGNNHFHNVF AVKQEHLGQV LKLKKFFEEL DMNFNDFTDP RTLVNVLESN RNINFLKSSQ  60
EAIIGGEALQ ISELIEKISN LIIKDILALP TYRWGESINQ DIISQVTDAI TNMFIHLNKQ  120
DAEPWIFWYN TGNSFPRYTY NLLIAIDTQD KDYLTDVLAI SFDVLVVKKT KKEVCSFTVN  180
DSAQCLIMMK HMLVGIKFED VYPS                                       204

SEQ ID NO: 169          moltype = AA  length = 204
FEATURE                 Location/Qualifiers
REGION                  1..204
                        note = Description of Artificial Sequence: Synthetic
                         polypeptide
source                  1..204
                        mol_type = protein
                        organism = synthetic construct
SEQUENCE: 169
MGNNHFHNVF AVKQEHLGQV LKLKKFFEEL DMNFNDFTDP RTLVNVLESN RNINFLKSSQ  60
EAIIGGEALQ ISELIEKISN LIIKDILALP TYRWGESINQ DIISQVTDAI TNMFIHLNKQ  120
DAEPWIFWYN TGNSFPRYTY NLLIAIDTQD KDYLTDVLAI SFDVLVVKKT KKEVCSFTVN  180
DSAQCLIMMK HMLVGIKFED VYPS                                       204

SEQ ID NO: 170          moltype = AA  length = 274
FEATURE                 Location/Qualifiers
source                  1..274
                        mol_type = protein
                        organism = Bacillus sp.
SEQUENCE: 170
MANFSSLQEA TSIYLSDKYI RVPNSYYISM IGVPDMFRNL EMSGPVTIPN VISTTEPRTV  60
VQTAAITNSS SSSITKQFSF SESVTDTVSS TLSYGFELGI TREISMGATI EIVKLDSKQT  120
ISTKFSTNSS QTTTNTKTRT WVDQYSVPVA AYTQATVIYT LSIGTFDGLL DVDLKLSGSV  180
LGGLEYSTVG SLANPGKGPF AFLDIPISDI VRYTQPTGFT VNPDNTVSFK GKLRLQGELG  240
IKSELLVNSK SLITGLITTT PLNTQTAPKT VLFA                            274

SEQ ID NO: 171          moltype = AA  length = 403
FEATURE                 Location/Qualifiers
source                  1..403
                        mol_type = protein
                        organism = Bacillus sp.
SEQUENCE: 171
LSTKLGGNIM KSISKKVMAG LLVGATSLSI WAPTSQAAAP EKNRYYSVHL AANTNLKWDV  60
YGNSPNDEAG ILLYNGSFGD NEQFVFFPLD GGLYAIVNKN SGKAVTIGGG YVAPLDFTYN  120
REGLKQSKWT GAADNKWYLR DKGNNNYEIV NQGYGKVASY ARIGITGPQY VDLDDSNPSD  180
NDRLFRIQRN PLGVDIPGFN FEYGTFSLPQ LPAVGNRPDA PNYTGGIDQQ LPQTSNSVVV  240
GASLLPCIMV NDSQASEYTK IHNSPYYTLV KEEYWDKTFS KVIQPGLSES YSYKTGVSSV  300
DQQKMTDTLS MKFGSDLGIK FGDVSASLKS EISRTIQTEI STTNSEATEE TRSYTAIGEP  360
GKATGYTQYQ LATKYTLKRA DGSTVSDPWV VKNDKITVTR KTS                  403

SEQ ID NO: 172          moltype = AA  length = 367
FEATURE                 Location/Qualifiers
REGION                  1..367
                        note = Description of Artificial Sequence: Synthetic
                         polypeptide
source                  1..367
                        mol_type = protein
                        organism = synthetic construct
SEQUENCE: 172
MAAPEKNRYY SVHLAANTNL KWDVYGNSPN DEAGILLYNG SFGDNEQFVF FPLDGGLYAI  60
VNKNSGKAVT IGGGYVAPLD FTYNREGLKQ SKWTGAADNK WYLRDKGNNN YEIVNQGYGK  120
VASYARIGIT GPQYVDLDDS NPSDNDRLFR IQRNPLGVDI PGFNFEYGTF SLPQLPAVGN  180
RPDAPNYTGG IDQQLPQTSN SVVVGASLLP CIMVNDSQAS EYTKIHNSPY YTLVKEEYWD  240
KTFSKVIQPG LSESYSYKTG VSSVDQQKMT DTLSMKFGSD LGIKFGDVSA SLKSEISRTI  300
QTEISTTNSE ATEETRSYTA IGEPGKATGY TQYQLATKYT LKRADGSTVS DPWVVKNDKI  360
TVTRKTS                                                          367

SEQ ID NO: 173          moltype = AA  length = 985
FEATURE                 Location/Qualifiers
source                  1..985
                        mol_type = protein
                        organism = Bacillus sp.
SEQUENCE: 173
MSIYNVEADL FDLCREYAIK HYDANDATFH GATIYDRSVL NSEVMPDQVE FNVIPDLSNT  60
VINTITNDTN IEQSMSTKLS TKTIETTSFT TTEGYKVGTS IKNTLEFKAG GLFSIGGVEH  120
KFEVSVSGEY NHSSSETTTN TTEKLWEYTA PIKVPPNTKV EGKIQIYSGA IPVPVTLKST  180
VLGLGQSPNG KLKNALTSLW YKDKAGKEWV DTYQTSHLYT LRGEWSGYKP IYVGSDGNGV  240
KLQGKGTVDL DLGLYAVVTF KEEPLPGNQL MEKGRTYSKF VFRDGRIMDV DGDADEISDV  300
PKATDEGYRY NSAAPSNNPN WMNGIPGATK LSEISIPGTH GSTALHGKTV FDEDLVRNQR  360
MSIATQLQAG IRYLDIRARR TGSSFAMHHG AVYQKLMFGD VLNQIQTFLR TNPRETILMR  420
LKEEHDPESG SQSFEDIFKK YKNDYGNLFW NYTSSNPTLD EVRGKIVLLQ NFSASQNYGI  480
QYGSLNIKDQ YDVKGSTPDA MYGKWLSVKN HLTAADNSNR SQIYLNYLSG TGGGEAITKG  540
```

```
TYPWFVASGY RSRSDDSGSA MIQEHRTDKW PDFPRGYYGQ VFYGGMNILT AQFILKLNLS  600
HTGIVAADFP GGPLINNVIR LNDRLSAGDI RYIRVEGARL KIGFQGNTFL QNTYVISRNG  660
KYIAHVEKGK SYYSSLAKTD FGYELTNSSV LFTDDKIEVY LDKNGQRTLL QSQVIRVEGQ  720
EGEVQVPNQT FIIKSKLPGA TSKAVDLAID SGYNYNVHLW SYNDQLNAEW YFEYKSDKRA  780
YVIWNSARPG RVMAWNDVGG GWNVFGTPFE SHKDEHYWKV RRTREGYASL VNLLKRDGKE  840
VVLDVAYGGT ADGTTINVYY SYPGELNQVF RLIERAKNER ASIVSLYRPQ SGQKNRSSNN  900
FSLNHIAAGT KVRVEINGAG ESSLVFRIMR DKRGDTDPTI WSNVKHGTVL TIPANAQLGS  960
LYIANPSGYS SNGSFTVKFY TLPNQ                                        985

SEQ ID NO: 174         moltype = AA  length = 523
FEATURE                Location/Qualifiers
source                 1..523
                       mol_type = protein
                       organism = Bacillus sp.
SEQUENCE: 174
MNADQRNYGQ NNQHMSNEQM NQNVNYNNHD GSCGCGCQQD NYEYEQKKEA YNSSYMSNEQ  60
MDSNYGEFCG DQQETTYPTS NEDMQDMDWK NTTYSEYDGC SSTQFNTPNL PIESRSFQMM  120
GFTPDFVFDS FPIRRLEFVP GVNIPSPCRS TRADWHTLLI RRDNSNDNQY FICYQIDNGN  180
FVIVGFGHGR TMEYRHNIDG RNDNSALVGS EFIGTNNQIF QTLNRGNNFF QLIPVSHRNM  240
VIDACARGTR EPNLITSSNN PGPGEFFMNY SNRRSISLPT LPPRTNLTPP RDLTSINDTG  300
DAPEQAPRAV EGSVLIPAIA VNDIIPVAQR MRESPYYVLT YRTYWHRVFS LILAGNGETT  360
TSPIVSLGMF SQAQDNMRDT LNMTIGADLR PQFVANGRTN LFQQQISRGL NTTISQTPTR  420
LGQTQHTYQF VNLGQQGRLV QYVKAHEFTL TRSNGTQVGQ TWVALDPNVD INRTFGSVII  480
TLKEDKIICA DNSYDLSVWK TPKRIKNGEI YIKNEQTTKP NYE                    523

SEQ ID NO: 175         moltype = AA  length = 387
FEATURE                Location/Qualifiers
REGION                 1..387
                       note = Description of Unknown: Organism from environmental
                        sample
source                 1..387
                       mol_type = protein
                       organism = unidentified
SEQUENCE: 175
MNKSKMHDEL KYITGFFSPI VFVDRGDSGA DYEIRQLTNK AGDKEMPDGN GWCYDANQEN  60
QIVIDRQKSS KGQDTYFTFY KTGRENEFVI ANKETGLVME HVKEEHVGSG HGSWKGSEYT  120
GNSGQIIRLH PESDKEFKLS VYDGNDKKFL DACKNKYDDK RKITSVWERG VEGNRQVLEY  180
PVASREEKIT LPKLPGKSSL EPIPELPGFN DPLPENEDAK RAVIGSTLIP CILVNDSISL  240
ADKIKKHPYY VLEYRQYWHL LWSDVFTAGS NKIKTEVTGI PSEAQEKMKD LIGASIRNDI  300
GLRFTDKSEP FGKQIASDLN VKHSYDYELG ETTTITNVEN PNDFTVRHAR YARAHEFVLK  360
RSDGQVVEEP WVAIDENDMY LKMYKKP                                      387

SEQ ID NO: 176         moltype = AA  length = 283
FEATURE                Location/Qualifiers
source                 1..283
                       mol_type = protein
                       organism = Bacillus sp.
SEQUENCE: 176
LAILDLKEVV RLGGEAIVQK YWPELGGVRN YGLNPRDFTS SWNNLQPAEI KDMQVHFPVT  60
TIDNPTSETS VASKTVTNGG SSDIKSTIVF SEDISDSVTT STTDGLTAGL EVSTEASANF  120
FFGSAKVSAK VNTSYTLTDT YSHQTITHH WADSTEVIVP AQKIVTAEYM IQSGPFDLPV  180
EYTAKVEGYG WIQFNNGNYA TYLISNLAVW AGLSNFNGDI FKGTGRVSGS MGLTSFVKVT  240
EEDLDTREVT RVYNLDYVNR FPSIAQPMNL QKSNFSGMSS VRR                    283

SEQ ID NO: 177         moltype = AA  length = 286
FEATURE                Location/Qualifiers
source                 1..286
                       mol_type = protein
                       organism = Bacillus sp.
SEQUENCE: 177
MDTNNCEFNP IANMIDLVSI FSNFANFWFT GTQSESSEIF SINPSAPPQG IEISSNSMTI  60
YSDATDTLSS FQTLGTLTFQ NLSSQNKLET AYFQLTTPTS QSWRMLEAVL SNGNDYFLIN  120
IPFDQSIPQE FRTNGDSRIQ IDCQETITRS TEQSWNIQRQ IQLSPYTITK VSFQAKLKKV  180
KRDFTFYFDV TGNLGVRTSK TVNGKTEHFI PVTEVMKWTE YPQIDINFEY NRLRCHNLGE  240
YKAEYYVDPI LLVETQSVTN PALMQQTVIP IFNIISAVPS KCKSFE                 286

SEQ ID NO: 178         moltype = AA  length = 647
FEATURE                Location/Qualifiers
source                 1..647
                       mol_type = protein
                       organism = Bacillus sp.
SEQUENCE: 178
MNSNNKTNPN VIGTSSDQSL LTNSVKKPLA SDQSNPLQHR DSNDCLSVSE GNRDSLNHDV  60
FISAPGLVDT TANITSVILS ALGVPMLGTV VKLYSKLFGF LWGSTPGQDP WKELMDRVEI  120
LIDQKLTEYA RSKALAELEG LQNVMKSYVD ALESWQNNSR NSQTRLLVQQ RLVVADSQFK  180
QAMPSFAIKD YEVSLLPVYA QAANLHLLLL RDSQIFEKDW GMPQHEIDLF YKEHLECIEK  240
YSDHCVEWYH TGLNKLKSST AKDWVDYNRF RREMTVAVLD IVALLPNYDV HMYPMPIHAE  300
LTREIYTNPV GSYLPYKGNF KDVMSWYEMK RYRQPTFQDL ESLIQKPSRF TWLKDLKMYT  360
RKRQNGKYEY YNYWVGHQLK KALIGEQYVR ETTISGEITS EEDTFTFEDY DIHRVLCNYI  420
```

```
GRYDNSLVGI NQVEFHYLDN NTPRKKEYKK DIWVTNQSQK IIDSEEELHS HRLSYVESFD  480
LYWNHNNEKG GTIPVFGWTH HSVAPKNIIY EDKITVISAT KASGYFTSEV IQGNGYSGGD  540
LIKGSKSMGN IPLTPPRDAH NKNYRLRVRY AADSDGLLEM TFTSGVGPSK LKTLYQATMK  600
KGDSFKYNSF QYVEKVVYIS SSQNGIMFSA GSGFYLDKVE FIPVNEN                647

SEQ ID NO: 179         moltype = AA  length = 540
FEATURE                Location/Qualifiers
source                 1..540
                       mol_type = protein
                       organism = Bacillus sp.
SEQUENCE: 179
LRRPSIFYGS LIKISAKSRI EIELKYNIRG DFNVKYKDRK KVKNKYQKTL LTTVATMILG  60
LGTVVSFTMD STYAAETVTE AQKQDAKDRI NKLDQLLKDK IGGTSGELKQ DFQNVMNQPE  120
VAFSVKAVSA IAPAILTAIK NDGTIPPMVL NSIAKNLVIA GVGMIPGVGG MASALVGLFW  180
PNITSGPSSL ELLEQKLTAL INDTVMNSEK NQLTAELKSA IDDIKALDYA LSTGIGYVPS  240
GVQFFSTGIV TDVKNANKSL KKVLDQIAGS QFKGEELPLY TTAATMHLMF LKFIEANKNN  300
IKMGMDAEDY SSINVANGGN IKELVIKYRN FINDAAQPIE KKLLDNVFYA WHTVDAQGNP  360
ITAVNNFTKY VNATEHNLEF NTIIDTIVSR QERDEPINIG EDIPVTISVN GKMLSANKNN  420
TSKIQCDAVN RTSDQLFFIK PISKKENIFA IQSIVNERHV TFNNQDVIRY TVGNIERETT  480
ESDVTWIKLI KLPGENQYAM QSIHSPYQNY IYADFNNNGT LMASSRIIGD WEKFTIIPVL  540

SEQ ID NO: 180         moltype = AA  length = 507
FEATURE                Location/Qualifiers
REGION                 1..507
                       note = Description of Artificial Sequence: Synthetic
                        polypeptide
source                 1..507
                       mol_type = protein
                       organism = synthetic construct
SEQUENCE: 180
MKYKDRKKVK NKYQKTLLTT VATMILGLGT VVSFTMDSTY AAETVTEAQK QDAKDRINKL  60
DQLLKDKIGG TSGELKQDFQ NVMNQPEVAF SVKAVSAIAP AILTAIKNDG TIPPMVLNSI  120
AKNLVIAGVG MIPGVGGMAS ALVGLFWPNI TSGPSSLELL EQKLTALIND TVMNSEKNQL  180
TAELKSAIDD IKALDYALST GIGYVPSGVQ FFSTGIVTDV KNANKSLKKV LDQIAGSQFK  240
GEELPLYTTA ATMHLMFLKF IEANKNNIKM GMDAEDYSSI NVANGGNIKE LVIKYRNFIN  300
DAAQPIEKKL LDNVFYAWHT VDAQGNPITA VNNFTKYVNA TEHNLEFNTI IDTIVSRQER  360
DEPINIGEDI PVTISVNGKM LSANKNNTSK IQCDAVNRTS DQLFFIKPIS KKENIFAIQS  420
IVNERHVTFN NQDVIRYTVG NIERETTESD VTWIKLIKLP GENQYAMQSI HSPYQNYIYA  480
DFNNNGTLMA SSRIIGDWEK FTIIPVL                                      507

SEQ ID NO: 181         moltype = AA  length = 216
FEATURE                Location/Qualifiers
source                 1..216
                       mol_type = protein
                       organism = Bacillus sp.
SEQUENCE: 181
MYNKRIINLE IPSYNAINFL EIYRLPQVHL NQALNITQHL QKSLSLQTLN LEFDQLNDLI  60
SEIPGGSILN TINQRVEYSE INTTCAINNI VDIVKSNCEM FKDDFLLQSK LESVISNVFL  120
NLANQEKNSY IFYHEKLSYK TSYSYHVIFV IDNMESSLNV FPISFNINVD SSYESLNKNS  180
INDLQYYNIK INGINFVISK NNESAEIMER VTESTL                            216

SEQ ID NO: 182         moltype = AA  length = 310
FEATURE                Location/Qualifiers
source                 1..310
                       mol_type = protein
                       organism = Bacillus sp.
SEQUENCE: 182
MTLPPMREPF CYFLTSSDRF SSHFICYYCE QNFKSKEHVV MTNVLDLIFT IDTFITNWVR  60
ENQACMGTLY LCSQDGGATH SFNVSSPFPA VYSKPTDTTT VQNSFCTYSF KNITNEFMEQ  120
EIIVEEETPI TESWYLTDMV CMAGDVFVTI SCPTDSLIPI HTVVLDPDNT VTLSNSQTWH  180
FNSTIQLPPN STTKVTFQTK ISKFSRNFEF AYWVTGNVGV VTEKQINGRN NFTFPVTKTL  240
QWVNNSLLDL DMDANKVTCI NKGVYQATYD IQPQLLIQTT DLDNPTIVQE SILDLNTGTM  300
TPVINPSGCC                                                         310

SEQ ID NO: 183         moltype = AA  length = 262
FEATURE                Location/Qualifiers
REGION                 1..262
                       note = Description of Unknown: Organism from environmental
                        sample
source                 1..262
                       mol_type = protein
                       organism = unidentified
SEQUENCE: 183
VKPNQNQFYR IVNKLSGMVM GVHDASQAKD VEQYPWGSYP ENHLLWRPES VQSFTLPSVP  60
TYPVPAVPQY TNINDVLPDQ TQIVTTHYTL APCIAVDDPH YNHQQKIKTN PYYLYVKKQY  120
WKRVASHTLA PGETYRYSMT TGMTQEDQNV VSKTVSHTIG ADVGFQFGKE NKGSVSASLS  180
YQYTTQLATQ ESHTTTQMTE ETKELSINNT NSYMVAWSKY VLVSEYSVQR SDGTLVREPW  240
TVTDPNTTQS SYYPLTAKLL DN                                           262
```

```
SEQ ID NO: 184         moltype = AA  length = 262
FEATURE                Location/Qualifiers
REGION                 1..262
                       note = Description of Artificial Sequence: Synthetic
                        polypeptide
source                 1..262
                       mol_type = protein
                       organism = synthetic construct
SEQUENCE: 184
MKPNQNQFYR IVNKLSGMVM GVHDASQAKD VEQYPWGSYP ENHLLWRPES VQSFTLPSVP  60
TYPVPAVPQY TNINDVLPDQ TQIVTTHYTL APCIAVDDPH YNHQQKIKTN PYYLYVKKQY  120
WKRVASHTLA PGETYRYSMT TGMTQEDQNV VSKTVSHTIG ADVGFQFGKE NKGSVSASLS  180
YQYTTQLATQ ESHTTTQMTE ETKELSINNT NSYMVAWSKY VLVSEYSVQR SDGTLVREPW  240
TVTDPNTTQS SYYPLTAKLL DN                                           262

SEQ ID NO: 185         moltype = AA  length = 341
FEATURE                Location/Qualifiers
source                 1..341
                       mol_type = protein
                       organism = Lysinibacillus sp.
SEQUENCE: 185
MRNKKNLVQK TLTLAAIASM GTTFAIASPS FASAYQINTS GEEHGVLAAE NTPTSMNKNA  60
VGITDVQSEL NKIGTYYYTN EIAGTKIESW PTLTFKAKPD SVETKLDFNI TGTLNKLNYD  120
TTTVDYVTIG ELDNTKTPTE QTLTTSSYTK SIQETVSTAT QNGFKFGGAG DLLLKVPLLL  180
NNIKINAEFN SSTTKTQTTS ETKTITLPSQ NIKVPPGKKY RAVVVFEQLN FWGDVSFTGE  240
GINPMTTIKG TATYWAPNGM GAWKEYTWNK YTALFWKELT DAQKKDLKGI EFIYYPNTGG  300
VKIKAQGTGK VEGVMGSKID VDILDVTNPS KHELVETRSY H                      341

SEQ ID NO: 186         moltype = AA  length = 315
FEATURE                Location/Qualifiers
REGION                 1..315
                       note = Description of Artificial Sequence: Synthetic
                        polypeptide
source                 1..315
                       mol_type = protein
                       organism = synthetic construct
SEQUENCE: 186
MSPSFASAYQ INTSGEEHGV LAAENTPTSM NKNAVGITDV QSELNKIGTY YYTNEIAGTK  60
IESWPTLTFK AKPDSVETKL DFNITGTLNK LNYDTTTVDY VTIGELDNTK TPTEQTLTTS  120
SYTKSIQETV STATQNGFKF GGAGDLLLKV PLLLNNIKIN AEFNSSTTKT QTTSETKTIT  180
LPSQNIKVPP GKKYRAVVVF EQLNFWGDVS FTGEGINPMT TIKGTATYWA PNGMGAWKEY  240
TWNKYTALFW KELTDAQKKD LKGIEFIYYP NTGGVKIKAQ GTGKVEGVMG SKIDVDILDV  300
TNPSKHELVE TRSYH                                                   315

SEQ ID NO: 187         moltype = AA  length = 287
FEATURE                Location/Qualifiers
REGION                 1..287
                       note = Description of Unknown: Organism from environmental
                        sample
source                 1..287
                       mol_type = protein
                       organism = unidentified
SEQUENCE: 187
MATLQDVLNQ YGQKLLFVGG TFGNSYYVQD IRPELSLSPL NVRGPVTIPT LISTDTPRTV  60
VQTSKITNSS SSDITKTFSF SETVTDTVTS SLETGFEIGI SKEMSMGASI EMVKMDTKQT  120
ISTKFSLKST QTTTNTKTRT WVEQYTVPVK ADTEATVIYT LSIGSFDGLV DVDFTLSGNI  180
WFKLMPTIYG INFDYVLSTP SGSKIPFVPN YGNQLISIPV SEVFNTINPA GFTLNPDNSI  240
RFQGKVRLQG ELGIMSELFI NSKSLITGVT TTTPLSTQTA PPTILFA                287

SEQ ID NO: 188         moltype = AA  length = 429
FEATURE                Location/Qualifiers
source                 1..429
                       mol_type = protein
                       organism = Brevibacillus sp.
SEQUENCE: 188
LMHADTWNNR IKSITEAAAK KIPYVGAIVS FAIGQLWPTD KLDIFSLIKD QVKGLVDQAI  60
LDKEMEERKH EIEGLKDTMN QYVDAGNHEK GGFMTSMLTQ LNIMHHKLTE STNSIHLIPL  120
TITISNIHLT LLRERLSHGK KIYTEDNTAV WQKDLTKRYQ DYHKFFLEIY PKWKTWRESK  180
IEIKWYTDKN PTTVPPFFYW AAHGDAKDTF AGKNIHYRDD FNSIETTFQG VCQAIKESWM  240
NDAIAKIAAS IATTFTLHHY LPGREDEPAI VDPNLETIWM GPYSLSITGN DSKVSCAVNV  300
TDQPGELKQV YVREYNSIDG MQFIYTDHSG NFIGNPKGGE PHYLNATQDK YVTGMKMRFS  360
SGIMCRVEVL FSDGSSSGML GNRKNWSGTD VDAVVESNYK LICGAYKTGS GPSGTSGISV  420
IKLGFKYSN                                                          429

SEQ ID NO: 189         moltype = AA  length = 327
FEATURE                Location/Qualifiers
source                 1..327
                       mol_type = protein
                       organism = Bacillus sp.
```

```
SEQUENCE: 189
MKAYKKIIKI APVAVLSTTI LLSPTSILAA ENAQTAKIQT NIQKDSVAPQ ERVLQGYLFK  60
NGVQTPIYKG GVQTRAAQLN EAPYPELPSN PNDPYPEKGS VASENGNVGS TLYFSTFEGT  120
ANVYIEKVSD SQINIGCYNP NTLERSTTTS LTKGQNDQMD KRFQIYQSFF NGTTVKRETA  180
FEKIASALQN KTDGYQFSQG VSSGLSKTDA IGFSFTMGWK WSITAGGGAV VPASMTEEFS  240
ASLTSTYTHT IAVTSQTTNT QTITHPKPAD TYKHDKYRAV VYQLNSIYTI VPGDELSKVL  300
TSGIAVLSQK SFKYSDSDIY LAVTPGS                                      327

SEQ ID NO: 190          moltype = AA  length = 299
FEATURE                 Location/Qualifiers
REGION                  1..299
                        note = Description of Artificial Sequence: Synthetic
                         polypeptide
source                  1..299
                        mol_type = protein
                        organism = synthetic construct
SEQUENCE: 190
MAENAQTAKI QTNIQKDSVA PQERVLQGYL FKNGVQTPIY KGGVQTRAAQ LNEAPYPELP  60
SNPNDPYPEK GSVASENGNV GSTLYFSTFE GTANVYIEKV SDSQINIGCY NPNTLERSTT  120
TSLTKGQNDQ MDKRFQIYQS FFNGTTVKRE TAFEKIASAL QNKTDGYQFS QGVSSGLSKT  180
DAIGFSFTMG WKWSITAGGG AVVPASMTEE FSASLTSTYT HTIAVTSQTT NTQTITHPKP  240
ADTYKHDKYR AVVYQLNSIY TIVPGDELSK VLTSGIAVLS QKSFKYSDSD IYLAVTPGS   299

SEQ ID NO: 191          moltype = AA  length = 404
FEATURE                 Location/Qualifiers
source                  1..404
                        mol_type = protein
                        organism = Bacillus sp.
SEQUENCE: 191
MKSVSKKVMA GLAVGAMSLS IWAPASQAAS PEKNRYYSIH LKSNPKLAWD VSGNSLDNDR  60
AIVLWNTSSR GDNEQFVFFP LDGQNYAIVN KNSGKPVTFG EGGWLEGYNG LPGRDNLQQK  120
SWTGSPTEQW YLRDQGSNNY EIVNQGNQKV ASYSWTGTLA QYVESVDLDE SNPSDSDRVF  180
NIAKNGFGGV GGDIQIPGFN FDYGTFSLPT LPATGTRPNA PDYEGADPNQ QLPQTSSSVV  240
VGASLVPCIM VNDSQTSDYT KIHNSPYYTL VKEEYWDKAA STVLTPGATQ SVAFKTGMSS  300
SDQQKMTETL SMKVGADFGL KFGDKTAALK AEISKTLQTE TSTTNTELSE DTVTHNFKDE  360
VGKDTGYTLY QLATKYTLKR ADGSVVSGSW TVKNNKITKV SKSK                   404

SEQ ID NO: 192          moltype = AA  length = 377
FEATURE                 Location/Qualifiers
REGION                  1..377
                        note = Description of Artificial Sequence: Synthetic
                         polypeptide
source                  1..377
                        mol_type = protein
                        organism = synthetic construct
SEQUENCE: 192
MASPEKNRYY SIHLKSNPKL AWDVSGNSLD NDRAIVLWNT SSRGDNEQFV FFPLDGQNYA  60
IVNKNSGKPV TFGEGGWLEG YNGLPGRDNL QQKSWTGSPT EQWYLRDQGS NNYEIVNQGN  120
QKVASYSWTG TLAQYVESVD LDESNPSDSD RVFNIAKNGF GGVGGDIQIP GFNFDYGTFS  180
LPTLPATGTR PNAPDYEGAD PNQQLPQTSS SVVVGASLVP CIMVNDSQTS DYTKIHNSPY  240
YTLVKEEYWD KAASTVLTPG ATQSVAFKTG MSSSDQQKMT ETLSMKVGAD FGLKFGDKTA  300
ALKAEISKTL QTETSTTNTE LSEDTVTHNF KDEVGKDTGY TLYQLATKYT LKRADGSVVS  360
GSWTVKNNKI TKVSKSK                                                 377

SEQ ID NO: 193          moltype = AA  length = 367
FEATURE                 Location/Qualifiers
source                  1..367
                        mol_type = protein
                        organism = Bacillus sp.
SEQUENCE: 193
MTNELNSNTQ DSNEIDNGIL TLDPFTFYHI RTFCGKMLDV TNSSISDHAP IIQHASNNHF  60
NQQFLIFALD DGYSIITSVI SGKVLDISQS GPLKGYVIQH YLNDGNHQRF LIGNNGTIAA  120
KYNGKVFDVY KASTANNVPI KEDNPHNGAN QKFTFERVKT FTVPSPSIGT LPPAPDFNND  180
INEVLPDKTN PVITHDSNIP CIMIDDKTFS NPLKIQRSPY YKLVKIQYWE KVTQRILGPK  240
DTYSYQKKKG VSRTDQVSMT ETVSMSIGAD FGFMFKGFSA SLSTRVTKEL SVTKSTSHTE  300
MTEETYTESY TNPFDYSLAR AQYMLVNEFY VTRMDGTRIT NNWTVRDDKQ TVTRIFPKPK  360
SLTDSNE                                                            367

SEQ ID NO: 194          moltype = AA  length = 317
FEATURE                 Location/Qualifiers
REGION                  1..317
                        note = Description of Unknown: Organism from environmental
                         sample
source                  1..317
                        mol_type = protein
                        organism = unidentified
SEQUENCE: 194
MKRMKKVIPA AFVLSSALFV APGFSSAATD TTNVGNLPVV ISAQEGKAPM TAEQVQENGT  60
QLPYIPTGPY EEFPNEWHVS TEDGKLIDYV YVDVVAKSNG ARVYGLKMDA NSKHKILKAD  120
```

-continued

```
GTWLKVGEEY EKTGNKGEVL YTIAIPKNDP ILEDTKLKKE VNWKLIDSNI VDKNSGYHWS  180
KAVTSGISHN VTVGLSYTIG MEVGLEGIAT VNQSLTASFG YGVTLNSEET VTKTFDFNPK  240
YDYAYDQYRT GLYQQVATYS VVPGEKLQKW MSEQNGVWDN LFGQLGEEFK GLTSPTEYKV  300
KTSVDYPVDV LVALTSK                                                317

SEQ ID NO: 195         moltype = AA  length = 291
FEATURE                Location/Qualifiers
REGION                 1..291
                       note = Description of Artificial Sequence: Synthetic
                        polypeptide
source                 1..291
                       mol_type = protein
                       organism = synthetic construct
SEQUENCE: 195
MATDTTNVGN LPVVISAQEG KAPMTAEQVQ ENGTQLPYIP TGPYEEFPNE WHVSTEDGKL  60
IDYVYVDVVA KSNGARVYGL KMDANSKHKI LKADGTWLKV GEEYEKTGNK GEVLYTIAIP  120
KNDPILEDTK LKKEVNWKLI DSNIVDKNSG YHWSKAVTSG ISHNVTVGLS YTIGMEVGLE  180
GIATVNQSLT ASFGYGVTLN SEETVTKTFD FNPKYDYAYD QYRTGLYQQV ATYSVVPGEK  240
LQKWMSEQNG VWDNLFGQLG EEFKGLTSPT EYKVKTSVDY PVDVLVALTS K          291

SEQ ID NO: 196         moltype = AA  length = 328
FEATURE                Location/Qualifiers
source                 1..328
                       mol_type = protein
                       organism = Bacillus sp.
SEQUENCE: 196
MYLSSSCTQT NRIILLIFLP KRYIRRSYHH IIDVYPKCKC LNVICNLKFN ELKYKTYTGR  60
RMFMNVNVTD LIELFGRYAN QWSQQRGGGN SKLSLMLPVF EHLAFTSFTK PVKYDEPTIY  120
MPEDVAVDSH TYTNTGNKPL NVTIGLMGTL KNWLHLKVNE GTSEGGKRFL NIDLPNDIPS  180
FSNEQLVPIG GALHESSHMQ PWEVNHPFTI NPKFKVTATL MIKTKKVTRS FKMQRILSRY  240
IAIHTSQAIN GSLTSLHHVS RMLKDYYSPY IQVDGNKVTV TDKGKLQSLF GIEQYIHIQG  300
ISLNNPNIKE DYNIYNPETS VKQSFKLS                                    328

SEQ ID NO: 197         moltype = AA  length = 205
FEATURE                Location/Qualifiers
source                 1..205
                       mol_type = protein
                       organism = Bacillus sp.
SEQUENCE: 197
MNRGTISDKK KSGYSEEKYY LKLISDVKPE YTVQTLNLMD KFKFIVNPMT KELDTSKILQ  60
IVNEHPGLAI VSTLNQQFTS NQKMPIKNLI DSSREFVFSA IGGSYLDKGI KKTCINGIEN  120
VVVNLNSQIE HPWISFYTEA KDETSYRYNI LFIFQRASFL VMTPISFEIT IFSNKDTVLD  180
LKLTNKVEYH VSIKLIQVIQ SLNTC                                       205

SEQ ID NO: 198         moltype = AA  length = 391
FEATURE                Location/Qualifiers
source                 1..391
                       mol_type = protein
                       organism = Bacillus sp.
SEQUENCE: 198
MYYNICKEYD DMAYQKVTMS RETNMDSLQV YYGEEAQQND ASWPQVPSDP SLPWPSSGST  60
ILTSPVNEQN FINIPLVASR IILLSDWDNV KSMIKNLIIK TFGLQNPIYL YNSDASLVDT  120
SNPLFGYNLS YPSTNPQLIA KGTVLGYIGL ETNNPANAKY LPGSSLERQT FYQLLSSDTV  180
DRRIAYHWEH EVSSGVTETF QHTFGTTVGF EISFTEGGFP LPAKAEQKIT ASLSYTFGYS  240
NAVTSGEITK QTFDFRVPGP NYQYQVYKCG VYQLNSKYKF KPGAPLLALA DTLNNGFNEV  300
AGLFIPSELP AVVVEFSIEY TYLEKSLYAT QTPDPTPNQD NEHPIQYKMY NDLFQSLVPP  360
VHCSLGCSCL CPSLTPLNSD IMLNDIVIDS N                                391

SEQ ID NO: 199         moltype = AA  length = 380
FEATURE                Location/Qualifiers
REGION                 1..380
                       note = Description of Artificial Sequence: Synthetic
                        polypeptide
source                 1..380
                       mol_type = protein
                       organism = synthetic construct
SEQUENCE: 199
MAYQKVTMSR ETNMDSLQVY YGEEAQQNDA SWPQVPSDPS LPWPSSGSTI LTSPVNEQNF  60
INIPLVASRI ILLSDWDNVK SMIKNLIIKT FGLQNPIYLY NSDASLVDTS NPLFGYNLSY  120
PSTNPQLIAK GTVLGYIGLE TNNPANAKYL PGSSLERQTF YQLLSSDTVD RRIAYHWEHE  180
VSSGVTETFQ HTFGTTVGFE ISFTEGGFPL PAKAEQKITA SLSYTFGYSN AVTSGEITKQ  240
TFDFRVPGPN YQYQVYKCGV YQLNSKYKFK PGAPLLALAD TLNNGFNEVA GLFIPSELPA  300
VVVEFSIEYT YLEKSLYATQ TPDPTPNQDN EHPIQYKMYN DLFQSLVPPV HCSLGCSCLC  360
PSLTPLNSDI MLNDIVIDSN                                             380

SEQ ID NO: 200         moltype = AA  length = 340
FEATURE                Location/Qualifiers
source                 1..340
                       mol_type = protein
```

```
                         organism = Bacillus sp.
SEQUENCE: 200
MKNKVLATAA IAFSLGITSL GYGGTAFAET PGYDQMGSFK NDVQNSERWN GFWQLIDNGT  60
MTNMFNIAPH STTKFKVTST KKEPLLIDTA RLDNSKGLEP SEHPAPIKTH SETNSLTVSA  120
GVEVSIGYEI ESTQGVPGVA SMTEKLTGGV KVSAGFQDLK SETIQTSYGG ATMKAQPGEI  180
VGFDYMLTKT KSSGKMHTGR RITKIGSDLK VWDIHKYENG YAYYGVYEPG EQKSTDDVYN  240
TFKYLKKMND EHDIGLVWTK GTGGYDGNGR PAILQAGKFD EYFFIDDETK NVYTMENQRD  300
FSAISGTDFV AVPVKIDPKT GVKTKDLNKS EIRNFPQVTF                        340

SEQ ID NO: 201           moltype = AA  length = 313
FEATURE                  Location/Qualifiers
REGION                   1..313
                         note = Description of Artificial Sequence: Synthetic
                          polypeptide
source                   1..313
                         mol_type = protein
                         organism = synthetic construct
SEQUENCE: 201
METPGYDQMG SFKNDVQNSE RWNGFWQLID NGTMTNMFNI APHSTTKFKV TSTKKEPLLI  60
DTARLDNSKG LEPSEHPAPI KTHSETNSLT VSAGVEVSIG YEIESTQGVP GVASMTEKLT  120
GGVKVSAGFQ DLKSETIQTS YGGATMKAQP GEIVGFDYML TKTKSSGKMH TGRRITKIGS  180
DLKVWDIHKY ENGYAYYGVY EPGEQKSTDD VYNTFKYLKK MNDEHDIGLV WTKGTGGYDG  240
NGRPAILQAG KFDEYFFIDD ETKNVYTMEN QRDFSAISGT DFVAVPVKID PKTGVKTKDL  300
NKSEIRNFPQ VTF                                                     313

SEQ ID NO: 202           moltype = AA  length = 978
FEATURE                  Location/Qualifiers
source                   1..978
                         mol_type = protein
                         organism = Bacillus sp.
SEQUENCE: 202
MLIYSKIILL GVTNMSSNTM VPYNVLRNLD MHTISGTRWN KEMFTNALNN TSSLLTLIEK  60
GINDGDDVLG LLSFIGLTAL EAIPVVGGVL SSLVSMLFFP TKSSIDFKKI WEHLEKAINQ  120
IVDKKIEEAL MSQLMQEIAG LANVLKEYRD AYDSYNGKKV FDIPDRLTPE EYLVQVFTSA  180
NLLFIQRIPT FQNPKYDVLF LPFFVHVAEM HILLIRDAAI HGLEWGIDET LHQKFKKDLK  240
GLINKYSGHL LNTYKKGLKE ATERKLDSND FPTSNNQHHY INTVRWNVIN QYKRGMALTV  300
FDFAYKWKYY QEVYQNNITL NPVRTIYSDI AGSVYPYEKT TNEIDNIIKE QNLKYRGLLK  360
ELLINHGDRI DSIQSKYIRN NEIIDSNRTG GAGGRATFFD LKSPINNPFI QVNMWSELVP  420
FSLAFKYYNG EESKPIWGGG TPGKHKFGSY HYVGNKVSSI IGFGKNGTGG FNSLDAMVVG  480
FKRDDYIPEN RFVGVNKNGE PVTKVIDAEN FYQEKFQSNI KMIDEPMFGE AVLQFENYSN  540
NLNKDSYVTY QIDAKIEGTY ELHAIIGAKK TKDKVAFKMS LNEQQPENFI TDSFDDGDIW  600
DGMSLSEGIV YKRILVGRFQ LKKGMNHISI HNGALQTSAN IKTWNLAALE LTITADSLND  660
PDITTLYDKD NYTGTKKFIF EDTKRLTDFN DKTSAIKVAS DMAGFRVYQD YDHKGKSLDL  720
VGGEKLSLKN HSFNNKISSV KFANIVLYNQ DNYQGSRKLV FEDIPDLGKQ GFNDKTSSIV  780
VSSNVSGARL YEHAYYKGKY VDVVGGQKLN LKNHVLNKKI SSIKFFKEGE VLNGVYQIIT  840
AINNTSVIDK HLQDSIVHLW ENAENKNQKW RIEYDVAKKA YQIKNMLDEK LVLSTHELFP  900
IFSELYCLPN KGYDSQYWIF VHVGNGYYII KNKLFSDLVL DVDGLNSDNG TRIKLYSQHD  960
LTDPLINAQK FKLKDINN                                                978

SEQ ID NO: 203           moltype = AA  length = 964
FEATURE                  Location/Qualifiers
REGION                   1..964
                         note = Description of Artificial Sequence: Synthetic
                          polypeptide
source                   1..964
                         mol_type = protein
                         organism = synthetic construct
SEQUENCE: 203
MSSNTMVPYN VLRNLDMHTI SGTRWNKEMF TNALNNTSSL LTLIEKGIND GDDVLGLLSF  60
IGLTALEAIP VVGGVLSSLV SMLFFPTKSS IDFKKIWEHL EKAINQIVDK KIEEALMSQL  120
MQEIAGLANV LKEYRDAYDS YNGKKVFDIP DRLTPEEYLV QVFTSANLLF IQRIPTFQNP  180
KYDVLFLPFF VHVAEMHILL IRDAAIHGLE WGIDETLHQK FKKDLKGLIN KYSGHLLNTY  240
KKGLKEATER KLDSNDFPTS NNQHHYINTV RWNVINQYKR GMALTVFDFA YKWKYYQEVY  300
QNNITLNPVR TIYSDIAGSV YPYEKTTNEI DNIIKEQNLK YRGLLKELLI NHGDRIDSIQ  360
SKYIRNNEII DSNRTGGAGG RATFFDLKSP INNPFIQVNM WSELVPFSLA FKYYNGEESK  420
PIWGGGTPGK HKFGSYHYVG NKVSSIIGFG KNGTGGFNSL DAMVVGFKRD DYIPENRFVG  480
VNKNGEPVTK VIDAENFYQE KFQSNIKMID EPMFGEAVLQ FENYSNNLNK DSYVTYQIDA  540
KIEGTYELHA IIGAKKTKDK VAFKMSLNEQ QPENFITDSF DDGDIWDGMS LSEGIVYKRI  600
LVGRFQLKKG MNHISIHNGA LQTSANIKTW NLAALELTIT ADSLNDPDIT TLYDKDNYTG  660
TKKFIFEDTK RLTDFNDKTS AIKVASDMAG FRVYQDYDHK GKSLDLVGGE KLSLKNHSFN  720
NKISSVKFAN IVLYNQDNYQ GSRKLVFEDI PDLGKQGFND KTSSIVVSSN VSGARLYEHA  780
YYKGKYVDVV GGQKLNLKNH VLNKKISSIK FFKEGEVLNG VYQIITAINN TSVIDKHLQD  840
SIVHLWENAE NKNQKWRIEY DVAKKAYQIK NMLDEKLVLS THELFPIFSE LYCLPNKGYD  900
SQYWIFVHVG NGYYIIKNKL FSDLVLDVDG LNSDNGTRIK LYSQHDLTDP LINAQKFKLK  960
DINN                                                               964

SEQ ID NO: 204           moltype = AA  length = 399
FEATURE                  Location/Qualifiers
source                   1..399
```

```
                         mol_type = protein
                         organism = Bacillus sp.
SEQUENCE: 204
MKSISKKVMA GLLVGATSLS IWTPSSEAEA PKNDRYYNIQ LKSNPKKVWN VTRASNDNDR  60
AILLWQGGSA DNEKFAFFQL DGGAYAIVNK NSGKIVTYGN GSWFADRDRL GGETLQQQSW  120
NGEAKQKWNL RDLGSNNYEI VNQANGKVPS YRWAGSLVDN VEYLQMDNSN PSDADKVFTL  180
FNGSTTVFFN DQFIPILKDM IPLQNLPSTG NRPDAPNYTG GVDQQLPQTS NSVVVGASLI  240
PCIMVNDNQA SDYTKIHNSP YYTLVKEEYW DKTFSAVIPA GLTRNYSFKT GMTSVDQQKM  300
TDTLSMKIGA DFGLKFGDAS ASLKTEISKT IQTEISTTNT EASEETITST VTSEAGKTTG  360
YTEYQLATKY TLKRADGSIV SDPWVVKNNK ITIARKNAQ                        399

SEQ ID NO: 205           moltype = AA  length = 370
FEATURE                  Location/Qualifiers
REGION                   1..370
                         note = Description of Artificial Sequence: Synthetic
                          polypeptide
source                   1..370
                         mol_type = protein
                         organism = synthetic construct
SEQUENCE: 205
MPKNDRYYNI QLKSNPKKVW NVTRASNDND RAILLWQGGS ADNEKFAFFQ LDGGAYAIVN  60
KNSGKIVTYG NGSWFADRDR LGGETLQQQS WNGEAKQKWN LRDLGSNNYE IVNQANGKVP  120
SYRWAGSLVD NVEYLQMDNS NPSDADKVFT LFNGSTTVFF NDQFIPILKD MIPLQNLPST  180
GNRPDAPNYT GGVDQQLPQT SNSVVVGASL IPCIMVNDNQ ASDYTKIHNS PYYTLVKEEY  240
WDKTFSAVIP AGLTRNYSFK TGMTSVDQQK MTDTLSMKIG ADFGLKFGDA SASLKTEISK  300
TIQTEISTTN TEASEETITS TVTSEAGKTT GYTEYQLATK YTLKRADGSI VSDPWVVKNN  360
KITIARKNAQ                                                        370

SEQ ID NO: 206           moltype = AA  length = 1051
FEATURE                  Location/Qualifiers
source                   1..1051
                         mol_type = protein
                         organism = Bacillus sp.
SEQUENCE: 206
MSKKPKNLLK CLSAAAILSQ ISMNPIASHA EVNSAKDSVS QENIARNGLV AYYFKDSSYK  60
ELSSIQVEKD STLFKKQEIK TNQQPVQSIR LIGKIKPTQN GEYAFSISSN DANTIIQING  120
QTVLQEGKKN TPIHLEKNKN YDIKIEYRSK QEVNSNIQLF WSKDGEKKEL IPQNQLLLPD  180
FKAQEKVIDE QSHTLLLPKH TLFNSASDSG LADTDKDGIP DEWEATGYTF KDQQIVKWDD  240
AFLTQGYKKY LSNPNKIRTV ADPYTDFEKV IGYMPAATKD EARDPMVAAY PAVGVGMEKF  300
FFSKNENVSD GTSGTISKSV TDTNSTTNGV DVSAELGWSK GWSLKGSLKY SHSWTNSTAI  360
QDTESESWSK QIGINTAESA FLNANVRYYN AGTAPIYDLR PTTNFVFDKS GTSIATITAG  420
SNQIGNSLAP SDTYPKREQA PISLDKANEA GTMKISINAE QLDALQQGTD TLSLETTQNK  480
GQYGILDENG NLVTDTSKQW DPVRTNIDAV TGAITLDYGT GKDSLERRVA AKNENDPEDK  540
TPEITIREAI KKAFDTTELD GRLYYTDAKG NKVCIDEPTI NIVTDDNTKK QIEQQLEQMQ  600
DKKIYNAKWK RGMKITLHMP TAYYDFEKTA GTEWYSTYQE NGGFSGKRHG RINTDGNGYA  660
QKELQLKPYT SYTARAYVRT ASTTGKNDVT LYVDDTINAN GKGSRETFSV EGNEWKLIEF  720
SFNTMSNPEY FKKLGIKNNG NANLHFDDVS VTEWGQGENI EQAHKFEKWD ASSDGSGKIG  780
SVTFSKVPAQ DIRYQVQRTN EKGEWVWDNI VDAPPVDANG KRTLNITGTH GVRVFAVNKD  840
TDNLKVKLAE YIPFSEDHKD SQWILEPIIQ NTRGVSGMQF NNVMRRNVNY KLVLDGRDYG  900
TKSGAEIDNE GNRFLNLKEY NGGNLFPVGL INNQVFNIFA IDADNPNIFE KIKIGDFRTL  960
VLADHKNAQG PYDIYSDSAE VSSMPDHNDT ITTIVLPPKS TITIYQDKNY GGKSKTYVND  1020
NSQVPMHIDF SKQDEWWNDT ISSFKYTKNS L                                1051

SEQ ID NO: 207           moltype = AA  length = 1022
FEATURE                  Location/Qualifiers
REGION                   1..1022
                         note = Description of Artificial Sequence: Synthetic
                          polypeptide
source                   1..1022
                         mol_type = protein
                         organism = synthetic construct
SEQUENCE: 207
MEVNSAKDSV SQENIARNGL VAYYFKDSSY KELSSIQVEK DSTLFKKQEI KTNQQPVQSI  60
RLIGKIKPTQ NGEYAFSISS NDANTIIQIN GQTVLQEGKK NTPIHLEKNK NYDIKIEYRS  120
KQEVNSNIQL FWSKDGEKKE LIPQNQLLLP DFKAQEKVID EQSHTLLLPK HTLFNSASDS  180
GLADTDKDGI PDEWEATGYT FKDQQIVKWD DAFLTQGYKK YLSNPNKIRT VADPYTDFEK  240
VIGYMPAATK DEARDPMVAA YPAVGVGMEK FFFSKNENVS DGTSGTISKS VTDTNSTTNG  300
VDVSAELGWS KGWSLKGSLK YSHSWTNSTA IQDTESESWS KQIGINTAES AFLNANVRYY  360
NAGTAPIYDL RPTTNFVFDK SGTSIATITA GSNQIGNSLA PSDTYPKREQ APISLDKANE  420
AGTMKISINA EQLDALQQGT DTLSLETTQN KGQYGILDEN GNLVTDTSKQ WDPVRTNIDA  480
VTGAITLDYG TGKDSLERRV AAKNENDPED KTPEITIREA IKKAFDTTEL DGRLYYTDAK  540
GNKVCIDEPT INIVTDDNTK KQIEQQLEQM QDKKIYNAKW KRGMKITLHM PTAYYDFEKT  600
AGTEWYSTYQ ENGGFSGKRH GRINTDGNGY AQKELQLKPY TSYTARAYVR TASTTGKNDV  660
TLYVDDTINA NGKGSRETFS VEGNEWKLIE FSFNTMSNPE YFKKLGIKNN GNANLHFDDV  720
SVTEWGQGEN IEQAHKFEKW DASSDGSGKI GSVTFSKVPA QDIRYQVQRT NEKGEWVWDN  780
IVDAPPVDAN GKRTLNITGT HGVRVFAVNK DTDNLKVKLA EYIPFSEDHK DSQWILEPII  840
QNTRGVSGMQ FNNVMRRNVN YKLVLDGRDY GTKSGAEIDN EGNRFLNLKE YNGGNLFPVG  900
LINNQVFNIF AIDADNPNIF EKIKIGDFRT LVLADHKNAQ GPYDIYSDSA EVSSMPDHND  960
TITTIVLPPK STITIYQDKN YGGKSKTYVN DNSQVPMHID FSKQDEWWND TISSFKYTKN  1020
```

```
SL                                                                      1022

SEQ ID NO: 208          moltype = AA  length = 646
FEATURE                 Location/Qualifiers
source                  1..646
                        mol_type = protein
                        organism = Bacillus sp.
SEQUENCE: 208
MHSNNNNNMS TLVVSSLSTN TVKHPLANNP ITSEQNIDYK DYLNSSSEPD LTPQDGVNIG  60
IDIVAGILKF LGIPGTGIVA TFYKFVIGKL WPSKNSSEIW ESFIKQMEAL IDNKIAEQVK  120
KDALSKLQGL QEGLESYVNA LESWQSNSRD YQTKSLVKER FVSLDMIFKT TMPQFAIKDS  180
EALLLPIYAQ AANLHLYLMK DAQIFGEEWG MEQKEIKLFH EEQLKATGKY INHCVQSYTN  240
EEYKLSQNQT AKGWLIHHRF RREMTLMVLD LISLFPNYDV HVYPIPTTNQ ITRTVYTDPI  300
GYNVSGEIGI NKPWTSLKLI DNNQLERELI RPPHLFEVLD SIQIYTTKGT LVMNKEAYIN  360
FWVGHSLSYK NINGSRTHKS NYGITNTPDI YRLELNEEDI VETYTTAACL QNYYNGYYGV  420
PAASFMLLKR DESMVYNKVY SKPHTAHKTQ DYKSGNEIPG ENSQRYSHRI SHITLSRFHP  480
ENGLGVNLPV FGWTHMSADL NNVIYPDKIT QIPLVKAHSL AADTTIEGGA GFTGGDLIFR  540
NKPGRFAQLK VTINSSLSQK YQLRIRYSST TKGKFFILVS DTSVCTELFD KTRENNEPIT  600
YESYDLVTID TPFKFRKKVD TISVEASYFA HGQAVYIDKI EFIPVN                646

SEQ ID NO: 209          moltype = AA  length = 367
FEATURE                 Location/Qualifiers
REGION                  1..367
                        note = Description of Unknown: Organism from environmental
                         sample
source                  1..367
                        mol_type = protein
                        organism = unidentified
SEQUENCE: 209
LKRSFFFCVT CIVYFIFIVD IENNSPNLLF EGDIHMKAYK RLATLAPMAV LSTSIFCSPA  60
MTFAAEKTTI TKQTAVQQNV VQKGRTIQGY LIKNGKKTPI YKESIINNQT AQSNDAPYPQ  120
LSSNPNDAIP ITGATHSENG SIGSVLYFSK APFYFSLDIK LTNLYIEKNN DGTITRGKYD  180
PKTLKRTPLS GTMSSGDPDY ARFNAYFKGT TTTRDTFFSK IGSGVVPKNS SYTFSQAVTS  240
GLTTADAIGG AVTLGYTMSL TEGGGIFPAA ASEEFSSQLT ASYEHTITVS SEVTNTQTLG  300
IPQAADSYQY DKYAAAVYQL RSKYKMNPSA KLREDLANGT VVLDTRAQSF QYDDSTLYLA  360
VTPGAGI                                                           367

SEQ ID NO: 210          moltype = AA  length = 332
FEATURE                 Location/Qualifiers
REGION                  1..332
                        note = Description of Artificial Sequence: Synthetic
                         polypeptide
source                  1..332
                        mol_type = protein
                        organism = synthetic construct
SEQUENCE: 210
MKAYKRLATL APMAVLSTSI FCSPAMTFAA EKTTITKQTA VQQNVVQKGR TIQGYLIKNG  60
KKTPIYKESI INNQTAQSND APYPQLSSNP NDAIPITGAT HSENGSIGSV LYFSKAPFYF  120
SLDIKLTNLY IEKNNDGTIT RGKYDPKTLK RTPLSGTMSS GDPDYARFNA YFKGTTTTRD  180
TFFSKIGSGV VPKNSSYTFS QAVTSGLTTA DAIGGAVTLG YTMSLTEGGG IFPAAASEEF  240
SSQLTASYEH TITVSSEVTN TQTLGIPQAA DSYQYDKYAA AVYQLRSKYK MNPSAKLRED  300
LANGTVVLDT RAQSFQYDDS TLYLAVTPGA GI                                332

SEQ ID NO: 211          moltype = AA  length = 304
FEATURE                 Location/Qualifiers
REGION                  1..304
                        note = Description of Artificial Sequence: Synthetic
                         polypeptide
source                  1..304
                        mol_type = protein
                        organism = synthetic construct
SEQUENCE: 211
MAEKTTITKQ TAVQQNVVQK GRTIQGYLIK NGKKTPIYKE SIINNQTAQS NDAPYPQLSS  60
NPNDAIPITG ATHSENGSIG SVLYFSKAPF YFSLDIKLTN LYIEKNNDGT ITRGKYDPKT  120
LKRTPLSGTM SSGDPDYARF NAYFKGTTTT RDTFFSKIGS GVVPKNSSYT FSQAVTSGLT  180
TADAIGGAVT LGYTMSLTEG GGIFPAAASE EFSSQLTASY EHTITVSSEV TNTQTLGIPQ  240
AADSYQYDKY AAAVYQLRSK YKMNPSAKLR EDLANGTVVL DTRAQSFQYD DSTLYLAVTP  300
GAGI                                                              304

SEQ ID NO: 212          moltype = AA  length = 362
FEATURE                 Location/Qualifiers
source                  1..362
                        mol_type = protein
                        organism = Bacillus sp.
SEQUENCE: 212
MMMKSYKKLL MVAPLACTLA TGIAAVPHAA LAASPTAQVN QQFSNRDAGF SDAQLQKDIG  60
DRMKAAMINR PDLFSMSGHP TQADLNKWKI QFKNATVDYG GYTNSGAINT DVTVDHYTDA  120
GQVELLSYRN ETPVNQTFNT PEKSLKSSET FTYSNQEGVK LGVASETKVS ASIPFVAEGG  180
ETIKVSSEFS YTHTSTNTTT NEETNTFKSQ PVVCVPGYTT QFFGTVQNAV FSGSFTGTTI  240
```

```
ANGDITYSVT TSVGGHDFPV EVNTASNADS NVRGHAVYNI FKYSGQPLPS YVHLDDANKR  300
VLIDGVKSSY NGVGGHYSRV VVKVFPNTRS NEEAITMPYA EYMQKVKDGT LQQDLEQHYK  360
KA                                                                362

SEQ ID NO: 213          moltype = AA  length = 360
FEATURE                 Location/Qualifiers
REGION                  1..360
                        note = Description of Artificial Sequence: Synthetic
                         polypeptide
source                  1..360
                        mol_type = protein
                        organism = synthetic construct
SEQUENCE: 213
MKSYKKLLMV APLACTLATG IAAVPHAALA ASPTAQVNQQ FSNRDAGFSD AQLQKDIGDR  60
MKAAMINRPD LFSMSGHPTQ ADLNKWKIQF KNATVDYGGY TNSGAINTDV TVDHYTDAGQ  120
VELLSYRNET PVNQTFNTPE KSLKSSETFT YSNQEGVKLG VASETKVSAS IPFVAEGGET  180
IKVSSEFSYT HTSTNTTTNE ETNTFKSQPV VCVPGYTTQF FGTVQNAVFS GSFTGTTIAN  240
GDITYSVTTS VGGHDFPVEV NTASNADSNV RGHAVYNIFK YSGQPLPSYV HLDDANKRVL  300
IDGVKSSYNG VGGHYSRVVV KVFPNTRSNE EAITMPYAEY MQKVKDGTLQ QDLEQHYKKA  360

SEQ ID NO: 214          moltype = AA  length = 331
FEATURE                 Location/Qualifiers
REGION                  1..331
                        note = Description of Artificial Sequence: Synthetic
                         polypeptide
source                  1..331
                        mol_type = protein
                        organism = synthetic construct
SEQUENCE: 214
MASPTAQVNQ QFSNRDAGFS DAQLQKDIGD RMKAAMINRP DLFSMSGHPT QADLNKWKIQ  60
FKNATVDYGG YTNSGAINTD VTVDHYTDAG QVELLSYRNE TPVNQTFNTP EKSLKSSETF  120
TYSNQEGVKL GVASETKVSA SIPFVAEGGE TIKVSSEFSY THTSTNTTTN EETNTFKSQP  180
VVCVPGYTTQ FFGTVQNAVF SGSFTGTTIA NGDITYSVTT SVGGHDFPVE VNTASNADSN  240
VRGHAVYNIF KYSGQPLPSY VHLDDANKRV LIDGVKSSYN GVGGHYSRVV VKVFPNTRSN  300
EEAITMPYAE YMQKVKDGTL QQDLEQHYKK A                                331

SEQ ID NO: 215          moltype = AA  length = 369
FEATURE                 Location/Qualifiers
source                  1..369
                        mol_type = protein
                        organism = Bacillus sp.
SEQUENCE: 215
MEDTKMKTYK KIATIVPIAA LSTSVLFSPV MTLAAENSAT ATSKKLAIQT NTDEWLPNPF  60
TDPNPTVHSI SVSDLKSAIE QILVIRYGSD SNKAFQQKIR DAVNSWTPTF QNENTDIPLG  120
NVTVNNYQND NIELANFKNT STKEQTFETP ATKKTKTDSI TYTNTEGVKL GLENTSKIKA  180
SIPFLVDGET TIKVGFEATY NHTSSNTSTN STEITYPSQK LICPPGYKVS LLVKTANANF  240
SGTMSATKQV ANESVLTNKL NQLVGQGSPQ KVPNDLTLYK ILSDRSGLSS GQLISFQDAY  300
NKVHPDFDNY TQTVTFGKVN IPYTGVVGHL SDAEMSSVKI ESLNSNDSTT IPLKSYQNLS  360
TEQIIQKLK                                                         369

SEQ ID NO: 216          moltype = AA  length = 364
FEATURE                 Location/Qualifiers
REGION                  1..364
                        note = Description of Artificial Sequence: Synthetic
                         polypeptide
source                  1..364
                        mol_type = protein
                        organism = synthetic construct
SEQUENCE: 216
MKTYKKIATI VPIAALSTSV LFSPVMTLAA ENSATATSKK LAIQTNTDEW LPNPFTDPNP  60
TVHSISVSDL KSAIEQILVI RYGSDSNKAF QQKIRDAVNS WTPTFQNENT DIPLGNVTVN  120
NYQNDNIELA NFKNTSTKEQ TFETPATKKT KTDSITYTNT EGVKLGLENT SKIKASIPFL  180
VDGETTIKVG FEATYNHTSS NTSTNSTEIT YPSQKLICPP GYKVSLLVKT ANANFSGTMS  240
ATKQVANESV LTNKLNQLVG QGSPQKVPND LTLYKILSDR SGLSSGQLIS FQDAYNKVHP  300
DFDNYTQTVT FGKVNIPYTG VVGHLSDAEM SSVKIESLNS NDSTTIPLKS YQNLSTEQII  360
QKLK                                                              364

SEQ ID NO: 217          moltype = AA  length = 336
FEATURE                 Location/Qualifiers
REGION                  1..336
                        note = Description of Artificial Sequence: Synthetic
                         polypeptide
source                  1..336
                        mol_type = protein
                        organism = synthetic construct
SEQUENCE: 217
MAENSATATS KKLAIQTNTD EWLPNPFTDP NPTVHSISVS DLKSAIEQIL VIRYGSDSNK  60
AFQQKIRDAV NSWTPTFQNE NTDIPLGNVT VNNYQNDNIE LANFKNTSTK EQTFETPATK  120
KTKTDSITYT NTEGVKLGLE NTSKIKASIP FLVDGETTIK VGFEATYNHT SSNTSTNSTE  180
```

```
ITYPSQKLIC PPGYKVSLLV KTANANFSGT MSATKQVANE SVLTNKLNQL VGQGSPQKVP  240
NDLTLYKILS DRSGLSSGQL ISFQDAYNKV HPDFDNYTQT VTFGKVNIPY TGVVGHLSDA  300
EMSSVKIESL NSNDSTTIPL KSYQNLSTEQ IIQKLK                           336

SEQ ID NO: 218         moltype = AA  length = 1293
FEATURE                Location/Qualifiers
source                 1..1293
                       mol_type = protein
                       organism = Bacillus sp.
SEQUENCE: 218
MNQNYGNYGN NEMEILDSGM RNPRYPYRNA PSTDLQNMNY KEWMNMCGEN DVSVMPVGSE  60
TKSSSEAISI VLGITADIIG LKFPITGLII GIMGHLWPKG EQDQQEVWET LMNAVEDLID  120
QKIDELVRSQ AIAELRALQS NLDVYNAALE AWRTTLDDNN RQWVIAEFDN CDQQFRNALA  180
QLSLIGWEVL LLPAYVEAAN LYHMFLRDFM LYWQDWGMSQ EEFNYRNDER KRLLQETSDY  240
CVTMYNQGLQ DAKNPSVNIE DAVRYPWANS DQPGDPPCNS NYRDAEGEYI SIEKWNAYNA  300
YRRDMTIMVL DMVAIWPTYD VDYYPVEVIR TYDPGTGALI GIEPQATPVK IELTREVYTD  360
ATGSVWRSDP SQITIDAIEN RLLGNRNTPH LFDWLQQLKF YMRRTGNADH RTVGDLMVGL  420
EKTTMKTYGS STTHPLEGQN TDYSSIATPG ADYNSYYWST ANTKQWFETR WLQLYINTGI  480
RSLEVGTIEE YYPPTANPTC PDNWEINQIY NEGYRANNIP HHRLSWIKFE PTGPDADNAW  540
PQYKQVTAFL FGWTHTSVDY NNTIAADKIT QIPAVKGYVI NGGQVIKGPG STGGDLVELA  600
PNGGVSFFVR VDSALANHRL RIRYASVGNS QLGVGTNLSF ITYPVNATYS GGTLTYNGFS  660
YLEANYSQIS SGMTAAINLG NFGNSPIVID KIEVIPIEGS VEEYEAKQNL KKARKAVNAL  720
FTNNAKNALR LDVTDYDVDQ AANKVDCMSD DLCTKEKMIL LDQVKHAKRL SQARNLLNYG  780
DFESSDWLSA KGWQASNNVS VLSGSPMFKG NYLNMPGAKT IDGTVVPTYV YQKVDESKLK  840
PYTRYLVRGF VGNSTDLELF VSRYGKEVHD KMNISLSQIN TYSQTARVPD SCGRGQVSSY  900
AMSSDPCQTN SYSANPSSLA MSPMKGLCED KQHFVFHIDV GEVDPRANLG IGVGFKIASS  960
SGMAQLDNLE VIEANPLTGE ALARVKKREQ KWKREMEQKC TLTEKTVVVS KQAVDHLFTN  1020
AQKNRLRVTT TMQDILHAKA KVENIPYVYN PYFEEVPGMN FAIYQALQSD VVRASRLYDN  1080
RNVLRNGDFS IGLSHWHATA RADVQEREGN PHVLVISNWD ANVSQEVCVE PERGYVLRVT  1140
ARKEGSGNGY VTISDCTEAN TETVTFTANE PVGTPRTTPP SRRTIEPAAC DKIRYNESFG  1200
IVPDTNMMNY TAKNASMETC SCGCNNTIHT PSTSYQTKAY SSQPIRPNMT GPSTGYITKT  1260
IEMFPETNRM RIEIGETEGT FLVESIELIC MED                              1293

SEQ ID NO: 219         moltype = AA  length = 698
FEATURE                Location/Qualifiers
REGION                 1..698
                       note = Description of Artificial Sequence: Synthetic
                        polypeptide
source                 1..698
                       mol_type = protein
                       organism = synthetic construct
SEQUENCE: 219
MNQNYGNYGN NEMEILDSGM RNPRYPYRNA PSTDLQNMNY KEWMNMCGEN DVSVMPVGSE  60
TKSSSEAISI VLGITADIIG LKFPITGLII GIMGHLWPKG EQDQQEVWET LMNAVEDLID  120
QKIDELVRSQ AIAELRALQS NLDVYNAALE AWRTTLDDNN RQWVIAEFDN CDQQFRNALA  180
QLSLIGWEVL LLPAYVEAAN LYHMFLRDFM LYWQDWGMSQ EEFNYRNDER KRLLQETSDY  240
CVTMYNQGLQ DAKNPSVNIE DAVRYPWANS DQPGDPPCNS NYRDAEGEYI SIEKWNAYNA  300
YRRDMTIMVL DMVAIWPTYD VDYYPVEVIR TYDPGTGALI GIEPQATPVK IELTREVYTD  360
ATGSVWRSDP SQITIDAIEN RLLGNRNTPH LFDWLQQLKF YMRRTGNADH RTVGDLMVGL  420
EKTTMKTYGS STTHPLEGQN TDYSSIATPG ADYNSYYWST ANTKQWFETR WLQLYINTGI  480
RSLEVGTIEE YYPPTANPTC PDNWEINQIY NEGYRANNIP HHRLSWIKFE PTGPDADNAW  540
PQYKQVTAFL FGWTHTSVDY NNTIAADKIT QIPAVKGYVI NGGQVIKGPG STGGDLVELA  600
PNGGVSFFVR VDSALANHRL RIRYASVGNS QLGVGTNLSF ITYPVNATYS GGTLTYNGFS  660
YLEANYSQIS SGMTAAINLG NFGNSPIVID KIEVIPIE                         698

SEQ ID NO: 220         moltype = AA  length = 187
FEATURE                Location/Qualifiers
source                 1..187
                       mol_type = protein
                       organism = Bacillus sp.
SEQUENCE: 220
LNHSRYREHT VYAHESLIEG MDQSAATIEY TESKNTTLSF CGMVHIPHGF TYVPKGTKKL  60
AYSLAGLSVV KETSQKTIVV EDCGPVDVTL NVLKVVGSIP YIVTAKVQGD DGEMYGSSSK  120
QENQIDLSYI GNIPVDTVLK LSVASLPDYR MQEQNIKISD FLVTPVQDQG ANLLRFTGTL  180
AFQGIPQ                                                           187

SEQ ID NO: 221         moltype = AA  length = 804
FEATURE                Location/Qualifiers
source                 1..804
                       mol_type = protein
                       organism = Bacillus sp.
SEQUENCE: 221
LLMNQNYKNN EYEILDNDNT VYQPRYPLAQ APDSELRNMN YKDWLAKFPD RAPVIPAESY  60
NADLREAIIT SINILTSLLS LTIPVAGVAG GIISAMLGWL WPTNTEAVWE AFMDAVEALV  120
DQKIDDFARS QAIGKLRGMH DVLELYETAV SNLQKDPQNE ALKETVRTQF IATNTFIVGS  180
LPSLHPPGYE VPMLASYAQA VNLHLLLLRD AVKFGTSWGM ESATVAGYQG DLETGILFHT  240
DNCVKTYNKG IEKTKMLKAN VKDYDRYPWA QYHDLLPSLG GTPEKDFQNV ENWNLLNSFR  300
RDMTIMALDL VSIWPTYNSK EYPLPVKAQL TREIYTDLRG CYAGDINSTE AQIIRPPHLF  360
TFFKSATLYT GTPPIFPYVG IQQSGHYTLG PSFTTTVKGT SEGAPNTVTA TPSDAIINKV  420
```

```
DIDTGNELYR FMFYQENYTQ PFKNVGENSS LGYVRTINRI PIEGNQTLAN HRISWISGSL  480
RPASSGGPMV GQIPPYISCA ALGWTHISAN LDNKIVSDKI TQIPAVKGFG LGGNAKVIPG  540
PGSTGGDLVQ LPNPGYVKIA IPAARNTQSY RVRIRYASSQ AGTLRVIKWR DGTYTHAFYN  600
VPQTYSSLLT YGAFKYLESF AITPDTNIEV WLENSGGGPI IIDKIEFIPL TPMPDPELKV  660
PVGTYQIITA LNNSSVVDMM RNQSIRNVQI FGNGNGTNQK WNFVYDASKA AYQIKNIANE  720
NLVLTWSYDV ERPFDVNATT NYYWNRQYWI IEDAGNGYVY LKNKEDLNIG LNVKNANTAN  780
GTLINAVSFN SGTSSQKFRM NRLN                                        804

SEQ ID NO: 222          moltype = AA  length = 802
FEATURE                 Location/Qualifiers
REGION                  1..802
                        note = Description of Artificial Sequence: Synthetic
                         polypeptide
source                  1..802
                        mol_type = protein
                        organism = synthetic construct
SEQUENCE: 222
MNQNYKNNEY EILDNDNTVY QPRYPLAQAP DSELRNMNYK DWLAKFPDRA PVIPAESYNA  60
DLREAIITSI NILTSLLSLT IPVAGVAGGI ISAMLGWLWP TNTEAVWEAF MDAVEALVDQ  120
KIDDFARSQA IGKLRGMHDV LELYETAVSN LQKDPQNEAL KETVRTQFIA TNTFIVGSLP  180
SLHPPGYEVP MLASYAQAVN LHLLLLRDAV KFGTSWGMES ATVAGYQGDL ETGILFHTDN  240
CVKTYNKGIE KTKMLKANVK DYDRYPWAQY HDLLPSLGGT PEKDFQNVEN WNLLNSFRRD  300
MTIMALDLVS IWPTYNSKEY PLPVKAQLTR EIYTDLRGCY AGDINSTEAQ IIRPPHLFTF  360
FKSATLYTGT PPIFPYVGIQ QSGHYTLGPS FTTTVKGTSE GAPNTVTATP SDAIINKVDI  420
DTGNELYRFM FYQENYTQPF KNVGENSSLG YVRTINRIPI EGNQTLANHR ISWISGSLRP  480
ASSGGPMVGQ IPPYISCAAL GWTHISANLD NKIVSDKITQ IPAVKGFGLG GNAKVIPGPG  540
STGGDLVQLP NPGYVKIAIP AARNTQSYRV RIRYASSQAG TLRVIKWRDG TYTHAFYNVP  600
QTYSSLLTYG AFKYLESFAI TPDTNIEVWL ENSGGGPIII DKIEFIPLTP MPDPELKVPV  660
GTYQIITALN NSSVVDMMRN QSIRNVQIFG NGNGTNQKWN FVYDASKAAY QIKNIANENL  720
VLTWSYDVER PFDVNATTNY YWNRQYWIIE DAGNGYVYLK NKEDLNIGLN VKNANTANGT  780
LINAVSFNSG TSSQKFRMNR LN                                          802

SEQ ID NO: 223          moltype = AA  length = 648
FEATURE                 Location/Qualifiers
REGION                  1..648
                        note = Description of Artificial Sequence: Synthetic
                         polypeptide
source                  1..648
                        mol_type = protein
                        organism = synthetic construct
SEQUENCE: 223
MNQNYKNNEY EILDNDNTVY QPRYPLAQAP DSELRNMNYK DWLAKFPDRA PVIPAESYNA  60
DLREAIITSI NILTSLLSLT IPVAGVAGGI ISAMLGWLWP TNTEAVWEAF MDAVEALVDQ  120
KIDDFARSQA IGKLRGMHDV LELYETAVSN LQKDPQNEAL KETVRTQFIA TNTFIVGSLP  180
SLHPPGYEVP MLASYAQAVN LHLLLLRDAV KFGTSWGMES ATVAGYQGDL ETGILFHTDN  240
CVKTYNKGIE KTKMLKANVK DYDRYPWAQY HDLLPSLGGT PEKDFQNVEN WNLLNSFRRD  300
MTIMALDLVS IWPTYNSKEY PLPVKAQLTR EIYTDLRGCY AGDINSTEAQ IIRPPHLFTF  360
FKSATLYTGT PPIFPYVGIQ QSGHYTLGPS FTTTVKGTSE GAPNTVTATP SDAIINKVDI  420
DTGNELYRFM FYQENYTQPF KNVGENSSLG YVRTINRIPI EGNQTLANHR ISWISGSLRP  480
ASSGGPMVGQ IPPYISCAAL GWTHISANLD NKIVSDKITQ IPAVKGFGLG GNAKVIPGPG  540
STGGDLVQLP NPGYVKIAIP AARNTQSYRV RIRYASSQAG TLRVIKWRDG TYTHAFYNVP  600
QTYSSLLTYG AFKYLESFAI TPDTNIEVWL ENSGGGPIII DKIEFIPL              648

SEQ ID NO: 224          moltype = AA  length = 330
FEATURE                 Location/Qualifiers
source                  1..330
                        mol_type = protein
                        organism = Bacillus sp.
SEQUENCE: 224
MNNNHESNMQ DVYNGGMENN QNSNVQSTYD GYVYNNSSNI QTMHTEGRQT RGIKIPRNAR  60
VITRINFVDA MRLVAEGYAM WRYSAPSAQI RNLNITGINE TKLVVERERF IGPIENPQLI  120
VNLTHRGVNT SPGELQISHA FSQTVTNESS YSSSRSITNT AGIEQAFEVN FQLPALGNVG  180
STTTLKYEYS NTKEELSSQS KSVGWQYEVS ATGILPPYTS ADLYTRLYKT KTRYEQTGYS  240
YFEGTISFDY LVDLPGAQWN QLTISLREIG GRINENIEER LYKDYNMYFS SYEDSTSGQL  300
RPALAYRGLF YLDMDDSYYA ETGMTSPTRI                                  330

SEQ ID NO: 225          moltype = AA  length = 299
FEATURE                 Location/Qualifiers
source                  1..299
                        mol_type = protein
                        organism = Bacillus sp.
SEQUENCE: 225
LQRKSYLLGG ETMIHDLKED ILNFTKWYAE KHYNANPDTF HDEKVFNPSV SNTEVVPDKI  60
EFDTTPKLTA RATDILINDT SVSQSITPKI STKTVETTSI TTTEGYKIGA GIKYTSTMKL  120
KLFLIGEISN SIEIAVTSEY NHSTSETQTN TTEKIWEYTR PVIVPPRTKV TATLEVYAGP  180
VKVPVTLRST ITGMGIASTG YGYILGSVAY KDRDGKNWID SCRSRSLYDF KSTWPGFKPV  240
YVGTDGEYGV KVQGTAQVEL ELGLYGVVTY QEEPLSGNDS NKSQTYREIM PRQGLHTRI   299

SEQ ID NO: 226          moltype = AA  length = 287
```

```
FEATURE                 Location/Qualifiers
REGION                  1..287
                        note = Description of Artificial Sequence: Synthetic
                         polypeptide
source                  1..287
                        mol_type = protein
                        organism = synthetic construct
SEQUENCE: 226
MIHDLKEDIL NFTKWYAEKH YNANPDTFHD EKVFNPSVSN TEVVPDKIEF DTTPKLTARA  60
TDILINDTSV SQSITPKIST KTVETTSITT TEGYKIGAGI KYTSTMKLKL FLIGEISNSI  120
EIAVTSEYNH STSETQTNTT EKIWEYTRPV IVPPRTKVTA TLEVYAGPVK VPVTLRSTIT  180
GMGIASTGYG YILGSVAYKD RDGKNWIDSC RSRSLYDFKS TWPGFKPVYV GTDGEYGVKV  240
QGTAQVELEL GLYGVVTYQE EPLSGNDSNK SQTYREIMPR QGLHTRI               287

SEQ ID NO: 227          moltype = AA  length = 354
FEATURE                 Location/Qualifiers
source                  1..354
                        mol_type = protein
                        organism = Bacillus sp.
SEQUENCE: 227
MISTIATPST TAFAAEVTSP NLITKEESST SRAISYIDIV QDRMKQRDIE SKRTGKPINM  60
QEQIIDGWFL ARFWIFKDQN NNHQTNRFIT WFKNNVASSK GYDNIAEQMG LKIEALSDMD  120
ISNVNYKSKL GDTIYNGISK LTNYTGSVQK MKTDSFQRDY TKSQSTSVTN GLQVGFKVTA  180
KSVITLVAGA GVDFETSVAY NLSSTTTEIN TLSDKFTVPS QEVTLPPGHK AIIKHDLRKM  240
VYSGSHDLKG DLKVTFNDKE FVRKFIYTNY RYIDLSDIRK AMIEIDKVNH VQPIDFYQLV  300
GVKNHIKKGN TLYIDTPAEF NFNGANPYYR GFWCKIFIRY FSFYYLLRYR QCIY        354

SEQ ID NO: 228          moltype = AA  length = 341
FEATURE                 Location/Qualifiers
REGION                  1..341
                        note = Description of Artificial Sequence: Synthetic
                         polypeptide
source                  1..341
                        mol_type = protein
                        organism = synthetic construct
SEQUENCE: 228
MAEVTSPNLI TKEESSTSRA ISYIDIVQDR MKQRDIESKR TGKPINMQEQ IIDGWFLARF  60
WIFKDQNNNH QTNRFITWFK NNVASSKGYD NIAEQMGLKI EALSDMDISN VNYKSKLGDT  120
IYNGISKLTN YTGSVQKMKT DSFQRDYTKS QSTSVTNGLQ VGFKVTAKSV ITLVAGAGVD  180
FETSVAYNLS STTTEINTLS DKFTVPSQEV TLPPGHKAII KHDLRKMVYS GSHDLKGDLK  240
VTFNDKEFVR KFIYTNYRYI DLSDIRKAMI EIDKVNHVQP IDFYQLVGVK NHIKKGNTLY  300
IDTPAEFNFN GANPYYRGFW CKIFIRYFSF YYLLRYRQCI Y                      341

SEQ ID NO: 229          moltype = AA  length = 689
FEATURE                 Location/Qualifiers
source                  1..689
                        mol_type = protein
                        organism = Bacillus sp.
SEQUENCE: 229
MNHNNNEYEI INSYTSPYPS NKNNNHSRYP YTNNPNQPLQ NTNYKDWHNM CQQNQQYGKN  60
FEITPTSLKD AVVTATNING AIFVAIPTPY TVIIGTGLLI IGSLLAFLWP SEEPGKNTQP  120
VWQEFMRNVE EHLKRAIDEQ VRNHAINTLK GIDNNIKLYS TSFATWFKNQ NDKSALDNLT  180
NNFSELDNLF EASMPHFASN KHETLLLSIY AQAANLHLLL LRDMLIYGEK WGYSKAVIKE  240
FYDRQLERTN DYTYHCTYWY NQGLNELINT PNIDWNRFND YRREMIITVL DTVSLFTSYD  300
IYKYPLGLIP EFTREIYTTS LADPYLSPNI IIGHLEQSLT RRPSLFTWLK GLDLYTLNTD  360
DSKEISLIAH SNLHSFTTND GLFFSGPIFG DSSNGILKII NFSKDEYVFK VSIEAFIKQG  420
IQYTFPKITE IVFDITNNKQ EFLITYNTGN TRSDTFDTLF YLPSTYYQQP TPDYNNYSHV  480
LSCITSHTSN IERAQISYAL GWTHVSVNPS NQIYTDTITQ ISAVKGMYLD TNSKVIEGPG  540
HTGGNLVYLQ KQGRLEIRCK TLVPTQSYFV RIRYATNGYL NTAPMISLTI PGVTGQSMRL  600
NNTFSGTSYS NLQYKNFAYL EFEQEIKLSS NQNITCIFNR LDSFDSILLI DKIEFLPITP  660
TFEKNLEIQK LEKIQQTVDT LFSNQTKIL                                    689

SEQ ID NO: 230          moltype = AA  length = 388
FEATURE                 Location/Qualifiers
source                  1..388
                        mol_type = protein
                        organism = Bacillus sp.
SEQUENCE: 230
MKSISKKVMA GLGVGAMSLS IWAPSSEAAA PANNEYHTIH LAANTNIAWD VYKGWQSDDA  60
GIVLWDGARG DNEQFVFFPL DGGAYAIVNK NSGKPVGIGN AIIGSDGVRH FTSMNNEGLR  120
QTSWTGAANE QWYLRDKGNN NFEIVNQGSG KVASWAGMEL YGYKDYVDLD ESNPSDNDRL  180
FNIPAARSTF SLPTLPTVGT RPNAPDYNKS GPIDQQLPQT SESVVVGASL IPSIMVKDNG  240
ASDYTKIHNS PYYVLVKEEY WEKEYSDIIP AGGSRKYTLK TGVSNVDQQK MTETLAMSFG  300
TDLGLKFGDS SLSIKSSVSK TLQTEISTTN TESKEETIEK VALSLPGKNT GFTEYQLKTK  360
YTLKRTDGSA VSAPWIVKDP KQTLPRTI                                     388

SEQ ID NO: 231          moltype = AA  length = 360
FEATURE                 Location/Qualifiers
REGION                  1..360
```

```
                         note = Description of Artificial Sequence: Synthetic
                          polypeptide
source                   1..360
                         mol_type = protein
                         organism = synthetic construct
SEQUENCE: 231
MAPANNEYHT IHLAANTNIA WDVYKGWQSD DAGIVLWDGA RGDNEQFVFF PLDGGAYAIV  60
NKNSGKPVGI GNAIIGSDGV RHFTSMNNEG LRQTSWTGAA NEQWYLRDKG NNNFEIVNQG  120
SGKVASWAGM ELYGYKDYVD LDESNPSDND RLFNIPAARS TFSLPTLPTV GTRPNAPDYN  180
KSGPIDQQLP QTSESVVVGA SLIPSIMVKD NGASDYTKIH NSPYYVLVKE EYWEKEYSDI  240
IPAGGSRKYT LKTGVSNVDQ QKMTETLAMS FGTDLGLKFG DSSLSIKSSV SKTLQTEIST  300
TNTESKEETI EKVALSLPGK NTGFTEYQLK TKYTLKRTDG SAVSAPWIVK DPKQTLPRTI  360

SEQ ID NO: 232           moltype = AA  length = 274
FEATURE                  Location/Qualifiers
REGION                   1..274
                         note = Description of Unknown: Organism from environmental
                          sample
source                   1..274
                         mol_type = protein
                         organism = unidentified
SEQUENCE: 232
MANFSSLQDA TMVYLTDKYI RVPNSDYISI LGTPDMFRYL NSKGPVTIPN LISTDTPRTV  60
VQTSKITNTS SSTISKTFSF SESVTDTVTS SFESGFELGM SKEMSMGASI EMVKMDVKQT  120
ISTKVSLKST QTTTNTKTRT WVEQYTVPVA ANTAATIIYT LSIGTFDGFV DVDLKLSGNV  180
LTGLVYSPIG QIANPGAGPI KDLEIPIVDI VRYTNPAGFT VNSDNTVSFK GKVRLQGELG  240
IMSELFVNST SLITGVTTTT PLSTQTAPPT ILFA                            274

SEQ ID NO: 233           moltype = AA  length = 1282
FEATURE                  Location/Qualifiers
source                   1..1282
                         mol_type = protein
                         organism = Bacillus sp.
SEQUENCE: 233
MEMRRMPIAS FRHSFLYSMH GRTICFLFLL LFTTLFGYIN QYICITKAFL TYDVYINDCT  60
KETLPEPYIY IANGHVDGLA VTKGVLSLLS FVPEAAPFVA AGTAVLDFLW PKIFGSNNSD  120
SEADRAKRMF EAMKPKIQEM IDVSLDEYQT DVVNTKFAGV VREMGSYQQA VLKGSVDEIK  180
RQTSAIHDDF LGKIDEFIVR KYEVVGLPYF ALTANFHILI LRDYVLNASQ WSVDSKDVDL  240
YKGYLTEAIK SYTDTVLRVF KQGLEERTKL EATTENFNKV VQYVNFMTDM VLDMAALWPT  300
FDVQVYPTGA KLDFTRSITS LKQELWPISY IRDPYPVLNP YKGELSKIDF FVYKTYYNNT  360
GSSTGGEFTG IQNYHIQSDG TEQLGLGYGA NHNTSTKSED LSGPYKTIEV ANHTPTRYGT  420
EVHGNHAMNN IDKQNNVVIY FNDGTYDGMG LGSAPGSGNN TWSPQDKAPA NHKLQYIQPL  480
NAFSSGAQIL SYLNVYTLID TMAQNIIGTI DEDTHQPETK LRGFPFEKAS YGGTPVKEWL  540
TGANVMKLSP GQSIGIPIIN MTKQKYEIRC RYANNSNDSV TMFVNLDTNK GNLIFQNIDF  600
ESTIDNGSVG NEDAKLGANG ETGFYVVKKL SDSQIELPVS EKDKPLYVHF TNKGSSDLFL  660
DRIEFVPIEF YSLDFNFDST ANFVPMPNMS SWFSLDLWKS TDGKLAHYIE APNIQSSQGV  720
QYVINFYKNG TWLSSEIYRT HFSDDFTQKF PFTATIPQGF DLVTVTDIVD TSLFFTSGSI  780
SIDAPENRDI TFTNSTDLAN ITTQVNALFA SGTQDTLAPD VSDYEIEEVV LKVDALSDEV  840
FGKEKKALRK LVNQAKRLSK ARNLLVGGNF ENWDAWYKGK NVVTVSDHEL FKSAHVLLPP  900
PTLYPSYIFQ KVEESKLKPN TRYTVSGFIA HAIDLEIVVS RYEQEVKKVV QVPYGEAFPL  960
TSNGSNCCSS DMSRFIRSGA PADPRFFSYS IDVGALDLEA NLGIEFGLRI VGRTGMARVS  1020
NLEIRENRSL TANELRKVQR AARDWRTAYD QERAEVTALI QPVLNQINAL YENENWNGPI  1080
RSDISYHDIE SIVLPTLPKL NHWFMSDMLG EQGSILAQFQ EALDRAYAQL EGSTLLHNGH  1140
FTTDAANWTI EGDAHHAILE DGRRVLRLPD WSSSVSQTIE IENFDPDKEY QLVFHAQGEG  1200
TASLQHGEEG EYVETHTHKF ANFTTSQRQG VTFETNKVTV EIASEDGEFL VDHIALVEAP  1260
LPTDDQSSDG NTNSTTSMNN NQ                                         1282

SEQ ID NO: 234           moltype = AA  length = 1246
FEATURE                  Location/Qualifiers
REGION                   1..1246
                         note = Description of Artificial Sequence: Synthetic
                          polypeptide
source                   1..1246
                         mol_type = protein
                         organism = synthetic construct
SEQUENCE: 234
MYINQYICIT KAFLTYDVYI NDCTKETLPE PYIYIANGHV DGLAVTKGVL SLLSFVPEAA  60
PFVAAGTAVL DFLWPKIFGS NNSDSEADRA KRMFEAMKPK IQEMIDVSLD EYQTDVVNTK  120
FAGVVREMGS YQQAVLKGSV DEIKRQTSAI HDDFLGKIDE FIVRKYEVVG LPYFALTANF  180
HILILRDYVL NASQWSVDSK DVDLYKGYLT EAIKSYTDTV LRVFKQGLEE RTKLEATTEN  240
FNKVVQYVNF MTDMVLDMAA LWPTFDVQVY PTGAKLDFTR SITSLKQELW PISYIRDPYP  300
VLNPYKGELS KIDFFVYKTY YNNTGSSTGG EFTGIQNYHI QSDGTEQLGL GYGANHNTST  360
KSEDLSGPYK TIEVANHTPT RYGTEVHGNH AMNNIDKQNN VVIYFNDGTY DGMGLGSAPG  420
SGNNTWSPQD KAPANHKLQY IQPLNAFSSG AQILSYLNVY TLIDTMAQNI IGTIDEDTHQ  480
PETKLRGFPF EKASYGGTPV KEWLTGANVM KLSPGQSIGI PIINMTKQKY EIRCRYANNS  540
NDSVTMFVNL DTNKGNLIFQ NIDFESTIDN GSVGNEDAKL GANGETGFYV VKKLSDSQIE  600
LPVSEKDKPL YVHFTNKGSS DLFLDRIEFV PIEFYSLDFN FDSTANFVPM PNMSSWFSLD  660
LWKSTDGKLA HYIEAPNIQS SQGVQYVINF YKNGTWLSSE IYRTHFSDDF TQKFPFTATI  720
PQGFDLVTVT DIVDTSLFFT SGSISIDAPE NRDITFTNST DLANITTQVN ALFASGTQDT  780
```

```
LAPDVSDYEI EEVVLKVDAL SDEVFGKEKK ALRKLVNQAK RLSKARNLLV GGNFENWDAW  840
YKGKNVVTVS DHELFKSAHV LLPPPTLYPS YIFQKVEESK LKPNTRYTVS GFIAHAIDLE  900
IVVSRYEQEV KKVVQVPYGE AFPLTSNGSN CCSSDMSRFI RSGAPADPRF FSYSIDVGAL  960
DLEANLGIEF GLRIVGRTGM ARVSNLEIRE NRSLTANELR KVQRAARDWR TAYDQERAEV  1020
TALIQPVLNQ INALYENENW NGPIRSDISY HDIESIVLPT LPKLNHWFMS DMLGEQGSIL  1080
AQFQEALDRA YAQLEGSTLL HNGHFTTDAA NWTIEGDAHH AILEDGRRVL RLPDWSSSVS  1140
QTIEIENFDP DKEYQLVFHA QGEGTASLQH GEEGEYVETH THKFANFTTS QRQGVTFETN  1200
KVTVEIASED GEFLVDHIAL VEAPLPTDDQ SSDGNTNSTT SMNNNQ                1246

SEQ ID NO: 235          moltype = AA  length = 633
FEATURE                 Location/Qualifiers
REGION                  1..633
                        note = Description of Artificial Sequence: Synthetic
                         polypeptide
source                  1..633
                        mol_type = protein
                        organism = synthetic construct
SEQUENCE: 235
MYINQYICIT KAFLTYDVYI NDCTKETLPE PYIYIANGHV DGLAVTKGVL SLLSFVPEAA  60
PFVAAGTAVL DFLWPKIFGS NNSDSEADRA KRMFEAMKPK IQEMIDVSLD EYQTDVVNTK  120
FAGVVREMGS YQQAVLKGSV DEIKRQTSAI HDDFLGKIDE FIVRKYEVVG LPYFALTANF  180
HILILRDYVL NASQWSVDSK DVDLYKGYLT EAIKSYTDTV LRVFKQGLEE RTKLEATTEN  240
FNKVVQYVNF MTDMVLDMAA LWPTFDVQVY PTGAKLDFTR SITSLKQELW PISYIRDPYP  300
VLNPYKGELS KIDFFVYKTY YNNTGSSTGG EFTGIQNYHI QSDGTEQLGL GYGANHNTST  360
KSEDLSGPYK TIEVANHTPT RYGTEVHGNH AMNNIDKQNN VVIYFNDGTY DGMGLGSAPG  420
SGNNTWSPQD KAPANHKLQY IQPLNAFSSG AQILSYLNVY TLIDTMAQNI IGTIDEDTHQ  480
PETKLRGFPF EKASYGGTPV KEWLTGANVM KLSPGQSIGI PIINMTKQKY EIRCRYANNS  540
NDSVTMFVNL DTNKGNLIFQ NIDFESTIDN GSVGNEDAKL GANGETGFYV VKKLSDSQIE  600
LPVSEKDKPL YVHFTNKGSS DLFLDRIEFV PIE                              633

SEQ ID NO: 236          moltype = AA  length = 115
FEATURE                 Location/Qualifiers
source                  1..115
                        mol_type = protein
                        organism = Rhizobium sp.
SEQUENCE: 236
MSTARSTIWT ITNATDSDWS LTSSTLNHGV WASNPPQTIK AGATASLTAE SNGLATGDEG  60
TVVYSFSGGS VSFYFDNPFL GSDDYTATVP PGYDQTSNQQ TGNTQVLTTR VFKTS       115

SEQ ID NO: 237          moltype = AA  length = 420
FEATURE                 Location/Qualifiers
source                  1..420
                        mol_type = protein
                        organism = Bacillus sp.
SEQUENCE: 237
VTSVAFTLGL SGIGPINVLS KPIAVHADTT SRAIEIASDG TVKIINDEIA KDAWFKKTLV  60
TMGGTALKDA VKGAHQNGSM SINNFAKDMT VAGTSLIPYG SALISPMIDL LWPTDGPNAT  120
KQLVDQISSI TNEQINDYDY ESLTTDLNAV KKELEIFEKG LQGDTSYYNG GSIEESNRAQ  180
AQIVNTAFHK LIENCKKERH QKSELPIYTL VATAHLEFLA YMATNGTGPN LKLDATSLQK  240
YYKDDLGKVI TEYKDHIKKL TRDGYTYGYN ESRDTAMANF FSSTSGSLAF NKAYNFAKNT  300
YLSRGGNVEN IRKIDNGCYA IVTSDTDGGI LFKTGNTSGL SNDINIYVNG KFVTTVSAGE  360
QQGKSFVAPG GVGLSPDDVV TVTMTEPDGH EYVLLDGYKF KDIPKSPTSY ESIAQLGTDM  420

SEQ ID NO: 238          moltype = AA  length = 420
FEATURE                 Location/Qualifiers
REGION                  1..420
                        note = Description of Artificial Sequence: Synthetic
                         polypeptide
source                  1..420
                        mol_type = protein
                        organism = synthetic construct
SEQUENCE: 238
MTSVAFTLGL SGIGPINVLS KPIAVHADTT SRAIEIASDG TVKIINDEIA KDAWFKKTLV  60
TMGGTALKDA VKGAHQNGSM SINNFAKDMT VAGTSLIPYG SALISPMIDL LWPTDGPNAT  120
KQLVDQISSI TNEQINDYDY ESLTTDLNAV KKELEIFEKG LQGDTSYYNG GSIEESNRAQ  180
AQIVNTAFHK LIENCKKERH QKSELPIYTL VATAHLEFLA YMATNGTGPN LKLDATSLQK  240
YYKDDLGKVI TEYKDHIKKL TRDGYTYGYN ESRDTAMANF FSSTSGSLAF NKAYNFAKNT  300
YLSRGGNVEN IRKIDNGCYA IVTSDTDGGI LFKTGNTSGL SNDINIYVNG KFVTTVSAGE  360
QQGKSFVAPG GVGLSPDDVV TVTMTEPDGH EYVLLDGYKF KDIPKSPTSY ESIAQLGTDM  420

SEQ ID NO: 239          moltype = AA  length = 506
FEATURE                 Location/Qualifiers
REGION                  1..506
                        note = Description of Unknown: Organism from environmental
                         sample
source                  1..506
                        mol_type = protein
                        organism = unidentified
SEQUENCE: 239
```

```
MIILAYAESI SRLHFHFTFE EIVMQNVDLP KARVNFSANH HLQLLRLRAG LNEEVLPGVE  60
AIGLGYNPFL GYASVNSGTV QLFDWANAKM KKVLFKPSFV VPEIVDVQQN DAASYTNISG  120
STVAEYQKNL ATSVAIEGKY NFFSGSLSTD YEENSLRNAE SEFTRIQQSI SLWSLRLPSV  180
KSLRDLMLPA LRAQLDQLDV KNPAAISKYF DTVGSHFLTG IVMGGRAVLA SSTNKLKVKR  240
DYSISVVAKA SYEGLTGQLS AEAKAKYGES ISSFTQYSNT HQEVLGGDGT KAQGVFSGKE  300
GYQAWVDSVG TSPDFIDFVP TIPMLEIWSL CETEEQASAI KLHFEKVWAP AQSEKYQLKP  360
NYIDQLVVIT GGSSTIEPPA GYAKVPYDLN TGAGGDFIYL CYHEQAWDPS HLKSAVTAIK  420
IIYNQDPTPA GYTKLPQDLN KGAGGDYVYL CYKTDAYDIN SAINKVTVIG GNNADINAPY  480
GYDKVPGDLN KGAGGEFIYV CTFVGK                                     506

SEQ ID NO: 240         moltype = AA  length = 312
FEATURE                Location/Qualifiers
source                 1..312
                       mol_type = protein
                       organism = Bacillus sp.
SEQUENCE: 240
MKRMKKIIPA AFVLSSALLV APGFSSADTN TTNVGSLPVV ISSQEGKAPM TAEQVAQNGT  60
QLPYVPTGPY EEFPSQWNIS TEDGKVIDYV YVDVVAQQDN VSMDKIFKFS GYKYVKPDGT  120
WIKDDENYAP KGNKGDVLYS IAIPKTDSIV ADTKLKKDLS WKLIDSNVID KNAGYHWSKA  180
VTSGISHNIS VGLSQTIGME VGLFDIAKVS TSLTWSFGYQ HTISEESTVT KTFDFNPKYD  240
YAYDQYRTAL YQQVANYAVI PGAGLQKWMS DRTANDPINA VLRAIGKGNA YEYKVKKSVD  300
YPVDVLVALT SK                                                    312

SEQ ID NO: 241         moltype = AA  length = 286
FEATURE                Location/Qualifiers
REGION                 1..286
                       note = Description of Artificial Sequence: Synthetic
                        polypeptide
source                 1..286
                       mol_type = protein
                       organism = synthetic construct
SEQUENCE: 241
MDTNTTNVGS LPVVISSQEG KAPMTAEQVA QNGTQLPYVP TGPYEEFPSQ WNISTEDGKV  60
IDYVYVDVVA QQDNVSMDKI FKFSGYKYVK PDGTWIKDDE NYAPKGNKGD VLYSIAIPKT  120
DSIVADTKLK KDLSWKLIDS NVIDKNAGYH WSKAVTSGIS HNISVGLSQT IGMEVGLFDI  180
AKVSTSLTWS FGYQHTISEE STVTKTFDFN PKYDYAYDQY RTALYQQVAN YAVIPGAGLQ  240
KWMSDRTAND PINAVLRAIG KGNAYEYKVK KSVDYPVDVL VALTSK                286

SEQ ID NO: 242         moltype = AA  length = 537
FEATURE                Location/Qualifiers
source                 1..537
                       mol_type = protein
                       organism = Bacillus sp.
SEQUENCE: 242
MYMYFSLLTS IFYIFYQKNK QKGEINMKYK DRTQAKNKYK KMLLATAAAL TLGVGPVSTF  60
VGVNSAYAAE QVTDVQKKDA EEKLSKLDQY FKDKLGGTTS EYAADFTSLM NDPKFSLSVE  120
AVKSITPSII NSLITGKTIE PAMLNSIAKN LTMTGVSMIP GVGGIASTIV GLLWPNVSTP  180
NPLDVLKEQL TTLINTTVQE SEKNAMQAKI NTVINNLAAL DSYVKKDTSY YSAGGTNSYV  240
TAINTALKEI MDQAAGSQFK NELLPVYTTA ATLHLTFMKF IEANAKNPDL GMDEKDLNAF  300
KIARGGDIRE LAIKYRDFIR KTAPEIESKA RSNAQTAGGI KANPYFYQFN EYATKTEFSL  360
SFNSIAEAVI GSETNLPTDA PVSIVHQGKY LSSRANQPDY LAFDTDRVHT NDGHDGQKFT  420
IKYVNKSKDI ITIQAENVNG NCISFDDFVV ENQASMVYKS DFGRVRKTSG DKSTLIKLIP  480
LKDANGKVIP DQYSMRALNS YMDAYIYVNG SSLDASSRIL GGTVNGGKYE TFTIKKI     537

SEQ ID NO: 243         moltype = AA  length = 511
FEATURE                Location/Qualifiers
REGION                 1..511
                       note = Description of Artificial Sequence: Synthetic
                        polypeptide
source                 1..511
                       mol_type = protein
                       organism = synthetic construct
SEQUENCE: 243
MKYKDRTQAK NKYKKMLLAT AAALTLGVGP VSTFVGVNSA YAAEQVTDVQ KKDAEEKLSK  60
LDQYFKDKLG GTTSEYAADF TSLMNDPKFS LSVEAVKSIT PSIINSLITG KTIEPAMLNS  120
IAKNLTMTGV SMIPGVGGIA STIVGLLWPN VSTPNPLDVL KEQLTTLINT TVQESEKNAM  180
QAKINTVINN LAALDSYVKK DTSYYSAGGT NSYVTAINTA LKEIMDQAAG SQFKNELLPV  240
YTTAATLHLT FMKFIEANAK NPDLGMDEKD LNAFKIARGG DIRELAIKYR DFIRKTAPEI  300
ESKARSNAQT AGGIKANPYF YQFNEYATKT EFSLSFNSIA EAVIGSETNL PTDAPVSIVH  360
QGKYLSSRAN QPDYLAFDTD RVHTNDGHDG QKFTIKYVNK SKDIITIQAE NVNGNCISFD  420
DFVVENQASM VYKSDFGRVR KTSGDKSTLI KLIPLKDANG KVIPDQYSMR ALNSYMDAYI  480
YVNGSSLDAS SRILGGTVNG GKYETFTIKK I                               511

SEQ ID NO: 244         moltype = AA  length = 470
FEATURE                Location/Qualifiers
REGION                 1..470
                       note = Description of Artificial Sequence: Synthetic
                        polypeptide
source                 1..470
```

```
                         mol_type = protein
                         organism = synthetic construct
SEQUENCE: 244
MAEQVTDVQK KDAEEKLSKL DQYFKDKLGG TTSEYAADFT SLMNDPKFSL SVEAVKSITP  60
SIINSLITGK TIEPAMLNSI AKNLTMTGVS MIPGVGGIAS TIVGLLWPNV STPNPLDVLK  120
EQLTTLINTT VQESEKNAMQ AKINTVINNL AALDSYVKKD TSYYSAGGTN SYVTAINTAL  180
KEIMDQAAGS QFKNELLPVY TTAATLHLTF MKFIEANAKN PDLGMDEKDL NAFKIARGGD  240
IRELAIKYRD FIRKTAPEIE SKARSNAQTA GGIKANPYFY QFNEYATKTE FSLSFNSIAE  300
AVIGSETNLP TDAPVSIVHQ GKYLSSRANQ PDYLAFDTDR VHTNDGHDGQ KFTIKYVNKS  360
KDIITIQAEN VNGNCISFDD FVVENQASMV YKSDFGRVRK TSGDKSTLIK LIPLKDANGK  420
VIPDQYSMRA LNSYMDAYIY VNGSSLDASS RILGGTVNGG KYETFTIKKI            470

SEQ ID NO: 245           moltype = AA  length = 265
FEATURE                  Location/Qualifiers
source                   1..265
                         mol_type = protein
                         organism = Bacillus sp.
SEQUENCE: 245
MNVNVTDLIE LFGRYANQWS QQRGGGNSKL SLMLPGFEHL AFTSFTKPVK YDEPTIHMPE  60
DVAVASNTYT NTGNQPLDVT IGLMGTLKNW LHLKINEGTS EAGKRFLNID LPNDIPSFLN  120
EQLIPIGGAL HESAHMQSWE VNHQFTINPK FKVTATLMIK TKKVTRLFEI QRILSRYIAI  180
HTSQAINGHL TSLHHVSRIL KDYFSPYIQV DGNKVTVTDK GKLQSLFGIE QYIHIQGKSL  240
SNPNIKEDYN IYNPETPVKQ SLKLS                                       265

SEQ ID NO: 246           moltype = AA  length = 378
FEATURE                  Location/Qualifiers
source                   1..378
                         mol_type = protein
                         organism = Bacillus sp.
SEQUENCE: 246
MLKKKRMFFA GMTALTIVGS GLTVSIPTAF ANTQGNMTPL QSMQGQEFTD ENGQVISPGT  60
FANISPYWLI GDSNNELYNF YNQVKQRIVD KQNKEQNMLK LDEYLNDLWF VGAVSQLYET  120
PNDHNKRLEA SNLVRWYKNN NAAKPNFEIL ESKLDNVEPI LDITEPIGYF ATESEYTNNS  180
PHQGEYLIPG WSNTTSTTYN TTTTKGFSIG ANSGIEIPLP FVDKLGLTGS YNFSKTDNVT  240
TTDSTTLTIP VQTIQVSQFA HSKTSFYFQT HQYRAKFDVT ATFKAEVGRD AEYTRKRSAF  300
YLLAKYNNYL PKGIVVENGG KLTLEGKGEI SVPNHINGFK LVKETNETPL SGGEGKIIKE  360
SYTKHPNTNK FTPEIEKT                                               378

SEQ ID NO: 247           moltype = AA  length = 349
FEATURE                  Location/Qualifiers
REGION                   1..349
                         note = Description of Artificial Sequence: Synthetic
                          polypeptide
source                   1..349
                         mol_type = protein
                         organism = synthetic construct
SEQUENCE: 247
MANTQGNMTP LQSMQGQEFT DENGQVISPG TFANISPYWL IGDSNNELYN FYNQVKQRIV  60
DKQNKEQNML KLDEYLNDLW FVGAVSQLYE TPNDHNKRLE ASNLVRWYKN NNAAKPNFEI  120
LESKLDNVEP ILDITEPIGY FATESEYTNN SPHQGEYLIP GWSNTTSTTY NTTTTKGFSI  180
GANSGIEIPL PFVDKLGLTG SYNFSKTDNV TTTDSTTLTI PVQTIQVSQF AHSKTSFYFQ  240
THQYRAKFDV TATFKAEVGR DAEYTRKRSA FYLLAKYNNY LPKGIVVENG GKLTLEGKGE  300
ISVPNHINGF KLVKETNETP LSGGEGKIIK ESYTKHPNTN KFTPEIEKT             349

SEQ ID NO: 248           moltype = AA  length = 268
FEATURE                  Location/Qualifiers
source                   1..268
                         mol_type = protein
                         organism = Bacillus sp.
SEQUENCE: 248
MGIINIQDEI NDYMKGMYGA TSVKSTYDPS FKVFNESVTP QYDVIPTEPV NNHITTKVVD  60
NPGHGEITST VTFTWTETDT VTTAVTHGVK AGGSISTKST FKFAFVTTDV TLTVSAEYNY  120
SKTETTTKTE TRTWTDSTAV KIPPRTNVEA AYIIQTGNYN VPVNVECDMT GTLFCRGYRD  180
GALIAATYVS ITDLADYNPN LGLTNEGNGV AHFKGEGYIE GAQGLRSYVQ VTEYPLDNDG  240
RRSIPKTYII KGSLAPNVTL INDRKEGR                                    268

SEQ ID NO: 249           moltype = AA  length = 150
FEATURE                  Location/Qualifiers
source                   1..150
                         mol_type = protein
                         organism = Bacillus sp.
SEQUENCE: 249
LSGGSGILMA IDAASGSMDA IDKFKKIFND IDAARSVILE IDNHTDQTLI KLAEHHFDGG  60
WSVTPQGEIP PNYALIFGSK DKDFMTGTEG SITYAAEGIE FEVYWNNPFI GDNECKINLN  120
GPNADQYRVN KECGIGDTDA HMRFELFTNP                                  150

SEQ ID NO: 250           moltype = AA  length = 150
FEATURE                  Location/Qualifiers
REGION                   1..150
```

```
                         note = Description of Artificial Sequence: Synthetic
                          polypeptide
source                   1..150
                         mol_type = protein
                         organism = synthetic construct
SEQUENCE: 250
MSGGSGILMA IDAASGSMDA IDKFKKIFND IDAARSVILE IDNHTDQTLI KLAEHHFDGG  60
WSVTPQGEIP PNYALIFGSK DKDFMTGTEG SITYAAEGIE FEVYWNNPFI GDNECKINLN  120
GPNADQYRVN KECGIGDTDA HMRFELFTNP                                   150

SEQ ID NO: 251           moltype = AA  length = 328
FEATURE                  Location/Qualifiers
REGION                   1..328
                         note = Description of Unknown: Organism from environmental
                          sample
source                   1..328
                         mol_type = protein
                         organism = unidentified
SEQUENCE: 251
LRVLARHPEL VSSSGVKPIT NQKDLEIYDS QAGGFAQFIR DNNQNLPHIF NDPHMKLMTG  60
VTPFFNWAPQ YTNLSTQNVI NLDNPKVDDY KEDNIEIASY TNNTTSEQTF STPSKTEKVT  120
DSFTYSNSEG GKLGVSTTTT IKAGIPIAQA EETLTLSFEA NYNHTSSNTS STEKTVTYPS  180
QVLKCLPGYR TSLIVKLSQA NFSGTMDFEV EPTASSLIDG IEKNWKDIKD DTKIKGDKSG  240
DYTVPNRQEF LYNVYKYSDL PIPSYVKLDD KKKTASFGKV TTPYTGVAGH LSEANATQVK  300
LESLDKAKKP IIMPLKQYQQ KIQNHESF                                     328

SEQ ID NO: 252           moltype = AA  length = 328
FEATURE                  Location/Qualifiers
REGION                   1..328
                         note = Description of Artificial Sequence: Synthetic
                          polypeptide
source                   1..328
                         mol_type = protein
                         organism = synthetic construct
SEQUENCE: 252
MRVLARHPEL VSSSGVKPIT NQKDLEIYDS QAGGFAQFIR DNNQNLPHIF NDPHMKLMTG  60
VTPFFNWAPQ YTNLSTQNVI NLDNPKVDDY KEDNIEIASY TNNTTSEQTF STPSKTEKVT  120
DSFTYSNSEG GKLGVSTTTT IKAGIPIAQA EETLTLSFEA NYNHTSSNTS STEKTVTYPS  180
QVLKCLPGYR TSLIVKLSQA NFSGTMDFEV EPTASSLIDG IEKNWKDIKD DTKIKGDKSG  240
DYTVPNRQEF LYNVYKYSDL PIPSYVKLDD KKKTASFGKV TTPYTGVAGH LSEANATQVK  300
LESLDKAKKP IIMPLKQYQQ KIQNHESF                                     328

SEQ ID NO: 253           moltype = AA  length = 383
FEATURE                  Location/Qualifiers
source                   1..383
                         mol_type = protein
                         organism = Bacillus sp.
SEQUENCE: 253
MMNQPSSKQI EEECMINMSK KKNRNKGLIV TATACSIAFS GLGSATSAFA EAPKVQYTDY  60
HDINNQNMND QDRNQFNNFK RYFDYGSTIS TIRDIHAVGT PNIVDAGSET LDNTAGYSSQ  120
KLNTPSTTIK TTDTLTTTHA IENAAEFGLT LAVESKENIG IVEETQKFTA SIKDTLKTTD  180
SKTTTHSDEK TYVIPSQSIE VPAGKKYKIE YVYKQTALEG VMDQVKEIRE QRNENGKLYF  240
PDVAVGRDSH EQVTPNVGVG INFSNDKGES VGLTNAVYDP ILNATPYQMF NQLTNMTKQA  300
KKWAIANPIC AIVDGSANIT AIHADALLNN IYLDHSLGKA YMVEESIPFK AATGHEFTLK  360
VYDVTNGDKA LVAEKPVQNA VEK                                          383

SEQ ID NO: 254           moltype = AA  length = 366
FEATURE                  Location/Qualifiers
REGION                   1..366
                         note = Description of Artificial Sequence: Synthetic
                          polypeptide
source                   1..366
                         mol_type = protein
                         organism = synthetic construct
SEQUENCE: 254
MSKKKNRNKG LIVTATACSI AFSGLGSATS AFAEAPKVQY TDYHDINNQN MNDQDRNQFN  60
NFKRYFDYGS TISTIRDIHA VGTPNIVDAG SETLDNTAGY SSQKLNTPST TIKTTDTLTT  120
THAIENAAEF GLTLAVESKE NIGIVEETQK FTASIKDTLK TTDSKTTTHS DEKTYVIPSQ  180
SIEVPAGKKY KIEYVYKQTA LEGVMDQVKE IREQRNENGK LYFPDVAVGR DSHEQVTPNV  240
GVGINFSNDK GESVGLTNAV YDPILNATPY QMFNQLTNMT KQAKKWAIAN PICAIVDGSA  300
NITAIHADAL LNNIYLDHSL GKAYMVEESI PFKAATGHEF TLKVYDVTNG DKALVAEKPV  360
QNAVEK                                                             366

SEQ ID NO: 255           moltype = AA  length = 334
FEATURE                  Location/Qualifiers
REGION                   1..334
                         note = Description of Artificial Sequence: Synthetic
                          polypeptide
source                   1..334
```

```
                         mol_type = protein
                         organism = synthetic construct
SEQUENCE: 255
MEAPKVQYTD YHDINNQNMN DQDRNQFNNF KRYFDYGSTI STIRDIHAVG TPNIVDAGSE  60
TLDNTAGYSS QKLNTPSTTI KTTDTLTTTH AIENAAEFGL TLAVESKENI GIVEETQKFT  120
ASIKDTLKTT DSKTTTHSDE KTYVIPSQSI EVPAGKKYKI EYVYKQTALE GVMDQVKEIR  180
EQRNENGKLY FPDVAVGRDS HEQVTPNVGV GINFSNDKGE SVGLTNAVYD PILNATPYQM  240
FNQLTNMTKQ AKKWAIANPI CAIVDGSANI TAIHADALLN NIYLDHSLGK AYMVEESIPF  300
KAATGHEFTL KVYDVTNGDK ALVAEKPVQN AVEK                              334

SEQ ID NO: 256           moltype = AA  length = 305
FEATURE                  Location/Qualifiers
source                   1..305
                         mol_type = protein
                         organism = Bacillus sp.
SEQUENCE: 256
MKRIKKIIPA AFVLSSALLV APGFSSAATD TTTNVGNLPV VISSQEAKAP MSAEQVEQSG  60
LPIPQAPTGP YQEFPYEAYS STQYGDLIDY VYVDIYAKKA QTMSTKQLKD IPFLVILPDG  120
TRVNTVKDDY NVNFTPGKLA YTIGLSKETF KEVLSDTKLK KDIYWKLIDS NIVDKNSGYH  180
WSKSVTSGLS KSNTLGFSLT VGFEAGFGDS VSFSTELTTS FESNTTITDE TSTTKTFDFN  240
PKPDYAYDQY RTALYQQVAK YSVKPGPVLE KWINDGNAFF VNDYELKLRK TYDYPVDVLL  300
ALTSK                                                              305

SEQ ID NO: 257           moltype = AA  length = 279
FEATURE                  Location/Qualifiers
REGION                   1..279
                         note = Description of Artificial Sequence: Synthetic
                          polypeptide
source                   1..279
                         mol_type = protein
                         organism = synthetic construct
SEQUENCE: 257
MATDTTTNVG NLPVVISSQE AKAPMSAEQV EQSGLPIPQA PTGPYQEFPY EAYSSTQYGD  60
LIDYVYVDIY AKKAQTMSTK QLKDIPFLVI LPDGTRVNTV KDDYNVNFTP GKLAYTIGLS  120
KETFKEVLSD TKLKKDIYWK LIDSNIVDKN SGYHWSKSVT SGLSKSNTLG FSLTVGFEAG  180
FGDSVSFSTE LTTSFESNTT ITDETSTTKT FDFNPKPDYA YDQYRTALYQ QVAKYSVKPG  240
PVLEKWINDG NAFFVNDYEL KLRKTYDYPV DVLLALTSK                         279

SEQ ID NO: 258           moltype = AA  length = 497
FEATURE                  Location/Qualifiers
source                   1..497
                         mol_type = protein
                         organism = Mucilaginibacter sp.
SEQUENCE: 258
MKKNLNLKLL ITCSAIAITS TFTSCKKNDF SLNQSTKPKK LTTQSAGDPL YDLLGFGYDV  60
TGEYASSNST TYQVVDIAKI AQAESNRVVT DLNVTQYSES HSGSTAEDYS QNLSYSTGAS  120
LTVGAFSGTV SEKFHEFSSL SSKYSYADAS LIIRQKRLRF DAPLSLIKST YLTPVFKSDV  180
NSMTPQQLVT KYGTHVLTDI ILGAKLSLYY RSQTTIKDRA LSVKAGAEAK GLFGIFGAST  240
NISYQDSLIN SNFDQTIYYE TVGGDGTKGL FGEIVLDNSA PKISIANWQS SCTRENAAFI  300
QLGNSATNII LLSDLIDDPA KSTAVKNYID QYLANKHVHL SNTLATVKSN AFYNVYLRLN  360
GTNYVSSTSG SGTVNCQFTA APFEKMLFAK QSDGTYTIES NAFAGLFLRM DGSGVPTGPQ  420
GGGIVNLQNS VGPYEKFNVI KQSDGTYVIQ SVAFPGTYLR MDGTGVTSVL ANGGGKINCT  480
KQAPGPWEKF VIKPDLY                                                 497

SEQ ID NO: 259           moltype = AA  length = 379
FEATURE                  Location/Qualifiers
source                   1..379
                         mol_type = protein
                         organism = Bacillus sp.
SEQUENCE: 259
LIILKFKLVG EREMKKYKKA LLIAPLACVL STNFFTLPNG AQAEEVKQQA YYDPFNQGTV  60
ATQENIAQTL FIRLLRGIEN SPELRNKFKM ADGEDFQREQ GETWYNGTKY PAIDYGFKSQ  120
LAKAEVVLSG TSFTVNPTAI TLEDDGLVNV VSYANNSPEK QQIVTPEVTK KYLRTFSTTN  180
QFGMKLGFEA QTKIQVGLPV VGGEFSLKAT SEYSMGMTIG QTTTQEDTTT FKSQTVNAAP  240
NGTTDYFYRV KKAKFSGTYN ADAYLKGLTV TIPIQKQQGN TTVVTHTETV ALTAEDLYTI  300
YKSTSNYPLP PYMKLNDQAK KVLVNTEFSY EGEGGFYTQA SVTFTPNTKT YSDTMPGSFN  360
PSKTMTYEEY EKSIQNKSL                                               379

SEQ ID NO: 260           moltype = AA  length = 366
FEATURE                  Location/Qualifiers
REGION                   1..366
                         note = Description of Artificial Sequence: Synthetic
                          polypeptide
source                   1..366
                         mol_type = protein
                         organism = synthetic construct
SEQUENCE: 260
MKKYKKALLI APLACVLSTN FFTLPNGAQA EEVKQQAYYD PFNQGTVATQ ENIAQTLFIR  60
LLRGIENSPE LRNKFKMADG EDFQREQGET WYNGTKYPAI DYGFKSQLAK AEVVLSGTSF  120
```

```
TVNPTAITLE DDGLVNVVSY ANNSPEKQQI VTPEVTKKYL RTFSTTNQFG MKLGFEAQTK  180
IQVGLPVVGG EFSLKATSEY SMGMTIGQTT TQEDTTTFKS QTVNAAPNGT TDYFYRVKKA  240
KFSGTYNADA YLKGLTVTIP IQKQQGNTTV VTHTETVALT AEDLYTIYKS TSNYPLPPYM  300
KLNDQAKKVL VNTEFSYEGE GGFYTQASVT FTPNTKTYSD TMPGSFNPSK TMTYEEYEKS  360
IQNKSL                                                            366

SEQ ID NO: 261         moltype = AA  length = 337
FEATURE                Location/Qualifiers
REGION                 1..337
                       note = Description of Artificial Sequence: Synthetic
                        polypeptide
source                 1..337
                       mol_type = protein
                       organism = synthetic construct
SEQUENCE: 261
MEEVKQQAYY DPFNQGTVAT QENIAQTLFI RLLRGIENSP ELRNKFKMAD GEDFQREQGE  60
TWYNGTKYPA IDYGFKSQLA KAEVVLSGTS FTVNPTAITL EDDGLVNVVS YANNSPEKQQ  120
IVTPEVTKKY LRTFSTTNQF GMKLGFEAQT KIQVGLPVVG GEFSLKATSE YSMGMTIGQT  180
TTQEDTTTFK SQTVNAAPNG TTDYFYRVKK AKFSGTYNAD AYLKGLTVTI PIQKQQGNTT  240
VVTHTETVAL TAEDLYTIYK STSNYPLPPY MKLNDQAKKV LVNTEFSYEG EGGFYTQASV  300
TFTPNTKTYS DTMPGSFNPS KTMTYEEYEK SIQNKSL                          337

SEQ ID NO: 262         moltype = AA  length = 279
FEATURE                Location/Qualifiers
source                 1..279
                       mol_type = protein
                       organism = Chryseobacterium sp.
SEQUENCE: 262
MNSLQQITDA WGKWYSQQHG TTCRFTASTD YSSQSFLDDY HQYQVSTTAQ NIVYDDNSLP  60
TNGSEIAFKT IYNNNTQAAN QQSLIETATS TQSFEWSITE AVSIGVEISA TEGVPAVASS  120
TQKVTVNLSL SSTQKSTVTN SQSWSVNTIL TIPPQSTIKA DIVIGTQSYN INFTLSVMLN  180
GYVAIWNNDK VNGHWLWFIP ITQVFSDCIA NNIIDTSGYD FVGGGISTTA SGVFTGSQGI  240
SVGVNTTQYP LNSNTDAAKE PGFIDTPAVS KIVAMAGKE                        279

SEQ ID NO: 263         moltype = AA  length = 967
FEATURE                Location/Qualifiers
source                 1..967
                       mol_type = protein
                       organism = Bacillus sp.
SEQUENCE: 263
VMNMISNTMV PYNVLRNLDM PTISGTRWDK EMFKNAFDNT SSLLTLIEKG INDGNDVLGL  60
LSFIGLTALE AIPIVGGALS SLVSIIFFPK KQSINFKKIW EELEKAIEQI VDRKIEEALM  120
SQLMQEISGF ANVLEEYRDA YDLYNDNKVF EIPDNLTPGD YLVNVFITAN LLFIQRITQF  180
QNPKYDVVFL PFFVHIAEMH ILLVRDAAIH GLEWGMDEAI HQKFKKDLKE LIANYTSYLL  240
NTYKKGLKEA SERELNNQDF PTTNNKENYI NTVRWNVINQ YKRGMALTVF DFAYKWKYYQ  300
EVYQYNIALN PFRTIYSDIA GSVYPYEKTT IEIDNIVKDQ NLKYRGIFKK LQVNHAERID  360
SLQSTYIRNN EIIDSEKTGG TGRRETILDL ESPVKNPLIQ VNMWSELVPF SLGFKFYDEK  420
ERTIGSGSWG WSSPHKFGAY RYVGNKVSSI MGFGKNATGG FNSLDAMVVG FKRDDYTPEN  480
RFVGVGKNEE PITKVIDVGN FYKDQFESNI TMINEPMFGD GVLQFKNYPI NLISDSYVTY  540
QIHAEITGTY ELHAVIGAKK QKNKIAFKMA INEKQPENFI TDPLDDGDIW DGMSLSEGLV  600
YKRIFLGNVQ LKNGMNRITI HNGALQESAN INTWNLASLE LKINSDSLID PDITTLYDKD  660
DYTGAKKFIF ENTSRLADFN DKTSSVKVGS NVSGMRLYEH YGYSGNFIDL AGGEKIILKN  720
YGFNNRASSV KFASIALYNQ DNYEGSKKLI FEDVPELTDF NDKTSSIVVS ANVIGARLYE  780
HADYKGRYLD VISGQKLNLK NHILDKKISS IKFLKVNEVL NGVYQIVTAI NDTSVIDKHL  840
QEPIVHLWEN VKNENQKWRI EYNGTKKAYQ IKNLLDENLV LTNFSYLPGM IGSLYCVSNE  900
GKDSQYWIFE SVGNSYYIIK NKANPSLVLD VDGANPTNGT IIKLQQQHEI NSPDINAQKF  960
KLMGVKN                                                           967

SEQ ID NO: 264         moltype = AA  length = 964
FEATURE                Location/Qualifiers
REGION                 1..964
                       note = Description of Artificial Sequence: Synthetic
                        polypeptide
source                 1..964
                       mol_type = protein
                       organism = synthetic construct
SEQUENCE: 264
MISNTMVPYN VLRNLDMPTI SGTRWDKEMF KNAFDNTSSL LTLIEKGIND GNDVLGLLSF  60
IGLTALEAIP IVGGALSSLV SIIFFPKKQS INFKKIWEEL EKAIEQIVDR KIEEALMSQL  120
MQEISGFANV LEEYRDAYDL YNDNKVFEIP DNLTPGDYLV NVFITANLLF IQRITQFQNP  180
KYDVVFLPFF VHIAEMHILL VRDAAIHGLE WGMDEAIHQK FKKDLKELIA NYTSYLLNTY  240
KKGLKEASER ELNNQDFPTT NNKENYINTV RWNVINQYKR GMALTVFDFA YKWKYYQEVY  300
QYNIALNPFR TIYSDIAGSV YPYEKTTIEI DNIVKDQNLK YRGIFKKLQV NHAERIDSLQ  360
STYIRNNEII DSEKTGGTGR RETILDLESP VKNPLIQVNM WSELVPFSLG FKFYDEKERT  420
IGSGSWGWSS PHKFGAYRYV GNKVSSIMGF GKNATGGFNS LDAMVVGFKR DDYTPENRFV  480
GVGKNEEPIT KVIDVGNFYK DQFESNITMI NEPMFGDGVL QFKNYPINLI SDSYVTYQIH  540
AEITGTYELH AVIGAKKQKN KIAFKMAINE KQPENFITDP LDDGDIWDGM SLSEGLVYKR  600
IFLGNVQLKN GMNRITIHNG ALQESANINT WNLASLELKI NSDSLIDPDI TTLYDKDDYT  660
GAKKFIFENT SRLADFNDKT SSVKVGSNVS GMRLYEHYGY SGNFIDLAGG EKIILKNYGF  720
```

```
NNRASSVKFA SIALYNQDNY EGSKKLIFED VPELTDFNDK TSSIVVSANV IGARLYEHAD  780
YKGRYLDVIS GQKLNLKNHI LDKKISSIKF LKVNEVLNGV YQIVTAINDT SVIDKHLQEP  840
IVHLWENVKN ENQKWRIEYN GTKKAYQIKN LLDENLVLTN FSYLPGMIGS LYCVSNEGKD  900
SQYWIFESVG NSYYIIKNKA NPSLVLDVDG ANPTNGTIIK LQQQHEINSP DINAQKFKLM  960
GVKN                                                              964

SEQ ID NO: 265          moltype = AA  length = 603
FEATURE                 Location/Qualifiers
source                  1..603
                        mol_type = protein
                        organism = Bacillus sp.
SEQUENCE: 265
LRMKYKDRKD AKRKYKQALL ATVATMTLGV STLGSTASAF AAENTANVQQ APTASATDEP  60
VFKRESNGAI TVLKDKLFNI ETLEAIGSLG GATLKQAWAD SKVEGGNFNN TFRTLTMGSA  120
ALIPYGGVVI SPLIGLLWPE DTTDAKNRLE NLMKAIAAQT HAQIEGYDLE TLGQKLNKLY  180
KDLKEFEEIM NPNGRNMAKA PSVGDEAAVI RSKAEFIHDD FKALISESQK PSYKTAEFPI  240
FMIAATAHLN FLHYMELHGK DPKINYNDAG LQLQFLDPQK QVRKDYLNYA TEFAKPALDT  300
AANGRKEAME IRGKFSGILY DQAIKAYIGG ASATVETTLN NSINNIAFKQ ALGIQSEWTL  360
NQNGRTFYYN PQDGKMQTGW KEISTTFASR IQLNDRDTQE MFTKNWLKSL GLTYSWYYFS  420
PEKTDKFEKG EVYRDTTQTI NGKTYTFDSD GKCLNPDGGA VNVPILNGTY KIVSKLDNNM  480
VLNTRNHQAV LVGTNDATWG NSWTFQYDKE KQAYLITNGQ SGGPWKLAAS GITNVFATDD  540
RANKQEHYWT LEPAGDGYFF IQNKSQPGKV LDLTGNSKAA GTKIDLFNKS GQDNQKFKLE  600
KIN                                                               603

SEQ ID NO: 266          moltype = AA  length = 601
FEATURE                 Location/Qualifiers
REGION                  1..601
                        note = Description of Artificial Sequence: Synthetic
                         polypeptide
source                  1..601
                        mol_type = protein
                        organism = synthetic construct
SEQUENCE: 266
MKYKDRKDAK RKYKQALLAT VATMTLGVST LGSTASAFAA ENTANVQQAP TASATDEPVF  60
KRESNGAITV LKDKLFNIET LEAIGSLGGA TLKQAWADSK VEGGNFNNTF RTLTMGSAAL  120
IPYGGVVISP LIGLLWPEDT TDAKNRLENL MKAIAAQTHA QIEGYDLETL GQKLNKLYKD  180
LKEFEEIMNP NGRNMAKAPS VGDEAAVIRS KAEFIHDDFK ALISESQKPS YKTAEFPIFM  240
IAATAHLNFL HYMELHGKDP KINYNDAGLQ LQFLDPQKQV RKDYLNYATE FAKPALDTAA  300
NGRKEAMEIR GKFSGILYDQ AIKAYIGGAS ATVETTLNNS INNIAFKQAL GIQSEWTLNQ  360
NGRTFYYNPQ DGKMQTGWKE ISTTFASRIQ LNDRDTQEMF TKNWLKSLGL TYSWYYFSPE  420
KTDKFEKGEV YRDTTQTING KTYTFDSDGK CLNPDGGAVN VPILNGTYKI VSKLDNNMVL  480
NTRNHQAVLV GTNDATWGNS WTFQYDKEKQ AYLITNGQSG GPWKLAASGI TNVFATDDRA  540
NKQEHYWTLE PAGDGYFFIQ NKSQPGKVLD LTGNSKAAGT KIDLFNKSGQ DNQKFKLEKI  600
N                                                                 601

SEQ ID NO: 267          moltype = AA  length = 563
FEATURE                 Location/Qualifiers
REGION                  1..563
                        note = Description of Artificial Sequence: Synthetic
                         polypeptide
source                  1..563
                        mol_type = protein
                        organism = synthetic construct
SEQUENCE: 267
MAENTANVQQ APTASATDEP VFKRESNGAI TVLKDKLFNI ETLEAIGSLG GATLKQAWAD  60
SKVEGGNFNN TFRTLTMGSA ALIPYGGVVI SPLIGLLWPE DTTDAKNRLE NLMKAIAAQT  120
HAQIEGYDLE TLGQKLNKLY KDLKEFEEIM NPNGRNMAKA PSVGDEAAVI RSKAEFIHDD  180
FKALISESQK PSYKTAEFPI FMIAATAHLN FLHYMELHGK DPKINYNDAG LQLQFLDPQK  240
QVRKDYLNYA TEFAKPALDT AANGRKEAME IRGKFSGILY DQAIKAYIGG ASATVETTLN  300
NSINNIAFKQ ALGIQSEWTL NQNGRTFYYN PQDGKMQTGW KEISTTFASR IQLNDRDTQE  360
MFTKNWLKSL GLTYSWYYFS PEKTDKFEKG EVYRDTTQTI NGKTYTFDSD GKCLNPDGGA  420
VNVPILNGTY KIVSKLDNNM VLNTRNHQAV LVGTNDATWG NSWTFQYDKE KQAYLITNGQ  480
SGGPWKLAAS GITNVFATDD RANKQEHYWT LEPAGDGYFF IQNKSQPGKV LDLTGNSKAA  540
GTKIDLFNKS GQDNQKFKLE KIN                                         563

SEQ ID NO: 268          moltype = AA  length = 297
FEATURE                 Location/Qualifiers
source                  1..297
                        mol_type = protein
                        organism = Bacillus sp.
SEQUENCE: 268
MAIFDLDAYL VALAKKVYYM FAPNINRVIT STLTVKNAES YGFEIKDNKP QGTMFMGESE  60
LKNDTNETQT IHSDSFTKTI TDSITLAVTN GITTGVNISI GGKVFGMGVE TSMSFEVSTS  120
TTREQTSTES VAYTVPSQTV SVPAKKTYYV YTALQRNQLE GSIRLRADLS GPFSAIIQVG  180
DGWVPIELDD IYEFVKQYQS LHPLPSGISL NHNDKAIHFE GVAEYFYGTG TKFYVTITDT  240
PSSQGTQEHK PIDAKTGLGT YEIQLDGKKL GFDINDLKDK MDPKDFEKLK ALQNEIV     297

SEQ ID NO: 269          moltype = AA  length = 996
FEATURE                 Location/Qualifiers
```

```
REGION                1..996
                      note = Description of Unknown: Organism from environmental
                       sample
source                1..996
                      mol_type = protein
                      organism = unidentified
SEQUENCE: 269
LADNNLQYTP PLRLDAEEYV PWKDVDSDVI IDAVAGAEGA LINLLIPGSG KIVEWGVSKF  60
LKWATGDTYK PPSLSQEITR VEGMIATLQQ QMYNVISATK AEILQNVASL FFSNVVSAVN  120
DYHHYLERWL DNSDDSNRLA ELKSSLDTAI TEANAAVSAS YYSQNVQYTF AYNVNAATFS  180
LIMMRDKYLN YTQWGYGDSA GAQNFYEGTF LYRLKNYTTN ILTQYNTILK LAHDLAVDPY  240
SELYREVTNR NPLQVTTNPL YNGKSDQRSM YWPSAYYGGS DTMRKRCISP MASNPYKHFS  300
DSRIENQWND DQHRSCQTPL PNGGLEMQIN MPDQLRLSFQ WNAYNRTRNV LTQTGLDFIA  360
IWPYFDPIQY QPGEVTADLT RMLYSDLAGA ITKNDIKSVD DIDNHVKKQP DLFEFLKSSK  420
LYTKNVKIQT QQGPPFAYNP STVKTHVDGD IIVGIENTTE RTLETNTRNP GGIQGSSSDN  480
ADTIDPTEAS KSVYISQWLF PRIFNFNEKI IGSVNETTPG NVTGIYNNLT YDFTLPEHQI  540
SWLSYVQAQE NVLTPSDYNY LTGNLTAANQ GQIGALAIGW TKANIDANNT VKKGTITSIP  600
AVKSHSITDF PIPGIVVKGP GHTGGDLVKL PPNSRAKMVV TIEDTSTSYD VRIRYAAPND  660
GQIQFSYWNG GSDVKVADTK LQNTGGNTNF EHFQYAMLTT DNAKFKAPFS PVEILIENIG  720
NSDIYLDKVE FIPAMPTSSF NNQSFSVGSN TTHLRNYTVW ELLSTPFIEP VVINITGTLV  780
NSASLSFQFL DIHNNVLLTK TVSGDGPSCH VIHNEMPAHG NSCSDKSSEF IIYETISQDL  840
YKIQLFEESN ATTNTDSGPL DNKYENVQGL INPSTPNTVV IPAHTVTYEM ANDDRYYIVW  900
EKNRPLALSI QNLTVISNSS TPIHLYIKRN DNAVATGVKA TRVETNNDTQ QYTFIFENMS  960
PDGGFDFVSL DFSGNFDISR YPLQVSGTLL LAPNNS                           996

SEQ ID NO: 270        moltype = AA  length = 735
FEATURE               Location/Qualifiers
REGION                1..735
                      note = Description of Artificial Sequence: Synthetic
                       polypeptide
source                1..735
                      mol_type = protein
                      organism = synthetic construct
SEQUENCE: 270
MADNNLQYTP PLRLDAEEYV PWKDVDSDVI IDAVAGAEGA LINLLIPGSG KIVEWGVSKF  60
LKWATGDTYK PPSLSQEITR VEGMIATLQQ QMYNVISATK AEILQNVASL FFSNVVSAVN  120
DYHHYLERWL DNSDDSNRLA ELKSSLDTAI TEANAAVSAS YYSQNVQYTF AYNVNAATFS  180
LIMMRDKYLN YTQWGYGDSA GAQNFYEGTF LYRLKNYTTN ILTQYNTILK LAHDLAVDPY  240
SELYREVTNR NPLQVTTNPL YNGKSDQRSM YWPSAYYGGS DTMRKRCISP MASNPYKHFS  300
DSRIENQWND DQHRSCQTPL PNGGLEMQIN MPDQLRLSFQ WNAYNRTRNV LTQTGLDFIA  360
IWPYFDPIQY QPGEVTADLT RMLYSDLAGA ITKNDIKSVD DIDNHVKKQP DLFEFLKSSK  420
LYTKNVKIQT QQGPPFAYNP STVKTHVDGD IIVGIENTTE RTLETNTRNP GGIQGSSSDN  480
ADTIDPTEAS KSVYISQWLF PRIFNFNEKI IGSVNETTPG NVTGIYNNLT YDFTLPEHQI  540
SWLSYVQAQE NVLTPSDYNY LTGNLTAANQ GQIGALAIGW TKANIDANNT VKKGTITSIP  600
AVKSHSITDF PIPGIVVKGP GHTGGDLVKL PPNSRAKMVV TIEDTSTSYD VRIRYAAPND  660
GQIQFSYWNG GSDVKVADTK LQNTGGNTNF EHFQYAMLTT DNAKFKAPFS PVEILIENIG  720
NSDIYLDKVE FIPAM                                                  735

SEQ ID NO: 271        moltype = AA  length = 495
FEATURE               Location/Qualifiers
REGION                1..495
                      note = Description of Unknown: Organism from environmental
                       sample
source                1..495
                      mol_type = protein
                      organism = unidentified
SEQUENCE: 271
MKISRVVNPI FTKQEQLDQI TNIVNNLFSS SSSSLSQGVS DYWIDQVLLK VNALSDRIFP  60
APKEQLYQRL AQAKQISKAR NLLVGGNFET LERWKLSQNA VLVSDHELFQ GYHLELPPAI  120
DSVKHPSYAY QIIAENKLKA NTRYYVSGFI AQGYQLEIMV SRYGQEHSQI VYVPAEMAKP  180
ISADTEPNCC TPHPCSCAAC NEEDIDSHFF QIPIDVKNLY HAQSPGIEIG FKVTSTEGFA  240
KLSNIEVFEG RPLTAAEQRK VLRLENDWKE EQQTKQTEHA QFIQQIQQRF NMLYTTPEHH  300
TLRTETSYQQ LLETTIPPFH NIYHWFMPDV PDSDYAFYYD LQQKLERGWD QYFSRNLLEN  360
GDFLEPLDDS WYKQGTVSLQ TINQNTMLRL QHWDSLIRTN VSLPVVNEDA EYVIRVIGKG  420
TGSVLIQNVN TTNKLVFTNS RQMETKEFYL EPEGAQISLT IRSDTNEFLV NTVEIILIND  480
GSEKDQGPGM FPTMN                                                  495

SEQ ID NO: 272        moltype = AA  length = 216
FEATURE               Location/Qualifiers
source                1..216
                      mol_type = protein
                      organism = Bacillus sp.
SEQUENCE: 272
MYNKRIINLE IPSYNAINFL EIYRLPRVHL NQALNITQHL QKSLSLQTLN LELDQLNDLI  60
SEIPGGSILN TINQTVEYSE INTTSAINNI VDIVKNNCEM FKDDFLLQSK LESVISNVFL  120
NLANQEKNSY VFYHEKLSYK TSYSYHVIFV IDNMESSLSV FPISFNVDVD SGYENLNKNS  180
INDPQSYKIK ISGINFMISK NNELAEIMER VTESTF                           216

SEQ ID NO: 273        moltype = AA  length = 410
```

```
FEATURE                 Location/Qualifiers
source                  1..410
                        mol_type = protein
                        organism = Bacillus sp.
SEQUENCE: 273
LDNRDAKRPK SSRGLEKHTY CGGKSLPTIY KDLNSGNINN TFRTLSMVSA SLIPYAGAFI  60
SPVIGLLWPE NGPNIGQMLK EMEQRLGILM DEKIQDADLA AINAEITGMM KNLKEFENSL  120
NGNVYYESQG DVASLNRDRI VSIQNHFNTL IELARKVHPD DSSKNFKIAE LPLFTVIATA  180
HLNFLHVVEK NGTSPKINFN AEALKDFLQS MNKNQENYKN HIEKTYKEAE TKINNKIDAA  240
RNKAAAPTDR QSVGNTIEAV QKEITSLIAE GPKNHTTRAE NEFEIKLNKL TNKRDSLKDY  300
LTKYDDLMKQ KDDYYEKTWN NTAFKLAAGL IKIDEITKTD NGWYQEDGRY YFLKNYVKQT  360
GWIQDSGKWY YLNKKEEDGL KEGQMAADMK LTNNNKEYSF DADGLCQNPK            410

SEQ ID NO: 274          moltype = AA  length = 410
FEATURE                 Location/Qualifiers
REGION                  1..410
                        note = Description of Artificial Sequence: Synthetic
                         polypeptide
source                  1..410
                        mol_type = protein
                        organism = synthetic construct
SEQUENCE: 274
MDNRDAKRPK SSRGLEKHTY CGGKSLPTIY KDLNSGNINN TFRTLSMVSA SLIPYAGAFI  60
SPVIGLLWPE NGPNIGQMLK EMEQRLGILM DEKIQDADLA AINAEITGMM KNLKEFENSL  120
NGNVYYESQG DVASLNRDRI VSIQNHFNTL IELARKVHPD DSSKNFKIAE LPLFTVIATA  180
HLNFLHVVEK NGTSPKINFN AEALKDFLQS MNKNQENYKN HIEKTYKEAE TKINNKIDAA  240
RNKAAAPTDR QSVGNTIEAV QKEITSLIAE GPKNHTTRAE NEFEIKLNKL TNKRDSLKDY  300
LTKYDDLMKQ KDDYYEKTWN NTAFKLAAGL IKIDEITKTD NGWYQEDGRY YFLKNYVKQT  360
GWIQDSGKWY YLNKKEEDGL KEGQMAADMK LTNNNKEYSF DADGLCQNPK            410

SEQ ID NO: 275          moltype = AA  length = 827
FEATURE                 Location/Qualifiers
source                  1..827
                        mol_type = protein
                        organism = Bacillus sp.
SEQUENCE: 275
LCRKHSKNKN NGALFMRTED FMIKKQKKIL SMTFATGVFA GTYIPTAYTA FAEIEQKENQ  60
PKNINQNNLQ IEPYGWFENP YKGVTFSQFI DAFNNNQWQP LLVNIKNKGD AGSGTISFLK  120
GMMTTGLSLL PPPASLLGSI WSVFIPTTDA NGTDMWRQLE TYIDEKIDSK INDYHKYLMG  180
AEFNGAMSAI KEYQRVLQIY NDNKNVLKRV EDPGTPVIEA VRAADRKLKE FIAVIQTPEK  240
STDSVYQQIT APIFVQAANA HLLLQRDIIL YGEEWGMDKN QWQGYKDNQK KLIQEYTNYA  300
MKVYNDGLEK RKKEAEEINT QQPNRNTDRW NHINDYVREY TLSVLDFVDL FPATNPETYS  360
KGVMQENSRQ IYSSIKGAVI PQDGTGEGTT WENIQKILDS QEYKGDLHKV DIRSYDRIDA  420
IQPWYSDKQN GGSNWTTPGW TGNISGGNLN PLINPADNPI TRVKAQSSRT PNYIDFKFDT  480
GTNNPYFGRY VSGHVSYKED IFEYPNQKLS QVHAFNRSTY PGFQGIDAVV FGFVDKNLTQ  540
SSTYLMTNMI TTIPAEKYNR GKSKFEPQVE SIHAKQKAMK ADTTNSYLAY GVEISKEQEY  600
KIRYKVAANE NSKISLSHRK PGGNYAKIAD TTIPITGNAA DSVKGEYGSY KIVEGPTIKL  660
TKGAHDLKVE NIQGKFSLDQ IELEPVEQDQ VIAQDNFDNI RLSWSNMDGI VNGGNSGKAG  720
MISKNGNTWT YIQDQITPFT KYTLNIKVKL DSNDGNERQK VAIFTDNAKH ERITKTVELK  780
GKSGYQEIKL EFITKRDLAN THVGILTSNG TSNVLFDDVQ VIGAKKS                827

SEQ ID NO: 276          moltype = AA  length = 806
FEATURE                 Location/Qualifiers
REGION                  1..806
                        note = Description of Artificial Sequence: Synthetic
                         polypeptide
source                  1..806
                        mol_type = protein
                        organism = synthetic construct
SEQUENCE: 276
MIKKQKKILS MTFATGVFAG TYIPTAYTAF AEIEQKENQP KNINQNNLQI EPYGWFENPY  60
KGVTFSQFID AFNNNQWQPL LVNIKNKGDA GSGTISFLKG MMTTGLSLLP PPASLLGSIW  120
SVFIPTTDAN GTDMWRQLET YIDEKIDSKI NDYHKYLMGA EFNGAMSAIK EYQRVLQIYN  180
DNKNVLKRVE DPGTPVIEAV RAADRKLKEF IAVIQTPEKS TDSVYQQITA PIFVQAANAH  240
LLLQRDIILY GEEWGMDKNQ WQGYKDNQKK LIQEYTNYAM KVYNDGLEKR KKEAEEINTQ  300
QPNRNTDRWN HINDYVREYT LSVLDFVDLF PATNPETYSK GVMQENSRQI YSSIKGAVIP  360
QDGTGEGTTW ENIQKILDSQ EYKGDLHKVD IRSYDRIDAI QPWYSDKQNG GSNWTTPGWT  420
GNISGGNLNP LINPADNPIT RVKAQSSRTP NYIDFKFDTG TNNPYFGRYV SGHVSYKEDI  480
FEYPNQKLSQ VHAFNRSTYP GFQGIDAVVF GFVDKNLTQS STYLMTNMIT TIPAEKYNRG  540
KSKFEPQVES IHAKQKAMKA DTTNSYLAYG VEISKEQEYK IRYKVAANEN SKISLSHRKP  600
GGNYAKIADT TIPITGNAAD SVKGEYGSYK IVEGPTIKLT KGAHDLKVEN IQGKFSLDQI  660
ELEPVEQDQV IAQDNFDNIR LSWSNMDGIV NGGNSGKAGM ISKNGNTWTY IQDQITPFTK  720
YTLNIKVKLD SNDGNERQKV AIFTDNAKHE RITKTVELKG KSGYQEIKLE FITKRDLANT  780
HVGILTSNGT SNVLFDDVQV IGAKKS                                       806

SEQ ID NO: 277          moltype = AA  length = 776
FEATURE                 Location/Qualifiers
REGION                  1..776
                        note = Description of Artificial Sequence: Synthetic
```

```
                          polypeptide
source                   1..776
                         mol_type = protein
                         organism = synthetic construct
SEQUENCE: 277
MEIEQKENQP KNINQNNLQI EPYGWFENPY KGVTFSQFID AFNNNQWQPL LVNIKNKGDA  60
GSGTISFLKG MMTTGLSLLP PPASLLGSIW SVFIPTTDAN GTDMWRQLET YIDEKIDSKI  120
NDYHKYLMGA EFNGAMSAIK EYQRVLQIYN DNKNVLKRVE DPGTPVIEAV RAADRKLKEF  180
IAVIQTPEKS TDSVYQQITA PIFVQAANAH LLLQRDIILY GEEWGMDKNQ WQGYKDNQKK  240
LIQEYTNYAM KVYNDGLEKR KKEAEEINTQ QPNRNTDRWN HINDYVREYT LSVLDFVDLF  300
PATNPETYSK GVMQENSRQI YSSIKGAVIP QDGTGEGTTW ENIQKILDSQ EYKGDLHKVD  360
IRSYDRIDAI QPWYSDKQNG GSNWTTPGWT GNISGGNLNP LINPADNPIT RVKAQSSRTP  420
NYIDFKFDTG TNNPYFGRYV SGHVSYKEDI FEYPNQKLSQ VHAFNRSTYP GFQGIDAVVF  480
GFVDKNLTQS STYLMTNMIT TIPAEKYNRG KSKFEPQVES IHAKQKAMKA DTTNSYLAYG  540
VEISKEQEYK IRYKVAANEN SKISLSHRKP GGNYAKIADT TIPITGNAAD SVKGEYGSYK  600
IVEGPTIKLT KGAHDLKVEN IQGKFSLDQI ELEPVEQDQV IAQDNFDNIR LSWSNMDGIV  660
NGGNSGKAGM ISKNGNTWTY IQDQITPFTK YTLNIKVKLD SNDGNERQKV AIFTDNAKHE  720
RITKTVELKG KSGYQEIKLE FITKRDLANT HVGILTSNGT SNVLFDDVQV IGAKKS      776

SEQ ID NO: 278           moltype = AA  length = 665
FEATURE                  Location/Qualifiers
REGION                   1..665
                         note = Description of Artificial Sequence: Synthetic
                          polypeptide
source                   1..665
                         mol_type = protein
                         organism = synthetic construct
SEQUENCE: 278
MIKKQKKILS MTFATGVFAG TYIPTAYTAF AEIEQKENQP KNINQNNLQI EPYGWFENPY  60
KGVTFSQFID AFNNNQWQPL LVNIKNKGDA GSGTISFLKG MMTTGLSLLP PPASLLGSIW  120
SVFIPTTDAN GTDMWRQLET YIDEKIDSKI NDYHKYLMGA EFNGAMSAIK EYQRVLQIYN  180
DNKNVLKRVE DPGTPVIEAV RAADRKLKEF IAVIQTPEKS TDSVYQQITA PIFVQAANAH  240
LLLQRDIILY GEEWGMDKNQ WQGYKDNQKK LIQEYTNYAM KVYNDGLEKR KKEAEEINTQ  300
QPNRNTDRWN HINDYVREYT LSVLDFVDLF PATNPETYSK GVMQENSRQI YSSIKGAVIP  360
QDGTGEGTTW ENIQKILDSQ EYKGDLHKVD IRSYDRIDAI QPWYSDKQNG GSNWTTPGWT  420
GNISGGNLNP LINPADNPIT RVKAQSSRTP NYIDFKFDTG TNNPYFGRYV SGHVSYKEDI  480
FEYPNQKLSQ VHAFNRSTYP GFQGIDAVVF GFVDKNLTQS STYLMTNMIT TIPAEKYNRG  540
KSKFEPQVES IHAKQKAMKA DTTNSYLAYG VEISKEQEYK IRYKVAANEN SKISLSHRKP  600
GGNYAKIADT TIPITGNAAD SVKGEYGSYK IVEGPTIKLT KGAHDLKVEN IQGKFSLDQI  660
ELEPV                                                             665

SEQ ID NO: 279           moltype = AA  length = 635
FEATURE                  Location/Qualifiers
REGION                   1..635
                         note = Description of Artificial Sequence: Synthetic
                          polypeptide
source                   1..635
                         mol_type = protein
                         organism = synthetic construct
SEQUENCE: 279
MEIEQKENQP KNINQNNLQI EPYGWFENPY KGVTFSQFID AFNNNQWQPL LVNIKNKGDA  60
GSGTISFLKG MMTTGLSLLP PPASLLGSIW SVFIPTTDAN GTDMWRQLET YIDEKIDSKI  120
NDYHKYLMGA EFNGAMSAIK EYQRVLQIYN DNKNVLKRVE DPGTPVIEAV RAADRKLKEF  180
IAVIQTPEKS TDSVYQQITA PIFVQAANAH LLLQRDIILY GEEWGMDKNQ WQGYKDNQKK  240
LIQEYTNYAM KVYNDGLEKR KKEAEEINTQ QPNRNTDRWN HINDYVREYT LSVLDFVDLF  300
PATNPETYSK GVMQENSRQI YSSIKGAVIP QDGTGEGTTW ENIQKILDSQ EYKGDLHKVD  360
IRSYDRIDAI QPWYSDKQNG GSNWTTPGWT GNISGGNLNP LINPADNPIT RVKAQSSRTP  420
NYIDFKFDTG TNNPYFGRYV SGHVSYKEDI FEYPNQKLSQ VHAFNRSTYP GFQGIDAVVF  480
GFVDKNLTQS STYLMTNMIT TIPAEKYNRG KSKFEPQVES IHAKQKAMKA DTTNSYLAYG  540
VEISKEQEYK IRYKVAANEN SKISLSHRKP GGNYAKIADT TIPITGNAAD SVKGEYGSYK  600
IVEGPTIKLT KGAHDLKVEN IQGKFSLDQI ELEPV                            635

SEQ ID NO: 280           moltype = AA  length = 242
FEATURE                  Location/Qualifiers
REGION                   1..242
                         note = Description of Unknown: Organism from environmental
                          sample
source                   1..242
                         mol_type = protein
                         organism = unidentified
SEQUENCE: 280
MSLPDNIIPV SGSGRTIVKT DSVLNASTNI PIEKTFSLKE TTSDAVSTTR TQGVDTSIDI  60
ELNLGATIDF LNLGAKTGFS TKTSLSNSKT ISQTKERTWE ENIKITVPPQ TKATLMYTIT  120
TGPFDALIPV DFVISGSVTG YATWASDTFS SMSISQIEGI QPDLIRRRSE TINIVNLFKN  180
LNTPGFTFNG DSEAIFRGEV RVQGELGVQS SLQLTTVSLL GNGAPRVQNF PTTPTYNMVL  240
FA                                                                242

SEQ ID NO: 281           moltype = AA  length = 335
FEATURE                  Location/Qualifiers
```

```
REGION                  1..335
                        note = Description of Unknown: Organism from environmental
                         sample
source                  1..335
                        mol_type = protein
                        organism = unidentified
SEQUENCE: 281
MRKRKKLVQK TLNLAAIASM GTAFAIASPS LASANQLNTS GERGVLAAEN TSNSINKNAV  60
GIIDVQTSLN TIGTAYYNTF IAGTKTGSSP TLTFKNSPDS VETKVNFNIT GIANDLNFDS  120
TVVEYVGENV FENKTDQTQK FSTSKYTKTV TESTATSTTK GFKVGGDGSN LFSIPLILNN  180
GLKINAEFNS STTETKTKTE TKSIEASVQT IEVPPHKKYK VDVVLEQRNF WGDVTFTGEG  240
VNPQTTIKGT ASYWGPNGMG IWEQHTWSKN TALFHRELTN YPLNGIVFDF KNGVYNVKAT  300
GTGRVQGIFG SKLVVNVYDI TNPSKTELVE TRNYY                            335

SEQ ID NO: 282          moltype = AA  length = 302
FEATURE                 Location/Qualifiers
REGION                  1..302
                        note = Description of Artificial Sequence: Synthetic
                         polypeptide
source                  1..302
                        mol_type = protein
                        organism = synthetic construct
SEQUENCE: 282
MNQLNTSGER GVLAAENTSN SINKNAVGII DVQTSLNTIG TAYYNTFIAG TKTGSSPTLT  60
FKNSPDSVET KVNFNITGIA NDLNFDSTVV EYVGENVFEN KTDQTQKFST SKYTKTVTES  120
TATSTTKGFK VGGDGSNLFS IPLILNNGLK INAEFNSSTT ETKTKTETKS IEASVQTIEV  180
PPHKKYKVDV VLEQRNFWGD VTFTGEGVNP QTTIKGTASY WGPNGMGIWE QHTWSKNTAL  240
FHRELTNYPL NGIVFDFKNG VYNVKATGTG RVQGIFGSKL VVNVYDITNP SKTELVETRN  300
YY                                                                302

SEQ ID NO: 283          moltype = AA  length = 482
FEATURE                 Location/Qualifiers
source                  1..482
                        mol_type = protein
                        organism = Bacillus sp.
SEQUENCE: 283
MDYTEECLNG TQDAPFSSIG AGEVFKVEND GVVKVLKDML FDKDSLKAIA SLGGDTLKQA  60
YKDAYHSNDY SGTLRTLVLG AVALIPYGGA FVSQILGAVC PNNVENNQLK YVEHEINRLD  120
KKIEDLSAAL LNSHYEALIK ELRSFENSVN SLGTPDVYYS TGNVYENRRW HARHINQKFK  180
ELIRDCSKEM LQEKELPMYT TVATAHLLFL RFMEKNGRGP KIKFDNASFN EEFKEDIQKA  240
PREYRMHIEY LYDHEARRLR GEMVDIASRD SEIYIPGNTT AFDSLVEHVL QRMKNKYNKL  300
WENFMRDGTA SVLSGQSSIM NKTRKNIDDF EAKLNELHKY YNTTWGNSAF KTIAKIDTWI  360
QENRKWFYYD SDMSLIHNMR NLGGKWYYFS PKKTDKIEEG QLLTGWHSFS PQEMAIAMMF  420
MFNQSTSKDG RNVSEVLEMS KKTANTKFWL YFSSNGELVY NTKKTIDGKE YEFDKFGICL  480
NP                                                                482

SEQ ID NO: 284          moltype = AA  length = 410
FEATURE                 Location/Qualifiers
REGION                  1..410
                        note = Description of Unknown: Organism from environmental
                         sample
source                  1..410
                        mol_type = protein
                        organism = unidentified
SEQUENCE: 284
VYINLVNGEY SVCFYCFVTK QRKSWRLKMM KFNRRNENNA EFNNGKISTF GFDLPEESTK  60
FQTIGSVLST NGRILTATRY REGDKLGQDV GDFCRTVTVD NQVTNEPVGD SMGGQFIFFK  120
KDYGGYIIAN RQYGEVLESV AANASSLITA PYANKRQQEF GKYVYDDGKF RIYGDDGSIT  180
TCGDKWNSWT RITMSGSNAN EARYVFQHGS TFPITIPTKL EPTTLGPIPD LTNLDDTGTP  240
PPPALVGTAL LPCIFVNDRT PSQRIQDSPY YILECYDYWK LMKSGVLQPG ESEGWWEETG  300
IRSEIQGAMT NMINISIGAD KKLRFFNLSD PFRQTIVRDI NILASNSNSD LSYISIPKEH  360
KNPYSTRLRF AKYFVAREFV LKRIDQPNPV HKWEYIEDAS YVMKEYKSSI            410

SEQ ID NO: 285          moltype = AA  length = 381
FEATURE                 Location/Qualifiers
REGION                  1..381
                        note = Description of Artificial Sequence: Synthetic
                         polypeptide
source                  1..381
                        mol_type = protein
                        organism = synthetic construct
SEQUENCE: 285
MKFNRRNENN AEFNNGKIST FGFDLPEEST KFQTIGSVLS TNGRILTATR YREGDKLGQD  60
VGDFCRTVTV DNQVTNEPVG DSMGGQFIFF KKDYGGYIIA NRQYGEVLES VAANASSLIT  120
APYANKRQQE FGKYVYDDGK FRIYGDDGSI TTCGDKWNSW TRITMSGSNA NEARYVFQHG  180
STFPITIPTK LEPTTLGPIP DLTNLDDTGT PPPPALVGTA LLPCIFVNDR TPSQRIQDSP  240
YYILECYDYW KLMKSGVLQP GESEGWWEET GIRSEIQGAM TNMINISIGA DKKLRFFNLS  300
DPFRQTIVRD INILASNSNS DLSYISIPKE HKNPYSTRLR FAKYFVAREF VLKRIDQPNP  360
VHKWEYIEDA SYVMKEYKSS I                                           381
```

```
SEQ ID NO: 286         moltype = AA  length = 406
FEATURE                Location/Qualifiers
source                 1..406
                       mol_type = protein
                       organism = Bacillus sp.
SEQUENCE: 286
MADNLNEDQN ENTVTNEDSL AKDKRNTDLP EESRIFAYYQ PVNTNNKVWD ATELKGDIFR  60
PNCKTNAFPH ALFNFPYHGG LNQQFIWFQL DDGRFAIANK HNGDVITRNE ALYEEVRNAA  120
WGNHHTQLWR KESTSTTNFR LVNGPHAINV CSNATHDQVK FTFVHNDPSN NALLFKRRAI  180
AQNNVVPALP SKQPLPALPI LSNLNDPAPH ETARAITGSS LVPCIMVSDY IPVAQRIKDS  240
PYYILVKKQF WKRLWHDTFL PGEYREFQET TGMSKTQQES MTQTTNISLQ ADFGFAFKAL  300
TLGLGVSISK SIEISRSTTD TVMSQYTDTQ GYKNQNSITI SWAKYALATE FILMRKDGTP  360
SGSWEAVDKK VTRSISYPPT KTLSWAKSLG DQEDNTVFEP TTIKSE                406

SEQ ID NO: 287         moltype = AA  length = 584
FEATURE                Location/Qualifiers
source                 1..584
                       mol_type = protein
                       organism = Bacillus sp.
SEQUENCE: 287
MKYKDRKNAK RKYKQALLAT VATMTLGVST LGSTASVFAA EETEKTTVQA GGVLQPAEPL  60
PQQQPQMSQT PADSFDIINN ALTGLQKNAE SLNKLYKENK DTKKAQAEWD AFRAANKHTP  120
YSEIVAEKGK RPVSKSYFLP DTPAEGAQKA LSVTSSLVSV LAKYNKPGAT GFSPDATRDI  180
VISLVNAVPY LSVAGPFLAY LWPSQGNDDV LMGKIKDLIK GDIQKSTVEQ LELRYETTLR  240
KVALATATQL HPESSTSRIT EDAISAKNAL EDLVTYTESK NNNDLAIATL PLYITATGAD  300
LAFKESIMKK NLTGFINSAG RTVPLDLSAK DVHFSKEQFD KDVTQYRKHV KDIYELKLKK  360
FEDELTELSK SNDAKFVTQE TITLDNLRAM YFKANQVAEE TQKQMNGGLP QDASGKVIVS  420
QHYAAERVKE KLKSIDEAYK SYKKLTIESD SATVFNKYVF DSTENIDFPT SYWGKNSNGN  480
WVHYNSKKST DTGWFIDTDY NYYYLSPEDG TKNEAGKTFD KGEMMTGWIK LNGEEYYLDD  540
NKENNKDFKG TMGRMLHNET ARIKSLQSDK YYEQHFKPSG AVWH                  584

SEQ ID NO: 288         moltype = AA  length = 546
FEATURE                Location/Qualifiers
REGION                 1..546
                       note = Description of Artificial Sequence: Synthetic
                        polypeptide
source                 1..546
                       mol_type = protein
                       organism = synthetic construct
SEQUENCE: 288
MAEETEKTTV QAGGVLQPAE PLPQQQPQMS QTPADSFDII NNALTGLQKN AESLNKLYKE  60
NKDTKKAQAE WDAFRAANKH TPYSEIVAEK GKRPVSKSYF LPDTPAEGAQ KALSVTSSLV  120
SVLAKYNKPG ATGFSPDATR DIVISLVNAV PYLSVAGPFL AYLWPSQGND DVLMGKIKDL  180
IKGDIQKSTV EQLELRYETT LRKVALATAT QLHPESSTSR ITEDAISAKN ALEDLVTYTE  240
SKNNNDLAIA TLPLYITATG ADLAFKESIM KKNLTGFINS AGRTVPLDLS AKDVHFSKEQ  300
FDKDVTQYRK HVKDIYELKL KKFEDELTEL SKSNDAKFVT QETITLDNLR AMYFKANQVA  360
EETQKQMNGG LPQDASGKVI VSQHYAAERV KEKLKSIDEA YKSYKKLTIE SDSATVFNKY  420
VFDSTENIDF PTSYWGKNSN GNWVHYNSKK STDTGWFIDT DYNYYYLSPE DGTKNEAGKT  480
FDKGEMMTGW IKLNGEEYYL DDNKENNKDF KGTMGRMLHN ETARIKSLQS DKYYEQHFKP  540
SGAVWH                                                            546

SEQ ID NO: 289         moltype = AA  length = 273
FEATURE                Location/Qualifiers
REGION                 1..273
                       note = Description of Unknown: Organism from environmental
                        sample
source                 1..273
                       mol_type = protein
                       organism = unidentified
SEQUENCE: 289
MTFKVGTKYM FKNKNSRKYL DILANSTANN ANVQQYQFIQ NSPAERFTVE EAGSVALPSI  60
GTQPLPLVPQ YKTIDDQLPR ETERAVTCFT IVPSIAVKDP QYGGDTAKQI KENPYYMVVK  120
KQWWTQEVSR VLTPGETYRY TTKTGIKVID QETSTKTVSW SIGADMGFSF KGFSLGMSTQ  180
YSTQLQTTIS RTNEQLREEI SEHEIKNTSS NRMAYSRYIL TTEYSVQRKN GTIVNTPWTL  240
TDKTNTHSVT YPNSKENGLE ESTRQLLETE SVN                              273

SEQ ID NO: 290         moltype = AA  length = 497
FEATURE                Location/Qualifiers
source                 1..497
                       mol_type = protein
                       organism = Bacillus sp.
SEQUENCE: 290
MNRNGRHDEW SHNQNMENRQ MNQNHSGSCG CGCQQNQNEY NGANNGSYSS NGYNGTSNGS  60
YSYQENSYAS NQNNQNNQDM YMQNDMYGNH TYSNGSYYST GYADTDDPLA NLPDESKKFQ  120
RITNINSGDA FVMEASNRPI GYYLDPIGTC SRQTEIENTV TNGTATPATQ EIRDTQNFIF  180
YNTDMKDTFI IANRGNGRVL ELVDTRATTG VTDGTLASRA YNPNVLAQFY KRELVPGQTD  240
QFYLITTLNG IEVGINNCHN NPTAWQKYTA YPRDRFQNNV YKFLKEAEDT EKKNVINFPT  300
DLVVTAQPLS EPGELTSING NLIIPRAIQG KSLIPGIIVN DPTLNSEKQI EKNPYYVLEF  360
```

```
AETWYEATNT IINAGDAAYW SEFAGITFYD QNNMQDIMNV SIGGSLLGWG LKFGDSSNLF  420
KRTIITGLSI AAASSNDNRM DFSESLKNYY NLTGSPMRYI KYIKAYELVL KRLDNSQVTK  480
WTIYYDRVSS VRTFPRN                                                 497

SEQ ID NO: 291         moltype = AA  length = 272
FEATURE                Location/Qualifiers
REGION                 1..272
                       note = Description of Unknown: Organism from environmental
                        sample
source                 1..272
                       mol_type = protein
                       organism = unidentified
SEQUENCE: 291
MGNFLDLTRI FSTFANEWSM ENQGCAGTLF YLIDDPSIQE FSVSGNFTAT YDSPVESVQT  60
NTLSSFSFEN SSKEFKDQQI LINTTTPLTE SWELTSCVTP AGNTMGNTIT PPIIDIPGLP  120
PGDSVTLGHD EISTNSYTYT WDINPSIQLP PRSSTKVRFQ TQIKHVTQNF KATYWMTGNI  180
GIISMHPING NLEHYFPITQ VLQWYKSDQF ILNMEENRLT AFATGIYTAT YQIQPQLLVQ  240
TTNLDTPTIV EEYVLDINTG TTTPVSKPNG CC                                272

SEQ ID NO: 292         moltype = AA  length = 379
FEATURE                Location/Qualifiers
REGION                 1..379
                       note = Description of Unknown: Organism from environmental
                        sample
source                 1..379
                       mol_type = protein
                       organism = unidentified
SEQUENCE: 292
VSNKNSAEEN LNAPLINDEE LIPSEIKASG ARISFPDFNF YNIRTFSGKY VDVAKGSTDD  60
RAVAVQYTRN NSDNQKFLIF TLDNGYSVIA PKHSGKVLDI MSLSFPTPNN YLTQYYFQNS  120
DNQKFFIAND GSIAVKISGQ VWDIPNGSTS NDIPIISYRY QGSVNQKFTL ERSGSVSIKL  180
PTISTLPPAP DFKTTNLDEE LPDDTTPVIT HATYLPYFMV KDPYYNAQQK ITNSPYYILV  240
RRQYWEKKTQ RVLAPSDSYD YMETTGVSRT DQTSMTETTE ISIGADLGFM FKGFSLGLST  300
SITKSLSVTK STSNTESTEI SKKVFYTNPF KYEIAYAKYM LINEYYVTRS NGEMITSGDA  360
SYWKVPDPER TVSRIIPRR                                               379

SEQ ID NO: 293         moltype = AA  length = 379
FEATURE                Location/Qualifiers
REGION                 1..379
                       note = Description of Artificial Sequence: Synthetic
                        polypeptide
source                 1..379
                       mol_type = protein
                       organism = synthetic construct
SEQUENCE: 293
MSNKNSAEEN LNAPLINDEE LIPSEIKASG ARISFPDFNF YNIRTFSGKY VDVAKGSTDD  60
RAVAVQYTRN NSDNQKFLIF TLDNGYSVIA PKHSGKVLDI MSLSFPTPNN YLTQYYFQNS  120
DNQKFFIAND GSIAVKISGQ VWDIPNGSTS NDIPIISYRY QGSVNQKFTL ERSGSVSIKL  180
PTISTLPPAP DFKTTNLDEE LPDDTTPVIT HATYLPYFMV KDPYYNAQQK ITNSPYYILV  240
RRQYWEKKTQ RVLAPSDSYD YMETTGVSRT DQTSMTETTE ISIGADLGFM FKGFSLGLST  300
SITKSLSVTK STSNTESTEI SKKVFYTNPF KYEIAYAKYM LINEYYVTRS NGEMITSGDA  360
SYWKVPDPER TVSRIIPRR                                               379

SEQ ID NO: 294         moltype = AA  length = 365
FEATURE                Location/Qualifiers
source                 1..365
                       mol_type = protein
                       organism = Bacillus sp.
SEQUENCE: 294
MKKYKKLLMV APLACMLGTG VFTLPNAAHA DQPASYWQLR PESKTTYSKE NLANELANSG  60
LRYAIENTPE LRQKFKIADD ERIQMEQGKT SFIDRNGNTT TYPEVYYGLQ NQLSKMEIGA  120
KGTSFEVNPT IDSYEDLGQT NLLTINNDDG IEKQTAQTPE TTETFSETMS YSNQYGAKLG  180
VESTTAFKVN LPFNLGEAAQ TIKISTEFNY SHTDSNTKTQ SKAVTFKSQP VVAAPGGTTT  240
YYGTIKRAKF SGTFQTDAYL SGVTLKLPIV KKDGNGSDVV HTEEVTLTSE DIYTIYKNKP  300
TSIPSYLSFD DQNKKVIVNK AEFKFSGEGG YYSAIQIRFT PKDPNKSTQV MPYKEYIAKA  360
QQGTL                                                              365

SEQ ID NO: 295         moltype = AA  length = 336
FEATURE                Location/Qualifiers
REGION                 1..336
                       note = Description of Artificial Sequence: Synthetic
                        polypeptide
source                 1..336
                       mol_type = protein
                       organism = synthetic construct
SEQUENCE: 295
MDQPASYWQL RPESKTTYSK ENLANELANS GLRYAIENTP ELRQKFKIAD DERIQMEQGK  60
TSFIDRNGNT TTYPEVYYGL QNQLSKMEIG AKGTSFEVNP TIDSYEDLGQ TNLLTINNDD  120
GIEKQTAQTP ETTETFSETM SYSNQYGAKL GVESTTAFKV NLPFNLGEAA QTIKISTEFN  180
```

```
YSHTDSNTKT QSKAVTFKSQ PVVAAPGGTT TYYGTIKRAK FSGTFQTDAY LSGVTLKLPI  240
VKKDGNGSDV VHTEEVTLTS EDIYTIYKNK PTSIPSYLSF DDQNKKVIVN KAEFKFSGEG  300
GYYSAIQIRF TPKDPNKSTQ VMPYKEYIAK AQQGTL                            336

SEQ ID NO: 296          moltype = AA  length = 801
FEATURE                 Location/Qualifiers
REGION                  1..801
                        note = Description of Unknown: Organism from environmental
                         sample
source                  1..801
                        mol_type = protein
                        organism = unidentified
SEQUENCE: 296
MNQYNNKNDY EIIDNADMYY QPKYPLAEAP CSELQQISYE KVMNTSVGRK YQAVQQVNVG  60
ESVSAALGIL ATILKAVNPT LGAAAGVISK IFGFLWKQFG TDSQAQWKQF MEAVEYLVNQ  120
KITDAVRSKA VSELAGVQNA LELYQEAADD WNINPNDTSA KERIRRQFSS TNTTIEFAMP  180
SFRVSGFEVP LLTVFAQAAN LHLLLLRDAV KFGNEWGMPA AEVEDYYTRL QKRTAEYTDY  240
CTNTYDKGLK QAYDLAPNPT DYNKYPYLNP YSKDPIYGKY YTAPVDWNLF NDFRRDMILM  300
VLDIVAVWPT YNPKIYNNPY GVQIQLSREV YSTVYGRGWT NNSSVDAIEY TLVRPPHLVT  360
ELKKLTFDER NLFEAETVPI AFSKVTNTLQ YVGSSTTWEQ SFSVPPIASI KTVHNVSATD  420
IGNLSLSLGA VPFGFSFYNK NDNPITTVGY SGGWWNGIPK DEGSNQNSHH LSYVAALETQ  480
TTAGWFPTYP VPLLGEWGFG WLHNSLTSTN TIVTDRTTQV PAVKGNAAEF GATVVRGPGS  540
TGGDLVKLSA YNGGSTQLRI VVRPSATART RPYKLRIRYA SEGNANLFVG KYVVNRWWET  600
GNFAVDRTFS GAMTYNSFKY LDAFNFAANE EEFKIEFRCN SGGPIYIDKI EFIPVNPIPE  660
PPESGPGYGN YQIIYALSSG AVGITSSSTN TKMAITQNNH GNNQKWLFEY DSSKNAYQIR  720
NSERKDLVFD YNTFGILYAL PNEHKETQYW TIENVGDGNV YLKNNQGLYV TANSLPGSYE  780
LILSPLYSHL KSQRFTLQKS N                                            801

SEQ ID NO: 297          moltype = AA  length = 656
FEATURE                 Location/Qualifiers
REGION                  1..656
                        note = Description of Artificial Sequence: Synthetic
                         polypeptide
source                  1..656
                        mol_type = protein
                        organism = synthetic construct
SEQUENCE: 297
MNQYNNKNDY EIIDNADMYY QPKYPLAEAP CSELQQISYE KVMNTSVGRK YQAVQQVNVG  60
ESVSAALGIL ATILKAVNPT LGAAAGVISK IFGFLWKQFG TDSQAQWKQF MEAVEYLVNQ  120
KITDAVRSKA VSELAGVQNA LELYQEAADD WNINPNDTSA KERIRRQFSS TNTTIEFAMP  180
SFRVSGFEVP LLTVFAQAAN LHLLLLRDAV KFGNEWGMPA AEVEDYYTRL QKRTAEYTDY  240
CTNTYDKGLK QAYDLAPNPT DYNKYPYLNP YSKDPIYGKY YTAPVDWNLF NDFRRDMILM  300
VLDIVAVWPT YNPKIYNNPY GVQIQLSREV YSTVYGRGWT NNSSVDAIEY TLVRPPHLVT  360
ELKKLTFDER NLFEAETVPI AFSKVTNTLQ YVGSSTTWEQ SFSVPPIASI KTVHNVSATD  420
IGNLSLSLGA VPFGFSFYNK NDNPITTVGY SGGWWNGIPK DEGSNQNSHH LSYVAALETQ  480
TTAGWFPTYP VPLLGEWGFG WLHNSLTSTN TIVTDRTTQV PAVKGNAAEF GATVVRGPGS  540
TGGDLVKLSA YNGGSTQLRI VVRPSATART RPYKLRIRYA SEGNANLFVG KYVVNRWWET  600
GNFAVDRTFS GAMTYNSFKY LDAFNFAANE EEFKIEFRCN SGGPIYIDKI EFIPVN      656

SEQ ID NO: 298          moltype = AA  length = 305
FEATURE                 Location/Qualifiers
source                  1..305
                        mol_type = protein
                        organism = Bacillus sp.
SEQUENCE: 298
MTVVDFNQLI IEYAQSLASS PGNQGVTFTG QYGYIEAGDP SGAPPFTVSN AVANPDTTTY  60
NFSPGSSVFS SSQVVQNSSD VPITQNLALG QAVQDSNSTS TTNGLSTNYS ITTKSTFTIK  120
FGVTDGNSIS EEIDATFGQT FNFSTTDSNT QTESQNWTET TSLTVPPYSQ MTVLYTVLGG  180
TYSINTTLKW ELQGCIWFTL NYPGIGDVKE IVDIYFVIEN AGLNGSYPPP GDTGTPFSIS  240
QPGEVAFFGG TGEFTGTQGI QSIVTATSAP LPGYPGQTIT STTPLTSINS DGTVTPASSP  300
IPIYS                                                              305

SEQ ID NO: 299          moltype = AA  length = 569
FEATURE                 Location/Qualifiers
source                  1..569
                        mol_type = protein
                        organism = Bacillus sp.
SEQUENCE: 299
MLQCPCTMKS IYSINNTTRK DDLMKYKDRK DAKRKYKQVI LTTVATMTLG VSTLGPTASA  60
LAAEGDNISV ISSLETQTEN TKLSESNFVD TVKAKIDVLN SEKDKLKPVG KFMGTTILEL  120
IKYANKGPEQ MNDTLRAITM ASIEVIPYGG MFIAPLIGAI WPQTNDINSQ LKALREELTK  180
LVTNEIDNEQ LNFLNSEFKT LIDLQTDLEH AINADNSQNA DENTKNQRGA WANGIEQSFR  240
RLLDHTSSDK HKITNLPIYT KVALAHLLFL ESLNNKAVSS KMNITEQSLK ELYTKDGVKT  300
YANKYVLHIV KTYYDAPQIK KIKQVPEFHF NPDDAENQIK DLKDRLSKVK VQYKEWRDGV  360
MSAGGFGMVP NKEYEFNIAI MEDAISSYEF VEKLYNATVG DPMIKELIKD SGNQEIKELA  420
KDSSEVFVAD TTYKIVYSKA NKVVDFGEHG IELPLIWYDH SGKNQRWEFK YDADKKAYQI  480
INRADGRILA YNTTPNADDT ALVTENQHKP EHYWILEDAG AGNVLLVNYE NKNKVLDVYD  540
EKTDDGSRVY VRDKLNNSNA QKFKLVISL                                    569
```

```
SEQ ID NO: 300         moltype = AA  length = 546
FEATURE                Location/Qualifiers
REGION                 1..546
                       note = Description of Artificial Sequence: Synthetic
                        polypeptide
source                 1..546
                       mol_type = protein
                       organism = synthetic construct
SEQUENCE: 300
MKYKDRKDAK RKYKQVILTT VATMTLGVST LGPTASALAA EGDNISVISS LETQTENTKL  60
SESNFVDTVK AKIDVLNSEK DKLKPVGKFM GTTILELIKY ANKGPEQMND TLRAITMASI  120
EVIPYGGMFI APLIGAIWPQ TNDINSQLKA LREELTKLVT NEIDNEQLNF LNSEFKTLID  180
LQTDLEHAIN ADNSQNADEN TKNQRGAWAN GIEQSFRRLL DHTSSDKHKI TNLPIYTKVA  240
LAHLLFLESL NNKAVSSKMN ITEQSLKELY TKDGVKTYAN KYVLHIVKTY YDAPQIKKIK  300
QVPEFHFNPD DAENQIKDLK DRLSKVKVQY KEWRDGVMSA GGFGMVPNKE YEFNIAIMED  360
AISSYEFVEK LYNATVGDPM IKELIKDSGN QEIKELAKDS SEVFVADTTY KIVYSKANKV  420
VDFGEHGIEL PLIWYDHSGK NQRWEFKYDA DKKAYQIINR ADGRILAYNT TPNADDTALV  480
TENQHKPEHY WILEDAGAGN VLLVNYENKN KVLDVYDEKT DDGSRVYVRD KLNNSNAQKF  540
KLVISL                                                            546

SEQ ID NO: 301         moltype = AA  length = 510
FEATURE                Location/Qualifiers
REGION                 1..510
                       note = Description of Artificial Sequence: Synthetic
                        polypeptide
source                 1..510
                       mol_type = protein
                       organism = synthetic construct
SEQUENCE: 301
MLAAEGDNIS VISSLETQTE NTKLSESNFV DTVKAKIDVL NSEKDKLKPV GKFMGTTILE  60
LIKYANKGPE QMNDTLRAIT MASIEVIPYG GMFIAPLIGA IWPQTNDINS QLKALREELT  120
KLVTNEIDNE QLNFLNSEFK TLIDLQTDLE HAINADNSQN ADENTKNQRG AWANGIEQSF  180
RRLLDHTSSD KHKITNLPIY TKVALAHLLF LESLNNKAVS SKMNITEQSL KELYTKDGVK  240
TYANKYVLHI VKTYYDAPQI KKIKQVPEFH FNPDDAENQI KDLKDRLSKV KVQYKEWRDG  300
VMSAGGFGMV PNKEYEFNIA IMEDAISSYE FVEKLYNATV GDPMIKELIK DSGNQEIKEL  360
AKDSSEVFVA DTTYKIVYSK ANKVVDFGEH GIELPLIWYD HSGKNQRWEF KYDADKKAYQ  420
IINRADGRIL AYNTTPNADD TALVTENQHK PEHYWILEDA GAGNVLLVNY ENKNKVLDVY  480
DEKTDDGSRV YVRDKLNNSN AQKFKLVISL                                  510

SEQ ID NO: 302         moltype = AA  length = 555
FEATURE                Location/Qualifiers
source                 1..555
                       mol_type = protein
                       organism = Bacillus sp.
SEQUENCE: 302
MVQNNLGTKA LPSFIDDFNG IFGFVDGIFS IFDKISGANI DNPELEEILK NQELLNELHD  60
KLSAVSGDLD TIIQNGELNT ELLNHLMQIS NAQGDMLQNI QNQIDGLQNM IQGHFTEIIT  120
MLNKIVIQNQ IISSQLVYIT EQLLVISQKL DTINVNILIS STITEITPSY QRMNYINKKY  180
DELAFSNTNK YSNDLNIVNF DIENHSEINE LIDFAKNVTQ NSQNSFEFYL DTFQEVMVGN  240
TLFERSALHS IGELIRNKHM PKGNGSEVAR AYTFLVGLIS IQAKSYATLA ACRKILGLKD  300
IDYTTVLTQY IQDQLNIFVS VELPKFSNEF SGFNHVNIGL GLEFDHKKID RVVKADPGYV  360
LVGLEIINNG DDFDLIAYQA KLKQNYEINK ESISKLTVHK INEIFAPVWQ IGRLGKINTY  420
PVAFNPTELQ FPEGYVITQI NFALYPRMLD MSYEVIANHY DPFTGNLEPT KSLTKRAERE  480
ELGPRLPITE EDETYFPTKI SDTFLAPMYS FKIDADYDTY KSNILCKNYF PQYLKASDLS  540
NKETNLLYVV NDTVK                                                  555

SEQ ID NO: 303         moltype = AA  length = 381
FEATURE                Location/Qualifiers
source                 1..381
                       mol_type = protein
                       organism = Bacillus sp.
SEQUENCE: 303
MMSKDIINLF NNYSNSWSQR ENGGASEISL VLPGFEEHAL KTKFPIRTTY HDIQEDLKIV  60
PVATTTIENP YDVPQQEYIT LAADVEEWGS WKFTDVATNV GDHVVKIDMP HDMVIPALGD  120
IRKVPIHLLN EEARHSGLRT WSVKHPFELN PRTRVIATLQ VKQKEIKRDF SVEHDLSGYL  180
GVITEHLVDN HHMSLHHIKR VLQCYPHPLI RITDSGVTLT SNGDFSALFS IEQMIHIKIE  240
SLDFPEITEE YTIYNPETGK KSIRIKDINP NGPQKTLVAT VDSQPKPQSG QSFRSSNNFN  300
LDLAKAPYAY ALQFEVNNQP SNMHFSVAED IRNGNDKVIL AGMGNNVKTP ITTGMKTNNL  360
YIGGPQNATS VFKVYIYALH D                                           381

SEQ ID NO: 304         moltype = AA  length = 322
FEATURE                Location/Qualifiers
source                 1..322
                       mol_type = protein
                       organism = Bacillus sp.
SEQUENCE: 304
MKKYKKIAMV MPLAGMLTVG IGVLGGPVSS FADTIPETKV APMYTNLAKN TMSDNEQLKK  60
ELSQFFGGEV SNIQLEMINT NSSPIQVQIT SAQPIGSKDD VIDFIGYDNY TNEMQSHKTP  120
EQKVINKMSV TTTNASEMHT GLKSETEFSL GVPLFAEGKE NITVELGVTY KRSLDETVEN  180
```

```
STEVTYPSQT INAAPGGRTT LLNQVQKTKF DGIYTGRAVI KSFDRKNSEG QVQTYEGDVL  240
YQIYKYRSAI KNGKNLSDSI ENDALNNKLI VKNHVVPFTG KAGHTTQATA RFIPFDKTKS  300
EVKMPISEYN KRVANGISLY AK                                          322

SEQ ID NO: 305         moltype = AA  length = 291
FEATURE                Location/Qualifiers
REGION                 1..291
                       note = Description of Artificial Sequence: Synthetic
                        polypeptide
source                 1..291
                       mol_type = protein
                       organism = synthetic construct
SEQUENCE: 305
MDTIPETKVA PMYTNLAKNT MSDNEQLKKE LSQFFGGEVS NIQLEMINTN SSPIQVQITS  60
AQPIGSKDDV IDFIGYDNYT NEMQSHKTPE QKVINKMSVT TTNASEMHTG LKSETEFSLG  120
VPLFAEGKEN ITVELGVTYK RSLDETVENS TEVTYPSQTI NAAPGGRTTL LNQVQKTKFD  180
GIYTGRAVIK SFDRKNSEGQ VQTYEGDVLY QIYKYRSAIK NGKNLSDSIE NDALNNKLIV  240
KNHVVPFTGK AGHTTQATAR FIPFDKTKSE VKMPISEYNK RVANGISLYA K           291

SEQ ID NO: 306         moltype = AA  length = 366
FEATURE                Location/Qualifiers
source                 1..366
                       mol_type = protein
                       organism = Bacillus sp.
SEQUENCE: 306
MKKYKKLLMA APLACMLGTG VFALPNASFA EQPASYFQLR PESKTTYSKE TLANELANSG  60
LRYAIENTPE LRQKFKIADD ERIQFEQGGT TEGHNGVVTK FPEVYYGLQD QLNKMELGVK  120
GTTFEVNPTI DSYEDLGQTN LLTINNDDGI VAQQAQTPET TETFSETMSY SNQYGAKLGI  180
ESTTSFKVNL PFNLGGAEQS IKISTEFSYN HTDSNTSTHE KTVTFKSQPV VAAPGGTTTY  240
YGTIKRAKFS GTFQTDAYLA GVTLKLPIVK KSGNNRDVVH TEEATLTAED IYKIYKNRPT  300
SVSMPSYLSF DDQNKKVLLN KADFNFSGEG GYYSAIQVRF TPKDSNKNSQ VMPYKEYVAK  360
AQQGAL                                                            366

SEQ ID NO: 307         moltype = AA  length = 337
FEATURE                Location/Qualifiers
REGION                 1..337
                       note = Description of Artificial Sequence: Synthetic
                        polypeptide
source                 1..337
                       mol_type = protein
                       organism = synthetic construct
SEQUENCE: 307
MEQPASYFQL RPESKTTYSK ETLANELANS GLRYAIENTP ELRQKFKIAD DERIQFEQGG  60
TTEGHNGVVT KFPEVYYGLQ DQLNKMELGV KGTTFEVNPT IDSYEDLGQT NLLTINNDDG  120
IVAQQAQTPE TTETFSETMS YSNQYGAKLG IESTTSFKVN LPFNLGGAEQ SIKISTEFSY  180
NHTDSNTSTH EKTVTFKSQP VVAAPGGTTT YYGTIKRAKF SGTFQTDAYL AGVTLKLPIV  240
KKSGNNRDVV HTEEATLTAE DIYKIYKNRP TSVSMPSYLS FDDQNKKVLL NKADFNFSGE  300
GGYYSAIQVR FTPKDSNKNS QVMPYKEYVA KAQQGAL                           337

SEQ ID NO: 308         moltype = AA  length = 402
FEATURE                Location/Qualifiers
source                 1..402
                       mol_type = protein
                       organism = Bacillus sp.
SEQUENCE: 308
MKSISKKVMA GLLVGATSLS IWTPSSEAEA PKNDRYYNIQ LKSNPKKVWN VTRASNDNDR  60
AILLWQGGSA DNEKFAFFQL DGGAYAIVNK NSGKIVTFGD ASWFGDRSIL PGNETLQQQS  120
WNGEAKQKWN LRDLGSNNYE IVNQANGKVP SYRWAGSLVD NVEYLQMDNS NPSDPDKVFK  180
LFSGSSTVLL PGSVIPTTIL QEPISVPNLP ATGTRPDAPN YTGGVDQQLP QTSNSVVVGA  240
SLIPCIMVKD NQASDYTKIH NSPYYTLVKE EYWDKTFSAV IPAGLTRNYS FKTGMTSVDQ  300
QKMTDTLSMK IGADFGLKFG DATASIKSEI SRTLQTEIST TNTEASEETV TSTVISEPGK  360
TTGYTEYQLA TKYTLKRADG SIVSDPWVVK NNKITIARKN AQ                    402

SEQ ID NO: 309         moltype = AA  length = 375
FEATURE                Location/Qualifiers
REGION                 1..375
                       note = Description of Artificial Sequence: Synthetic
                        polypeptide
source                 1..375
                       mol_type = protein
                       organism = synthetic construct
SEQUENCE: 309
MEAPKNDRYY NIQLKSNPKK VWNVTRASND NDRAILLWQG GSADNEKFAF FQLDGGAYAI  60
VNKNSGKIVT FGDASWFGDR SILPGNETLQ QQSWNGEAKQ KWNLRDLGSN NYEIVNQANG  120
KVPSYRWAGS LVDNVEYLQM DNSNPSDPDK VFKLFSGSST VLLPGSVIPT TILQEPISVP  180
NLPATGTRPD APNYTGGVDQ QLPQTSNSVV VGASLIPCIM VKDNQASDYT KIHNSPYYTL  240
VKEEYWDKTF SAVIPAGLTR NYSFKTGMTS VDQQKMTDTL SMKIGADFGL KFGDATASIK  300
SEISRTLQTE ISTTNTEASE ETVTSTVISE PGKTTGYTEY QLATKYTLKR ADGSIVSDPW  360
VVKNNKITIA RKNAQ                                                  375
```

```
SEQ ID NO: 310          moltype = AA  length = 367
FEATURE                 Location/Qualifiers
source                  1..367
                        mol_type = protein
                        organism = Streptomyces sp.
SEQUENCE: 310
MTRTRVRKRR SLWRAATVLA AMVGAAVGIG AAPAAAAPEA VTGSTALIQL KFTNVSNGKL  60
LDVQGGSYDD NAAISVNPAP GSATTWRINT GTSLGSGFAI VNTTTGKCMD VTTAHYQLRQ  120
QPCDGRASEQ WYFQPIDGSA QKAFRIRQVG DNSCLTVQIP PASDNWVYTY RCDNTPYQQW  180
TLPSEVYSKA WNMAVDYAAG RCNKDTSTCS WSTTTQTPPF TLPEACVSPI WFNDTSTTIP  240
WEFSLNTSTG WTNTIGFKMG GTLTVGGDIG LAKLQLEVTA EVNGATSIDL KQDMGNKLTV  300
SVPPRQYGWV ALSELATKAT GTWTFDVQGF PWTADDTITV PLKYDVNGGA SIYSARTRAT  360
FTNCAGT                                                            367

SEQ ID NO: 311          moltype = AA  length = 332
FEATURE                 Location/Qualifiers
REGION                  1..332
                        note = Description of Artificial Sequence: Synthetic
                         polypeptide
source                  1..332
                        mol_type = protein
                        organism = synthetic construct
SEQUENCE: 311
MAPEAVTGST ALIQLKFTNV SNGKLLDVQG GSYDDNAAIS VNPAPGSATT WRINTGTSLG  60
SGFAIVNTTT GKCMDVTTAH YQLRQQPCDG RASEQWYFQP IDGSAQKAFR IRQVGDNSCL  120
TVQIPPASDN WVYTYRCDNT PYQQWTLPSE VYSKAWNMAV DYAAGRCNKD TSTCSWSTTT  180
QTPPFTLPEA CVSPIWFNDT STTIPWEFSL NTSTGWTNTI GFKMGGTLTV GGDIGLAKLQ  240
LEVTAEVNGA TSIDLKQDMG NKLTVSVPPR QYGWVALSEL ATKATGTWTF DVQGFPWTAD  300
DTITVPLKYD VNGGASIYSA RTRATFTNCA GT                                332

SEQ ID NO: 312          moltype = AA  length = 1155
FEATURE                 Location/Qualifiers
source                  1..1155
                        mol_type = protein
                        organism = Bacillus sp.
SEQUENCE: 312
MRNKQARKRK DQLKPVNVIT TIAIAVTTLF TPIVNGLPSK SNLIHAETKD EKTLDAPNVN  60
KMTDQDTNIT GIGEEGTTVK VVVDGQEIGT GKVDEKGNFK VDIPKQPVGK EIVLTLKDST  120
GNTSQPTKRK VEAKDEKAPD APNVNKVTDQ DTNITGIGEK GTTVKVVVDG QEIGTGKVDE  180
KGNFKVDIPK QPVGKEIVLT LTDVASNTSQ PTKRKIEAKD EKAPDAPNVN KVTDQDINIT  240
GIGEKGTTVK VVVDGQEIGT GKVDEKGNFK VDIPKQSVGK EIVLTLTDVA GNMSQPTKRK  300
IEAKDEKAPD APSVNKVTDQ DTNITGIGEK ETTVKVVVDG QEIGTGKVDE KGNFKVDIPK  360
QPVGKEIVLT LTDVASNMSQ PTKRKIEAKD KKAPDVPNVN KVTDQDTNIT GIGEKGTTVK  420
VVVDGQEIGT GKVDEKGNFK VDIPKQPVGK EIVLTLTDVA GNTSKPIKVV VQNNHHYQNV  480
LVKEAKQAIN GLFTDLIQTN YSHDFSNLTK VAIQLDVTQL KIDEAESKLE KIDDQRAEKI  540
ALKKEIDRAR QLLNERENEQ DGNMLQNGLF NFGFDNWKLW TGSEAIAPSI EEKDDKSVKV  600
AKVNPNSSVE QTITGLEPST TYELTLYAKT DNYEKFSIGV KNTGTPTVSV PVKSKEYSQT  660
KLRFITGENA TTATLYFYKS GGNGSGYADM AILKQVIDEK AIQQAIHHLF ADRIYSGGNG  720
EEKPTKQAIQ PNVKKQDIDR IENNVNLITD PKVKKQLKNE VKRAQDLYEE KQRQQTNNQL  780
KNGSFEEKLK NWKSWKSSAA NIAPIVLEKE GRLSNVLKFE IGASSVEQTL QVEPNTIYEL  840
AGYGKTENGE KLSLGVKKMI GVSDIGVANS SNDYVEQVLR FKTGPNTTSA TVYVYKGVGT  900
KPSYIDDIRL YKVNSITNQQ CHSIEPLDFK SVCKSEATDW GNKLFSLWDK LTPQIEKDAV  960
RGYTGIDYED INSYLRSDYF DVRDQEKIKR SIQQMDLAFS RVRLYEDMIV YRRASESAFG  1020
YQEGTLVNEG VIDMEQFEMF KNRFQGKYKK DPTYISTSIV KDVAEGFSNR PILLKIHVPK  1080
GVPAMYLDPL THFSGEMELL LPRNRTYKVK TISPVTEEDR EYVMLDVEIL DIPSNYQNKR  1140
ATDIRYEGSL PSLSK                                                   1155

SEQ ID NO: 313          moltype = AA  length = 448
FEATURE                 Location/Qualifiers
source                  1..448
                        mol_type = protein
                        organism = Bacillus sp.
SEQUENCE: 313
MSTNEVHQLP KGFLKDLGEE LKQKTQITSE DLAKIMRDAS RDSAKLNDLI RQASIAAVGK  60
IPSVGMAISP IISYLWPEQA GVDSKLNALE ARITAKIGQA VGEQHTRDIQ SKIKDLKHAM  120
EKLEDSLNTG TFYDGSVKDI HGVLRNQAKD VNDKFISLMH FTQQENNDIV DLPIYTKVAS  180
AHILFLKYLK THGTDSKLFR YDKSSTLNAE FKTDNIESII TTYAKYIEDT FKKGDNDLAM  240
LLKTRDNTIA QKRNLIVPGI PVNIGTESRI HTLEQEIKGI NDLKVEEKRA LYRDLTVGEG  300
SFEAVSCKKL TYTNFGWIED GGKRYYLSLY NGFKNYDGKT FDRGELVTGW LKPHEGNTYY  360
LSPANGTKND DGKVFNKGEI TTGWMQVGKK STWDGKHGAW YYLDNKEGNK DFKGTTGRML  420
HDETARVKNK EGDFKKHYFN ENGTWGDN                                     448

SEQ ID NO: 314          moltype = AA  length = 357
FEATURE                 Location/Qualifiers
source                  1..357
                        mol_type = protein
                        organism = Bacillus sp.
SEQUENCE: 314
```

```
MKAYKKFKKA LPFAVLSTAI LFSPAATTFA AEKTQPENLN VQMKNMDGDG IGIGGGQHGG  60
GNVTGTPGDG HILKGFLFKN DGSGHKTPVY SDAVSDESPY PELSANPNDP IPDHGTIETE  120
SGKPGTKLYF SKFEVPIPGY GNDGIPVKNV YLQKNDDGSI TVGTYDPSTL ATIEGSDVNT  180
YRASDTAPVA KRVFAYMNGN TVKRETAYNK LGSGVVPKGA SYTFSQAVTS GVTTSEIVGG  240
ALTLGYKVSV GASTGAIPGP SVTQEFSAQL QVSYSHNYTV SSSTTNTQTM SNPHAPASYP  300
HDKYAGAVYQ LGSKYTFVPG AALSQDIKDG HVVLGQNVFD YDQSTLYLAV TPGAGAE     357

SEQ ID NO: 315         moltype = AA  length = 328
FEATURE                Location/Qualifiers
REGION                 1..328
                       note = Description of Artificial Sequence: Synthetic
                        polypeptide
source                 1..328
                       mol_type = protein
                       organism = synthetic construct
SEQUENCE: 315
MAEKTQPENL NVQMKNMDGD GIGIGGGQHG GGNVTGTPGD GHILKGFLFK NDGSGHKTPV  60
YSDAVSDESP YPELSANPND PIPDHGTIET ESGKPGTKLY FSKFEVPIPG YGNDGIPVKN  120
VYLQKNDDGS ITVGTYDPST LATIEGSDVN TYRASDTAPV AKRVFAYMNG NTVKRETAYN  180
KLGSGVVPKG ASYTFSQAVT SGVTTSEIVG GALTLGYKVS VGASTGAIPG PSVTQEFSAQ  240
LQVSYSHNYT VSSSTTNTQT MSNPHAPASY PHDKYAGAVY QLGSKYTFVP GAALSQDIKD  300
GHVVLGQNVF DYDQSTLYLA VTPGAGAE                                     328

SEQ ID NO: 316         moltype = AA  length = 353
FEATURE                Location/Qualifiers
source                 1..353
                       mol_type = protein
                       organism = Bacillus sp.
SEQUENCE: 316
VWGVNQRYWN RRKSRTHSNI ANKIRILFVI SLIFYIKINV CIKEDIVKMA ELDLAKSNSA  60
ISLRGLHNLI GCDMELYQRW NFDTEFYPMP VSPKITPSCG MDMPYEGKDC SLQGLKLHGV  120
GVEIDPLDLI ANSVPWFISV GTFQNASDLT QTFQTTEFTE KITDTTTVTK TKTLKVGNTT  180
STKTTLDVFL IDAEVSTSIT VEGTWSTAET QTHTVEKTIR VPPMSVIVPP RKGMRVKAEY  240
FKGELNSKDI KINAQLSGKY KINNGHHWYD QDLYPIIKSL QLGSPNIWKG IEGNGIKLND  300
ATQTVTCYGL GTLNANFTTS TYNVLYEEFN LSTGRVEKVT KVAVYPWIIS SFS         353

SEQ ID NO: 317         moltype = AA  length = 305
FEATURE                Location/Qualifiers
REGION                 1..305
                       note = Description of Artificial Sequence: Synthetic
                        polypeptide
source                 1..305
                       mol_type = protein
                       organism = synthetic construct
SEQUENCE: 317
MAELDLAKSN SAISLRGLHN LIGCDMELYQ RWNFDTEFYP MPVSPKITPS CGMDMPYEGK  60
DCSLQGLKLH GVGVEIDPLD LIANSVPWFI SVGTFQNASD LTQTFQTTEF TEKITDTTTV  120
TKTKTLKVGN TTSTKTTLDV FLIDAEVSTS ITVEGTWSTA ETQTHTVEKT IRVPPMSVIV  180
PPRKGMRVKA EYFKGELNSK DIKINAQLSG KYKINNGHHW YDQDLYPIIK SLQLGSPNIW  240
KGIEGNGIKL NDATQTVTCY GLGTLNANFT TSTYNVLYEE FNLSTGRVEK VTKVAVYPWI  300
ISSFS                                                              305

SEQ ID NO: 318         moltype = AA  length = 735
FEATURE                Location/Qualifiers
source                 1..735
                       mol_type = protein
                       organism = Bacillus sp.
SEQUENCE: 318
MNLHDCNNSN LKNYETPFPR SSTHSRVQSL REKALALNYF TLEEEKESLA YIQQILQVQS  60
PELENTMDTV SVLSTNLSAH IKYSKKIGDL PCPENFQFKN DYLVPTSTTP LNLFPMLAGL  120
VPWAATSIAK YAANKALTEV LNIIFPGSST PTLDQVQDIV QKEIHKSLSA DLQGRLHAKY  180
NGLLEQLDQF NDLLCQFCPP SANPCTEYGI CPSTLPEKDF IALLTQFQYV DSEFRGAMEE  240
FIYDPSAPGF EEVLLPLYTL VGTTHLTFLK TAIYQAENWR FTENYTALLK SHYNENLYEY  300
TEDALNMYNK GFQNVIENKD LSTGDVLQFK NSMTLALDQV YAWSLMRYEG LQYRLARSYW  360
HWAGPQYFGI NEYKITLQKW SALYQYMNGP LNYRLQNILY GKKEGLNASF YYSQYMFRTF  420
PVTSYDSADK GQLAPYPGYT GTGYTTDLFN TENFEIINKV KTYMYYNSFG GQVYATIELW  480
KDNDSIFKLM GRWPTNNEIY YENTFLRSFI KDVSVYNISE KKFTEALEYI YTSSIPVQYQ  540
GNNSIILGFT PITEWEYFKN KVQTLKSYSE ENPALSIPPT QFFDITRLDN VQFQETQGQG  600
IDGNLRLDGN SGPNRVRYRI KLDSSLSIST EYRLFFRVGG GSGWSSPVIS PVTYSETDCS  660
TCDNDDLILK MNLIGSVALS DPQYFYDYIS DPFKMNQAPG KDIDLSIICT ENNFLQFAQI  720
QIVPATFFKT IINPK                                                   735

SEQ ID NO: 319         moltype = AA  length = 669
FEATURE                Location/Qualifiers
REGION                 1..669
                       note = Description of Artificial Sequence: Synthetic
                        polypeptide
source                 1..669
                       mol_type = protein
```

```
                         organism = synthetic construct
SEQUENCE: 319
MDTVSVLSTN LSAHIKYSKK IGDLPCPENF QFKNDYLVPT STTPLNLFPM LAGLVPWAAT  60
SIAKYAANKA LTEVLNIIFP GSSTPTLDQV QDIVQKEIHK SLSADLQGRL HAKYNGLLEQ  120
LDQFNDLLCQ FCPPSANPCT EYGICPSTLP EKDFIALLTQ FQYVDSEFRG AMEEFIYDPS  180
APGFEEVLLP LYTLVGTTHL TFLKTAIYQA ENWRFTENYT ALLKSHYNEN LYEYTEDALN  240
MYNKGFQNVI ENKDLSTGDV LQFKNSMTLA LDQVYAWSLM RYEGLQYRLA RSYWHWAGPQ  300
YFGINEYKIT LQKWSALYQY MNGPLNYRLQ NILYGKKEGL NASFYYSQYM FRTFPVTSYD  360
SADKGQLAPY PGYTGTGYTT DLFNTENFEI INKVKTYMYY NSFGGQVYAT IELWKDNDSI  420
FKLMGRWPTN NEIYYENTFL RSFIKDVSVY NISEKKFTEA LEYIYTSSIP VQYQGNNSII  480
LGFTPITEWE YFKNKVQTLK SYSEENPALS IPPTQFFDIT RLDNVQFQET QGQGIDGNLR  540
LDGNSGPNRV RYRIKLDSSL SISTEYRLFF RVGGGSGWSS PVISPVTYSE TDCSTCDNDD  600
LILKMNLIGS VALSDPQYFY DYISDPFKMN QAPGKDIDLS IICTENNFLQ FAQIQIVPAT  660
FFKTIINPK                                                         669

SEQ ID NO: 320           moltype = AA  length = 247
FEATURE                  Location/Qualifiers
source                   1..247
                         mol_type = protein
                         organism = Bacillus sp.
SEQUENCE: 320
MKNFNQLPIL NNTPLENNPF TTQSTTREIV LRVTEPTTSS NMKQIFEIED ENALLQAIFT  60
ANAFNQALIP IESDGYKSIY FDVELALKVV ETLNPPGAIF GSINQILTQK ENTVETMIEK  120
VTDVFLTQLN LTLSTDSLNS IRAALTNTFT NLDAQKTDAW IFYQQNDAFK ANYTYNILFS  180
FINEKTGTSM ITIPIGLYIQ AESKSKKILW VTYDDKVSYE VHIQALKVIQ PLINTSATLL  240
NTISRLV                                                           247

SEQ ID NO: 321           moltype = AA  length = 406
FEATURE                  Location/Qualifiers
source                   1..406
                         mol_type = protein
                         organism = Bacillus sp.
SEQUENCE: 321
MNDNMDENQN GDTITTEDSL ANDERNESLP EESRMFAYYQ PVNTNDKVWD ASEGGGGMPG  60
GCARASLANA MYNFPYHGGL NQQFIWFQLD DGRFAIANKH NGYVLQKYQV SNIISEIVNV  120
PWENNYAQLW RKESTSATNF RLVNEAEALE VCGGNTSAQA KMSFIPNRPD NGLLFKRRAI  180
AQNNVVPSLP SKQPLPPLPT LSNLNDPAPH ETARVITGSS LEPCIMVSDY IPVSQRIKES  240
PYYILAKKQF WKLLWHDTFI PGEYREFQET TGMSKTHQES MTETTNISLQ ADFGFAYKAI  300
TLGLGVSISK SIEISRSTTD TVMSQHTDTQ GYKNGNNFNL SWAKYALATE FVLMRKDGTT  360
AGSWEAVDKK VTRSISYPPT QTLSWAKSLG EQEDNTVFEP TTITSE                406

SEQ ID NO: 322           moltype = AA  length = 1239
FEATURE                  Location/Qualifiers
source                   1..1239
                         mol_type = protein
                         organism = Bacillus sp.
SEQUENCE: 322
MAYQNESEGE ILYTIPSKAP LANGAQRSPL TNSSRTELQN MNYKDFLNQC ESPVIGEIAP  60
SMNTSSAIRT ATLKSIEVIS SMLSSLPIPG APILGYAGKF FGAILGLLWP DGQEDVWKAF  120
MEAVEELVDQ KIEEFAKKLA ISSLEGIFNV AAEYDNALGR LEKDPNNAAL KEEVRVKYYD  180
TIAAIVQGMP YFKTQSYEVP FLTVFTEAAN LHLLMLRDGA MFGAQWGMDP TTVKNYRNNF  240
NVLLGEYTDY CVKWYNIGLD RASKLKADIN DRDKYPWIGP GHIALSPDKW QYTEDWNLYN  300
DYRRNMTLQV LDMVAVWSSL DDQYYPMPTK VQLTRDIYTN VWGIGTDSNG SLAQVEARFT  360
RPPHLVTQLL NLGYYTKTDT KGVETIEGSY STVRKCGRMA GGVSETNFNG EKTSAHRFWW  420
QPFSEVSGYH FAETSVLASP GKTQVGNFWI NGGAWSAFNI PGQIVNWFCS TYPGQLIPVR  480
GLRGANFILK SDTLDYQNVF YHDMINQFPA VMALDCYSVV RGPGSTGGSL VKLIPGTGLD  540
LMVSPDPDAK YKPFKVRIRY ASESNGILNV AKWDQDGTVF WQNQDNPVEQ TYTGSMTYKS  600
FKYVETIAVP ANEDSFRIVL YSKSGGPMYI DKIELIPLNG SLAEYEAEQD LEKARKAVNA  660
LFTDDAKNAL KLNITDYAVD QAANLAECVS DEFHAQEKTI LLDQVKFAKR LSQARNLLNF  720
GDFKSPDWFG ENGWKRSPHV DVASDNPIFK GHYLHMPGAN QPQMSNIIYP TYIYQKVDES  780
KLKSYTRYHV RGFVGNSKDF ELLVERYGKE VHVEMNVPND IRYSLPTNEC GGFERCTHGS  840
YKDTAYTDID CQCTDMKNRM TTGVYTNMPV DSSIYTNSYH THKSCRCGNK DVYQNGKHEH  900
KSCGCKDPHV FSFHIDTGCV DTEENLGLLF ALKIASTNGV ANIDNLEIIE GQPLTGEALA  960
RVKKREHKWK EEIKQKRYKT DEAVQAAQIA INALFTNTQY NRLKFDTLFP HILHADELVQ  1020
RIPYVYHPFL RDADPDVPGI NYVIFQQLVE LVGRARGFYD MRNLVQNGTF SSGTGSWCVT  1080
DDVTTESEGN ASVLVLLEWS DKAVQHLRID AERGYVLRVT ARKEGNGDGY VVIDDCDYQQ  1140
EKVTFTACDY SMMGASTGTQ TSVIPATNYP PCHSGTWGEE MTTPVTMLSG YVTKTAEIFP  1200
DSDRIRIEIG ETEGTFKVES VELICMDQME DAGNFEDEM                        1239

SEQ ID NO: 323           moltype = AA  length = 638
FEATURE                  Location/Qualifiers
REGION                   1..638
                         note = Description of Artificial Sequence: Synthetic
                          polypeptide
source                   1..638
                         mol_type = protein
                         organism = synthetic construct
SEQUENCE: 323
MAYQNESEGE ILYTIPSKAP LANGAQRSPL TNSSRTELQN MNYKDFLNQC ESPVIGEIAP  60
```

```
SMNTSSAIRT ATLKSIEVIS SMLSSLPIPG APILGYAGKF FGAILGLLWP DGQEDVWKAF  120
MEAVEELVDQ KIEEFAKKLA ISSLEGIFNV AAEYDNALGR LEKDPNNAAL KEEVRVKYYD  180
TIAAIVQGMP YFKTQSYEVP FLTVFTEAAN LHLLMLRDGA MFGAQWGMDP TTVKNYRNNF  240
NVLLGEYTDY CVKWYNIGLD RASKLKADIN DRDKYPWIGP GHIALSPDKW QYTEDWNLYN  300
DYRRNMTLQV LDMVAVWSSL DDQYYPMPTK VQLTRDIYTN VWGIGTDSNG SLAQVEARFT  360
RPPHLVTQLL NLGYYTKTDT KGVETIEGSY STVRKCGRMA GGVSETNFNG EKTSAHRFWW  420
QPFSEVSGYH FAETSVLASP GKTQVGNFWI NGGAWSAFNI PGQIVNWFCS TYPGQLIPVR  480
GLRGANFILK SDTLDYQNVF YHDMINQFPA VMALDCYSVV RGPGSTGGSL VKLIPGTGLD  540
LMVSPDPDAK YKPFKVRIRY ASESNGILNV AKWDQDGTVF WQNQDNPVEQ TYTGSMTYKS  600
FKYVETIAVP ANEDSFRIVL YSKSGGPMYI DKIELIPL                         638

SEQ ID NO: 324         moltype = AA  length = 286
FEATURE                Location/Qualifiers
source                 1..286
                       mol_type = protein
                       organism = Bacillus sp.
SEQUENCE: 324
MAIINLNNIV SNYRPPQELM KELGGRPLSS GPEGVGILQN SLSITGTSTN TAPIPIIGLG  60
RNIVLQQTVD NLQGKIPITK EFSFTETTED ESSTTVTSGV TTDIKADVNL SGVLDFVTLG  120
LTSAFSRSTT LTNQTTNKMT RTHVWGDKYT LTVPAGAKST VFFTITVGPF STLLDVDIIL  180
SGTVRYFYNL GHRIKGPTIY DLDLDIATTG YFYFESSPID IKTIFQSQNI PGVTYPSDGS  240
VRIQGQLQLT GEVGLISKLT QKTAGVTGPP VTKELSSKLA PKTIIF                286

SEQ ID NO: 325         moltype = AA  length = 569
FEATURE                Location/Qualifiers
source                 1..569
                       mol_type = protein
                       organism = Bacillus sp.
SEQUENCE: 325
MLQCPCTMKS IYSINNTTRK DDLMKYKDRK DAKRKYKQVI LTTVATMTLG VSTLGPTASA  60
LAAEGDNISV ISSLETQTEN TKLSESNFVD TVKAKIDVLN SEKDKLKPVG KFMGTTILEL  120
IKYANKGPEQ MNDTLRAITM ASIEVIPYGG MFIAPLIGAI WPQTNDINSQ LKALREELTK  180
LVTNEIDNEQ LNFLNSEFKT LIDLQRDLEK AINADNSQNA DENTKNQRGV WANGIEQSFR  240
RLLEHTSNPE HKITNLPIYT KVALAHLLFL DSLNNKAVSS KMNITQQSLK ELYTKDGVKT  300
LANDHVLLIM QTFYDAPQIK KIKQVPEFHF NPDDAENQIK DLKDRLSKVK VQYNEWRDGV  360
MSAGGFGMVP NKEYEFNIAI LEDAISSYEF VEKLYNATVG DPMIKELIKD SGNQEIKELA  420
KDSSEVFVAD TTYKIVYSKA NKVVDFGEHG IELPLIWYDH SGKNQRWEFK YDADKKAYQI  480
INRADGRILA YNTTPNADDT ALVTENQHKP EHYWILEDAG AGNVLLVNYE NKNKVLDVYD  540
EKTDDGSRVY VRDKLNNSNA QKFKLVISL                                   569

SEQ ID NO: 326         moltype = AA  length = 546
FEATURE                Location/Qualifiers
REGION                 1..546
                       note = Description of Artificial Sequence: Synthetic
                        polypeptide
source                 1..546
                       mol_type = protein
                       organism = synthetic construct
SEQUENCE: 326
MKYKDRKDAK RKYKQVILTT VATMTLGVST LGPTASALAA EGDNISVISS LETQTENTKL  60
SESNFVDTVK AKIDVLNSEK DKLKPVGKFM GTTILELIKY ANKGPEQMND TLRAITMASI  120
EVIPYGGMFI APLIGAIWPQ TNDINSQLKA LREELTKLVT NEIDNEQLNF LNSEFKTLID  180
LQRDLEKAIN ADNSQNADEN TKNQRGVWAN GIEQSFRRLL EHTSNPEHKI TNLPIYTKVA  240
LAHLLFLDSL NNKAVSSKMN ITQQSLKELY TKDGVKTLAN DHVLLIMQTF YDAPQIKKIK  300
QVPEFHFNPD DAENQIKDLK DRLSKVKVQY NEWRDGVMSA GGFGMVPNKE YEFNIAILED  360
AISSYEFVEK LYNATVGDPM IKELIKDSGN QEIKELAKDS SEVFVADTTY KIVYSKANKV  420
VDFGEHGIEL PLIWYDHSGK NQRWEFKYDA DKKAYQIINR ADGRILAYNT TPNADDTALV  480
TENQHKPEHY WILEDAGAGN VLLVNYENKN KVLDVYDEKT DDGSRVYVRD KLNNSNAQKF  540
KLVISL                                                            546

SEQ ID NO: 327         moltype = AA  length = 510
FEATURE                Location/Qualifiers
REGION                 1..510
                       note = Description of Artificial Sequence: Synthetic
                        polypeptide
source                 1..510
                       mol_type = protein
                       organism = synthetic construct
SEQUENCE: 327
MLAAEGDNIS VISSLETQTE NTKLSESNFV DTVKAKIDVL NSEKDKLKPV GKFMGTTILE  60
LIKYANKGPE QMNDTLRAIT MASIEVIPYG GMFIAPLIGA IWPQTNDINS QLKALREELT  120
KLVTNEIDNE QLNFLNSEFK TLIDLQRDLE KAINADNSQN ADENTKNQRG VWANGIEQSF  180
RRLLEHTSNP EHKITNLPIY TKVALAHLLF LDSLNNKAVS SKMNITQQSL KELYTKDGVK  240
TLANDHVLLI MQTFYDAPQI KKIKQVPEFH FNPDDAENQI KDLKDRLSKV KVQYNEWRDG  300
VMSAGGFGMV PNKEYEFNIA ILEDAISSYE FVEKLYNATV GDPMIKELIK DSGNQEIKEL  360
AKDSSEVFVA DTTYKIVYSK ANKVVDFGEH GIELPLIWYD HSGKNQRWEF KYDADKKAYQ  420
IINRADGRIL AYNTTPNADD TALVTENQHK PEHYWILEDA GAGNVLLVNY ENKNKVLDVY  480
DEKTDDGSRV YVRDKLNNSN AQKFKLVISL                                  510
```

```
SEQ ID NO: 328          moltype = AA  length = 972
FEATURE                 Location/Qualifiers
REGION                  1..972
                        note = Description of Unknown: Organism from environmental
                         sample
source                  1..972
                        mol_type = protein
                        organism = unidentified
SEQUENCE: 328
VNLHLLLLRD ASIFGEEWGF TPSEISRFYN RQLQLTAEYS DYCVNWYKIG LDKLKGTTSK  60
SWLNYHQFRR EMTLLVLDLV ALFPNYDTHM YPIETTAQLT RDVYTDPIAF NIVTSTGFCN  120
PWSTHSGILF SEVEKDVIRS PHLFDILSSV EINTSRGGIA LNNNAYINYW SGHYLKYHKT  180
NNSRLIGVNY GRITSEKNSF ALEDRDIFEI NSTAANLANY YQKAYGVPES WFHMVKRGTS  240
STTAYLYSKT HTTLQGCTQV YESNDEIPLD RTVPVAESYS HRLSHITSHS FSKISAKSYG  300
SFPVFVWTHV SADLNNTIYP DKITQIPAVK GDEYYLGSSV VQGPGFTGGD LLKRDNPSGL  360
GTFTVTVNGS LSQRYRARIR YASTTDVDIS LYFKYGTLLG KGRFNKTMDN GTSLTYNTFK  420
YASFTSDFQF PQTQNTISIN VTNFSSGQEV YIDRIEFIPV DETYEAEQDL EAAKKAVNAL  480
FTSTKDGLKP GVTDYEVNQA ANLVECLSDD LYPNEKRLLF DAVREAKRLS GARNLLQDPD  540
FQEINGENGW TASTGIEIVE GDAVFKGRYL RLPGAREIDT ETYPTYLYQK IDEGVLKPYT  600
RYRLRGFVGS SQGLEIYTIR HQTNRIVKNV PDDLLPDVSP VNSDGSINRC SEQKYVNSRL  660
EGENRSGDAH EFSLPIDIGE LDYNENAGIW VGFKITDPEG YATLGNLELV EEGPLSGDAL  720
ERLQREEQQW KLQMPKRCEE TDRKYMAAKQ AVDRLYVDYQ DQQLNPNVEI TDLTAAQNLT  780
QSIPYVYNEM FPEIQGMNYT KFTELTNRLQ QAWSLYDQQN AITNGDFRNE LSNWNTASGV  840
NVQKINNTSV LVIPNWDGQV SQQFTVQPNQ RYVLRVTARK EGVGNGYVSI RDGGNQTETL  900
TFSASDSDTN NAYNTQVSKT NGYNTNDMYN DQTGYITKTI KFIPYTDQVW IEMSETEGMF  960
YIESVELIVD VV                                                     972

SEQ ID NO: 329          moltype = AA  length = 461
FEATURE                 Location/Qualifiers
REGION                  1..461
                        note = Description of Artificial Sequence: Synthetic
                         polypeptide
source                  1..461
                        mol_type = protein
                        organism = synthetic construct
SEQUENCE: 329
MNLHLLLLRD ASIFGEEWGF TPSEISRFYN RQLQLTAEYS DYCVNWYKIG LDKLKGTTSK  60
SWLNYHQFRR EMTLLVLDLV ALFPNYDTHM YPIETTAQLT RDVYTDPIAF NIVTSTGFCN  120
PWSTHSGILF SEVEKDVIRS PHLFDILSSV EINTSRGGIA LNNNAYINYW SGHYLKYHKT  180
NNSRLIGVNY GRITSEKNSF ALEDRDIFEI NSTAANLANY YQKAYGVPES WFHMVKRGTS  240
STTAYLYSKT HTTLQGCTQV YESNDEIPLD RTVPVAESYS HRLSHITSHS FSKISAKSYG  300
SFPVFVWTHV SADLNNTIYP DKITQIPAVK GDEYYLGSSV VQGPGFTGGD LLKRDNPSGL  360
GTFTVTVNGS LSQRYRARIR YASTTDVDIS LYFKYGTLLG KGRFNKTMDN GTSLTYNTFK  420
YASFTSDFQF PQTQNTISIN VTNFSSGQEV YIDRIEFIPV D                     461

SEQ ID NO: 330          moltype = AA  length = 433
FEATURE                 Location/Qualifiers
source                  1..433
                        mol_type = protein
                        organism = Bacillus sp.
SEQUENCE: 330
LVLSFYIAKV ILFRNKSISN VQYNFIFCNL VGILPAKLGG NIMKSMSKKV TAGLLVGATS  60
LSIWAPSSEA AAPAKNEYHT IHLAANSSIV WDVYKGWESD DAGIILWNGS RGDNEQFVFF  120
PLDGGTYAIV NKNSGKPVGL NDGSAKYWTD GVRNSGVNNV EALRQKSWTG AANEQWYLRD  180
KGNNNYEIVN QGNGKVASWA GSSVTGGYLD YVDLDNSNPS DNNRLFNIPA ASSTFSLPTL  240
PAVGTRPEAP KYTEGGANDQ QLPQTSNSVV VGASLVPCIM VKDSQASDYT KIHNSPYYTL  300
VKEEYWDKTF SAVIPAGLTR NYTFKTGMTS VDQQKMTDTL SMKIGADFGL KFGDASASIK  360
SEISKTIQTE ISTTNTEATE ETITSSVTSE PGKTTGFTEY QLATKYTLKR ADGSVVSDPW  420
VVKNNKITVA RKI                                                    433

SEQ ID NO: 331          moltype = AA  length = 391
FEATURE                 Location/Qualifiers
REGION                  1..391
                        note = Description of Artificial Sequence: Synthetic
                         polypeptide
source                  1..391
                        mol_type = protein
                        organism = synthetic construct
SEQUENCE: 331
MKSMSKKVTA GLLVGATSLS IWAPSSEAAA PAKNEYHTIH LAANSSIVWD VYKGWESDDA  60
GIILWNGSRG DNEQFVFFPL DGGTYAIVNK NSGKPVGLND GSAKYWTDGV RNSGVNNVEA  120
LRQKSWTGAA NEQWYLRDKG NNNYEIVNQG NGKVASWAGS SVTGGYLDYV DLDNSNPSDN  180
NRLFNIPAAS STFSLPTLPA VGTRPEAPKY TEGGANDQQL PQTSNSVVVG ASLVPCIMVK  240
DSQASDYTKI HNSPYYTLVK EEYWDKTFSA VIPAGLTRNY TFKTGMTSVD QQKMTDTLSM  300
KIGADFGLKF GDASASIKSE ISKTIQTEIS TTNTEATEET ITSSVTSEPG KTTGFTEYQL  360
ATKYTLKRAD GSVVSDPWVV KNNKITVARK I                                391

SEQ ID NO: 332          moltype = AA  length = 363
FEATURE                 Location/Qualifiers
```

```
REGION                1..363
                      note = Description of Artificial Sequence: Synthetic
                       polypeptide
source                1..363
                      mol_type = protein
                      organism = synthetic construct
SEQUENCE: 332
MAPAKNEYHT IHLAANSSIV WDVYKGWESD DAGIILWNGS RGDNEQFVFF PLDGGTYAIV  60
NKNSGKPVGL NDGSAKYWTD GVRNSGVNNV EALRQKSWTG AANEQWYLRD KGNNNYEIVN  120
QGNGKVASWA GSSVTGGYLD YVDLDNSNPS DNNRLFNIPA ASSTFSLPTL PAVGTRPEAP  180
KYTEGGANDQ QLPQTSNSVV VGASLVPCIM VKDSQASDYT KIHNSPYYTL VKEEYWDKTF  240
SAVIPAGLTR NYTFKTGMTS VDQQKMTDTL SMKIGADFGL KFGDASASIK SEISKTIQTE  300
ISTTNTEATE ETITSSVTSE PGKTTGFTEY QLATKYTLKR ADGSVVSDPW VVKNNKITVA  360
RKI                                                                363

SEQ ID NO: 333        moltype = AA  length = 758
FEATURE               Location/Qualifiers
source                1..758
                      mol_type = protein
                      organism = Bacillus sp.
SEQUENCE: 333
MKRDSFIQIL NYRRYFMDQL QSQPVLPYNV LSTETYNQQN QLSVIPSNAD SITDLYAEIK  60
AYWDAHGDLS KDIVQKAWDF YKTGSIDYLE LTKTLISLGS FIPEVGAFVP YVNKFLDIVW  120
PKIFGGHQST PDVFEQLKPQ IQALIDQTLT QQEKDFLDSL QAGFSGVMQL YNNKVDVWKT  180
DPTNTAYQAD VRTQIDIVRS FYEEHSALYS QKGYEMLGLP YIANITTLML MTLQSAIQSG  240
SKWGYDQTQV DSLLNGKLGL RDLITKWSQY ITNQIITYTS SSTFKAKNWN DQNKFMRQIT  300
LTCLDYVALW PTLDPMNYTG DVDLDQTRAI LSDINEASPS SNNGLATGPA PGDAVYMNTA  360
YLGELSAINF SAHIYGNNSQ YANFNGVQQQ VLTPAGSTQN VVNGGGPTYP YSIPFPSSSY  420
AVSTHLTNWV TDGQRATGFI ATFADGTSQN AYVQSYVGSG GHAYGDATPT APAGHKLSQI  480
IPISSDPFRT YVDTFVHSDL QAQNVFGSVN SAGDIIAKGI PMEKATGGEY RIVTEWVNGA  540
NAVNLAAGKA VSMSLTNATA GKYTARIRHV SAPGQTINFY LYGLRGSMVN KSYLLDTNTS  600
GVLTGRQGDY VLTTIEDIAI PSGNGIELVI TNTSGAEIVL DRIEFIPAVS NPTSLINYTV  660
TSPIAQCQSG HTTIWDGNGI TATSAEVSIT GLTQSRYIWF AGSDDKGNTF NIYNTNVTNG  720
GPYKLQDRSG QLRPFSRIRV CTTDTNPITS GTFTGNTR                          758

SEQ ID NO: 334        moltype = AA  length = 742
FEATURE               Location/Qualifiers
REGION                1..742
                      note = Description of Artificial Sequence: Synthetic
                       polypeptide
source                1..742
                      mol_type = protein
                      organism = synthetic construct
SEQUENCE: 334
MDQLQSQPVL PYNVLSTETY NQQNQLSVIP SNADSITDLY AEIKAYWDAH GDLSKDIVQK  60
AWDFYKTGSI DYLELTKTLI SLGSFIPEVG AFVPYVNKFL DIVWPKIFGG HQSTPDVFEQ  120
LKPQIQALID QTLTQQEKDF LDSLQAGFSG VMQLYNNKVD VWKTDPTNTA YQADVRTQID  180
IVRSFYEEHS ALYSQKGYEM LGLPYIANIT TLMLMTLQSA IQSGSKWGYD QTQVDSLLNG  240
KLGLRDLITK WSQYITNQII TYTSSSTFKA KNWNDQNKFM RQITLTCLDY VALWPTLDPM  300
NYTGDVDLDQ TRAILSDINE ASPSSNNGLA TGPAPGDAVY MNTAYLGELS AINFSAHIYG  360
NNSQYANFNG VQQQVLTPAG STQNVVNGGG PTYPYSIPFP SSSYAVSTHL TNWVTDGQRA  420
TGFIATFADG TSQNAYVQSY VGSGGHAYGD ATPTAPAGHK LSQIIPISSD PFRTYVDTFV  480
HSDLQAQNVF GSVNSAGDII AKGIPMEKAT GGEYRIVTEW VNGANAVNLA AGKAVSMSLT  540
NATAGKYTAR IRHVSAPGQT INFYLYGLRG SMVNKSYLLD TNTSGVLTGR QGDYVLTTIE  600
DIAIPSGNGI ELVITNTSGA EIVLDRIEFI PAVSNPTSLI NYTVTSPIAQ CQSGHTTIWD  660
GNGITATSAE VSITGLTQSR YIWFAGSDDK GNTFNIYNTN VTNGGPYKLQ DRSGQLRPFS  720
RIRVCTTDTN PITSGTFTGN TR                                           742

SEQ ID NO: 335        moltype = AA  length = 632
FEATURE               Location/Qualifiers
REGION                1..632
                      note = Description of Artificial Sequence: Synthetic
                       polypeptide
source                1..632
                      mol_type = protein
                      organism = synthetic construct
SEQUENCE: 335
MDQLQSQPVL PYNVLSTETY NQQNQLSVIP SNADSITDLY AEIKAYWDAH GDLSKDIVQK  60
AWDFYKTGSI DYLELTKTLI SLGSFIPEVG AFVPYVNKFL DIVWPKIFGG HQSTPDVFEQ  120
LKPQIQALID QTLTQQEKDF LDSLQAGFSG VMQLYNNKVD VWKTDPTNTA YQADVRTQID  180
IVRSFYEEHS ALYSQKGYEM LGLPYIANIT TLMLMTLQSA IQSGSKWGYD QTQVDSLLNG  240
KLGLRDLITK WSQYITNQII TYTSSSTFKA KNWNDQNKFM RQITLTCLDY VALWPTLDPM  300
NYTGDVDLDQ TRAILSDINE ASPSSNNGLA TGPAPGDAVY MNTAYLGELS AINFSAHIYG  360
NNSQYANFNG VQQQVLTPAG STQNVVNGGG PTYPYSIPFP SSSYAVSTHL TNWVTDGQRA  420
TGFIATFADG TSQNAYVQSY VGSGGHAYGD ATPTAPAGHK LSQIIPISSD PFRTYVDTFV  480
HSDLQAQNVF GSVNSAGDII AKGIPMEKAT GGEYRIVTEW VNGANAVNLA AGKAVSMSLT  540
NATAGKYTAR IRHVSAPGQT INFYLYGLRG SMVNKSYLLD TNTSGVLTGR QGDYVLTTIE  600
DIAIPSGNGI ELVITNTSGA EIVLDRIEFI PA                                632
```

```
SEQ ID NO: 336         moltype = AA  length = 259
FEATURE                Location/Qualifiers
source                 1..259
                       mol_type = protein
                       organism = Bacillus sp.
SEQUENCE: 336
MYNRNQVNLN PFNFPASDFN TISTNNPFLP DTDPTREMTI RIENPEISSN MRQIFTFSDA  60
NMFAQGLSIA NTFQPAVNPV PGTTDVYYFN ANQGLKIVNE LNDPPVEIYG TVNTTLSQTN  120
KELRDIFDPI VSVLRTILPE NTTVLLYKYL KTEIQNAFVN LIDTEYEAWI NFLNQTSFKA  180
SYTYNFIFIF SDPLTSETLI SMPVGLTIEL TSQGAQKDKI LVLSPLSYVD CNVRIQALAI  240
SQEIIETDGL PLSVLSALT                                             259

SEQ ID NO: 337         moltype = AA  length = 330
FEATURE                Location/Qualifiers
source                 1..330
                       mol_type = protein
                       organism = Bacillus sp.
SEQUENCE: 337
MMHDHLGVLA QNLLRSTVTN LPDRIGIRLG RGKNRKEEVD IMAIIHLLRE LDTYGRRYAE  60
SHGYVYVGSS TDTQNPIRLS RFDGSIPNSI VTGGVENIEL DRRTISNGTS NPLEGEFSFS  120
NAYTNSTSSK TIEGVTAGTP ISITAFANLT FAQVGLTAQI PFEVAFTNEN KNTLDVSKDY  180
TDRRTIRIPS HHQATCKYIL ERASFEKQSV LECVASGNGL LRYYRPLPSG GTSPVTQRVG  240
IAEVLQANDT PGFRILSEQA GAHFTGSGTV SGQLGLQTYI DVTIEPMPGY AGQSQKHRIP  300
VSGRSGLDIP IFDRIGSRQT AEAVRNLMSV                                  330

SEQ ID NO: 338         moltype = AA  length = 289
FEATURE                Location/Qualifiers
REGION                 1..289
                       note = Description of Artificial Sequence: Synthetic
                        polypeptide
source                 1..289
                       mol_type = protein
                       organism = synthetic construct
SEQUENCE: 338
MAIIHLLREL DTYGRRYAES HGYVYVGSST DTQNPIRLSR FDGSIPNSIV TGGVENIELD  60
RRTISNGTSN PLEGEFSFSN AYTNSTSSKT IEGVTAGTPI SITAFANLTF AQVGLTAQIP  120
FEVAFTNENK NTLDVSKDYT DRRTIRIPSH HQATCKYILE RASFEKQSVL ECVASGNGLL  180
RYYRPLPSGG TSPVTQRVGI AEVLQANDTP GFRILSEQAG AHFTGSGTVS GQLGLQTYID  240
VTIEPMPGYA GQSQKHRIPV SGRSGLDIPI FDRIGSRQTA EAVRNLMSV             289

SEQ ID NO: 339         moltype = AA  length = 542
FEATURE                Location/Qualifiers
source                 1..542
                       mol_type = protein
                       organism = Bacillus sp.
SEQUENCE: 339
MKYKDRIQAK RNYKQAIFAA ATTLTLGVSA LAGPASAFAA EKEQAVTQQQ DTTQQKSTSI  60
PSYGINTYGI RSSLGKIEDW RKSMQDGSKN FKDGFTLIEK ELPFLFKDIS NHTDFNSTFR  120
NLTIISSSFI PYAGAFISPI ISLLWPDNAP NLNQILKEME QRLSNLMDEK IDKYDQTAVT  180
SEVTGMMKNL KPFESSVNGT VSYYSDGDVA SLNRDRAVAI EHSFQRLTEI SRKDGFQISE  240
LPLFTVIAAA HLNFLHLVEK IGTSDKIKFT DEALKDFLQN MKDNQATYIK YIADTYKQGE  300
DKINGKIANV GSHVRGLIID ETGSSTGDFD EQGANDAIAK LNASRPTQPT NTHDTSAMNK  360
WQAKIENINS KIKILQEGLN QYHDLVDQKT EYYNQTQNSD AFKLAAGLIT IKDIDKDDNN  420
QNTQKNGWYQ KDGNYYFNKD GVKQTGWKHI HDGNLVSDDA NGRWYYFEKD GKMHTGWLYS  480
KDGQEVSKET PGGNWYYFSK EKESGFEIGE MVRASDGYLS FKTEIDGKYY SFNAEGKCID  540
PD                                                                542

SEQ ID NO: 340         moltype = AA  length = 360
FEATURE                Location/Qualifiers
source                 1..360
                       mol_type = protein
                       organism = Bacillus sp.
SEQUENCE: 340
MKRQKSQKLK KLLMVAPLAC MLGTGVFTLP NAAHAASVGT SQSVTPPGGF DQYGQATIYT  60
KENLQTAVYM RLLNGINTSP ELRQKFKMAQ DEYIQGDSPD NHYIKPQVDA LQVAANGSSF  120
EVKPNIDSYE DLGQTNLLTI NNDDGIEKQT QVTPEVTQKY TETNTYTNQY GVKLGVDATT  180
KFSVNLPFNL GGAEQSVTIK TEFSYGRTDT NTTTNEKAVT FKSQSVVAAP GGTTTYYGTV  240
KKAKFSGSFQ TDAYVAGGLT LKLQMFNAST GNPNTHTETA TLTAEDIYTI FANNQTPLPA  300
YLSFDHQNKK VILKNATFNY QGEGGYWTAV QVKFTPKNKP AQAQLMSYDT YTKKVQDKSF  360

SEQ ID NO: 341         moltype = AA  length = 326
FEATURE                Location/Qualifiers
REGION                 1..326
                       note = Description of Artificial Sequence: Synthetic
                        polypeptide
source                 1..326
                       mol_type = protein
                       organism = synthetic construct
SEQUENCE: 341
```

```
MASVGTSQSV TPPGGFDQYG QATIYTKENL QTAVYMRLLN GINTSPELRQ KFKMAQDEYI  60
QGDSPDNHYI KPQVDALQVA ANGSSFEVKP NIDSYEDLGQ TNLLTINNDD GIEKQTQVTP  120
EVTQKYTETN TYTNQYGVKL GVDATTKFSV NLPFNLGGAE QSVTIKTEFS YGRTDTNTTT  180
NEKAVTFKSQ SVVAAPGGTT TYYGTVKKAK FSGSFQTDAY VAGGLTLKLQ MFNASTGNPN  240
THTETATLTA EDIYTIFANN QTPLPAYLSF DHQNKKVILK NATFNYQGEG GYWTAVQVKF  300
TPKNKPAQAQ LMSYDTYTKK VQDKSF                                      326

SEQ ID NO: 342          moltype = AA  length = 594
FEATURE                 Location/Qualifiers
source                  1..594
                        mol_type = protein
                        organism = Bacillus sp.
SEQUENCE: 342
MKYKDRKHAK RKYKQALLAT VATMTLGVST LGSTASVFAA EKDTKVQQQQ ADASPSTGPV  60
FKKEKDGTFT VLKKNIFNMA TLKAIGSLGG AGLKQAYADY QVDGGNFNNT FRTLAMGSAA  120
LIPYGGVVLS PLIGLLWSED KTAEANQLKK LMESISAQTH EQIAKYDTAK LSTALKDLHE  180
KVEEFENLVP IPGNGIFYSG DQLGTYENIQ ISAKALNNSF RTAIAACQTE GYKESELPIY  240
IVLATMHMNF MNYVIKNGEN LLHFDPKVLK SEFIDKQDEY IHGVHNVPGH SDKVGYIEYL  300
NSFAKKDLDD SSQVEKTVRE LEKKFAGSLR EQSIKHTVLG YSHKLEETLN ASINNIAFKQ  360
AANIKSEFTL NQNGRPLYYS LDGEMQTGWK EIGTSFATRH EIDSTNSGDQ FSRAWLKAQG  420
IQYSRYYFSP TKTDKFEQGE MYVDTTQTLP DGKTYTFDLN GKCLNPDGGK IHGLAHLGNG  480
WFYYAPKGGK ENSDHQKFDE GKIMTGWVTI DKETYYFSPQ KDSENDDHQK FDEGAMMTGW  540
VNFRSNWYYL DNSAGNKDFK GILGRMLNSE SATVKNNKGE FKLNHFKESG AAWE        594

SEQ ID NO: 343          moltype = AA  length = 556
FEATURE                 Location/Qualifiers
REGION                  1..556
                        note = Description of Artificial Sequence: Synthetic
                         polypeptide
source                  1..556
                        mol_type = protein
                        organism = synthetic construct
SEQUENCE: 343
MAEKDTKVQQ QQADASPSTG PVFKKEKDGT FTVLKKNIFN MATLKAIGSL GGAGLKQAYA  60
DYQVDGGNFN NTFRTLAMGS AALIPYGGVV LSPLIGLLWS EDKTAEANQL KKLMESISAQ  120
THEQIAKYDT AKLSTALKDL HEKVEEFENL VPIPGNGIFY SGDQLGTYEN IQISAKALNN  180
SFRTAIAACQ TEGYKESELP IYIVLATMHM NFMNYVIKNG ENLLHFDPKV LKSEFIDKQD  240
EYIHGVHNVP GHSDKVGYIE YLNSFAKKDL DDSSQVEKTV RELEKKFAGS LREQSIKHTV  300
LGYSHKLEET LNASINNIAF KQAANIKSEF TLNQNGRPLY YSLDGEMQTG WKEIGTSFAT  360
RHEIDSTNSG DQFSRAWLKA QGIQYSRYYF SPTKTDKFEQ GEMYVDTTQT LPDGKTYTFD  420
LNGKCLNPDG GKIHGLAHLG NGWFYYAPKG GKENSDHQKF DEGKIMTGWV TIDKETYYFS  480
PQKDSENDDH QKFDEGAMMT GWVNFRSNWY YLDNSAGNKD FKGILGRMLN SESATVKNNK  540
GEFKLNHFKE SGAAWE                                                  556

SEQ ID NO: 344          moltype = AA  length = 381
FEATURE                 Location/Qualifiers
source                  1..381
                        mol_type = protein
                        organism = Bacillus sp.
SEQUENCE: 344
VSNGNSNKEN LSAPLINDEE LIPSEIKASG ARVSFPDFNF YNIRTFADMY VDIKKGSMDD  60
RAGAVQYFKN NSDNQKFLIF TLDNDYSVIA AKHSGKVLDI MYFPNPMPGP KHFLVQYYFQ  120
NSDNQKFFIS NDGIIAGKID GKVWDVHNGE TWENAPIVSW DYHGAPNQKF SLVKSGSASI  180
TPPTLGTLPN APDFKTTDLN ELLPDSTEPV STHATYLPYF MVKDPYYNTK QKMQNSPYYI  240
LVRRQYWEKI TQRVLGAGES YKFEQTTGVS RTDQTSMTET TEISIGADLG FMFKGFSAGL  300
STSITKTLSV TKSTSTTEST SKTETVTDSN PFTHTIARAK YMLINEYHVT RANGQVISSG  360
DGAYWKVPNP NQTVTRTIPR S                                            381

SEQ ID NO: 345          moltype = AA  length = 381
FEATURE                 Location/Qualifiers
REGION                  1..381
                        note = Description of Artificial Sequence: Synthetic
                         polypeptide
source                  1..381
                        mol_type = protein
                        organism = synthetic construct
SEQUENCE: 345
MSNGNSNKEN LSAPLINDEE LIPSEIKASG ARVSFPDFNF YNIRTFADMY VDIKKGSMDD  60
RAGAVQYFKN NSDNQKFLIF TLDNDYSVIA AKHSGKVLDI MYFPNPMPGP KHFLVQYYFQ  120
NSDNQKFFIS NDGIIAGKID GKVWDVHNGE TWENAPIVSW DYHGAPNQKF SLVKSGSASI  180
TPPTLGTLPN APDFKTTDLN ELLPDSTEPV STHATYLPYF MVKDPYYNTK QKMQNSPYYI  240
LVRRQYWEKI TQRVLGAGES YKFEQTTGVS RTDQTSMTET TEISIGADLG FMFKGFSAGL  300
STSITKTLSV TKSTSTTEST SKTETVTDSN PFTHTIARAK YMLINEYHVT RANGQVISSG  360
DGAYWKVPNP NQTVTRTIPR S                                            381

SEQ ID NO: 346          moltype = AA  length = 243
FEATURE                 Location/Qualifiers
source                  1..243
                        mol_type = protein
```

```
                         organism = Bacillus sp.
SEQUENCE: 346
MKGECKMTSI YLKKNECIRN LHNPPYRRIT LTVPYENRGN LKNIFQLEPQ YIHQALAASN  60
AFQGAIGPDL NFDFNKAWEI GQNLPRLNML LSGLNDTVVQ ETLQVSSMIS KLKGILKEYL  120
YFIDISNTTF WNEVEATITN TFTNLYTQTN SAWIFFYRST STSTSYYYNT LFAIQYATFM  180
IVVPIVFEIT VRLEKQKVLF ITIKDRSEYR VTMKLIIAFL SLQGTHNKLI EDVFYPKPQI  240
ICR                                                               243

SEQ ID NO: 347           moltype = AA  length = 237
FEATURE                  Location/Qualifiers
REGION                   1..237
                         note = Description of Artificial Sequence: Synthetic
                          polypeptide
source                   1..237
                         mol_type = protein
                         organism = synthetic construct
SEQUENCE: 347
MTSIYLKKNE CIRNLHNPPY RRITLTVPYE NRGNLKNIFQ LEPQYIHQAL AASNAFQGAI  60
GPDLNFDFNK AWEIGQNLPR LNMLLSGLND TVVQETLQVS SMISKLKGIL KEYLYFIDIS  120
NTTFWNEVEA TITNTFTNLY TQTNSAWIFF YRSTSTSTSY YYNTLFAIQY ATFMIVVPIV  180
FEITVRLEKQ KVLFITIKDR SEYRVTMKLI IAFLSLQGTH NKLIEDVFYP KPQIICR     237

SEQ ID NO: 348           moltype = AA  length = 376
FEATURE                  Location/Qualifiers
source                   1..376
                         mol_type = protein
                         organism = Bacillus sp.
SEQUENCE: 348
VENNMNDDMN TVPSDSKDTL DSTINSRIID VGYYFDWLGD VLKNTGDRNM EFYPNFMGGG  60
GPYYHKRKCD LVRRVYDNYE VWGDNADSGA DTSRLIYTTP NPPSVNFSDL NSDHVSPNVV  120
FDNRFRNTTN DPQQQLTPSL SEKKTDTMRT STTTSLKVGT TITKQWSSSI SIKDVGGIGN  180
SITFEFSTEF TYTDTTEKTT TIEKTITIPS LAVNVPPKTE RRVIISLSQL TIPDRPVTFP  240
IDIGGIISGK CDVRAKDFDF DRAQSEDINI INSEVEIDRL EPWMFGTFND YLYNLMEKIQ  300
KSCPNSFVNV DNTYRLNPAQ RTLQVTGAGI LGGKVYSYLY KVETIDYSIT TGEVIGESTQ  360
YIPIPEDKDK KKIVRL                                                 376

SEQ ID NO: 349           moltype = AA  length = 372
FEATURE                  Location/Qualifiers
REGION                   1..372
                         note = Description of Artificial Sequence: Synthetic
                          polypeptide
source                   1..372
                         mol_type = protein
                         organism = synthetic construct
SEQUENCE: 349
MNDDMNTVPS DSKDTLDSTI NSRIIDVGYY FDWLGDVLKN TGDRNMEFYP NFMGGGGPYY  60
HKRKCDLVRR VYDNYEVWGD NADSGADTSR LIYTTPNPPS VNFSDLNSDH VSPNVVFDNR  120
FRNTTNDPQQ QLTPSLSEKK TDTMRTSTTT SLKVGTTITK QWSSSISIKD VGGIGNSITF  180
EFSTEFTYTD TTEKTTTIEK TITIPSLAVN VPPKTERRVI ISLSQLTIPD RPVTFPIDIG  240
GIISGKCDVR AKDFDFDRAQ SEDINIINSE VEIDRLEPWM FGTFNDYLYN LMEKIQKSCP  300
NSFVNVDNTY RLNPAQRTLQ VTGAGILGGK VYSYLYKVET IDYSITTGEV IGESTQYIPI  360
PEDKDKKKIV RL                                                     372

SEQ ID NO: 350           moltype = AA  length = 561
FEATURE                  Location/Qualifiers
REGION                   1..561
                         note = Description of Unknown: Organism from environmental
                          sample
source                   1..561
                         mol_type = protein
                         organism = unidentified
SEQUENCE: 350
MTHTDLNTRV LPPFVGEFNG IMGFWKNISS IIDMISGTST GTENTGNAEL EGILANQELL  60
STINGKLSGI NGDLSTIITN GNVNTDLLNQ LIGISNEQGI VLSGIQTQLA GIQNILATFV  120
PQVTKMLQKI EQKTDIMMHQ MVFLSKQLEE ISQKLDIINV NVLVNSTVTE ITPSYQRMTY  180
VNRQFDKLSS TYIKKYSTIK QDNSSIVDLD MTNLKALNEF AKNITQNSQN GFEFYLETFQ  240
DVMVGRTLFE RSALNTIVQL IQSKQTPKTN ASEVAKVYNF LTGLISVQAK SYATLAACRK  300
ILGLSEIDYN SILNQYIQQQ TNIFKTDVLP KLSNYVVGTN YIDPGIGRYV IPDYIKSLEA  360
DPGYVLVGFE IIKNDNDSDL IGYQAKLKQN YTIDKESVST IIVHKINEFF GKGYNKRDDG  420
TEYYPSRNCG IDELEFPEGY VITKVDFKGY VIEYRNEVTA TFYDSATGKL DKTKTITKKN  480
EKSRTFKATS MENGLHCSSK ITDTFLLPMY SFKIDTIENT IENTITSIVT CKNYLPQYLI  540
ANDLSGKEGS LVYITDDIAK E                                           561

SEQ ID NO: 351           moltype = AA  length = 509
FEATURE                  Location/Qualifiers
source                   1..509
                         mol_type = protein
                         organism = Bacillus sp.
SEQUENCE: 351
```

```
MGSAALIPYG GVVISPLIGL LSSEDKTAEA NHLKKLMESV SAQTHEQIAH YDTAKLSQAL  60
KDLKEKVAEF ENLIPIPGNG TFYSGDQIGD YENIQNSAIN LNNYFRTAIS ACQTEGYKES  120
ELPIYIILAT AHMNFMNYVI ENEKLLHFKP SVLEAEFKKK KDRYMHGSHG VSAGIDTVGY  180
IEYVNEFAKK DLDKTNQIAR DIPKSVRYQQ EASNQLDRDL RAQFVKLSTQ GASQQLEKNL  240
NKSLNNMAFK QAAGINSEFT LNQNGRPLYY SLDGKLQTGW KEIGSSFTTR HELDSDDTQI  300
PLSRGWLKNV VGLSYSWYYF SPKKTDKFEK GEMYIDTTET LPDGKTYKFD TDGKCLNPDG  360
GKISDPILSG TYKIVSKLDN NMVLNTSNHA TVLRGNNEAP WGNSWTFQYD KEKKAYLITN  420
RQNDHPGILA SDWGSKDHSF VFVTSDTSNK PEHYWTLERA EDDYFFIHNN ALPDKVLDIT  480
GNSAANGTKI NLYDKNGQNN QKFKLEKIN                                  509

SEQ ID NO: 352         moltype = AA  length = 380
FEATURE                Location/Qualifiers
source                 1..380
                       mol_type = protein
                       organism = Bacillus sp.
SEQUENCE: 352
MLPKKNKLFF TGISALTIMA SGLTIAIPTA SANTSESSPS IYPIQGTEFS DENGQVISPG  60
AFATISPYWL INDSNDQLLN FYNQVKQKLL DKQNTEQNML KLDEYLNDLW FVGAVSELYA  120
TPTDYNKRLE ASQLVRWYKN NNAARPTFEI LESKLENVEP ILDITEPIGY FATESEYTNN  180
SPHKGEYLIP GWSNTTSTTY NTTTTKGFSI GANSGIEIPL PFMDKLGLTG SYNFSKTENV  240
STTDSTTLTI PVQTIQVSPF SHSKTSFYFQ THQYRAKFDV TAKFKADVGR DAEYTKKRSA  300
FYLLAKYNEY LPKGIVVENG GKLTLEGKGE ISVPNHINGF KLVKETKETP LLGGESKTTK  360
EIYTKDPDTN KLIPDSSSKY                                            380

SEQ ID NO: 353         moltype = AA  length = 349
FEATURE                Location/Qualifiers
REGION                 1..349
                       note = Description of Artificial Sequence: Synthetic
                        polypeptide
source                 1..349
                       mol_type = protein
                       organism = synthetic construct
SEQUENCE: 353
MNTSESSPSI YPIQGTEFSD ENGQVISPGA FATISPYWLI NDSNDQLLNF YNQVKQKLLD  60
KQNTEQNMLK LDEYLNDLWF VGAVSELYAT PTDYNKRLEA SQLVRWYKNN NAARPTFEIL  120
ESKLENVEPI LDITEPIGYF ATESEYTNNS PHKGEYLIPG WSNTTSTTYN TTTTKGFSIG  180
ANSGIEIPLP FMDKLGLTGS YNFSKTENVS TTDSTTLTIP VQTIQVSPFS HSKTSFYFQT  240
HQYRAKFDVT AKFKADVGRD AEYTKKRSAF YLLAKYNEYL PKGIVVENGG KLTLEGKGEI  300
SVPNHINGFK LVKETKETPL LGGESKTTKE IYTKDPDTNK LIPDSSSKY              349

SEQ ID NO: 354         moltype = AA  length = 337
FEATURE                Location/Qualifiers
source                 1..337
                       mol_type = protein
                       organism = Bacillus sp.
SEQUENCE: 354
MRMRKKLVKK ALVIAAIASM GTTLAIVSPN LVSADTINTL INNSQKEMKN GSILDWKEEI  60
FYALEVVGEN EAVKIPGASA YNWTDSMGKE RGYYDVVYHQ FSVEAGDSPI ITNSTNVFVG  120
KTTLTNDTDL EQTLSTNSFE KTFVNTITNS TTSGYNLGVT ASAKFSILSI FETGIEMSTE  180
YDFSNTSVTE KKDEYKYIAT PQLIKVPAHS AVEVLVTLDT VKAHGGVKLL TKMSGRDTGH  240
FMYYDVDNRK DKPYNYDLTF HQIVDNASKS AQLENVSANP DGKTINLVGF GEYEATYGTE  300
FSVTVRPVEK HRNSIKKRDI ADGSYTYKIK PEILKIN                          337

SEQ ID NO: 355         moltype = AA  length = 304
FEATURE                Location/Qualifiers
REGION                 1..304
                       note = Description of Artificial Sequence: Synthetic
                        polypeptide
source                 1..304
                       mol_type = protein
                       organism = synthetic construct
SEQUENCE: 355
MDTINTLINN SQKEMKNGSI LDWKEEIFYA LEVVGENEAV KIPGASAYNW TDSMGKERGY  60
YDVVYHQFSV EAGDSPIITN STNVFVGKTT LTNDTDLEQT LSTNSFEKTF VNTITNSTTS  120
GYNLGVTASA KFSILSIFET GIEMSTEYDF SNTSVTEKKD EYKYIATPQL IKVPAHSAVE  180
VLVTLDTVKA HGGVKLLTKM SGRDTGHFMY YDVDNRKDKP YNYDLTFHQI VDNASKSAQL  240
ENVSANPDGK TINLVGFGEY EATYGTEFSV TVRPVEKHRN SIKKRDIADG SYTYKIKPEI  300
LKIN                                                             304

SEQ ID NO: 356         moltype = AA  length = 314
FEATURE                Location/Qualifiers
source                 1..314
                       mol_type = protein
                       organism = Viridibacillus sp.
SEQUENCE: 356
MDLIVVKNIL EVRGYFMRKI TSVLLASTLV TGVIFGAGPA SVKAAEHSQK SVYQDLDERV  60
KKMSISAALP GTEYRYHTIN DAELNGSNIE SSIIENSQLL TVQESILENN LAHEVTLPTS  120
GYEHEFKETT STTNTTGWTF GYNYNATLSV MMLTASQSFS VDYNMSTSNT TEKSETRKFT  180
IPSQGIPVPA GKKYKVEYVF EKIKISGKNR INADLYGDAN YYYNNQPMSP QLLYSALNRA  240
```

```
SDKQGFEPVI RDNAEGNNRF GIRATGIGQF STEFGTRLYS KITDITNSKK PVTIETKAIP  300
VEFKTISVNT SVVE                                                    314

SEQ ID NO: 357         moltype = AA  length = 298
FEATURE                Location/Qualifiers
REGION                 1..298
                       note = Description of Artificial Sequence: Synthetic
                        polypeptide
source                 1..298
                       mol_type = protein
                       organism = synthetic construct
SEQUENCE: 357
MRKITSVLLA STLVTGVIFG AGPASVKAAE HSQKSVYQDL DERVKKMSIS AALPGTEYRY  60
HTINDAELNG SNIESSIIEN SQLLTVQESI LENNLAHEVT LPTSGYEHEF KETTSTTNTT  120
GWTFGYNYNA TLSVMMLTAS QSFSVDYNMS TSNTTEKSET RKFTIPSQGI PVPAGKKYKV  180
EYVFEKIKIS GKNRINADLY GDANYYYNNQ PMSPQLLYSA LNRASDKQGF EPVIRDNAEG  240
NNRFGIRATG IGQFSTEFGT RLYSKITDIT NSKKPVTIET KAIPVEFKTI SVNTSVVE    298

SEQ ID NO: 358         moltype = AA  length = 271
FEATURE                Location/Qualifiers
REGION                 1..271
                       note = Description of Artificial Sequence: Synthetic
                        polypeptide
source                 1..271
                       mol_type = protein
                       organism = synthetic construct
SEQUENCE: 358
MAEHSQKSVY QDLDERVKKM SISAALPGTE YRYHTINDAE LNGSNIESSI IENSQLLTVQ  60
ESILENNLAH EVTLPTSGYE HEFKETTSTT NTTGWTFGYN YNATLSVMML TASQSFSVDY  120
NMSTSNTTEK SETRKFTIPS QGIPVPAGKK YKVEYVFEKI KISGKNRINA DLYGDANYYY  180
NNQPMSPQLL YSALNRASDK QGFEPVIRDN AEGNNRFGIR ATGIGQFSTE FGTRLYSKIT  240
DITNSKKPVT IETKAIPVEF KTISVNTSVV E                                 271

SEQ ID NO: 359         moltype = AA  length = 661
FEATURE                Location/Qualifiers
REGION                 1..661
                       note = Description of Unknown: Organism from environmental
                        sample
source                 1..661
                       mol_type = protein
                       organism = unidentified
SEQUENCE: 359
MNKNNNSSEL GINDTGASHP SNSIVEVPCS ECGGIDYRDV MNMSTQNAYV EQQSVVGAAT  60
TTSFQVIREL YRSNKGILST AGGIIKSIFG FLWKKEHAQT QWEEFMKSVE LMIDEKIDTA  120
VMSAAISKLA SLEALLALHQ DYLDDLAADP SNSNLQELVR EHVINLQDFF VYTMPQLSQS  180
PYQVQQLVAY AEAANLHLAF LRDVVMFGSQ WGMQPATIDT YYKNLENNIK VYTNYCVNTY  240
NIGLEKTKNL MGSINPKNYD KYPYLNPHAN NSTNNYKKVL QWNVWNDFRR NMTIMVLDLV  300
VVFPTYDPKV YTNLEGIEIE LSREVYSTSY NRYGDSTHGG DWKGWEILET SVVRPPHLVS  360
FLSNLAFYMA NYANAPTNTG LDQYNGVINT LRNIDSTSTW EDGFAPITKK EYTTVKDIPG  420
DFIKEINMNS GVDPCFLNFI TNSSGTHSVG TCYRSSIQGP IYNLSATIPY HRLSYVNGMD  480
DNFSESFSGW GISAWGFGWL HESLKTSNVI HATRSSFIPA VKSYGLWGGA TVIKGPGSTG  540
GDLVRLPAAP GVIQVRLPVT RQAVKQYKIR IRYAAQENGE LFVGKWANRW WETANLSLIK  600
TTSSNTPSYS EFKLIDAFIM TTNESAFQIE LRNDSGGPIL IDRIEFIPIQ GTLEEYEATQ  660
N                                                                  661

SEQ ID NO: 360         moltype = AA  length = 287
FEATURE                Location/Qualifiers
REGION                 1..287
                       note = Description of Unknown: Organism from environmental
                        sample
source                 1..287
                       mol_type = protein
                       organism = unidentified
SEQUENCE: 360
MFDINRLINE YQGYLQATGF VGIPGLPNIP YNAVFINEKR IEVTGAVDIP QYQIPISAIT  60
TAPLVVKTSN FTNRSSTPQE ETFSYSETVT DSISTTRTEG ATFDISSKTT VAVKIPEIVD  120
ISEEITVTTS ISNTNSTEIS YSKQTAWSNS LRLTVPAGKK MVAQATLTQA NFSTTVDADV  180
ILSGYVVYRA VIPLRNGGFQ NNDISVPIQT LIDWAKSRPD IASSVGFVSS NATNLSDGTV  240
RYAGKMKIQG RMGLASDVIV TETDLTGKPI STTTLDSTQA PRTILFQ                287

SEQ ID NO: 361         moltype = AA  length = 346
FEATURE                Location/Qualifiers
source                 1..346
                       mol_type = protein
                       organism = Bacillus sp.
SEQUENCE: 361
MRFYRTSKEK IIMKRYKKLL IVAPLACMLS VGMFTSPNAA HADATVRNTH VLNTKEEAPF  60
SPAQLQADIK ERLLTSMQTR FPEAGFQKTD IIGDLDLSKI QFGTISVDQN IKADAQVDSY  120
TDLGQTNLLT YNNNDGIVPQ QASTPETTIK QTETSSYSNT EGLKLGASAS FKLGVSIPFI  180
```

```
GEGGTKMTVS SEFNYAHSDT QTSSKETDVT FKSQSVVAAP GGTTTYYGSV KTANFSALFH  240
GSKAPLENVN LAFNVYGNPG GSGGVSMVGE FLYDIFKYGG KAVPSYLTLD DTNKRVLVNH  300
DSSFKVTGQG GFYTQIMVKF TPKDKNKAPQ TMPYEEYVKK ERTKTL                 346

SEQ ID NO: 362          moltype = AA  length = 334
FEATURE                 Location/Qualifiers
REGION                  1..334
                        note = Description of Artificial Sequence: Synthetic
                         polypeptide
source                  1..334
                        mol_type = protein
                        organism = synthetic construct
SEQUENCE: 362
MKRYKKLLIV APLACMLSVG MFTSPNAAHA DATVRNTHVL NTKEEAPFSP AQLQADIKER  60
LLTSMQTRFP EAGFQKTDII GDLDLSKIQF GTISVDQNIK ADAQVDSYTD LGQTNLLTYN  120
NNDGIVPQQA STPETTIKQT ETSSYSNTEG LKLGASASFK LGVSIPFIGE GGTKMTVSSE  180
FNYAHSDTQT SSKETDVTFK SQSVVAAPGG TTTYYGSVKT ANFSALFHGS KAPLENVNLA  240
FNVYGNPGGS GGVSMVGEFL YDIFKYGGKA VPSYLTLDDT NKRVLVNHDS SFKVTGQGGF  300
YTQIMVKFTP KDKNKAPQTM PYEEYVKKER TKTL                              334

SEQ ID NO: 363          moltype = AA  length = 305
FEATURE                 Location/Qualifiers
REGION                  1..305
                        note = Description of Artificial Sequence: Synthetic
                         polypeptide
source                  1..305
                        mol_type = protein
                        organism = synthetic construct
SEQUENCE: 363
MDATVRNTHV LNTKEEAPFS PAQLQADIKE RLLTSMQTRF PEAGFQKTDI IGDLDLSKIQ  60
FGTISVDQNI KADAQVDSYT DLGQTNLLTY NNNDGIVPQQ ASTPETTIKQ TETSSYSNTE  120
GLKLGASASF KLGVSIPFIG EGGTKMTVSS EFNYAHSDTQ TSSKETDVTF KSQSVVAAPG  180
GTTTYYGSVK TANFSALFHG SKAPLENVNL AFNVYGNPGG SGGVSMVGEF LYDIFKYGGK  240
AVPSYLTLDD TNKRVLVNHD SSFKVTGQGG FYTQIMVKFT PKDKNKAPQT MPYEEYVKKE  300
RTKTL                                                              305

SEQ ID NO: 364          moltype = AA  length = 473
FEATURE                 Location/Qualifiers
source                  1..473
                        mol_type = protein
                        organism = Bacillus sp.
SEQUENCE: 364
MVNRNMNNGS SKVEMNQTTG YQNDASKYGA DMNNTIYENG TNISNNEEKI SCENAGCITA  60
TEDNLNPDPF ENSLLSNQWN MLPEESKMFA SYGSIYGGLY IWRQTNLPIQ FNEGCLGNYR  120
ENPLFNSIPL ISDLNHHRFI FFQIDDGRFV IVNRMDGKLI EWFTVGDGEY QICSNGWKGE  180
LDQTWSKIQI NSTNFRLAER SKSMNVCGWR NNQEVKYTAI NSSNNNDTNL HFRKSSLLES  240
LPVQMPILPA KQPLPPLPII DSLHDVPPVE SEKAITGGSL VPCIMINDTG VPLAQRIKDN  300
PYYIIVKRQY WKRLWSYVFT PGYSQKVMEK TGITNTTQTS IKNTLNIGIN ADFKLNFLKI  360
LDSLKLSTSY ALETSLTQTT VELTESTIEQ TYTNPNNHDT AWARYALATE YSLVRPNTNI  420
TVNKWEVVDG TVLRDQSFPH NQSLEWTDSQ TISSDNYNNG DPFTTPKLIK SLK         473

SEQ ID NO: 365          moltype = AA  length = 188
FEATURE                 Location/Qualifiers
source                  1..188
                        mol_type = protein
                        organism = Bacillus sp.
SEQUENCE: 365
VNDCIMALHS NSSSDNIDNS IITSKQSMTD NYSAEPLTPN NKIPFSFFVQ LPNGFIYPTK  60
QQTKLVYNMN YLTLSQEIVK HPIQVNHLGT IDIDLQVLKV KGCLPVYFNI PISPISLEHM  120
CTIHREFPLL YMGYQDIISV DHIIKCSTGT LPYYLLDCEH IKVCDLQVQS VQNDKSIQIS  180
GEFELLYA                                                           188

SEQ ID NO: 366          moltype = AA  length = 180
FEATURE                 Location/Qualifiers
source                  1..180
                        mol_type = protein
                        organism = Lysobacter sp.
SEQUENCE: 366
MKVREQHYGR LVFPSCQATI ATRPVGYRRC REGDRTLDSP PTKETAAMSD STSRKQSKDA  60
ARSVVVTLRN NTPFDLQLNR NTESLPHGKW DEYPPAFIRS GDKGAWKTES DELMSGTEGR  120
VSYNILDQSH NSVSVNWDDP FQGSDADGGS VSDTNRYKLD TPGPISGNNV EMDFTLRYLG  180

SEQ ID NO: 367          moltype = AA  length = 133
FEATURE                 Location/Qualifiers
REGION                  1..133
                        note = Description of Artificial Sequence: Synthetic
                         polypeptide
source                  1..133
                        mol_type = protein
```

```
                         organism = synthetic construct
SEQUENCE: 367
MSDSTSRKQS KDAARSVVVT LRNNTPFDLQ LNRNTESLPH GKWDEYPPAF IRSGDKGAWK  60
TESDELMSGT EGRVSYNILD QSHNSVSVNW DDPFQGSDAD GGSVSDTNRY KLDTPGPISG  120
NNVEMDFTLR YLG                                                    133

SEQ ID NO: 368           moltype = AA  length = 526
FEATURE                  Location/Qualifiers
source                   1..526
                         mol_type = protein
                         organism = Bacillus sp.
SEQUENCE: 368
MNVNHDISCG CGCQQDNNEY EPKQYNEEYN NSHVSNEYRQ QNYQELSCGS NQGMTYPMID  60
KSMQKDRNGE NTSYSGYDGY SPTQFSTFSP SLPVESTRFQ RITNMGIFNR NLNAVNNSDG  120
DFLGNLQDWR CQHIDYDNTV TSELPDLSQD TAFFIYYQLD DGSFVIANRG NGRVLEVRNS  180
RINIFVTISN AFNPNHFNNT SDLDQREQRF RIERTTSNEF YLVAASNPRR VVHVCSGNQI  240
NVLNKIVAGD VSGRVFTFHN VNVPTIPVNT TLPAPTELAL PPALTSIDDL GVDPEHAPRA  300
VVGSTLIPAI AVNDPVIPVA NRVRESPYYV LTRNRYWHKV FAITVPGTNI PQSSIVNLGI  360
SDGAQNSMNQ TIGVQIGADN GLQFSLTGLT NPFQRQISTG LNTTVSQTGT RLGTMQREFT  420
YQNRGDLGRV VQYVRADEYV LTRANGTQVT TPWVVLDSHV DVVRTCAPGV NAGGQGCNGI  480
MILSLAQDKI ICASNSYDLS VRKTPKKIKD GEINMKNECN FKPYYE                526

SEQ ID NO: 369           moltype = AA  length = 897
FEATURE                  Location/Qualifiers
source                   1..897
                         mol_type = protein
                         organism = Bacillus sp.
SEQUENCE: 369
VLDMNDNKNC TCTYTCTCGY SNEQPMPYHY PIPGSYPNDG ISTVLSSYSS EDATTISLAV  60
NQEKLVGLVG YYFKDREFKE LMFIQVGEKS NLVARARGNE NLQYIQSIRW MGNIKVTKTG  120
SYTFSTSFDR DVILQINGKT TMERGSEPKS IYLEENKICE IKLEYLCAVD LIKKLPLHPQ  180
LQLMYSIDNA TKMPIPDIQI LSPNFAEKAE LPSEKADQVL LPNYNLFNPE SRSGLATELD  240
YDKDGIPDDW EINGYTFRKR QIVPWDDAYA QEGRKKYVSN PAKARTAADP YTDFEKVAGL  300
MPEATKLDAR DPLIAAYPSV GVGMESFHFS KNDTVQEGAS GTKTKSVTKT STTSETAELS  360
MKFGFSKDAF VFDFSPKYSQ SWSNSTSVQD TESSTWSSQI GINTAERAYL NANIRYYNEG  420
NAPIYDVSPT TNFILQKFGQ SIATITAGPN QIGHSLAPGD TYPAKGLGPI SLDKANATGT  480
IKISVDALTL DKIQSNGEVL QLETPQSSGQ FGKLDEMGTP IIGGEWNPYL TNIDATSGAL  540
TLYLGKGKGS LERRVAAPSL TDPDDETPII TLKEAIKKAF NATEIDGRLF YMDEGGNYIF  600
IDESAVNIIT DEATKQEINN QLSNLSDKKV YNVTWKRKMK ITICAPTKYY DFEDSTDSGW  660
SYPSHDGGFT GQKKMDIPPV GSATTKQNLN LKKNTTYTAR AYVKNSNSSG KNNVTFFVDN  720
NMGSGSGVKV TGILEGTQGN QWQLVEIKFN TDENPEFFSR IGFLNNGTGY LHVDDVSVTE  780
WRTYPSLPSY YRFHKWHGWN YDGKNLDYTK VYFQKGLDPS IYESVPKYKI SINGRTPYTV  840
DRPALQSDGR LSLPLSTGYQ IGEGSLIEIW AITSTEKVVK ILTRWTSRED AEISFWP     897

SEQ ID NO: 370           moltype = AA  length = 894
FEATURE                  Location/Qualifiers
REGION                   1..894
                         note = Description of Artificial Sequence: Synthetic
                          polypeptide
source                   1..894
                         mol_type = protein
                         organism = synthetic construct
SEQUENCE: 370
MNDNKNCTCT YTCTCGYSNE QPMPYHYPIP GSYPNDGIST VLSSYSSEDA TTISLAVNQE  60
KLVGLVGYYF KDREFKELMF IQVGEKSNLV ARARGNENLQ YIQSIRWMGN IKVTKTGSYT  120
FSTSFDRDVI LQINGKTTME RGSEPKSIYL EENKICEIKL EYLCAVDLIK KLPLHPQLQL  180
MYSIDNATKM PIPDIQILSP NFAEKAELPS EKADQVLLPN YNLFNPESRS GLATELDYDK  240
DGIPDDWEIN GYTFRKRQIV PWDDAYAQEG RKKYVSNPAK ARTAADPYTD FEKVAGLMPE  300
ATKLDARDPL IAAYPSVGVG MESFHFSKND TVQEGASGTK TKSVTKTSTT SETAELSMKF  360
GFSKDAFVFD FSPKYSQSWS NSTSVQDTES STWSSQIGIN TAERAYLNAN IRYYNEGNAP  420
IYDVSPTTNF ILQKFGQSIA TITAGPNQIG HSLAPGDTYP AKGLGPISLD KANATGTIKI  480
SVDALTLDKI QSNGEVLQLE TPQSSGQFGK LDEMGTPIIG GEWNPYLTNI DATSGALTLY  540
LGKGKGSLER RVAAPSLTDP DDETPIITLK EAIKKAFNAT EIDGRLFYMD EGGNYIFIDE  600
SAVNIITDEA TKQEINNQLS NLSDKKVYNV TWKRKMKITI CAPTKYYDFE DSTDSGWSYP  660
SHDGGFTGQK KMDIPPVGSA TTKQNLNLKK NTTYTARAYV KNSNSSGKNN VTFFVDNNMG  720
SGSGVKVTGI LEGTQGNQWQ LVEIKFNTDE NPEFFSRIGF LNNGTGYLHV DDVSVTEWRT  780
YPSLPSYYRF HKWHGWNYDG KNLDYTKVYF QKGLDPSIYE SVPKYKISIN GRTPYTVDRP  840
ALQSDGRLSL PLSTGYQIGE GSLIEIWAIT STEKVVKILT RWTSREDAEI SFWP        894

SEQ ID NO: 371           moltype = AA  length = 669
FEATURE                  Location/Qualifiers
source                   1..669
                         mol_type = protein
                         organism = Bacillus sp.
SEQUENCE: 371
VKKMNSYQNT NEYEILESSS NNTNMPNRYP FANDRDMSPM SWNDCQGTSW QDVWESSTSI  60
AGIGIDLINF VAEPSLGGVN LLFSIIGKLI PPNRQSISAL SICDLLSIIR KEVAESVLNA  120
AIADFNGKLK NYREYYLSYL EAWLKDGKPL KKTNNSDIGK LVEYFELSER EFNEILGGSL  180
ARSNAQILLL PTFAQAANVQ LLLLRDAVQY KEQWFPFLSA ENVKSELKSP NSGCDFTGDY  240
```

```
YERLKCKTAE YTNYCVYWYQ AGLDQIKQAG TGADTWSKFN KFRREMTLAV LDIIAIFPTY  300
DFEKYPLATD VELTREIYTD AVGYSSGTYS WLNYWTGAFN ALEANGTRGP GLVTWLSSIG  360
IYNEYVSRYF SGWVGTRHYE DYTKGNGTFQ RMSGTTSNDL RNVTFSPFDI FKISSLAIMN  420
LAGETNPRPE YRVSRTEFSS TSLPSKHLYD ANNNGLSRMT IESTLPGIWN PKPSYTDYSH  480
RLSNAACVVY GNSRVNVYGW THTSMSKHNP IYPDKISQIP AVKAFALESG AYVSAGPGHT  540
GGNVVWLPYL GRLKIRLTSA PTNKNYRVRV RYAGLYSGRL MVQRWSLSGS ATGDFPYSST  600
GSNNTFGYVE TLVTTFNQSG VEIIIQNQTS PQLIIDKIEF IPVDLTNLEY EGEQNLEKTK  660
NAVNDLFIN                                                         669

SEQ ID NO: 372         moltype = AA  length = 666
FEATURE                Location/Qualifiers
REGION                 1..666
                       note = Description of Artificial Sequence: Synthetic
                        polypeptide
source                 1..666
                       mol_type = protein
                       organism = synthetic construct
SEQUENCE: 372
MNSYQNTNEY EILESSSNNT NMPNRYPFAN DRDMSPMSWN DCQGTSWQDV WESSTSIAGI  60
GIDLINFVAE PSLGGVNLLF SIIGKLIPPN RQSISALSIC DLLSIIRKEV AESVLNAAIA  120
DFNGKLKNYR EYYLSYLEAW LKDGKPLKKT NNSDIGKLVE YFELSEREFN EILGGSLARS  180
NAQILLLPTF AQAANVQLLL LRDAVQYKEQ WFPFLSAENV KSELKSPNSG CDFTGDYYER  240
LKCKTAEYTN YCVYWYQAGL DQIKQAGTGA DTWSKFNKFR REMTLAVLDI IAIFPTYDFE  300
KYPLATDVEL TREIYTDAVG YSSGTYSWLN YWTGAFNALE ANGTRGPGLV TWLSSIGIYN  360
EYVSRYFSGW VGTRHYEDYT KGNGTFQRMS GTTSNDLRNV TFSPFDIFKI SSLAIMNLAG  420
ETNPRPEYRV SRTEFSSTSL PSKHLYDANN NGLSRMTIES TLPGIWNPKP SYTDYSHRLS  480
NAACVVYGNS RVNVYGWTHT SMSKHNPIYP DKISQIPAVK AFALESGAYV SAGPGHTGGN  540
VVWLPYLGRL KIRLTSAPTN KNYRVRVRYA GLYSGRLMVQ RWSLSGSATG DFPYSSTGSN  600
NTFGYVETLV TTFNQSGVEI IIQNQTSPQL IIDKIEFIPV DLTNLEYEGE QNLEKTKNAV  660
NDLFIN                                                            666

SEQ ID NO: 373         moltype = AA  length = 640
FEATURE                Location/Qualifiers
REGION                 1..640
                       note = Description of Artificial Sequence: Synthetic
                        polypeptide
source                 1..640
                       mol_type = protein
                       organism = synthetic construct
SEQUENCE: 373
MNSYQNTNEY EILESSSNNT NMPNRYPFAN DRDMSPMSWN DCQGTSWQDV WESSTSIAGI  60
GIDLINFVAE PSLGGVNLLF SIIGKLIPPN RQSISALSIC DLLSIIRKEV AESVLNAAIA  120
DFNGKLKNYR EYYLSYLEAW LKDGKPLKKT NNSDIGKLVE YFELSEREFN EILGGSLARS  180
NAQILLLPTF AQAANVQLLL LRDAVQYKEQ WFPFLSAENV KSELKSPNSG CDFTGDYYER  240
LKCKTAEYTN YCVYWYQAGL DQIKQAGTGA DTWSKFNKFR REMTLAVLDI IAIFPTYDFE  300
KYPLATDVEL TREIYTDAVG YSSGTYSWLN YWTGAFNALE ANGTRGPGLV TWLSSIGIYN  360
EYVSRYFSGW VGTRHYEDYT KGNGTFQRMS GTTSNDLRNV TFSPFDIFKI SSLAIMNLAG  420
ETNPRPEYRV SRTEFSSTSL PSKHLYDANN NGLSRMTIES TLPGIWNPKP SYTDYSHRLS  480
NAACVVYGNS RVNVYGWTHT SMSKHNPIYP DKISQIPAVK AFALESGAYV SAGPGHTGGN  540
VVWLPYLGRL KIRLTSAPTN KNYRVRVRYA GLYSGRLMVQ RWSLSGSATG DFPYSSTGSN  600
NTFGYVETLV TTFNQSGVEI IIQNQTSPQL IIDKIEFIPV                       640

SEQ ID NO: 374         moltype = AA  length = 567
FEATURE                Location/Qualifiers
source                 1..567
                       mol_type = protein
                       organism = Bacillus sp.
SEQUENCE: 374
VSPMFTSGTK NTLKIETTDY EIDQAAISIE CMSDEQNSQE KMMLWDEVKQ AKQLSQSRNL  60
LGNGDFGDFS GNDWTFGNDI IIGSNSPIFK GHYLHMFGAR DIYGTLFPTY IYQKIEESKL  120
KPYTRYRVRG FVGSSKDLKL MVTRYGKEID AMMDVPDDLA YMQPGPSCGD YRCESSSQYV  180
SQGYPTLYAD GYASDRYACP ADRVKKHVKC HDRHSFDFHI DTGELDINQN LGIWVLFKIS  240
NPDGYATLGN LEVIEEGPLT DEALAHVKQK EKKWHQHMEK KRLETKQAYD PAKQAVDALF  300
TNVQGEELHY HITLDHIQNA NQLVQSIPYV HHAWLPDAPG MNYDLYQGLN ARIMQAYNLY  360
AVRNVITNGD FTQGLQGWHT TGKAVVQQMD GTSVLVLSNW SAGVSQNLHV QDHHGYVLRV  420
IAKKEGPGKG YVTMMDCNGN QETLRFTSCE EGYITKTVEA FPESNRVRIE IGETEGTFYV  480
DSIELLCMQG YASNNNRHTG NRYEESYNGN YKQNTSDVYH QGHTNNDNQD SSSMYNQNYI  540
NNDDLHFGCA CNQGHNSGCT CNQGYNR                                     567

SEQ ID NO: 375         moltype = AA  length = 487
FEATURE                Location/Qualifiers
source                 1..487
                       mol_type = protein
                       organism = Bacillus sp.
SEQUENCE: 375
VKHMNSDQQK YEQNNEYRHQ NHGVSCNCGC QQGKYEYEQK QNHEGIGYPV ANQVMRNDMY  60
DSVKKEFRVY NMCHENKNYY SCSPRQFNTF TLPEESLRFQ TITCHLSNEK RGIDALRTYV  120
GQQLGQGLAN YCRIVKVQNQ VTNDYVHDGG NRQRFLFYST DSGDFVIANQ QYGEVLAYVD  180
DGESIVTQLY NGNSRQFFRK VNTSTDKFRL MIDSETAIAP CGNVNNWTRM AGFAFANNET  240
```

```
ELFYNQTDQN VSITIPALST PTELGPPPVL TSLSDAGPSP EQATRAVIGS ALIPCIFVND  300
IIPLDRRIQE SPYYKLEYRQ YWHRLWTDEI PSGDRRSFDE VTGISPDAQT SMRNMIDISI  360
GADFGLRFGN NSTPFKSGIL HGLNKLESYA NTDLGSKKAT DFRLNPNPFP VRYARFVIAH  420
EYRLTRANGT LVITPWVALD HRAPQTSKFP PDAQSLQKHK IISSDNSYDL PILEHSETVT  480
RETGNCF                                                            487

SEQ ID NO: 376         moltype = AA  length = 484
FEATURE                Location/Qualifiers
REGION                 1..484
                       note = Description of Artificial Sequence: Synthetic
                        polypeptide
source                 1..484
                       mol_type = protein
                       organism = synthetic construct
SEQUENCE: 376
MNSDQQKYEQ NNEYRHQNHG VSCNCGCQQG KYEYEQKQNH EGIGYPVANQ VMRNDMYDSV  60
KKEFRVYNMC HENKNYYSCS PRQFNTFTLP EESLRFQTIT CHLSNEKRGI DALRTYVGQQ  120
LGQGLANYCR IVKVQNQVTN DYVHDGGNRQ RFLFYSTDSG DFVIANQQYG EVLAYVDDGE  180
SIVTQLYNGN SRQFFRKVNT STDKFRLMID SETAIAPCGN VNNWTRMAGF AFANNETELF  240
YNQTDQNVSI TIPALSTPTE LGPPPVLTSL SDAGPSPEQA TRAVIGSALI PCIFVNDIIP  300
LDRRIQESPY YKLEYRQYWH RLWTDEIPSG DRRSFDEVTG ISPDAQTSMR NMIDISIGAD  360
FGLRFGNNST PFKSGILHGL NKLESYANTD LGSKKATDFR LNPNPFPVRY ARFVIAHEYR  420
LTRANGTLVI TPWVALDHRA PQTSKFPPDA QSLQKHKIIS SDNSYDLPIL EHSETVTRET  480
GNCF                                                               484

SEQ ID NO: 377         moltype = AA  length = 275
FEATURE                Location/Qualifiers
source                 1..275
                       mol_type = protein
                       organism = Bacillus sp.
SEQUENCE: 377
MNMAILNLVD ALTQAAERFA DQNNLLFGKD TLPNIRLINS KLEIPNNTIN IETNGTTIVS  60
RKEISNFTDK PTQVQVISFE RAVENSWGSK TTQGFELGAS IESSVSVDVF FGKFDVKVST  120
NFKYDTSTEQ SYESKETIIW KEDIPVVVPP RTTTIVDYII SIGGQSAIPI NFWAILNDGL  180
LAYDTPDHQI TYYIPLTGRF SPNFPSVADN LAEMFQLTIE QNPGTSIEIQ GEIEFNVAIS  240
LNSNTSIRNK PLLGNPLPES IQNLPVKPGP RTIFF                             275

SEQ ID NO: 378         moltype = AA  length = 326
FEATURE                Location/Qualifiers
source                 1..326
                       mol_type = protein
                       organism = Bacillus sp.
SEQUENCE: 378
MKRKILTAVL VGIPLCIISG NTANAQINTS PGTIPEQSSL QKLSSYQTQG SQVVNVDQVL  60
RQAIPGYAKF INGLGETSKV GVHINDVKLL DVEEKYIDPD YPIQSKLIGK GPEKLVESIE  120
EYIYNEHPSA ELTKSHTFQH GISNTSTITN SVTHNHKAGV KFTYKAKVNL LVKAAEVGGE  180
VAYEYTNSNQ TGTSDSKTLT KTFSSTASAK LPPNSKGKLV SSVYTTPATY EIKSRSFFTG  240
SVQFSYVLAN DPGTLRTTTI SLYELFSRTD EKTVDDIANN YHMWASTFWN PENGQPVNAL  300
LFEGKSILNI DETYRTETRL TDIKGI                                       326

SEQ ID NO: 379         moltype = AA  length = 302
FEATURE                Location/Qualifiers
REGION                 1..302
                       note = Description of Artificial Sequence: Synthetic
                        polypeptide
source                 1..302
                       mol_type = protein
                       organism = synthetic construct
SEQUENCE: 379
MQINTSPGTI PEQSSLQKLS SYQTQGSQVV NVDQVLRQAI PGYAKFINGL GETSKVGVHI  60
NDVKLLDVEE KYIDPDYPIQ SKLIGKGPEK LVESIEEYIY NEHPSAELTK SHTFQHGISN  120
TSTITNSVTH NHKAGVKFTY KAKVNLLVKA AEVGGEVAYE YTNSNQTGTS DSKTLTKTFS  180
STASAKLPPN SKGKLVSSVY TTPATYEIKS RSFFTGSVQF SYVLANDPGT LRTTTISLYE  240
LFSRTDEKTV DDIANNYHMW ASTFWNPENG QPVNALLFEG KSILNIDETY RTETRLTDIK  300
GI                                                                 302

SEQ ID NO: 380         moltype = AA  length = 340
FEATURE                Location/Qualifiers
source                 1..340
                       mol_type = protein
                       organism = Bacillus sp.
SEQUENCE: 380
MEFNLFDLDD YLNHNVDNVL HGPIGLWSRS MGYAPLGSWK FDQEFVPTPT SAQIPSPCNA  60
GNTLYSTCEW QPNNYDTWTV ETSNLVAGGT DVYEQIEDVA IETPIIADQH IYQNESSLQQ  120
AYVTPAYSES VTTTTNTTT NGCKINPKAS ISRKSSYKVK IYNKDKGFNL EVGAEYNFTN  180
TNTYTTTTTR TVTYPSFTTQ VPAYTTAIVT ITLNRGYYAN YNVPVEVDLF GRFRNQHAKW  240
YDPNDPDVYN YFDLYPFVEL VQTCCKSCSQ CVPNTIRALP DNKTVRYNGT GSFIADIASN  300
DYVVKTQFVD NKTGATIAEQ VEYIPAIYTN PVIETVTTSE                        340
```

```
SEQ ID NO: 381         moltype = AA  length = 375
FEATURE                Location/Qualifiers
source                 1..375
                       mol_type = protein
                       organism = Bacillus sp.
SEQUENCE: 381
VMSNENNMDT SMINDENLIP SEVLASGKQI SFPDFNFYKI RTFCGKYVDI RGGSTNEMAA  60
VQYSGNNGDN QKFLILTLDN NYSVIAAKHS GKVLDVMKLP FPINEDFLIQ YDFKNGENQK  120
FFISNDGTIA VKQDGKVWDV RGASTQNDVS IVSYDYKGAA NQKFTLEKSG SVSIKLPTTG  180
TLPPAPDFKT TNLDEELPDD TIPVITHATY LPYFMVKDPY YNAQQKITNS PYYILVRRQY  240
WEKKTQRVLA PSETYDYMET TGVSRTDQTS MTETTEISIG ADLGFMFKGF SLGLSTSITK  300
SLSVTKSTSN TESTEISKRV VYTNPFKYQI AYAKYMLINE YYVTRSNGEM ITSGDASYWK  360
VPDPERTVSR IIPRR                                                   375

SEQ ID NO: 382         moltype = AA  length = 374
FEATURE                Location/Qualifiers
REGION                 1..374
                       note = Description of Artificial Sequence: Synthetic
                        polypeptide
source                 1..374
                       mol_type = protein
                       organism = synthetic construct
SEQUENCE: 382
MSNENNMDTS MINDENLIPS EVLASGKQIS FPDFNFYKIR TFCGKYVDIR GGSTNEMAAV  60
QYSGNNGDNQ KFLILTLDNN YSVIAAKHSG KVLDVMKLPF PINEDFLIQY DFKNGENQKF  120
FISNDGTIAV KQDGKVWDVR GASTQNDVSI VSYDYKGAAN QKFTLEKSGS VSIKLPTTGT  180
LPPAPDFKTT NLDEELPDDT IPVITHATYL PYFMVKDPYY NAQQKITNSP YYILVRRQYW  240
EKKTQRVLAP SETYDYMETT GVSRTDQTSM TETTEISIGA DLGFMFKGFS LGLSTSITKS  300
LSVTKSTSNT ESTEISKRVV YTNPFKYQIA YAKYMLINEY YVTRSNGEMI TSGDASYWKV  360
PDPERTVSRI IPRR                                                    374

SEQ ID NO: 383         moltype = AA  length = 1129
FEATURE                Location/Qualifiers
REGION                 1..1129
                       note = Description of Unknown: Organism from environmental
                        sample
source                 1..1129
                       mol_type = protein
                       organism = unidentified
SEQUENCE: 383
MATLSDLYPV NVLSSSAYEK YNLIPSEAAN MDEIFKQIKD AWGKYGSVPK ELLTQAWNYY  60
NNGTIDYLAL VKSVISLAGV IPEVSAFVPF ANQFLDFIWP KIFGDSTSTT PDLFEQLKPQ  120
IKALVDEAIY KANEQLLADT AKGFEGVVQL YNEKVGQVKK APTVQHVLEL HNQIDAVRNF  180
FLHDAPHFVS SGTVAIPHLT MMVTLQLMVL RDAILSDSSW DYTASDKDTL LNGALGFRQI  240
LKTYSKWVFD TLTEELNTNY ATFDTVDKWN ARNNFLTIVT LTSLDLVALW PTLDPELYPV  300
NTDIDFTRTL KSPILQPVWN PDPFIVPNDF LSYQGELSSM QFSNQYDTAG YSSVLSGIIN  360
RLDRSNYTTR ELNYGYGRTV YGVNIDKPPI PVKSTNPVIK TSLTNTSYNR IEASAFTATF  420
ADGSDDGLVV QGNYGAAWDH AYTASDTAPS QHKLNYFYTS TKDVLLWNFV NVYTPIDTPR  480
VNIIGQPDDT GKISIKGFPA EKGYSDSNLE YVNEPLNGAA AVKLSYNQIF RLPFTNQISR  540
NYAIRIRYAS NITATNWFHL YTRSGSPING PLTFLTTNTD TAISVQGENG RYGLVTATES  600
VTIPAGDSEI IIKNTHQTDL FIDRIEFVPV PPKPTFAPDS QQVTLDVYLK EQNNQKLETE  660
QDLQNITNQV NELFTSSTQN TLASDVSDYW IDQVVMKIDA LSDEVFGKEK TELRKRVNKA  720
KQLSKIRNLL IAGNFENLND WYVGRNVVRV ANHELFKGEY LLLPPPSLFP SYAYQIVEEF  780
KLKPNTRYTV SGFIAQAEGL ELIISRYGQE IQKVFHVPEG TAYPLTSEEI ANCCAPSSDP  840
NATDSHFFNY SIDIGSLQPE ANLGIEVGFR IVKPTGFAKL SNIEIREERA LTMSEISSVQ  900
RTEQTWRRKY NQERTEVTTV IQTVIDQINE LYENEDWNGT IRSTISYADV QDIVLPTLPK  960
EKHWFMDDRT GEHASIRQRF QRALDRAFQQ LEARNLFHNG HFTNGLTDWT IEGNTAMITL  1020
ETGQQVLQLE HWDASAAQSI EIANFNQNQE YQLRVYAKGK GKITIKHGVD GERIEVMNID  1080
STNFIKQHSA PLKFDTATIE VYVMSEDGVF QVDSIELIKF FVEDTPDNN              1129

SEQ ID NO: 384         moltype = AA  length = 631
FEATURE                Location/Qualifiers
REGION                 1..631
                       note = Description of Artificial Sequence: Synthetic
                        polypeptide
source                 1..631
                       mol_type = protein
                       organism = synthetic construct
SEQUENCE: 384
MATLSDLYPV NVLSSSAYEK YNLIPSEAAN MDEIFKQIKD AWGKYGSVPK ELLTQAWNYY  60
NNGTIDYLAL VKSVISLAGV IPEVSAFVPF ANQFLDFIWP KIFGDSTSTT PDLFEQLKPQ  120
IKALVDEAIY KANEQLLADT AKGFEGVVQL YNEKVGQVKK APTVQHVLEL HNQIDAVRNF  180
FLHDAPHFVS SGTVAIPHLT MMVTLQLMVL RDAILSDSSW DYTASDKDTL LNGALGFRQI  240
LKTYSKWVFD TLTEELNTNY ATFDTVDKWN ARNNFLTIVT LTSLDLVALW PTLDPELYPV  300
NTDIDFTRTL KSPILQPVWN PDPFIVPNDF LSYQGELSSM QFSNQYDTAG YSSVLSGIIN  360
RLDRSNYTTR ELNYGYGRTV YGVNIDKPPI PVKSTNPVIK TSLTNTSYNR IEASAFTATF  420
ADGSDDGLVV QGNYGAAWDH AYTASDTAPS QHKLNYFYTS TKDVLLWNFV NVYTPIDTPR  480
VNIIGQPDDT GKISIKGFPA EKGYSDSNLE YVNEPLNGAA AVKLSYNQIF RLPFTNQISR  540
NYAIRIRYAS NITATNWFHL YTRSGSPING PLTFLTTNTD TAISVQGENG RYGLVTATES  600
```

```
VTIPAGDSEI IIKNTHQTDL FIDRIEFVPV P                           631

SEQ ID NO: 385         moltype = AA  length = 243
FEATURE                Location/Qualifiers
source                 1..243
                       mol_type = protein
                       organism = Bacillus sp.
SEQUENCE: 385
MKKYKKIAVI MPLAFMLTTG AGVLGGPTST FADKIPQVKV SPMYTNLVKN TMNVNEQLKK  60
ELSQFFGGEV SNIQLEMINT TSNPIQVYIT NAQPIGSKYD VIDFISYDNY TNEMQSHKTP  120
EQKVINKMSV TTTNASEMQT GLKSETEFSL GIPLFAEGKE KITVELGVNY KKSLDETVEN  180
STEVTYPSQT INAAPGGRTT LLNQVQKTKF DGIYTGSAVI KSFDRKNSEG QVQTYEGNAL  240
YQV                                                          243

SEQ ID NO: 386         moltype = AA  length = 212
FEATURE                Location/Qualifiers
REGION                 1..212
                       note = Description of Artificial Sequence: Synthetic
                        polypeptide
source                 1..212
                       mol_type = protein
                       organism = synthetic construct
SEQUENCE: 386
MDKIPQVKVS PMYTNLVKNT MNVNEQLKKE LSQFFGGEVS NIQLEMINTT SNPIQVYITN  60
AQPIGSKYDV IDFISYDNYT NEMQSHKTPE QKVINKMSVT TTNASEMQTG LKSETEFSLG  120
IPLFAEGKEK ITVELGVNYK KSLDETVENS TEVTYPSQTI NAAPGGRTTL LNQVQKTKFD  180
GIYTGSAVIK SFDRKNSEGQ VQTYEGNALY QV                           212

SEQ ID NO: 387         moltype = AA  length = 905
FEATURE                Location/Qualifiers
source                 1..905
                       mol_type = protein
                       organism = Bacillus sp.
SEQUENCE: 387
MANLTELYPS YHNVLAHPIR LDSSLDPFVE TFNDLKEAWD EFGKTGYMDP LKQHLKIAWD  60
AGQNGTVDYL ALTKASISLI GLIPGGEAVV PFVNMFVDFI FPKLFGGGSQ QNPQAQFFEL  120
IIKKVKEIVD QEFRDFTLNN LLNYLDGMQT ALEHFQNDVQ IAICQEEQPG HMLDQTPTAC  180
TPTTDHLISV RESFKDARSA IETALPHFKN PMLSTNENTP DFNSNTVLLT LPMYTTAATL  240
NLILHQGYLQ FSERWKSVSY DESFINQTKT DLQHRIQDYS ITVATTFETF KPTLNPSNKK  300
SVNTYNRYVR SMTLQSLDIA ATWPTLDIVN YPSDVNIQLD QTRLVFSDIA GPWESNENIT  360
SNIIDVLKPV NTTIGYQERS DPRNFIYPQM ELQSVQFHGQ YVGSKDVTHC YSDGIKLEYN  420
NKTITAGVSN IDESNQYNKH NYGPEILSPL TDINANSQNS IYLDINSILL NGGQKIAGCS  480
PLSSDGSSNN IALPNQKINV IYPVQSNDKP EKHADTYRKW GYMSSHIPYD LVPENIIGQP  540
DTDGNIMGRG FPAEKGTLAN NIGSWQTVSE PINGANAVKL TYQQILAIPI TNVTNGYYSL  600
RIRYASSSDI TGYFHVQTPA GDSNRGSITF PNTQNISNTM YVKGENGNYS LFQAAESIKI  660
PPGQSTVYIQ NNSNADLFLD RIEVFPITAS QLPDPSSANQ FTLVGPYTML PEPMGKDFVI  720
WQTSQTCAST PNSTLSFTIL GSGEFQVLDK NNNIIAKKTE NQNNLTTETW NLPQNVEKIR  780
FVANDYVVLR NIIGKINCQE PIKPCTLGGQ TLVDIDYNTN GEQFLWSSTE PMGNCTVDIV  840
LDSDFISSIA TLQFQDNTGT VVRSIDFGPG EQNLTVSVAS TTRIVLKPTN FGPISGHLKI  900
QIVTN                                                        905

SEQ ID NO: 388         moltype = AA  length = 687
FEATURE                Location/Qualifiers
REGION                 1..687
                       note = Description of Artificial Sequence: Synthetic
                        polypeptide
source                 1..687
                       mol_type = protein
                       organism = synthetic construct
SEQUENCE: 388
MANLTELYPS YHNVLAHPIR LDSSLDPFVE TFNDLKEAWD EFGKTGYMDP LKQHLKIAWD  60
AGQNGTVDYL ALTKASISLI GLIPGGEAVV PFVNMFVDFI FPKLFGGGSQ QNPQAQFFEL  120
IIKKVKEIVD QEFRDFTLNN LLNYLDGMQT ALEHFQNDVQ IAICQEEQPG HMLDQTPTAC  180
TPTTDHLISV RESFKDARSA IETALPHFKN PMLSTNENTP DFNSNTVLLT LPMYTTAATL  240
NLILHQGYLQ FSERWKSVSY DESFINQTKT DLQHRIQDYS ITVATTFETF KPTLNPSNKK  300
SVNTYNRYVR SMTLQSLDIA ATWPTLDIVN YPSDVNIQLD QTRLVFSDIA GPWESNENIT  360
SNIIDVLKPV NTTIGYQERS DPRNFIYPQM ELQSVQFHGQ YVGSKDVTHC YSDGIKLEYN  420
NKTITAGVSN IDESNQYNKH NYGPEILSPL TDINANSQNS IYLDINSILL NGGQKIAGCS  480
PLSSDGSSNN IALPNQKINV IYPVQSNDKP EKHADTYRKW GYMSSHIPYD LVPENIIGQP  540
DTDGNIMGRG FPAEKGTLAN NIGSWQTVSE PINGANAVKL TYQQILAIPI TNVTNGYYSL  600
RIRYASSSDI TGYFHVQTPA GDSNRGSITF PNTQNISNTM YVKGENGNYS LFQAAESIKI  660
PPGQSTVYIQ NNSNADLFLD RIEVFPI                                687

SEQ ID NO: 389         moltype = AA  length = 122
FEATURE                Location/Qualifiers
source                 1..122
                       mol_type = protein
                       organism = Burkholderia sp.
SEQUENCE: 389
```

```
VIRMAARSVV AKFSNNTKFD LMLGDSELWH GHWVTSPPSS IAPGAEGQWE TDSDDYESGT  60
AGDLQYQFTN EEGTQTVRVS WAVPYLGSNN FEVYCEAAGV RPGYTGGGQD TNATVNYYLN  120
QA                                                                122

SEQ ID NO: 390          moltype = AA  length = 119
FEATURE                 Location/Qualifiers
REGION                  1..119
                        note = Description of Artificial Sequence: Synthetic
                         polypeptide
source                  1..119
                        mol_type = protein
                        organism = synthetic construct
SEQUENCE: 390
MAARSVVAKF SNNTKFDLML GDSELWHGHW VTSPPSSIAP GAEGQWETDS DDYESGTAGD  60
LQYQFTNEEG TQTVRVSWAV PYLGSNNFEV YCEAAGVRPG YTGGGQDTNA TVNYYLNQA   119

SEQ ID NO: 391          moltype = AA  length = 1202
FEATURE                 Location/Qualifiers
REGION                  1..1202
                        note = Description of Unknown: Organism from environmental
                         sample
source                  1..1202
                        mol_type = protein
                        organism = unidentified
SEQUENCE: 391
MNGGKNMNQN NQNEMQIIDS SSNDFSQSNR YPRYPLAKES NYKDWLASCD ESNVDTLSTT  60
SDVKGSVSRV LGIVNQILGF LGLGFIGTGL GVLGDLFNSF WPSNNNAVWE AFLRSVEELI  120
NRRIGEVERF RIESQFNGLK NVMSNYNGAL RDWNGNRNNT ALQSEVRSRF DNADDAFAVR  180
MPEFRIQGFE VQSLAIYAQA ATLHLLLLRD GVVNGRLWGF APETVERLYN KLVCLSGAYA  240
DHCTFFYRQG LEELRGRGNW NAFNTYRRNM TIQVLDVISL FSNYNPRLYE INTNTQLTRE  300
IYTEPLAVPG WLNSHSNPTQ FQQIENDLIR SPSVFSHLRT LFMEAGFAFH DTQTPRQTVL  360
RTLTESWNTG RTNTIMTPWQ GALNPNVSER LQVHFENRNV FNINSVVARQ ISNPNSSLFG  420
VQQAIFNFVY EGGSAASTTQ FNLPSARYLT SITSNIPGTN STTPTASDYT HRLSLITSTS  480
VGTWQRDRTN IMAYGWTHVS AERTNRILPN RITQIPAVKS QSLTTDAPPN QLQTQVVRGP  540
GHTGGNLMVM GIGTSRFHMS ITSSTRQRYR VRLRYANLIP HPCQIIIPAL GVNVSFTLPA  600
TTTHYREDPP YSSFGYVDVP MSFATPDGQN TWEFQLVTTR ASSAFDRVEF IPVNATNLEY  660
AGKQNLEKAK KAVDNLFTNT GKNALKVDTT DYDVDQAANL VECVPGELYT KEKMILLDEV  720
KHAKQLSASR NLIQNGNFAF YTDEWTTSNN VSIQTDNQIF KGNYLKMPGA RETEGGTTRF  780
PTYVLQKIDE SKLKPYTRYK VRGFVGSSHD VKLIVERYGK EVDAILNVRN DLALDTVSSS  840
CVEVNQCQSQ MYPIMHDGYL ANVIDTNSYE EAQSDHANFK KEHGMCHQSH QFDFHIDTGE  900
VHLNKNPGIW VLFKISSPEG HATLDNIELI EDGPLVGESL ALVKKREKKW KHEMKTRWLQ  960
TKEVYEKAKG AIDALFTDAQ DHAIKFDTNI SHIISAEHLV QSMPYVYNNW LSDVPGMNYD  1020
IYTELERRIT QAYSLYEHRN IIKNGDFDYD LNHWHATPHA KVQQMDGTAV LVIPNWSSNV  1080
SQNLCVEHNH GYVLRVTAKK EGPGKGYVTI SDCNENQETL TFTSCDNYVS NEITNDQLEY  1140
PFSQEMNEQR SYNPNETINE QRNYITRTID FFPDTDQVRI DIGENEGTFK VESIELICMK  1200
SQ                                                                1202

SEQ ID NO: 392          moltype = AA  length = 650
FEATURE                 Location/Qualifiers
REGION                  1..650
                        note = Description of Artificial Sequence: Synthetic
                         polypeptide
source                  1..650
                        mol_type = protein
                        organism = synthetic construct
SEQUENCE: 392
MNQNNQNEMQ IIDSSSNDFS QSNRYPRYPL AKESNYKDWL ASCDESNVDT LSTTSDVKGS  60
VSRVLGIVNQ ILGFLGLGFI GTGLGVLGDL FNSFWPSNNN AVWEAFLRSV EELINRRIGE  120
VERFRIESQF NGLKNVMSNY NGALRDWNGN RNNTALQSEV RSRFDNADDA FAVRMPEFRI  180
QGFEVQSLAI YAQAATLHLL LLRDGVVNGR LWGFAPETVE RLYNKLVCLS GAYADHCTFF  240
YRQGLEELRG RGNWNAFNTY RRNMTIQVLD VISLFSNYNP RLYEINTNTQ LTREIYTEPL  300
AVPGWLNSHS NPTQFQQIEN DLIRSPSVFS HLRTLFMEAG FAFHDTQTPR QTVLRTLTES  360
WNTGRTNTIM TPWQGALNPN VSERLQVHFE NRNVFNINSV VARQISNPNS SLFGVQQAIF  420
NFVYEGGSAA STTQFNLPSA RYLTSITSNI PGTNSTTPTA SDYTHRLSLI TSTSVGTWQR  480
DRTNIMAYGW THVSAERTNR ILPNRITQIP AVKSQSLTTD APPNQLQTQV VRGPGHTGGN  540
LMVMGIGTSR FHMSITSSTR QRYRVRLRYA NLIPHPCQII IPALGVNVSF TLPATTTHYR  600
EDPPYSSFGY VDVPMSFATP DGQNTWEFQL VTTRASSAFD RVEFIPVNSQ            650

SEQ ID NO: 393          moltype = AA  length = 284
FEATURE                 Location/Qualifiers
source                  1..284
                        mol_type = protein
                        organism = Bacillus sp.
SEQUENCE: 393
MPINLNEIIF NYGKNLVYPL PSNIIDTTFT PGTTTGSFTS YAETTIISND VKVQGSTAVV  60
PNYQIPLTGT QTIAVKTDTI SNTSDTPLTK NFSYSETVTN TVTTTRTDGV DYTVGSETSI  120
SGTIIAASVS QKITFSTKIS TTNSTAITNT KSQTWTDSYT ATIPPKTNAT ATYIVNVGTF  180
DTTVDTDIIL SGSVTYQIKY NDPSIPAFRL GPPITVPVSQ ILSGIPGITL LPDGTVKYVG  240
KVNIKGEVGL NSYINFSSTS ISSGTSSSPI IIPGSSSPKT LLFA                  284
```

```
SEQ ID NO: 394          moltype = AA  length = 330
FEATURE                 Location/Qualifiers
source                  1..330
                        mol_type = protein
                        organism = Bacillus sp.
SEQUENCE: 394
MKKYRKIVTV VPLTCMLSGG VGMLLTPQSS FAASIVDTKT ANTLLAGKNT DGVKFAIEKK  60
ILHALEVRDH ATYYPIQGQK VDYNSINYNY VGKNFSTTAT ANSYTNAGEV ELLLYRNASP  120
VDQTQLTIEK QVTDSESFTY SNTEGVKLGT AVKANVDVGI PFVAEGGTEI TVNTEFSYEH  180
SSSNTSSHET TVKFPSQSVI CAKGYITKYV GRVQNANFSG VLHGKVELTG NVSIVVANMN  240
TNRAETKTIS VADVFKYSAD YPGPTAGYEY DSQNEKVYAT VDSTYSGVGG HYQTVDVEVV  300
PIGKSESEMR KVSLKEYEKR VKNGTLAELF                                 330

SEQ ID NO: 395          moltype = AA  length = 299
FEATURE                 Location/Qualifiers
REGION                  1..299
                        note = Description of Artificial Sequence: Synthetic
                         polypeptide
source                  1..299
                        mol_type = protein
                        organism = synthetic construct
SEQUENCE: 395
MASIVDTKTA NTLLAGKNTD GVKFAIEKKI LHALEVRDHA TYYPIQGQKV DYNSINYNYV  60
GKNFSTTATA NSYTNAGEVE LLLYRNASPV DQTQLTIEKQ VTDSESFTYS NTEGVKLGTA  120
VKANVDVGIP FVAEGGTEIT VNTEFSYEHS SSNTSSHETT VKFPSQSVIC AKGYITKYVG  180
RVQNANFSGV LHGKVELTGN VSIVVANMNT NRAETKTISV ADVFKYSADY PGPTAGYEYD  240
SQNEKVYATV DSTYSGVGGH YQTVDVEVVP IGKSESEMRK VSLKEYEKRV KNGTLAELF   299

SEQ ID NO: 396          moltype = AA  length = 1125
FEATURE                 Location/Qualifiers
source                  1..1125
                        mol_type = protein
                        organism = Bacillus sp.
SEQUENCE: 396
MNKHNSYINQ TKSENSPCSS NNTHINSNTI LNATINQEYK YLLEHIPSAK DYNETYYIII  60
KNIVTTAVSF VPQIGSILSG ISSMYYDSIG PSLKPSEIWK SIREYAENLV NEKISDADYN  120
RLFTTLKGLA NSLKEYKVHF DAHYNSSTKI DSGEIVYEKF SNVSSLFDKH ISDFQMEGKE  180
IVSLPLFAQA AQLHLLLLRD VAVYGKEWGV PDNQLNVYKN SLKEKIQIYT MYCRFWYKDG  240
LAKRKKNIPT NPPYPPGYEI PSNNDDYYYA KSSIQWNYVN DYVRIMTHAV LNFVSLFPFC  300
DPDFYPLNTS LQQSRKVYTQ LAGWAYPPSL TFEDINKKVY SGCGSNDRPG NYQGDLETLD  360
IHAYDRIDAV KNSFERGDGK YSCTPVGGSG GILHQISTYK MNPINEVSGY SQIVPWALNF  420
GYTDGKKKSM GTYDDPRVKP FCYKYPLQKL SEVKGLGLNP TGGFYGLDAV TFGFEAENLT  480
HKHILSTNSV NIISAELYSQ QSNCSSQEEF INGQNAILLN DNQSSLTYTI YVPTPGMYAL  540
DFRISIENAT TLNPAKIEIA EFSNNQFDKV DFKEYLNTSD REDSVAGEYG DYSKLEGTKL  600
MLSRGKNTIR ISNLTDVEVC IDTIIITPLK LSIITMDFID QYYELEDLAN GQKNIVFRAY  660
PQYPGKKLEW PLTLYADGNP KLNFKENQSL EEVTNLINKQ NITEKSVVLS YGLPVEIINL  720
PTNTKKLLSF KRLDFDNIYA YTDEPNAKIG NNDNKIIYIY IDGKCVYSFA ETTELKIVTK  780
AFNYLGARGN NLRIQDSLKI TFDILQDRTL GLFDIWNPND LNLATTDFDI REIEYELENL  840
KDSDNIPEEK IEALKNKLNY ARSIINGDKM IIKNSDSSLN LGIAISHQKQ QFTTLDLTSL  900
TLRNEIMKQI DLYFSFTLID AKTGNEKFAL SFQTNSELQN FLTALRKFHF EYDDIIMIKH  960
KNAYIDVYDN NDLLDFNDSI THYFLIKPNG FIKIFNIKNW QTTAYYIDGV TFSQVPQGKK  1020
IKYKVKLNGN DIGTASPYQT DGKGNDTVLF TQDFYDMEGW GVSKHDNHII VFAIDPDTGL  1080
EYEIAHHEPQ RTRDGDIDIP EKYLHHNVQI NFYHSTCNIY VNKKK                1125

SEQ ID NO: 397          moltype = AA  length = 956
FEATURE                 Location/Qualifiers
REGION                  1..956
                        note = Description of Artificial Sequence: Synthetic
                         polypeptide
source                  1..956
                        mol_type = protein
                        organism = synthetic construct
SEQUENCE: 397
MNKHNSYINQ TKSENSPCSS NNTHINSNTI LNATINQEYK YLLEHIPSAK DYNETYYIII  60
KNIVTTAVSF VPQIGSILSG ISSMYYDSIG PSLKPSEIWK SIREYAENLV NEKISDADYN  120
RLFTTLKGLA NSLKEYKVHF DAHYNSSTKI DSGEIVYEKF SNVSSLFDKH ISDFQMEGKE  180
IVSLPLFAQA AQLHLLLLRD VAVYGKEWGV PDNQLNVYKN SLKEKIQIYT MYCRFWYKDG  240
LAKRKKNIPT NPPYPPGYEI PSNNDDYYYA KSSIQWNYVN DYVRIMTHAV LNFVSLFPFC  300
DPDFYPLNTS LQQSRKVYTQ LAGWAYPPSL TFEDINKKVY SGCGSNDRPG NYQGDLETLD  360
IHAYDRIDAV KNSFERGDGK YSCTPVGGSG GILHQISTYK MNPINEVSGY SQIVPWALNF  420
GYTDGKKKSM GTYDDPRVKP FCYKYPLQKL SEVKGLGLNP TGGFYGLDAV TFGFEAENLT  480
HKHILSTNSV NIISAELYSQ QSNCSSQEEF INGQNAILLN DNQSSLTYTI YVPTPGMYAL  540
DFRISIENAT TLNPAKIEIA EFSNNQFDKV DFKEYLNTSD REDSVAGEYG DYSKLEGTKL  600
MLSRGKNTIR ISNLTDVEVC IDTIIITPLK LSIITMDFID QYYELEDLAN GQKNIVFRAY  660
PQYPGKKLEW PLTLYADGNP KLNFKENQSL EEVTNLINKQ NITEKSVVLS YGLPVEIINL  720
PTNTKKLLSF KRLDFDNIYA YTDEPNAKIG NNDNKIIYIY IDGKCVYSFA ETTELKIVTK  780
AFNYLGARGN NLRIQDSLKI TFDILQDRTL GLFDIWNPND LNLATTDFDI REIEYELENL  840
KDSDNIPEEK IEALKNKLNY ARSIINGDKM IIKNSDSSLN LGIAISHQKQ QFTTLDLTSL  900
```

```
TLRNEIMKQI DLYFSFTLID AKTGNEKFAL SFQTNSELQN FLTALRKFHF EYDDII      956

SEQ ID NO: 398         moltype = AA  length = 665
FEATURE                Location/Qualifiers
REGION                 1..665
                       note = Description of Unknown: Organism from environmental
                        sample
source                 1..665
                       mol_type = protein
                       organism = unidentified
SEQUENCE: 398
MKKNKDTSYN PLGMATNLGH KINRYPLANN QVSKLKGTNY KDSLVMCNNA NPVWFHEPEN  60
LEFTWLNAAV AALTVVSTIT ALLVAPPIVV GGVVAAGAAI LAGTLPLLWP AGEPTKDNTF  120
DELMGAAEKL IKKEISEFVR QTAGAKIESL RQLMNHYQSA LEYWKKNPNN QAAIYEVSSR  180
FRIVNAFFVE AMSALSVKGY ETVQLSAYAQ AANLHLLLLK DGITYANAWS LAYESSGNPG  240
DLHYREFIDF RREYINYCSK WYNEGFIDAE NKLVYQTAMT IYVLDIIALF SAYDVRQYKY  300
PLKMETLTRT LYTHLLSENG KQFKHKPSLF RKLKKIKLYT YKGSSDSWLC GQKNVYETMN  360
FQLIEDKVQG STSDINNTLD FGSGGAYSVT TNIKNNDPIN IQKMTFYAKD HGENLEYTAM  420
DSGNTIEFKR NIPNIDAPSR NLNTNKYTHY LSDCIIDTEE KLGSKSIKSY TFGWNHHSID  480
STGNYVTDVI DPKETNSPFQ ISQIPAVKAS HLSSKGSAGG VSVFNGPYFT GGDVILSKVK  540
VNNNESITGK TTMNITLPLV PKGYRTRSFR IRMYYAANHD GSIKYKYKEK SGEATFKKTF  600
DRYEPYKIKF EDFQYLDFDW PVTFDSDGTL ANVNLTWEYI HSYIQGQGEK LLMIDKFEFI  660
PIETH                                                             665

SEQ ID NO: 399         moltype = AA  length = 569
FEATURE                Location/Qualifiers
source                 1..569
                       mol_type = protein
                       organism = Bacillus sp.
SEQUENCE: 399
MLQCPCTMKS IYSINNTTRK DDLMKYKDRK DAKRKYKQAI LTTVATMTLG VSTLGPTASA  60
FAAEGDNNSV ISHAETQTEN TKLLESNFVD KVKAKIDVLS SEKDKLKPVG KFMGTTILEL  120
IQYANKGPEQ MNDTLRAITI ASTELIPYGG MFIAPLIGAI WPQTNGINSQ LNALREDLTK  180
LVTNEIDKEQ LNFLNSEFKT LIDLQTDLEH AINTDNSQNV DENTKNQRGV WANGIEQSFR  240
RLLDHTSSDK HKITNLPIYT KVALAHLLFL DSLNNKAVSS KMNITQQSLK ELYTKDGVKT  300
LANDYVLHIM QTFYDAPQIK KIKQVPEFHF NPDDAENQIK DLKDRLSKVK VQYKEWQDGV  360
MSAGGFGMVP NKEYEFNIAI LEDAISSYEF VEKLYNATVG DPMIKELIKD SGNQEIKELA  420
KDSSEVFVAD TTYKIVYSKA NKVVDFGEHG IELPLIWYDH SGKNQRWEFK YDADKKAYQI  480
INRADGRILA YNTTPNADDT ALVTENQHKP EHYWILEDAG AGNVLLVNYE NKNKVLDVYD  540
EKTDDGSRVY VRDKLNNSNA QKFKLVISL                                   569

SEQ ID NO: 400         moltype = AA  length = 546
FEATURE                Location/Qualifiers
REGION                 1..546
                       note = Description of Artificial Sequence: Synthetic
                        polypeptide
source                 1..546
                       mol_type = protein
                       organism = synthetic construct
SEQUENCE: 400
MKYKDRKDAK RKYKQAILTT VATMTLGVST LGPTASAFAA EGDNNSVISH AETQTENTKL  60
LESNFVDKVK AKIDVLSSEK DKLKPVGKFM GTTILELIQY ANKGPEQMND TLRAITIAST  120
ELIPYGGMFI APLIGAIWPQ TNGINSQLNA LREDLTKLVT NEIDKEQLNF LNSEFKTLID  180
LQTDLEHAIN TDNSQNVDEN TKNQRGVWAN GIEQSFRRLL DHTSSDKHKI TNLPIYTKVA  240
LAHLLFLDSL NNKAVSSKMN ITQQSLKELY TKDGVKTLAN DYVLHIMQTF YDAPQIKKIK  300
QVPEFHFNPD DAENQIKDLK DRLSKVKVQY KEWQDGVMSA GGFGMVPNKE YEFNIAILED  360
AISSYEFVEK LYNATVGDPM IKELIKDSGN QEIKELAKDS SEVFVADTTY KIVYSKANKV  420
VDFGEHGIEL PLIWYDHSGK NQRWEFKYDA DKKAYQIINR ADGRILAYNT TPNADDTALV  480
TENQHKPEHY WILEDAGAGN VLLVNYENKN KVLDVYDEKT DDGSRVYVRD KLNNSNAQKF  540
KLVISL                                                            546

SEQ ID NO: 401         moltype = AA  length = 508
FEATURE                Location/Qualifiers
REGION                 1..508
                       note = Description of Artificial Sequence: Synthetic
                        polypeptide
source                 1..508
                       mol_type = protein
                       organism = synthetic construct
SEQUENCE: 401
MAEGDNNSVI SHAETQTENT KLLESNFVDK VKAKIDVLSS EKDKLKPVGK FMGTTILELI  60
QYANKGPEQM NDTLRAITIA STELIPYGGM FIAPLIGAIW PQTNGINSQL NALREDLTKL  120
VTNEIDKEQL NFLNSEFKTL IDLQTDLEHA INTDNSQNVD ENTKNQRGVW ANGIEQSFRR  180
LLDHTSSDKH KITNLPIYTK VALAHLLFLD SLNNKAVSSK MNITQQSLKE LYTKDGVKTL  240
ANDYVLHIMQ TFYDAPQIKK IKQVPEFHFN PDDAENQIKD LKDRLSKVKV QYKEWQDGVM  300
SAGGFGMVPN KEYEFNIAIL EDAISSYEFV EKLYNATVGD PMIKELIKDS GNQEIKELAK  360
DSSEVFVADT TYKIVYSKAN KVVDFGEHGI ELPLIWYDHS GKNQRWEFKY DADKKAYQII  420
NRADGRILAY NTTPNADDTA LVTENQHKPE HYWILEDAGA GNVLLVNYEN KNKVLDVYDE  480
KTDDGSRVYV RDKLNNSNAQ KFKLVISL                                    508
```

```
SEQ ID NO: 402          moltype = AA  length = 1259
FEATURE                 Location/Qualifiers
source                  1..1259
                        mol_type = protein
                        organism = Bacillus sp.
SEQUENCE: 402
MNLNDNKNEF EIMGNGSMAY QPRYPLAQAP GSAFQGMDYK DWMNRCASGE FGELFVDPDA  60
VKNGVVAGLA ITSYLLSISF PFPSAALGII SVLLPILWPG QAGDPGTIEA QFTWDQWMNA  120
AEKMADQKIE NSVKIQAIDT TKTLQYHVNE YTRAICNLKS EPNNERYKEA VRRQFNDAND  180
WAKTTLIRFG NPAYAIPLLA DYAQAANLHL LLLQEGIKLG ESWGLSALEV QQLYSNNGVG  240
NPGMKELLAI YTDHCVRYYN EGLKKRYETG NWYTFNDYRR NMTIMVMDIV SFWPTYDPIL  300
YPVPTKSQLT RTVYTDFLRN GILPPAISDV ENSVTVPLGL FRWMSRLGYH GIPVASSNVW  360
KGLEQIYQYT LRDDLYEERQ GEFPNGSKLL GSLNIQDTTA GDDVWSIIPN YIPIEDGSEV  420
GYMPNTASFF HDFRFQLLKS GEQRVNIAYE EGISRKFGLP CKSNPGTDCI PCQTCEAFPN  480
VSDPCDEKSL YSHRFSYMGI YKSPEPYNDE TLSPCFGWTH VSADANNLID AEKITQIPAV  540
KAYGIAINSR VVKGPGSTGG DVVQLSSGTE MGSMSMWITT PPGALAYRVR LRYASSMQTN  600
VKIYMVGANK QFDVPATTTD LTNLTYDKFK YLDTVVYSYS QLEENRNHIR IEATGSGSGS  660
FILDKIEFIP IGGSVEEFEA NQALEKVRKA VNALFTNNAK NVLQLNVTDY EIDQAANLAE  720
CVSEEFHAQE KMILFDQVKF AKRLSHARNL LHYGDFESSD WSGENGWRTS PHVHVASDNP  780
IFKGRYLHMS GAMSPQFSNN IYPTYAYQKV DESKLKSYTR YLVRGFVGNS KDLELLVERY  840
GKDVYVEMDV PNDIRYTLPR NECGDFDRCK PASYQTKPPH TCTCKDPAVA HTDCQCKDKG  900
NHTSTNMYTN GPTGSEVSTN GFHAHKSCGC GDKHMDKNGT HPHKSCGCKD PHIFTYHIDT  960
GCVDTEENLG LFFALKIASE NGVANIDNLE IIEAQPLTGE ALARVKKREQ RWKHEMTKKQ  1020
LETETAVQAA QDAIQNLFTN TQYNRLKFET LFPQIVNAEL LVQQIPYVYH PFLSGVLPVV  1080
PGMNFDIFQQ LSFLIDTAKG LYEERNFVQN GTFSSGTGSW YVTAGVEVHR LQNTSVLVLS  1140
EWSHEASQQV RIDSDRGYVL RVTARKEGAG KGTVTLSDCA DYTETLSFTS CDYNTVGTQT  1200
MTKGTLSGFV TKTLENFPET DRIRIDIGET EGTFKVESVE LICMEQMEDH LYDMAGNLE   1259

SEQ ID NO: 403          moltype = AA  length = 671
FEATURE                 Location/Qualifiers
REGION                  1..671
                        note = Description of Artificial Sequence: Synthetic
                         polypeptide
source                  1..671
                        mol_type = protein
                        organism = synthetic construct
SEQUENCE: 403
MNLNDNKNEF EIMGNGSMAY QPRYPLAQAP GSAFQGMDYK DWMNRCASGE FGELFVDPDA  60
VKNGVVAGLA ITSYLLSISF PFPSAALGII SVLLPILWPG QAGDPGTIEA QFTWDQWMNA  120
AEKMADQKIE NSVKIQAIDT TKTLQYHVNE YTRAICNLKS EPNNERYKEA VRRQFNDAND  180
WAKTTLIRFG NPAYAIPLLA DYAQAANLHL LLLQEGIKLG ESWGLSALEV QQLYSNNGVG  240
NPGMKELLAI YTDHCVRYYN EGLKKRYETG NWYTFNDYRR NMTIMVMDIV SFWPTYDPIL  300
YPVPTKSQLT RTVYTDFLRN GILPPAISDV ENSVTVPLGL FRWMSRLGYH GIPVASSNVW  360
KGLEQIYQYT LRDDLYEERQ GEFPNGSKLL GSLNIQDTTA GDDVWSIIPN YIPIEDGSEV  420
GYMPNTASFF HDFRFQLLKS GEQRVNIAYE EGISRKFGLP CKSNPGTDCI PCQTCEAFPN  480
VSDPCDEKSL YSHRFSYMGI YKSPEPYNDE TLSPCFGWTH VSADANNLID AEKITQIPAV  540
KAYGIAINSR VVKGPGSTGG DVVQLSSGTE MGSMSMWITT PPGALAYRVR LRYASSMQTN  600
VKIYMVGANK QFDVPATTTD LTNLTYDKFK YLDTVVYSYS QLEENRNHIR IEATGSGSGS  660
FILDKIEFIP I                                                  671

SEQ ID NO: 404          moltype = AA  length = 199
FEATURE                 Location/Qualifiers
source                  1..199
                        mol_type = protein
                        organism = Bacillus sp.
SEQUENCE: 404
MSENEYFRDA MFHSNHEPLN ILPEASEEFA SIAHTKNKPE CYEEVNTNIP FCCVVNIPHG  60
FDYVPNGTHK IAYNLDCVSV VKETCRKTIQ VDGCGPVEVT LNLLKVVGCI PYIVNATVAG  120
ECGSNCDYDP HGKHHINVCC SGSICVDNVL KCSIECLPHY EIDCHNVVVS DFKVQSLQEH  180
GCHMLQFTGT IEFKHIPHS                                          199

SEQ ID NO: 405          moltype = AA  length = 312
FEATURE                 Location/Qualifiers
source                  1..312
                        mol_type = protein
                        organism = Bacillus sp.
SEQUENCE: 405
MKYKKLLLVA PTIMMLCTPL VATISPVTAL AEAKGGVAVD QPVTKADIIN WLNNDLGRYN  60
AGVYYDDTPA YSVVVGDVSF DYAGTNSLKL TASPKVVSVG LIHNTTNVNQ TLKTDSKSES  120
VTDTFTTTNS EGIKVSLSST VKVSAGIPGV IGAENSLTMS VDGSYTHTSS NSVSKTQTLT  180
FPSQELVGAP HGTTKMEVLV YQQKFAGTDT NAQVELVGKM QPIRGGYIPA SIYVYVKDTV  240
NSGYTLPSYL TLDHENKRVL VKGLKVDFSG VVGYMTKGEV TFTPDDPNEK SVKMSVEEYK  300
NPTIRMQKLN QQ                                                 312

SEQ ID NO: 406          moltype = AA  length = 291
FEATURE                 Location/Qualifiers
REGION                  1..291
                        note = Description of Artificial Sequence: Synthetic
```

```
                         polypeptide
source                   1..291
                         mol_type = protein
                         organism = synthetic construct
SEQUENCE: 406
MTISPVTALA EAKGGVAVDQ PVTKADIINW LNNDLGRYNA GVYYDDTPAY SVVVGDVSFD  60
YAGTNSLKLT ASPKVVSVGL IHNTTNVNQT LKTDSKSESV TDTFTTTNSE GIKVSLSSTV  120
KVSAGIPGVI GAENSLTMSV DGSYTHTSSN SVSKTQTLTF PSQELVGAPH GTTKMEVLVY  180
QQKFAGTDTN AQVELVGKMQ PIRGGYIPAS IYVYVKDTVN SGYTLPSYLT LDHENKRVLV  240
KGLKVDFSGV VGYMTKGEVT FTPDDPNEKS VKMSVEEYKN PTIRMQKLNQ Q           291

SEQ ID NO: 407           moltype = AA  length = 397
FEATURE                  Location/Qualifiers
source                   1..397
                         mol_type = protein
                         organism = Bacillus sp.
SEQUENCE: 407
MKSISKKVMA GLLVGATSLS IWAPISEAAA PENNRYYNIQ LKSNQKKVWN VTRASNDNDR  60
AILLWQGGSA DNEKFAFFQL DGGAYAIVNK NSGKIVTYGD GSWFADRDRL GGETLQQQSW  120
NGEAKQKWNL RDLGSNTYEI VNQANGKVPT YRWAGSTVDN VEFLQMDNSN PSDADKVFTL  180
FNGTANIFGQ NITFFNDTFS VPNLPATGAR PDAPNYTGGV DQQLPQTSNS VVVGASLIPC  240
IMVNDNQASD YTKIHNSPYY TLVKEEYWDK TFSAVIPAGL TRNYSFKTGM TSVDQQKMTD  300
TLSMKIGADF GLKFGDATAS IKSEISKTIQ TEISTTNTEA SEETITSTVT SEAGKTTGYT  360
EYQLATKYTL KRADGSIVSD PWVVKNNKIT IARKNAQ                           397

SEQ ID NO: 408           moltype = AA  length = 370
FEATURE                  Location/Qualifiers
REGION                   1..370
                         note = Description of Artificial Sequence: Synthetic
                          polypeptide
source                   1..370
                         mol_type = protein
                         organism = synthetic construct
SEQUENCE: 408
MAAPENNRYY NIQLKSNQKK VWNVTRASND NDRAILLWQG GSADNEKFAF FQLDGGAYAI  60
VNKNSGKIVT YGDGSWFADR DRLGGETLQQ QSWNGEAKQK WNLRDLGSNT YEIVNQANGK  120
VPTYRWAGST VDNVEFLQMD NSNPSDADKV FTLFNGTANI FGQNITFFND TFSVPNLPAT  180
GARPDAPNYT GGVDQQLPQT SNSVVVGASL IPCIMVNDNQ ASDYTKIHNS PYYTLVKEEY  240
WDKTFSAVIP AGLTRNYSFK TGMTSVDQQK MTDTLSMKIG ADFGLKFGDA TASIKSEISK  300
TIQTEISTTN TEASEETITS TVTSEAGKTT GYTEYQLATK YTLKRADGSI VSDPWVVKNN  360
KITIARKNAQ                                                         370

SEQ ID NO: 409           moltype = AA  length = 717
FEATURE                  Location/Qualifiers
source                   1..717
                         mol_type = protein
                         organism = Bacillus sp.
SEQUENCE: 409
MNSYQNNDEI TDVAENYHNN INKYPYADDP NITMQNTNYK NWINECENIT SSSLSGILTS  60
IGMFNKVLML TGVLGVTPIV INIILDMVRL IDMGTGNDLL AHTEQLIQQT LATEYRSAAV  120
GAIYGISRAY ENYLMFFKQW EHNRTPQNGQ QVESAFTTVN TLCITALASQ ASLSRRGFET  180
LLLPNYALAA NFHLLLLRDA VIYRNNWLSS NVSTRSVNLT ILRTAINEYS NHCNRWYNDG  240
LNRFGRTSFN DWVRFNAYRR DMTLSVLDFV TAFPIYDPVI YPKPTNIELT RIVYTDPIIP  300
PRGFPRTTPP TFNQMENLII SRTSFLNRTN IFTNYYHSPN HISRDFWAGN RNYLSNGTSQ  360
QYASTSPWST HLNMENIDVF KVNMTTHDIN NVFESYGGIH RADFINNQRK SLLYNQHVDT  420
TRFITRNETV FLPGDSGLEP NEHNYTHRLF QMMTVYRTNP NARRAAFLHA WTHRSLRRRN  480
DFRSDQIIQI PAVKTINTHD NCAVILNTGE NMIKLDDLTT GLFYKLTAAN SKAMNTCFIV  540
RIRYASMNNN RLNLVLNDAQ VASLTVERTV QSGELLTDFQ YDNFKYATFA GNFKMGSQSI  600
LGIFKEIPNT EFILDKIELI PMNFMSSLEQ TQDYNNNYEQ NYSTYNQGYD MYDQDIENTY  660
QPDYDSYNPN FSSTYEDMYN QEHNYYNQDY NNDYKDNYNE NAGCTCNQRY NNNYYSK     717

SEQ ID NO: 410           moltype = AA  length = 622
FEATURE                  Location/Qualifiers
REGION                   1..622
                         note = Description of Artificial Sequence: Synthetic
                          polypeptide
source                   1..622
                         mol_type = protein
                         organism = synthetic construct
SEQUENCE: 410
MNSYQNNDEI TDVAENYHNN INKYPYADDP NITMQNTNYK NWINECENIT SSSLSGILTS  60
IGMFNKVLML TGVLGVTPIV INIILDMVRL IDMGTGNDLL AHTEQLIQQT LATEYRSAAV  120
GAIYGISRAY ENYLMFFKQW EHNRTPQNGQ QVESAFTTVN TLCITALASQ ASLSRRGFET  180
LLLPNYALAA NFHLLLLRDA VIYRNNWLSS NVSTRSVNLT ILRTAINEYS NHCNRWYNDG  240
LNRFGRTSFN DWVRFNAYRR DMTLSVLDFV TAFPIYDPVI YPKPTNIELT RIVYTDPIIP  300
PRGFPRTTPP TFNQMENLII SRTSFLNRTN IFTNYYHSPN HISRDFWAGN RNYLSNGTSQ  360
QYASTSPWST HLNMENIDVF KVNMTTHDIN NVFESYGGIH RADFINNQRK SLLYNQHVDT  420
TRFITRNETV FLPGDSGLEP NEHNYTHRLF QMMTVYRTNP NARRAAFLHA WTHRSLRRRN  480
DFRSDQIIQI PAVKTINTHD NCAVILNTGE NMIKLDDLTT GLFYKLTAAN SKAMNTCFIV  540
```

```
RIRYASMNNN RLNLVLNDAQ VASLTVERTV QSGELLTDFQ YDNFKYATFA GNFKMGSQSI  600
LGIFKEIPNT EFILDKIELI PM                                           622

SEQ ID NO: 411         moltype = AA  length = 712
FEATURE                Location/Qualifiers
source                 1..712
                       mol_type = protein
                       organism = Bacillus sp.
SEQUENCE: 411
MKSIVNFERV PKPFRKIKTI LILSAFMLSS FSPPVSANND QGYAYDASIG YSNPNWMSRI  60
SGSKKISELS IPGTHGSTAL HGVTFFDEDW VRNQRMTITT QLNSGIRYLD IRARRTGNSF  120
AMHHGEVYQK KMFGDILNEV TAFLRQNPGE TILMRLKEEH TAESGSNSFE EIMTKYWNDY  180
NSYFWKPSGS TNKMNPTLDE VRGKIVLLQN FNTSGGSGQF GIPYNSLQTQ DQDIVDNTGD  240
SMYAKWTAVG NHLKAADASN RQNIYLNHLS GNGGFSGAKP WFVSSGKRGR STNDGMEMIT  300
EHRDPNKWPQ FPRGYYGQIF YGGMNIMSNQ YIQQWPIHHT GILAADFPGK GLIDLVIKLN  360
DRHMGEDIRF IEPQGTTGIR IGFGGDSYLN KHYVVRRNGQ YYGEVNQGKP YYASWHQTDF  420
GHELRIGATL FTGDKIEVFV KNGDNLTLIK SQMLTVNEQE GEEIKVPDGH YNIQSALNLN  480
KVVHMHQNEA RNINLWDNGN QLHLEFTLQY DQNREAYQLW NRWDPTHVMA WNAIPESVNV  540
FGTPFDVSKD EHYWKIKRAG NGYVYLENLK NGHVLDVTGA GTANGTNLIV HPLNQNTNQK  600
FKLVQRNETK RATIISQPNP QSGQKNRSSG NFSLDSARGK QVRVLIRDAN GKEAKISFRV  660
MRDKNNDTDP TIWSNVKNGS LVTVSTDANS SNLYIANPSN ANSNFTVEFY TL          712

SEQ ID NO: 412         moltype = AA  length = 676
FEATURE                Location/Qualifiers
REGION                 1..676
                       note = Description of Artificial Sequence: Synthetic
                        polypeptide
source                 1..676
                       mol_type = protein
                       organism = synthetic construct
SEQUENCE: 412
MNNDQGYAYD ASIGYSNPNW MSRISGSKKI SELSIPGTHG STALHGVTFF DEDWVRNQRM  60
TITTQLNSGI RYLDIRARRT GNSFAMHHGE VYQKKMFGDI LNEVTAFLRQ NPGETILMRL  120
KEEHTAESGS NSFEEIMTKY WNDYNSYFWK PSGSTNKMNP TLDEVRGKIV LLQNFNTSGG  180
SGQFGIPYNS LQTQDQDIVD NTGDSMYAKW TAVGNHLKAA DASNRQNIYL NHLSGNGGFS  240
GAKPWFVSSG KRGRSTNDGM EMITEHRDPN KWPQFPRGYY GQIFYGGMNI MSNQYIQQWP  300
IHHTGILAAD FPGKGLIDLV IKLNDRHMGE DIRFIEPQGT TGIRIGFGGD SYLNKHYVVR  360
RNGQYYGEVN QGKPYYASWH QTDFGHELRI GATLFTGDKI EVFVKNGDNL TLIKSQMLTV  420
NEQEGEEIKV PDGHYNIQSA LNLNKVVHMH QNEARNINLW DNGNQLHLEF TLQYDQNREA  480
YQLWNRWDPT HVMAWNAIPE SVNVFGTPFD VSKDEHYWKI KRAGNGYVYL ENLKNGHVLD  540
VTGAGTANGT NLIVHPLNQN TNQKFKLVQR NETKRATIIS QPNPQSGQKN RSSGNFSLDS  600
ARGKQVRVLI RDANGKEAKI SFRVMRDKNN DTDPTIWSNV KNGSLVTVST DANSSNLYIA  660
NPSNANSNFT VEFYTL                                                  676

SEQ ID NO: 413         moltype = AA  length = 422
FEATURE                Location/Qualifiers
REGION                 1..422
                       note = Description of Artificial Sequence: Synthetic
                        polypeptide
source                 1..422
                       mol_type = protein
                       organism = synthetic construct
SEQUENCE: 413
MNNDQGYAYD ASIGYSNPNW MSRISGSKKI SELSIPGTHG STALHGVTFF DEDWVRNQRM  60
TITTQLNSGI RYLDIRARRT GNSFAMHHGE VYQKKMFGDI LNEVTAFLRQ NPGETILMRL  120
KEEHTAESGS NSFEEIMTKY WNDYNSYFWK PSGSTNKMNP TLDEVRGKIV LLQNFNTSGG  180
SGQFGIPYNS LQTQDQDIVD NTGDSMYAKW TAVGNHLKAA DASNRQNIYL NHLSGNGGFS  240
GAKPWFVSSG KRGRSTNDGM EMITEHRDPN KWPQFPRGYY GQIFYGGMNI MSNQYIQQWP  300
IHHTGILAAD FPGKGLIDLV IKLNDRHMGE DIRFIEPQGT TGIRIGFGGD SYLNKHYVVR  360
RNGQYYGEVN QGKPYYASWH QTDFGHELRI GATLFTGDKI EVFVKNGDNL TLIKSQMLTV  420
NE                                                                 422

SEQ ID NO: 414         moltype = AA  length = 448
FEATURE                Location/Qualifiers
source                 1..448
                       mol_type = protein
                       organism = Bacillus sp.
SEQUENCE: 414
MSTNKVHQLP KEFLKDLGEE LKQKTQITSE DLAKIMRDAS RDSAKLNDLI RQASIAAVGK  60
IPSVGMAISP IISYLWPEQA GVDSKLNALE ARITAKIGQA VGEQHTRDIQ SKIKDLKHAM  120
EKLEDSLNTG TFYDGSVKDI HGVLRNQAKD VNDKFISLMH FTQQEHNEIV DLPIYTKVAA  180
AHILFLKYLK THGTDPKLFR YDKSSTLNAE FKTDNIESII NTYAKYIEDT FKKGDNELTT  240
LLKTRDKKIA EKRNLIVPGI PPNPGTESRI HTLDKEINGI NDLKVEEKRV LYRDLTVGEG  300
SFEAISGKKL TYTNFGWIKD DGKWYYLSLY SGFQNYDHKT FDKGELVTGW LQPYEGNTYY  360
LSPANGTKND DGKVFNKGEM TTGWMQVGKK GIWDGKHGAW YYLDNKEGNK DFKGTTGRML  420
HDETARVKNK QGEFKKHYFN ENGTWGDN                                     448

SEQ ID NO: 415         moltype = AA  length = 379
FEATURE                Location/Qualifiers
```

```
source                  1..379
                        mol_type = protein
                        organism = Bacillus sp.
SEQUENCE: 415
MKFASKKVMT GLMVGAMGLS IWAPTSEAAP ANNKYYSINL KADTNKVWDV QGESTDLGLI  60
LLYNGSRGDN EQFAFFPLDG GLYAIVNRNS GKSVMSAAKS VMGSVLFQNS WIGDSTQKWY  120
LRDQGSNNYE IVNQGFGKVA SWGWNGILGP ASQEFVDLDN SNPSDSNNVF FIGNSYGTFS  180
LPTLPAIGTR PNAPDYNKSG AIDQQLPQTS ESVVVGASLI PCIMVQDNQA SDYTKIHNSP  240
YYVLVKEEYW EKAYSDIIPA GGSRKYTLKT GVSTVDQQKM TDTLSMSFGA DLGFKFKDAT  300
ASIKTSITKT LQTEASTTNT EATEETTEKI APSIPGKDTG FTEYQLKTKY TLKRTDGSAV  360
SEPWIVKDPK QTLPRTIAK                                              379

SEQ ID NO: 416          moltype = AA  length = 352
FEATURE                 Location/Qualifiers
REGION                  1..352
                        note = Description of Artificial Sequence: Synthetic
                         polypeptide
source                  1..352
                        mol_type = protein
                        organism = synthetic construct
SEQUENCE: 416
MAPANNKYYS INLKADTNKV WDVQGESTDL GLILLYNGSR GDNEQFAFFP LDGGLYAIVN  60
RNSGKSVMSA AKSVMGSVLF QNSWIGDSTQ KWYLRDQGSN NYEIVNQGFG KVASWGWNGI  120
LGPASQEFVD LDNSNPSDSN NVFFIGNSYG TFSLPTLPAI GTRPNAPDYN KSGAIDQQLP  180
QTSESVVVGA SLIPCIMVQD NQASDYTKIH NSPYYVLVKE EYWEKAYSDI IPAGGSRKYT  240
LKTGVSTVDQ QKMTDTLSMS FGADLGFKFK DATASIKTSI TKTLQTEAST TNTEATEETT  300
EKIAPSIPGK DTGFTEYQLK TKYTLKRTDG SAVSEPWIVK DPKQTLPRTI AK          352

SEQ ID NO: 417          moltype = AA  length = 454
FEATURE                 Location/Qualifiers
source                  1..454
                        mol_type = protein
                        organism = Bacillus sp.
SEQUENCE: 417
VFIFSYSGDK LVQHTCKGRL RKMKAYKKIA TIVPIAVLST SVLFAPAMSF AAEKQGHQRM  60
NMTGSSQQTN QHMNKGLKKH RQTNVADSIS SSNAQSNTTD ITSQPSGSST IASTTSQPAT  120
SNTTGKTAGI RALATTNSVD DWTNSNTQSN QKVDLDAFIN TLGNAFNNKT PGYYMGLTQQ  180
GGDTFDPNQS LGPDGPLNHA DGKYDSHDAI GYTYLGSSSL TLTGKAVGDG SPKSVTLMTE  240
HNGSDLEQTF NTEEKSEQTT NSFTVSNTEG VAVKLSSTTE AKVDVPFVAG VKTSVTMGLD  300
TSYSHTSSNT ATKTDTVIFK SQPVKVAPHT TTTVSAAVYE QKFDGVDTAS KVAIDSTLKF  360
NTTSAGGSAN IKLYDVARAY VKLGNKLPDG ITLDTNTKQV IVNNSIQTTF SGVMGYKTDL  420
DISVTPDGGG QTVKMSMEDY NNPTTRAKIL AQTK                             454

SEQ ID NO: 418          moltype = AA  length = 432
FEATURE                 Location/Qualifiers
REGION                  1..432
                        note = Description of Artificial Sequence: Synthetic
                         polypeptide
source                  1..432
                        mol_type = protein
                        organism = synthetic construct
SEQUENCE: 418
MKAYKKIATI VPIAVLSTSV LFAPAMSFAA EKQGHQRMNM TGSSQQTNQH MNKGLKKHRQ  60
TNVADSISSS NAQSNTTDIT SQPSGSSTIA STTSQPATSN TTGKTAGIRA LATTNSVDDW  120
TNSNTQSNQK VDLDAFINTL GNAFNNKTPG YYMGLTQQGG DTFDPNQSLG PDGPLNHADG  180
KYDSHDAIGY TYLGSSSLTL TGKAVGDGSP KSVTLMTEHN GSDLEQTFNT EEKSEQTTNS  240
FTVSNTEGVA VKLSSTTEAK VDVPFVAGVK TSVTMGLDTS YSHTSSNTAT KTDTVIFKSQ  300
PVKVAPHTTT TVSAAVYEQK FDGVDTASKV AIDSTLKFNT TSAGGSANIK LYDVARAYVK  360
LGNKLPDGIT LDTNTKQVIV NNSIQTTFSG VMGYKTDLDI SVTPDGGGQT VKMSMEDYNN  420
PTTRAKILAQ TK                                                     432

SEQ ID NO: 419          moltype = AA  length = 404
FEATURE                 Location/Qualifiers
REGION                  1..404
                        note = Description of Artificial Sequence: Synthetic
                         polypeptide
source                  1..404
                        mol_type = protein
                        organism = synthetic construct
SEQUENCE: 419
MAEKQGHQRM NMTGSSQQTN QHMNKGLKKH RQTNVADSIS SSNAQSNTTD ITSQPSGSST  60
IASTTSQPAT SNTTGKTAGI RALATTNSVD DWTNSNTQSN QKVDLDAFIN TLGNAFNNKT  120
PGYYMGLTQQ GGDTFDPNQS LGPDGPLNHA DGKYDSHDAI GYTYLGSSSL TLTGKAVGDG  180
SPKSVTLMTE HNGSDLEQTF NTEEKSEQTT NSFTVSNTEG VAVKLSSTTE AKVDVPFVAG  240
VKTSVTMGLD TSYSHTSSNT ATKTDTVIFK SQPVKVAPHT TTTVSAAVYE QKFDGVDTAS  300
KVAIDSTLKF NTTSAGGSAN IKLYDVARAY VKLGNKLPDG ITLDTNTKQV IVNNSIQTTF  360
SGVMGYKTDL DISVTPDGGG QTVKMSMEDY NNPTTRAKIL AQTK                  404

SEQ ID NO: 420          moltype = AA  length = 349
```

```
FEATURE                 Location/Qualifiers
source                  1..349
                        mol_type = protein
                        organism = Bacillus sp.
SEQUENCE: 420
MKNSCKTNEV NPTSFTLFDL DEYLDHNMIN VNINPIDLGG ISDGSKPSGS WKFDRNFLPT  60
PTSGQIPNIC KPVHGYHPEC DFVPYQERAW WVDTSNLVAG GTDVYEEINS VVLQTPIIAD  120
QHIYENESSL QQAYVTPAYT ESVTTTTTNT TTNGCKINPK ASISRKSKYK VKIKEIEKGF  180
NLEVGAEYNF TDTNTNTVTT TRTVTYPSFT TQVPPRTTAI VTVTLNKGYY ANYNVPVEVD  240
LFGRFSQVDI RDNPPSARYY YDLYPYVELV QTCCKSCSQC VPNTIRALPD NKTVRYNGTG  300
SFIADIASNN FVVKTKFVDN KTGATLAEQV EYIPAIYTNP VIETVTTSE             349

SEQ ID NO: 421          moltype = AA  length = 118
FEATURE                 Location/Qualifiers
source                  1..118
                        mol_type = protein
                        organism = Bacillus sp.
SEQUENCE: 421
MQKKYFRNST AKTKSQDYNY NIPSQAIEIQ SGHYAIAKGS AILANYKVDV NLYGEFTGHI  60
PNKNLSAFKS LAAFRGNLPK CITFADGGTV ILNGKGRMNG VEQVLLKMLN QLRLQSCS    118

SEQ ID NO: 422          moltype = AA  length = 343
FEATURE                 Location/Qualifiers
source                  1..343
                        mol_type = protein
                        organism = Enterococcus sp.
SEQUENCE: 422
MKNNTKLLLF STLLIGIITI GNEVEANEIN HFTQNQMLDS SQNRNYGEDW NKVLHDAGQV  60
SVSSAKYLNP PSGYRRITTT TEARDLLNRY YGPNGWLQPV DQYVEQVGDL EIVNQQTIAA  120
GQTVVSNHTG QAMNILTPAF EYSKTYTTST TTTNAFKLGL KASYSLKIFS ATIGTELTTE  180
YNFTHAGTRS VAETVKYTIP SQSVPALPGR TYKVQHQLSV GEARGKVRYV GDINGFIPYA  240
VAVNANASHS SRAGNAILAA ERDPQYISAG YKNKFEYKDA DNIRYFGGDG SFSAQYGTNS  300
RVDIYDITDG EENAPVVASY EIDEITKEII ETKEIKKNNF FIG                   343

SEQ ID NO: 423          moltype = AA  length = 318
FEATURE                 Location/Qualifiers
REGION                  1..318
                        note = Description of Artificial Sequence: Synthetic
                         polypeptide
source                  1..318
                        mol_type = protein
                        organism = synthetic construct
SEQUENCE: 423
MNEINHFTQN QMLDSSQNRN YGEDWNKVLH DAGQVSVSSA KYLNPPSGYR RITTTTEARD  60
LLNRYYGPNG WLQPVDQYVE QVGDLEIVNQ QTIAAGQTVV SNHTGQAMNI LTPAFEYSKT  120
YTTSTTTTNA FKLGLKASYS LKIFSATIGT ELTTEYNFTH AGTRSVAETV KYTIPSQSVP  180
ALPGRTYKVQ HQLSVGEARG KVRYVGDING FIPYAVAVNA NASHSSRAGN AILAAERDPQ  240
YISAGYKNKF EYKDADNIRY FGGDGSFSAQ YGTNSRVDIY DITDGEENAP VVASYEIDEI  300
TKEIIETKEI KKNNFFIG                                               318

SEQ ID NO: 424          moltype = AA  length = 308
FEATURE                 Location/Qualifiers
source                  1..308
                        mol_type = protein
                        organism = Bacillus sp.
SEQUENCE: 424
MKRKRMLLKW MCGLTIGIGS LTGGSLNVFA DEVSDSLADV GFLYGDYLYK TKQHPFGTLS  60
ITYPMREVNN YQIIDKSVSQ VGSTEYEEGE TLFVDDDVFD NKTGTDQTFK TVQFEKEFSE  120
TATASTTHSV GTSLEESVKF DFFVGEGSAK FTVNYNFSKT DSLSTSNKIK YTLPSQSINV  180
PANKKYEVIC VLETKKAKAN VQFNIDVLGN AKYVYSNNSP YTPKYESAAT MVKTLNEKTP  240
TPSVSWLGKE WEKWEYYGEK VRYKNGSGTV SAEYGTRMVL VINDITNNKT RGSKEIARIP  300
VTPIKKQI                                                          308

SEQ ID NO: 425          moltype = AA  length = 279
FEATURE                 Location/Qualifiers
REGION                  1..279
                        note = Description of Artificial Sequence: Synthetic
                         polypeptide
source                  1..279
                        mol_type = protein
                        organism = synthetic construct
SEQUENCE: 425
MDEVSDSLAD VGFLYGDYLY KTKQHPFGTL SITYPMREVN NYQIIDKSVS QVGSTEYEEG  60
ETLFVDDDVF DNKTGTDQTF KTVQFEKEFS ETATASTTHS VGTSLEESVK FDFFVGEGSA  120
KFTVNYNFSK TDSLSTSNKI KYTLPSQSIN VPANKKYEVI CVLETKKAKA NVQFNIDVLG  180
NAKYVYSNNS PYTPKYESAA TMVKTLNEKT PTPSVSWLGK EWEKWEYYGE KVRYKNGSGT  240
VSAEYGTRMV LVINDITNNK TRGSKEIARI PVTPIKKQI                        279

SEQ ID NO: 426          moltype = AA  length = 525
```

```
FEATURE                 Location/Qualifiers
source                  1..525
                        mol_type = protein
                        organism = Mucilaginibacter sp.
SEQUENCE: 426
MFKNLNLNLK ILTVVGLSLI VTSCKKGNVD DPGSSNIVKK LTTQSAGDNK YDLLGFGYDI  60
TGEYASSQAA TYRVIDVDKM ILDEPDRFVP DVNVTQYTEY HVGGDANEYM HNLAESYSLT 120
YTPVPTVPAV IPSFLGSATL HVNFRESTNI SSKYSYASAS VMIKQRRIKF NTPLALIKST 180
YLTAIFKSDV STLSAQQLVT KYGTHVLTDI ILGAKLNVYY RSQTLSTKKG ESVNAGLDVK 240
GLFKVFGVNS NISWKDSSVN SNYDQKLYYN TVGGDGTKGL IGEASLDDST PKISIAAWQS 300
TCTRDNAAFI QISNSSGSVI PLADLIDDPA KKQAVSDYII QYIASRQITL VPEPVNGSGL 360
PSDWVSRALL MPSGKIPGAV NASDDAILVS NGTNNLYSVN RAYRMAMQTD GNLVVYNASN 420
NKPLWASNTS STATGWIYKL YLQLDGNVVI KKRSSSGVEA VVWGAGTETR EGSDRRENAR 480
RTYLVMQNDG NMALYYNGFD GGQYSLQYST ATEGGRVSAR YGRLK                525

SEQ ID NO: 427          moltype = AA  length = 499
FEATURE                 Location/Qualifiers
REGION                  1..499
                        note = Description of Artificial Sequence: Synthetic
                         polypeptide
source                  1..499
                        mol_type = protein
                        organism = synthetic construct
SEQUENCE: 427
MNVDDPGSSN IVKKLTTQSA GDNKYDLLGF GYDITGEYAS SQAATYRVID VDKMILDEPD  60
RFVPDVNVTQ YTEYHVGGDA NEYMHNLAES YSLTYTPVPT VPAVIPSFLG SATLHVNFRE 120
STNISSKYSY ASASVMIKQR RIKFNTPLAL IKSTYLTAIF KSDVSTLSAQ QLVTKYGTHV 180
LTDIILGAKL NVYYRSQTLS TKKGESVNAG LDVKGLFKVF GVNSNISWKD SSVNSNYDQK 240
LYYNTVGGDG TKGLIGEASL DDSTPKISIA AWQSTCTRDN AAFIQISNSS GSVIPLADLI 300
DDPAKKQAVS DYIIQYIASR QITLVPEPVN GSGLPSDWVS RALLMPSGKI PGAVNASDDA 360
ILVSNGTNNL YSVNRAYRMA MQTDGNLVVY NASNNKPLWA SNTSSTATGW IYKLYLQLDG 420
NVVIKKRSSS GVEAVVWGAG TETREGSDRR ENARRTYLVM QNDGNMALYY NGFDGGQYSL 480
QYSTATEGGR VSARYGRLK                                             499

SEQ ID NO: 428          moltype = AA  length = 669
FEATURE                 Location/Qualifiers
REGION                  1..669
                        note = Description of Unknown: Organism from environmental
                         sample
source                  1..669
                        mol_type = protein
                        organism = unidentified
SEQUENCE: 428
VKKMNSYQNT NEYEILESSS NNTNMPNRYP FANDRDMSPM SWNDCQGTSW QDVWESSTSI  60
AGIGIDLINF VAEPSLGGVN LLFSIIGKLI PPNRQSISAL SICDLLSIIR KEVAESVLNA 120
AIADFNGKLK NYREYYLSYL EAWLKDGKPL KKTNNSDIGK LVEYFELSER EFNEILGGSL 180
ARSNAQILLL PTFAQAANVQ LLLLRDAVQY KEQWFPFLSA ENVKSELKSP NSGCDFTGDY 240
YERLKCKTAE YTNYCVYWYQ AGLDQIKQAG TGADTWSKFN KFRREMTLAV LDIIAIFPTY 300
DFEKYPLATD VELTREIYTD AVGYSSGTYS WLNYWTGAFN ALEANGTRGP GLVTWLSSIG 360
IYNEYVSRYF SGWVGTRHYE DYTKGNGTFQ RMSGTTSNDL RNVTFSPFDI FKISSLAIMN 420
LAGETNPRPE YRVSRTEFSS TSLPSKHLYD ANNNGLSRMT IESTLPGIWN PKPSYTDYSH 480
RLSNAACVVY GNSRVNVYGW THTSMSKHNP IYPDKISQIP AVKAFALESG AYVSAGPGHT 540
GGNVVWLPYL GRLKIRLTSA PTNKNYRVRV RYAGLYSGRL MVQRWSLSGS ATGDFPYSST 600
GSNNTFGYVE TLVTTFNQSG VEIIIQNQTS PQLIIDKIEF IPVDLTNLEY EGEQNLEKTK 660
NAVNDLFIN                                                        669

SEQ ID NO: 429          moltype = AA  length = 666
FEATURE                 Location/Qualifiers
REGION                  1..666
                        note = Description of Artificial Sequence: Synthetic
                         polypeptide
source                  1..666
                        mol_type = protein
                        organism = synthetic construct
SEQUENCE: 429
MNSYQNTNEY EILESSSNNT NMPNRYPFAN DRDMSPMSWN DCQGTSWQDV WESSTSIAGI  60
GIDLINFVAE PSLGGVNLLF SIIGKLIPPN RQSISALSIC DLLSIIRKEV AESVLNAAIA 120
DFNGKLKNYR EYYLSYLEAW LKDGKPLKKT NNSDIGKLVE YFELSEREFN EILGGSLARS 180
NAQILLLPTF AQAANVQLLL LRDAVQYKEQ WFPFLSAENV KSELKSPNSG CDFTGDYYER 240
LKCKTAEYTN YCVYWYQAGL DQIKQAGTGA DTWSKFNKFR REMTLAVLDI IAIFPTYDFE 300
KYPLATDVEL TREIYTDAVG YSSGTYSWLN YWTGAFNALE ANGTRGPGLV TWLSSIGIYN 360
EYVSRYFSGW VGTRHYEDYT KGNGTFQRMS GTTSNDLRNV TFSPFDIFKI SSLAIMNLAG 420
ETNPRPEYRV SRTEFSSTSL PSKHLYDANN NGLSRMTIES TLPGIWNPKP SYTDYSHRLS 480
NAACVVYGNS RVNVYGWTHT SMSKHNPIYP DKISQIPAVK AFALESGAYV SAGPGHTGGN 540
VVWLPYLGRL KIRLTSAPTN KNYRVRVRYA GLYSGRLMVQ RWSLSGSATG DFPYSSTGSN 600
NTFGYVETLV TTFNQSGVEI IIQNQTSPQL IIDKIEFIPV DLTNLEYEGE QNLEKTKNAV 660
NDLFIN                                                           666

SEQ ID NO: 430          moltype = AA  length = 567
```

```
FEATURE                Location/Qualifiers
REGION                 1..567
                       note = Description of Unknown: Organism from environmental
                        sample
source                 1..567
                       mol_type = protein
                       organism = unidentified
SEQUENCE: 430
VSPMFTSGTK NTLKIETTDY EIDQAAISIE CMSDEQNSQE KMMLWDEVKQ AKQLSQSRNL  60
LGNGDFGDFS GNDWTFGNDI IIGSNSPIFK GHYLHMFGAR DIYGTLFPTY IYQKIEESKL  120
KPYTRYRVRG FVGSSKDLKL MVTRYGKEID AMMDVPDDLA YMQPGPSCGD YRCESSSQYV  180
SQGYPTLYAD GYASDRYACP ADRVKKHVKC HDRHSFDFHI DTGELDINQN LGIWVLFKIS  240
NPDGYATLGN LEVIEEGPLT DEALAHVKQK EKKWHQHMEK KRLETKQAYD PAKQAVDALF  300
TNVQGEELHY HITLDHIQNA NQLVQSIPYV HHAWLPDAPG MNYDLYQGLN ARIMQAYNLY  360
AVRNVITNGD FTQGLQGWHT TGKAVVQQMD GTSVLVLSNW SAGVSQNLHV QDHHGYVLRV  420
IAKKEGPGKG YVTMMDCNGN QETLRFTSCE EGYITKTVEA FPESNRVRIE IGETEGTFYV  480
DSIELLCMQG YASNNNRHTG NRYEESYNGN YKQNTSDVYH QGHTNNDNQD SSSMYNQNYI  540
NNDDLHFGCA CNQGHNSGCT CNQGYNR                                     567

SEQ ID NO: 431         moltype = AA  length = 424
FEATURE                Location/Qualifiers
source                 1..424
                       mol_type = protein
                       organism = Pseudomonas sp.
SEQUENCE: 431
LMQKEPNPMD SLIFKDLLIN FTSDFTPLWN DRGSGAQLSV SYWRPIPTEH FHGFHILGDF  60
ASSDYNSIVR NRIVAIVSDA NGPDGTALHP PVDYQRLWSD TGTGADTHGA IWKPIAPEGY  120
VALGMLCTLG YEKPLLSTMR CIRADLVIAS YVGDMIWNDR GSGGDSDFSA WSVQPPKAAS  180
GELYFSSGTF IGVPSYEKPD IHINAHALRM QMPLEAFTPS PVPALANFNK PPSVEPSRVT  240
YITRLPWFIV KDPNLQNHEQ LRLSPEYRLE RSDRFILVGF GHNTSSVTQA FDWTATHGES  300
GGHSHTLSDT TLVEVGFEWQ FSVFKNSIKF SAKFNNSVTH TKTSSIGWST TTSLKVTAVV  360
PSQKAVAVYL IQSDYRLLRR DNGQISTSIS YTDGNSVYWS EFPPTPEREV TVSCTPIEQP  420
PSLE                                                              424

SEQ ID NO: 432         moltype = AA  length = 416
FEATURE                Location/Qualifiers
REGION                 1..416
                       note = Description of Artificial Sequence: Synthetic
                        polypeptide
source                 1..416
                       mol_type = protein
                       organism = synthetic construct
SEQUENCE: 432
MDSLIFKDLL INFTSDFTPL WNDRGSGAQL SVSYWRPIPT EHFHGFHILG DFASSDYNSI  60
VRNRIVAIVS DANGPDGTAL HPPVDYQRLW SDTGTGADTH GAIWKPIAPE GYVALGMLCT  120
LGYEKPLLST MRCIRADLVI ASYVGDMIWN DRGSGGDSDF SAWSVQPPKA ASGELYFSSG  180
TFIGVPSYEK PDIHINAHAL RMQMPLEAFT PSPVPALANF NKPPSVEPSR VTYITRLPWF  240
IVKDPNLQNH EQLRLSPEYR LERSDRFILV GFGHNTSSVT QAFDWTATHG ESGGHSHTLS  300
DTTLVEVGFE WQFSVFKNSI KFSAKFNNSV THTKTSSIGW STTTSLKVTA VVPSQKAVAV  360
YLIQSDYRLL RRDNGQISTS ISYTDGNSVY WSEFPPTPER EVTVSCTPIE QPPSLE     416

SEQ ID NO: 433         moltype = AA  length = 449
FEATURE                Location/Qualifiers
source                 1..449
                       mol_type = protein
                       organism = Bacillus sp.
SEQUENCE: 433
MITNEVHQLP KGFLKDLGEE LKQKTQITSE DLAKIMREAS RDSAKLNDLI RQASIAAVGK  60
IPSVGMAISP IISYLWPEQA GVDSKLNALE AKITAKIGQA VGEQHTRDIQ SKIKDLKHAM  120
EKLEDSLNTG TFYDGSVKDI HGVLRNQAKD VNDKFISLLH FTQQEHNEIV DLPIYTKVAA  180
AHILFLKYLK THGTDPKLFR YDKSSTLNAE FKTDNIESII ATYAKHIEDT FKNGDNKLVT  240
ILKTRAEKIA KKRNLIVPGI PTNIGTESQI HTLENEIKGI DDLKVEEKRA LYRDLTVNEG  300
SFEAISGKKL TYTNFGWIID GGKWYYLSPY KDFKNYDGKT FDKGELVTGW LKPYEEKNYY  360
YLSPADGTKN DDGKVFNKGE MTTGWMQVGK KSTWDGKHGA WYYLDNKEGN KDFKGTTGRM  420
LHDETARVKN KQGDFKKHYF NENGTWGDN                                   449

SEQ ID NO: 434         moltype = AA  length = 292
FEATURE                Location/Qualifiers
source                 1..292
                       mol_type = protein
                       organism = Bacillus sp.
SEQUENCE: 434
MLNLTQLINA YGNYLRTIPI PAFQGAFGLP GDVLYDSVYV QRNGVSVTGI APTSNIEIPT  60
NLLTQTPIIG KSTSYTNGSS LPQKETFTYN EQFTDSVTTT RTEGIVYDVS TTTNIGVNIP  120
GIANINQSIT FSTNISNTTS TAQTYTKQTS WSSGLELNIP PFRKLTAQAI ILQGAFEMPV  180
VSNVILSGNV VYIGQIQILL IARDTIERSI VSIIQWALNN PNDPNVQASG FDPSKAIILP  240
NGTVQYNGTV SIKGTVGLHL QVVSQEFTLD GRPVSEPKPI STVSSPKTIL FQ          292

SEQ ID NO: 435         moltype = AA  length = 486
```

```
FEATURE                 Location/Qualifiers
source                  1..486
                        mol_type = protein
                        organism = Bacillus sp.
SEQUENCE: 435
MIHPQEYLSD TQSSTYQSIG AGKVFKVEND GVVKVLKDML FDKDTLKSIA SLGGNTLNQV  60
YKDAYHSNDF SGTLRTVVLG AVALIPYGGA FISQILGAVC PNNVEDNQLK YVQDQINRLD  120
KKIEDLSAAI LKSHYDSLLK ELQSFERSVN SSDTSDVYYS TGDVYENRRW HARHINQKFK  180
ELIRDCNKEV LQAKELPMYT TVTTAYLLFL KFIEKNGKGS EVRFDNKSFN EEFMHDIQNA  240
AKEYKIHIEH IYNNEAQRLR DEMIAIAQKT RKVTGIYLVG NESRFDSQVE DVLKRMQAKY  300
NELFKEFMRD GTASVLSGRN AIMNDLRKNI SLYTDLLNQK NKYYNVTWGS KLFRLVAKID  360
TWILDNGKWY YYDEYMSLVK HMFYSAGKWY YLSPKKSDKL EEGQMLTGWL SLTHGETVNV  420
MMWMAVRNEG DKYRDDLAKM PELIKKLANT KSWIYASSNG ELVYNTKRVI DGKEYEFNKF  480
GICLNP                                                             486

SEQ ID NO: 436          moltype = AA  length = 277
FEATURE                 Location/Qualifiers
source                  1..277
                        mol_type = protein
                        organism = Bacillus sp.
SEQUENCE: 436
MANPQENPID LIEIFSTFAN NWSMENQGCA GTLFLFPHDD SQQGLEVSSD FTAVYDTPVE  60
QGKANPQSSF TFDNTTNAFK DQQILINTTT PISESWELTQ SVCPGGNDFF TINTPALTNV  120
PGIPSADSIQ ICEHETVAHS HMYTWDINQT IQLLPRSSTK VTFQTTLKEV TRNFQFVYWM  180
TGNIGVTSMK PINGSSETYF PVTQVLQWIQ SDLITLDFEY NKVTCLNKGI YKATYQDQPQ  240
LLIQSTSLDN SSIVQESILD LNTGTMMPVN NPNGCCN                           277

SEQ ID NO: 437          moltype = AA  length = 271
FEATURE                 Location/Qualifiers
source                  1..271
                        mol_type = protein
                        organism = Bacillus sp.
SEQUENCE: 437
MAILNLRDIL QRTADAMVPS NAAGPAILNN LKLASRLDIA TNREITLDNT GVPIIITEKA  60
DNLTDKATQE QTINFKKEVM NTFNTKTTQG FEIGNQVEVG TSVNLVFGQL NTKMSTSFKY  120
NISTEKTIES TETITYARDV PFITPAKTQT LISYIIRTTG PFTTTVPFFA NLSGGYSFRN  180
KGGEPSVEPV TIYPFTTTEF LNRLIIENQD LNISINPDNP VELRLQGELE ITGGLSLDSY  240
VTIQNIPLGN NPSLSTTQTL PSQSGPLTLF F                                 271

SEQ ID NO: 438          moltype = AA  length = 439
FEATURE                 Location/Qualifiers
source                  1..439
                        mol_type = protein
                        organism = Pseudomonas sp.
SEQUENCE: 438
LTMTTENSVT TAVRQMESIK LDNLLINFTT DFHRIWDTRG SASKPAAFWR PTPAPDLLPG  60
FFPLGDVAIS GYGNINGSRI VAVVCESHSS SVDATLGKAL SRPEDFEEVW KDEGSNAHQD  120
GSIWRPIPPD GYVALGLVCS NDHEKPSLNA VRCVRADLVI GSSVGDLIWS DLGSHAEQDF  180
SAWSVQPPFG TAGQIYFAPG TFVGANGHSR PAADFPTYSL RMQIPLQASP PPAAPVLTGE  240
GQPPAAGTAV VTYVAQLPWF AITDPELSPI EQLRASPFYV MERADQYFLV GNEHNSTPQA  300
KTFKWTAPRA QNAERLESFA KATSIEIGSQ WPFRVQPASI KFSARLNHTF AHTEITSNQW  360
FNSAAVEIIS IAPKNKTVAV YQVQCDYRLL RENGTQVSTG ISYTDTNSLY MSLYPPETDR  420
EVICPVPATE PPVITDTAP                                               439

SEQ ID NO: 439          moltype = AA  length = 437
FEATURE                 Location/Qualifiers
REGION                  1..437
                        note = Description of Artificial Sequence: Synthetic
                         polypeptide
source                  1..437
                        mol_type = protein
                        organism = synthetic construct
SEQUENCE: 439
MTTENSVTTA VRQMESIKLD NLLINFTTDF HRIWDTRGSA SKPAAFWRPT PAPDLLPGFF  60
PLGDVAISGY GNINGSRIVA VVCESHSSSV DATLGKALSR PEDFEEVWKD EGSNAHQDGS  120
IWRPIPPDGY VALGLVCSND HEKPSLNAVR CVRADLVIGS SVGDLIWSDL GSHAEQDFSA  180
WSVQPPFGTA GQIYFAPGTF VGANGHSRPA ADFPTYSLRM QIPLQASPPP AAPVLTGEGQ  240
PPAAGTAVVT YVAQLPWFAI TDPELSPIEQ LRASPFYVME RADQYFLVGN EHNSTPQAKT  300
FKWTAPRAQN AERLESFAKA TSIEIGSQWP FRVQPASIKF SARLNHTFAH TEITSNQWFN  360
SAAVEIISIA PKNKTVAVYQ VQCDYRLLRE NGTQVSTGIS YTDTNSLYMS LYPPETDREV  420
ICPVPATEPP VITDTAP                                                 437

SEQ ID NO: 440          moltype = AA  length = 327
FEATURE                 Location/Qualifiers
REGION                  1..327
                        note = Description of Unknown: Organism from environmental
                         sample
source                  1..327
                        mol_type = protein
```

```
                         organism = unidentified
SEQUENCE: 440
MRTLKKTIAL ACTLALAEGV VGGASPTFAQ ELPKSQLEHF KVNNKSDASP VDIRAVVRNG  60
LDLLDKKEET RGFPFGRSYN IHLNTYSQKL DSVIEEGEPI FSDGTSEFVG SSVLTNNGDI  120
EQTLSTNSYS KQTTNSVTTT TTNGWEAGME VSAEIPIDFF KIGMKMSGKV NGTQGKSITS  180
SENITYTATP QNIKVAPHSS VQVTVKLKRA KATGDLKYRA YNDGYLVNTD SSPYAAPVLP  240
GKPNPWLGEF INYLKKYEDI PGVEVSPNER GVYTFGSGKY EADYGSTFEV TVTPIQKKKA  300
SHTPNTKKEQ LNNTTYKFEV TAQVTGH                                     327

SEQ ID NO: 441           moltype = AA  length = 299
FEATURE                  Location/Qualifiers
REGION                   1..299
                         note = Description of Artificial Sequence: Synthetic
                          polypeptide
source                   1..299
                         mol_type = protein
                         organism = synthetic construct
SEQUENCE: 441
MQELPKSQLE HFKVNNKSDA SPVDIRAVVR NGLDLLDKKE ETRGFPFGRS YNIHLNTYSQ  60
KLDSVIEEGE PIFSDGTSEF VGSSVLTNNG DIEQTLSTNS YSKQTTNSVT TTTTNGWEAG  120
MEVSAEIPID FFKIGMKMSG KVNGTQGKSI TSSENITYTA TPQNIKVAPH SSVQVTVKLK  180
RAKATGDLKY RAYNDGYLVN TDSSPYAAPV LPGKPNPWLG EFINYLKKYE DIPGVEVSPN  240
ERGVYTFGSG KYEADYGSTF EVTVTPIQKK KASHTPNTKK EQLNNTTYKF EVTAQVTGH   299

SEQ ID NO: 442           moltype = AA  length = 276
FEATURE                  Location/Qualifiers
source                   1..276
                         mol_type = protein
                         organism = Bacillus sp.
SEQUENCE: 442
MTIVNIWTEV DKFATKFCTS RGLTYSGERG RVEQLPLIMR NIVATAVDSI VSSPPKTAFS  60
QSQIFTNITE DTQRSIFEYH KELTESTSST TSTGVTTGLS VSSTQEFNIK FVEVGVTQTV  120
TAEVNVTTEQ TKTTTETQRM GTTQEITVPP HSQVKATIII QEGDYSFATK LTCDISGFVY  180
FTSTSGLTFW SSIYDVLKTN NTPNFTFTFE DPSDPTCHFN GTGGIKGNQG LQSFVTVEQS  240
PLPGKPGQSR KYTLSGQTAN SLGIIQPGTI QIPVFN                           276

SEQ ID NO: 443           moltype = AA  length = 818
FEATURE                  Location/Qualifiers
source                   1..818
                         mol_type = protein
                         organism = Bacillus sp.
SEQUENCE: 443
MSTGGSKMNP YQSKNDYEIL DATRKNCHMS NCYPKYPLAN DPQMYLRNTH YKDWLAMCNK  60
NNPVGWIPPG SFEFTWLNAT VAALTIISVT TALLIAPPLL VGGVIAAGAA ILAGTLPLLW  120
PAGSTPEDNT FNEIMNATEA LLNTKISDFV RQTADTKIIS LQNLISYYQS ALENWKKNPN  180
NSAAINTVSS RFQIVNAFFV EAMPALSMRG YEVAQLGAYA QAANLHLLLL RDGILYADKW  240
NLAKGPVHAS GNLHYKEFLD YKNKYINHCS TWYNEGQLSA NNKGNGLAYQ RTMTILVLDI  300
ISMFSTYDPR LYTMPIKTEI LTRTIYTDGV NRNQTRSIHN PGLFRRLEQM KFHIYEYQNV  360
QFLSGHQNIF RSMNDTHPLI YGPLQGYRSS NINKITTINL GDYDKIYSIK TESRDRIVQG  420
SITFDKINFY GAFNKSWLFY VYNQNGPIIK HSNIPGVEAP SATLDYRNYT HYLSNCIFQS  480
NRNGVSEPDY NTQSYIFGWN HYTIDPTGNY VTDAWVDYTS TEERYVPQIS QVPAVKASDI  540
YNPGHVVNAT VEYGPYFTGG DVIVSKAQLD GTGLVRTLIT FPIIPKRYAA SGFRVRMYYA  600
ANHTGQVSYG VENINTTGYA IFEKTFDGWE YDRARHEQFK YIEFDRTFSL RHSGQVEDHL  660
LHIYYPNTAR VSGDQLLIID KIEFIPVGIR LNQAPEGYDT YDQNISSYNQ NYNNYDENTD  720
TTYQPSYDNN YNHNSSNMYD QNYNNSYNQS CGCNDNSGYG TYDQNMDNTY DQSYNNYNPD  780
NSNYNQHSND MYNQEYTNNY NQNSGCTCNQ GYNNNYPK                         818

SEQ ID NO: 444           moltype = AA  length = 811
FEATURE                  Location/Qualifiers
REGION                   1..811
                         note = Description of Artificial Sequence: Synthetic
                          polypeptide
source                   1..811
                         mol_type = protein
                         organism = synthetic construct
SEQUENCE: 444
MNPYQSKNDY EILDATRKNC HMSNCYPKYP LANDPQMYLR NTHYKDWLAM CNKNNPVGWI  60
PPGSFEFTWL NATVAALTII SVTTALLIAP PLLVGGVIAA GAAILAGTLP LLWPAGSTPE  120
DNTFNEIMNA TEALLNTKIS DFVRQTADTK IISLQNLISY YQSALENWKK NPNNSAAINT  180
VSSRFQIVNA FFVEAMPALS MRGYEVAQLG AYAQAANLHL LLLRDGILYA DKWNLAKGPV  240
HASGNLHYKE FLDYKNKYIN HCSTWYNEGQ LSANNKGNGL AYQRTMTILV LDIISMFSTY  300
DPRLYTMPIK TEILTRTIYT DGVNRNQTRS IHNPGLFRRL EQMKFHIYEY QNVQFLSGHQ  360
NIFRSMNDTH PLIYGPLQGY RSSNINKITT INLGDYDKIY SIKTESRDRI VQGSITFDKI  420
NFYGAFNKSW LFYVYNQNGP IIKHSNIPGV EAPSATLDYR NYTHYLSNCI FQSNRNGVSE  480
PDYNTQSYIF GWNHYTIDPT GNYVTDAWVD YTSTEERYVP QISQVPAVKA SDIYNPGHVV  540
NATVEYGPYF TGGDVIVSKA QLDGTGLVRT LITFPIIPKR YAASGFRVRM YYAANHTGQV  600
SYGVENINTT GYAIFEKTFD GWEYDRARHE QFKYIEFDRT FSLRHSGQVE DHLLHIYYPN  660
TARVSGDQLL IIDKIEFIPV GIRLNQAPEG YDTYDQNISS YNQNYNNYDE NTDTTYQPSY  720
DNNYNHNSSN MYDQNYNNSY NQSCGCNDNS GYGTYDQNMD NTYDQSYNNY NPDNSNYNQH  780
```

```
SNDMYNQEYT NNYNQNSGCT CNQGYNNNYP K                         811

SEQ ID NO: 445          moltype = AA  length = 680
FEATURE                 Location/Qualifiers
REGION                  1..680
                        note = Description of Artificial Sequence: Synthetic
                         polypeptide
source                  1..680
                        mol_type = protein
                        organism = synthetic construct
SEQUENCE: 445
MNPYQSKNDY EILDATRKNC HMSNCYPKYP LANDPQMYLR NTHYKDWLAM CNKNNPVGWI  60
PPGSFEFTWL NATVAALTII SVTTALLIAP PLLVGGVIAA GAAILAGTLP LLWPAGSTPE  120
DNTFNEIMNA TEALLNTKIS DFVRQTADTK IISLQNLISY YQSALENWKK NPNNSAAINT  180
VSSRFQIVNA FFVEAMPALS MRGYEVAQLG AYAQAANLHL LLLRDGILYA DKWNLAKGPV  240
HASGNLHYKE FLDYKNKYIN HCSTWYNEGQ LSANNKGNGL AYQRTMTILV LDIISMFSTY  300
DPRLYTMPIK TEILTRTIYT DGVNRNQTRS IHNPGLFRRL EQMKFHIYEY QNVQFLSGHQ  360
NIFRSMNDTH PLIYGPLQGY RSSNINKITT INLGDYDKIY SIKTESRDRI VQGSITFDKI  420
NFYGAFNKSW LFYVYNQNGP IIKHSNIPGV EAPSATLDYR NYTHYLSNCI FQSNRNGVSE  480
PDYNTQSYIF GWNHYTIDPT GNYVTDAWVD YTSTEERYVP QISQVPAVKA SDIYNPGHVV  540
NATVEYGPYF TGGDVIVSKA QLDGTGLVRT LITFPIIPKR YAASGFRVRM YYAANHTGQV  600
SYGVENINTT GYAIFEKTFD GWEYDRARHE QFKYIEFDRT FSLRHSGQVE DHLLHIYYPN  660
TARVSGDQLL IIDKIEFIPV                                      680

SEQ ID NO: 446          moltype = AA  length = 350
FEATURE                 Location/Qualifiers
REGION                  1..350
                        note = Description of Unknown: Organism from environmental
                         sample
source                  1..350
                        mol_type = protein
                        organism = unidentified
SEQUENCE: 446
LNFKPLYKVL VVTTLVSSSV ALPTVSFAEL DNSKKVQDYT NIRASEVNLE NILQQIGQTP  60
LHELIMQDFD LYNCYGNEVW GNSVGNFYPL PVSPKLQEQP WTEYSPEPAK YVKLNGINLI  120
KMDVESPNLL ADFKPLYFSV ANFKNKTSAP QTFQTIEFAE EIKDVTTITK TKAIKAGVDA  180
SAKSELDVFG LVGIEFSAKL TVEGNFSDTD TETHEYVRKM RIPPMSVIVQ PGKGVRVKAE  240
VLKGEVENVD LKADASVQGP YIIKNKGPED KGDVYGYLKT MQIVYPQKFK EITGGNVSFD  300
DRLKVTKLRG LGMLTASITS SNYNVFLEEY DLDTGKVTKQ IPVETRTLNV       350

SEQ ID NO: 447          moltype = AA  length = 323
FEATURE                 Location/Qualifiers
REGION                  1..323
                        note = Description of Artificial Sequence: Synthetic
                         polypeptide
source                  1..323
                        mol_type = protein
                        organism = synthetic construct
SEQUENCE: 447
MELDNSKKVQ DYTNIRASEV NLENILQQIG QTPLHELIMQ DFDLYNCYGN EVWGNSVGNF  60
YPLPVSPKLQ EQPWTEYSPE PAKYVKLNGI NLIKMDVESP NLLADFKPLY FSVANFKNKT  120
SAPQTFQTIE FAEEIKDVTT ITKTKAIKAG VDASAKSELD VFGLVGIEFS AKLTVEGNFS  180
DTDTETHEYV RKMRIPPMSV IVQPGKGVRV KAEVLKGEVE NVDLKADASV QGPYIIKNKG  240
PEDKGDVYGY LKTMQIVYPQ KFKEITGGNV SFDDRLKVTK LRGLGMLTAS ITSSNYNVFL  300
EEYDLDTGKV TKQIPVETRT LNV                                  323

SEQ ID NO: 448          moltype = AA  length = 670
FEATURE                 Location/Qualifiers
source                  1..670
                        mol_type = protein
                        organism = Bacillus sp.
SEQUENCE: 448
MNQYNNDGYE ILDSNTSPYP SNKNNQYSNS RYPYTNNPNQ PTNYKDWLNM SQKNQQYGAN  60
AENFASADTI TGVTTMMNVV GTIMTGFATT TIYGLGLLVI GAVLPLFWKP GADPKTVWTQ  120
FMNIGETALK KEISEVIRAQ AFAYIQGYKN SIEEYKNLFS LWQNNPNSDT ARAVQISFLA  180
VNQDFLSNLP LFQIQSYEIL LLPVFTAVSL LHITLLQQAS LYYDQWNKDQ SISPTPTSSS  240
NHYYELLTTK IEEYIDYSSI TYQRGLEILK NNRTPWDIYN TYRREMTLTV LDIISIFPNF  300
DSRKYQMKSN YELTREIYTA LMEDNSTIPI DDLEIQLTRE KEPHLFNKLT KLTLSISLRH  360
NLFLGNQVGV TYMNVPMNSP GFPILSPIYG SIDSIQNVDY GGNVNYPLYK ANIADISPPE  420
TRPTNKIIRM NFNPIVGGTI FNIDLNSKLT PSEIRNTSFG FSKDIYNPNT PNINNYSHII  480
SYMKTNDIYI GEERRISFAW THKDVDFNNT IHFDRITQIP AVKSWDLRVG SKIIKGPGHT  540
GGDLILLNGA GYLEMRCKVT NFSSPNKKYI IRLRYAANDK LRTDIRVNET LNGGTINGET  600
QTLDVTFSTT KNDIPHLTYN MFEYTEFFKN NNPLIIQPNQ TISLIIRSLT SPSSTTDFII  660
IDKIEFIPVD                                                 670

SEQ ID NO: 449          moltype = AA  length = 206
FEATURE                 Location/Qualifiers
source                  1..206
                        mol_type = protein
```

```
                        organism = Bacillus sp.
SEQUENCE: 449
MYLYKGGEPI FMENKHSHLN SDYPNHTEYE SESQSSLSYS HPSSHLHQHT LHPNDKNHIL  60
PFSVILNLPK GFHIQKQIHP KLVYDLSYLS MSKEICKKSI EVDNCGYVDV DLHVLKIKGC  120
LSFLLNVCIE PIHKQKMCST DHKDDFIFLC AQDTLYVDHI LKYSIDTLPY YVIDEDHIQV  180
RKLEIEMLEP SHGIIKISGE FYFEYE                                      206

SEQ ID NO: 450          moltype = AA  length = 323
FEATURE                 Location/Qualifiers
source                  1..323
                        mol_type = protein
                        organism = Bacillus sp.
SEQUENCE: 450
LIQLIQRRGV SHVRKKYLKK TMIISTMTLS MSLTGLSSSS SVFAAENILT PIQHVQNKQN  60
NEENYFKERF FNNAFAKSIG PTSIENIQIT EKVPRFVGSV ISNNYTNEAF TDVTPEKSYK  120
TVDSVTTSTT WEWNLENTIE VSGGVEVNVG FGKITGGVKE SFKAGVKNTK NKTEFHSDEY  180
TVTEKSRSIP LNPHQSKRLD TMLLTTKMNG TLSHTDELTG KNTFTILTDQ SEFIQLEDVN  240
AYELFKKLES LGDMIVNITN SSDITYWYLN TKELRDAVII NDEKKKVYLK TETTTFTADL  300
GSTQTISSLY DITDGGSKLL KTF                                         323

SEQ ID NO: 451          moltype = AA  length = 323
FEATURE                 Location/Qualifiers
REGION                  1..323
                        note = Description of Artificial Sequence: Synthetic
                         polypeptide
source                  1..323
                        mol_type = protein
                        organism = synthetic construct
SEQUENCE: 451
MIQLIQRRGV SHVRKKYLKK TMIISTMTLS MSLTGLSSSS SVFAAENILT PIQHVQNKQN  60
NEENYFKERF FNNAFAKSIG PTSIENIQIT EKVPRFVGSV ISNNYTNEAF TDVTPEKSYK  120
TVDSVTTSTT WEWNLENTIE VSGGVEVNVG FGKITGGVKE SFKAGVKNTK NKTEFHSDEY  180
TVTEKSRSIP LNPHQSKRLD TMLLTTKMNG TLSHTDELTG KNTFTILTDQ SEFIQLEDVN  240
AYELFKKLES LGDMIVNITN SSDITYWYLN TKELRDAVII NDEKKKVYLK TETTTFTADL  300
GSTQTISSLY DITDGGSKLL KTF                                         323

SEQ ID NO: 452          moltype = AA  length = 280
FEATURE                 Location/Qualifiers
REGION                  1..280
                        note = Description of Artificial Sequence: Synthetic
                         polypeptide
source                  1..280
                        mol_type = protein
                        organism = synthetic construct
SEQUENCE: 452
MAENILTPIQ HVQNKQNNEE NYFKERFFNN AFAKSIGPTS IENIQITEKV PRFVGSVISN  60
NYTNEAFTDV TPEKSYKTVD SVTTSTTWEW NLENTIEVSG GVEVNVGFGK ITGGVKESFK  120
AGVKNTKNKT EFHSDEYTVT EKSRSIPLNP HQSKRLDTML LTTKMNGTLS HTDELTGKNT  180
FTILTDQSEF IQLEDVNAYE LFKKLESLGD MIVNITNSSD ITYWYLNTKE LRDAVIINDE  240
KKKVYLKTET TTFTADLGST QTISSLYDIT DGGSKLLKTF                       280

SEQ ID NO: 453          moltype = AA  length = 283
FEATURE                 Location/Qualifiers
source                  1..283
                        mol_type = protein
                        organism = Pseudomonas sp.
SEQUENCE: 453
MSFEININVG SDAQSSTITA SGKVRDLISA EERETFGIDD FALTRAIKNM RGEAPDEVHL  60
RDNSLFDQYG WTKTHRVMEV LSAEILSIDL QPVALATHQY ENLRDNLPSS HTATLSYAAL  120
VSAATNWSAG SKLTLEQKFT YKIGLPSNNI GGETRIGLET TYGEGASKTL TSTITTADAV  180
TLVVEPGTRA TATLSASKGT LEAKVTYRAY LEGDVYYDYH TPFEGHHHWA EPIDEIMAAG  240
DISNEVVCSE TIEVGFYADT KVIVSDDQGN AERQIAPAFL TMD                  283

SEQ ID NO: 454          moltype = AA  length = 299
FEATURE                 Location/Qualifiers
source                  1..299
                        mol_type = protein
                        organism = Bacillus sp.
SEQUENCE: 454
MTQIIDIDRY LCTGALIYMS EGIFPKPCQE VKMWYESVLN GGGMWSEYYN NSKLTISDQK  60
LDYQLPPLSS DNVTPLVIVG GIFENTTNET QNFTSLEIVK RTSTVTRSST TYGFKTSTKI  120
GSSTTVKAEI PFVGGGETTL SMEFSFETDF SKTNEIVKTD ETELKIPPQS ITVEPGQKKR  180
LEVELYKVAI PEATFTIDGD VAGRVYTPQT NEVVVYDFLS KINNRCPGTY ANVDKNLQLD  240
SGKKTLHFKG EGKAAFEIMA VEYVMRIITL DNKTGATLNE ETAVRQLSRT IEKKSPSLS   299

SEQ ID NO: 455          moltype = AA  length = 449
FEATURE                 Location/Qualifiers
source                  1..449
                        mol_type = protein
```

```
                        organism = Bacillus sp.
SEQUENCE: 455
MITNEIHQLP KGFLKDLGEE LKQKTQITSE DLAKIMRDAS HDSAKLNDLI RQVSIAAVGK  60
IPSVGMAISP IISYLWPEQA GVDSKLNALE ARITAKIGQA VGEQHTRDIQ SKIKDLKHAM  120
EKLEDSLNTG TFYDGSVKDI HGVLRNQAKD VNDKFISLMH FTQQEHNEIV DLPIYTKVAA  180
AHILFLKYLK THGTDPKLFR YDKSSTLNAE FKTDNIESII ATYAKHIEDT FKKGDNKLVA  240
ILKTRAEKIA KKRSLIVPGI PANIGTESQI HTLENEIKGI DDLKVEEKRA LYRDLTVNEG  300
SFEAITGKKL TYTNFGWIID GGKWYYMSPY KDFINYDGKT FDKGELVTGW LKPYEEKNYY  360
YLSPVDGTKN DDGKVFNKGE MTTGWMQVGK KSTWDGKHGA WYYLDNKEGN KDFKGTTGRM  420
LHDETARVKN KQGDFKKHYF NENGTWGDN                                  449

SEQ ID NO: 456          moltype = AA  length = 332
FEATURE                 Location/Qualifiers
source                  1..332
                        mol_type = protein
                        organism = Bacillus sp.
SEQUENCE: 456
MHEMNKWIKL ILCVGILTTS VITFNTSNIV YAQSSSQLIY DLQDNVMDCL NSIGRNQNND  60
VNFQENRSAG TYNFKSVSFS SPLDIKFEKY DAEKIGPEKQ IDEKIVFSFT DELINGSSTS  120
QKLSTGTRSE MVSNTTTATI TRGFKIGGKT SGKISIPFIG ETGIEVSPEY NQSDATSNTK  180
TTMKTLIATP QNIDVPAGKK ALVTVEFTQR TIEGKIKLNA IASGHAKGTF DYIGMPFITS  240
GADKWVKREF DMNLNQIYIK FAELSNEANN PLIITMNPDN ETITLHGEAK YTSENTASSF  300
RVHVNIVDID TNSNNRIHKR DIINSYSYTV NP                              332

SEQ ID NO: 457          moltype = AA  length = 329
FEATURE                 Location/Qualifiers
REGION                  1..329
                        note = Description of Artificial Sequence: Synthetic
                         polypeptide
source                  1..329
                        mol_type = protein
                        organism = synthetic construct
SEQUENCE: 457
MNKWIKLILC VGILTTSVIT FNTSNIVYAQ SSSQLIYDLQ DNVMDCLNSI GRNQNNDVNF  60
QENRSAGTYN FKSVSFSSPL DIKFEKYDAE KIGPEKQIDE KIVFSFTDEL INGSSTSQKL  120
STGTRSEMVS NTTTATITRG FKIGGKTSGK ISIPFIGETG IEVSPEYNQS DATSNTKTTM  180
KTLIATPQNI DVPAGKKALV TVEFTQRTIE GKIKLNAIAS GHAKGTFDYI GMPFITSGAD  240
KWVKREFDMN LNQIYIKFAE LSNEANNPLI ITMNPDNETI TLHGEAKYTS ENTASSFRVH  300
VNIVDIDTNS NNRIHKRDII NSYSYTVNP                                  329

SEQ ID NO: 458          moltype = AA  length = 301
FEATURE                 Location/Qualifiers
REGION                  1..301
                        note = Description of Artificial Sequence: Synthetic
                         polypeptide
source                  1..301
                        mol_type = protein
                        organism = synthetic construct
SEQUENCE: 458
MQSSSQLIYD LQDNVMDCLN SIGRNQNNDV NFQENRSAGT YNFKSVSFSS PLDIKFEKYD  60
AEKIGPEKQI DEKIVFSFTD ELINGSSTSQ KLSTGTRSEM VSNTTTATIT RGFKIGGKTS  120
GKISIPFIGE TGIEVSPEYN QSDATSNTKT TMKTLIATPQ NIDVPAGKKA LVTVEFTQRT  180
IEGKIKLNAI ASGHAKGTFD YIGMPFITSG ADKWVKREFD MNLNQIYIKF AELSNEANNP  240
LIITMNPDNE TITLHGEAKY TSENTASSFR VHVNIVDIDT NSNNRIHKRD IINSYSYTVN  300
P                                                                301

SEQ ID NO: 459          moltype = AA  length = 401
FEATURE                 Location/Qualifiers
source                  1..401
                        mol_type = protein
                        organism = Bacillus sp.
SEQUENCE: 459
MKSISKKVMA GLLVGATSLS IWAPISEAAA PENNRYYNIQ LKSNQKKVWN VTRASNDNDR  60
AILLWQGGSA DNEKFAFFQL DGGAYAIVNK NSGKIVTFGD ASWFGDRSIL PGNETLQQQS  120
WTGAAKQKWN LRDLGSNNYE IVNQANGKVP TYQWAGSLVD NVEYLKLDNS NPSDPDKVFK  180
LSDGSVPILL PGSVIPILIG QDSISVPNLP ATGTRPDAPN YTGGVDQQLP QVSNSVVVGA  240
SLIPCIMVND NEASDYTKIH NSPYYTLVKE EYWDRTFSKV IQPGLSESYS YKTGVSSVDQ  300
QKMTDTLSMK FGADLGIKFG DASASLKSEI SRTIQTEIST TNSEATEETR SYVATGEPGK  360
ATGYTQYQLA TKYTLKRADG SIVSDSWVVK NDKITVTRKT S                     401

SEQ ID NO: 460          moltype = AA  length = 372
FEATURE                 Location/Qualifiers
REGION                  1..372
                        note = Description of Artificial Sequence: Synthetic
                         polypeptide
source                  1..372
                        mol_type = protein
                        organism = synthetic construct
SEQUENCE: 460
```

```
MPENNRYYNI QLKSNQKKVW NVTRASNDND RAILLWQGGS ADNEKFAFFQ LDGGAYAIVN  60
KNSGKIVTFG DASWFGDRSI LPGNETLQQQ SWTGAAKQKW NLRDLGSNNY EIVNQANGKV  120
PTYQWAGSLV DNVEYLKLDN SNPSDPDKVF KLSDGSVPIL LPGSVIPILI GQDSISVPNL  180
PATGTRPDAP NYTGGVDQQL PQVSNSVVVG ASLIPCIMVN DNEASDYTKI HNSPYYTLVK  240
EEYWDRTFSK VIQPGLSESY SYKTGVSSVD QQKMTDTLSM KFGADLGIKF GDASASLKSE  300
ISRTIQTEIS TTNSEATEET RSYVATGEPG KATGYTQYQL ATKYTLKRAD GSIVSDSWVV  360
KNDKITVTRK TS                                                    372

SEQ ID NO: 461         moltype = AA  length = 665
FEATURE                Location/Qualifiers
source                 1..665
                       mol_type = protein
                       organism = Bacillus sp.
SEQUENCE: 461
MKYKDRKNAK RKYKQALLAT VATMTLGVST LGSTASVFAA EKTEKTQQLT SNADLDSAIE  60
ILKDGSIEII NKDLIKGETA QAVVSLGGNA LFQAWKDSQK GNYNNTFRTL AIGSTALIPY  120
GGIFISPILG LLWPENVDSK DHMMTQLITD MTDLMDDKIN QYDLETIKKS WDALIKLQEK  180
FENAVNKKPL TFDDSIQAAN IKYAGDINNK FNELIALCQK SSKKIIELPM FTTIAAAHVQ  240
FLKFMEKNAR THPRIKMDNE HYQYYFGEDL KKLPLTYANH VMKIHKEGRD QAYSKIKTLA  300
KTDDIKARKL WRAYTKFYYQ SFDCQAFWDI IDLPSLYKDT TGWIQEGPNY YYLVKGQKKT  360
GWFQVDGKWY YTNLKTTGTS KQGQMKTGWF QVDGKWYFAS PKATDTFKQG QMVTGWLKDY  420
TGYGTLEDDA TQSLLKTYTL GNRRDDWYYL SPNGNTTNSA GQKFKEGEMV TGWFQVDGKW  480
YFANTGRFQG TRIEYTGPLG LNPKVVDVTF DLHGALITDA GVKIDGKTYY FNKGGVCTNP  540
NGQKMIDSEE HPEKSEQGSD IPLWEETKIY NTTGTKVVYQ GNFFESIHHI NAGVVPNKDD  600
RHGNETGWKL TGGPAFTEIP EWKPTIAYSG ADQVTYKGKT YEAKNWTKGN NPETSGEDGP  660
WKLTQ                                                            665

SEQ ID NO: 462         moltype = AA  length = 627
FEATURE                Location/Qualifiers
REGION                 1..627
                       note = Description of Artificial Sequence: Synthetic
                        polypeptide
source                 1..627
                       mol_type = protein
                       organism = synthetic construct
SEQUENCE: 462
MAEKTEKTQQ LTSNADLDSA IEILKDGSIE IINKDLIKGE TAQAVVSLGG NALFQAWKDS  60
QKGNYNNTFR TLAIGSTALI PYGGIFISPI LGLLWPENVD SKDHMMTQLI TDMTDLMDDK  120
INQYDLETIK KSWDALIKLQ EKFENAVNKK PLTFDDSIQA ANIKYAGDIN NKFNELIALC  180
QKSSKKIIEL PMFTTIAAAH VQFLKFMEKN ARTHPRIKMD NEHYQYYFGE DLKKLPLTYA  240
NHVMKIHKEG RDQAYSKIKT LAKTDDIKAR KLWRAYTKFY YQSFDCQAFW DIIDLPSLYK  300
DTTGWIQEGP NYYYLVKGQK KTGWFQVDGK WYYTNLKTTG TSKQGQMKTG WFQVDGKWYF  360
ASPKATDTFK QGQMVTGWLK DYTGYGTLED DATQSLLKTY TLGNRRDDWY YLSPNGNTTN  420
SAGQKFKEGE MVTGWFQVDG KWYFANTGRF QGTRIEYTGP LGLNPKVVDV TFDLHGALIT  480
DAGVKIDGKT YYFNKGGVCT NPNGQKMIDS EEHPEKSEQG SDIPLWEETK IYNTTGTKVV  540
YQGNFFESIH HINAGVVPNK DDRHGNETGW KLTGGPAFTE IPEWKPTIAY SGADQVTYKG  600
KTYEAKNWTK GNNPETSGED GPWKLTQ                                     627

SEQ ID NO: 463         moltype = AA  length = 324
FEATURE                Location/Qualifiers
source                 1..324
                       mol_type = protein
                       organism = Bacillus sp.
SEQUENCE: 463
MIGVIGTSFA FASPNSASAA STPQVNPIAA GQENPYIENW DEPFKKMFTM LQNGDTQYKN  60
YKNPKFELKK VVKTSVEEDG SPITNAKTLY VGKTVLRNTT DRDQTLTTDQ FSKTIEHSVS  120
SSTTHGFNLG VTASASFGVP VIGETSVEIS TEYNFSNTNE TTRTESITYT ASPQNIVVPA  180
HSAVEVSVIL NTVKISGNVD LTSTITGTVN YEDGSRKSNN HLQNLWYDAF RYSNSKTSAF  240
NVRPVYEYSD GLYDKVTLKG KGKYSAEYGT QFSVSVKPIV EQPRALAVQS SGTVAENGKS  300
TDDDYTTTNE GYTYTVKPEV KKEQ                                        324

SEQ ID NO: 464         moltype = AA  length = 306
FEATURE                Location/Qualifiers
REGION                 1..306
                       note = Description of Artificial Sequence: Synthetic
                        polypeptide
source                 1..306
                       mol_type = protein
                       organism = synthetic construct
SEQUENCE: 464
MASTPQVNPI AAGQENPYIE NWDEPFKKMF TMLQNGDTQY KNYKNPKFEL KKVVKTSVEE  60
DGSPITNAKT LYVGKTVLRN TTDRDQTLTT DQFSKTIEHS VSSSTTHGFN LGVTASASFG  120
VPVIGETSVE ISTEYNFSNT NETTRTESIT YTASPQNIVV PAHSAVEVSV ILNTVKISGN  180
VDLTSTITGT VNYEDGSRKS NNHLQNLWYD AFRYSNSKTS AFNVRPVYEY SDGLYDKVTL  240
KGKGKYSAEY GTQFSVSVKP IVEQPRALAV QSSGTVAENG KSTDDDYTTT NEGYTYTVKP  300
EVKKEQ                                                            306

SEQ ID NO: 465         moltype = AA  length = 280
FEATURE                Location/Qualifiers
```

```
source                  1..280
                        mol_type = protein
                        organism = Bacillus sp.
SEQUENCE: 465
MEVFTMAILD IWEEVDKYAF NFCRLRGLTY SGKAGSVPQY PLKLAKFEAS LPDDKVLTPP  60
ESIVTLPIMF ENKSNEAQEA DLSFAQEITE STSTTTTEGV TIGNEVSASQ SFKVKFVEVG  120
FTQTIRAEYT TTSSKTVTLE EKRTITVSHK VTVPPQTRIK SVLIVENGIY DLITDIKCDL  180
SGLIYFDATN GTRFFATIYE VLKTNNTPNF TFSFNDPEDP VCHFDGSGKL KGNSGLNSYI  240
VVDETPLSGS LGQHRQYILP GQDLTTGIIY SGNIGIPVIN                       280

SEQ ID NO: 466          moltype = AA  length = 275
FEATURE                 Location/Qualifiers
REGION                  1..275
                        note = Description of Artificial Sequence: Synthetic
                         polypeptide
source                  1..275
                        mol_type = protein
                        organism = synthetic construct
SEQUENCE: 466
MAILDIWEEV DKYAFNFCRL RGLTYSGKAG SVPQYPLKLA KFEASLPDDK VLTPPESIVT  60
LPIMFENKSN EAQEADLSFA QEITESTSTT TTEGVTIGNE VSASQSFKVK FVEVGFTQTI  120
RAEYTTTSSK TVTLEEKRTI TVSHKVTVPP QTRIKSVLIV ENGIYDLITD IKCDLSGLIY  180
FDATNGTRFF ATIYEVLKTN NTPNFTFSFN DPEDPVCHFD GSGKLKGNSG LNSYIVVDET  240
PLSGSLGQHR QYILPGQDLT TGIIYSGNIG IPVIN                            275

SEQ ID NO: 467          moltype = AA  length = 322
FEATURE                 Location/Qualifiers
source                  1..322
                        mol_type = protein
                        organism = Bacillus sp.
SEQUENCE: 467
MKYKKIALIV PMLVMISTPA VFSPAVALAA EPTTSISQNQ TVLGYRIKDG IQTPIYPNGQ  60
PKIKNFAQSG SPMPAVPTLP SDPNAAIPVK GEAVLETGEM GNMLYFDGSA GTSTKNEKLK  120
FYLLKKDNGT IEYGGYNPDT FELYPFNVQA PQDDYGRPFD GNTKVKREVY YKKLGGGRQD  180
NAFSYKFNEA IKHGVTTSNL FSFTGTVGWK LTVKAGGSVI PAEVTQEFST SLSTMYSHTI  240
AVSDEQTITN EVTIGPVNNA SYSYPYYQTA VYQLMSPYTC NPGSGLQQFI NDHPEFGSLA  300
HTVYEYKDNE YLSLVTPGSH TM                                          322

SEQ ID NO: 468          moltype = AA  length = 294
FEATURE                 Location/Qualifiers
REGION                  1..294
                        note = Description of Artificial Sequence: Synthetic
                         polypeptide
source                  1..294
                        mol_type = protein
                        organism = synthetic construct
SEQUENCE: 468
MAEPTTSISQ NQTVLGYRIK DGIQTPIYPN GQPKIKNFAQ SGSPMPAVPT LPSDPNAAIP  60
VKGEAVLETG EMGNMLYFDG SAGTSTKNEK LKFYLLKKDN GTIEYGGYNP DTFELYPFNV  120
QAPQDDYGRP FDGNTKVKRE VYYKKLGGGR QDNAFSYKFN EAIKHGVTTS NLFSFTGTVG  180
WKLTVKAGGS VIPAEVTQEF STSLSTMYSH TIAVSDEQTI TNEVTIGPVN NASYSYPYYQ  240
TAVYQLMSPY TCNPGSGLQQ FINDHPEFGS LAHTVYEYKD NEYLSLVTPG SHTM       294

SEQ ID NO: 469          moltype = AA  length = 246
FEATURE                 Location/Qualifiers
source                  1..246
                        mol_type = protein
                        organism = Bacillus sp.
SEQUENCE: 469
MNNFRKFSTL NNTQLENNPF VSQNTARETV LRITEPEKPA GFKEIFDIED PQQMAQAINL  60
ANVFTQVLNA VDENDEDTFY FDVTDALEVI KNLEPKAALV EYIDETISQE RKEVSAILDP  120
LIDLLKSMLK GDIDARTLDK IKGAVTGTFT NVEAENNNSW IFYSETTAYK VAYIYNLFFA  180
YPNEFNTAII CMPITMTIEA QSYEEKYLFI TTSSKVSYKV RVQALTVVQG VVDTSNTALD  240
VLSELT                                                            246

SEQ ID NO: 470          moltype = AA  length = 257
FEATURE                 Location/Qualifiers
source                  1..257
                        mol_type = protein
                        organism = Bacillus sp.
SEQUENCE: 470
MKLNKNFCGI SNQSLYSRII KLNILNSETN NYMKEIVDLP IEFLAQAINL GNQLQSSLII  60
ISDKYGNNSP RLDANKTVER LLYNTEYSIQ NKILDCYVPD WTTPIYITAT NKIIQKLQIR  120
TIQQHEISIA NLIKRIESNI NKYFGIDIFL QKNISNSIRD VFLNLDIQKN EAWIFWGTTT  180
ASQTNYIYNL LYGFKDETSI ICLGMGFEVE VYASKSVVLG FTTSSSQRLT VDCNIVMIKE  240
PILNFKNLKI GSLSQLI                                                257

SEQ ID NO: 471          moltype = AA  length = 370
FEATURE                 Location/Qualifiers
```

```
source                  1..370
                        mol_type = protein
                        organism = Bacillus sp.
SEQUENCE: 471
MTIGVSTFGS TTSAFAAEED NISIISSHTL NDIGIQVEKI IPDQTLRDKF LKAFATKGTM  60
KVGVNGAFQF IKDAQEDIPN FNDTFRSLAM AGTDLIPYAG LVISPLIGLL WSENDGVSAQ  120
IKEMSNQILT QVDEKFDTEY VNNLKTDFKT LNSNILTLEK SLNTDTNKNA MYYAGNDIYA  180
TRGNWANHIQ HSFESLIDRA SGNHEVASLP LYTKLAVAHI TFLKYMHEHA KGPKLKYDEQ  240
SLQHFFDKGN LEVITKKYAD HIKKVYNQGL QMFYNNIDKL NDLRTKKENL LSTPGDGIGK  300
ENELNILNAK IAKLEAKNIF RNMQNFSSST WDDPTFQAQI QGEWKLENNA WTFINKKGEK  360
KTGWLVLSQP                                                        370

SEQ ID NO: 472          moltype = AA  length = 556
FEATURE                 Location/Qualifiers
source                  1..556
                        mol_type = protein
                        organism = Bacillus sp.
SEQUENCE: 472
MVQNNLETKA LPSFIDDFNG IFGFVDGIFS IFDKISGANI DSPELEEILK NQELLNELQN  60
KLSVVSEDLD TIIQNGELNT EALKHLIQIS NAQGDMLQNI QGQIDGLQNM IQGYFIEIIS  120
MLNKIVIQNQ IISSQLVYIT EQLLVISQKL DTINVNILIS STITEITPSY QRMNYINKKY  180
DELVFSNTNK YSNDLNIVNF DIENHSEINE LIDFAKNVTQ NSQNSFEFYL DTFQEVMVGN  240
TLFERSALHS IGELIRNEHM PKGNGSEVAR AYAFLVSLIS IQAKSYATLA ACRKILGLKD  300
IDYTTVLTQY IQDQLNIFAS VELPKFSSEF SGFNHVNIGL GLHVDHEKID RVVKADPGYV  360
LVGLEIINNG DDFDLIAYQA KLKQNYEINK ESISKFTVHK IHEIFAPQWK IDRLGRKYIY  420
PLYFQPTELQ FPEGYVITQI NFTHDPKSLV DVYYEVIANY YDPFTGNLDS TKSLTKLSER  480
EYPSPQLPIT EEDETYFPTK ISDTFLAPMY SFKLDADYDT CKCNISCKNY LPQYLKASDL  540
SNKETNLLYV VNDTVK                                                 556

SEQ ID NO: 473          moltype = AA  length = 972
FEATURE                 Location/Qualifiers
source                  1..972
                        mol_type = protein
                        organism = Bacillus sp.
SEQUENCE: 473
MILNNVYKCL AVTALLTQTM VLPASSFAEQ FQEKNAEKEH LFQEQVRTDV STGLIGQYFT  60
DNQFQQLSFI QVGEKNILIN KDKVKEDITN VESIRWIGNI KPAETGEYKI STSENESVII  120
QIDGDIIVKQ NEETKPIQLE KDKIYEIKIE QRVEKGNAKE LNLFWSKDHG KETLIPEEEI  180
ISPDFAQKTQ VTQDEQLLLP NQNLFEANRQ KRETSRKRVD TDKDGIPDFL EEKGYTFKDN  240
AIVAWKDVYA ERGYKKYISN PRKARTVADP YTDFEKVTGR MPAATKYDAR DPLVAASPSI  300
GVGVEKFHFS KNETVQEGAS GTKSKTVTNS NTTTNSVDIG AKFGFNKDGF SFDFSPKYTR  360
SWSSSTAIAN AESESWSKQI NINLSERAFL NANIRYYNGG TASIYDLRPT SNFVLQHSGE  420
SIATVTANGN TIGNSLGPGA TYPEKGKAPI SLTQANEAGT VKISVNAENL DKIQDGREIL  480
NIETTQYRGQ YGKITEDGRL VSGGEWGPIR TNIDAVSGVL TLNIGSSKES LERRIAAKDP  540
RDPEDKTPEI TVKEAIKKAF DVIEKDGRMI YTDEDGNDIV LEESAVNIIT NENTKKEIEK  600
QLANMQNKKI YDVKWKRGME MTLYIPETYY DFENGKYHFS DIYTVNGGYT GTAHAMLEGN  660
SSPGYAVIKN NLKPYTSYTA RAYVKADKWT STETTFFVGE LDAIGNGGCG AKIHGKVDGD  720
DWQLVELSFN TGANPEYFGS IGLKNHGNTR LYFDDVSLTE WKRTENIEKS HAFKEWDTMY  780
DDNVGKYKLQ SVKFSKFPNQ KVNYQILFND DTWGPILPDS SVVDNSGERT ISFGTRSNAP  840
GAENKIGVFA VDEKNPNLKV KIAEFGMMTE QQIKKAHTLD SWILSEKGTY VDGLYFENMD  900
RNVLSHITGY KVSINDGLQS VKRRYGLDDK NKLKINILEY NLGKGIAKNV KLKIWAVVQN  960
KDILVYEGLS GR                                                     972

SEQ ID NO: 474          moltype = AA  length = 970
FEATURE                 Location/Qualifiers
REGION                  1..970
                        note = Description of Artificial Sequence: Synthetic
                         polypeptide
source                  1..970
                        mol_type = protein
                        organism = synthetic construct
SEQUENCE: 474
MNNVYKCLAV TALLTQTMVL PASSFAEQFQ EKNAEKEHLF QEQVRTDVST GLIGQYFTDN  60
QFQQLSFIQV GEKNILINKD KVKEDITNVE SIRWIGNIKP AETGEYKIST SENESVIIQI  120
DGDIIVKQNE ETKPIQLEKD KIYEIKIEQR VEKGNAKELN LFWSKDHGKE TLIPEEEIIS  180
PDFAQKTQVT QDEQLLLPNQ NLFEANRQKR ETSRKRVDTD KDGIPDFLEE KGYTFKDNAI  240
VAWKDVYAER GYKKYISNPR KARTVADPYT DFEKVTGRMP AATKYDARDP LVAASPSIGV  300
GVEKFHFSKN ETVQEGASGT KSKTVTNSNT TTNSVDIGAK FGFNKDGFSF DFSPKYTRSW  360
SSSTAIANAE SESWSKQINI NLSERAFLNA NIRYYNGGTA SIYDLRPTSN FVLQHSGESI  420
ATVTANGNTI GNSLGPGATY PEKGKAPISL TQANEAGTVK ISVNAENLDK IQDGREILNI  480
ETTQYRGQYG KITEDGRLVS GGEWGPIRTN IDAVSGVLTL NIGSSKESLE RRIAAKDPRD  540
PEDKTPEITV KEAIKKAFDV IEKDGRMIYT DEDGNDIVLE ESAVNIITNE NTKKEIEKQL  600
ANMQNKKIYD VKWKRGMEMT LYIPETYYDF ENGKYHFSDI YTVNGGYTGT AHAMLEGNSS  660
PGYAVIKNNL KPYTSYTARA YVKADKWTST ETTFFVGELD AIGNGGCGAK IHGKVDGDDW  720
QLVELSFNTG ANPEYFGSIG LKNHGNTRLY FDDVSLTEWK RTENIEKSHA FKEWDTMYDD  780
NVGKYKLQSV KFSKFPNQKV NYQILFNDDT WGPILPDSSV VDNSGERTIS FGTRSNAPGA  840
ENKIGVFAVD EKNPNLKVKI AEFGMMTEQQ IKKAHTLDSW ILSEKGTYVD GLYFENMDRN  900
VLSHITGYKV SINDGLQSVK RRYGLDDKNK LKINILEYNL GKGIAKNVKL KIWAVVQNKD  960
ILVYEGLSGR                                                        970
```

```
SEQ ID NO: 475          moltype = AA  length = 946
FEATURE                 Location/Qualifiers
REGION                  1..946
                        note = Description of Artificial Sequence: Synthetic
                         polypeptide
source                  1..946
                        mol_type = protein
                        organism = synthetic construct
SEQUENCE: 475
MAEQFQEKNA EKEHLFQEQV RTDVSTGLIG QYFTDNQFQQ LSFIQVGEKN ILINKDKVKE  60
DITNVESIRW IGNIKPAETG EYKISTSENE SVIIQIDGDI IVKQNEETKP IQLEKDKIYE  120
IKIEQRVEKG NAKELNLFWS KDHGKETLIP EEEIISPDFA QKTQVTQDEQ LLLPNQNLFE  180
ANRQKRETSR KRVDTDKDGI PDFLEEKGYT FKDNAIVAWK DVYAERGYKK YISNPRKART  240
VADPYTDFEK VTGRMPAATK YDARDPLVAA SPSIGVGVEK FHFSKNETVQ EGASGTKSKT  300
VTNSNTTTNS VDIGAKFGFN KDGFSFDFSP KYTRSWSSST AIANAESESW SKQININLSE  360
RAFLNANIRY YNGGTASIYD LRPTSNFVLQ HSGESIATVT ANGNTIGNSL GPGATYPEKG  420
KAPISLTQAN EAGTVKISVN AENLDKIQDG REILNIETTQ YRGQYGKITE DGRLVSGGEW  480
GPIRTNIDAV SGVLTLNIGS SKESLERRIA AKDPRDPEDK TPEITVKEAI KKAFDVIEKD  540
GRMIYTDEDG NDIVLEESAV NIITNENTKK EIEKQLANMQ NKKIYDVKWK RGMEMTLYIP  600
ETYYDFENGK YHFSDIYTVN GGYTGTAHAM LEGNSSPGYA VIKNNLKPYT SYTARAYVKA  660
DKWTSTETTF FVGELDAIGN GGCGAKIHGK VDGDDWQLVE LSFNTGANPE YFGSIGLKNH  720
GNTRLYFDDV SLTEWKRTEN IEKSHAFKEW DTMYDDNVGK YKLQSVKFSK FPNQKVNYQI  780
LFNDDTWGPI LPDSSVVDNS GERTISFGTR SNAPGAENKI GVFAVDEKNP NLKVKIAEFG  840
MMTEQQIKKA HTLDSWILSE KGTYVDGLYF ENMDRNVLSH ITGYKVSIND GLQSVKRRYG  900
LDDKNKLKIN ILEYNLGKGI AKNVKLKIWA VVQNKDILVY EGLSGR                 946

SEQ ID NO: 476          moltype = AA  length = 380
FEATURE                 Location/Qualifiers
source                  1..380
                        mol_type = protein
                        organism = Bacillus sp.
SEQUENCE: 476
VMSNENNNGE NTNTSMRNDE DSILSEVLKS GKQISFPDFN FYKIRTFCGK YIDIQDGSTA  60
NEKVAFQYTV NNNDNQRFLI FTLDNNYSVI AAKHSGKVLD IMDLPIFPGL PFMLIQYDFQ  120
NGDNQKFLIA NEGAIAVKKT GQVWDVASGS TKDKTPIIPY NYSGASNQKF KLEPSGAASV  180
KPPEFGTLPN APDFITNDIN EELPDDTPPV ITHATYMPYF MVKDPYYNAQ QKIKNTPYYI  240
LVRRQYWQKV TQRILAPSDT YDYTETTGVS RTDQTSMTET TEISIGADLG FMFKGFSLGL  300
SASITKSLSV TKSTSTTEST EITQKVVYTN PFKHQIAYAK YMLINEYYVT RANGEMITSG  360
DASYWKVPDP SRTVARIIPR                                              380

SEQ ID NO: 477          moltype = AA  length = 379
FEATURE                 Location/Qualifiers
REGION                  1..379
                        note = Description of Artificial Sequence: Synthetic
                         polypeptide
source                  1..379
                        mol_type = protein
                        organism = synthetic construct
SEQUENCE: 477
MSNENNNGEN TNTSMRNDED SILSEVLKSG KQISFPDFNF YKIRTFCGKY IDIQDGSTAN  60
EKVAFQYTVN NNDNQRFLIF TLDNNYSVIA AKHSGKVLDI MDLPIFPGLP FMLIQYDFQN  120
GDNQKFLIAN EGAIAVKKTG QVWDVASGST KDKTPIIPYN YSGASNQKFK LEPSGAASVK  180
PPEFGTLPNA PDFITNDINE ELPDDTPPVI THATYMPYFM VKDPYYNAQQ KIKNTPYYIL  240
VRRQYWQKVT QRILAPSDTY DYTETTGVSR TDQTSMTETT EISIGADLGF MFKGFSLGLS  300
ASITKSLSVT KSTSTTESTE ITQKVVYTNP FKHQIAYAKY MLINEYYVTR ANGEMITSGD  360
ASYWKVPDPS RTVARIIPR                                               379

SEQ ID NO: 478          moltype = AA  length = 1521
FEATURE                 Location/Qualifiers
source                  1..1521
                        mol_type = protein
                        organism = Bacillus sp.
SEQUENCE: 478
LVIYMTRLED FYPRSDDAFR AERLETEAST SESLLQDLKT GIEKGTYQNS IDTIFQNIAD  60
EKIDYVTFVN STLRLAPMST PDTGLFSPLV GLFFSGLNQI PTTRDATTNV FQSMNPLITD  120
ALGRSLTSNE LDQMNAEVSG LRAVLIPFQT AMSTIQTQYG GFENATAAAR QAFVNAIENV  180
DAILADRLPS LLYTDPAQAI MGLPYYCSFA RMHLQLYKDI IMHGITWDPD YYDAQVIGIK  240
KNTLKKFIQL YAQQAYDGFT KGLSLLGGGD LKTSDTATFS QQKQYIQFLT INALDIARFF  300
PTFDPDLYPV GITTNLQTNH QFVSPILPGF CLPKTFPSGF DYPISDNGTI RKDPELAAIE  360
SDTSTNKTYG SPVFIQMVDR NGTVRRWGND SGDQYSLPSI DHVDPLIGFG AAAAVSFDSN  420
GHPTYEICSS DPIFGFQFLT ASKKLTTWER VELPAEFMPW LRAPRNYKIR TIYPLYDSSK  480
PDMPFGGYVV VFTPIDPPSI GFLAPDSSGN LSIIGIPCAP FGYEQGWVVP EWTTGSNVVK  540
LPPGQTLHIP VFNTLEGQFT MRMNYACNAD VDVFVNLDTG GQNPVYNTVT FSATNSNDFP  600
GKNGYYRSQL ITDHLDMGTF SMKIDYIYLT NKGTSDIFLD RVEFIPAPSD TAQTGTFIAQ  660
GFTIPNDKSP ITIYSGDAIY NTIKLVYSLQ GSDTFPVEFR FYSHGFYVDS VTPATNTPIT  720
KQYPQGITQI TAQATTNLTG THVVDVVAKL TYDSSMPITP NINVNAPVPS ASLEINAFDG  780
PKALVWAAPY GMTIADRFTV VAKPGDSNVD AVTLVLNANS TQGISWICAK TASNNNDPNS  840
NLYYDATDGT FHFENIWGYS DTNAITARVS PKLQPTTVQN INVINAPVPS ASLEINAFDG  900
```

```
PKALVWAMHG AVPAPNTRFT VVAKPSDSNV EAVTLVLNAN STQGISWICA KTASNNNDPN  960
SNLYYDATDG TFHFENIWGY PDTNAITARV SPELSSAITL QLQGNIDLID ENTGDPISVT  1020
PFHLEGTVTV TKAPELTSTK VSFIEPEDLQ HITKHVQDLF ASQNQTALSD ETDDYWIDQV  1080
VMKVDALSDE TFGKEKKALR KLVNKAKQLS KARNLLTGGS FDTLDAWQLG KNVVRKEDGD  1140
LFKGEHLLLP PPTVLSPSYA YQKIDESKLK PYTRYTVSGF VAHGEPLDIV VSRYGKEIEK  1200
TLHVPYADAH PITSDPTPNC CMPGIPSTCN GGATDSHFFH YTIDVGSLQT EANLGISFGL  1260
RIGETAENTL GLARIGNLEI REDRPLTASE KRKVQKVEKK WKKEVEKEHA DLTAKLHPVI  1320
NQINALYVND DWNGLLQPDV TEADIHAITL PDLPKQRHWF MTDRKGAHRA MTEQMQQALT  1380
RAADLLENQN LIHNGHFTDE LEKWTVAGDA AIQVLSGGNK ALFLPHWDST ATQTIQITDF  1440
DEDATYTLRV IGKGKGKMTI QHGAAGERVE TMMFSQKNMQ KQELSNLQFE TAEIEIEISS  1500
EDGGLTIDSI ELIEVKEGTE N                                            1521

SEQ ID NO: 479          moltype = AA  length = 1517
FEATURE                 Location/Qualifiers
REGION                  1..1517
                        note = Description of Artificial Sequence: Synthetic
                         polypeptide
source                  1..1517
                        mol_type = protein
                        organism = synthetic construct
SEQUENCE: 479
MTRLEDFYPR SDDAFRAERL ETEASTSESL LQDLKTGIEK GTYQNSIDTI FQNIADEKID  60
YVTFVNSTLR LAPMSTPDTG LFSPLVGLFF SGLNQIPTTR DATTNVFQSM NPLITDALGR  120
SLTSNELDQM NAEVSGLRAV LIPFQTAMST IQTQYGGFEN ATAAARQAFV NAIENVDAIL  180
ADRLPSLLYT DPAQAIMGLP YYCSFARMHL QLYKDIIMHG ITWDPDYYDA QVIGIKKNTL  240
KKFIQLYAQQ AYDGFTKGLS LLGGGDLKTS DTATFSQQKQ YIQFLTINAL DIARFFPTFD  300
PDLYPVGITT NLQTNHQFVS PILPGFCLPK TFPSGFDYPI SDNGTIRKDP ELAAIESDTS  360
TNKTYGSPVF IQMVDRNGTV RRWGNDSGDQ YSLPSIDHVD PLIGFGAAAA VSFDSNGHPT  420
YEICSSDPIF GFQFLTASKK LTTWERVELP AEFMPWLRAP RNYKIRTIYP LYDSSKPDMP  480
FGGYVVVFTP IDPPSIGFLA PDSSGNLSII GIPCAPFGYE QGWVVPEWTT GSNVVKLPPG  540
QTLHIPVFNT LEGQFTMRMN YACNADVDVF VNLDTGGQNP VYNTVTFSAT NSNDFPGKNG  600
YYRSQLITDH LDMGTFSMKI DYIYLTNKGT SDIFLDRVEF IPAPSDTAQT GTFIAQGFTI  660
PNDKSPITIY SGDAIYNTIK LVYSLQGSDT FPVEFRFYSH GFYVDSVTPA TNTPITKQYP  720
QGITQITAQA TTNLTGTHVV DVVAKLTYDS SMPITPNINV NAPVPSASLE INAFDGPKAL  780
VWAAPYGMTI ADRFTVVAKP GDSNVDAVTL VLNANSTQGI SWICAKTASN NNDPNSNLYY  840
DATDGTFHFE NIWGYSDTNA ITARVSPKLQ PTTVQNINVI NAPVPSASLE INAFDGPKAL  900
VWAMHGAVPA PNTRFTVVAK PSDSNVEAVT LVLNANSTQG ISWICAKTAS NNNDPNSNLY  960
YDATDGTFHF ENIWGYPDTN AITARVSPEL SSAITLQLQG NIDLIDENTG DPISVTPFHL  1020
EGTVTVTKAP ELTSTKVSFI EPEDLQHITK HVQDLFASQN QTALSDETDD YWIDQVVMKV  1080
DALSDETFGK EKKALRKLVN KAKQLSKARN LLTGGSFDTL DAWQLGKNVV RKEDGDLFKG  1140
EHLLLPPPTV LSPSYAYQKI DESKLKPYTR YTVSGFVAHG EPLDIVVSRY GKEIEKTLHV  1200
PYADAHPITS DPTPNCCMPG IPSTCNGGAT DSHFFHYTID VGSLQTEANL GISFGLRIGE  1260
TAENTLGLAR IGNLEIREDR PLTASEKRKV QKVEKKWKKE VEKEHADLTA KLHPVINQIN  1320
ALYVNDDWNG LLQPDVTEAD IHAITLPDLP KQRHWFMTDR KGAHRAMTEQ MQQALTRAAD  1380
LLENQNLIHN GHFTDELEKW TVAGDAAIQV LSGGNKALFL PHWDSTATQT IQITDFDEDA  1440
TYTLRVIGKG KGKMTIQHGA AGERVETMMF SQKNMQKQEL SNLQFETAEI EIEISSEDGG  1500
LTIDSIELIE VKEGTEN                                                 1517

SEQ ID NO: 480          moltype = AA  length = 643
FEATURE                 Location/Qualifiers
REGION                  1..643
                        note = Description of Artificial Sequence: Synthetic
                         polypeptide
source                  1..643
                        mol_type = protein
                        organism = synthetic construct
SEQUENCE: 480
MTRLEDFYPR SDDAFRAERL ETEASTSESL LQDLKTGIEK GTYQNSIDTI FQNIADEKID  60
YVTFVNSTLR LAPMSTPDTG LFSPLVGLFF SGLNQIPTTR DATTNVFQSM NPLITDALGR  120
SLTSNELDQM NAEVSGLRAV LIPFQTAMST IQTQYGGFEN ATAAARQAFV NAIENVDAIL  180
ADRLPSLLYT DPAQAIMGLP YYCSFARMHL QLYKDIIMHG ITWDPDYYDA QVIGIKKNTL  240
KKFIQLYAQQ AYDGFTKGLS LLGGGDLKTS DTATFSQQKQ YIQFLTINAL DIARFFPTFD  300
PDLYPVGITT NLQTNHQFVS PILPGFCLPK TFPSGFDYPI SDNGTIRKDP ELAAIESDTS  360
TNKTYGSPVF IQMVDRNGTV RRWGNDSGDQ YSLPSIDHVD PLIGFGAAAA VSFDSNGHPT  420
YEICSSDPIF GFQFLTASKK LTTWERVELP AEFMPWLRAP RNYKIRTIYP LYDSSKPDMP  480
FGGYVVVFTP IDPPSIGFLA PDSSGNLSII GIPCAPFGYE QGWVVPEWTT GSNVVKLPPG  540
QTLHIPVFNT LEGQFTMRMN YACNADVDVF VNLDTGGQNP VYNTVTFSAT NSNDFPGKNG  600
YYRSQLITDH LDMGTFSMKI DYIYLTNKGT SDIFLDRVEF IPA                    643

SEQ ID NO: 481          moltype = AA  length = 413
FEATURE                 Location/Qualifiers
source                  1..413
                        mol_type = protein
                        organism = Bacillus sp.
SEQUENCE: 481
LPTKLGGNIM KSISKKVMAG LLVGATSLSI WAPASQAAAP ENNRYYSVHL TNNIEKVWDV  60
YNGWTSNDAG ILLYNVNGKD NQQFVFFQLD GGTYAIVNKN SGKPVGLGGG INYNDGVRHM  120
SNIAGNPADA LGQNDWTGAD TDKWYLRDKG NANYEIVNQG NGKVASYAAT NIAPYFHYVD  180
LDESNPSDGD RLFKISKSPW VYGDIPGLNL DYGTFSLPQL PATGNRPDAP NYTGGIDQQL  240
```

```
PQTSNSVVVG ASLIPCIMVK DSQASDYTKI HNSPYYTLIK EEYWDKTFSS VIPSGYTKNY  300
SFKTGMTSVD QQRMTDTLSM KIGADFGLKF GDASASLKTE ISRTIQTEIT STNTEASEET  360
VTSTVTSEPG KTTGFTEYQL ATKYTLKRAD GTIVSDPWVV KNNKITIARK NSQ         413

SEQ ID NO: 482         moltype = AA  length = 404
FEATURE                Location/Qualifiers
REGION                 1..404
                       note = Description of Artificial Sequence: Synthetic
                        polypeptide
source                 1..404
                       mol_type = protein
                       organism = synthetic construct
SEQUENCE: 482
MKSISKKVMA GLLVGATSLS IWAPASQAAA PENNRYYSVH LTNNIEKVWD VYNGWTSNDA  60
GILLYNVNGK DNQQFVFFQL DGGTYAIVNK NSGKPVGLGG GINYNDGVRH MSNIAGNPAD  120
ALGQNDWTGA DTDKWYLRDK GNANYEIVNQ GNGKVASYAA TNIAPYFHYV DLDESNPSDG  180
DRLFKISKSP WVYGDIPGLN LDYGTFSLPQ LPATGNRPDA PNYTGGIDQQ LPQTSNSVVV  240
GASLIPCIMV KDSQASDYTK IHNSPYYTLI KEEYWDKTFS SVIPSGYTKN YSFKTGMTSV  300
DQQRMTDTLS MKIGADFGLK FGDASASLKT EISRTIQTEI TSTNTEASEE TVTSTVTSEP  360
GKTTGFTEYQ LATKYTLKRA DGTIVSDPWV VKNNKITIAR KNSQ                    404

SEQ ID NO: 483         moltype = AA  length = 321
FEATURE                Location/Qualifiers
source                 1..321
                       mol_type = protein
                       organism = Bacillus sp.
SEQUENCE: 483
MTNNKKLKRK IFSLATLATI GTSCITLPNY ASAATSDKVP QDINKIQKQN PQVRGMQGWK  60
DPINYAIGLF FQKNTGNNVE AFLNDIHDPE FIQTTAEPSS SPNITEMEGA YIGRSVLTNH  120
TDHEQTLHTD GYEETFTNST TSSTTHGFKI GEKSTATLSL PIVGANFSQE VNMEYNISDL  180
KSKTTTETKS YKITPQNIKV PAHSSVEVIV KLDKIKANGT VDLFTKMKDT TYLALVWYKD  240
RPDGMLSGNV YDAVNEVTSI RPLPDIKANK DKTISLIGKG KYSATMGTNF SVTVRPVDKN  300
KRAIDEGYTF KVTPQITNVK K                                             321

SEQ ID NO: 484         moltype = AA  length = 289
FEATURE                Location/Qualifiers
REGION                 1..289
                       note = Description of Artificial Sequence: Synthetic
                        polypeptide
source                 1..289
                       mol_type = protein
                       organism = synthetic construct
SEQUENCE: 484
MATSDKVPQD INKIQKQNPQ VRGMQGWKDP INYAIGLFFQ KNTGNNVEAF LNDIHDPEFI  60
QTTAEPSSSP NITEMEGAYI GRSVLTNHTD HEQTLHTDGY EETFTNSTTS STTHGFKIGE  120
KSTATLSLPI VGANFSQEVN MEYNISDLKS KTTTETKSYK ITPQNIKVPA HSSVEVIVKL  180
DKIKANGTVD LFTKMKDTTY LALVWYKDRP DGMLSGNVYD AVNEVTSIRP LPDIKANKDK  240
TISLIGKGKY SATMGTNFSV TVRPVDKNKR AIDEGYTFKV TPQITNVKK               289

SEQ ID NO: 485         moltype = AA  length = 317
FEATURE                Location/Qualifiers
source                 1..317
                       mol_type = protein
                       organism = Bacillus sp.
SEQUENCE: 485
MNRIKKIIPA AFVLSTALFV APGFSSADTN TTNVGSAPVV ISAQEGKAPM TAAQVAKNGT  60
QLPYIPTGPY EEFPNEWHVS TEDGKLIDYV YVDVVAKSNG ARVYGLKIDA NSKHKILKAD  120
GTWLNVGEEY EKTGNKGDVL YTIAIPKTDP ILEDTKLKKE VNWKLIDSNI VDKNSGYHWS  180
KAVTSGISHN VTVGLSYTIG MEVGLEGVAK VNQSLTASFG YGITLNSENT VTKTFDFNPK  240
TDYAYDQYRT ALYQQVATYS VIPGGKLQKW MSEQNGVWDN LFGQLGEEFK GLTSPTEYKV  300
KTSVDYPVDV LVALTSK                                                  317

SEQ ID NO: 486         moltype = AA  length = 291
FEATURE                Location/Qualifiers
REGION                 1..291
                       note = Description of Artificial Sequence: Synthetic
                        polypeptide
source                 1..291
                       mol_type = protein
                       organism = synthetic construct
SEQUENCE: 486
MDTNTTNVGS APVVISAQEG KAPMTAAQVA KNGTQLPYIP TGPYEEFPNE WHVSTEDGKL  60
IDYVYVDVVA KSNGARVYGL KIDANSKHKI LKADGTWLNV GEEYEKTGNK GDVLYTIAIP  120
KTDPILEDTK LKKEVNWKLI DSNIVDKNSG YHWSKAVTSG ISHNVTVGLS YTIGMEVGLE  180
GVAKVNQSLT ASFGYGITLN SENTVTKTFD FNPKTDYAYD QYRTALYQQV ATYSVIPGGK  240
LQKWMSEQNG VWDNLFGQLG EEFKGLTSPT EYKVKTSVDY PVDVLVALTS K             291

SEQ ID NO: 487         moltype = AA  length = 299
FEATURE                Location/Qualifiers
```

```
source                  1..299
                        mol_type = protein
                        organism = Bacillus sp.
SEQUENCE: 487
MAIVDFDAYL LAFAKKWFPD PISKLITKVD TSSYLTVKNA ESYGFEIKSS KPQGTMFIGE  60
SVLKNDTNET QLIHSDSFTK TITDSVTLSV TNGISTGVNI SIGGKVFGMG VETSMSFEVS  120
TSTTREQTST ESVEYKVPSQ PVSVPAKKTY YVYTALQRSQ LEGSIRLRAD LSGAYVVYIN  180
MDGQEMPVGA FPIYEFIKEY QSLHPLPSGI SLNHNDKSIH FEGLAELIYG TGTKFYVTIT  240
DTPSSQGTQE HKPFDAKTGL GTYEINLDGK KSGFDLNDLK DQMEPEVFEK LKELRNEIV   299

SEQ ID NO: 488          moltype = AA  length = 664
FEATURE                 Location/Qualifiers
source                  1..664
                        mol_type = protein
                        organism = Bacillus sp.
SEQUENCE: 488
MSSYNKNQFE KPKELLSNSN LSIKCPLHPL ANEPTAVLQG MDYKDWLVMC ENNKGLGNPE  60
NFESIVEKAT VAAASVVAAI VALMAAPVTG GTSAAAGFAI LAGVLPLMFP EDEEKPSIFN  120
DVMKATEELI DQKIDKIVKK KAESELEGLY NLLEHYHFAI ENWKEKEKNS HVDVSLAIDE  180
VRFRFRAAHV AFTSAMAQFR IIGYELALLP VYAQAANLHL IFLKDAVMYE RQWNLEKELH  240
LEELLRVKEM YINHCTKWYR RGLEKIKDNN DKNWVDYNRY RRNMTILVLD VIALFPMYDA  300
EKYNMLTKIE TLTRKVYSDP LNYIKGESIA EDEKQYTRLP ELYASLNKIG CQTKTTPDGK  360
EEYLIGHNNT FFRTDSETSY TKINGIGGDR GEPIELANKA VWGLETYHSI KNPSIRKMVF  420
NYNNTDKLYY NKENNKGTSQ KNHSIAEGNK GKHHLSDMIL VAREGFEVEK PKAYSFAWRH  480
NSIKSVNEIV DDKITQIPAV KASKIGSTVE VKEGEKGPTV KVERGPAFIG GDVVVSTAEK  540
ANIAGGQFTN IINIPVKVNV NGERDFKIRI RYATDHDINV CYTIRNGAGS VYVHDDIKRP  600
ILEVDKLNYG DFKYIEFDQA VKLNARDHDL NIRLNYYNSQ FNDSSKSKFV LDKVEFIPVE  660
KKQV                                                              664

SEQ ID NO: 489          moltype = AA  length = 659
FEATURE                 Location/Qualifiers
REGION                  1..659
                        note = Description of Artificial Sequence: Synthetic
                         polypeptide
source                  1..659
                        mol_type = protein
                        organism = synthetic construct
SEQUENCE: 489
MSSYNKNQFE KPKELLSNSN LSIKCPLHPL ANEPTAVLQG MDYKDWLVMC ENNKGLGNPE  60
NFESIVEKAT VAAASVVAAI VALMAAPVTG GTSAAAGFAI LAGVLPLMFP EDEEKPSIFN  120
DVMKATEELI DQKIDKIVKK KAESELEGLY NLLEHYHFAI ENWKEKEKNS HVDVSLAIDE  180
VRFRFRAAHV AFTSAMAQFR IIGYELALLP VYAQAANLHL IFLKDAVMYE RQWNLEKELH  240
LEELLRVKEM YINHCTKWYR RGLEKIKDNN DKNWVDYNRY RRNMTILVLD VIALFPMYDA  300
EKYNMLTKIE TLTRKVYSDP LNYIKGESIA EDEKQYTRLP ELYASLNKIG CQTKTTPDGK  360
EEYLIGHNNT FFRTDSETSY TKINGIGGDR GEPIELANKA VWGLETYHSI KNPSIRKMVF  420
NYNNTDKLYY NKENNKGTSQ KNHSIAEGNK GKHHLSDMIL VAREGFEVEK PKAYSFAWRH  480
NSIKSVNEIV DDKITQIPAV KASKIGSTVE VKEGEKGPTV KVERGPAFIG GDVVVSTAEK  540
ANIAGGQFTN IINIPVKVNV NGERDFKIRI RYATDHDINV CYTIRNGAGS VYVHDDIKRP  600
ILEVDKLNYG DFKYIEFDQA VKLNARDHDL NIRLNYYNSQ FNDSSKSKFV LDKVEFIPV   659

SEQ ID NO: 490          moltype = AA  length = 278
FEATURE                 Location/Qualifiers
source                  1..278
                        mol_type = protein
                        organism = Bacillus sp.
SEQUENCE: 490
MANQRENPLD LIEVFSTFVN NWSMQNQGCA GTLFLLPHDA TQQGLEVSSD FTAVYAAPVE  60
QKQTISHSSF SFSNTSNTFK EQQILVNTAT DVSESWELTQ SVCPGGNDFF TITTPALTDV  120
PGVPSKDSIQ ICDHETVTHS HSYTWNVNQT ISLPPRSTTT VTFQTTLKNV TRDFQFVFWM  180
TGNIGVTSMN PINSSTETYF PITQVLQWYP SDLLTLDFDF NKVTCLNKGI YKATYQVSPQ  240
LLIETTSSDN AGITQNLVMD LSTGTTTFVN NSNGCCPA                         278

SEQ ID NO: 491          moltype = AA  length = 397
FEATURE                 Location/Qualifiers
REGION                  1..397
                        note = Description of Unknown: Organism from environmental
                         sample
source                  1..397
                        mol_type = protein
                        organism = unidentified
SEQUENCE: 491
MKSISKKVMA GLLVGATGLS IWAPASEAAE LEKNRYYAIT LKANSNIGWD VYEQATYDDA  60
GIRLFGNGIK DNERFLFFPL DGGSYAIVNK NSGKAVTTGS GWIAPNTMSH DPEALKQAKW  120
TGAATDKWNL RDAGNGYHEI VNQGYGKVAS YAKAGIGPLA VDYVDLDNSN PSDPDRVFSI  180
FDGTVEFFGQ EMKLFDDTFS LPNLPVTGTR PDAPNYTGGI DQQLPQTSNS VVVGASLVPC  240
IMVNDNQASD YTKIHNSPYY TLVKEEYWDK TFSAVIPAGL TRNYTFKTGV TSVDQQKMTD  300
TLSMKIGADF GLKFGDASAA IKSEISRTIQ TEISTTNTEA SEETITSTVT SEPGKTTGFT  360
EYQLATKYTL KRADGSIVSD PWVVKNNKIT VARKNTQ                          397
```

```
SEQ ID NO: 492         moltype = AA  length = 370
FEATURE                Location/Qualifiers
REGION                 1..370
                       note = Description of Artificial Sequence: Synthetic
                        polypeptide
source                 1..370
                       mol_type = protein
                       organism = synthetic construct
SEQUENCE: 492
MAELEKNRYY AITLKANSNI GWDVYEQATY DDAGIRLFGN GIKDNERFLF FPLDGGSYAI  60
VNKNSGKAVT TGSGWIAPNT MSHDPEALKQ AKWTGAATDK WNLRDAGNGY HEIVNQGYGK  120
VASYAKAGIG PLAVDYVDLD NSNPSDPDRV FSIFDGTVEF FGQEMKLFDD TFSLPNLPVT  180
GTRPDAPNYT GGIDQQLPQT SNSVVVGASL VPCIMVNDNQ ASDYTKIHNS PYYTLVKEEY  240
WDKTFSAVIP AGLTRNYTFK TGVTSVDQQK MTDTLSMKIG ADFGLKFGDA SAAIKSEISR  300
TIQTEISTTN TEASEETITS TVTSEPGKTT GFTEYQLATK YTLKRADGSI VSDPWVVKNN  360
KITVARKNTQ                                                        370

SEQ ID NO: 493         moltype = AA  length = 616
FEATURE                Location/Qualifiers
source                 1..616
                       mol_type = protein
                       organism = Bacillus sp.
SEQUENCE: 493
MKYKDRKDAK RKYKKALLAT VATMTLGVST LGSTASAFAE EKDQNVTQQQ NTGQQKSVGT  60
FYAAPTQITN MATAFEKTLE LLKNQKLTNA EGKQVSIFEG NKYITPEFLK GSISTTGVVL  120
KQIYSDAYSK DFNNASRELA VSLTALIPYG GSIASPLLAL IWPENVDNSQ MKKIEKLIDA  180
KIIKYDITTL KIEYNNLMTR QIAYEKSMTE PNIDKNTRKT NAINAQNAFT DMIAESNKSK  240
ELELAELPVY TTVAAAHIAF LKSMQVQQTR SAAGIDQGTI NSNFNSGNLT DQIAIYTKHI  300
QDVYDKREKE IFKQIEDIGK PFGGSISINN YQTVLTNKYN AIAANRSGND GIEHLKDSLV  360
KAKHQCDELS TELKALYDQT LGNAAFITML GQWQKDIKTN KWSYIDTKGE TKTDWLRLGD  420
KWYYLSKGTN GDTKNLEGAT FAKGEMVTGT MNLSGKTYYF NSDGEMIDYN SSSMNRTYKV  480
VAKLNSSKVL DNDFNHDRLS LLWNDNGGDN QKWFLQYNTD KKAYKIINQQ APHDELAVNG  540
QDNTVFATDD RNDSSDLRYW TLEPAGNGYV FIKNKASGRV LDVTDGNTAN GTVIKTHSQN  600
TPAVAAQMFK LETVQQ                                                 616

SEQ ID NO: 494         moltype = AA  length = 580
FEATURE                Location/Qualifiers
REGION                 1..580
                       note = Description of Artificial Sequence: Synthetic
                        polypeptide
source                 1..580
                       mol_type = protein
                       organism = synthetic construct
SEQUENCE: 494
MFAEEKDQNV TQQQNTGQQK SVGTFYAAPT QITNMATAFE KTLELLKNQK LTNAEGKQVS  60
IFEGNKYITP EFLKGSISTT GVVLKQIYSD AYSKDFNNAS RELAVSLTAL IPYGGSIASP  120
LLALIWPENV DNSQMKKIEK LIDAKIIKYD ITTLKIEYNN LMTRQIAYEK SMTEPNIDKN  180
TRKTNAINAQ NAFTDMIAES NKSKELELAE LPVYTTVAAA HIAFLKSMQV QQTRSAAGID  240
QGTINSNFNS GNLTDQIAIY TKHIQDVYDK REKEIFKQIE DIGKPFGGSI SINNYQTVLT  300
NKYNAIAANR SGNDGIEHLK DSLVKAKHQC DELSTELKAL YDQTLGNAAF ITMLGQWQKD  360
IKTNKWSYID TKGETKTDWL RLGDKWYYLS KGTNGDTKNL EGATFAKGEM VTGTMNLSGK  420
TYYFNSDGEM IDYNSSSMNR TYKVVAKLNS SKVLDNDFNH DRLSLLWNDN GGDNQKWFLQ  480
YNTDKKAYKI INQQAPHDEL AVNGQDNTVF ATDDRNDSSD LRYWTLEPAG NGYVFIKNKA  540
SGRVLDVTDG NTANGTVIKT HSQNTPAVAA QMFKLETVQQ                       580

SEQ ID NO: 495         moltype = AA  length = 824
FEATURE                Location/Qualifiers
source                 1..824
                       mol_type = protein
                       organism = Bacillus sp.
SEQUENCE: 495
MRISTEPIQY PFIPSNPDLS SNKTFTFDWN WGLHHALEAI TGLVEFIPGI GFLAGPYSAL  60
LNYVYGDVID ELFPKVDDNG NTIDITLLFQ TFMAAAEIMM DQKIAETEKA KAVADLGSLH  120
IAMMSFKQQL DNLKNNTKPE DEDHLKSLVQ SQYQIVNTAF STMMSQFSKQ GEEVLLLSSY  180
AQAANLHLLF LQEVYQKGSD WGFPQATIDG YYDSPGSGLG FTQLIQTYTN HCLKFYNQGL  240
SDIKNQPVAL CATGDDVNNQ SFYNQYLYDP IDAANFGTAT CQHSIGTLST GCGGVNFATH  300
GPVCKDEVVA SRIHSNYMQS IANWNQYNEY VQTMQVTVLD LVAIWPYWDP KNYPNGAKKE  360
LPREIYTDIV GSADGKSKDI DTLSQELLPQ PRLFTFLNQI NVKTDSYKQT VDTHNVMNGT  420
INASYNYIDG EIITGIDQQF QNAKGDPFTH PQGSDGSSTY PKPTSTRIDV AFWFEPRSIT  480
FDGSVLDAIG TVWDDTPFKQ IGDNSLAIAY KSRGYDNSSH LLGPTYQLDQ HSISYVKFTP  540
TTFPDVRFVN SGKQLGSLTV GWTSTTVDAM NKIQPDATTS IPAVKAYNNT NQGLAAIITG  600
PGFTGGDIVK LSPGTRIDMG VTPPDSTSEF DIRVRYACKG EGQIRAIRVN NGQWTYGATQ  660
AITSTGGFTD FDHFQYSPAS LLRFQTDPVI IIENTGSVDI YLDKIEFIPT DPSSPPSLPD  720
NEFVIDTTLI DDNTGISLIK NTGKTYTKFT VDQFTFSGAN GTYLGTFLFY KDNQPVSPTD  780
DDFYKLHFLT SPFSITINLP TEFDEVFLNV WSPITRVHLE GRVD                  824

SEQ ID NO: 496         moltype = AA  length = 710
FEATURE                Location/Qualifiers
REGION                 1..710
```

```
                        note = Description of Artificial Sequence: Synthetic
                         polypeptide
source                  1..710
                        mol_type = protein
                        organism = synthetic construct
SEQUENCE: 496
MRISTEPIQY PFIPSNPDLS SNKTFTFDWN WGLHHALEAI TGLVEFIPGI GFLAGPYSAL  60
LNYVYGDVID ELFPKVDDNG NTIDITLLFQ TFMAAAEIMM DQKIAETEKA KAVADLGSLH  120
IAMMSFKQQL DNLKNNTKPE DEDHLKSLVQ SQYQIVNTAF STMMSQFSKQ GEEVLLLSSY  180
AQAANLHLLF LQEVYQKGSD WGFPQATIDG YYDSPGSGLG FTQLIQTYTN HCLKFYNQGL  240
SDIKNQPVAL CATGDDVNNQ SFYNQYLYDP IDAANFGTAT CQHSIGTLST GCGGVNFATH  300
GPVCKDEVVA SRIHSNYMQS IANWNQYNEY VQTMQVTVLD LVAIWPYWDP KNYPNGAKKE  360
LPREIYTDIV GSADGKSKDI DTLSQELLPQ PRLFTFLNQI NVKTDSYKQT VDTHNVMNGT  420
INASYNYIDG EIITGIDQQF QNAKGDPFTH PQGSDGSSTY PKPTSTRIDV AFWFEPRSIT  480
FDGSVLDAIG TVWDDTPFKQ IGDNSLAIAY KSRGYDNSSH LLGPTYQLDQ HSISYVKFTP  540
TTFPDVRFVN SGKQLGSLTV GWTSTTVDAM NKIQPDATTS IPAVKAYNNT NQGLAAIITG  600
PGFTGGDIVK LSPGTRIDMG VTPPDSTSEF DIRVRYACKG EGQIRAIRVN NGQWTYGATQ  660
AITSTGGFTD FDHFQYSPAS LLRFQTDPVI IIENTGSVDI YLDKIEFIPT             710

SEQ ID NO: 497          moltype = AA  length = 480
FEATURE                 Location/Qualifiers
source                  1..480
                        mol_type = protein
                        organism = Bacillus sp.
SEQUENCE: 497
MTLSNIANVS FTKPEELKKI TTIVNNLFAP TVSPTLAADV TDYWIDQVFM KIQALSDDVF  60
SAQKTQLRQR VSQAKQLAKK RNLLVGGNFE TLENWKLSRN ALLRSGNPLF QEAHLELPPA  120
INANLPSYAY QKVDENKLKA NTRYYATGFI AQGDPLEVVV SRYGQEYHRI LHVPAEAALS  180
ISLNEQPNCC GSHPCTCAAC EGKETDSHFF KIPIDVGMLQ LGMNPGIEIG FKISSSEGLA  240
KLSNLEIYED RPLTDKEKRK TLSLEQQWKQ AQQTKATERA RTLQQIKGRF NTLFTTPQHH  300
TLHVNTSYQD LLNTKISPLP DTYHWFMPDV PASDYAVSYE YEEKLQRAWQ QYYARNLVAN  360
GNFVEELSQS WQTKGNVMVK VSNHKPVLQL LGWDSTISQT VTLPVIDQNA EYLVRIVGQG  420
AGYVQIKNGE VSEERLFSEK NIGMDIQELV IDAENEQLMI TLGSNGNKFV VMSVEVILMD  480

SEQ ID NO: 498          moltype = AA  length = 297
FEATURE                 Location/Qualifiers
source                  1..297
                        mol_type = protein
                        organism = Bacillus sp.
SEQUENCE: 498
MLTLTRLVAD YTVDVMYKQL QGSGPFGPFE GGHLLSIMDT QNISVQGETT LNPPPVDIPV  60
TSVTPIISKT ELIVNNDPNN SITKQFTFSE QTTNTVTTTR TAGIEYNVGS ETSISGTIIA  120
ATISEKITFS TKISNTSSTA ITNTKTQTWT DVITITVPPN TKSTIRYIIN AGNFDAIVNA  180
NVIMSGSVTF NPAYGNNCEG LPSQYCQVKN GTPVTVSIAD IMQWALNNPN ISSASGMDST  240
NVTLLPDGNV LYKGTIRVQG QTGINSYIEN TPVPLSGGTG TPIITPGSSS PKTILFA     297

SEQ ID NO: 499          moltype = AA  length = 616
FEATURE                 Location/Qualifiers
source                  1..616
                        mol_type = protein
                        organism = Bacillus sp.
SEQUENCE: 499
MFMPNIDQIL QDLPKATSAS NYKISLTAVE KVVPNIIKGV NEGNINNAAK ALAVYGTSLI  60
PYAGVLISPL ISLLWPELGG SKTLQQMRKE ISDEIDTKIK DSFKTYDETL LKKQIKPFFQ  120
RIQQFEELIN GTTGINYKGI DDIAYSDHSD HSAYSDHSAY SAYSVYSDMS SNILSPGDYY  180
AEGTSDQTAR SEALDINSKF NEIISSCTKD PSGLLVDMDI WELPIYVLLA TAHLQFLYFI  240
TINGKKEKSE KIQFDADTLE TYFSKPFKQK IVEYRDYIER TYKKGYQQFE SKMGALANGN  300
SDRERLQYLK NQIDYYKYHN GPHTSDSGLV KKYEDTLKKY ENLITERDKY LELTINTKTF  360
NMAVPGKWNV TWQNAYDEDP TVHKYRWLND NNHFYLDPT KDGRIKFGWF LDLNEKWYYF  420
NPEREDIDHN PLFAQGEMLA DTSSVINSIR YYFNADGSCK DPFSRESVGR LILREGTYRI  480
ELDNNRFLAI SEKKLTNYHV PYNVVATFPG DSADLSQKWT AKFDSKKEAY QFVNQDNNWV  540
LAWNKTEKHY DQMLIGAPNE HKDEHYWILS STSDGRFYAK NYADQNSNLY LSYAPQSSVY  600
LSVLPRSSGA KLKFVN                                                616

SEQ ID NO: 500          moltype = AA  length = 430
FEATURE                 Location/Qualifiers
REGION                  1..430
                        note = Description of Unknown: Organism from environmental
                         sample
source                  1..430
                        mol_type = protein
                        organism = unidentified
SEQUENCE: 500
LIHADTWNNR IKSISEAAAK KIPYVGAIVS FAIGQLWPTD KADIFSLIKD QVKGLVDQAI  60
LDKEMEERKH EIEGLNDTMN QYVDAGNHEK GGFMTSMLTQ LNIMHHKLTE STNSIHLIPL  120
TITIANIHLT LLRERLSHGK EIYTEDNTAV WQKDLTKRYQ DYHKFFLEIY PKWKAWRESK  180
IEIKWYTDKN PTTVPPFFYW AAHGYAKDSF AAEKPIHYRD DFNSIETTFQ GVCQAIKESW  240
MNDAITKIAA SIATTFTLHR YLPGREDEPA IVDPNLETIW MGPYSLSILG NDSKVSYAVN  300
VTEQPGELKQ VYIREYNSID GMQLIYTDHS GNFIGNPKGG EPHYLDTTQD KYVIGMKMRF  360
```

```
SSGIISRLEV LFSDGSSSGM LGNRKNWSGT DVDAVVESNY KLVCGAYKTG SGPSGTTGIS  420
VIKLGFKYSN                                                         430

SEQ ID NO: 501          moltype = AA  length = 685
FEATURE                 Location/Qualifiers
source                  1..685
                        mol_type = protein
                        organism = Bacillus sp.
SEQUENCE: 501
MNSNNNKESN IKGKLSEQSL LAKSVKYPLA NNQTIALENM NYKDYLKMSE EHNNNYLRNV  60
EAVVETKDSI ILGMNIVGNI LSALGVPFVG PIVGFYTKIL NLLWPSSGKN PWEILMEHVE  120
ELVDQKISEY AKNKALAELE GLGKNFELYK ISLEEWENNP NVSRATRDVR TRFEILDALF  180
TQYMPSFKVI NCEVPQLTVY AQAATLHLLL LKDVSIFGEE WGLSTTTINN YYKRQMNLTA  240
EYSDHCVKWY DIGLDELKGS DAKSWLNYHR FRREMTLMVL DLVALYPSFD VRTYPIETTA  300
QLTREVYTDP IGYNPSEDSS KIGIAWTKLF FHDFDQIEKA VIRPPHAFEI LNSVEIRTVK  360
QPLVFNEKAY INYWCGHSLE YTYANYSEIH NKDYGFQNFT EKNMYSLKNN DVYKIISSAG  420
CLANGYGSVY GLPEATFYGA VRNNLEPTSL SYSKTHTILP SKIQNYDTVE ELPQKTTEQP  480
ENKSYNHRLS HITVYPFGSN GHGGVLPVFA WTHRSVDLNN FIDSKKITQI PAVKSIESAI  540
NDSSISIEKC SGYTGGDVVV CNNIKSVLRV AYLFATAAEN EVSQKYRVRV RYASELAGEL  600
LLSVRESNSD WKEQRALAKV IQTKELEENL TYKNFQYADF EAYNIFDGLV APLVPNFLIE  660
ITALNMKGSG KKIYIDKIEF IPVFE                                        685

SEQ ID NO: 502          moltype = AA  length = 501
FEATURE                 Location/Qualifiers
source                  1..501
                        mol_type = protein
                        organism = Bacillus sp.
SEQUENCE: 502
MEHTDKNINE AQQGTQGNLG ALARFDTWAQ DLGKTTGAGN YKTTLGMAEK LLPTIYKDLD  60
SGNFNNTARS ITMLSTALIP YGGAFISPII GILWPENGPN IKEMLQEMEN KLVGIMDEKI  120
EAKDLDDLEA AVKGLMVTLK EFENSLNGNI GGEYYSAPAD VDSLNRGRIT AIQKGFNDLI  180
SAASKPKFKI AELPIYTIIA TAHLNFLHTV KKQGTSPKIN YTEAALKDLL QNMKKNHKEY  240
AAYIEKTYKE GEARIDSKLE DKQQIEKELD KVHEQLSALG PKPKNHTHIE ENKFIKKKDE  300
LYERARSLKE RLSKYNELMY QKSDFYSKTK GSAAFQIAST GKTVANPSWV KTEGSWVHNG  360
FWYYIDAKGQ VKTGWFNDKA PDGKDRWYYL STGTTGLDSV RGNSLLPKGT MLTGWFHDTR  420
KNKWYYLSPE KDLKNSAGEL FNHGQMMTKW VEIKDTQTGE PHWYYFNPDD GSMTHDKKAV  480
KIGNLKYDFD SNGVCTTPNG Y                                            501

SEQ ID NO: 503          moltype = AA  length = 455
FEATURE                 Location/Qualifiers
REGION                  1..455
                        note = Description of Artificial Sequence: Synthetic
                         polypeptide
source                  1..455
                        mol_type = protein
                        organism = synthetic construct
SEQUENCE: 503
MAEKLLPTIY KDLDSGNFNN TARSITMLST ALIPYGGAFI SPIIGILWPE NGPNIKEMLQ  60
EMENKLVGIM DEKIEAKDLD DLEAAVKGLM VTLKEFENSL NGNIGGEYYS APADVDSLNR  120
GRITAIQKGF NDLISAASKP KFKIAELPIY TIIATAHLNF LHTVKKQGTS PKINYTEAAL  180
KDLLQNMKKN HKEYAAYIEK TYKEGEARID SKLEDKQQIE KELDKVHEQL SALGPKPKNH  240
THIEENKFIK KKDELYERAR SLKERLSKYN ELMYQKSDFY SKTKGSAAFQ IASTGKTVAN  300
PSWVKTEGSW VHNGFWYYID AKGQVKTGWF NDKAPDGKDR WYYLSTGTTG LDSVRGNSLL  360
PKGTMLTGWF HDTRKNKWYY LSPEKDLKNS AGELFNHGQM MTKWVEIKDT QTGEPHWYYF  420
NPDDGSMTHD KKAVKIGNLK YDFDSNGVCT TPNGY                             455

SEQ ID NO: 504          moltype = AA  length = 449
FEATURE                 Location/Qualifiers
source                  1..449
                        mol_type = protein
                        organism = Bacillus sp.
SEQUENCE: 504
MSTNKVHQLP KGFLKDLGEE LKQKTQITSE DLAKIMRDAS HDSAKLNDLI RQASIAAVGK  60
IPSVGMAISP IISYLWPEQA GVDSKLNALE ARITAKIGQA VGEQHTRDIQ SKIKDLKHAM  120
EKLEDSLNTG TFYDGSVKDI HGVLRNQAKD VNDKFISLMH FTQQEHNEIV DLPIYTKVAA  180
AHILFLKYLK THGTDPKLFR YDKPSTLNAE FKTDNIESNI ATYAKYIEDT FKKGDNKLAT  240
ILKTRAEKIA KKRNLIVPGI PTNIGTESQI HTLENEIKGI NDLKVEEKRA LYRDLTVNEG  300
SFEAISGKKL TYTNFGWIID GGKWYYLSPY KDFINFDGKT FDKGELVTGW LKPYEEKNYY  360
YLSPADGTKN DDGKVFNKGE MTTGWMQVGK KSTWDGKHGA WYYLDNKEGN KDFKGTTGRM  420
LHDETARVKN KQGDFKKHYF NENGTWGDN                                    449

SEQ ID NO: 505          moltype = AA  length = 622
FEATURE                 Location/Qualifiers
source                  1..622
                        mol_type = protein
                        organism = Bacillus sp.
SEQUENCE: 505
MKYKDRKHAK RKYKQALLAT VATMTLGVST LGSTASTFAE EKDQNVAQQQ NTVQPQQGTD  60
SLGAGGGATS SKAFEVLTDG TVKLLNDNIF DSKTKQAIVQ LGGDGLKQTY KDLQSGNFEE  120
```

```
TARTLTLGAV ALIPYGGAFV SPILGLLWPG SESDKMKELQ DQIKAVDEKV NALQNANLKA  180
KYDALMADLH QFENGMNNKS GSSSFRMAGS IEESNRTAAM HINSKFKELI QQCKIEMLKN  240
EELPMYTLVA TAHLVFLQII EKNQSNPRLQ LDQQSYNTYY KEDIQNLPGE YANYVMKTYT  300
TTIENYKKQM QDIAKNAPEG NYISADENQT LKMMQDKYQE KLKNFLRDGT ASVISGQNDI  360
MNKLQKASND YSTLMSKKNK YYQETAGSEA FQMLALGTWK KDGDKWNFID TKGQKKTDWL  420
QLGATWYYLS KGGDSDTKNV EGTTFAKGEM VTGTMNLGGK TYTFDSDGKC LNPDGGAVNA  480
QILNGTYKIV SKLDNNMVLN TSDHRAVLKG TNEATWGNRW TFQYDNEKHA YLIKNEQQSG  540
GPWKLAEYSN TDTVFQTDDG TNRQEHYWTL EPAGDGYFFI HNKSQPDKVL DITGSNKAAG  600
TKIGLFNKNG QDNQKFKLEK TN                                          622

SEQ ID NO: 506          moltype = AA  length = 588
FEATURE                 Location/Qualifiers
REGION                  1..588
                        note = Description of Artificial Sequence: Synthetic
                         polypeptide
source                  1..588
                        mol_type = protein
                        organism = synthetic construct
SEQUENCE: 506
MSTFAEEKDQ NVAQQQNTVQ PQQGTDSLGA GGGATSSKAF EVLTDGTVKL LNDNIFDSKT  60
KQAIVQLGGD GLKQTYKDLQ SGNFEETART LTLGAVALIP YGGAFVSPIL GLLWPGSESD  120
KMKELQDQIK AVDEKVNALQ NANLKAKYDA LMADLHQFEN GMNNKSGSSS FRMAGSIEES  180
NRTAAMHINS KFKELIQQCK IEMLKNEELP MYTLVATAHL VFLQIIEKNQ SNPRLQLDQQ  240
SYNTYYKEDI QNLPGEYANY VMKTYTTTIE NYKKQMQDIA KNAPEGNYIS ADENQTLKMM  300
QDKYQEKLKN FLRDGTASVI SGQNDIMNKL QKASNDYSTL MSKKNKYYQE TAGSEAFQML  360
ALGTWKKDGD KWNFIDTKGQ KKTDWLQLGA TWYYLSKGGD SDTKNVEGTT FAKGEMVTGT  420
MNLGGKTYTF DSDGKCLNPD GGAVNAQILN GTYKIVSKLD NNMVLNTSDH RAVLKGTNEA  480
TWGNRWTFQY DNEKHAYLIK NEQQSGGPWK LAEYSNTDTV FQTDDGTNRQ EHYWTLEPAG  540
DGYFFIHNKS QPDKVLDITG SNKAAGTKIG LFNKNGQDNQ KFKLEKTN              588

SEQ ID NO: 507          moltype = AA  length = 334
FEATURE                 Location/Qualifiers
source                  1..334
                        mol_type = protein
                        organism = Bacillus sp.
SEQUENCE: 507
MYEMNKWIKP IVCMGILTTS VTTYNNSRTA YAQSASQFIY DLQDNATDWL HSIGRNQNND  60
VNFQENKSAG TYNFKSVSFS SPFDIKFEKY SAEKIGPENQ TDEKIVFSFT DELINRSSIS  120
QKLSTGTRSE AISNTTTATI TKGFKIGGKA STKISIPFIG ETGIEVSPEY NHSNAISDVK  180
TTMKTLTATP QSIDVPAGKK ALVTVEFIQR TIEGKVKLDA VASGHAKGTF DYIGMPFITS  240
GAGKWVKREF DMNLNQIYKR SAELSNEVND PSIITINPDH ETITLHGEVK YISEKIDSSY  300
RVHVDIVDID TDTSNKNRVK KRDIINSYSY TVNP                              334

SEQ ID NO: 508          moltype = AA  length = 331
FEATURE                 Location/Qualifiers
REGION                  1..331
                        note = Description of Artificial Sequence: Synthetic
                         polypeptide
source                  1..331
                        mol_type = protein
                        organism = synthetic construct
SEQUENCE: 508
MNKWIKPIVC MGILTTSVTT YNNSRTAYAQ SASQFIYDLQ DNATDWLHSI GRNQNNDVNF  60
QENKSAGTYN FKSVSFSSPF DIKFEKYSAE KIGPENQTDE KIVFSFTDEL INRSSISQKL  120
STGTRSEAIS NTTTATITKG FKIGGKASTK ISIPFIGETG IEVSPEYNHS NAISDVKTTM  180
KTLTATPQSI DVPAGKKALV TVEFIQRTIE GKVKLDAVAS GHAKGTFDYI GMPFITSGAG  240
KWVKREFDMN LNQIYKRSAE LSNEVNDPSI ITINPDHETI TLHGEVKYIS EKIDSSYRVH  300
VDIVDIDTDT SNKNRVKKRD IINSYSYTVN P                                 331

SEQ ID NO: 509          moltype = AA  length = 303
FEATURE                 Location/Qualifiers
REGION                  1..303
                        note = Description of Artificial Sequence: Synthetic
                         polypeptide
source                  1..303
                        mol_type = protein
                        organism = synthetic construct
SEQUENCE: 509
MQSASQFIYD LQDNATDWLH SIGRNQNNDV NFQENKSAGT YNFKSVSFSS PFDIKFEKYS  60
AEKIGPENQT DEKIVFSFTD ELINRSSISQ KLSTGTRSEA ISNTTTATIT KGFKIGGKAS  120
TKISIPFIGE TGIEVSPEYN HSNAISDVKT TMKTLTATPQ SIDVPAGKKA LVTVEFIQRT  180
IEGKVKLDAV ASGHAKGTFD YIGMPFITSG AGKWVKREFD MNLNQIYKRS AELSNEVNDP  240
SIITINPDHE TITLHGEVKY ISEKIDSSYR VHVDIVDIDT DTSNKNRVKK RDIINSYSYT  300
VNP                                                                303

SEQ ID NO: 510          moltype = AA  length = 736
FEATURE                 Location/Qualifiers
source                  1..736
                        mol_type = protein
```

```
                          organism = Bacillus sp.
SEQUENCE: 510
LAHIIETRKN RITVGYKNFI QNNKYSDLGY TKQLFNISNS LSWNDLEPLV EKGAGALADA  60
ALSSLLTPVG GAIAGAAVSK LISILWPADA PDTLGPILTE MIGLTDQMIR YNNINNSIAA  120
AQAILEGFRE SLQSFQIIID NPNSSATSIR SKADIILGLF ENQLPKLKNS DLTQAIAILP  180
VYAQVANLHV VLLRDCIRNK NKWGFDAEDV QNLTTNIKRV IPDYTKYCID TYNNKKSQML  240
NIVVPMCSCQ LPGELQVPGD CKQSCNTCPT TCQNCGEVYP WANDQHSWTT SDKSLFKNCY  300
IYVSQLKGCD KTLQSEKSRC SKAIVATRSG VGLYQSVENW NAYNRFIRNT TLSVLDIISL  360
WKYLDPTQYT DNIGVKSELS RPIYSDIIGN TYLPDASQNT ISAISSRMLP KPDLFKYLNS  420
ISFATNYYQS GTWNTDPDSL NVFASVSSVS GDLIVGMKLQ YNYGGGNIGI TNPQVAGTFT  480
MSGLGSSGVS IQSAKISSSN NIYSIFISRR FEPRIMTFYD KNQKQIFTVG STQGEGNTQP  540
PYSNETLSLA NHILSYIKYE PVSPAESWVF VNTNPLNQYR NQQLGAMLLE WTSETVDPLN  600
TINPTTITSI PAVKAQAYEP IKVVAGPGHT GGNLVQLLPN SRIVLVLKNT ITKAFKIRIR  660
CVCPNGTQVN TGSIGDTPMK TTISKSGSLD FQYTDFQYVD LPQYTLAHSD TDLPTYQISN  720
TGANDIYIDI IDFIPQ                                                736

SEQ ID NO: 511          moltype = AA  length = 736
FEATURE                 Location/Qualifiers
REGION                  1..736
                        note = Description of Artificial Sequence: Synthetic
                         polypeptide
source                  1..736
                        mol_type = protein
                        organism = synthetic construct
SEQUENCE: 511
MAHIIETRKN RITVGYKNFI QNNKYSDLGY TKQLFNISNS LSWNDLEPLV EKGAGALADA  60
ALSSLLTPVG GAIAGAAVSK LISILWPADA PDTLGPILTE MIGLTDQMIR YNNINNSIAA  120
AQAILEGFRE SLQSFQIIID NPNSSATSIR SKADIILGLF ENQLPKLKNS DLTQAIAILP  180
VYAQVANLHV VLLRDCIRNK NKWGFDAEDV QNLTTNIKRV IPDYTKYCID TYNNKKSQML  240
NIVVPMCSCQ LPGELQVPGD CKQSCNTCPT TCQNCGEVYP WANDQHSWTT SDKSLFKNCY  300
IYVSQLKGCD KTLQSEKSRC SKAIVATRSG VGLYQSVENW NAYNRFIRNT TLSVLDIISL  360
WKYLDPTQYT DNIGVKSELS RPIYSDIIGN TYLPDASQNT ISAISSRMLP KPDLFKYLNS  420
ISFATNYYQS GTWNTDPDSL NVFASVSSVS GDLIVGMKLQ YNYGGGNIGI TNPQVAGTFT  480
MSGLGSSGVS IQSAKISSSN NIYSIFISRR FEPRIMTFYD KNQKQIFTVG STQGEGNTQP  540
PYSNETLSLA NHILSYIKYE PVSPAESWVF VNTNPLNQYR NQQLGAMLLE WTSETVDPLN  600
TINPTTITSI PAVKAQAYEP IKVVAGPGHT GGNLVQLLPN SRIVLVLKNT ITKAFKIRIR  660
CVCPNGTQVN TGSIGDTPMK TTISKSGSLD FQYTDFQYVD LPQYTLAHSD TDLPTYQISN  720
TGANDIYIDI IDFIPQ                                                736

SEQ ID NO: 512          moltype = AA  length = 338
FEATURE                 Location/Qualifiers
source                  1..338
                        mol_type = protein
                        organism = Enterococcus sp.
SEQUENCE: 512
MIHTVINKSI GNDFTIGLSI MIKGINKMKK VIKLMLGVVG ATSVGLFKGE SVACADDSLP  60
QIGEGYLKSV NQSTIDRMST MAYALSYQMY QWGDIGVNER LTGNEYNPKN VSSQSYSVGV  120
NSDMGTKQTS KTVNTSVFHN QTNQDQTFTT PSYTETYIDS LTTSTTHSAG ISTSASTEIS  180
VPMFGSASMG LELSYNFSTT TSHTRETQKG WTVPGQAINV RPGHTVEVNW VFYTGEATGS  240
VDLQERIRAD IPYKKDSAGR IHTYGLGTVV GDRQVLSDSY WDRYITESRN NWKKVDANVA  300
GQKIGAGTYR VDYGSGFVLE AFDRTTGTKE IIATGYRI                        338

SEQ ID NO: 513          moltype = AA  length = 318
FEATURE                 Location/Qualifiers
REGION                  1..318
                        note = Description of Artificial Sequence: Synthetic
                         polypeptide
source                  1..318
                        mol_type = protein
                        organism = synthetic construct
SEQUENCE: 513
MIKGINKMKK VIKLMLGVVG ATSVGLFKGE SVACADDSLP QIGEGYLKSV NQSTIDRMST  60
MAYALSYQMY QWGDIGVNER LTGNEYNPKN VSSQSYSVGV NSDMGTKQTS KTVNTSVFHN  120
QTNQDQTFTT PSYTETYIDS LTTSTTHSAG ISTSASTEIS VPMFGSASMG LELSYNFSTT  180
TSHTRETQKG WTVPGQAINV RPGHTVEVNW VFYTGEATGS VDLQERIRAD IPYKKDSAGR  240
IHTYGLGTVV GDRQVLSDSY WDRYITESRN NWKKVDANVA GQKIGAGTYR VDYGSGFVLE  300
AFDRTTGTKE IIATGYRI                                              318

SEQ ID NO: 514          moltype = AA  length = 284
FEATURE                 Location/Qualifiers
REGION                  1..284
                        note = Description of Artificial Sequence: Synthetic
                         polypeptide
source                  1..284
                        mol_type = protein
                        organism = synthetic construct
SEQUENCE: 514
MDDSLPQIGE GYLKSVNQST IDRMSTMAYA LSYQMYQWGD IGVNERLTGN EYNPKNVSSQ  60
SYSVGVNSDM GTKQTSKTVN TSVFHNQTNQ DQTFTTPSYT ETYIDSLTTS TTHSAGISTS  120
```

```
ASTEISVPMF GSASMGLELS YNFSTTTSHT RETQKGWTVP GQAINVRPGH TVEVNWVFYT  180
GEATGSVDLQ ERIRADIPYK KDSAGRIHTY GLGTVVGDRQ VLSDSYWDRY ITESRNNWKK  240
VDANVAGQKI GAGTYRVDYG SGFVLEAFDR TTGTKEIIAT GYRI                   284

SEQ ID NO: 515         moltype = AA  length = 430
FEATURE                Location/Qualifiers
source                 1..430
                       mol_type = protein
                       organism = Brevibacillus sp.
SEQUENCE: 515
LIHADTWNNR IKSISEAAAK KIPYVGSIVS FAIGQLWPTD KADIFSLIKD QVKGLVDQAI  60
LNKEMEERKH EIEGLNDTMN QYVDAGNHEK GGFMTSMLTQ LNIMHHKLTE STNSIHLIPL  120
TITIANIHLT LLRERLSHGK EIYTEDNTTV WQKDLTKRYQ DYHKFFLEIY PKWKTWRESK  180
IEIKWYTDKN PTTVPPFFYW AAHGYAKDTF AAEKPIHYRD DFNSIETTFQ GVCQAIKESW  240
MNDAIAKIAA SIATTFTLHR YIPGREDEPA IVDPNLETIW MGPYSLSILG NDSKVSYAVN  300
VEDQPGELKQ VYIREYNSID GMQLIYTDHS GNFIGNPKGG EPHYLPTTQD KYVIGMKMRF  360
SSGIICRLEV LFSDGSSSGM LGNRKNWSGT DVDAVVESNY KLVCGAYKTG AGPSGTTGIS  420
VIKLGFKYSN                                                         430

SEQ ID NO: 516         moltype = AA  length = 430
FEATURE                Location/Qualifiers
REGION                 1..430
                       note = Description of Artificial Sequence: Synthetic
                        polypeptide
source                 1..430
                       mol_type = protein
                       organism = synthetic construct
SEQUENCE: 516
MIHADTWNNR IKSISEAAAK KIPYVGSIVS FAIGQLWPTD KADIFSLIKD QVKGLVDQAI  60
LNKEMEERKH EIEGLNDTMN QYVDAGNHEK GGFMTSMLTQ LNIMHHKLTE STNSIHLIPL  120
TITIANIHLT LLRERLSHGK EIYTEDNTTV WQKDLTKRYQ DYHKFFLEIY PKWKTWRESK  180
IEIKWYTDKN PTTVPPFFYW AAHGYAKDTF AAEKPIHYRD DFNSIETTFQ GVCQAIKESW  240
MNDAIAKIAA SIATTFTLHR YIPGREDEPA IVDPNLETIW MGPYSLSILG NDSKVSYAVN  300
VEDQPGELKQ VYIREYNSID GMQLIYTDHS GNFIGNPKGG EPHYLPTTQD KYVIGMKMRF  360
SSGIICRLEV LFSDGSSSGM LGNRKNWSGT DVDAVVESNY KLVCGAYKTG AGPSGTTGIS  420
VIKLGFKYSN                                                         430

SEQ ID NO: 517         moltype = AA  length = 430
FEATURE                Location/Qualifiers
REGION                 1..430
                       note = Description of Unknown: Organism from environmental
                        sample
source                 1..430
                       mol_type = protein
                       organism = unidentified
SEQUENCE: 517
LIHADTWNNR IKSISEAAAK KIPYVGAIVS FAIGQLWPTD KADIFSLIKD QIKGLVDQAI  60
LEKEMEERKH EIEGLNDTMN QYVDAGNHEK GGFMTSMLTQ LNIMHHKLTE STNSIHLIPL  120
TITIANIHLT LLRERFSHGK EIYTEDNTTV WQKDLTKRYQ DYHKFFREIY PKWKAWRESK  180
IEIKWYTDKN PTTVPPFFYW AAHGYAKDTF AAEKPIHYRD DFNSIETTFQ GVCQAIKESW  240
MNDAIAKIAA SIATTFTLHR YLPGREDEPA IVDPNLETIW MGPYSLSILG NDSKVSYAVN  300
VTDQPGELKQ VYIREYNSID GMQLIYTDHS GNFIGNPKGG EPHYLDTTQD KYVTGMKMRF  360
SSGIISRLEV LFSDGSSSGM LGNRKNWSGT DVDAVVESNY KLVCGAYKTG SGPSGTTGIS  420
VIKLGFKYSN                                                         430

SEQ ID NO: 518         moltype = AA  length = 430
FEATURE                Location/Qualifiers
REGION                 1..430
                       note = Description of Artificial Sequence: Synthetic
                        polypeptide
source                 1..430
                       mol_type = protein
                       organism = synthetic construct
SEQUENCE: 518
MIHADTWNNR IKSISEAAAK KIPYVGAIVS FAIGQLWPTD KADIFSLIKD QIKGLVDQAI  60
LEKEMEERKH EIEGLNDTMN QYVDAGNHEK GGFMTSMLTQ LNIMHHKLTE STNSIHLIPL  120
TITIANIHLT LLRERFSHGK EIYTEDNTTV WQKDLTKRYQ DYHKFFREIY PKWKAWRESK  180
IEIKWYTDKN PTTVPPFFYW AAHGYAKDTF AAEKPIHYRD DFNSIETTFQ GVCQAIKESW  240
MNDAIAKIAA SIATTFTLHR YLPGREDEPA IVDPNLETIW MGPYSLSILG NDSKVSYAVN  300
VTDQPGELKQ VYIREYNSID GMQLIYTDHS GNFIGNPKGG EPHYLDTTQD KYVTGMKMRF  360
SSGIISRLEV LFSDGSSSGM LGNRKNWSGT DVDAVVESNY KLVCGAYKTG SGPSGTTGIS  420
VIKLGFKYSN                                                         430

SEQ ID NO: 519         moltype = AA  length = 430
FEATURE                Location/Qualifiers
REGION                 1..430
                       note = Description of Unknown: Organism from environmental
                        sample
source                 1..430
```

```
                        mol_type = protein
                        organism = unidentified
SEQUENCE: 519
LIHADTWNNR IKSISEAAAK KIPYVGAIVS FAIGQLWPTD KADIFSLIKD QVKGLVDQAI  60
LNKEMEERKH EIEGLNDTMN QYVDAGNHEK GGFMTSMLTQ LNIMHHKLTE STNSIHLIPL  120
TITIANIHLT LLRERLSHGK EIYTEDNTTV WQKDLTKRYQ DYHRFFLEIY PKWKTWRESK  180
IEIKWYTDKN PTTVPPFFYW AAHGYARDTF AEEKPIHYRD DFNSIETTFQ GVCQAIKESW  240
MNDAIAKIAA SIATTFTLHR YLPGREDEPA IVDPNLETIW MGPYSLSISG NDSKVSYAVN  300
VTDQPGELKQ VYIREYNSID GMQLIYTDHS GNFVGNPKGG ESHYLPATQD KYVTGMKMRF  360
SSGIISRLEV LFSDGSSSGM LGNRKDWSGT DVDAVVESNY KLVCGAYKTG SGPSGTTGIS  420
VIKLGFKYSN                                                         430

SEQ ID NO: 520          moltype = AA  length = 430
FEATURE                 Location/Qualifiers
REGION                  1..430
                        note = Description of Artificial Sequence: Synthetic
                         polypeptide
source                  1..430
                        mol_type = protein
                        organism = synthetic construct
SEQUENCE: 520
MIHADTWNNR IKSISEAAAK KIPYVGAIVS FAIGQLWPTD KADIFSLIKD QVKGLVDQAI  60
LNKEMEERKH EIEGLNDTMN QYVDAGNHEK GGFMTSMLTQ LNIMHHKLTE STNSIHLIPL  120
TITIANIHLT LLRERLSHGK EIYTEDNTTV WQKDLTKRYQ DYHRFFLEIY PKWKTWRESK  180
IEIKWYTDKN PTTVPPFFYW AAHGYARDTF AEEKPIHYRD DFNSIETTFQ GVCQAIKESW  240
MNDAIAKIAA SIATTFTLHR YLPGREDEPA IVDPNLETIW MGPYSLSISG NDSKVSYAVN  300
VTDQPGELKQ VYIREYNSID GMQLIYTDHS GNFVGNPKGG ESHYLPATQD KYVTGMKMRF  360
SSGIISRLEV LFSDGSSSGM LGNRKDWSGT DVDAVVESNY KLVCGAYKTG SGPSGTTGIS  420
VIKLGFKYSN                                                         430

SEQ ID NO: 521          moltype = AA  length = 431
FEATURE                 Location/Qualifiers
REGION                  1..431
                        note = Description of Unknown: Organism from environmental
                         sample
source                  1..431
                        mol_type = protein
                        organism = unidentified
SEQUENCE: 521
MYLMLADTWN NRIKSITEGA TKKIPYVGAI VSFAIGQLWP TDKADIFSLI KEQVKGLVDQ  60
AILDKEMEER KHEIEGLEDT MKQYVDAGNR EKGGFMTSML TQLNIMHHKL TESSNSIHLI  120
PLTITIANIH LTLLRERLSH GKEIYTEDNT TVWQKDLTKR YQDYHKFFLE IYPKWKAWRE  180
SKIEIKWYTD KNPTTVPPFF YWAAHGKAKD TFTGKSVHYR DDFNSIEATF QGVCEAIKES  240
WMNDAIAKIA ASIATTFTLH HYLPGRESEP AIVDPNLETI WMGPYSLSIN GNDRKVSYAV  300
NVTDQPGELK QVYIREYNSI DGMQLIYTDH SGNFIGNPKG GEPHYLHATQ DKYVTGMKLR  360
FSSGIICRVE VLFSDGSTSG MLGNRKNWSG TDVDAVVESN YKLVSGAYKT GSGPSGTSGI  420
SVIKLGFKYS N                                                       431

SEQ ID NO: 522          moltype = AA  length = 430
FEATURE                 Location/Qualifiers
source                  1..430
                        mol_type = protein
                        organism = Brevibacillus sp.
SEQUENCE: 522
LIHADTWNNR IKSISEAAAK KIPYVGAIVS FAIGQLWPTD KADIFSLIKD QIKGLVDQAI  60
LEKEMEERKH EIEGLNDTMN QYVDAGNHEK GGFMTSMLTQ LNIMHHKLTE STNSIHLIPL  120
TITIANIHLT LLRERFSHGK EIYTEDNTTV WQKDLTKRYQ DYHRFFLEIY PKWKTWRESK  180
IEIKWYTDKN PTTVPPFFYW AAHGYARDTF AEEKPIHYRD DFNSIETTFQ GVCQAIKESW  240
MNDAIAKIAA SIATTFTLHR YLPGREDEPA IVDPNLETIW MGPYSLSISG NDSKVSYAVN  300
VTDQPGELKQ VYIREYNSID GMQLIYTDHS GNFVGNPKGG ESHYLPATQD KYVTGMKMRF  360
SSGIISRLEV LFSDGSSSGM LGNRKDWSGT DVDAVVESNY KLVCGAYKTG SGPSGTTGIS  420
VIKLGFKYSN                                                         430

SEQ ID NO: 523          moltype = AA  length = 430
FEATURE                 Location/Qualifiers
REGION                  1..430
                        note = Description of Artificial Sequence: Synthetic
                         polypeptide
source                  1..430
                        mol_type = protein
                        organism = synthetic construct
SEQUENCE: 523
MIHADTWNNR IKSISEAAAK KIPYVGAIVS FAIGQLWPTD KADIFSLIKD QIKGLVDQAI  60
LEKEMEERKH EIEGLNDTMN QYVDAGNHEK GGFMTSMLTQ LNIMHHKLTE STNSIHLIPL  120
TITIANIHLT LLRERFSHGK EIYTEDNTTV WQKDLTKRYQ DYHRFFLEIY PKWKTWRESK  180
IEIKWYTDKN PTTVPPFFYW AAHGYARDTF AEEKPIHYRD DFNSIETTFQ GVCQAIKESW  240
MNDAIAKIAA SIATTFTLHR YLPGREDEPA IVDPNLETIW MGPYSLSISG NDSKVSYAVN  300
VTDQPGELKQ VYIREYNSID GMQLIYTDHS GNFVGNPKGG ESHYLPATQD KYVTGMKMRF  360
SSGIISRLEV LFSDGSSSGM LGNRKDWSGT DVDAVVESNY KLVCGAYKTG SGPSGTTGIS  420
```

-continued

```
VIKLGFKYSN                                                          430

SEQ ID NO: 524          moltype = AA  length = 430
FEATURE                 Location/Qualifiers
REGION                  1..430
                        note = Description of Unknown: Organism from environmental
                         sample
source                  1..430
                        mol_type = protein
                        organism = unidentified
SEQUENCE: 524
LIHADTWNNR IKSISEAAAK KIPYVGAIVS FAIGQLWPTD KADIFSLIKD QVKGLVDQAI  60
LNKEMEERKH EIEGLNDTMN QYVDAGNHEK GGFMTSMLTQ LNIMHHKLTE STNSIHLIPL  120
TITIANIHLT LLRERLSHGK EIYTEDNTTV WQKDLTKRYQ DYHRFFLVIY PKWKTWRESK  180
IEIKWYTDKN PTTVPPFFYW AAHGYAKDTF AEEKPIHYRD DFNSIETTFQ GVCQAIKESW  240
MNDAIAKIAA SIATTFTLHR YLPGREDEPA IVDPNLETIW MGPYSLSIFG NDSKVSYAVN  300
VTDQPGELKQ VYIREYNSID GMQLVYTDHS GNFIGNPKGG EPHYLHATED KYVTGMKMRF  360
SSGIICRLEV LFSDGSSSGM LGNRKDWSGT DVDAVVESNY KLVCGAYKTG AGPSGTTGIS  420
VIKLGFKYSN                                                          430

SEQ ID NO: 525          moltype = AA  length = 430
FEATURE                 Location/Qualifiers
REGION                  1..430
                        note = Description of Artificial Sequence: Synthetic
                         polypeptide
source                  1..430
                        mol_type = protein
                        organism = synthetic construct
SEQUENCE: 525
MIHADTWNNR IKSISEAAAK KIPYVGAIVS FAIGQLWPTD KADIFSLIKD QVKGLVDQAI  60
LNKEMEERKH EIEGLNDTMN QYVDAGNHEK GGFMTSMLTQ LNIMHHKLTE STNSIHLIPL  120
TITIANIHLT LLRERLSHGK EIYTEDNTTV WQKDLTKRYQ DYHRFFLVIY PKWKTWRESK  180
IEIKWYTDKN PTTVPPFFYW AAHGYAKDTF AEEKPIHYRD DFNSIETTFQ GVCQAIKESW  240
MNDAIAKIAA SIATTFTLHR YLPGREDEPA IVDPNLETIW MGPYSLSIFG NDSKVSYAVN  300
VTDQPGELKQ VYIREYNSID GMQLVYTDHS GNFIGNPKGG EPHYLHATED KYVTGMKMRF  360
SSGIICRLEV LFSDGSSSGM LGNRKDWSGT DVDAVVESNY KLVCGAYKTG AGPSGTTGIS  420
VIKLGFKYSN                                                          430
```